(12) United States Patent
Pinkerton et al.

(10) Patent No.: US 11,731,986 B2
(45) Date of Patent: Aug. 22, 2023

(54) INHIBITORS OF LOW MOLECULAR WEIGHT PROTEIN TYROSINE PHOSPHATASE (LMPTP) AND USES THEREOF

(71) Applicant: Sanford Burnham Prebys Medical Discovery Institute, La Jolla, CA (US)

(72) Inventors: Anthony B. Pinkerton, Rancho Santa Fe, CA (US); Robert J. Ardecky, Encinitas, CA (US); Jiwen Zou, San Diego, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 164 days.

(21) Appl. No.: 17/342,226

(22) Filed: Jun. 8, 2021

(65) Prior Publication Data

US 2023/0029557 A1  Feb. 2, 2023

Related U.S. Application Data

(62) Division of application No. 16/610,055, filed as application No. PCT/US2018/029749 on Apr. 27, 2018, now Pat. No. 11,066,420.

(60) Provisional application No. 62/492,618, filed on May 1, 2017.

(51) Int. Cl.
| | | |
|---|---|---|
| *C07D 471/04* | (2006.01) |
| *A61K 31/5377* | (2006.01) |
| *C07D 519/00* | (2006.01) |
| *A61P 3/04* | (2006.01) |
| *A61K 45/06* | (2006.01) |

(52) U.S. Cl.
CPC .............. *C07D 519/00* (2013.01); *A61P 3/04* (2018.01); *A61K 45/06* (2013.01)

(58) Field of Classification Search
CPC . C07D 471/04; C07D 401/12; A61K 31/5377
USPC ........................................................ 514/300
See application file for complete search history.

(56) References Cited

U.S. PATENT DOCUMENTS

| | | |
|---|---|---|
| 3,340,260 A | 9/1967 | Morton et al. |
| 6,440,955 B1 | 8/2002 | Stasiak et al. |
| 6,440,995 B1 | 8/2002 | Alanine et al. |
| 6,559,163 B2 | 5/2003 | Cai et al. |
| 6,828,329 B2 | 12/2004 | Cai et al. |
| 7,037,922 B1 | 5/2006 | Yuan et al. |
| 7,169,797 B2 | 1/2007 | Xin et al. |
| 7,402,696 B2 | 7/2008 | Suzuki et al. |
| 7,446,112 B2 | 11/2008 | Grootenhuis et al. |
| 7,511,145 B2 | 3/2009 | Schmitz et al. |
| 8,193,199 B2 | 6/2012 | Chen et al. |
| 8,343,980 B2 | 1/2013 | Gonzalez, III et al. |
| 8,796,180 B2 | 8/2014 | Gross et al. |
| 8,877,707 B2 | 11/2014 | Zhong et al. |
| 8,901,145 B2 | 12/2014 | Balding et al. |
| 9,403,758 B2 * | 8/2016 | Patterson .............. C07C 323/42 |
| 10,626,094 B2 | 4/2020 | Bottini et al. |
| 11,066,420 B2 | 7/2021 | Pinkerton et al. |
| 2006/0128702 A1 | 6/2006 | Pal et al. |
| 2006/0194805 A1 | 8/2006 | Bakthavatchalam et al. |
| 2008/0207614 A1 | 8/2008 | Lee et al. |
| 2009/0209536 A1 | 8/2009 | Gahman et al. |
| 2009/0306133 A1 | 12/2009 | Blomberg et al. |
| 2011/0288090 A1 | 11/2011 | Armstrong et al. |
| 2020/0290977 A1 | 9/2020 | Bottini et al. |

FOREIGN PATENT DOCUMENTS

| | | |
|---|---|---|
| JP | H083163 A | 1/1996 |
| JP | 2002286821 A | 10/2002 |
| JP | 2007514759 A | 6/2007 |
| JP | 2008179621 A | 8/2008 |
| WO | WO-0076982 A1 | 12/2000 |
| WO | WO-0192232 A1 | 12/2001 |
| WO | WO-2004056352 A1 | 7/2004 |
| WO | WO-2004081009 A1 | 9/2004 |
| WO | WO-2004112710 A2 | 12/2004 |
| WO | WO-2005035521 A1 | 4/2005 |
| WO | WO-2005056552 A1 | 6/2005 |
| WO | WO-2005108370 A1 | 11/2005 |
| WO | WO-2007009911 A1 | 1/2007 |
| WO | WO-2010024356 A1 | 3/2010 |
| WO | WO-2011054433 A1 | 5/2011 |
| WO | WO-2011127070 A2 | 10/2011 |
| WO | WO-2014048532 A1 | 4/2014 |
| WO | WO-2014117090 A1 | 7/2014 |
| WO | WO-2014147611 A1 | 9/2014 |
| WO | WO-2014164749 A1 | 10/2014 |
| WO | WO-2014164767 A1 | 10/2014 |
| WO | WO-2015033228 A2 | 3/2015 |
| WO | WO-2016061280 A1 | 4/2016 |
| WO | WO-2018204176 A1 | 11/2018 |

OTHER PUBLICATIONS

Abbiati et al. An Efficient Synthesis of 2,4-Substituted [1,8]Naphthyridines from 3-(2-Amino-5-methylpyridin-3-yl)-1-arylprop-2-yn-1-ones. Synthesis 2002(13):1912-1916 (2002).

Alafeefy et al. Synthesis, Analgesic and Anti-inflammatory Evaluation of Some Novel Quinazoline Derivatives. European Journal of Medicinal Chemistry 45(11):4947-4952 (2010).

Batt et al. Immunosuppressive structure-activity relationships of Brequinarand related cinchoninic acid derivatives. Bioorg Med Chem Lett 5(14):1549-54 (1995).

(Continued)

*Primary Examiner* — Niloofar Rahmani
(74) *Attorney, Agent, or Firm* — Wilson Sonsini Goodrich & Rosati

(57) ABSTRACT

Protein tyrosine phosphatases (PTPs) are key regulators of metabolism and insulin signaling. As a negative regulator of insulin signaling, the low molecular weight protein tyrosine phosphatase (LMPTP) is a target for insulin resistance and related conditions. Described herein are compounds capable of modulating the level of activity of low molecular weight protein tyrosine phosphatase (LMPTP) and compositions, and methods of using these compounds and compositions.

18 Claims, No Drawings

(56) References Cited

OTHER PUBLICATIONS

Bauer et al. Discovery of 4-hydroxy-1,6-naphthyridine-3-carbonitrile derivatives as novel PDE10A inhibitors. Bioorg Med Chem Lett 22(5):1944-1948 (2012).
Berge et al. Pharmaceutical Salts. Journal of Pharmaceutical Sciences 66(1):1-19 (Jan. 1977).
Brouwer et al. Development of N-methyl-(2-arylquinolin-4-yl)oxypropanamides as leads to PET radioligands for translocator protein (18 kDa). J Med Chem 57(14):6240-6251 (2014).
Chaires et al. Triplex Selective 2-(2-Naphthyl)quinoline Compounds: Origins Of Affinity And New Design Principles. J Am Chem Soc 125(24):7272-7283 (2003).
Cho. Recent Advances in Oral Prodrug Discovery. Annual Reports in Medicinal Chemistry 41:395-407 (2006).
Geschwindner et al. Development of a plate-based optical biosensor fragment screening methodology to identify phosphodiesterase 10A inhibitors. J Med Chem 56(8):3228-3234 (2013).
Hamersak et al. Efficient Synthesis of Chiral Amides of 2-(2'-Carboxyphenyl)-4-Hydroxy-Quinoline. Synthesis 15:2174-2176 (2002).
Hanns et al. Quinoline Derivatives, XXXIV Derivatives of 2-Phenylquinoline-4-carboxylic acid and 2-Phenyl-4'-anninoquinoline. Journal fuer Praktische Chemie 133:13-18 (1932).
Ishihara et al. Synthesis of Isoindolo[2,1-a]quinoline Derivatives and Their Effects on N.sub.2-Induced Hypoxia. Chemical Pharmaceutical Bulletin 38(11):3024-3030 (1990).
Kireev et al. Molecular Modeling And Quantitative Structure-Activity Studies Of Anti-HIV-1 2-Heteroarylquinoline-4-Amines. Eur J Med Chem 30(5):395-402 (1995).
Kumar et al. A Convenient Route To Biologically Important Quinazolines Using N -Arylamino-1,3-Diazabuta-1,3-Dienes. Synthesis 2005(18):3059-3062 (2005).
Lee et al. Discovery of Potent Cyclic GMP Phosphodiesterase Inhibitors. 2-Pyridyl- and 2-Innidazolylquinazolines Possessing Cyclic GMP Phosphodiesterase and Thromboxane Synthesis Inhibitory Activities. J Med Chem 38(18):3547-3557 (1995).
Liu et al. Overcoming the Limitations of Directed C—H Functionalizations of Heterocycles. Nature 515(7527):389-393 (2014).
Maccari et al. Low molecular weight phosphotyrosine protein phosphatases as emerging targets for the design of novel therapeutic agents. J Med Chem 55(1):2-22 (2012).
Mokrosz et al. Structure-activity relationship studies of CNS agents. Part 29. N-Methylpiperazino-substituted derivatives of quinazoline, phthalazine and quinoline as novel $\alpha$1, 5-HT1A and 5-HT2A receptor ligands. Eur J Med Chem 31(12):973-980 (1996).
Mphahlele et al. One-Pot Palladium-Catalyzed Ci And Ch Bond Activation And Subsequent Suzukimiyaura Cross-Coupling Of 2-Aryl-3-Iodo-4-(Phenylamino)Quinolines With Arylboronic Acids. Tetrahedron 67(25):4689-4695 (2011).
Nielsen et al. Phosphoramides. XIII.* Phosphorus Pentaoxide—Amine Hydrochloride Mixtures as Reagents in the Synthesis of 4(3H)-Quinazolinones and 4-Quinazolinamines. Acta Chemica Scandinavica B34(9):637-642 (1980).
Nogrady. Medicinal Chemistry A Biochemical Approach, Oxford University Press, New York, pp. 388-392 (1985).
Paliakov et al. Boron Tribromide Mediated Debenzylation Of Benzylamino And Benzyloxy Groups. Tetrahedron Letters 45(21):4093-4095 (2004).
Paliakov et al. Fujita-Ban QSAR Analysis And CoMFA Study Of Quinoline Antagonists Of Immunostimulatory CpG-Oligodeoxynucleotides. Bioorg Med Chem 15(1):324-332 (2006).
Paliwal et al. Pharmacophore and Molecular Docking Based Identification of Novel Structurally Diverse PDE-5 Inhibitors. Medicinal Chemistry Research 24(2):576-587 (2015).
PCT/US2015/055607 International Search Report and Written Opinion dated Feb. 9, 2016.
PCT/US2018/029749 International Search Report and Written Opinion dated Aug. 14, 2018.
PubChem CID 7047. (69 pgs.) (Created Sep. 16, 2004).
PubChem CID 73050850. (9 pgs.) (Created Mar. 10, 2014).
Rivalle et al. Ethyl (4-N-acylaminopyridin-3-yl)glyoxylate and 5-azaisatin as new synthons for a route to various new polyheterocycles. Journal of Heterocyclic Chemistry 34(2):441-444 (1997).
Rooseboom et al. Enzyme-catalyzed activation of anticancer prodrugs. Pharmacological Reviews 56:53-102 (2004).
Rossi et al. Divergent Sequential Reactions Of ß-(2-Aminophenyl)-$\alpha$,ß-Ynones With Nitrogen Nucleophiles. Tetrahedron 60(50):11391-11398 (2004).
Rossi et al. Concise Synthesis Of Fused Polycyclic Quinolines. Tetrahedron Let 42(22):3705-3708 (2001).
Saeed et al. Synthesis of Benzo-Fused Six-Membered Aromatic Heterocycles . Der Chemica Sinica 2(1):66-69 (2011).
Say et al. Synthesis Of 2-Phenylquinolin-4-Amines Substituted With Diverse Amino And Aminoalkyl Groups. Journal Heterocyclic Chemistry 43(6):1613-1620 (2006).
Silverman. Chapter 8: Prodrugs and Drug Delivery Systems. The Organic Chemistry of Drug Design and Drug Action, Academic Press, Inc., San Diego (pp. 352-401) (1992).
Soliman et al. Nitriles in Heterocyclic synthesis: studies on ethyl 3-amino-4,4-dicyano-3-butenoate. Chinese Journal of Chemistry 9(5):461-6 (1991).
Soliman et al. Nitriles In Heterocyclic Synthesis-Studies On Ethoxycarbonyl-3-Amino-4, 4-Dicyano-Prop-3-Ene. Revue Rounaine de Chimie 38(9):1097-104 (1993).
Stanford et al. Diabetes reversal by inhibition of the low-molecular-weight tyrosine phosphatase. Nat Chem Biol 13(6):624-632 (2017).
STN printout of Registry No. 345341-94-8 (2001); 1789298-88-9 (2015); 1787785-59-4 (2015); 1787609-44-2 (2015); 1125451-90-2 (2009); 1125438-39-2 (2009); 1125418-33-8 (2009); 860724-06-7 (2005); 856096-27-0 (2005); and 753417-30-0 (10 pgs) (2004).
STN printout of RN 959562-00-6 (2007).
STN printout of RN 959568-30-0 (2007).
Strekowski et al. Structure-Activity Relationship Analysis Of Substituted 4-Quinolinamines, Antagonists Of Immunostimulatory CpG-Oligodeoxynucleotides. Bioorg Med Chem Lett 9(13):1819-1824 (1999).
Strekowski et al. Synthesis And Activity Of Substituted 2-Phenylquinolin-4-Amines, Antagonists Of Immunostimulatory Cpg-Oligodeoxynucleotides. J Med Chem 46(7):1242-1249 (2003).
Strekowski et al. Synthesis And Quantitative Structure-Activity Relationship Analysis of 2-(Aryl Or Heteroaryl)Quinolin-4-Amines, A New Class Of Anti-Hiv-1 Agents. J Med Chem 34(5):1739-1746 (2003).
Strekowski et al. Amination By Lithium Alkylamide Reagents Of Ketimines Derived From 2-(Trifluoromethyl)Anilines And Methyl Halophenyl Ketones And Their Cyclization Products 2-(Halophenyl)Quinolin-4-Amines. Tetrahedron 52(9):3273-3282 (1996).
Van Baelan et al. Synthesis of 4-Aminoquinazolines by Palladium-Catalyzed Intramolecular Imidoylation of N-(2-Bromoaryl) amidines. Chemistry 17(52):15039-15044 (2011).
Von Hanns. Chinolinderivate, XXXIV. Derivate der 2-Phenyl-Chinolin-4'-Carbonsaure And 2-Phenyl-4'-Amino-Chinolin. Journal Fur Praktische Chemie : Practical Applications And Applied Chemistry : Covering All Aspects Of Applied Chemistry 133(1-2):13-18 (1932).
Wade et al. Deletion of low molecular weight protein tyrosine phosphatase (Acp1) protects against stress-induced cardiomyopathy. J Pathol 237(4):482-494 (2015).
Wallkup et al. Translating slow-binding inhibition kinetics into cellular and in vivo effects. Nat Chem Biol 11(6):416-423 (2015).
Wan et al. An Efficient Direct Amination Of Cyclic Amides And Cyclic Ureas. Organic Letters (8):11:2425-2428 (2006).
Wan et al. The Scope and Mechanism of Phosphonium-Mediated SNAr Reactions in Heterocyclic Amides and Ureas. J Org Chem 72(26):10194-10210 (2007).
Youssef et al. Utility of 3-aroylprop-2-enoic acid in heterocyclic synthesis. Afinidad: Revista de quimica teorica y aplicada 61(512):304-316 (2004).
Zhang et al. Pyridinylquinazolines Selectively Inhibit Human Methionine Aminopeptidase-1 In Cells. J Med Chem 56(10):3996-4016 (2013).

(56) References Cited

OTHER PUBLICATIONS

Zong et al. Direct access to 4-carboxy-1,8-naphthyridines and related compounds through Pfitzinger-type chemistry. J Org Chem 73(11):4334-7 (2008).
Abbiati et al. Palladium-assisted multicomponent synthesis of 2-aryl-4-aminoquinolines and 2-aryl-4-amino[1,8]naphthyridines. J Org Chem 70(16):6454-6460 (2005).

\* cited by examiner

INHIBITORS OF LOW MOLECULAR WEIGHT PROTEIN TYROSINE PHOSPHATASE (LMPTP) AND USES THEREOF

CROSS-REFERENCE

This application is a divisional of U.S. patent application Ser. No. 16/610,055, filed Oct. 31, 2019, which is a U.S. National Stage Application of International Application No. PCT/US2018/029749, filed Apr. 27, 2018, and claims benefit of U.S. Provisional Patent Application No. 62/492,618 filed on May 1, 2017, all of which are incorporated herein by reference in their entirety.

STATEMENT AS TO FEDERALLY SPONSORED RESEARCH

This invention was made with government support under R01 DK106233 awarded by the National Institutes of Health. The government has certain rights in the invention.

FIELD OF THE INVENTION

Described herein are inhibitors of low molecular weight protein tyrosine phosphatase (LMPTP), methods of making such compounds, pharmaceutical compositions and medicaments comprising such compounds, and methods of using such compounds in the treatment of conditions, diseases, or disorders associated with LMPTP activity.

BACKGROUND OF THE INVENTION

Obesity is frequently complicated by a combination of metabolic and cardiovascular anomalies, called the metabolic syndrome, which significantly increases morbidity and mortality of affected individuals. Insulin resistance is an important component of the metabolic syndrome. Protein tyrosine phosphatases (PTPs), including low molecular weight protein tyrosine phosphatase (LMPTP) regulate insulin signaling. LMPTP is highly expressed in liver, muscle, adipocytes, heart and other tissues. Genetic association studies in humans support a negative role for LMPTP in insulin resistance and the metabolic complications of obesity.

BRIEF SUMMARY OF THE INVENTION

Described herein are compounds capable of modulating the level of activity of low molecular weight protein tyrosine phosphatase (LMPTP) and compositions, and methods of using these compounds and compositions.

In one aspect, described herein is a compound that has the structure of Formula (I), or a pharmaceutically acceptable salt, or solvate thereof:

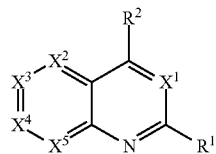

Formula (I)

wherein,
$R^1$ is

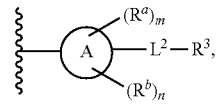

and $R^2$ is $-Z^1-L^4-R^4$;
or
$R^1$ is $-Z^1-L^4-R^4$, and $R^2$ is

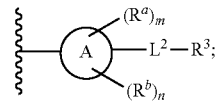

Ⓐ is an aryl or a heteroaryl;
each $R^a$ is independently H, halogen, —CN, —OH, —OR$^{13}$, —SR$^{13}$, —S(=O)R$^{13}$, —S(=O)$_2$R$^{13}$, —N(R$^{12}$)S(=O)$_2$R$^{13}$, —S(=O)$_2$NR$^{12}$R$^{13}$, —C(=O)R$^{13}$, —OC(=O)R$^{13}$, —CO$_2$R$^{12}$, —OCO$_2$R$^{13}$, —NR$^{12}$R$^{12}$, —NR$^{12}$R$^{13}$, —C(=O)NR$^{12}$R$^{12}$, —C(=O)NR$^{12}$R$^{13}$, —OC(=O)NR$^{12}$R$^{12}$, —OC(=O)NR$^{12}$R$^{13}$, —NR$^{12}$C(=O)NR$^{12}$R$^{12}$, —NR$^{12}$C(=O)NR$^{12}$R$^{13}$, —NR$^{12}$C(=O)R$^{13}$, —NR$^{12}$C(=O)OR$^{13}$, substituted or unsubstituted $C_1$-$C_6$alkyl, substituted or unsubstituted $C_1$-$C_6$fluoroalkyl, or substituted or unsubstituted $C_1$-$C_6$heteroalkyl;
m is 0, 1, or 2;
each $R^b$ is independently H, substituted or unsubstituted $C_1$-$C_6$alkyl, substituted or unsubstituted $C_1$-$C_6$fluoroalkyl, or substituted or unsubstituted $C_1$-$C_6$heteroalkyl;
n is 0, 1, or 2;
$L^2$ is -$L^7$-$Y^1$—;
$L^7$ is absent, substituted or unsubstituted $C_1$-$C_4$alkylene, —CH=CH—, —C≡C—, substituted or unsubstituted $C_3$-$C_6$cycloalkylene, —$Y^2$-$L^8$-, or -$L^8$-$Y^2$-$L^8$-;
$Y^1$ is —C(=O)NR$^c$—, —C(=O)—, —SO$_2$NR$^c$—, —C(=O)O—, —C(=NR$^c$)—, —C(=N—OR$^c$)—, —C(=NR$^c$)NR$^c$—, or —C(=N—OR$^c$)—NR$^c$—;
each $L^8$ is independently substituted or unsubstituted $C_1$-$C_4$alkylene or substituted or unsubstituted $C_3$-$C_6$cycloalkylene;
$Y^2$ is —O—, —S—, —S(=O)—, —SO$_2$—, —NR$^c$—, —C(=O)NR$^c$—, —C(=O)—, —NR$^c$C(=O)—, —SO$_2$NR$^c$—, —NR$^c$SO$_2$—, —OC(=O)—, —C(=O)O—, —OC(=O)O—, —OC(=O)NR$^c$—, —NR$^c$C(=O)O—, or —NR$^c$C(=O)NR$^c$—;
each $R^c$ is independently H or substituted or unsubstituted $C_1$-$C_6$alkyl;
$R^3$ is H or -$L^3$-$R^5$;
$L^3$ is absent, substituted or unsubstituted $C_1$-$C_6$alkylene, or substituted or unsubstituted $C_1$-$C_6$heteroalkylene;
$R^5$ is H, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl;
or $R^3$ and $R^c$ are taken together with the N atom to which they are attached to form a substituted or unsubstituted N-containing heterocycle;

$Z^1$ is $-NR^d-$, $-O-$, $-S-$, $-SO_2-$, $-SO_2NR^d-$, $-C(=O)NR^d-$, $-NR^dC(=O)-$, $-OC(=O)-$, $-C(=O)O-$, $-OC(=O)O-$, $-C(=O)-$, $-OC(=O)NR^d-$, $-NR^dC(=O)O-$, or $-NR^dC(=O)NR^d-$; each $R^d$ is independently H or substituted or unsubstituted $C_1$-$C_6$alkyl;

$L^4$ is absent or -$L^5$-$L^6$-;

$L^5$ is substituted or unsubstituted $C_1$-$C_6$alkylene, substituted or unsubstituted $C_1$-$C_6$heteroalkylene, substituted or unsubstituted arylene or substituted or unsubstituted heteroarylene;

$L^6$ is absent, substituted or unsubstituted $C_1$-$C_6$alkylene, substituted or unsubstituted $C_1$-$C_6$heteroalkylene, $-NR^6-$, $-C(=O)NR^6-$, $-NR^6C(=O)-$, or $-NR^6C(=O)NR^6-$;

$R^4$ is H, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl;

or $R^4$ and $R^6$ are taken together with the N atom to which they are attached to form a substituted or unsubstituted N-containing heterocycle;

$X^1$ is $CR^7$ or N;
$X^2$ is N or $CR^8$;
$X^3$ is N or $CR^9$;
$X^4$ is N or $CR^{10}$;
$X^5$ is N or $CR^{11}$;
where at least one of $X^2$, $X^3$, $X^4$, and $X^5$ is N;

$R^7$, $R^8$, $R^9$, $R^{10}$, and $R^{11}$ are independently selected from H, halogen, $-CN$, $-OH$, $-OR^{13}$, $-SR^{13}$, $-S(=O)R^{13}$, $-S(=O)_2R^{13}$, $-N(R^{12})S(=O)_2R^{13}$, $-S(=O)_2NR^{12}R^{12}$, $-S(=O)_2NR^{12}R^{13}$, $-C(=O)R^{13}$, $-OC(=O)R^{13}$, $-CO_2R^{12}$, $-OCO_2R^{13}$, $-NR^{12}R^{12}$, $-C(=O)NR^{12}R^{12}$, $-C(=O)NR^{12}R^{13}$, $-OC(=O)NR^{12}R^{12}$, $-OC(=O)NR^{12}R^{13}$, $-NR^{12}C(=O)NR^{12}R^{12}$, $-NR^{12}C(=O)NR^{12}R^{13}$, $-NR^{12}C(=O)R^{13}$, $-NR^{12}C(=O)OR^{13}$, substituted or unsubstituted $C_1$-$C_6$alkyl, substituted or unsubstituted $C_1$-$C_6$fluoroalkyl, substituted or unsubstituted $C_1$-$C_6$heteroalkyl, a substituted or unsubstituted $C_3$-$C_6$cycloalkyl, a substituted or unsubstituted $C_2$-$C_6$heterocycloalkyl, a substituted or unsubstituted aryl, and a substituted or unsubstituted heteroaryl;

each $R^{12}$ is independently selected from the group consisting of H, $C_1$-$C_6$alkyl, and $C_1$-$C_6$fluoroalkyl, and $C_1$-$C_6$heteroalkyl;

each $R^{13}$ is independently selected from the group consisting of $C_1$-$C_6$alkyl, $C_1$-$C_6$fluoroalkyl, $C_1$-$C_6$heteroalkyl, a substituted or unsubstituted $C_3$-$C_6$cycloalkyl, a substituted or unsubstituted $C_2$-$C_6$heterocycloalkyl, a substituted or unsubstituted aryl, a substituted or unsubstituted heteroaryl, a substituted or unsubstituted $-C_1$-$C_4$alkylene-$C_3$-$C_{10}$cycloalkyl, a substituted or unsubstituted $-C_1$-$C_4$alkylene-$C_2$-$C_{10}$heterocycloalkyl, a substituted or unsubstituted $-C_1$-$C_4$alkylene-aryl, and a substituted or unsubstituted $-C_1$-$C_4$alkylene-heteroaryl;

or when $R^{12}$ and $R^{13}$ are attached to the same N atom then $R^{12}$ and $R^{13}$ are taken together with the N atom to which they are attached to form a substituted or unsubstituted $C_2$-$C_{10}$heterocycle.

Any combination of the groups described above or below for the various variables is contemplated herein. Throughout the specification, groups and substituents thereof are chosen by one skilled in the field to provide stable moieties and compounds.

In one aspect, provided herein is a pharmaceutical composition comprising a compound of Formula (I), or a pharmaceutically acceptable salt, or solvate thereof, and at least one pharmaceutically acceptable excipient.

In some embodiments, the compound of Formula (I), or a pharmaceutically acceptable salt thereof, is formulated for administration to a mammal by intravenous administration, subcutaneous administration, oral administration, inhalation, nasal administration, dermal administration, or ophthalmic administration. In some embodiments, the compound of Formula (I), or a pharmaceutically acceptable salt thereof, is in the form of a tablet, a pill, a capsule, a liquid, a suspension, a gel, a dispersion, a solution, an emulsion, an ointment, or a lotion.

In one aspect, described herein is a method of inhibiting low molecular weight protein tyrosine phosphatase (LMPTP) activity in a mammal comprising administering to the mammal a compound of Formula (I), or a pharmaceutically acceptable salt or solvate thereof.

In some embodiments of the method of inhibiting low molecular weight protein tyrosine phosphatase (LMPTP) activity, a mammal has insulin resistance, metabolic syndrome, type 2 diabetes, cardiovascular disease, or combinations thereof.

In some embodiments of a method of inhibiting low molecular weight protein tyrosine phosphatase (LMPTP) activity, the mammal has an impaired glucose tolerance.

In some embodiments of a method of inhibiting low molecular weight protein tyrosine phosphatase (LMPTP) activity, the mammal is pre-diabetic.

In some embodiments of a method of inhibiting low molecular weight protein tyrosine phosphatase (LMPTP) activity, the mammal is obese.

In some embodiments of a method of inhibiting low molecular weight protein tyrosine phosphatase (LMPTP) activity, the method further comprises administering an additional therapeutic agent to the mammal. In some embodiments of a method of inhibiting low molecular weight protein tyrosine phosphatase (LMPTP) activity, the additional therapeutic agent is a peroxisome proliferator activated receptor (PPAR) agonist (gamma, dual, or pan), a dipeptidyl peptidase (IV) inhibitor, a glucagon-like peptide-1 (GLP-I) analog, insulin or an insulin analog, an insulin secretagogue, a sodium glucose co-transporter 2 (SGLT2) inhibitor, a human amylin analog, a biguanide, a glucophage, an alpha-glucosidase inhibitor, a meglitinide, a thiazolidinedione, a sulfonylurea, or any combination thereof. In some embodiments of a method of inhibiting low molecular weight protein tyrosine phosphatase (LMPTP) activity, the additional therapeutic agent is an angiotensin-converting enzyme (ACE) inhibitor, angiotensin II receptor blocker (ARB), beta-blocker, diuretic, calcium channel blocker, inhibitor of renin-angiotensin system (RAS), blood-thinning medication, a statin, a fibrate, or any combination thereof.

In another aspect, described herein is a method of treating insulin resistance, metabolic syndrome, type 2 diabetes or a combination thereof in a mammal comprising administering to the mammal a compound of Formula (I), or a pharmaceutically acceptable salt or solvate thereof.

In some embodiments of a method of treating insulin resistance, metabolic syndrome, type 2 diabetes or a combination thereof in a mammal, the mammal has abdominal obesity, elevated blood pressure, elevated fasting plasma glucose, high serum triglycerides, low high-density cholesterol levels (HDL), or combinations thereof.

In some embodiments of a method of treating insulin resistance, metabolic syndrome, type 2 diabetes or a combination thereof in a mammal, the mammal has an impaired glucose tolerance.

In some embodiments of a method of treating insulin resistance, metabolic syndrome, type 2 diabetes or a combination thereof in a mammal, the mammal is obese.

In some embodiments of a method of treating insulin resistance, metabolic syndrome, type 2 diabetes or a combination thereof in a mammal, the compound modulates glucose and lipid metabolism.

In some embodiments of a method of treating insulin resistance, metabolic syndrome, type 2 diabetes or a combination thereof in a mammal, the method further comprises administering an additional therapeutic agent to the mammal. In some embodiments of a method of treating insulin resistance, metabolic syndrome, type 2 diabetes or a combination thereof in a mammal, the additional therapeutic agent is a peroxisome proliferator activated receptor (PPAR) agonist (gamma, dual, or pan), a dipeptidyl peptidase (IV) inhibitor, a glucagon-like peptide-1 (GLP-I) analog, insulin or an insulin analog, an insulin secretagogue, a sodium glucose co-transporter 2 (SGLT2) inhibitor, a human amylin analog, a biguanide, a glucophage, an alpha-glucosidase inhibitor, a meglitinide, a thiazolidinedione, a sulfonylurea, or any combination thereof. In some embodiments of a method of treating insulin resistance, metabolic syndrome, type 2 diabetes or a combination thereof in a mammal, the additional therapeutic agent is an angiotensin-converting enzyme (ACE) inhibitor, angiotensin II receptor blocker (ARB), beta-blocker, diuretic, calcium channel blocker, inhibitor of renin-angiotensin system (RAS), blood-thinning medication, a statin, a fibrate, or any combination thereof.

DETAILED DESCRIPTION

Protein phosphorylation represents a key post-translational modification that is critical to the control of many cellular functions. The reversible phosphorylation of tyrosine residues of proteins is a significant regulatory event in eukaryotes compared to other protein phosphorylation processes and is crucially important for the regulation and progression of various cellular signaling cascades, especially those induced by receptor activation mechanisms. The appropriate functioning of these signaling pathways is controlled by the concerted and dynamic activities of protein tyrosine kinases (PTKs) and phosphotyrosine protein phosphatases (PTPs) which play vital roles in numerous fundamental physiological cellular processes, such as growth, differentiation, survival, migration, metabolism, cell-cell communication and adhesion, immune response, and gene transcription.

PTPs are implicated in the pathogenesis of human diseases, including diabetes, obesity, cancer, inflammation, autoimmune, and cardiovascular diseases.

Low molecular weight PTPs (LMPTPs) have emerged as attractive targets for the pharmacological control of post-receptor events involved in the development of metabolic and neoplastic pathologies as well as for therapeutic intervention in infectious diseases.

LMPTP is a small (18 kD) cytosolic enzyme that is expressed ubiquitously but has particularly high expression in adipocytes. As a result of an alternative mRNA splicing mechanism, LMPTP is usually found as two isozymes, called LMPTP-A and -B (the rodent isoforms are called respectively LMPTP-IF1 and -IF2). In humans the total enzymatic activity of LMPTP is variable and is determined by a common genetic polymorphism.

LMPTPs have been identified and isolated from a wide variety of prokaryotic and eukaryotic organisms, such as bacteria, yeasts, and mammalians. LMPTPs from different organisms generally display a high degree of homology, especially in their tertiary structure.

Human LMPTPs exert sophisticated control over cell growth and differentiation through the modulation of signaling pathways induced by several growth factors and kinases. The enzyme also negatively regulates the metabolic responses to insulin, and the sensitivity of specific tissues to the hormone is consequently enhanced as a result of the LMPTP suppression.

LMPTP is an inhibitor of insulin signaling. In cell lines LMPTP is able to inhibit both the metabolic and growth-inducing effects of insulin. Also in vitro the phosphatase dephosphorylates peptides derived from the phosphorylated IGF-1 receptor and insulin receptor (IR). Increased insulin signaling was observed in the adipose tissue of obese mice treated with anti-LMPTP antisense oligonucleotides (ASO). It was shown that LMPTP can also easily be co-precipitated with the IR. Multiple lines of evidence suggest that LMPTP plays an important role in the metabolic syndrome. The first line of evidence comes from human genetic studies. The ACP1 gene is located in one of the candidate genome regions for obesity on chromosome 2p25 and is currently included in the obesity gene map. Carriers of ACP1 alleles associated with low enzymatic activity tend to have lower non-fasting glucose levels and are protected from obesity-associated lipid anomalies. Strong in vivo evidence suggesting that inhibition of LMPTP decreases the insulin resistance associated with obesity, by treating mice with anti-LMPTP ASOs. Leptin-deficient or diet-induced obese mice treated with specific anti-LMPTP ASOs showed a marked improvement of lipid profiles, and of glucose and insulin tolerance, in the absence of significant side effects.

Obesity is frequently complicated by a constellation of metabolic and cardiovascular anomalies, called the metabolic syndrome, which significantly increases morbidity and mortality of affected individuals. Insulin resistance is an important component of the metabolic syndrome. Protein tyrosine phosphatases (PTPs) that regulate insulin signaling are targets for insulin resistance syndromes. One of the PTPs, the low molecular weight protein tyrosine phosphatase (LMPTP), is encoded by the ACP1 gene. LMPTP is highly expressed in adipocytes. There is strong in vitro and in vivo evidence that LMPTP is a negative regulator of insulin signaling. Genetic association studies in humans support a negative role for LMPTP in insulin resistance and the metabolic complications of obesity. In vivo, partial knock-down of LMPTP expression by specific antisense oligonucleotides (ASOs) led to improved glycemic and lipid profiles and decreased insulin resistance in diet-induced obese C57BL/6 mice. Interestingly, anti-LMPTP ASOs did not induce any metabolic phenotype in lean mice. LMPTP is considered to play a critical negative role in adipocyte insulin signaling, while it is less important in liver and muscle, where it can be at least partially compensated for by PTP1B, a critical negative regulator of insulin signaling in liver and skeletal muscle, and/or other prominent PTPs. Inhibition of LMPTP can significantly reduce obesity associated insulin resistance and decrease the severity of the metabolic syndrome in obesity.

It has been estimated that every year in the U.S. more than 70 billion dollars are spent for the treatment of obesity-related conditions and almost 300,000 deaths/year can be attributed to the complications of obesity. Obese patients often show multiple metabolic and cardiovascular anomalies known as "the metabolic syndrome", including glucose intolerance, hyperlipidemia (especially high triglycerides with low HDL), and hypertension.

Obesity-induced insulin resistance is believed to be a central pathogenic factor in the metabolic syndrome. Obese patients are routinely treated with oral hypoglycemic agents, however even combinations of multiple agents are often insufficient to ensure adequate glycemic control, requiring the addition of parenteral insulin to the regimen. Reduced signal transduction at several levels after engagement of the insulin receptor (IR) has been observed in multiple insulin resistance syndromes, including the metabolic syndrome.

The IR is a protein tyrosine kinase, and tyrosine phosphorylation plays an important role in insulin signal transduction. Modification of the activity of the IR and/or tyrosine phosphorylation of IR targets are viewed as a promising way to reduce insulin resistance.

Provided herein are methods for improving insulin sensitivity in a subject comprising administering to the subject a LMPTP inhibitor; and thereby improving insulin sensitivity in the subject. In certain embodiments, the subject has insulin resistance. In some embodiments, the individual with insulin resistance has fasting insulin levels of at least 20 µU/mL. In some embodiments, the individual with insulin resistance has fasting insulin levels that exceed 100 µU/mL. In some embodiments, the LMPTP inhibitor treats a metabolic disorder by improving insulin resistance. In some embodiments, the LMPTP inhibitor treats a metabolic disorder by improving insulin sensitivity. In certain embodiments, the methods comprise selecting a subject having insulin resistance.

Provided herein are methods for treating metabolic disorders with a LMPTP inhibitor. The LMPTP inhibitor can treat, delay or prevent the onset of a metabolic disorder, wherein such metabolic disorders include, but are not limited to, metabolic syndrome, elevated blood glucose levels, insulin resistance, glucose intolerance, type 2 diabetes, type 1 diabetes, pre-diabetes, non-alcoholic fatty liver disease, nonalcoholic steatohepatitis, and obesity.

Insulin resistance may be detected using a procedure known as the hyperinsulinemic euglycemic clamp, which measures the amount of glucose necessary to compensate for an increased insulin level without causing hypoglycemia. In some embodiments, the methods disclosed herein comprise administering a LMPTP inhibitor to a subject with insulin resistance. In some embodiments, the LMPTP inhibitor improves insulin sensitivity. In some embodiments, the LMPTP inhibitor treats a metabolic disorder. In some embodiments, the LMPTP inhibitor treats a metabolic disorder by improving insulin sensitivity. In some embodiments, the LMPTP inhibitor delays or prevents the onset of the metabolic disorder by improving insulin sensitivity.

In some embodiments, described herein is a method of improving glucose tolerance in an individual comprising administering a LMPTP inhibitor to the subject with impaired glucose tolerance. In some embodiments, the individual has a metabolic disorder and the metabolic disorder is treated by improving glucose tolerance. In some embodiments, the LMPTP inhibitor delays or prevents the onset of a metabolic disorder in an individual by improving glucose tolerance.

In some embodiments, described herein is a method of treatment of a metabolic disorder in a subject that is overweight or obese. In some embodiments, a LMPTP inhibitor is used to treat obesity in a subject. In some embodiments, the LMPTP inhibitor decreases adipose tissue expansion in the subject that is overweight or obese. In some embodiments, the metabolic disorder is treated by decreasing adipose tissue expansion.

In some embodiments, administration of a LMPTP inhibitor to a subject delays or prevents the onset of a metabolic disorder by decreasing adipose tissue expansion. In some embodiments, the subject is at risk for developing a metabolic disorder.

Compounds

Described herein are small molecule LMPTP inhibitors. In one aspect, described herein is a compound of Formula (I), or a pharmaceutically acceptable salt, or solvate thereof:

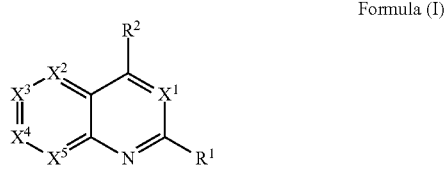

Formula (I)

wherein,
$R^1$ is

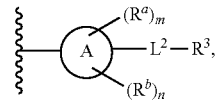

and $R^2$ is $—Z^1-L^4-R^4$;
or
$R^1$ is $—Z^1-L^4-R^4$, and $R^2$ is

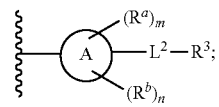

Ⓐ is an aryl or a heteroaryl;
each $R^a$ is independently H, halogen, —CN, —OH, —OR$^{13}$, —SR$^{13}$, —S(=O)R$^{13}$, —S(=O)$_2$R$^{13}$, —N(R$^{12}$)S(=O)$_2$R$^{13}$, —S(=O)$_2$NR$^{12}$R$^{13}$, —C(=O)R$^{13}$, —OC(=O)R$^{13}$, —CO$_2$R$^{12}$, —OCO$_2$R$^{13}$, —NR$^{12}$R$^{12}$, —NR$^{12}$R$^{13}$, —C(=O)NR$^{12}$R$^{12}$, —C(=O)NR$^{12}$R$^{13}$, —OC(=O)NR$^{12}$R$^{12}$, —OC(=O)NR$^{12}$R$^{13}$, —NR$^{12}$C(=O)NR$^{12}$R$^{12}$, —NR$^{12}$C(=O)NR$^{12}$R$^{13}$, —NR$^{12}$C(=O)R$^{13}$, —NR$^{12}$C(=O)OR$^{13}$, substituted or unsubstituted $C_1$-$C_6$alkyl, substituted or unsubstituted $C_1$-$C_6$fluoroalkyl, or substituted or unsubstituted $C_1$-$C_6$heteroalkyl;
each $R^b$ is independently H, substituted or unsubstituted $C_1$-$C_6$alkyl, substituted or unsubstituted $C_1$-$C_6$fluoroalkyl, or substituted or unsubstituted $C_1$-$C_6$heteroalkyl;
m is 0, 1, or 2; n is 0, 1, or 2;
$L^2$ is -$L^7$-$Y^1$—;
$L^7$ is absent, substituted or unsubstituted $C_1$-$C_4$alkylene, —CH=CH—, —C≡C—, substituted or unsubstituted $C_3$-$C_6$cycloalkylene, —$Y^2$-$L^8$-, or -$L^8$-$Y^2$-$L^8$-;

$Y^1$ is —C(=O)NR$^c$—, —C(=O)—, —SO$_2$NR$^c$—, —C(=O)O—, —C(=NR)—, —C(=N—OR$^c$)—, —C(=NR$^c$)NR$^c$—, or —C(=N—OR$^c$)—NR$^c$—;

each $L^8$ is independently substituted or unsubstituted C$_1$-C$_4$alkylene or substituted or unsubstituted C$_3$-C$_6$cycloalkylene;

$Y^2$ is —O—, —S—, —S(=O)—, —SO$_2$—, —NR$^c$—, —C(=O)NR$^c$—, —C(=O)—, —NR$^c$C(=O)—, —SO$_2$NR$^c$—, —NR$^c$SO$_2$—, —OC(=O)—, —C(=O)O—, —OC(=O)O—, —OC(=O)NR$^c$—, —NR$^c$C(=O)O—, or —NR$^c$C(=O)NR$^c$—;

each $R^c$ is independently H or substituted or unsubstituted C$_1$-C$_6$alkyl;

$R^3$ is H or -L$^3$-R$^5$;

$L^3$ is absent, substituted or unsubstituted C$_1$-C$_6$alkylene, or substituted or unsubstituted C$_1$-C$_6$heteroalkylene;

$R^5$ is H, substituted or unsubstituted C$_3$-C$_{10}$cycloalkyl, substituted or unsubstituted C$_2$-C$_{10}$heterocycloalkyl, substituted or unsubstituted aryl, or substituted or unsubstituted heteroaryl;

or $R^3$ and $R^c$ are taken together with the N atom to which they are attached to form a substituted or unsubstituted N-containing heterocycle;

$Z^1$ is —NR$^d$—, —O—, —S—, —SO$_2$—, —SO$_2$NR$^d$—, —C(=O)NR$^d$—, —NR$^d$C(=O)—, —OC(=O)—, —C(=O)O—, —OC(=O)O—, —C(=O)—, —OC(=O)NR$^d$—, —NR$^d$C(=O)O—, or —NR$^d$C(=O)NR$^d$—;

each $R^d$ is independently H or substituted or unsubstituted C$_1$-C$_6$alkyl;

$L^4$ is absent or -L$^5$-L$^6$-;

$L^5$ is substituted or unsubstituted C$_1$-C$_6$alkylene, substituted or unsubstituted C$_1$-C$_6$heteroalkylene, substituted or unsubstituted arylene or substituted or unsubstituted heteroarylene;

$L^6$ is absent, substituted or unsubstituted C$_1$-C$_6$alkylene, substituted or unsubstituted C$_1$-C$_6$heteroalkylene, —NR$^6$—, —C(=O)NR$^6$—, —NR$^6$C(=O)—, or —NR$^6$C(=O)NR$^6$—;

$R^4$ is H, substituted or unsubstituted C$_3$-C$_{10}$cycloalkyl, substituted or unsubstituted C$_2$-C$_{10}$heterocycloalkyl, substituted or unsubstituted aryl, or substituted or unsubstituted heteroaryl;

or $R^4$ and $R^6$ are taken together with the N atom to which they are attached to form a substituted or unsubstituted N-containing heterocycle;

$X^1$ is CR$^7$ or N;

$X^2$ is N or CR$^8$;

$X^3$ is N or CR$^9$;

$X^4$ is N or CR$^{10}$;

$X^5$ is N or CR$^{11}$;

where at least one of $X^2$, $X^3$, $X^4$, and $X^5$ is N;

$R^7$, $R^8$, $R^9$, $R^{10}$, and $R^{11}$ are independently selected from hydrogen, halogen, —CN, —OH, —OR$^{13}$, —SR$^{13}$, —S(=O)R$^{13}$, —S(=O)$_2$R$^{13}$, —N(R$^{12}$)S(=O)$_2$R$^{13}$, —S(=O)$_2$NR$^{12}$R$^{12}$, —S(=O)$_2$NR$^{12}$R$^{13}$, —C(=O)R$^{13}$, —OC(=O)R$^{13}$, —CO$_2$R$^{12}$, —OCO$_2$R$^{13}$, —NR$^{12}$R$^{12}$, —NR$^{12}$R$^{13}$, —C(=O)NR$^{12}$R$^{12}$, —C(=O)NR$^{12}$R$^{13}$, —OC(=O)NR$^{12}$R$^{12}$, —OC(=O)NR$^{12}$R$^{13}$, —NR$^{12}$C(=O)NR$^{12}$R$^{12}$, —NR$^{12}$C(=O)NR$^{12}$R$^{13}$, —NR$^{12}$C(=O)R$^{13}$, —NR$^{12}$C(=O)OR$^{13}$, substituted or unsubstituted C$_1$-C$_6$alkyl, substituted or unsubstituted C$_1$-C$_6$fluoroalkyl, substituted or unsubstituted C$_1$-C$_6$heteroalkyl, a substituted or unsubstituted C$_3$-C$_6$cycloalkyl, a substituted or unsubstituted C$_2$-C$_6$heterocycloalkyl, a substituted or unsubstituted aryl, and a substituted or unsubstituted heteroaryl;

each $R^{12}$ is independently selected from the group consisting of H, C$_1$-C$_6$alkyl, C$_1$-C$_6$fluoroalkyl, and C$_1$-C$_6$heteroalkyl;

each $R^{13}$ is independently selected from the group consisting of C$_1$-C$_6$alkyl, C$_1$-C$_6$fluoroalkyl, C$_1$-C$_6$heteroalkyl, a substituted or unsubstituted C$_3$-C$_6$cycloalkyl, a substituted or unsubstituted C$_2$-C$_6$heterocycloalkyl, a substituted or unsubstituted aryl, a substituted or unsubstituted heteroaryl, a substituted or unsubstituted —C$_1$-C$_4$alkylene-C$_3$-C$_{10}$cycloalkyl, a substituted or unsubstituted —C$_1$-C$_4$alkylene-C$_2$-C$_{10}$heterocycloalkyl, a substituted or unsubstituted —C$_1$-C$_4$alkylene-aryl, and a substituted or unsubstituted —C$_1$-C$_4$alkylene-heteroaryl;

or when $R^{12}$ and $R^{13}$ are attached to the same N atom then $R^{12}$ and $R^{13}$ are taken together with the N atom to which they are attached to form a substituted or unsubstituted C$_2$-C$_{10}$heterocycle.

For any and all of the embodiments, substituents are selected from among a subset of the listed alternatives. For example, in some embodiments, m is 0, 1 or 2. In other embodiments, m is 0. In some other embodiments, m is 1. In some other embodiments, m is 2.

In some embodiments, n is 0, 1 or 2. In other embodiments, n is 0. In some other embodiments, n is 1. In some other embodiments, n is 2.

In some embodiments, $L^2$ is -L$^7$-Y$^1$—; $L^7$ is absent, substituted or unsubstituted C$_1$-C$_4$alkylene, —CH=CH—, —C≡C—, substituted or unsubstituted C$_3$-C$_6$cycloalkylene, —Y$^2$-L$^8$- or -L$^8$-Y$^2$-L$^8$-; $Y^1$ is —C(=O)NR$^c$—, —C(=O)—, —SO$_2$NR$^c$—, —C(=O)O—, —C(=NR$^c$)—, —C(=N—OR$^c$)—, —C(=NR$^c$)NR$^c$—, or —C(=N—OR$^c$)—NR$^c$—; each $L^8$ is independently substituted or unsubstituted C$_1$-C$_4$alkylene or substituted or unsubstituted C$_3$-C$_6$cycloalkylene; $Y^2$ is —O—, —S—, —S(=O)—, —SO$_2$—, —NR$^c$—, —C(=O)NR$^c$—, —C(=O)—, —NR$^c$C(=O)—, —SO$_2$NR$^c$—, —NR$^c$SO$_2$—, —OC(=O)—, —C(=O)O—, —OC(=O)O—, —OC(=O)NR$^c$—, —NR$^c$C(=O)O—, or —NR$^c$C(=O)NR$^c$—; each $R^c$ is independently H or substituted or unsubstituted C$_1$-C$_6$alkyl.

In some embodiments, $R^1$ is

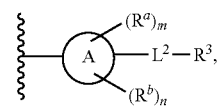

and $R^2$ is —Z$^1$-L$^4$-R$^4$.

In some embodiments, $R^1$ is —Z$^1$-L$^4$-R$^4$, and $R^2$ is

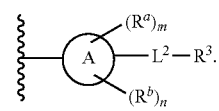

In some embodiments, the compound of Formula (I) has one of the following structures, or a pharmaceutically acceptable salt or solvate thereof:

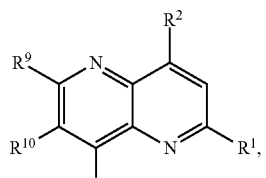
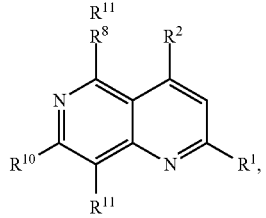
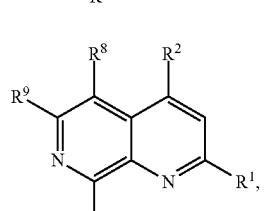
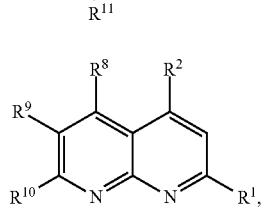
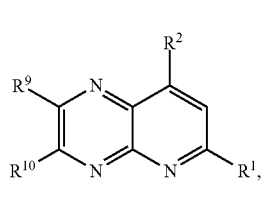
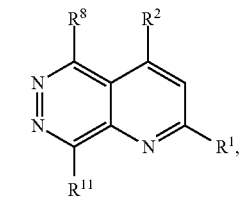
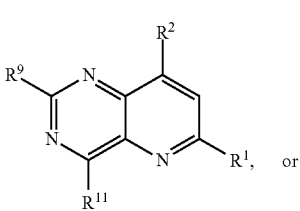
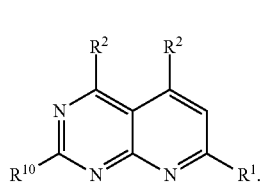
In some embodiments, the compound of Formula (I) has the structure of Formula (II), or a pharmaceutically acceptable salt or solvate thereof, wherein:
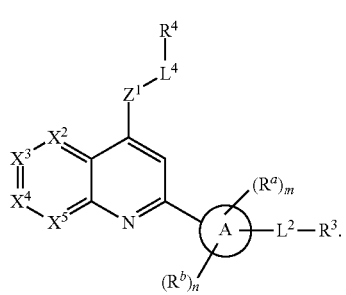
In some embodiments, the compound of Formula (II) has one of the following structures, or a pharmaceutically acceptable salt or solvate thereof:
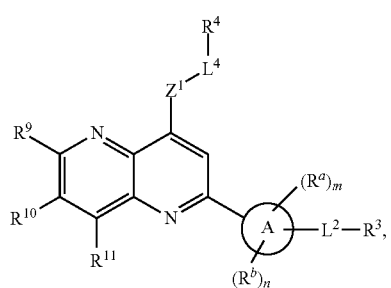
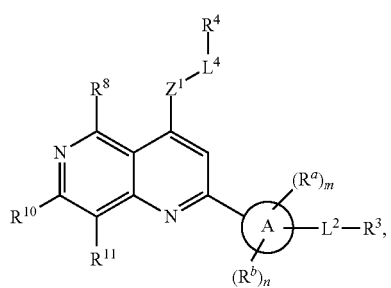
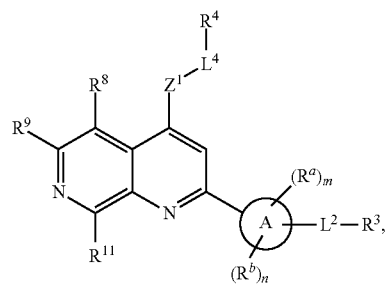
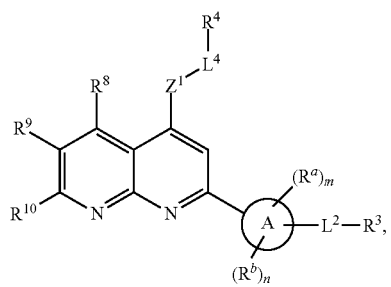

-continued

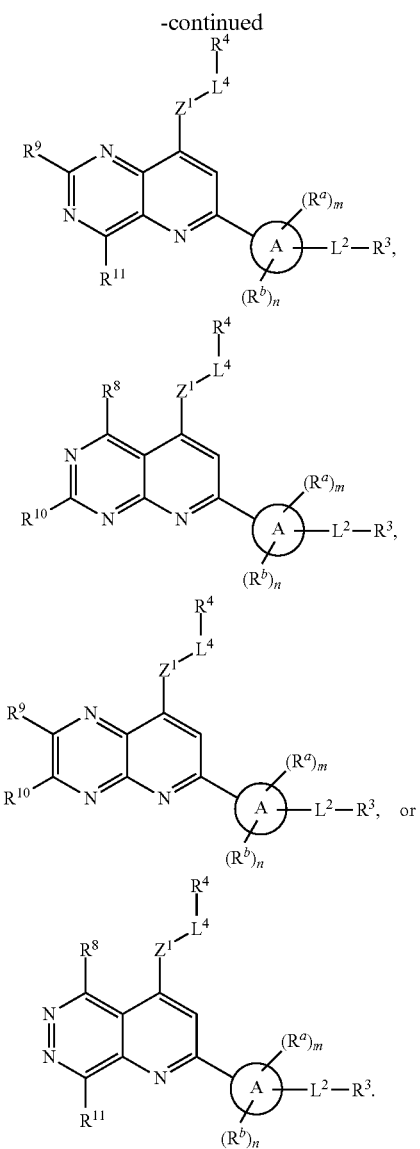

In some embodiments, 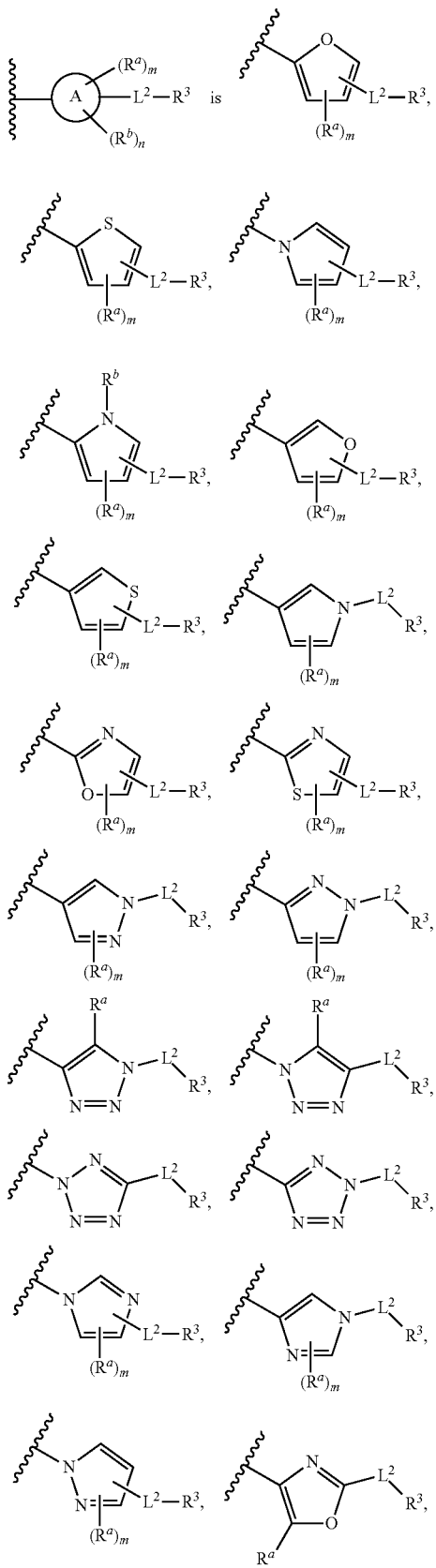

In some embodiments, (A) is a phenyl, naphthyl, monocyclic heteroaryl or bicyclic heteroaryl. In some embodiments, ring A is phenyl. In some embodiments, ring A is naphthyl. In some embodiments, ring A is monocyclic heteroaryl. In some embodiments, ring A is bicyclic heteroaryl.

In some embodiments, (A) is a monocyclic 5- or 6-membered heteroaryl containing 0-4 N and 0 or 1 O or S atom.

In some embodiments, (A) is a monocyclic 5-membered heteroaryl. In some embodiments, ring A is furanyl, thienyl, pyrrolyl, oxazolyl, imidazolyl, triazolyl, tetrazolyl, isoxazolyl, isothiazolyl, oxadiazolyl, or thiadiazolyl. In some embodiments, ring A is furanyl. In some embodiments, ring A is thienyl. In some embodiments, ring A is pyrrolyl. In some embodiments, ring A is oxazolyl. In some embodiments, ring A is imidazolyl. In some embodiments, ring A is triazolyl. In some embodiments, ring A is tetrazolyl. In some embodiments, ring A is isoxazolyl. In some embodiments, ring A is isothiazolyl. In some embodiments, ring A is oxadiazolyl. In some embodiments, ring A is thiadiazolyl.

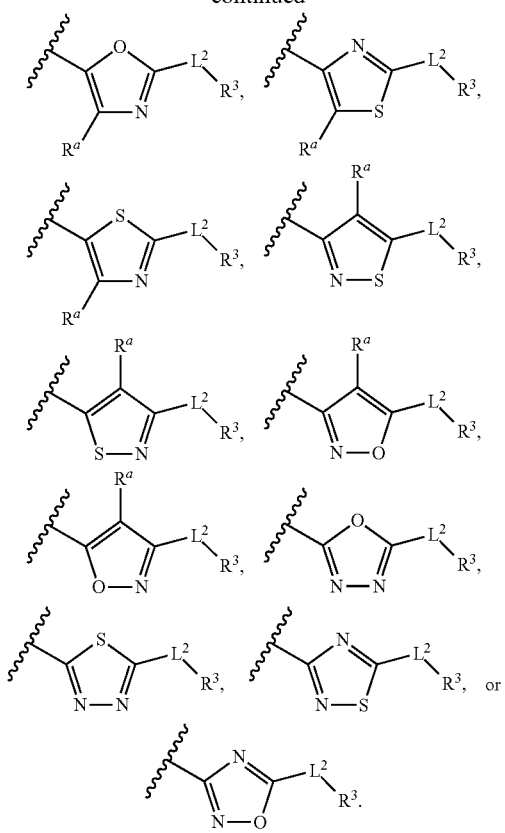

In some embodiments, Ⓐ is a monocyclic 6-membered heteroaryl that is pyridinyl, pyrimidinyl, pyrazinyl, pyridazinyl, or triazinyl. In some embodiments, ring A is pyridinyl. In some embodiments, ring A is pyrimidinyl. In some embodiments, ring A is pyrazinyl. In some embodiments, ring A is pyridazinyl. In some embodiments, ring A is triazinyl.

In some embodiments,

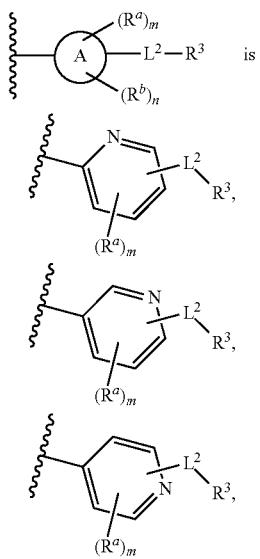

is

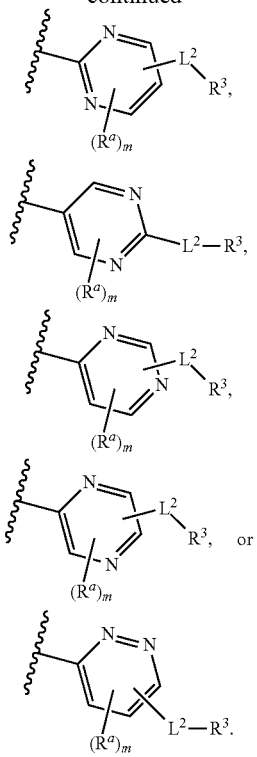

In some embodiments, Ⓐ is a bicyclic heteroaryl containing 0-4 N and 0 or 1 O or S atom.

In some embodiments, Ⓐ is a bicyclic heteroaryl that is quinolinyl, isoquinolinyl, cinnolinyl, phthalazinyl, quinazolinyl, quinoxalinyl, naphthyridinyl, pteridinyl, indolizinyl, azaindolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, or purinyl. In some embodiments, ring A is quinolinyl. In some embodiments, ring A is isoquinolinyl. In some embodiments, ring A is cinnolinyl. In some embodiments, ring A is phthalazinyl. In some embodiments, ring A is quinazolinyl. In some embodiments, ring A is quinoxalinyl. In some embodiments, ring A is naphthyridinyl. In some embodiments, ring A is pteridinyl. In some embodiments, ring A is indolizinyl. In some embodiments, ring A is azaindolizinyl. In some embodiments, ring A is indolyl. In some embodiments, ring A is azaindolyl. In some embodiments, ring A is indazolyl. In some embodiments, ring A is azaindazolyl. In some embodiments, ring A is benzimidazolyl. In some embodiments, ring A is azabenzimidazolyl. In some embodiments, ring A is benzotriazolyl. In some embodiments, ring A is azabenzotriazolyl. In some embodiments, ring A is benzoxazolyl. In some embodiments, ring A is azabenzoxazolyl. In some embodiments, ring A is benzisoxazolyl. In some embodiments, ring A is azabenzisoxazolyl. In some embodiments, ring A is benzofuranyl. In some embodiments, ring A is azabenzofuranyl. In some embodiments, ring A is benzothienyl. In some embodiments, ring A is azabenzothienyl. In some embodiments, ring A is benzothiazolyl. In some embodiments, ring A is azabenzothiazolyl. In some embodiments, ring A is purinyl.

In some embodiments,
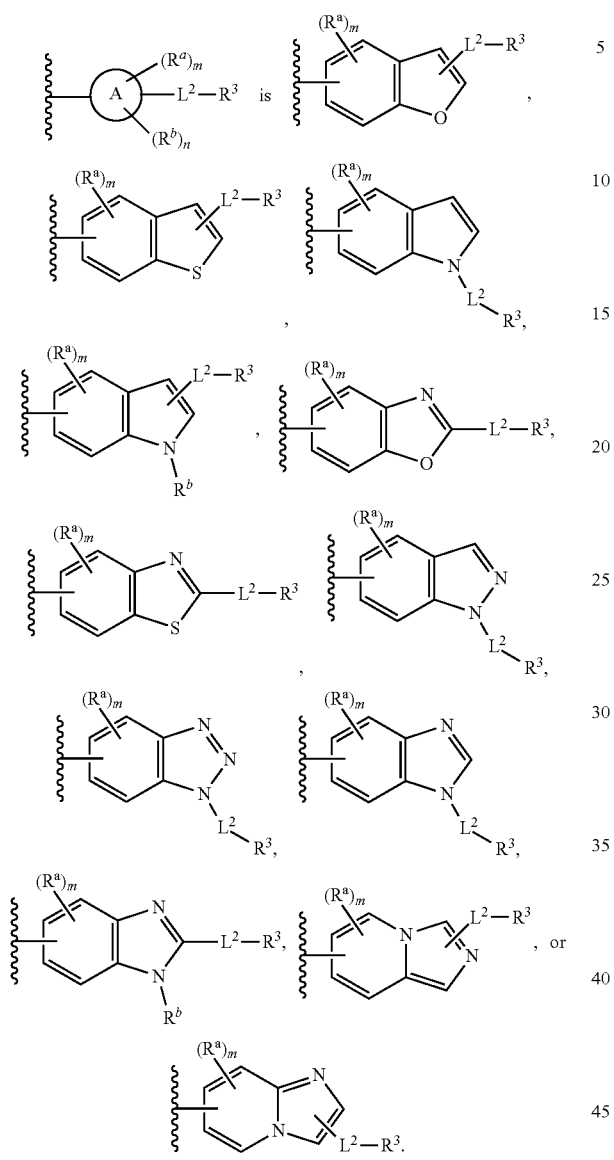
In some embodiments, the compound of Formula (I) has the structure of Formula (III) or a pharmaceutically acceptable salt or solvate thereof, wherein:
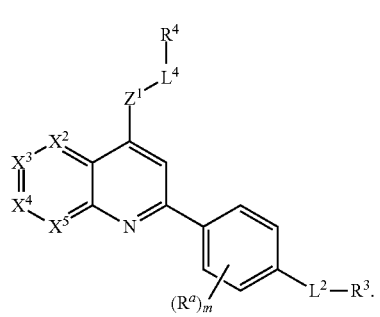
Formula (III)
In some embodiments, the compound of Formula (III) has one of the following structures, or a pharmaceutically acceptable salt or solvate thereof:
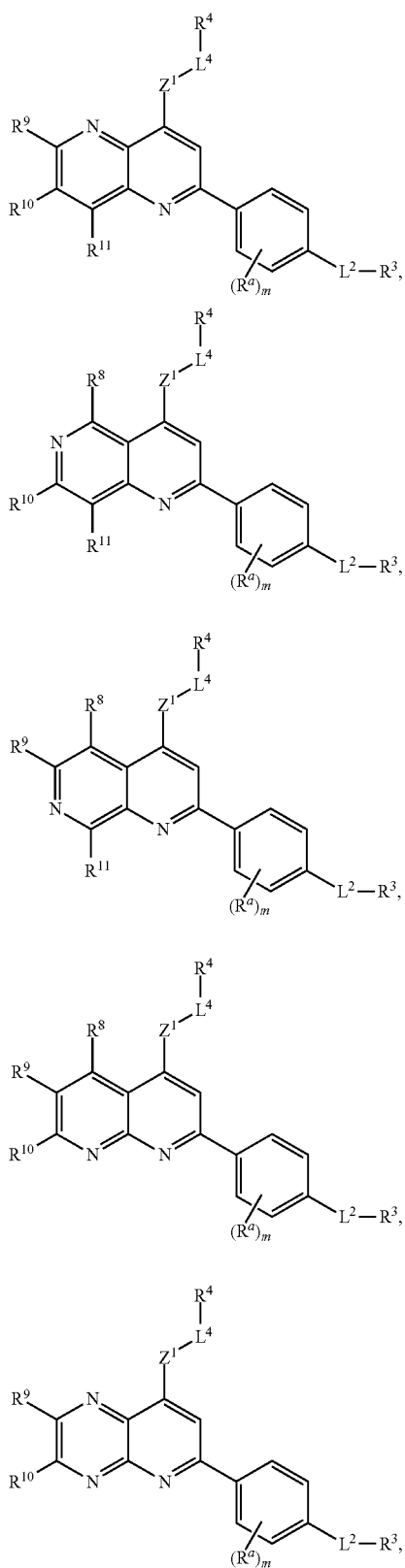

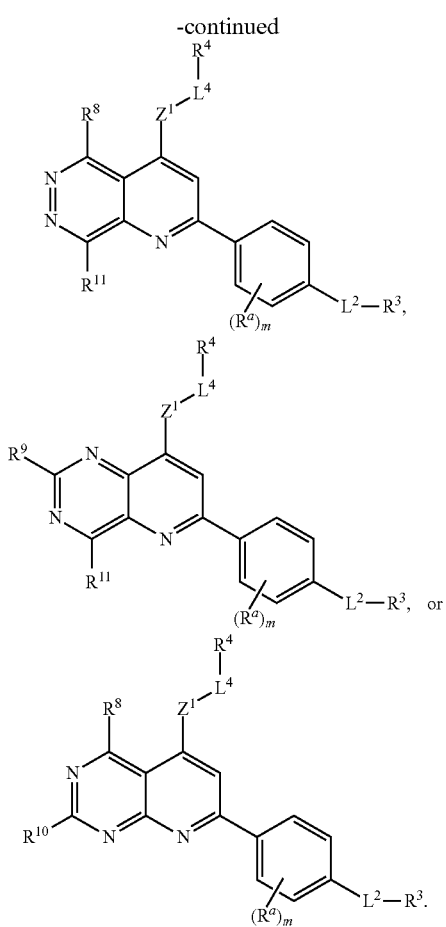

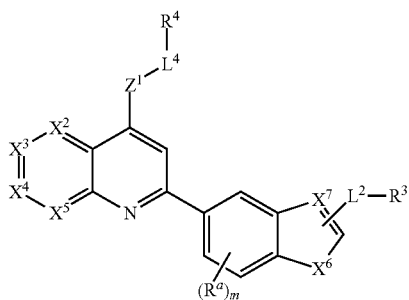

In some embodiments, the compound of Formula (I) has the structure of Formula (IV) or a pharmaceutically acceptable salt or solvate thereof, wherein:

Formula (IV)

wherein,
$X^6$ is $NR^b$, N, O, or S; and
$X^7$ is N or $CR^b$.

In some embodiments, $X^2$ is N; $X^3$ is $CR^9$; $X^4$ is $CR^{10}$; and $X^5$ is $CR^{11}$.

In some embodiments, $X^2$ is $CR^8$; $X^3$ is N; $X^4$ is $CR^{10}$; and $X^5$ is $CR^{11}$.

In some embodiments, $X^2$ is $CR^8$; $X^3$ is $CR^9$; $X^4$ is N; and $X^5$ is $CR^{11}$.

In some embodiments, $X^2$ is $CR^8$; $X^3$ is $CR^9$; $X^4$ is $CR^{10}$; and $X^5$ is N.

In some embodiments, $X^2$ is N; $X^3$ is $CR^9$; $X^4$ is N; and $X^5$ is $CR^{11}$.

In some embodiments, $X^2$ is $CR^8$; $X^3$ is N; $X^4$ is $CR^{10}$; and $X^5$ is N.

In some embodiments, $X^2$ is N; $X^3$ is $CR^9$; $X^4$ is $CR^{10}$; and $X^5$ is N.

In some embodiments, $X^2$ is $CR^8$; $X^3$ is N; $X^4$ is N; and $X^5$ is $CR^{11}$.

In some embodiments, the compound of Formula (IV) has one of the following structures, or a pharmaceutically acceptable salt or solvate thereof:

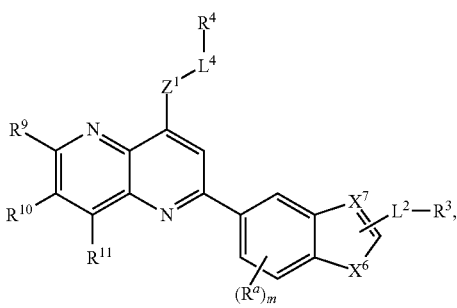

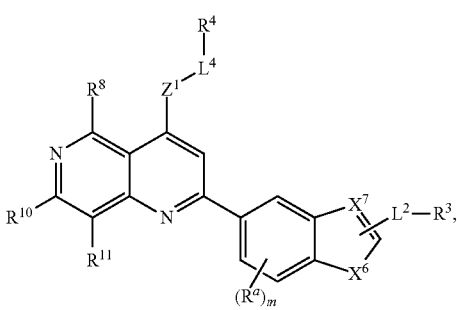

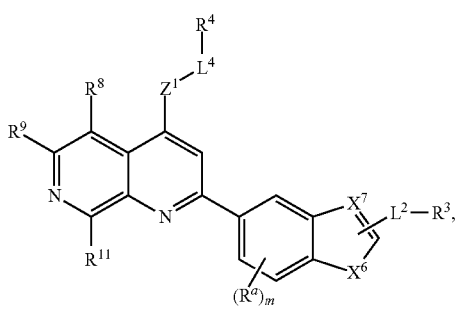

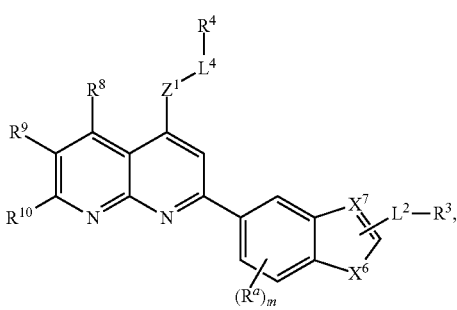

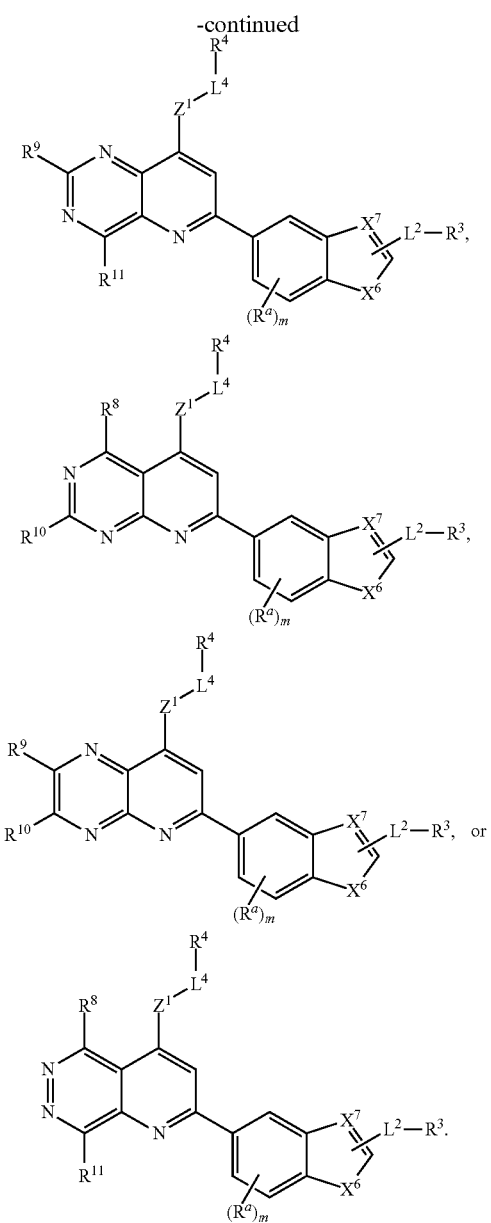

In some embodiments, $R^7$, $R^8$, $R^9$, $R^{10}$, and $R^{11}$ are independently selected from H, halogen, —CN, —OH, —$OR^{13}$, substituted or unsubstituted $C_1$-$C_6$alkyl, substituted or unsubstituted $C_1$-$C_6$fluoroalkyl, and substituted or unsubstituted $C_1$-$C_6$heteroalkyl.

In some embodiments, $R^7$, $R^8$, $R^9$, $R^{10}$, and $R^{11}$ are independently selected from H, F, Cl, Br, —CN, —OH, —$OCH_3$, —$OCH_2CH_3$, —$OCF_3$, —$CH_3$, —$CH_2CH_3$, —$CH(CH_3)_2$, —$CFH_2$, —$CF_2H$, —$CF_3$, —$CH_2OH$, —$CH_2OCH_3$, —$CH_2CH_2OH$, —$CH_2CH_2OCH_3$, —$CH_2NH_2$, —$CH_2NHCH_3$, and —$CH_2N(CH_3)_2$. In some embodiments, $R^7$, $R^8$, $R^9$, $R^{10}$, and $R^{11}$ are independently selected from H, F, Cl, Br, —CN, —OH, —$OCH_3$, —$OCH_2CH_3$, —$OCF_3$, —$CH_3$, —$CH_2CH_3$, —$CH(CH_3)_2$, —$CFH_2$, —$CF_2H$, and —$CF_3$. In some embodiments, $R^7$, $R^8$, $R^9$, $R^{10}$, and $R^{11}$ are independently selected from H, F, Cl, Br, —CN, —OH, —$OCH_3$, —$OCF_3$, —$CH_3$, —$CFH_2$, —$CF_2H$, and —$CF_3$. In some embodiments, $R^7$, $R^8$, $R^9$, $R^{10}$, and $R^{11}$ are H.

In some embodiments, $L^2$ is -$L^7$-$Y^1$—, —$Y^2$-$L^8$-$Y^1$—, or -$L^8$-$Y^2$-$L^8$-$Y^1$—; $L^7$ is absent, substituted or unsubstituted $C_1$-$C_4$alkylene, —CH═CH—, —C≡C—, or substituted or unsubstituted $C_3$-$C_6$cycloalkylene; $Y^1$ is —C(═O)$NR^c$—, —C(═O)—, or —C(═O)O—; each $L^8$ is independently substituted or unsubstituted $C_1$-$C_4$alkylene or substituted or unsubstituted $C_3$-$C_6$cycloalkylene; $Y^2$ is —O—, —S—, or —$NR^c$—; and $R^3$ is H or -$L^3$-$R^5$.

In some embodiments, $L^2$ is -$L^7$-$Y^1$—. In some embodiments, —$Y^2$-$L^8$-$Y^1$— or -$L^8$-$Y^2$-$L^8$-$Y^1$—. In some embodiments, —$Y^2$-$L^8$-$Y^1$—. In some embodiments, -$L^8$-$Y^2$-$L^8$-$Y^1$—.

In some embodiments, $L^7$ is absent, —$CH_2$—, —$CH_2$—$CH_2$—, —$CH_2CH_2$—, —CH═CH—, —C≡C—, cyclopropylene, cyclobutylene, cyclopentylene, or cyclohexylene.

In some embodiments, $Y^1$ is —C(═O)$NR^c$—, —C(═O)—, —$SO_2NR^c$—, —C(═O)O—, —C(═$NR^c$)—, —C(═N—$OR^c$)—, —C(═$NR^c$)$NR^c$—, or —C(═N—$OR^c$)—$NR^c$—. In some embodiments, $Y^1$ is —C(═O)$NR^c$—, —C(═O)—, —C(═O)O—, or —C(═N—$OR^c$)—$NR^c$—. In some embodiments, $Y^1$ is —C(═O)$NR^c$—. In some embodiments, $Y^1$ is —C(═O)—. In some embodiments, $Y^1$ is —C(═O)O—. In some embodiments, $Y^1$ is —C(═N—$OR^c$)—$NR^c$—.

In some embodiments, —$CH_2$—, —$CH_2$—$CH_2$—, —$CH_2CH_2$—, cyclopropylene, cyclobutylene, cyclopentylene, or cyclohexylene.

In some embodiments, $Y^2$ is —O—. In some embodiments, $Y^2$ is —S—. In some embodiments, $Y^2$ is —$NR^c$—.

In some embodiments, $R^3$ is H. In some embodiments, $R^3$-$L^3$-$R^5$.

In some embodiments, $L^3$ is absent, substituted or unsubstituted $C_1$-$C_6$alkylene, or substituted or unsubstituted $C_1$-$C_6$heteroalkylene. In some embodiments, $L^3$ is absent. In some embodiments, $L^3$ is substituted or unsubstituted $C_1$-$C_6$alkylene. In some embodiments, $L^3$ is substituted or unsubstituted $C_1$-$C_6$heteroalkylene.

In some embodiments, $R^5$ is H, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl. In some embodiments, R is H. In some embodiments, $R^5$ is substituted or unsubstituted $C_3$-$C_{10}$cycloalkyl. In some embodiments, $R^5$ is substituted or unsubstituted $C_2$-$C_{10}$heterocycloalkyl. In some embodiments, $R^5$ is substituted or unsubstituted aryl. In some embodiments, R is substituted or unsubstituted heteroaryl.

In some embodiments, $R^3$ and $R^c$ are taken together with the N atom to which they are attached to form a substituted or unsubstituted N-containing heterocycle.

In some embodiments, $R^5$ is a substituted or unsubstituted monocyclic $C_2$-$C_8$heterocycloalkyl containing at least 1 N atom in the ring.

In some embodiments, $R^5$ is substituted or unsubstituted aziridinyl, substituted or unsubstituted azetidinyl, substituted or unsubstituted pyrrolidinyl, substituted or unsubstituted morpholinyl, substituted or unsubstituted thiomorpholinyl, substituted or unsubstituted piperidinyl, substituted or unsubstituted piperazinyl, or substituted or unsubstituted azepanyl. In some embodiments, R is substituted or unsubstituted aziridinyl. In some embodiments, R is substituted or unsubstituted azetidinyl. In some embodiments, $R^5$ is substituted or unsubstituted pyrrolidinyl. In some embodiments, $R^5$ is substituted or unsubstituted morpholinyl. In some embodiments, $R^5$ is substituted or unsubstituted thiomorpholinyl. In some embodiments, $R^5$ is substituted or unsubstituted piperidinyl. In some embodiments, $R^5$ is substituted or unsubstituted piperazinyl. In some embodiments, $R^5$ is substituted or unsubstituted azepanyl.

In some embodiments, $R^5$ is substituted or unsubstituted monocyclic $C_2$-$C_5$heterocycloalkyl containing 1 N atom in the ring that is a β-lactam, γ-lactam, δ-lactam or ε-lactam. In some embodiments, $R^5$ is substituted or unsubstituted monocyclic $C_2$-$C_8$heterocycloalkyl containing 1 N atom in the ring that is a β-lactam. In some embodiments, $R^5$ is substituted or unsubstituted monocyclic $C_2$-$C_8$heterocycloalkyl containing 1 N atom in the ring that is a γ-lactam. In some embodiments, R is substituted or unsubstituted monocyclic $C_2$-$C_8$heterocycloalkyl containing 1 N atom in the ring that is a δ-lactam. In some embodiments, $R^5$ is substituted or unsubstituted monocyclic $C_2$-$C_5$heterocycloalkyl containing 1 N atom in the ring that is a ε-lactam.

In some embodiments, $R^5$ is a substituted or unsubstituted bicyclic $C_5$-$C_{10}$heterocycloalkyl.

In some embodiments, $R^5$ is a substituted or unsubstituted bicyclic $C_5$-$C_{10}$heterocycloalkyl that is a substituted or unsubstituted fused bicyclic $C_5$-$C_{10}$heterocycloalkyl. In some embodiments, $R^5$ is a substituted or unsubstituted bicyclic $C_5$-$C_{10}$heterocycloalkyl that is substituted or unsubstituted bridged bicyclic $C_5$-$C_{10}$heterocycloalkyl. In some embodiments, $R^5$ is a substituted or unsubstituted bicyclic $C_5$-$C_{10}$heterocycloalkyl that is substituted or unsubstituted spiro bicyclic $C_5$-$C_{10}$heterocycloalkyl.

In some embodiments, $Z^1$ is —$NR^d$— or —O—; and $L^4$ is absent or -$L^5$-$L^6$-. In some embodiments, $Z^1$ is —$NR^d$—. In some embodiments, $Z^1$ is —O—. In some embodiments, $L^4$ is absent. In some embodiments, $L^4$ is -$L^5$-$L^6$-.

In some embodiments, $L^5$ is substituted or unsubstituted $C_1$-$C_6$alkylene, substituted or unsubstituted $C_1$-$C_6$heteroalkylene, substituted or unsubstituted phenylene or substituted or unsubstituted monocyclic heteroarylene. In some embodiments, $L^5$ is substituted or unsubstituted $C_1$-$C_6$alkylene. In some embodiments, $L^5$ is substituted or unsubstituted $C_1$-$C_6$heteroalkylene. In some embodiments, $L^5$ is substituted or unsubstituted phenylene. In some embodiments, $L^5$ is substituted or unsubstituted monocyclic heteroarylene.

In some embodiments, $L^6$ is absent, substituted or unsubstituted $C_1$-$C_6$alkylene, substituted or unsubstituted $C_1$-$C_6$heteroalkylene, —$NR^6$—, —C(=O)$NR^6$—, —$NR^6$C(=O)—, or —$NR^6$C(=O)$NR^6$—. In some embodiments, $L^6$ is absent. In some embodiments, $L^6$ is substituted or unsubstituted $C_1$-$C_6$alkylene. In some embodiments, $L^6$ is substituted or unsubstituted $C_1$-$C_6$heteroalkylene. In some embodiments, $L^6$ is —$NR^6$—. In some embodiments, $L^6$ is —C(=O)$NR^6$—. In some embodiments, $L^6$ is —$NR^6$C(=O)—. In some embodiments, $L^6$ is —$NR^6$C(=O)$NR^6$—.

In some embodiments, $R^4$ is H, substituted or unsubstituted $C_3$-$C_{10}$cycloalkyl, substituted or unsubstituted $C_2$-$C_{10}$heterocycloalkyl, substituted or unsubstituted phenyl, or substituted or unsubstituted monocyclic heteroaryl. In some embodiments, $R^4$ is H. In some embodiments, $R^4$ is substituted or unsubstituted $C_3$-$C_{10}$cycloalkyl. In some embodiments, $R^4$ is substituted or unsubstituted $C_2$-$C_{10}$heterocycloalkyl. In some embodiments, $R^4$ is substituted or unsubstituted phenyl. In some embodiments, $R^4$ is substituted or unsubstituted monocyclic heteroaryl.

In some embodiments, $R^4$ and $R^6$ are taken together with the N atom to which they are attached to form a substituted or unsubstituted N-containing heterocycle.

In some embodiments, $L^4$ is absent or -$L^5$-$L^6$-. In some embodiments, $L^4$ is absent. In some embodiments, $L^4$ is -$L^5$-$L^6$-. In some embodiments, $L^5$ is substituted or unsubstituted $C_1$-$C_6$alkylene. In some embodiments, $L^6$ is absent or —$NR^6$—. In some embodiments, $L^6$ is absent. In some embodiments, $L^6$ is —$NR^6$—.

In some embodiments, $R^4$ is substituted or unsubstituted monocyclic $C_2$-$C_6$heterocycloalkyl.

In some embodiments, $R^4$ and $R^6$ are taken together with the N atom to which they are attached to form a substituted or unsubstituted monocyclic N-containing $C_2$-$C_6$heterocycloalkyl.

In some embodiments, $L^5$ is —$CH_2CH_2$—, —$CH_2CH_2CH_2$—, or —$CH_2CH_2CH_2CH_2$—. In some embodiments, $L^5$ is —$CH_2CH_2$—. In some embodiments, $L^5$ is —$CH_2CH_2CH_2$—. In some embodiments, $L^5$ is —$CH_2CH_2CH_2CH_2$—.

In some embodiments, $R^4$ is substituted or unsubstituted monocyclic $C_2$-$C_6$heterocycloalkyl that is a substituted or unsubstituted aziridinyl, substituted or unsubstituted azetidinyl, substituted or unsubstituted pyrrolidinyl, substituted or unsubstituted morpholinyl, substituted or unsubstituted thiomorpholinyl, substituted or unsubstituted piperidinyl, substituted or unsubstituted piperazinyl, or substituted or unsubstituted azepanyl. In some embodiments, $R^4$ is substituted or unsubstituted aziridinyl. In some embodiments, $R^4$ is substituted or unsubstituted azetidinyl. In some embodiments, $R^4$ is substituted or unsubstituted pyrrolidinyl. In some embodiments, $R^4$ is substituted or unsubstituted morpholinyl. In some embodiments, $R^4$ is substituted or unsubstituted thiomorpholinyl. In some embodiments, $R^4$ is substituted or unsubstituted piperidinyl. In some embodiments, $R^4$ is substituted or unsubstituted piperazinyl. In some embodiments, $R^4$ is substituted or unsubstituted azepanyl.

In some embodiments, $R^4$ and $R^6$ are taken together with the N atom to which they are attached to form a substituted or unsubstituted monocyclic N-containing $C_2$-$C_6$ heterocycloalkyl that is a substituted or unsubstituted aziridinyl, substituted or unsubstituted azetidinyl, substituted or unsubstituted pyrrolidinyl, substituted or unsubstituted morpholinyl, substituted or unsubstituted thiomorpholinyl, substituted or unsubstituted piperidinyl, substituted or unsubstituted piperazinyl, or substituted or unsubstituted azepanyl. In some embodiments, $R^4$ and $R^6$ are taken together with the N atom to which they are attached to form substituted or unsubstituted aziridinyl. In some embodiments, $R^4$ and $R^6$ are taken together with the N atom to which they are attached to form substituted or unsubstituted azetidinyl. In some embodiments, $R^4$ and $R^6$ are taken together with the N atom to which they are attached to form substituted or unsubstituted pyrrolidinyl. In some embodiments, $R^4$ and $R^6$ are taken together with the N atom to which they are attached to form substituted or unsubstituted morpholinyl. In some embodiments, $R^4$ and $R^6$ are taken together with the N atom to which they are attached to form substituted or unsubstituted thiomorpholinyl. In some embodiments, $R^4$ and $R^6$ are taken together with the N atom to which they are attached to form substituted or unsubstituted piperidinyl. In some embodiments, $R^4$ and $R^6$ are taken together with the N atom to which they are attached to form substituted or unsubstituted piperazinyl. In some embodiments, $R^4$ and $R^6$ are taken together with the N atom to which they are attached to form substituted or unsubstituted azepanyl.

Any combination of the groups described above for the various variables is contemplated herein. Throughout the specification, groups and substituents thereof are chosen by one skilled in the field to provide stable moieties and compounds.

In some embodiments, compounds of Formula (I), or a pharmaceutically acceptable salt, or solvate thereof, include but are not limited to those found in the following tables.

TABLE 1
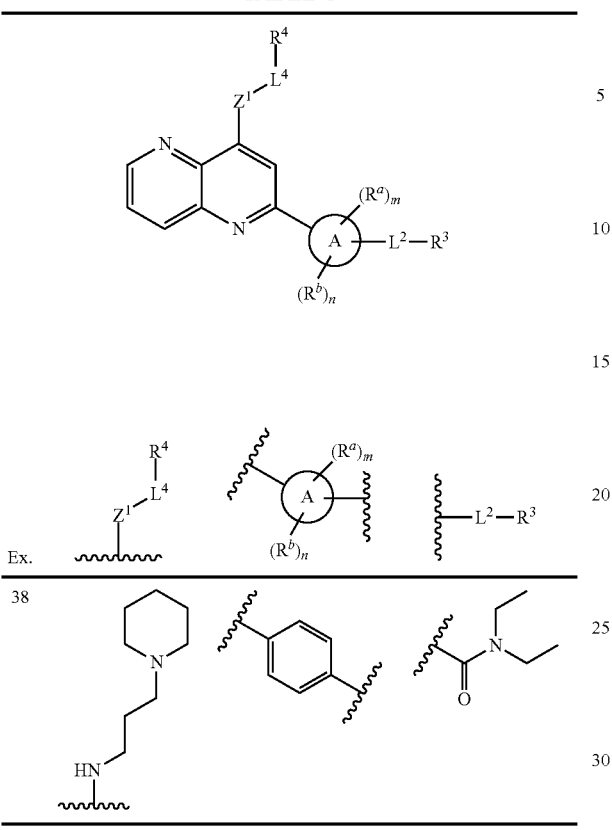
TABLE 2
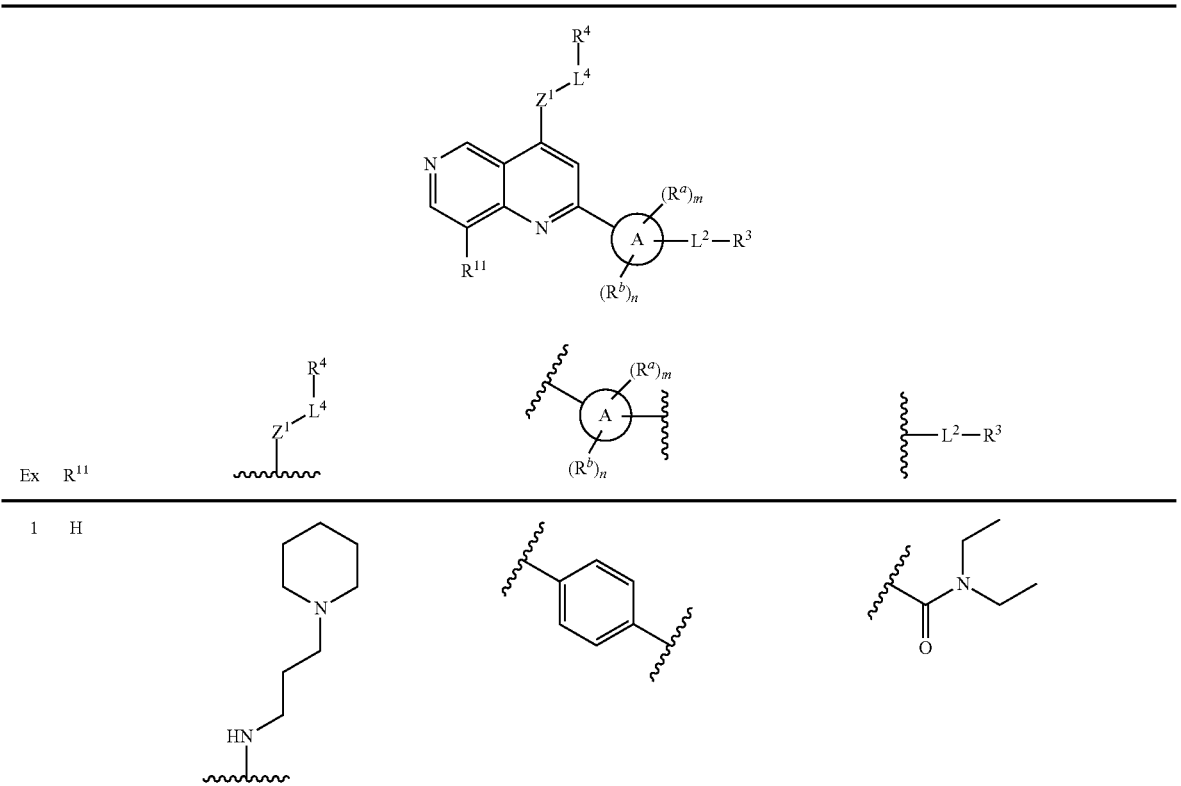

TABLE 2-continued

| Ex | R11 | Z1-L4-R4 | A with (Ra)m and (Rb)n | L2-R3 |
|---|---|---|---|---|
| 2 | H | piperidine-(CH2)3-NH- | 1-methyl-indole (5,2-linked) | -C(O)NH-CH2CH2-N(CH3)2 |
| 3 | H | piperidine-(CH2)3-NH- | 1-methyl-indole (5,2-linked) | -C(O)NH-(1-methylpiperidin-4-yl) |
| 4 | H | piperidine-(CH2)3-NH- | 1-methyl-indole (5,2-linked) | -C(O)NH-(piperidin-4-yl) |
| 5 | H | piperidine-(CH2)3-NH- | 1-methyl-indole (5,2-linked) | -C(O)O-ethyl |

TABLE 2-continued
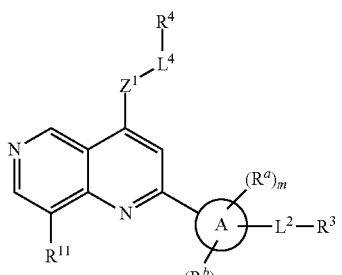
| Ex | R[11] | Z[1]-L[4]-R[4] | A with (R[a])[m], (R[b])[n] | L[2]—R[3] |
|----|-------|----------------|------------------------------|-----------|
| 6 | H | 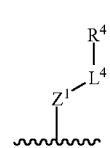 | 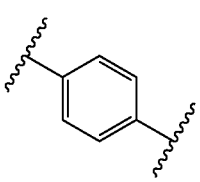 [SMILES: *c1ccc(*)cc1] | 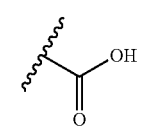 |
| 7 | H | 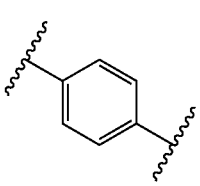 [SMILES: *c1ccc(*)cc1] | 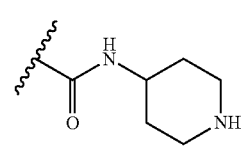 [SMILES: *C(=O)NC1CCNCC1] | 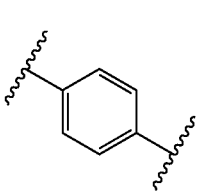 [SMILES: *c1ccc(*)cc1] |
| 8 | H | 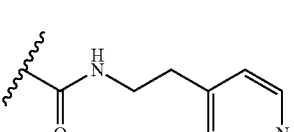 | 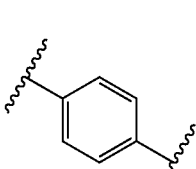 | 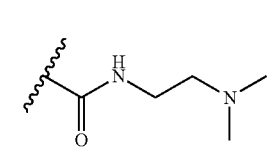 [SMILES: *C(=O)NCCN(C)C] |
| 9 | H | | | |

TABLE 2-continued
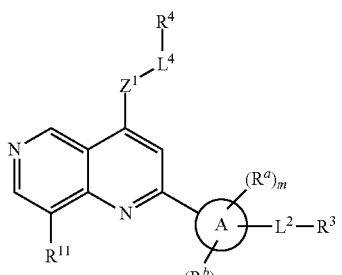
| Ex | R[11] | Z[1]—L[4]—R[4] | A ring | L[2]—R[3] |
|---|---|---|---|---|
| 10 | H | 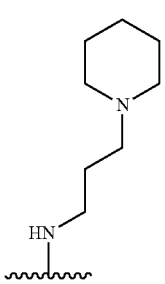 [SMILES: *NCCCN1CCCCC1] | 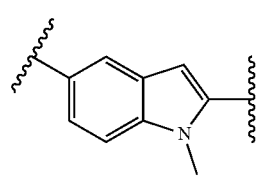 [SMILES: *c1ccc2c(c1)cc(*)n2C] | 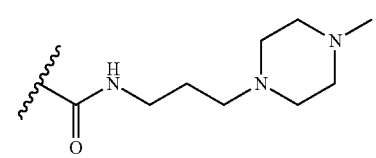 [SMILES: *C(=O)NCCCN1CCN(C)CC1] |
| 11 | H | 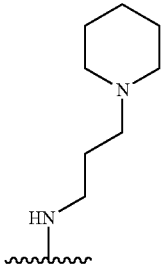 [SMILES: *NCCCN1CCCCC1] | 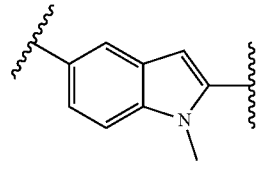 [SMILES: *c1ccc2c(c1)cc(*)n2C] | 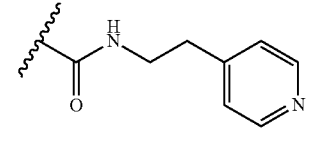 [SMILES: *C(=O)NCCc1ccncc1] |
| 12 | H | 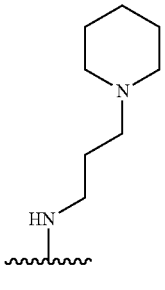 [SMILES: *NCCCN1CCCCC1] | 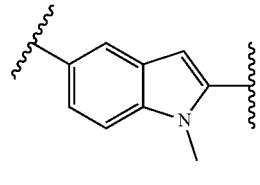 [SMILES: *c1ccc2c(c1)cc(*)n2C] | 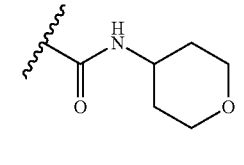 [SMILES: *C(=O)NC1CCOCC1] |
| 13 | H | 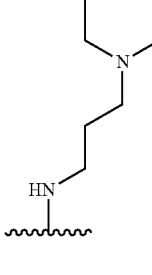 | 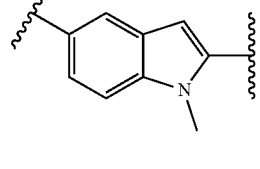 | 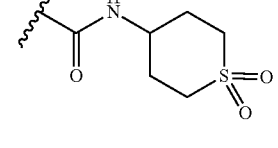 |

TABLE 2-continued
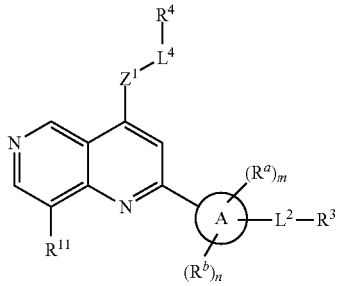
| Ex | R[11] | Z[1]—L[4] (R[4]) | A with (R[a])m, (R[b])n | L[2]—R[3] |
|----|-------|------------------|-------------------------|-----------|
| 14 | H | 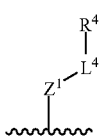 | 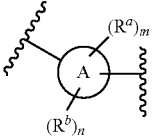 | 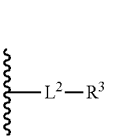 |
| 15 | H | 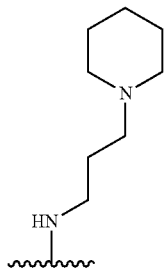 [SMILES: *NCCCN1CCCCC1] | 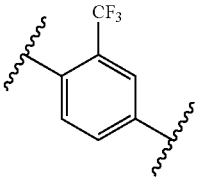 | 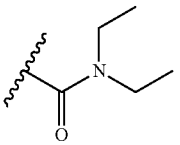 [SMILES: *C(=O)N(CC)CC] |
| 16 | H | 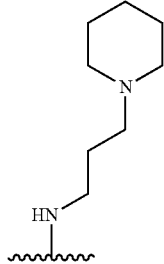 [SMILES: *NCCCN1CCCCC1] | 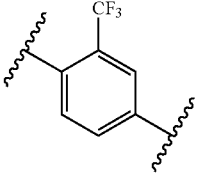 [SMILES: *c1ccc(*)c(C(F)(F)F)c1] | 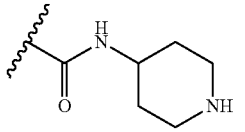 [SMILES: *C(=O)NC1CCNCC1] |
| 17 | H | 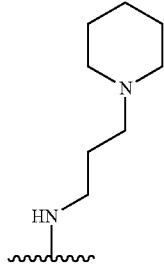 [SMILES: *NCCCN1CCCCC1] | 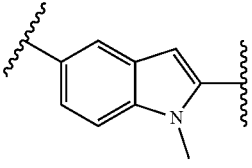 [SMILES: *c1ccc2c(c1)cc(*)n2C] | 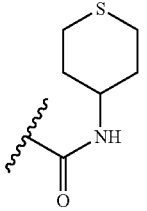 [SMILES: *C(=O)NC1CCSCC1] |
| 18 | H | 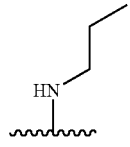 | 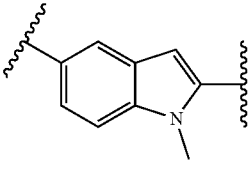 [SMILES: *c1ccc2c(c1)cc(*)n2C] | 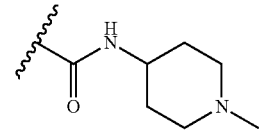 [SMILES: *C(=O)NC1CCN(C)CC1] |

TABLE 2-continued
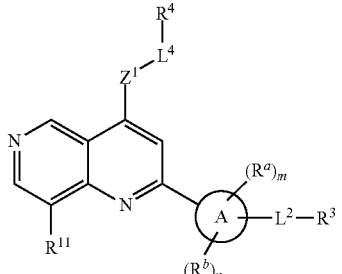
| Ex | R¹¹ | Z¹–L⁴ ~ | ~ A ~ | ~ L²–R³ |
|----|-----|---------|-------|---------|
| 19 | H | 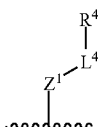 | 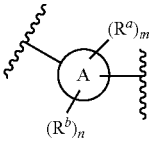 | 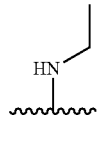 |
| 20 | H | 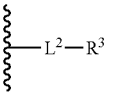 | 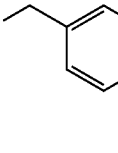 | 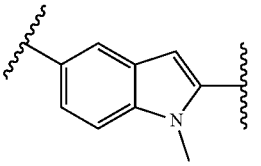 [SMILES: *c1ccc2c(c1)cc(*)n2C] |
| 21 | H | 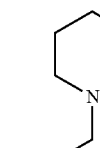 | 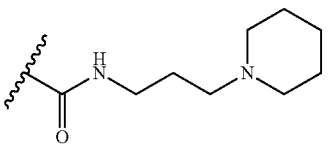 [SMILES: *C(=O)NCCCN1CCCCC1] | 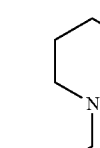 |
| 22 | H | 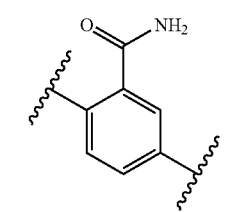 [SMILES: *c1ccc(*)c(C(N)=O)c1] | 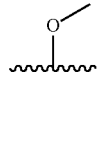 | 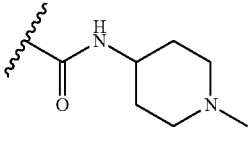 [SMILES: *C(=O)NC1CCN(C)CC1] |
| 23 | H |  |  |  |

TABLE 2-continued
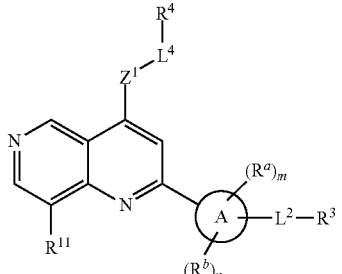
| Ex | R[11] | 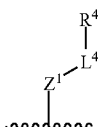 | 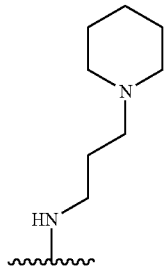 [SMILES: *NCCCN1CCCCC1] | 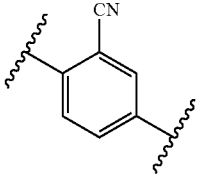 [SMILES: *c1ccc(*)c(C#N)c1] |
|---|---|---|---|---|
| 24 | H | 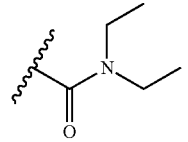 [SMILES: *C(=O)N(CC)CC] | 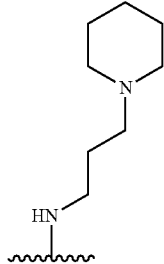 [SMILES: *NCCCN1CCCCC1] | 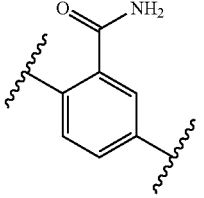 [SMILES: *c1ccc(*)c(C(N)=O)c1] |
| 25 | H | 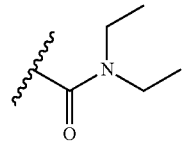 [SMILES: *C(=O)N(CC)CC] |  | 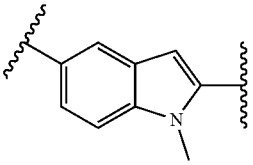 [SMILES: *c1ccc2c(c1)cc(*)n2C] |
| 26 | H | 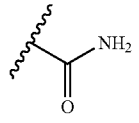 | 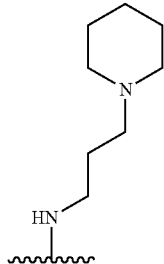 [SMILES: *NCCCN1CCCCC1] | 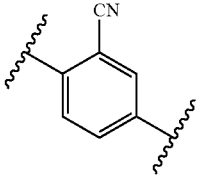 [SMILES: *c1ccc(*)c(C#N)c1] |
| 27 | H | 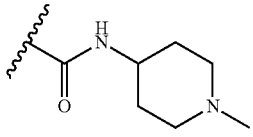 [SMILES: *C(=O)NC1CCN(C)CC1] | | |

US 11,731,986 B2
TABLE 2-continued
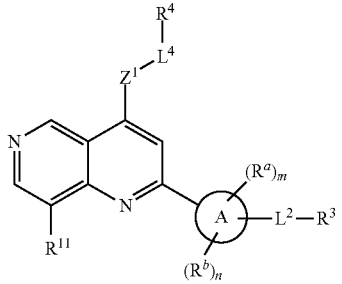
| Ex | R[11] | Z[1]–L[4]/R[4] | A ring with (R[a])m, (R[b])n | L[2]–R[3] |
|----|-------|----------------|-------------------------------|-----------|
| 28 | H | 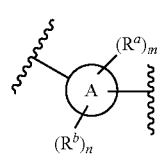 | 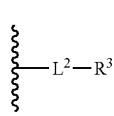 | 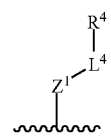 |
| 29 | H | 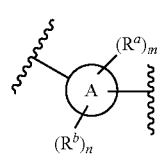 | 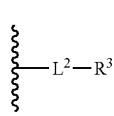 | 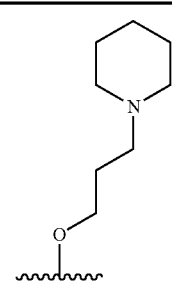 |
| 30 | H | 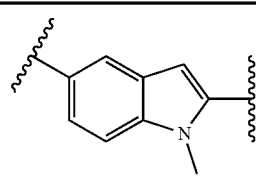 | 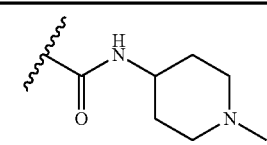 | 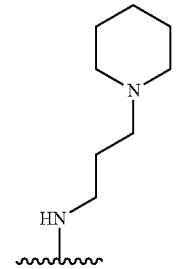 [SMILES: *NCCCN1CCCCC1] |
| 31 | H | 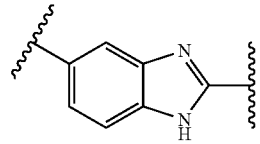 [SMILES: *c1ccc2[nH]c(*)nc2c1] | 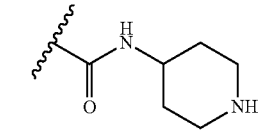 [SMILES: *C(=O)NC1CCNCC1] | 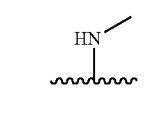 |
| 32 | H | 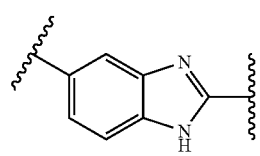 [SMILES: *c1ccc2[nH]c(*)nc2c1] | 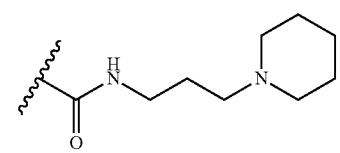 [SMILES: *C(=O)NCCCN1CCCCC1] | 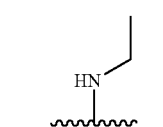 |

TABLE 2-continued

| Ex | R11 | Z1-L4-R4 | A with (Ra)m (Rb)n | L2-R3 |
|----|-----|----------|---------------------|-------|
| 33 | H | piperidine-propyl-NH- | 5,2-benzimidazole (1H) | -C(O)NH-CH2CH2CH2-N(4-methylpiperazine) |
| 34 | H | piperidine-propyl-NH- | 5,2-benzimidazole (1H) | -C(O)-piperazine-NH |
| 35 | H | piperidine-propyl-NH- | 5,2-benzimidazole (1H) | -C(O)N(Et)2 |
| 36a | H | piperidine-propyl-NH- | 5,2-benzimidazole (1H) | -C(O)-N(4-ethylpiperazine) |

TABLE 2-continued
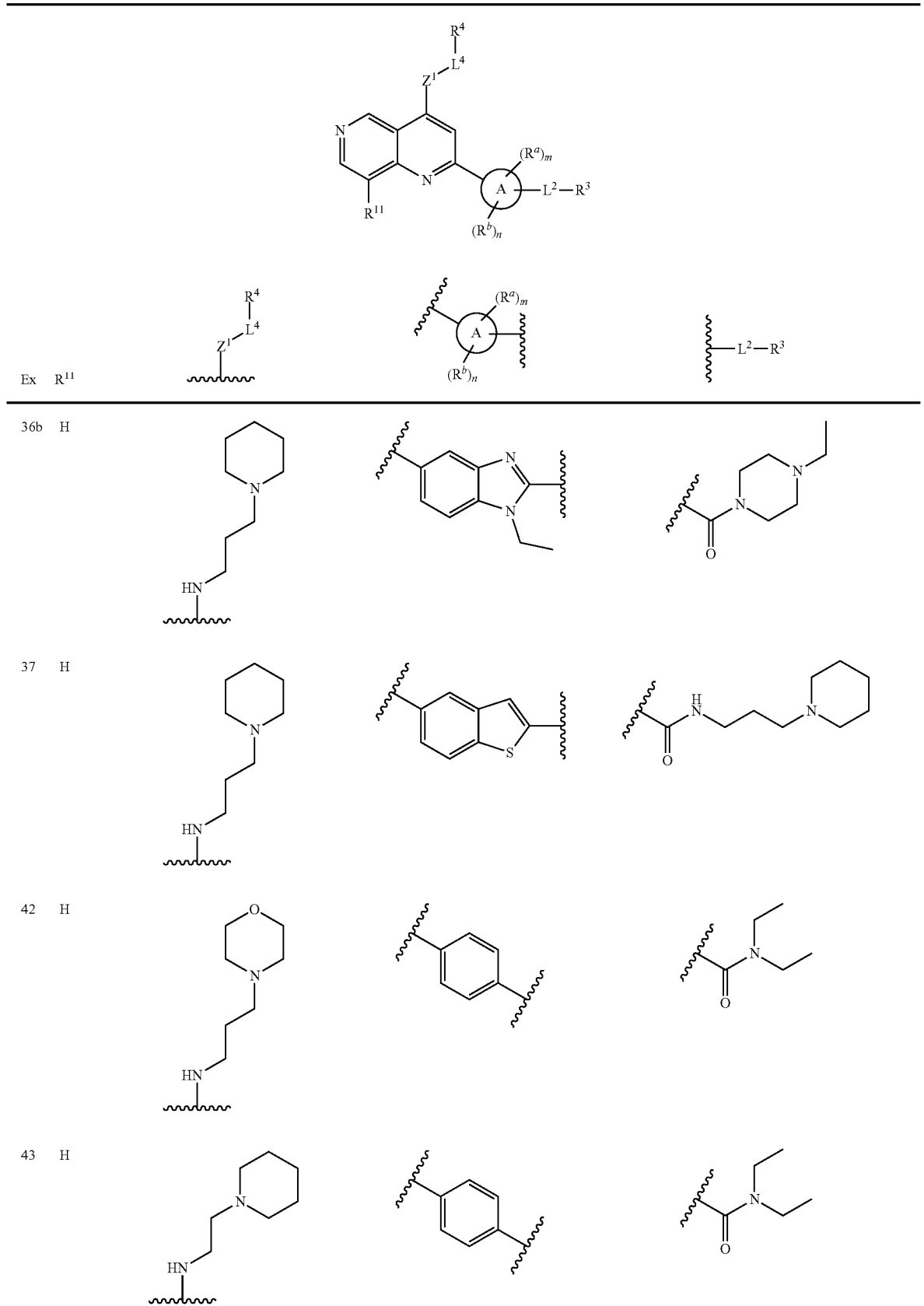

TABLE 2-continued

| Ex | R[11] | Z[1]–L[4]–R[4] | A (R[a])m (R[b])n | L[2]–R[3] |
|----|-------|----------------|-------------------|-----------|
| 44 | H | 4-(piperazin-1-yl)propyl-NH– | 1,4-phenylene | –CH₂C(O)N(Et)₂ |
| 45 | H | 4-(methylsulfonyl)piperazin-1-yl propyl-NH– | 1,4-phenylene | –CH₂C(O)N(Et)₂ |
| 46 | H | (1-methylpiperidin-4-yl)-NH– | 1,4-phenylene | –CH₂C(O)N(Et)₂ |
| 47 | H | (2-(dimethylamino)ethyl)-NH– | 1,4-phenylene | –CH₂C(O)N(Et)₂ |

TABLE 2-continued
| Ex | R¹¹ | Z¹-L⁴-R⁴ | A (Rᵃ)ₘ (Rᵇ)ₙ | L²-R³ |
|---|---|---|---|---|
| 48 | H | 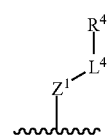 | 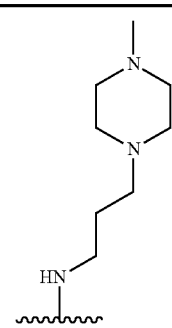 | 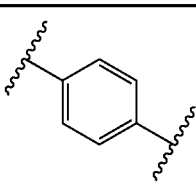 |
| 49 | H | 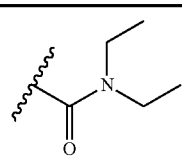 | 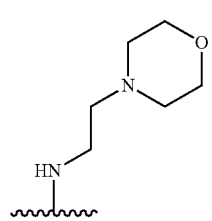 [SMILES: *NCCN1CCOCC1] | 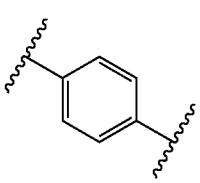 [SMILES: *c1ccc(*)cc1] |
| 50 | H | 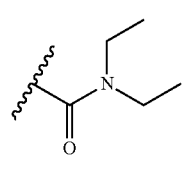 [SMILES: *C(=O)N(CC)CC] | 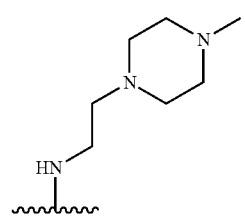 [SMILES: *NCCN1CCN(C)CC1] | 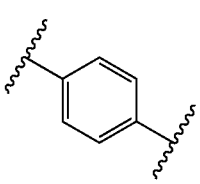 [SMILES: *c1ccc(*)cc1] |
| 51 | H | 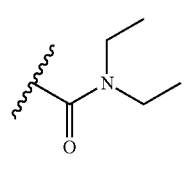 [SMILES: *C(=O)N(CC)CC] | 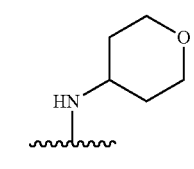 [SMILES: *NC1CCOCC1] | 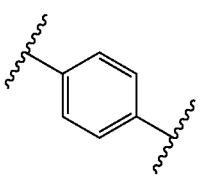 [SMILES: *c1ccc(*)cc1] |
| 52 | H | 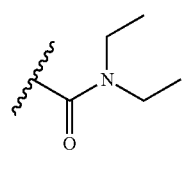 [SMILES: *C(=O)N(CC)CC] | 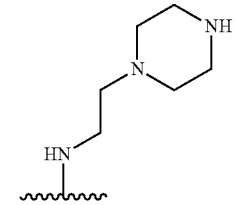 | 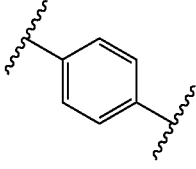 [SMILES: *c1ccc(*)cc1] |
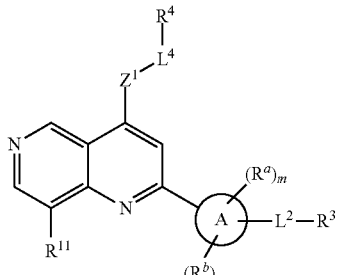

TABLE 2-continued

| Ex | R¹¹ | $Z^1{-}L^4{-}R^4$ | A with $(R^a)_m$, $(R^b)_n$ | $L^2{-}R^3$ |
|---|---|---|---|---|
| 53 | H | 4-(methylsulfonyl)piperazin-1-yl-ethyl-NH– | 1,4-phenylene | –C(O)N(Et)₂ |
| 54 | H | 4-methoxyphenyl-NH– | 1,4-phenylene | –C(O)N(Et)₂ |
| 55 | H | 4-(dimethylamino)phenyl-NH– | 1,4-phenylene | –C(O)N(Et)₂ |
| 56 | H | 4-((dimethylamino)methyl)phenyl-NH– | 1,4-phenylene | –C(O)N(Et)₂ |
| 57 | H | 4-((2-methoxyethyl)amino)phenyl-NH– | 1,4-phenylene | –C(O)N(Et)₂ |

TABLE 2-continued

| Ex | R[11] | Z[1]-L[4]-R[4] | A (R[a])[m] (R[b])[n] | L[2]-R[3] |
|---|---|---|---|---|
| 58 | H | thiomorpholine-1,1-dioxide-N-CH2CH2-NH- | 1,4-phenylene | -C(O)N(Et)2 |
| 59 | H | thiomorpholine-1,1-dioxide-N-CH2CH2CH2-NH- | 1,4-phenylene | -C(O)N(Et)2 |
| 60 | H | 1-methylpyrrolidin-3-yl-NH- | 1,4-phenylene | -C(O)N(Et)2 |
| 61 | H | piperidin-4-yl-NH- | 1,4-phenylene | -C(O)N(Et)2 |
| 62 | H | 1-methylpyrrolidin-3-yl-NH- | 1,4-phenylene | -C(O)NH-(1-methylpiperidin-4-yl) |

TABLE 2-continued

| Ex | R[11] | Z[1]–L[4]–R[4] | A with (R[a])[m], (R[b])[n] | L[2]–R[3] |
|---|---|---|---|---|
| 63 | H | 1-methylpyrrolidin-3-ylamino | 1,4-phenylene | –C(O)NH(CH2)3-piperidin-1-yl |
| 64 | H | piperidin-4-ylamino | 1,4-phenylene | –C(O)NH(CH2)3-piperidin-1-yl |
| 65 | H | piperidin-4-ylamino | 1,4-phenylene | –C(O)NH-(1-methylpiperidin-4-yl) |
| 66 | H | pyrrolidin-3-ylamino | 1,4-phenylene | –C(O)N(Et)2 |
| 67 | H | pyrrolidin-3-ylamino | 1,4-phenylene | –C(O)NH(CH2)3-piperidin-1-yl |
| 68 | H | pyrrolidin-3-ylamino | 1,4-phenylene | –C(O)NH-(1-methylpiperidin-4-yl) |

TABLE 2-continued
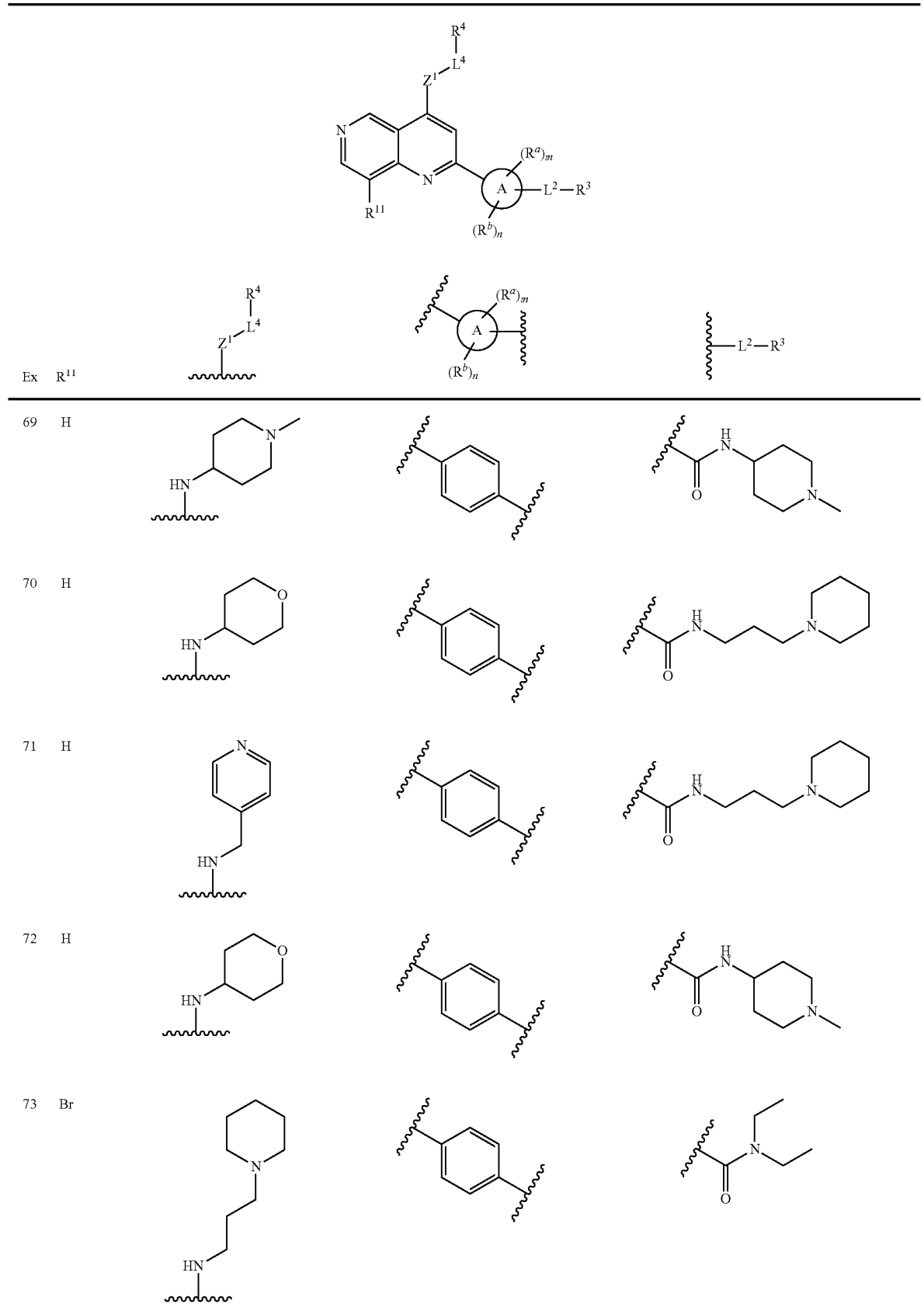

TABLE 2-continued
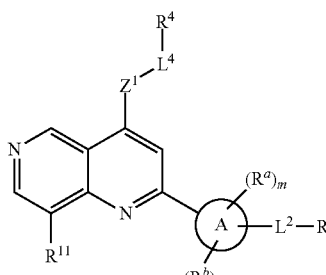
| Ex | R[11] | Z[1]–L[4]–R[4] | A with (R[a])[m], (R[b])[n] | L[2]–R[3] |
|----|-------|----------------|-----------------------------|-----------|
| 74 | Br | 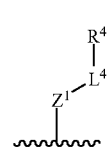 | 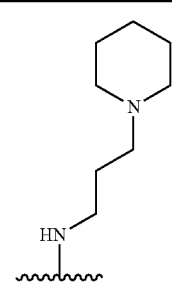 | 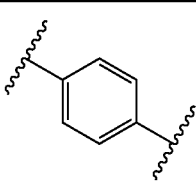 |
| 75 | Me | 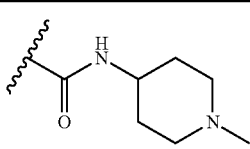 | 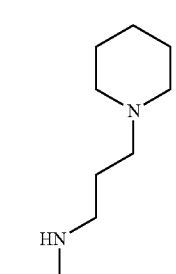 | 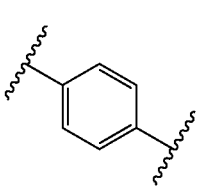 [SMILES: *c1ccc(*)cc1] |
| 76 | Me | 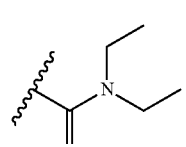 | 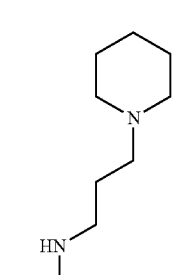 | 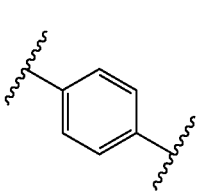 [SMILES: *c1ccc(*)cc1] |
| 77 | Me | 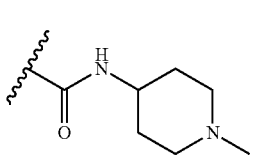 [SMILES: *C(=O)NC1CCN(C)CC1] | 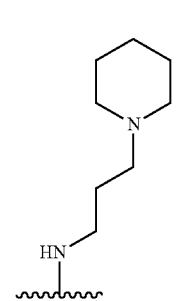 [SMILES: *NCCCN1CCCCC1] | 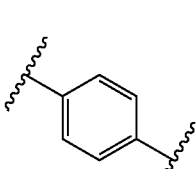 |

TABLE 2-continued
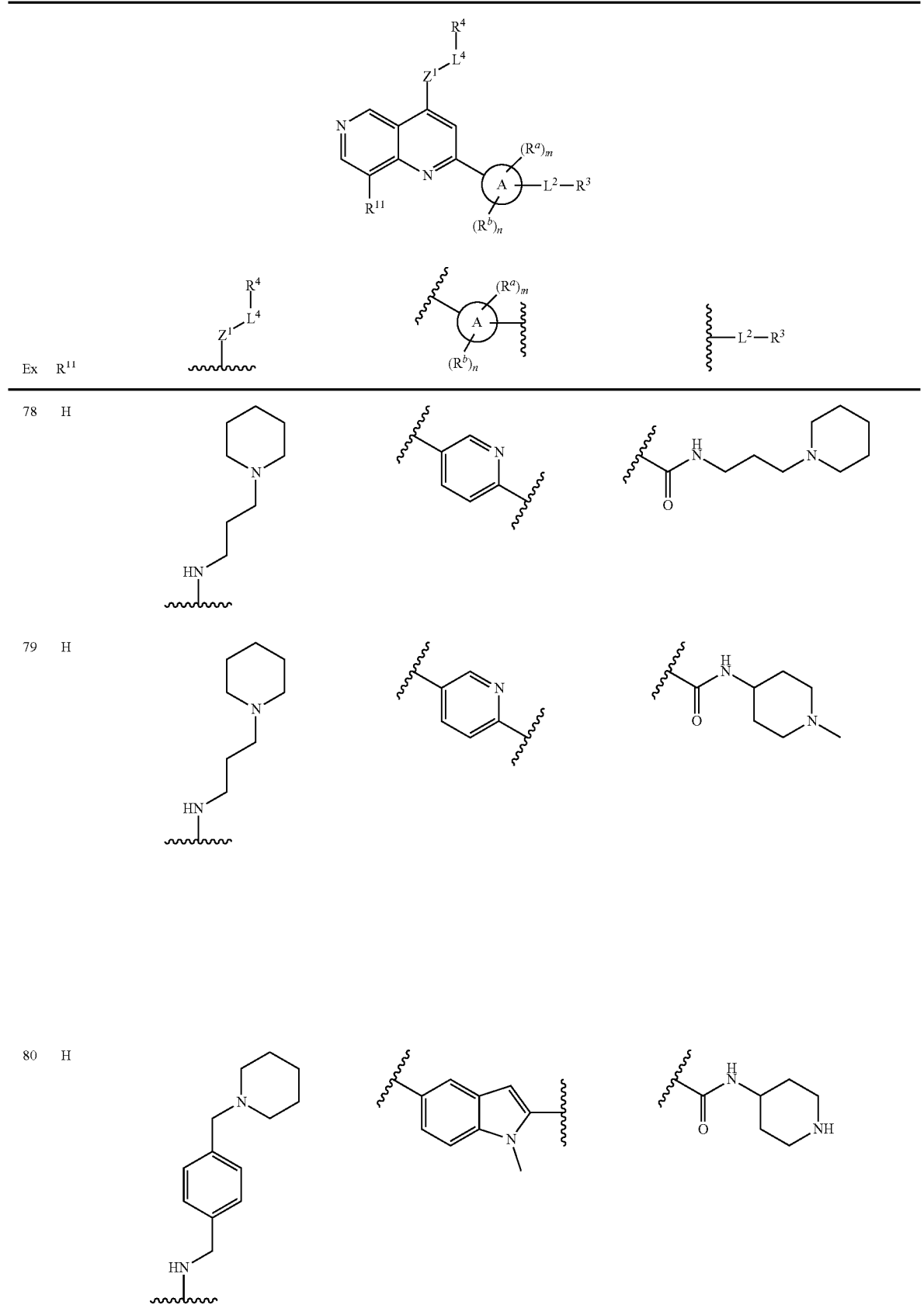

TABLE 2-continued

| Ex | R[11] | Z[1]—L[4]—R[4] | A with (R[a])m, (R[b])n | L[2]—R[3] |
|---|---|---|---|---|
| 81 | H | 4-(piperidin-1-ylmethyl)benzylamino | 1-methyl-1H-indol-5,2-diyl | C(=O)NH-(1-methylpiperidin-4-yl) |
| 82 | H | 4-(piperidin-1-ylmethyl)benzylamino | 1-methyl-1H-indol-5,2-diyl | C(=O)-(4-methylpiperazin-1-yl) |
| 83 | H | 4-(piperidin-1-ylmethyl)benzylamino | 1-methyl-1H-indol-5,2-diyl | C(=O)NH-CH2-(1-methylpiperidin-4-yl) |

TABLE 2-continued

| Ex | R[11] | Z[1]—L[4]—R[4] | A with (R[a])m, (R[b])n | L[2]—R[3] |
|---|---|---|---|---|
| 84 | H | N-methyl-N-(3-piperidin-1-ylpropyl)amino | 1-methyl-1H-indole-2,5-diyl | C(O)NH-(1-methylpiperidin-4-yl) |
| 85 | H | (4-piperidin-1-ylbutan-2-yl)amino | 1-methyl-1H-indole-2,5-diyl | C(O)NH-(1-methylpiperidin-4-yl) |
| 86 | H | (1-methylpiperidin-4-yl)amino | 1-methyl-1H-indole-2,5-diyl | C(O)NH-(1-methylpiperidin-4-yl) |
| 87 | H | (1-methylpiperidin-4-yl)amino | 1-methyl-1H-indole-2,5-diyl | C(O)-(4-methylpiperazin-1-yl) |
| 88 | H | (1-methylpiperidin-4-yl)amino | 1-methyl-1H-indole-2,5-diyl | C(O)NHCH2-(1-methylpiperidin-4-yl) |

TABLE 2-continued

| Ex | R[11] | Z[1]–L[4]–R[4] | A with (R[a])m, (R[b])n | L[2]–R[3] |
|----|-------|----------------|-------------------------|-----------|
| 89 | H | 4-(1-methylpiperidinyl)amino | 1-methyl-indol-2,5-diyl | –C(O)NH-(CH2)3-piperidinyl |
| 90 | H | 3-(piperidin-1-yl)propylamino | 1H-indol-2,6-diyl | –C(O)NH-(1-methylpiperidin-4-yl) |
| 91 | H | 3-(piperidin-1-yl)propylamino | 1H-indol-2,6-diyl | –C(O)NH-(CH2)3-piperidinyl |
| 92 | H | 3-(piperidin-1-yl)propylamino | 1H-indol-2,6-diyl | –C(O)NH-(CH2)2-N(CH3)2 |

TABLE 2-continued

| Ex | R11 | Z1-L4-R4 | A (R^a)_m (R^b)_n | L2—R3 |
|---|---|---|---|---|
| 93 | H | piperidine-N-CH2CH2CH2-NH- | 6,2-indole | -C(O)NH-CH2CH2-(4-pyridyl) |
| 94 | H | piperidine-N-CH2CH2CH2-NH- | 6,2-indole | -C(O)NH-(4-piperidinyl) |
| 95 | H | piperidine-N-CH2CH2CH2-NH- | 6,2-indole | -C(O)-N(4-ethylpiperazinyl) |
| 96 | H | piperidine-N-CH2CH2CH2-NH- | 1,4-phenylene | -O-CH2CH2-C(O)-N(Et)2 |

TABLE 2-continued
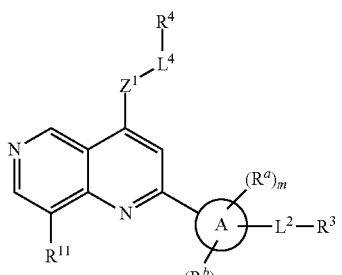
| Ex | R[11] | Z[1]-L[4]-R[4] | A with (R[a])m (R[b])n | L[2]—R[3] |
|---|---|---|---|---|
| 97 | H | 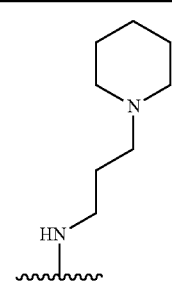 | 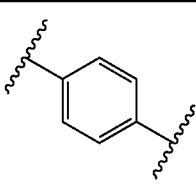 | 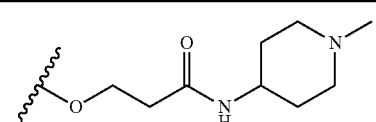 |
| 98a | H | 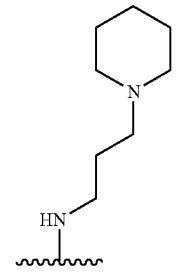 [SMILES: *NCCCN1CCCCC1] | 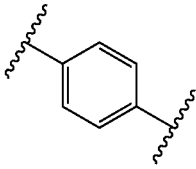 [SMILES: *c1ccc(*)cc1] | 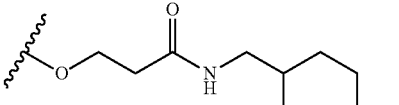 |
| 98b | H | 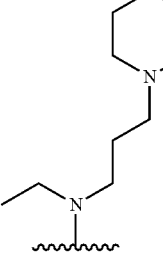 | 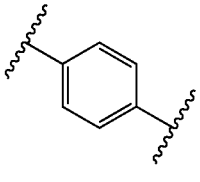 [SMILES: *c1ccc(*)cc1] | 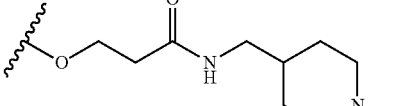 |
| 99 | H | 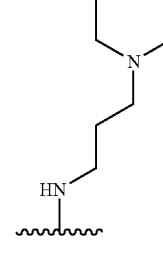 | 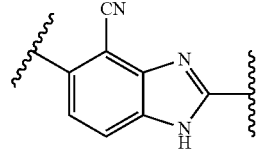 [SMILES: *c1nc2c(C#N)c(*)ccc2[nH]1] | 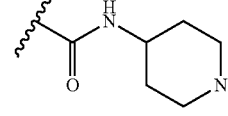 |

TABLE 2-continued
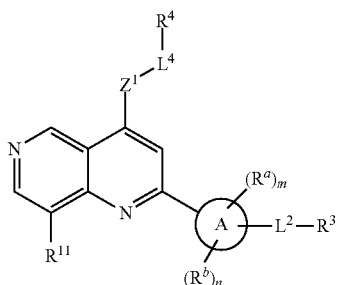
| Ex | R[11] | Z[1]-L[4] (R[4]) | A (R[a])m (R[b])n | L[2]-R[3] |
|----|-------|------------------|-------------------|-----------|
| 100 | H | 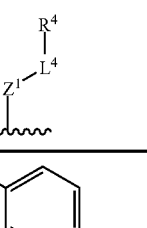 | 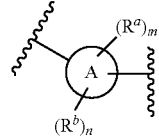 | 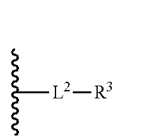 |
| 101 | H | 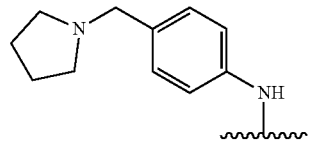 [SMILES: *Nc1ccc(CN2CCCC2)cc1] | 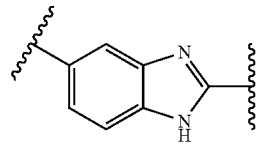 [SMILES: *c1ccc2[nH]c(*)nc2c1] | 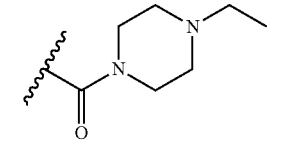 [SMILES: *C(=O)N1CCN(CC)CC1] |
| 102 | H | 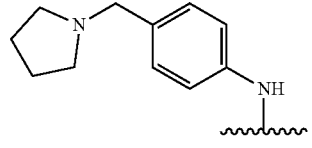 [SMILES: *Nc1ccc(CN2CCCC2)cc1] | 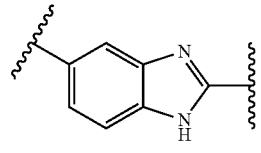 [SMILES: *c1ccc2[nH]c(*)nc2c1] | 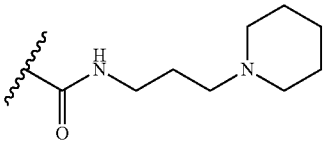 [SMILES: *C(=O)NCCCN1CCCCC1] |
| 103 | H | 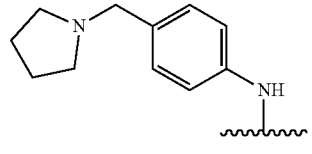 [SMILES: *Nc1ccc(CN2CCCC2)cc1] |  | 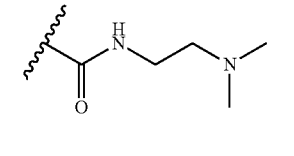 [SMILES: *C(=O)NCCN(C)C] |
| 104 | H | 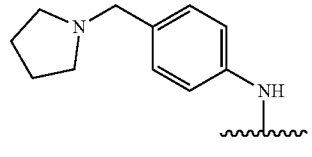 [SMILES: *Nc1ccc(CN2CCCC2)cc1] | 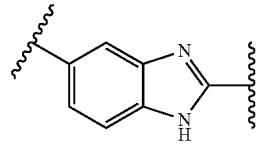 [SMILES: *c1ccc2[nH]c(*)nc2c1] | 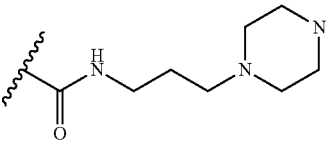 |
| 105 | H | 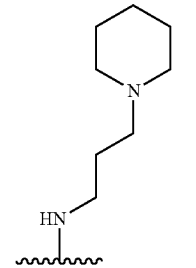 [SMILES: *NCCCN1CCCCC1] |  | 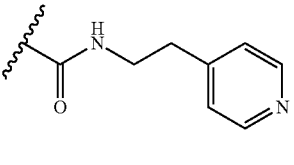 |

TABLE 2-continued
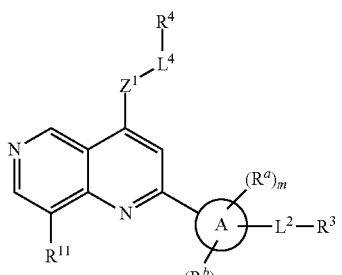
| Ex | R[11] | Z[1]—L[4]—R[4] | A with (R[a])[m], (R[b])[n] | L[2]—R[3] |
|---|---|---|---|---|
| 106 | H | piperidine-CH₂CH₂CH₂-NH- | 1,4-phenylene | -OCH₂C(O)NH-(1-methylpiperidin-4-yl) |
| 107 | H | piperidine-CH₂CH₂CH₂-NH- | 1,4-phenylene | -CH₂OCH₂C(O)NH-CH₂CH₂CH₂-piperidine |
| 108 | H | piperidine-CH₂CH₂CH₂-NH- | 1,4-phenylene | -CH₂OCH₂C(O)N(Et)₂ |
| 109 | H | piperidine-CH₂CH₂CH₂-NH- | 1,4-phenylene | -CH₂OCH₂C(O)NH-(1-methylpiperidin-4-yl) |

TABLE 2-continued

| Ex | R11 | Z1-L4-R4 | A with (Ra)m, (Rb)n | L2-R3 |
|----|-----|----------|---------------------|-------|
| 110 | H | piperidine-(CH2)3-NH- | 1,4-phenylene | -CH2-O-CH2-C(O)-NH-CH2-(1-ethylpiperidin-4-yl) |
| 111 | H | piperidine-(CH2)3-NH- | 1,4-phenylene | -CH2-O-CH2-C(O)-NH-CH2-(1-methylpiperidin-4-yl) |
| 112 | H | piperidine-(CH2)3-NH- | 1,4-phenylene | -CH2-O-CH2-C(O)-NH-(CH2)2-(4-methyl-1,4-diazepan-1-yl) |
| 113 | H | piperidine-(CH2)3-NH- | 1,4-phenylene | -CH2-O-CH2-C(O)-NH-CH2-(piperidin-4-yl) |

TABLE 2-continued

| Ex | R¹¹ | Z¹-L⁴-R⁴ | A ring with (Rᵃ)ₘ, (Rᵇ)ₙ | L²—R³ |
|----|-----|----------|--------------------------|-------|
| 114 | H | piperidine-CH₂CH₂CH₂-NH- | 1,4-phenylene | -CH₂-O-CH₂-C(=O)-NH-CH₂CH₂-(1-methylpiperidin-4-yl) |
| 115 | H | piperidine-CH₂CH₂CH₂-NH- | 1,4-phenylene | -CH₂-O-CH₂CH₂-C(=O)-NH-(1-methylpiperidin-4-yl) |
| 116 | H | piperidine-CH₂CH₂CH₂-NH- | 1-methyl-1H-pyrrolo[3,2-b]pyridine-2,5-diyl | -C(=O)-NH-(1-methylpiperidin-4-yl) |
| 117 | H | piperidine-CH₂CH₂CH₂-NH- | 1-methyl-1H-pyrrolo[3,2-b]pyridine-2,5-diyl | -C(=O)-NH₂ |

TABLE 2-continued
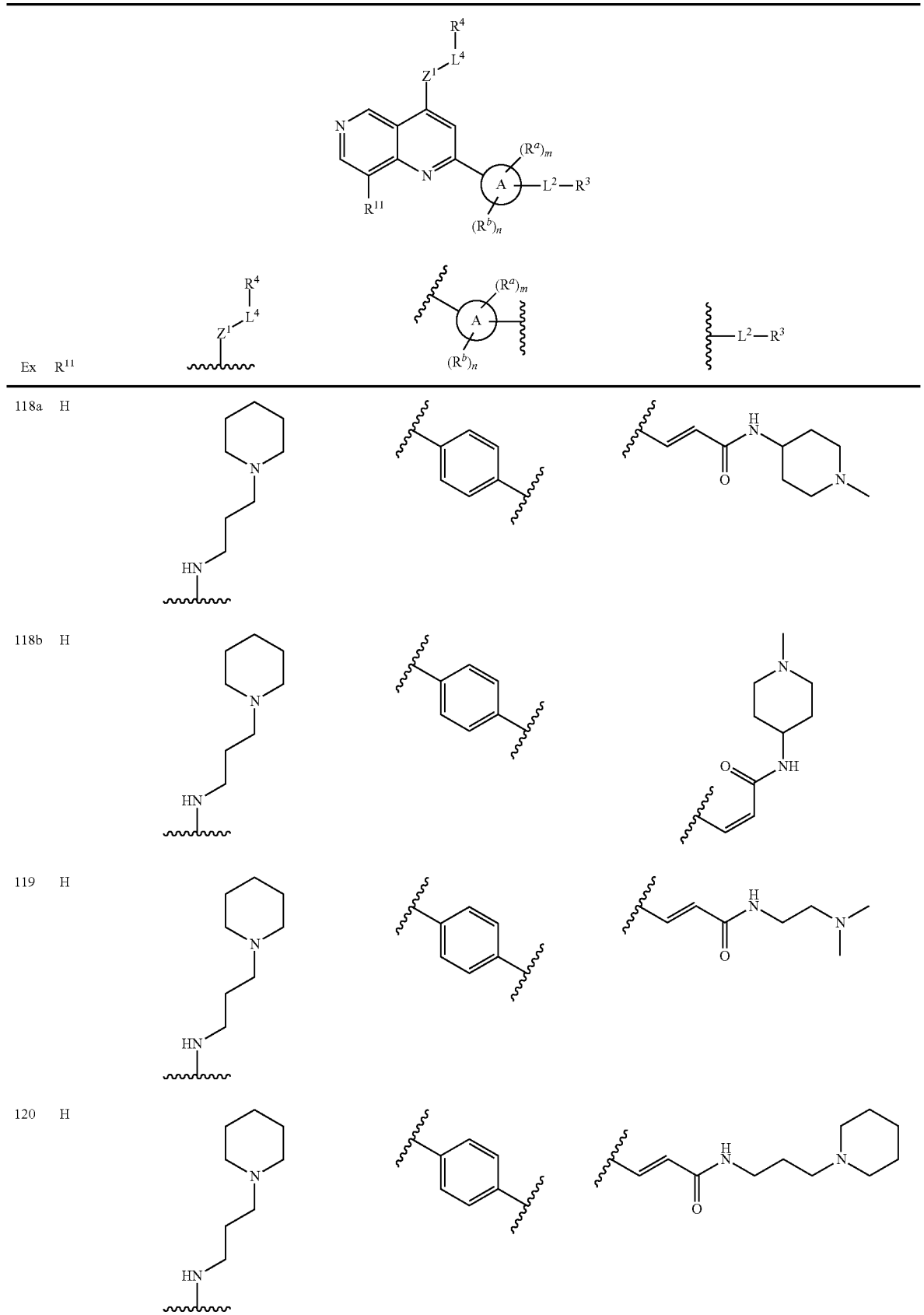

TABLE 2-continued
| Ex | R[11] | Z[1]-L[4]-R[4] | A (R[a])[m] (R[b])[n] | L[2]-R[3] |
|---|---|---|---|---|
| 121 | H | 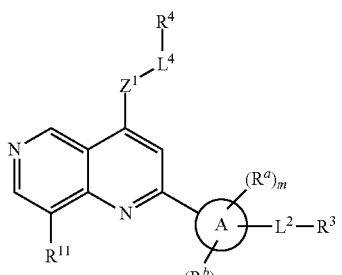 | 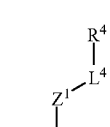 | 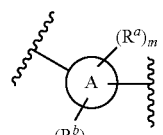 |
| 122 | H | 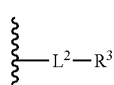 | 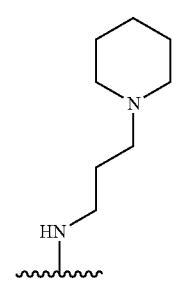 [SMILES: *NCCCN1CCCCC1] | 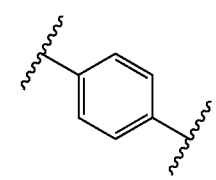 [SMILES: *c1ccc(*)cc1] |
| 123 | H | 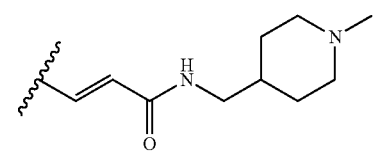 [SMILES: */C=C/C(=O)NCC1CCN(C)CC1] | 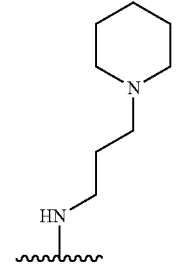 [SMILES: *NCCCN1CCCCC1] | 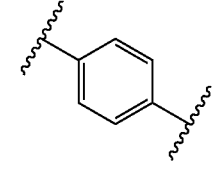 |
| 124 | H | 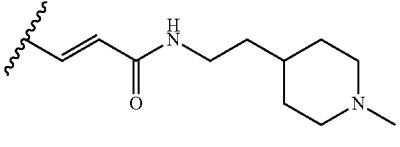 [SMILES: */C=C/C(=O)NCCC1CCN(C)CC1] | 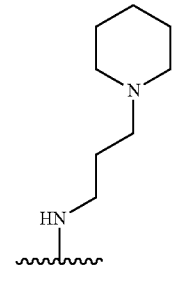 [SMILES: *NCCCN1CCCCC1] | 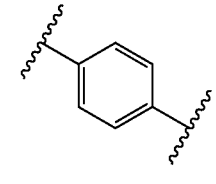 [SMILES: *c1ccc(*)cc1] |

TABLE 2-continued

| Ex | R[11] | Z[1]—L[4]—R[4] | A with (R[a])[m] and (R[b])[n] | L[2]—R[3] |
|---|---|---|---|---|
| 125 | H | 4-(pyrrolidin-1-ylmethyl)phenyl-NH- | 1,4-phenylene | -CH=CH-C(O)N(Et)[2] |
| 126 | H | (1-methylpiperidin-4-yl)-NH- | 1,4-phenylene | -(CH[2])[2]C(O)NH-(1-methylpiperidin-4-yl) |
| 127 | H | (1-methylpiperidin-4-yl)-NH- | 1,4-phenylene | -(CH[2])[2]C(O)N(Et)[2] |
| 128 | H | 3-(piperidin-1-yl)propyl-NH- | 1,4-phenylene | -(CH[2])[2]C(O)NH-CH[2]-(1-methylpiperidin-4-yl) |
| 129 | H | 3-(piperidin-1-yl)propyl-NH- | 1,4-phenylene | -(CH[2])[2]C(O)NH-CH[2]CH[2]-(1-methylpiperidin-4-yl) |

TABLE 2-continued
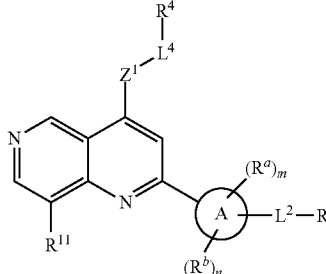
| Ex | R[11] | Z[1]-L[4]-R[4] | A with (R[a])[m], (R[b])[n] | L[2]—R[3] |
|---|---|---|---|---|
| 130 | H | 1-(3-aminopropyl)piperidine linker | 1,4-phenylene | -CH2CH2C(O)NH-(piperidin-4-yl) |
| 131 | H | 1-(3-aminopropyl)piperidine linker | 1,4-phenylene | -CH2CH2C(O)NHCH2C(O)N(Et)2 |
| 132 | H | 1-(3-aminopropyl)piperidine linker | 1,4-phenylene | -CH2CH2C(O)NH-(1-ethylpiperidin-4-yl) |
| 133 | H | 1-(3-aminopropyl)piperidine linker | 1,4-phenylene | -CH2CH2C(O)NHCH2CH2-(4-methyl-1,4-diazepan-1-yl) |

TABLE 2-continued
| Ex | R[11] | Z[1]-L[4]-R[4] | A with (R[a])[m], (R[b])[n] | L[2]-R[3] |
|---|---|---|---|---|
| 134 | H | 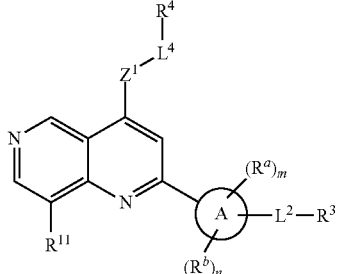 | 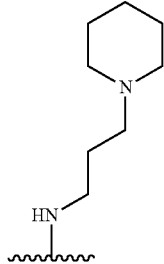 [SMILES: *NCCCN1CCCCC1] | 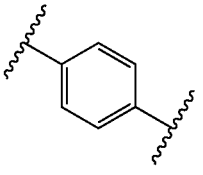 [SMILES: *c1ccc(*)cc1] |
| 135 | H | 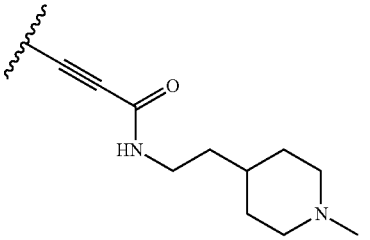 [SMILES: *C#CC(=O)NCCC1CCN(C)CC1] | 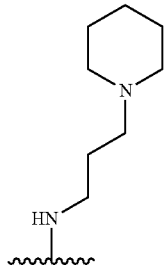 [SMILES: *NCCCN1CCCCC1] | 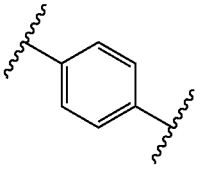 [SMILES: *c1ccc(*)cc1] |
| 136 | H | 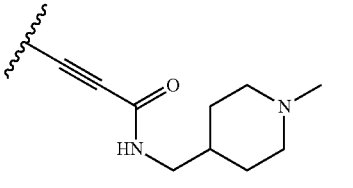 [SMILES: *C#CC(=O)NCC1CCN(C)CC1] | 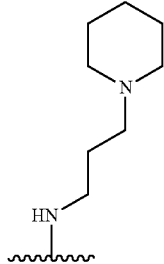 [SMILES: *NCCCN1CCCCC1] | 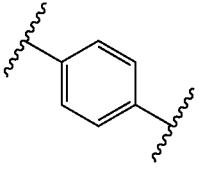 [SMILES: *c1ccc(*)cc1] |
| 137 | H | 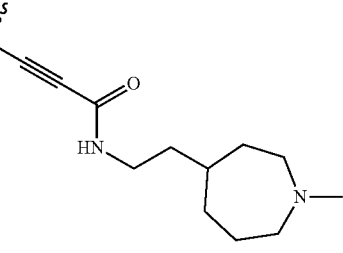 | 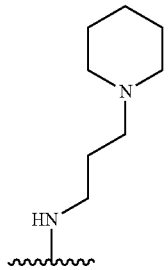 [SMILES: *NCCCN1CCCCC1] | 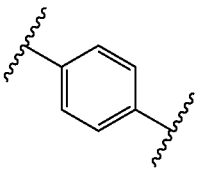 [SMILES: *c1ccc(*)cc1] |

TABLE 2-continued
| Ex | R[11] | Z[1]-L[4]-R[4] | A (R[a])[m] (R[b])[n] | L[2]-R[3] |
|---|---|---|---|---|
| 138 | Cl | 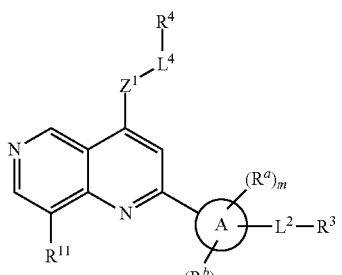 | 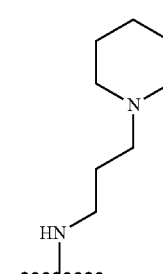 | 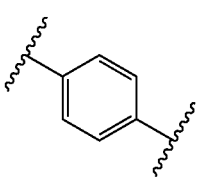 [SMILES: *c1ccc(*)cc1] |
| 139 | H | 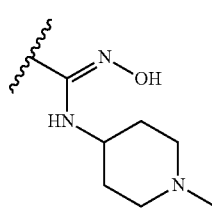 | 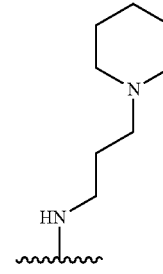 | 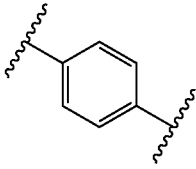 [SMILES: *c1ccc(*)cc1] |
| 140 | H | 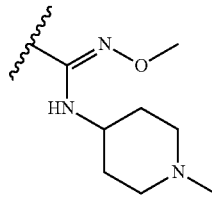 | 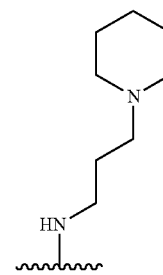 | 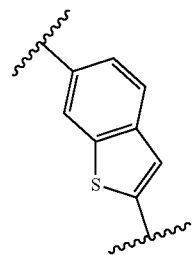 [SMILES: *c1ccc2cc(*)sc2c1] |
| 141 | H | 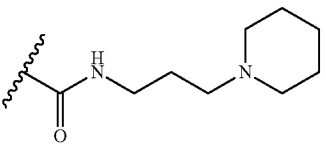 [SMILES: *C(=O)NCCCN1CCCCC1] | 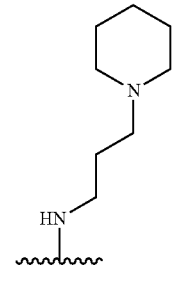 [SMILES: *NCCCN1CCCCC1] | 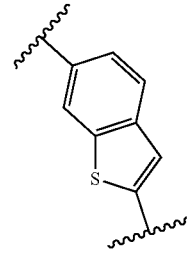 [SMILES: *c1ccc2cc(*)sc2c1] |

TABLE 2-continued
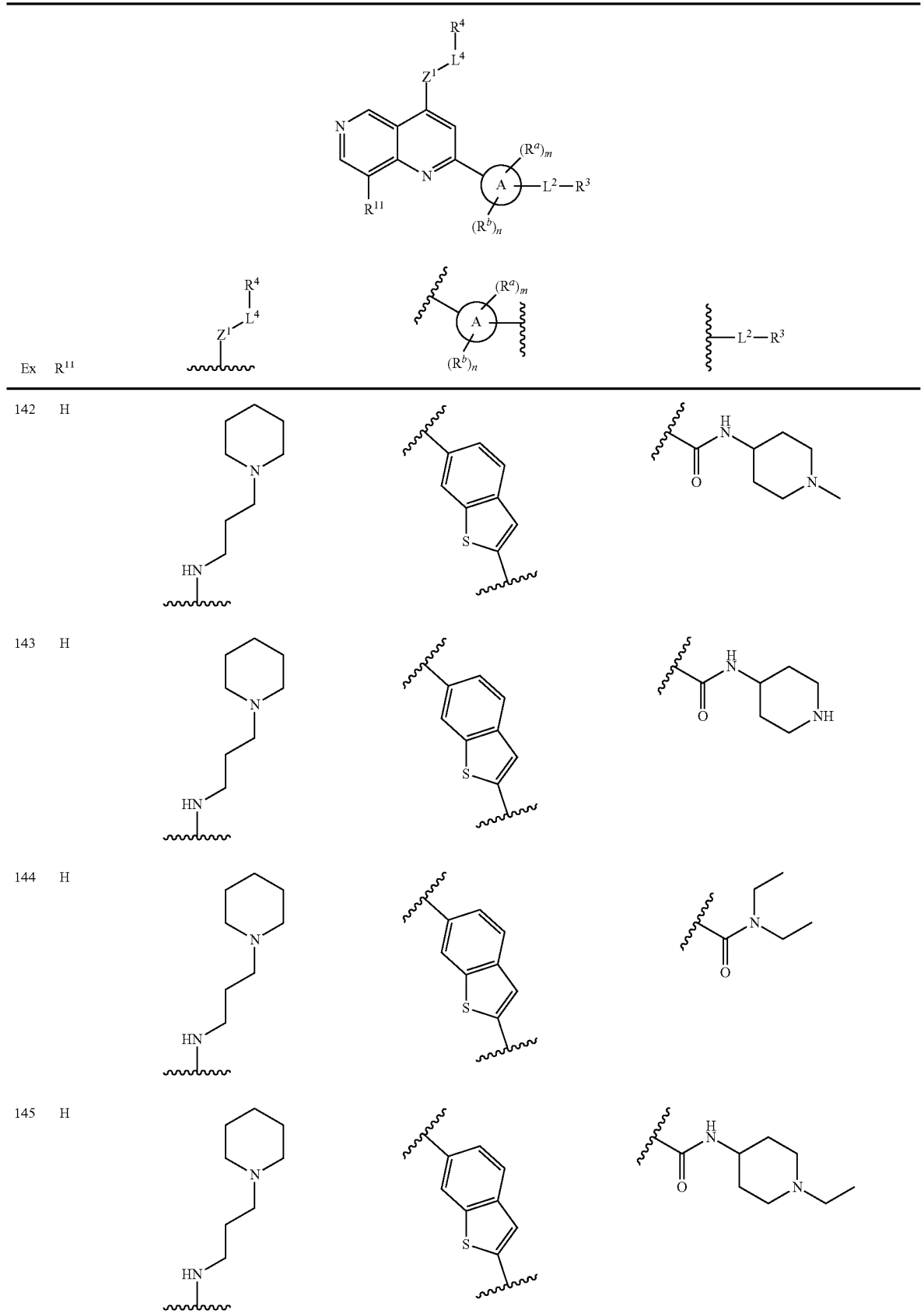

TABLE 2-continued
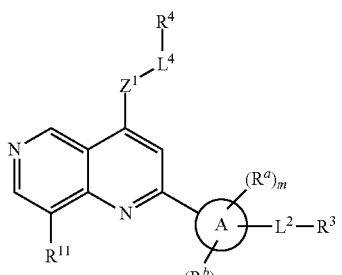
| Ex | R[11] | Z[1]-L[4]-R[4] | A ring | L[2]-R[3] |
|---|---|---|---|---|
| 146 | H | 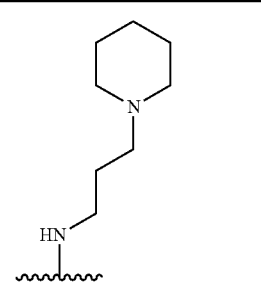 | 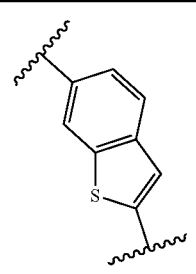 | 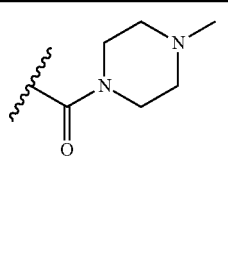 |
| 147 | H | 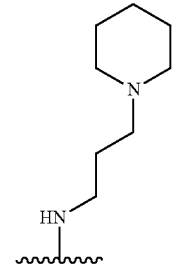 [SMILES: *NCCCN1CCCCC1] | 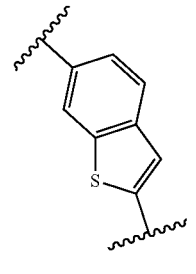 [SMILES: *c1ccc2cc(*)sc2c1] | 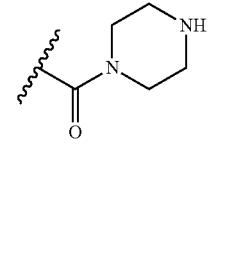 [SMILES: *C(=O)N1CCNCC1] |
| 148 | H | 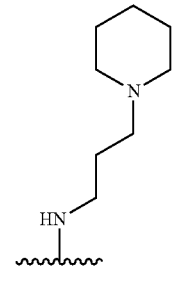 [SMILES: *NCCCN1CCCCC1] | 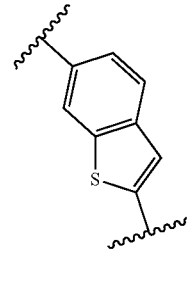 [SMILES: *c1ccc2cc(*)sc2c1] | 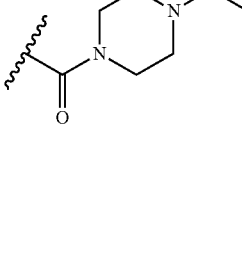 |
| 149 | H | 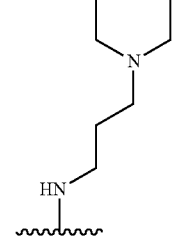 | 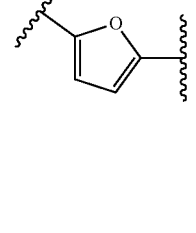 | 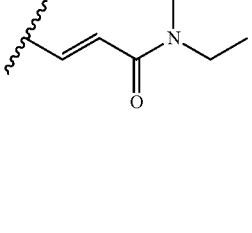 |

TABLE 2-continued
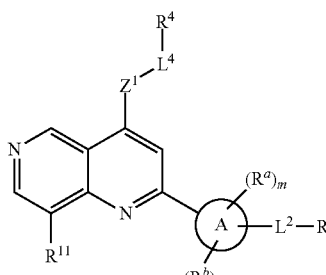
| Ex | R[11] | Z[1]–L[4]–R[4] | A (R[a])m (R[b])n | L[2]–R[3] |
|---|---|---|---|---|
| 150 | H | 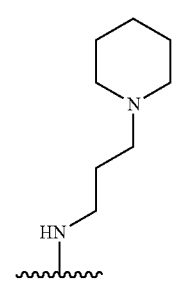 [SMILES: *NCCCN1CCCCC1] | furan | 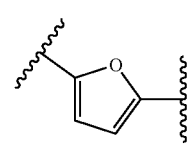 |
| 151 | H | 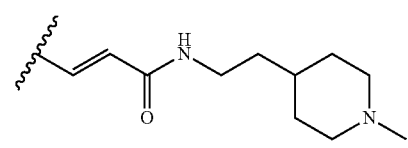 [SMILES: */C=C/C(=O)NCCC1CCN(C)CC1] | furan | 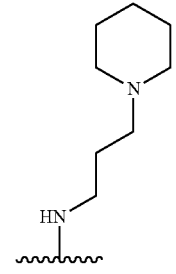 [SMILES: *NCCCN1CCCCC1] |
| 152 | H | 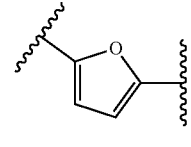 | thiophene | 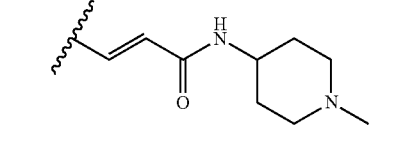 [SMILES: */C=C/C(=O)NC1CCN(C)CC1] |
| 153 | H | 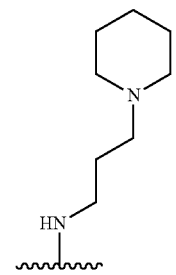 [SMILES: *NCCCN1CCCCC1] | thiophene | 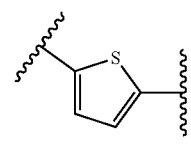 [SMILES: *c1ccc(*)s1] |

TABLE 2-continued

| Ex | R[11] | Z[1]-L[4]-R[4] | A (R[a])[m] (R[b])[n] | L[2]—R[3] |
|---|---|---|---|---|
| 154 | H | 1-piperidinyl-propyl-NH- | 2,5-thienyl | -CH=CH-C(O)-NH-(1-methylpiperidin-4-yl) |
| 155 | H | 1-piperidinyl-propyl-NH- | benzothiazol-2,6-diyl | -C(O)-piperazinyl |
| 156 | H | 1-piperidinyl-propyl-NH- | benzothiazol-2,6-diyl | -C(O)-morpholinyl |
| 157 | H | 1-piperidinyl-propyl-NH- | benzoxazol-2,6-diyl | -C(O)-N(Et)2 |

TABLE 3
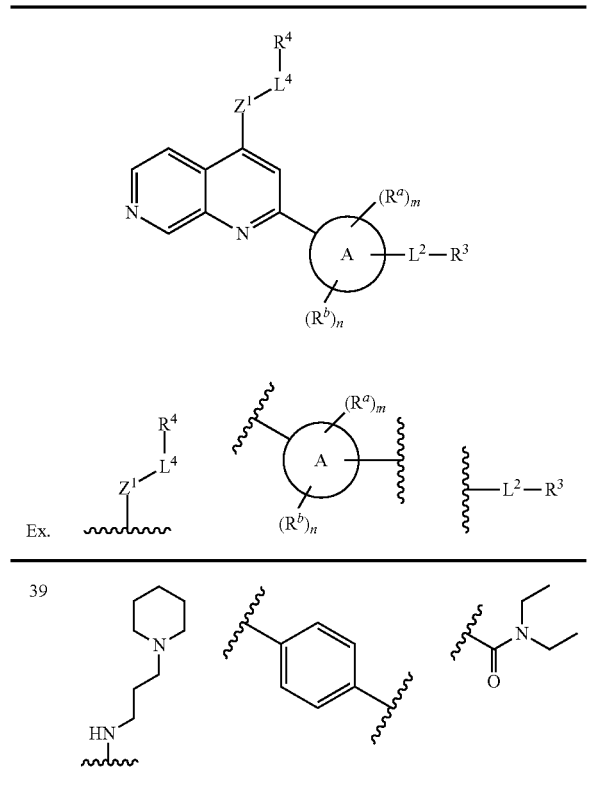
TABLE 4
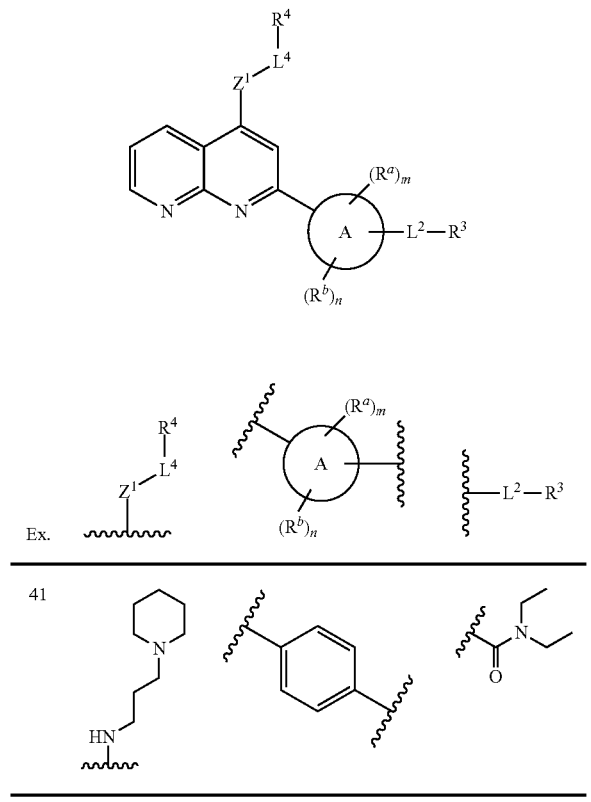
TABLE 5
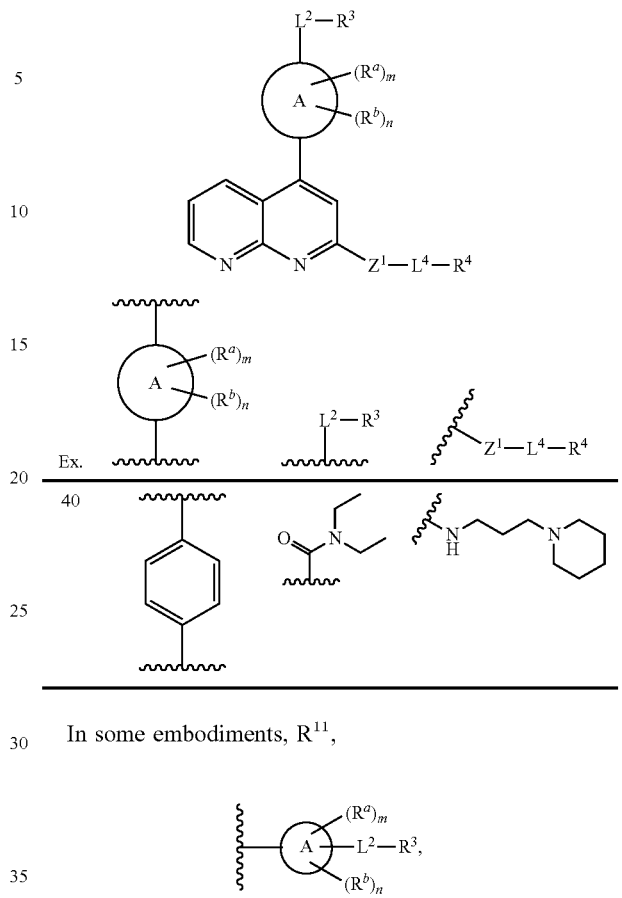
In some embodiments, $R^{11}$,
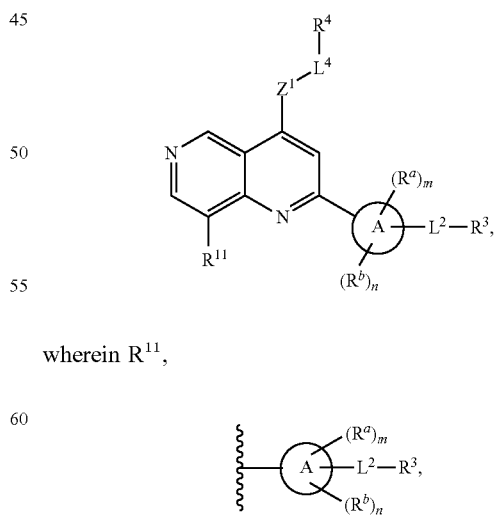
and $-Z^1\text{-}L^4\text{-}R^4$ are defined as in Table 1, Table 2, Table 3, Table 4, or Table 5.
In some embodiments, compounds of Formula (I), or a pharmaceutically acceptable salt, or solvate thereof, have the structure
wherein $R^{11}$,
and $-Z^1\text{-}L^4\text{-}R^4$ are defined as in Table 1, Table 2, Table 3, Table 4, or Table 5. In some embodiments, $R^{11}$,

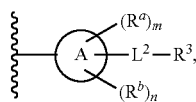

and —$Z^1$-$L^4$-$R^4$ are defined as in Table 2.

In some embodiments, compounds of Formula (I) include, but are not limited to:

N,N-diethyl-4-(4-(3-(piperidin-1-yl)propylamino)-1,6-naphthyridin-2-yl)benzamide;
N-(2-(dimethylamino)ethyl)-1-methyl-5-(4-((3-(piperidin-1-yl)propyl)amino)-1,6-naphthyridin-2-yl)-1H-indole-2-carboxamide;
1-methyl-N-(1-methylpiperidin-4-yl)-5-(4-((3-(piperidin-1-yl)propyl)amino)-1,6-naphthyridin-2-yl)-1H-indole-2-carboxamide;
1-methyl-5-(4-((3-(piperidin-1-yl)propyl)amino)-1,6-naphthyridin-2-yl)-N-(piperidin-4-yl)-1H-indole-2-carboxamide;
ethyl 1-methyl-5-(4-((3-(piperidin-1-yl)propyl)amino)-1,6-naphthyridin-2-yl)-1H-indole-2-carboxylate;
4-(4-((3-(piperidin-1-yl)propyl)amino)-1,6-naphthyridin-2-yl)benzoic acid;
4-(4-((3-(piperidin-1-yl)propyl)amino)-1,6-naphthyridin-2-yl)-N-(piperidin-4-yl)benzamide;
4-(4-((3-(piperidin-1-yl)propyl)amino)-1,6-naphthyridin-2-yl)-N-(2-(pyridin-4-yl)ethyl)benzamide;
N-(2-(dimethylamino)ethyl)-4-(4-((3-(piperidin-1-yl)propyl)amino)-1,6-naphthyridin-2-yl)benzamide;
1-methyl-N-(3-(4-methylpiperazin-1-yl)propyl)-5-(4-((3-(piperidin-1-yl)propyl)amino)-1,6-naphthyridin-2-yl)-1H-indole-2-carboxamide;
1-methyl-5-(4-((3-(piperidin-1-yl)propyl)amino)-1,6-naphthyridin-2-yl)-N-(2-(pyridin-4-yl)ethyl)-1H-indole-2-carboxamide;
1-methyl-5-(4-((3-(piperidin-1-yl)propyl)amino)-1,6-naphthyridin-2-yl)-N-(tetrahydro-2H-pyran-4-yl)-1H-indole-2-carboxamide;
N-(1,1-dioxidotetrahydro-2H-thiopyran-4-yl)-1-methyl-5-(4-((3-(piperidin-1-yl)propyl)amino)-1,6-naphthyridin-2-yl)-1H-indole-2-carboxamide;
N,N-diethyl-4-(4-((3-(piperidin-1-yl)propyl)amino)-1,6-naphthyridin-2-yl)-3-(trifluoromethyl)benzamide;
4-(4-((3-(piperidin-1-yl)propyl)amino)-1,6-naphthyridin-2-yl)-N-(piperidin-4-yl)-3-(trifluoromethyl)benzamide;
1-methyl-5-(4-(3-(piperidin-1-yl)propylamino)-1,6-naphthyridin-2-yl)-N-(tetrahydro-2H-thiopyran-4-yl)-1H-indole-2-carboxamide;
1-methyl-N-(1-methylpiperidin-4-yl)-5-(4-(propylamino)-1,6-naphthyridin-2-yl)-1H-indole-2-carboxamide;
1-methyl-5-(4-(methylamino)-1,6-naphthyridin-2-yl)-N-(1-methylpiperidin-4-yl)-1H-indole-2-carboxamide;
5-(4-(ethylamino)-1,6-naphthyridin-2-yl)-1-methyl-N-(1-methylpiperidin-4-yl)-1H-indole-2-carboxamide;
1-methyl-N-(1-methylpiperidin-4-yl)-5-(4-((4-(pyrrolidin-1-ylmethyl)phenyl)amino)-1,6-naphthyridin-2-yl)-1H-indole-2-carboxamide;
N-(3-(piperidin-1-yl)propyl)-5-(4-((3-(piperidin-1-yl)propyl)amino)-1,6-naphthyridin-2-yl)-1H-benzo[d]imidazole-2-carboxamide;
methyl 3-carbamoyl-4-(4-((3-(piperidin-1-yl)propyl)amino)-1,6-naphthyridin-2-yl)benzoate;
5-(4-methoxy-1,6-naphthyridin-2-yl)-1-methyl-N-(1-methylpiperidin-4-yl)-1H-indole-2-carboxamide;
3-cyano-N,N-diethyl-4-(4-((3-(piperidin-1-yl)propyl)amino)-1,6-naphthyridin-2-yl)benzamide;
N1,N1-diethyl-4-(4-((3-(piperidin-1-yl)propyl)amino)-1,6-naphthyridin-2-yl)isophthalamide;
1-methyl-5-(4-(methylamino)-1,6-naphthyridin-2-yl)-1H-indole-2-carboxamide;
3-cyano-N-(1-methylpiperidin-4-yl)-4-(4-((3-(piperidin-1-yl)propyl)amino)-1,6-naphthyridin-2-yl)benzamide;
1-methyl-N-(1-methylpiperidin-4-yl)-5-(4-(3-(piperidin-1-yl)propoxy)-1,6-naphthyridin-2-yl)-1H-indole-2-carboxamide;
5-(4-((3-(piperidin-1-yl)propyl)amino)-1,6-naphthyridin-2-yl)-N-(piperidin-4-yl)-1H-benzo[d]imidazole-2-carboxamide;
5-(4-(methylamino)-1,6-naphthyridin-2-yl)-N-(3-(piperidin-1-yl)propyl)-1H-benzo[d]imidazole-2-carboxamide;
5-(4-(ethylamino)-1,6-naphthyridin-2-yl)-N-(3-(piperidin-1-yl)propyl)-1H-benzo[d]imidazole-2-carboxamide;
N-(2-(dimethylamino)ethyl)-5-(4-(3-(piperidin-1-yl)propylamino)-1,6-naphthyridin-2-yl)-1H-benzo[d]imidazole-2-carboxamide;
N-(3-(4-methylpiperazin-1-yl)propyl)-5-(4-((3-(piperidin-1-yl)propyl)amino)-1,6-naphthyridin-2-yl)-1H-benzo[d]imidazole-2-carboxamide;
piperazin-1-yl(5-(4-((3-(piperidin-1-yl)propyl)amino)-1,6-naphthyridin-2-yl)-1H-benzo[d]imidazol-2-yl)methanone;
N,N-diethyl-5-(4-((3-(piperidin-1-yl)propyl)amino)-1,6-naphthyridin-2-yl)-1H-benzo[d]imidazole-2-carboxamide;
(1-ethyl-5-(4-((3-(piperidin-1-yl)propyl)amino)-1,6-naphthyridin-2-yl)-1H-benzo[d]imidazol-2-yl)(4-ethylpiperazin-1-yl)methanone;
(4-ethylpiperazin-1-yl)(5-(4-((3-(piperidin-1-yl)propyl)amino)-1,6-naphthyridin-2-yl)-1H-benzo[d]imidazol-2-yl)methanone;
N-(3-(piperidin-1-yl)propyl)-5-(4-(3-(piperidin-1-yl)propylamino)-1,6-naphthyridin-2-yl)benzo[b]thiophene-2-carboxamide;
N,N-diethyl-4-(4-(3-(piperidin-1-yl)propylamino)-1,5-naphthyridin-2-yl)benzamide;
N,N-diethyl-4-(4-(3-(piperidin-1-yl)propylamino)-1,7-naphthyridin-2-yl)benzamide;
N,N-diethyl-4-(2-(3-(piperidin-1-yl)propylamino)-1,8-naphthyridin-4-yl)benzamide;
N,N-diethyl-4-(4-(3-(piperidin-1-yl)propylamino)-1,8-naphthyridin-2-yl)benzamide;
N,N-Diethyl-4-(4-((3-morpholinopropyl)amino)-1,6-naphthyridin-2-yl)benzamide;
N,N-Diethyl-4-(4-((2-(piperidin-1-yl)ethyl)amino)-1,6-naphthyridin-2-yl)benzamide;
N,N-Diethyl-4-(4-((3-(piperazin-1-yl)propyl)amino)-1,6-naphthyridin-2-yl)benzamide;
N,N-Diethyl-4-(4-((3-(4-(methylsulfonyl)piperazin-1-yl)propyl)amino)-1,6-naphthyridin-2-yl)benzamide;
N,N-Diethyl-4-(4-((1-methylpiperidin-4-yl)amino)-1,6-naphthyridin-2-yl)benzamide;
4-(4-((2-(Dimethylamino)ethyl)amino)-1,6-naphthyridin-2-yl)-N,N-diethylbenzamide;
N,N-diethyl-4-(4-(3-(4-methylpiperazin-1-yl)propylamino)-1,6-naphthyridin-2-yl)benzamide;
N,N-diethyl-4-(4-(2-morpholinoethylamino)-1,6-naphthyridin-2-yl)benzamide;
N,N-diethyl-4-(4-(2-(4-methylpiperazin-1-yl)ethylamino)-1,6-naphthyridin-2-yl)benzamide;
N,N-diethyl-4-(4-(tetrahydro-2H-pyran-4-ylamino)-1,6-naphthyridin-2-yl)benzamide;

N,N-diethyl-4-(4-(2-(piperazin-1-yl)ethylamino)-1,6-naphthyridin-2-yl)benzamide;
N,N-diethyl-4-(4-(2-(4-(methylsulfonyl)piperazin-1-yl)ethylamino)-1,6-naphthyridin-2-yl)benzamide;
N,N-Diethyl-4-(4-(4-methoxyphenylamino)-1,6-naphthyridin-2-yl)benzamide;
4-(4-(4-(Dimethylamino)phenylamino)-1,6-naphthyridin-2-yl)-N,N-diethylbenzamide;
4-(4-(4-((Dimethylamino)methyl)phenylamino)-1,6-naphthyridin-2-yl)-N,N-diethylbenzamide;
N,N-Diethyl-4-(4-(4-(2-methoxyethylamino)phenylamino)-1,6-naphthyridin-2-yl)benzamide;
4-(4-((2-(1,1-Dioxidothiomorpholino)ethyl)amino)-1,6-naphthyridin-2-yl)-N,N-diethylbenzamide;
4-(4-((3-(1,1-Dioxidothiomorpholino)propyl)amino)-1,6-naphthyridin-2-yl)-N,N-diethylbenzamide;
N,N-Diethyl-4-(4-(1-methylpyrrolidin-3-ylamino)-1,6-naphthyridin-2-yl)benzamide;
N,N-Diethyl-4-(4-(piperidin-4-ylamino)-1,6-naphthyridin-2-yl)benzamide;
N-(1-Methylpiperidin-4-yl)-4-(4-((1-methylpyrrolidin-3-yl)amino)-1,6-naphthyridin-2-yl)benzamide;
4-(4-((1-Methylpyrrolidin-3-yl)amino)-1,6-naphthyridin-2-yl)-N-(3-(piperidin-1-yl)propyl)benzamide;
N-(3-(Piperidin-1-yl)propyl)-4-(4-(piperidin-4-ylamino)-1,6-naphthyridin-2-yl)benzamide;
N-(1-Methylpiperidin-4-yl)-4-(4-(piperidin-4-ylamino)-1,6-naphthyridin-2-yl)benzamide;
N,N-diethyl-4-(4-(pyrrolidin-3-ylamino)-1,6-naphthyridin-2-yl)benzamide;
N-(3-(Piperidin-1-yl)propyl)-4-(4-(pyrrolidin-3-ylamino)-1,6-naphthyridin-2-yl)benzamide;
N-(1-Methylpiperidin-4-yl)-4-(4-(pyrrolidin-3-ylamino)-1,6-naphthyridin-2-yl)benzamide;
N-(1-Methylpiperidin-4-yl)-4-(4-((1-methylpiperidin-4-yl)amino)-1,6-naphthyridin-2-yl)benzamide;
N-(3-(Piperidin-1-yl)propyl)-4-(4-((tetrahydro-2H-pyran-4-yl)amino)-1,6-naphthyridin-2-yl)benzamide;
N-(3-(Piperidin-1-yl)propyl)-4-(4-((pyridin-4-ylmethyl)amino)-1,6-naphthyridin-2-yl)benzamide;
N-(1-Methylpiperidin-4-yl)-4-(4-((tetrahydro-2H-pyran-4-yl)amino)-1,6-naphthyridin-2-yl)benzamide;
4-(8-Bromo-4-((3-(piperidin-1-yl)propyl)amino)-1,6-naphthyridin-2-yl)-N,N-diethylbenzamide;
4-(8-Bromo-4-((3-(piperidin-1-yl)propyl)amino)-1,6-naphthyridin-2-yl)-N-(1-methylpiperidin-4-yl)benzamide;
N,N-Diethyl-4-(8-methyl-4-((3-(piperidin-1-yl)propyl)amino)-1,6-naphthyridin-2-yl)benzamide;
4-(8-Methyl-4-((3-(piperidin-1-yl)propyl)amino)-1,6-naphthyridin-2-yl)-N-(1-methylpiperidin-4-yl)benzamide;
4-(8-Methyl-4-((3-(piperidin-1-yl)propyl)amino)-1,6-naphthyridin-2-yl)-N-(3-(piperidin-1-yl)propyl)benzamide;
N-(3-(piperidin-1-yl)propyl)-5-(4-((3-(piperidin-1-yl)propyl)amino)-1,6-naphthyridin-2-yl)picolinamide;
N-(1-methylpiperidin-4-yl)-5-(4-((3-(piperidin-1-yl)propyl)amino)-1,6-naphthyridin-2-yl)picolinamide;
1-methyl-5-(4-(4-(piperidin-1-ylmethyl)benzylamino)-1,6-naphthyridin-2-yl)-N-(piperidin-4-yl)-1H-indole-2-carboxamide;
1-methyl-N-(1-methylpiperidin-4-yl)-5-(4-(4-(piperidin-1-ylmethyl)benzylamino)-1,6-naphthyridin-2-yl)-1H-indole-2-carboxamide;
(1-methyl-5-(4-(4-(piperidin-1-ylmethyl)benzylamino)-1,6-naphthyridin-2-yl)-1H-indol-2-yl)(4-methylpiperazin-1-yl)methanone;
1-methyl-N-((1-methylpiperidin-4-yl)methyl)-5-(4-(4-(piperidin-1-ylmethyl)benzylamino)-1,6-naphthyridin-2-yl)-1H-indole-2-carboxamide;
1-methyl-5-(4-(methyl(3-(piperidin-1-yl)propyl)amino)-1,6-naphthyridin-2-yl)-N-(1-methylpiperidin-4-yl)-1H-indole-2-carboxamide;
1-Methyl-N-(1-methylpiperidin-4-yl)-5-(4-(4-(piperidin-1-yl)butan-2-ylamino)-1,6-naphthyridin-2-yl)-1H-indole-2-carboxamide;
1-Methyl-N-(1-methylpiperidin-4-yl)-5-(4-((1-methylpiperidin-4-yl)amino)-1,6-naphthyridin-2-yl)-1H-indole-2-carboxamide;
(1-Methyl-5-(4-((1-methylpiperidin-4-yl)amino)-1,6-naphthyridin-2-yl)-1H-indol-2-yl)(4-methylpiperazin-1-yl)methanone;
1-Methyl-5-(4-((1-methylpiperidin-4-yl)amino)-1,6-naphthyridin-2-yl)-N-((1-methylpiperidin-4-yl)methyl)-1H-indole-2-carboxamide;
1-Methyl-5-(4-((1-methylpiperidin-4-yl)amino)-1,6-naphthyridin-2-yl)-N-(3-(piperidin-1-yl)propyl)-1H-indole-2-carboxamide;
N-(1-Methylpiperidin-4-yl)-6-(4-(3-(piperidin-1-yl)propylamino)-1,6-naphthyridin-2-yl)-1H-indole-2-carboxamide;
N-(3-(Piperidin-1-yl)propyl)-6-(4-(3-(piperidin-1-yl)propylamino)-1,6-naphthyridin-2-yl)-1H-indole-2-carboxamide;
N-(2-(Dimethylamino)ethyl)-6-(4-(3-(piperidin-1-yl)propylamino)-1,6-naphthyridin-2-yl)-1H-indole-2-carboxamide;
6-(4-(3-(Piperidin-1-yl)propylamino)-1,6-naphthyridin-2-yl)-N-(2-(pyridin-4-yl)ethyl)-1H-indole-2-carboxamide;
6-(4-(3-(Piperidin-1-yl)propylamino)-1,6-naphthyridin-2-yl)-N-(piperidin-4-yl)-1H-indole-2-carboxamide;
(4-Ethylpiperazin-1-yl)(6-(4-(3-(piperidin-1-yl)propylamino)-1,6-naphthyridin-2-yl)-1H-indol-2-yl)methanone;
N,N-diethyl-3-(4-(4-((3-(piperidin-1-yl)propyl)amino)-1,6-naphthyridin-2-yl)phenoxy)propanamide;
N-(1-methylpiperidin-4-yl)-3-(4-(4-((3-(piperidin-1-yl)propyl)amino)-1,6-naphthyridin-2-yl)phenoxy)propanamide;
N-((1-ethylpiperidin-4-yl)methyl)-3-(4-(4-((3-(piperidin-1-yl)propyl)amino)-1,6-naphthyridin-2-yl)phenoxy)propanamide;
3-(4-(4-(ethyl(3-(piperidin-1-yl)propyl)amino)-1,6-naphthyridin-2-yl)phenoxy)-N-((1-ethylpiperidin-4-yl)methyl)propanamide;
4-cyano-5-(4-((3-(piperidin-1-yl)propyl)amino)-1,6-naphthyridin-2-yl)-N-(piperidin-4-yl)-1H-benzo[d]imidazole-2-carboxamide;
(4-ethylpiperazin-1-yl)(5-(4-((4-(pyrrolidin-1-ylmethyl)phenyl)amino)-1,6-naphthyridin-2-yl)-1H-benzo[d]imidazol-2-yl)methanone;
N-(3-(piperidin-1-yl)propyl)-5-(4-((4-(pyrrolidin-1-ylmethyl)phenyl)amino)-1,6-naphthyridin-2-yl)-1H-benzo[d]imidazole-2-carboxamide;
N-(2-(dimethylamino)ethyl)-5-(4-((4-(pyrrolidin-1-ylmethyl)phenyl)amino)-1,6-naphthyridin-2-yl)-1H-benzo[d]imidazole-2-carboxamide;
N-(3-(4-methylpiperazin-1-yl)propyl)-5-(4-((4-(pyrrolidin-1-ylmethyl)phenyl)amino)-1,6-naphthyridin-2-yl)-1H-benzo[d]imidazole-2-carboxamide;
5-(4-((3-(piperidin-1-yl)propyl)amino)-1,6-naphthyridin-2-yl)-N-(2-(pyridin-4-yl)ethyl)-1H-benzo[d]imidazole-2-carboxamide;

N-(1-Methylpiperidin-4-yl)-6-(4-(3-(piperidin-1-yl)propylamino)-1,6-naphthyridin-2-yl)-3H-imidazo[4,5-b]pyridine-2-carboxamide;
N-(1-methylpiperidin-4-yl)-2-(4-(4-(3-(piperidin-1-yl)propylamino)-1,6-naphthyridin-2-yl)phenoxy)acetamide;
N-(3-(piperidin-1-yl)propyl)-2-((4-(4-((3-(piperidin-1-yl)propyl)amino)-1,6-naphthyridin-2-yl)benzyl)oxy)acetamide;
N,N-diethyl-2-((4-(4-((3-(piperidin-1-yl)propyl)amino)-1,6-naphthyridin-2-yl)benzyl)oxy)acetamide;
N-(1-methylpiperidin-4-yl)-2-((4-(4-((3-(piperidin-1-yl)propyl)amino)-1,6-naphthyridin-2-yl)benzyl)oxy)acetamide;
N-((1-ethylpiperidin-4-yl)methyl)-2-(4-(4-(3-(piperidin-1-yl)propylamino)-1,6-naphthyridin-2-yl)benzyloxy)acetamide;
N-((1-methylpiperidin-4-yl)methyl)-2-(4-(4-(3-(piperidin-1-yl)propylamino)-1,6-naphthyridin-2-yl)benzyloxy)acetamide;
N-(2-(4-methyl-1,4-diazepan-1-yl)ethyl)-2-(4-(4-(3-(piperidin-1-yl)propylamino)-1,6-naphthyridin-2-yl)benzyloxy)acetamide;
2-(4-(4-(3-(piperidin-1-yl)propylamino)-1,6-naphthyridin-2-yl)benzyloxy)-N-(piperidin-4-ylmethyl)acetamide;
N-(2-(1-methylpiperidin-4-yl)ethyl)-2-(4-(4-(3-(piperidin-1-yl)propylamino)-1,6-naphthyridin-2-yl)benzyloxy)acetamide;
N-(1-Methylpiperidin-4-yl)-3-(4-(4-(3-(piperidin-1-yl)propylamino)-1,6-naphthyridin-2-yl)benzyloxy)propanamide;
methyl-N-(1-methylpiperidin-4-yl)-5-(4-((3-(piperidin-1-yl)propyl)amino)-1,6-naphthyridin-2-yl)-1H-pyrrolo[3,2-b]pyridine-2-carboxamide;
1-methyl-5-(4-((3-(piperidin-1-yl)propyl)amino)-1,6-naphthyridin-2-yl)-1H-pyrrolo[3,2-b]pyridine-2-carboxamide;
(E)-N-(1-Methylpiperidin-4-yl)-3-(4-(4-(3-(piperidin-1-yl)propylamino)-1,6-naphthyridin-2-yl)phenyl)acrylamide;
(E)-N-(2-(Dimethylamino)ethyl)-3-(4-(4-(3-(piperidin-1-yl)propylamino)-1,6-naphthyridin-2-yl)phenyl)acrylamide;
(E)-N-(3-(Piperidin-1-yl)propyl)-3-(4-(4-(3-(piperidin-1-yl)propylamino)-1,6-naphthyridin-2-yl)phenyl)acrylamide;
(E)-N-((1-Methylpiperidin-4-yl)methyl)-3-(4-(4-(3-(piperidin-1-yl)propylamino)-1,6-naphthyridin-2-yl)phenyl)acrylamide;
(E)-N-(2-(1-Methylpiperidin-4-yl)ethyl)-3-(4-(4-(3-(piperidin-1-yl)propylamino)-1,6-naphthyridin-2-yl)phenyl)acrylamide;
(E)-N-((1-Ethylpiperidin-4-yl)methyl)-3-(4-(4-(3-(piperidin-1-yl)propylamino)-1,6-naphthyridin-2-yl)phenyl)acrylamide;
(E)-N-(2-(4-Methyl-1,4-diazepan-1-yl)ethyl)-3-(4-(4-(3-(piperidin-1-yl)propylamino)-1,6-naphthyridin-2-yl)phenyl)acrylamide;
(E)-N,N-Diethyl-3-(4-(4-((4-(pyrrolidin-1-ylmethyl)phenyl)amino)-1,6-naphthyridin-2-yl)phenyl)acrylamide;
N-(1-Methylpiperidin-4-yl)-3-(4-(4-(1-methylpiperidin-4-ylamino)-1,6-naphthyridin-2-yl)phenyl)propanamide;
N,N-Diethyl-3-(4-(4-(1-methylpiperidin-4-ylamino)-1,6-naphthyridin-2-yl)phenyl)propanamide;
N-((1-Methylpiperidin-4-yl)methyl)-3-(4-(4-(3-(piperidin-1-yl)propylamino)-1,6-naphthyridin-2-yl)phenyl)propanamide;
N-(2-(1-Methylpiperidin-4-yl)ethyl)-3-(4-(4-(3-(piperidin-1-yl)propylamino)-1,6-naphthyridin-2-yl)phenyl)propanamide;
3-(4-(4-(3-(Piperidin-1-yl)propylamino)-1,6-naphthyridin-2-yl)phenyl)-N-(piperidin-4-yl)propanamide;
N-(2-(Diethylamino)-2-oxoethyl)-3-(4-(4-(3-(piperidin-1-yl)propylamino)-1,6-naphthyridin-2-yl)phenyl)propanamide;
N-(1-Ethylpiperidin-4-yl)-3-(4-(4-(3-(piperidin-1-yl)propylamino)-1,6-naphthyridin-2-yl)phenyl)propanamide;
N-(2-(4-Methyl-1,4-diazepan-1-yl)ethyl)-3-(4-(4-(3-(piperidin-1-yl)propylamino)-1,6-naphthyridin-2-yl)phenyl)propanamide;
N-(2-(1-methylpiperidin-4-yl)ethyl)-3-(4-(4-((3-(piperidin-1-yl)propyl)amino)-1,6-naphthyridin-2-yl)phenyl)propiolamide;
N-((1-methylpiperidin-4-yl)methyl)-3-(4-(4-((3-(piperidin-1-yl)propyl)amino)-1,6-naphthyridin-2-yl)phenyl)propiolamide;
N-(2-(1-methylazepan-4-yl)ethyl)-3-(4-(4-((3-(piperidin-1-yl)propyl)amino)-1,6-naphthyridin-2-yl)phenyl)propiolamide;
(Z)—N'-hydroxy-N-(1-methylpiperidin-4-yl)-4-(4-((3-(piperidin-1-yl)propyl)amino)-1,6-naphthyridin-2-yl)benzimidamide;
(Z)-4-(8-chloro-4-((3-(piperidin-1-yl)propyl)amino)-1,6-naphthyridin-2-yl)-N'-hydroxy-N-(1-methylpiperidin-4-yl)benzimidamide;
(Z)—N'-methoxy-N-(1-methylpiperidin-4-yl)-4-(4-((3-(piperidin-1-yl)propylamino)-1,6-naphthyridin-2-yl)benzimidamide;
N-(3-(piperidin-1-yl)propyl)-6-(4-(3-(piperidin-1-yl)propylamino)-1,6-naphthyridin-2-yl)benzo[b]thiophene-2-carboxamide;
N-(2-(dimethylamino)ethyl)-6-(4-(3-(piperidin-1-yl)propylamino)-1,6-naphthyridin-2-yl)benzo[b]thiophene-2-carboxamide;
N-(1-methylpiperidin-4-yl)-6-(4-(3-(piperidin-1-yl)propylamino)-1,6-naphthyridin-2-yl)benzo[b]thiophene-2-carboxamide;
6-(4-(3-(piperidin-1-yl)propylamino)-1,6-naphthyridin-2-yl)-N-(piperidin-4-yl)benzo[b]thiophene-2-carboxamide;
N,N-diethyl-6-(4-(3-(piperidin-1-yl)propylamino)-1,6-naphthyridin-2-yl)benzo[b]thiophene-2-carboxamide;
N-(1-ethylpiperidin-4-yl)-6-(4-(3-(piperidin-1-yl)propylamino)-1,6-naphthyridin-2-yl)benzo[b]thiophene-2-carboxamide;
(4-methylpiperazin-1-yl)(6-(4-(3-(piperidin-1-yl)propylamino)-1,6-naphthyridin-2-yl)benzo[b]thiophen-2-yl)methanone;
Piperazin-1-yl(6-(4-(3-(piperidin-1-yl)propylamino)-1,6-naphthyridin-2-yl)benzo[b]thiophen-2-yl)methanone;
(4-ethylpiperazin-1-yl)(6-(4-(3-(piperidin-1-yl)propylamino)-1,6-naphthyridin-2-yl)benzo[b]thiophen-2-yl)methanone;
(E)-N,N-Diethyl-3-(5-(4-((3-(piperidin-1-yl)propyl)amino)-1,6-naphthyridin-2-yl)furan-2-yl)acrylamide;
(E)-N-(2-(1-Methylpiperidin-4-yl)ethyl)-3-(5-(4-((3-(piperidin-1-yl)propyl)amino)-1,6-naphthyridin-2-yl)furan-2-yl)acrylamide;
(E)-N-(1-Methylpiperidin-4-yl)-3-(5-(4-((3-(piperidin-1-yl)propyl)amino)-1,6-naphthyridin-2-yl)furan-2-yl)acrylamide;
(E)-3-(5-(4-(3-(Piperidin-1-yl)propylamino)-1,6-naphthyridin-2-yl)thiophen-2-yl)acrylic acid;
(E)-N,N-Diethyl-3-(5-(4-(3-(piperidin-1-yl)propylamino)-1,6-naphthyridin-2-yl)thiophen-2-yl)acrylamide;
(E)-N-(1-Methylpiperidin-4-yl)-3-(5-(4-(3-(piperidin-1-yl)propylamino)-1,6-naphthyridin-2-yl)thiophen-2-yl)acrylamide;
Piperazin-1-yl(6-(4-(3-(piperidin-1-yl)propylamino)-1,6-naphthyridin-2-yl)benzo[d]thiazol-2-yl)methanone;

Morpholino(6-(4-(3-(piperidin-1-yl)propylamino)-1,6-naphthyridin-2-yl)benzo[d]thiazol-2-yl)methanone;

N,N-Diethyl-6-(4-(3-(piperidin-1-yl)propylamino)-1,6-naphthyridin-2-yl)benzo[d]oxazole-2-carboxamide;

N,N-Diethyl-6-(4-(3-(piperidin-1-yl)propylamino)-1,6-naphthyridin-2-yl)benzo[d]thiazole-2-carboxamide;

or a pharmaceutically acceptable salt or solvate thereof.

Any combination of the groups described above for the various variables is contemplated herein. Throughout the specification, groups and substituents thereof are chosen by one skilled in the field to provide stable moieties and compounds.

Further Forms of Compounds

In one aspect, the compound of Formula (I), (II), (III), or (IV), possesses one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In one aspect, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

In one aspect, prodrugs are designed to alter the metabolic stability or the transport characteristics of a drug, to mask side effects or toxicity, to improve the flavor of a drug or to alter other characteristics or properties of a drug. By virtue of knowledge of pharmacokinetic, pharmacodynamic processes and drug metabolism in vivo, once a pharmaceutically active compound is known, the design of prodrugs of the compound is possible. (see, for example, Nogrady (1985) Medicinal Chemistry A Biochemical Approach, Oxford University Press, New York, pages 388-392; Silverman (1992), The Organic Chemistry of Drug Design and Drug Action, Academic Press, Inc., San Diego, pages 352-401, Rooseboom et al., Pharmacological Reviews, 56:53-102, 2004; Aesop Cho, "Recent Advances in Oral Prodrug Discovery", Annual Reports in Medicinal Chemistry, Vol. 41, 395-407, 2006; T. Higuchi and V. Stella, Pro-drugs as Novel Delivery Systems, Vol. 14 of the A.C.S. Symposium Series).

In some embodiments, some of the herein-described compounds may be a prodrug for another derivative or active compound.

In some embodiments, sites on the aromatic ring portion of compounds described herein are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine, chlorine, and iodine such as, for example, $^2H$, $^3H$, $^{13}C$, $^{14}C$, $^{15}N$, $^{18}O$, $^{17}O$, $^{35}S$, $^{18}F$, $^{36}Cl$, and $^{125}I$. In one aspect, isotopically-labeled compounds described herein, for example those into which radioactive isotopes such as $^3H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

"Pharmaceutically acceptable" as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound of Formula (I), (II), (III), or (IV) with acids. Pharmaceutically acceptable salts are also obtained by reacting a compound of Formula (I), (II), (III), or (IV) with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms, particularly solvates. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Methods of Synthesis

In some embodiments, the syntheses of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FisherScientific (Fisher Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4th Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein. As a guide the following synthetic methods may be utilized.

In the reactions described, it may be necessary to protect reactive functional groups, for example hydroxy, amino, imino, thio or carboxy groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Definitions

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed invention.

The terms below, as used herein, have the following meanings, unless indicated otherwise:

"Oxo" refers to the =O substituent.

"Alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl or ethyl. Unless stated otherwise specifically in the specification, an alkyl group may be optionally substituted as described below.

"Alkylene" refers to a straight or branched divalent hydrocarbon chain linking the rest of the molecule to a radical group. In some embodiments, the alkylene is —CH$_2$—, —CH$_2$CH$_2$—, or —CH$_2$CH$_2$CH$_2$—. In some embodiments, the alkylene is —CH$_2$—. In some embodiments, the alkylene is —CH$_2$CH$_2$—. In some embodiments, the alkylene is —CH$_2$CH$_2$CH$_2$—.

"Alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

"Heteroalkyl" refers to an alkyl radical as described above where one or more carbon atoms of the alkyl is replaced with a O, N (i.e. NH, —Nalkyl) or S atom. "Heteroalkylene" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to —OCH$_2$OMe, —OCH$_2$CH$_2$OMe, or —OCH$_2$CH$_2$OCH$_2$CH$_2$NH$_2$. Representative heteroalkylene groups include, but are not limited to —OCH$_2$CH$_2$O—, —OCH$_2$CH$_2$OCH$_2$CH$_2$O—, or —OCH$_2$CH$_2$OCH$_2$CH$_2$OCH$_2$CH$_2$O—.

"Alkylamino" refers to a radical of the formula —NHR or —NRR where each R is, independently, an alkyl radical as defined above. Unless stated otherwise specifically in the specification, an alkylamino group may be optionally substituted as described below.

The term "aromatic" refers to a planar ring having a delocalized π-electron system containing 4n+2 π electrons, where n is an integer. Aromatics can be optionally substituted. The term "aromatic" includes both aryl groups (e.g., phenyl, naphthalenyl) and heteroaryl groups (e.g., pyridinyl, quinolinyl).

"Aryl" refers to an aromatic ring wherein each of the atoms forming the ring is a carbon atom. Aryl groups can be optionally substituted. Examples of aryl groups include, but are not limited to phenyl, and naphthyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to:

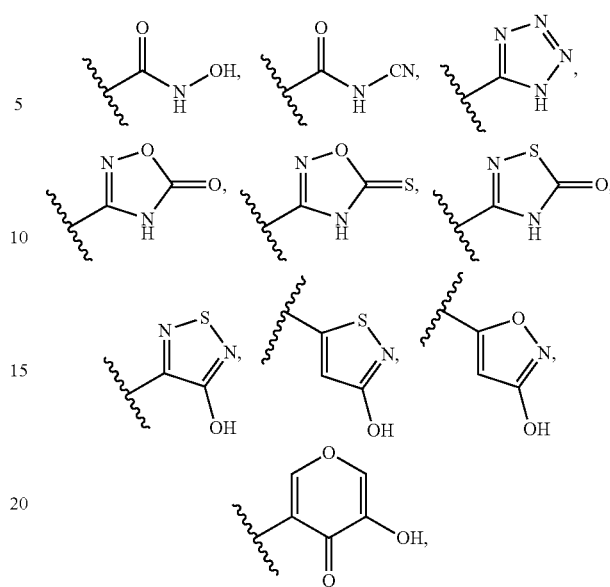

and the like.

"Cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. Monocyclic cycloalkyl radicals include, for example, cyclopropyl, cyclobutyl, cyclopentyl, cyclohexyl, cycloheptyl, and cyclooctyl. In some embodiments, the monocyclic cycloalkyl is cyclopropyl, cyclobutyl, cyclopentyl or cyclohexyl. In some embodiments, the monocyclic cycloalkyl is cyclopentyl. Polycyclic radicals include, for example, adamantyl, norbornyl, decalinyl, and 3,4-dihydronaphthalen-1(2H)-one. Unless otherwise stated specifically in the specification, a cycloalkyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" refers to an alkoxy radical, as defined above, that is substituted by one or more halo radicals, as defined above, e.g., trifluoromethoxy, difluoromethoxy, fluoromethoxy, trichloromethoxy, 2,2,2-trifluoroethoxy, 1,2-difluoroethoxy, 3-bromo-2-fluoropropoxy, 1,2-dibromoethoxy, and the like. Unless stated otherwise specifically in the specification, a haloalkoxy group may be optionally substituted.

"Heterocycloalkyl" or "heterocyclyl" or "heterocyclic ring" refers to a stable 3- to 14-membered non-aromatic ring radical comprising 2 to 10 carbon atoms and from one to 4 heteroatoms selected from the group consisting of nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. In some embodiments, heterocycloalkyls have from 2 to 10 carbons, 0-2 N atoms, 0-2 O atoms, and 0-1 S atoms in the ring. In some embodiments, heterocycloalkyls have from 2 to 10 carbons, 1-2 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to an aryl group that includes one or more ring heteroatoms selected from nitrogen, oxygen and sulfur. The heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, a bicyclic heteroaryl is a $C_6$-$C_9$heteroaryl.

The term "optionally substituted" or "substituted" means that the referenced group may be substituted with one or more additional group(s) individually and independently selected from alkyl, haloalkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halogen, acyl, acyloxy, —$CO_2H$, —$CO_2$alkyl, nitro, and amino, including mono- and di-substituted amino groups (e.g. —$NH_2$, —NHR, —$N(R)_2$), and the protected derivatives thereof. In some embodiments, optional substituents are independently selected from alkyl, alkoxy, haloalkyl, cycloalkyl, halogen, —CN, —$NH_2$, —$NH(CH_3)$, —$N(CH_3)_2$, —OH, —$CO_2H$, and —$CO_2$alkyl. In some embodiments, optional substituents are independently selected from fluoro, chloro, bromo, iodo, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic) includes oxo (=O).

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

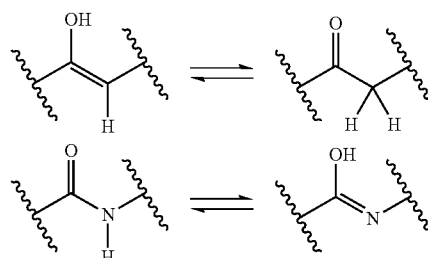

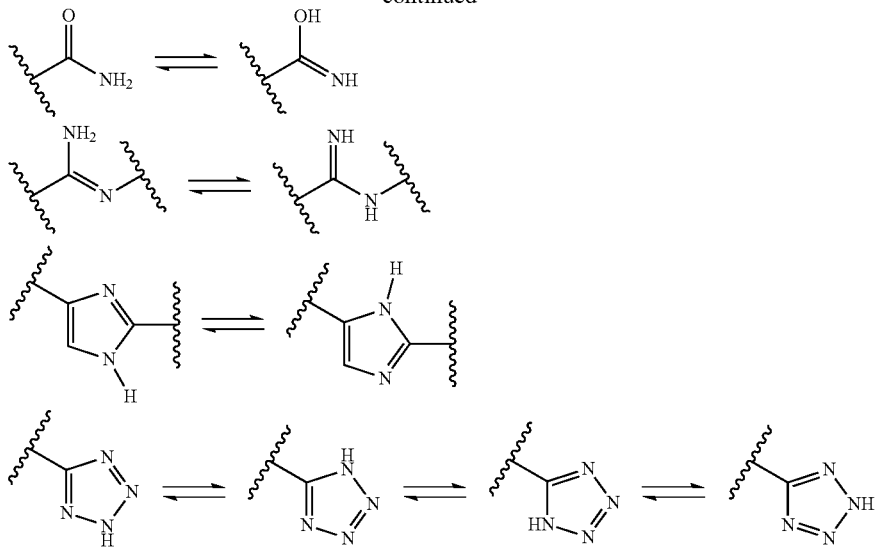

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I) and a co-agent, are both administered to a patient simultaneously in the form of a single entity or dosage. The term "non-fixed combination" means that the active ingredients, e.g. a compound of Formula (I) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "subject" or "patient" encompasses mammals. Examples of mammals include, but are not limited to, humans. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

Pharmaceutical Compositions

In one aspect, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound of Formula (I), (II), (III), or (IV) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism.

Pharmaceutical formulations described herein are administrable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compounds of Formula (I), (II), (III), or (IV) are administered orally.

In some embodiments, the compounds of Formula (I), (II), (III), or (IV) are administered topically. In such embodiments, the compound of Formula (I), (II), (III), or (IV) is formulated into a variety of topically administrable compositions, such as solutions, suspensions, lotions, gels, pastes, shampoos, scrubs, rubs, smears, medicated sticks, medicated bandages, balms, creams or ointments. In one aspect, the compounds of Formula (I), (II), (III), or (IV) are administered topically to the skin.

In another aspect, the compounds of Formula (I), (II), (III), or (IV) are administered by inhalation.

In another aspect, the compounds of Formula (I), (II), (III), or (IV) are formulated for intranasal administration. Such formulations include nasal sprays, nasal mists, and the like.

In another aspect, the compounds of Formula (I), (II), (III), or (IV) are formulated as eye drops.

In any of the aforementioned aspects are further embodiments in which the effective amount of the compound of Formula (I), (II), (III), or (IV) is: (a) systemically administered to the mammal; and/or (b) administered orally to the mammal; and/or (c) intravenously administered to the mammal; and/or (d) administered by inhalation to the mammal; and/or (e) administered by nasal administration to the mammal; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound of Formula (I), (II), (III), or (IV), including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound of Formula (I), (II), (III), or (IV), including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound of Formula (I), (II), (III), or (IV) is temporarily suspended or the dose of the compound being administered is temporarily reduced; at the end of the drug holiday, dosing of the compound is resumed. In one embodiment, the length of the drug holiday varies from 2 days to 1 year.

In certain embodiments, the compound of Formula (I), (II), (III), or (IV) is administered in a local rather than systemic manner.

In some embodiments, the compound of Formula (I), (II), (III), or (IV) is administered topically. In some embodiments, the compound of Formula (I), (II), (III), or (IV) is administered systemically.

In some embodiments, the pharmaceutical formulation is in the form of a tablet. In other embodiments, pharmaceutical formulations of the compounds of Formula (I), (II), (III), or (IV) are in the form of a capsule.

In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, a compound of Formula (I), (II), (III), or (IV) is formulated for use as an aerosol, a mist or a powder.

For buccal or sublingual administration, the compositions may take the form of tablets, lozenges, or gels formulated in a conventional manner.

In some embodiments, compounds of Formula (I), (II), (III), or (IV) are prepared as transdermal dosage forms.

In one aspect, a compound of Formula (I), (II), (III), or (IV) is formulated into a pharmaceutical composition suitable for intramuscular, subcutaneous, or intravenous injection.

In some embodiments, the compound of Formula (I), (II), (III), or (IV) is be administered topically and can be formulated into a variety of topically administrable compositions, such as solutions, suspensions, lotions, gels, pastes, medicated sticks, balms, creams or ointments.

In some embodiments, the compounds of Formula (I), (II), (III), or (IV) are formulated in rectal compositions such as enemas, rectal gels, rectal foams, rectal aerosols, suppositories, jelly suppositories, or retention enemas.

Methods of Dosing and Treatment Regimens

In one aspect, the compounds of Formula (I), (II), (III), or (IV) are used in the preparation of medicaments for the treatment of diseases or conditions described herein. In addition, a method for treating any of the diseases or conditions described herein in a subject in need of such treatment, involves administration of pharmaceutical compositions that include at least one compound of Formula (I), (II), (III), or (IV) or a pharmaceutically acceptable salt, active metabolite, prodrug, or solvate thereof, in therapeutically effective amounts to said subject.

In certain embodiments, the compositions containing the compound of Formula (I), (II), (III), or (IV) are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds of Formula (I), (II), (III), or (IV) are administered to a patient susceptible to or otherwise at risk of a particular disease, disorder or condition.

In certain embodiments, the dose of drug being administered may be temporarily reduced or temporarily suspended for a certain length of time (i.e., a "drug holiday").

Doses employed for adult human treatment are typically in the range of 0.01 mg-5000 mg per day or from about 1 mg to about 1000 mg per day. In one embodiment, the desired dose is conveniently presented in a single dose or in divided doses.

Combination Treatments

In certain instances, it is appropriate to administer at least one compound of Formula (I) in combination with another therapeutic agent.

In one specific embodiment, a compound of Formula (I), (II), (III), or (IV) is co-administered with a second therapeutic agent, wherein the compound of Formula (I), (II), (III), or (IV) and the second therapeutic agent modulate different aspects of the disease, disorder or condition being treated, thereby providing a greater overall benefit than administration of either therapeutic agent alone.

For combination therapies described herein, dosages of the co-administered compounds vary depending on the type of co-drug(s) employed, on the specific drug(s) employed, on the disease or condition being treated and so forth. In additional embodiments, when co-administered with one or more other therapeutic agents, the compound provided herein is administered either simultaneously with the one or more other therapeutic agents, or sequentially.

If administration is simultaneous, the multiple therapeutic agents are, by way of example only, provided in a single, unified form, or in multiple forms.

In some embodiments, the one or more agents used in the treatment of a metabolic disorder include, but are not limited to, a statin, an insulin sensitizing drug, (such as sitagliptin, vildagliptin, saxagliptin, linagliptin, anagliptin, teneligliptin, alogliptin, gemigliptin, or dutogliptin), meglitinide, sulfonylurea, peroxisome proliferator-activated receptor (alpha-glucosidase inhibitor, amylin agonist, dipeptidyl-peptidase 4 (DPP-4) inhibitor PPAR)-gamma agonist (e.g., a thiazolidinedione (TZD) [such as ioglitazone, rosiglitazone, rivoglitazone, or troglitazone], aleglitazar, farglitazar, muraglitazar, or tesaglitazar), a glucagon-like peptide (GLP) agonist, anti-inflammatory agent (e.g., oral corticosteroid), or a combination thereof. In some embodiments, the one or more agents used in the treatment of a metabolic disorder include, but are not limited to, a statin, HMG-CoA reductase inhibitor, fish oil, fibrate, niacin or other treatment for dyslipidemia. In some embodiments retinoic acid is also administered. In one example, nicotinamide ribonucleoside and/or nicotinamide ribonucleoside analogs are also administered.

In some embodiments, the additional therapeutic agent is a peroxisome proliferator activated receptor (PPAR) agonist (gamma, dual, or pan), a dipeptidyl peptidase (IV) inhibitor, a glucagon-like peptide-1 (GLP-I) analog, insulin or an insulin analog, an insulin secretagogue, a sodium glucose co-transporter 2 (SGLT2) inhibitor, a human amylin analog, a biguanide, a glucophage, an alpha-glucosidase inhibitor, a meglitinide, a thiazolidinedione, a sulfonylurea, or any combination thereof.

In some embodiments, the additional therapeutic agent is an angiotensin-converting enzyme (ACE) inhibitor, angiotensin II receptor blocker (ARB), beta-blocker, diuretic, calcium channel blocker, inhibitor of renin-angiotensin system (RAS), blood-thinning medication, a statin, a fibrate, or any combination thereof.

Methods of Inhibition

In one aspect, described herein is a method of inhibiting low molecular weight protein tyrosine phosphatase (LMPTP) activity comprising contacting the low molecular weight protein tyrosine phosphatase (LMPTP) with a compound of Formula (I), (II), (III), or (IV), or a pharmaceutically acceptable salt or solvate thereof.

In some embodiments, the mammal has insulin resistance, metabolic syndrome, type 2 diabetes, cardiovascular disease, or combinations thereof. In some embodiments, the mammal has insulin resistance. In some embodiments, the mammal has metabolic syndrome. In some embodiments, the mammal has type 2 diabetes. In some embodiments, the mammal has cardiovascular disease. In some embodiments, the mammal has an impaired glucose tolerance. In some embodiments, the mammal is pre-diabetic. In some embodiments, the mammal is obese. In some embodiments, the mammal has a disease or condition that would benefit from inhibition of LMPTP activity. In some embodiments, the disease or condition is described herein.

Methods of Treatment

In one aspect, described herein is a method of treating a disease or condition including administering to a subject in need thereof an effective amount of a compound of Formula (I), (II), (III), or (IV).

In some embodiments, the disease or condition is type II diabetes, heart disease, coronary artery disease, hyperlipidemia, lipodystrophy, insulin resistance, rheumatic disease, atherosclerosis, myocardial infarction, stroke, high blood pressure (hypertension), obesity, elevated fasting plasma glucose, high serum triglycerides, elevated blood cholesterol, cardiac hypertrophy, heart failure (e.g., hypertrophy-induced heart failure) or metabolic syndrome.

In an aspect is provided a method of treating a disease associated with low molecular weight protein tyrosine phosphatase (LMPTP) activity including administering to a subject in need thereof an effective amount of a compound described herein. In some embodiments, the disease is associated with aberrant low molecular weight protein tyrosine phosphatase (LMPTP) activity. For example, studies have shown that inhibition of low molecular weight protein tyrosine phosphatase (LMPTP) activity may be a target for cardiac diseases (e.g., heart failure). See, e.g., Wade et al., *J. Pathol.*, 2015, pages 1-13 (DOI: 10.1002/path.4594), which is hereby incorporated by reference in its entirety.

In some embodiments, the method includes administering a second agent (e.g. therapeutic agent). In some embodiments, the method includes administering a second agent (e.g. therapeutic agent) in a therapeutically effective amount. Examples of a second agent include therapeutic agents known in the art for the treatment of diabetes, heart disease, coronary artery disease, hyperlipidemia, lipodystrophy, insulin resistance, rheumatic disease, atherosclerosis, myocardial infarction, stroke, high blood pressure (hypertension), obesity, elevated fasting plasma glucose, high serum triglycerides, elevated blood cholesterol, cardiac hypertrophy, heart failure (e.g., hypertrophy-induced heart failure) or metabolic syndrome. Thus, in some embodiments, the method includes administering to a subject in need thereof an effective amount of a compound described herein in combination with a second therapeutic agent for the treatment of diabetes, heart disease, coronary artery disease, hyperlipidemia, lipodystrophy, insulin resistance, rheumatic disease, atherosclerosis, myocardial infarction, stroke, high blood pressure (hypertension), obesity, elevated fasting plasma glucose, high serum triglycerides, elevated blood cholesterol, cardiac hypertrophy, heart failure (e.g., hypertrophy-induced heart failure) or metabolic syndrome.

EXAMPLES

These examples are provided for illustrative purposes only and not to limit the scope of the claims provided herein. The starting materials and reagents used for the synthesis of the compounds described herein may be synthesized or can be obtained from commercial sources, such as, but not limited to, Sigma-Aldrich, Acros Organics, Fluka, and Fischer Scientific.

Example 1: Synthesis of N,N-diethyl-4-(4-(3-(piperidin-1-yl)propylamino)-1,6-naphthyridin-2-yl)benzamide

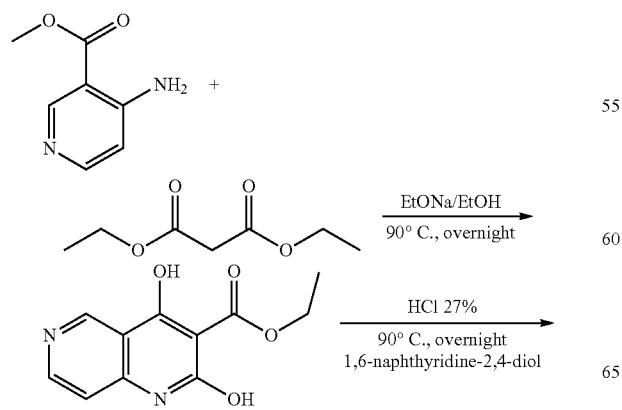

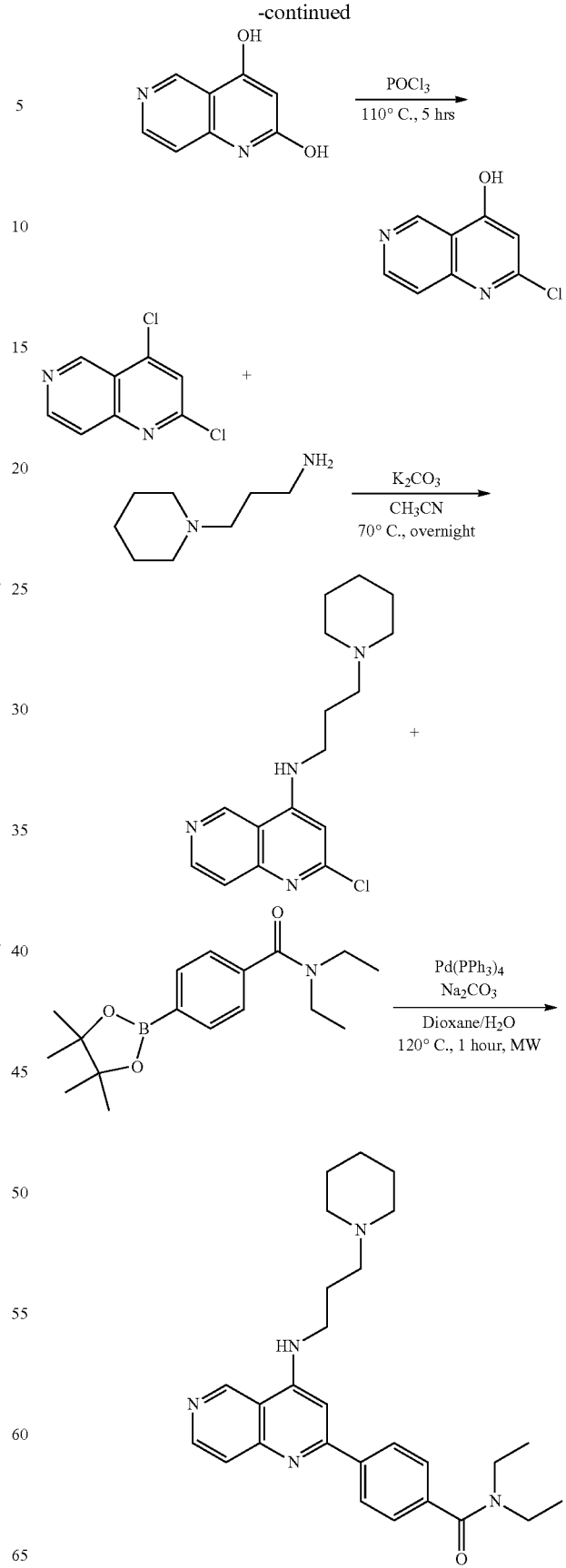

Step 1

To a solution of Na (1.035 g, 45 mmol) in EtOH (30 mL) until the mixture was clear. Then diethyl malonate (5.76 g, 36 mmol), EtOH (10 mL) and methyl 4-aminonicotinate (5 g, 30 mmol) in EtONa (1.5 M, 30 mL). Then the mixture was stirred at 90° C. for overnight. Then the solvent was removed under reduce pressure in vacuum, the mixture was dissolved in 50 mL H$_2$O and adjusted to pH=5-6 with 1 M HCl. Extracted with EA (100 mL), filtered and the residue was desired compound which used to next step directly. A white solid (5 g), yield: 65%.

Step 2

To a solution of Ethyl 2,4-dihydroxy-1,6-naphthyridine-3-carboxylate (4.7 g, 20 mmol) in 27% HCl (100 mL). Then the mixture was stirred at 90° C. for overnight. Then the mixture was adjusted to pH=5-6 with 30% NaOH under ice-water bath. Filtered and the residue was desired compound which used to next step directly. A white solid (2.5 g), yield: 69.4%. LC-MS (ESI): 163 (M+1)$^+$.

Step 3

A mixture of 1,6-naphthyridine-2,4-diol (810 mg, 5 mmol) and in POCl$_3$ (20 mL) was stirred at 110° C. for 5 hrs. Then the solvent was removed under reduce pressure in vacuum, the mixture was dissolved in 100 mL DCM and adjusted to pH=8-9 with NaHCO$_3$ saturated aqueous solution. Extracted with DCM (100 mL), washed with brine, dried over Na$_2$SO$_4$. Evaporation of the organic phase and the residue was purified by flash column to afford a white solid (700 mg). Yield: 70%; LC-MS (ESI): 198, 200 (M+1)$^+$.

Step 4

A mixture of 2,4-dichloro-1,6-naphthyridine (500 mg, 2.52 mmol) and 3-(piperidin-1-yl)propan-1-amine (358 mg, 2.52 mmol) in CH$_3$CN (30 mL) and was stirred at 70° C. for 2 hours. Filtered and the mixture was evaporated and the residue was purified by Pre-TLC to afford the desired compound as a white solid (300 mg), yield: 39%; LC-MS (ESI): 305 (M+1)$^+$.

Step 5

The mixture of 2-chloro-N-(3-(piperidin-1-yl)propyl)-1,6-naphthyridin-4-amine (152 mg, 0.5 mmol), N,N-diethyl-4-(4,4,5,5-tetramethyl-1,3,2-dioxaborolan-2-yl)benzamide (152 mg, 0.5 mmol), Pd(PPh$_3$)$_4$ (58 mg, 0.05 mmol) and Na$_2$CO$_3$ (106 mg, 1 mmol) in Dioxane/H$_2$O (3 mL/0.3 mL) was stirred at for 120° C. 1 hour by MW. The mixture was diluted with DCM, washed with water (20 mL×3) and brine (20 mL×1), dried over Na$_2$SO$_4$, filtered and concentrated. The crude product was purified by Prep-TLC to afford N,N-diethyl-4-(4-(3-(piperidin-1-yl)propylamino)-1,6-naphthyridin-2-yl)benzamide (28.5 mg, 40%) as a white solid. HPLC/UV purity=96%; LC-MS (ESI): 446.2 (M+1)$^+$; $^1$H NMR (CD$_3$OD) δ 9.57 (s, 1H), 8.61 (d, J=6.1 Hz, 1H), 8.15-8.24 (m, 2H), 7.81 (d, J=6.1 Hz, 1H), 7.54-7.61 (m, 2H), 7.15 (s, 1H), 3.69 (t, J=6.7 Hz, 2H), 3.55-3.66 (m, 3H), 3.50 (m, 1H), 3.37 (d, J=6.7 Hz, 2H), 3.26-3.32 (m, 2H), 3.15 (m, 1H), 3.05 (m, 1H), 2.23-2.36 (m, 2H), 1.90 (m, 6H), 1.31 (t, J=6.9 Hz, 3H), 1.19 (t, J=6.9 Hz, 3H).

Example 2: Synthesis of N-(2-(dimethylamino)ethyl)-1-methyl-5-(4-((3-(piperidin-1-yl)propyl)amino)-1,6-naphthyridin-2-yl)-1H-indole-2-carboxamide

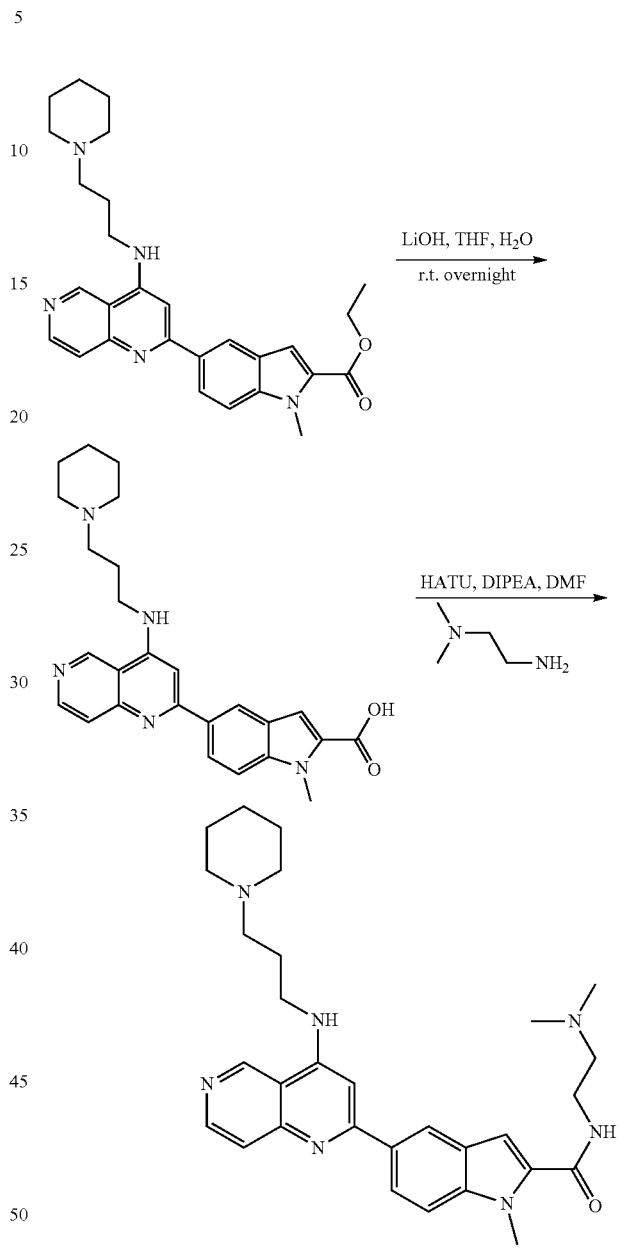

Step 1

The mixture of Ethyl 1-methyl-5-(4-((3-(piperidin-1-yl)propyl)amino)-1,6-naphthyridin-2-yl)-1H-indole-2-carboxylate (350 mg, 0.74 mmol) and LiOH·H$_2$O (94 mg, 2.23 mmol) in THF/H$_2$O (12 mL/3 mL) was stirred at room temperature overnight. The mixture was acidified with HCl solution (2 M) to pH=2, then concentrated to give the crude product that was used directly in the next step without further purification. LC-MS (ESI): 444.2 (M+1)$^+$.

Step 2

The mixture of 1-methyl-5-(4-((3-(piperidin-1-yl)propyl)amino)-1,6-naphthyridin-2-yl)-1H-indole-2-carboxylic acid (100 mg, 0.24 mmol), N',N'-dimethylethane-1,2-diamine (132 mg, 0.36 mmol), HATU (137 mg, 0.36 mmol) and DIPEA (65 mg, 0.48 mmol) in DMF (3 mL) was stirred at room temperature overnight. Water (30 mL) was added, and then the mixture was extracted with EA three times. The combined organic layers were washed with water (20 mL×3) and brine (20 mL×1), dried over Na$_2$SO$_4$, filtered and concentrated. The residue was purified by the Prep-HPLC to afford N-(2-(dimethylamino)ethyl)-1-methyl-5-(4-((3-(piperidin-1-yl)propyl)amino)-1,6-naphthyridin-2-yl)-1H-indole-2-carboxamide as a white solid (20 mg, 16% yield). LC-MS (ESI): 514.3 (M+1)$^+$; $^1$H NMR (CD$_3$OD) δ 9.70 (br, s, 1H), 8.86 (d, J=6.0 Hz, 1H), 8.41 (d, J=1.2 Hz, 1H), 7.90-7.96 (m, 2H), 7.79 (d, J=9.2 Hz, 1H), 7.34 (s, 1H), 7.26 (s, 1H), 4.15 (s, 3H), 3.78-3.87 (m, 4H), 3.57 (d, J=12 Hz, 3H), 3.42 (t, J=11.6 Hz, 2H), 3.02 (s, 6H), 2.92-2.96 (m, 3H), 2.27-2.34 (m, 2H), 1.76-1.86 (m, 4H), 1.50-1.61 (m, 2H).

Example 3: Synthesis of 1-methyl-N-(1-methylpiperidin-4-yl)-5-(4-((3-(piperidin-1-yl)propyl)amino)-1,6-naphthyridin-2-yl)-1H-indole-2-carboxamide

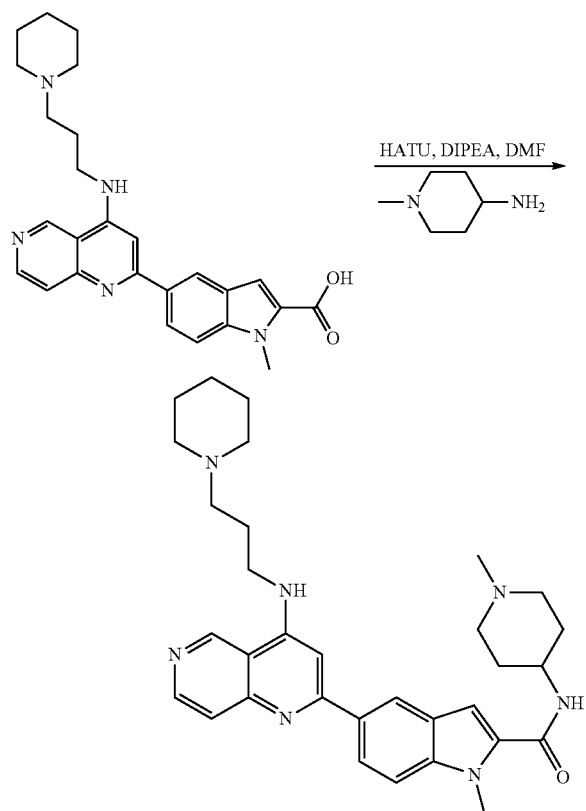

The mixture of 1-methyl-5-(4-((3-(piperidin-1-yl)propyl)amino)-1,6-naphthyridin-2-yl)-1H-indole-2-carboxylic acid (100 mg, 0.24 mmol), 1-methylpiperidin-4-amine (72 mg, 0.5 mmol), HATU (114 mg, 0.30 mmol) and DIPEA (96 mg, 0.75 mmol) in DMF (3 mL) was stirred at room temperature overnight. Water (30 mL) was added, and then the mixture was extracted with EA three times. The combined organic layers were washed with water (20 mL×3) and brine (20 mL×1), dried over Na$_2$SO$_4$, filtered and concentrated. The residue was purified by the Prep-HPLC to afford 1-methyl-N-(1-methylpiperidin-4-yl)-5-(4-((3-(piperidin-1-yl)propyl)amino)-1,6-naphthyridin-2-yl)-1H-indole-2-carboxamide as a white solid (30 mg, 12% yield). LC-MS (ESI): 540.3 (M+1)$^+$; $^1$H NMR (CD$_3$OD) δ 9.70 (br, s, 1H), 8.87 (d, J=5.2 Hz, 1H), 8.40 (d, J=1.6 Hz, 1H), 7.90-7.96 (m, 2H), 7.78 (d, J=8.8 Hz, 1H), 7.26 (d, J=11.2 Hz, 2H), 4.15-4.23 (m, 1H), 4.10 (s, 3H), 3.84 (t, J=6.8 Hz, 2H), 3.57 (t, J=13.2 Hz, 4H), 3.18-3.25 (m, 3H), 2.91-2.99 (m, 3H), 2.27-2.33 (m, 4H), 1.94-1.97 (m, 5H), 1.76-1.83 (m, 4H), 1.50-1.60 (m, 2H).

Example 4: Synthesis of 1-methyl-5-(4-((3-(piperidin-1-yl)propyl)amino)-1,6-naphthyridin-2-yl)-N-(piperidin-4-yl)-1H-indole-2-carboxamide

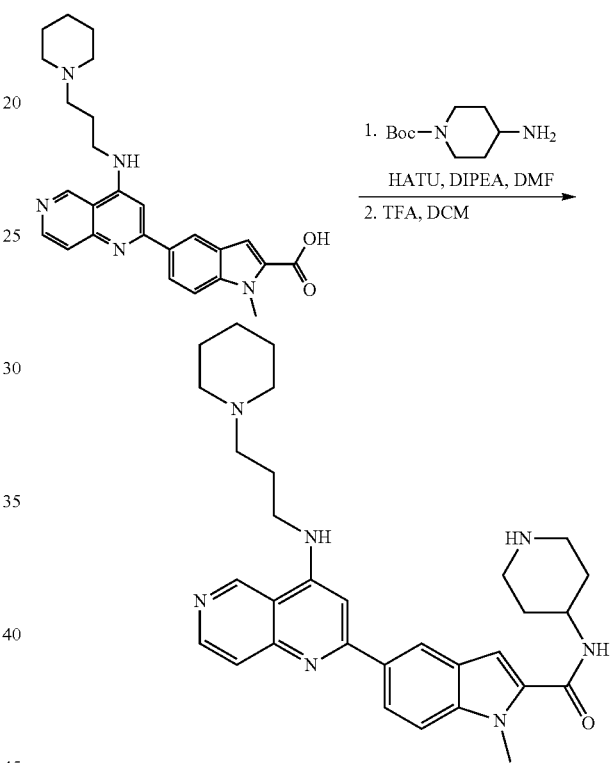

The mixture of 1-methyl-5-(4-((3-(piperidin-1-yl)propyl)amino)-1,6-naphthyridin-2-yl)-1H-indole-2-carboxylic acid (100 mg, 0.24 mmol), tert-butyl 4-aminopiperidine-1-carboxylate (100 mg, 0.5 mmol), HATU (114 mg, 0.30 mmol) and DIPEA (96 mg, 0.75 mmol) in DMF (3 mL) was stirred at room temperature overnight. Water (30 mL) was added, and then the mixture was extracted with EA three times. The combined organic layers were washed with water (20 mL×3) and brine (20 mL×1), dried over Na$_2$SO$_4$, filtered and concentrated. The residue was added TFA (1 mL) and DCM (10 mL) and stirred at room temperature overnight. The mixture was concentrated and purified by the Prep-HPLC to afford 1-methyl-5-(4-((3-(piperidin-1-yl)propyl)amino)-1,6-naphthyridin-2-yl)-N-(piperidin-4-yl)-1H-indole-2-carboxamide as a white solid (30 mg, 24% yield). LC-MS (ESI): 526.3 (M+1)$^+$; $^1$H NMR (CD$_3$OD) δ 9.72 (br, s, 1H), 8.84 (d, J=6.0 Hz, 1H), 8.40 (d, J=1.6 Hz, 1H), 7.92-7.95 (m, 2H), 7.75 (d, J=8.8 Hz, 1H), 7.25 (d, J=15.6 Hz, 2H), 4.17-4.24 (m, 1H), 4.09 (s, 3H), 3.84 (t, J=13.6 Hz, 2H), 3.49-3.60 (m, 5H), 3.32-3.34 (m, 2H), 3.16-3.21 (m, 3H), 2.93-2.99 (m, 2H), 2.22-2.36 (m, 5H), 1.81-1.96 (m, 5H).

127

Example 5: Synthesis of ethyl 1-methyl-5-(4-((3-(piperidin-1-yl)propyl)amino)-1,6-naphthyridin-2-yl)-1H-indole-2-carboxylate

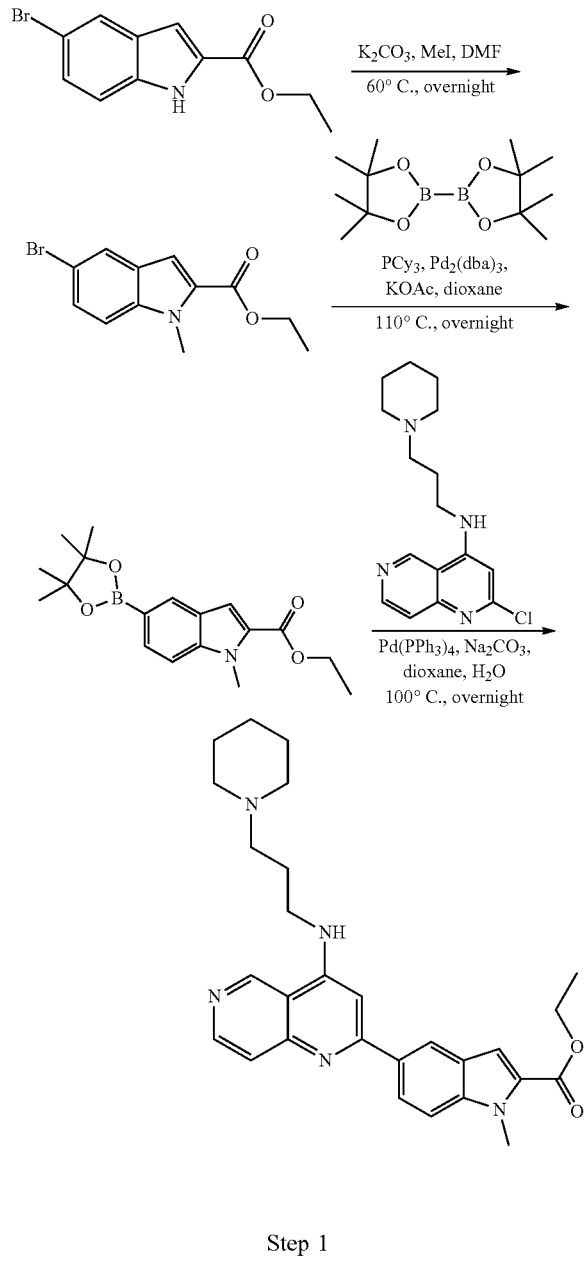

Step 1

To the mixture of ethyl 5-bromo-1H-indole-2-carboxylate (8.04 g, 30 mmol) and K$_2$CO$_3$ (11.5 g, 90 mmol) in DMF (50 mL) was added MeI (2.43 mL, 39 mmol), then the mixture was heated to 60° C. overnight. After cooling to room temperature, water (500 mL) was added. The mixture was extracted with EA three times. The combined organic layers were washed with water (×3) and brine (×1), dried over Na$_2$SO$_4$, filtered and concentrated. The residue was purified by the flash column chromatography (silica gel, eluting with PE to 10% EA in PE) to afford ethyl 5-bromo-1-methyl-1H-indole-2-carboxylate as a white solid (7.5 g, 88% yield). LC-MS (ESI): 282.0 (M+1)$^+$.

128

Step 2

The mixture of ethyl 5-bromo-1-methyl-1H-indole-2-carboxylate (7.5 g, 26.7 mmol), 4,4,4',4',5,5,5',5'-octamethyl-2,2'-bi(1,3,2-dioxaborolane) (7.46 g, 29.4 mmol), Pd$_2$(dba)$_3$ (0.49 g, 0.53 mmol), PCy$_3$ (0.60 g, 2.14 mmol) and KOAc (3.92 g, 40 mmol) in dioxane (60 mL) protected under N$_2$ atmosphere was heated to 110° C. overnight. After cooling to room temperature, the mixture was concentrated. The residue was purified by the flash column chromatography (silica gel, eluting with PE to 10% EA in PE) to afford ethyl 1-methyl-5-(4,4,5,5-tetramethyl-1,3,2-dioxaborolan-2-yl)-1H-indole-2-carboxylate as a yellow solid (7.8 g, 89% yield). LC-MS (ESI): 330.2 (M+1)$^+$.

Step 3

The mixture of 2-chloro-N-(3-(piperidin-1-yl)propyl)-1,6-naphthyridin-4-amine (1.5 g, 5 mmol, the mixture of two isomers) and ethyl 1-methyl-5-(4,4,5,5-tetramethyl-1,3,2-dioxaborolan-2-yl)-1H-indole-2-carboxylate (1.8 g, 5.5 mmol), Na$_2$CO$_3$ (1.6 g, 15 mmol) and Pd(PPh$_3$)$_4$ (0.15 g, 0.13 mmol) in dioxane/H$_2$O (40 mL/8 mL) protected by N$_2$ atmosphere was heated to 100° C. overnight. After cooling to room temperature, water (60 mL) was added, and then the mixture was extracted with EA three times. The combined organic layers were washed with water (×3) and brine (×1), dried over Na$_2$SO$_4$, filtered and concentrated. The residue was purified by the flash column chromatography (silica gel, eluting with DCM to 10% MeOH in DCM) to afford ethyl 1-methyl-5-(4-((3-(piperidin-1-yl)propyl)amino)-1,6-naphthyridin-2-yl)-1H-indole-2-carboxylate as a white solid (0.35 g, 30% yield). LC-MS (ESI): 472.3 (M+1)$^+$; $^1$H NMR (CD$_3$OD) δ 9.41 (s, 1H), 8.48 (d, J=6.0 Hz, 1H), 8.28 (d, J=1.2 Hz, 1H), 7.97 (dd, J=8.8, 1.6 Hz, 1H), 7.68 (d, J=6.0 Hz, 1H), 7.51 (d, J=8.8 Hz, 1H), 7.29 (s, 1H), 6.97 (s, 1H), 4.31 (q, J=7.2 Hz, 2H), 4.02 (s, 3H), 3.60-3.63 (m, 3H), 3.15-3.25 (m, 6H), 2.21-2.29 (m, 2H), 1.84-1.88 (m, 5H), 1.56 (t, J=7.0 Hz, 3H).

Example 6: Synthesis of 4-(4-((3-(piperidin-1-yl)propyl)amino)-1,6-naphthyridin-2-yl)benzoic acid

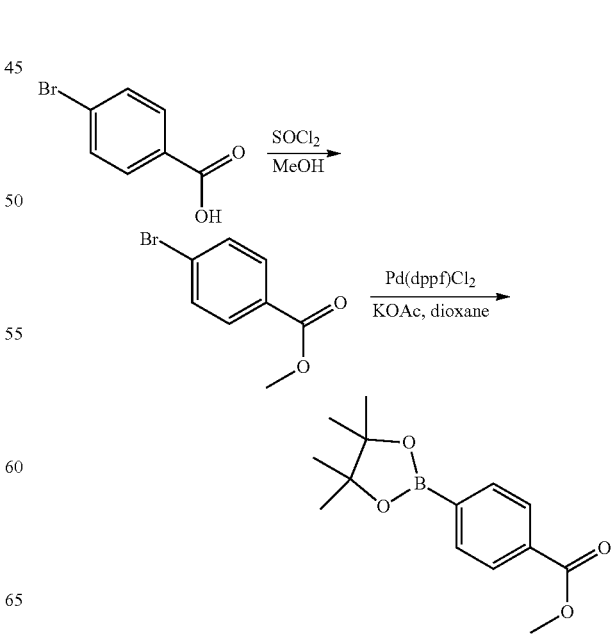

129
-continued

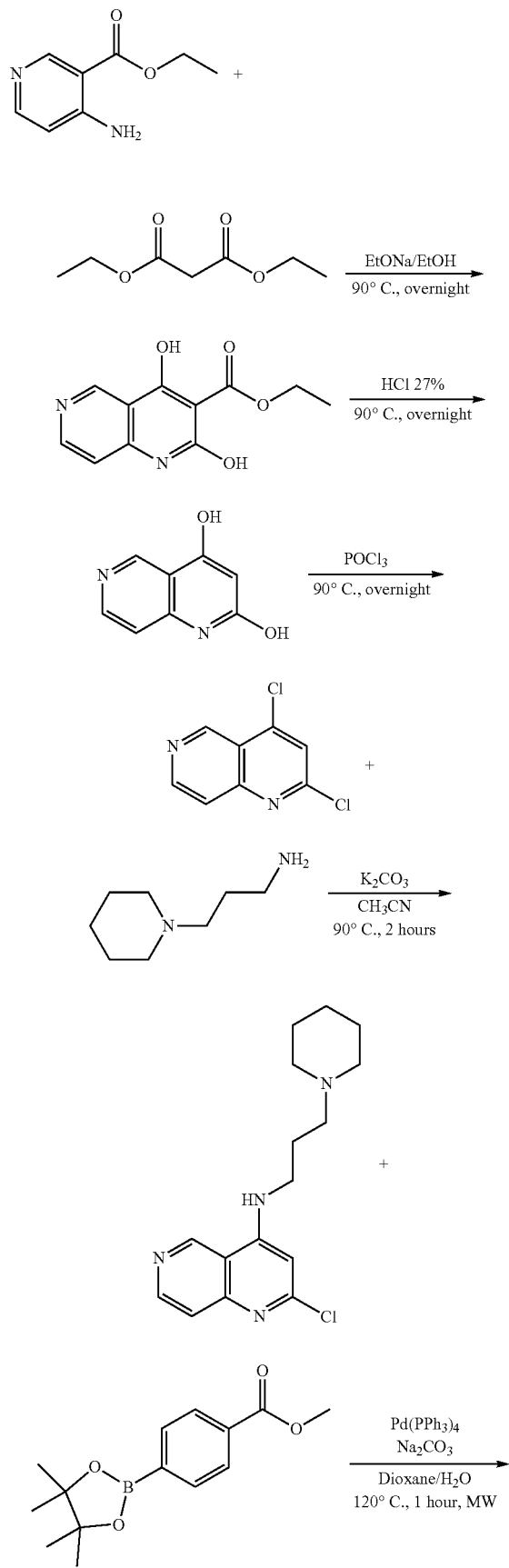

130
-continued

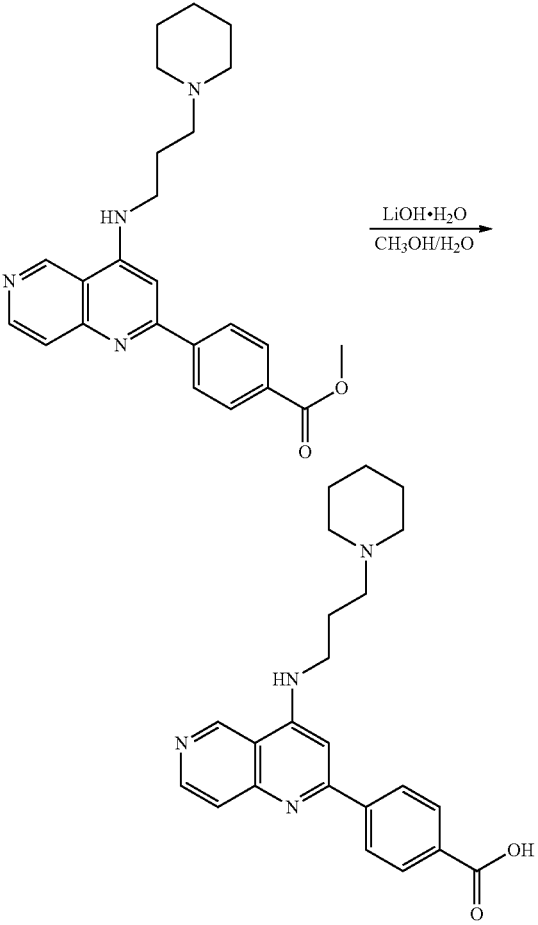

Step 1

To a solution of 4-bromobenzoic acid (2.21 g, 11 mmol) in SOCl$_2$ and MeOH (50 mL) and was stirred at 80° C. for 2 hours. Evaporated the solvent to give desired compound which was used to next step directly. Isolated weight: 2.3 g, yield: 99%, color: white, state: solid.

Step 2

The mixture of methyl 4-bromobenzoate (2.15 g, 10 mmol), 4,4,4',4',5,5,5',5'-octamethyl-2,2'-bi(1,3,2-dioxaborolane) (2.54 g, 10 mmol), Pd(dppf)Cl$_2$ (816 mg, 1 mmol) and KOAc (1.96 g, 20 mmol) in Dioxane (150 mL) was stirred at 90° C. for 6 hours. The mixture was diluted with DCM (200 mL), washed with water (50 mL×3) and brine (30 mL×1), dried over Na$_2$SO$_4$, filtered and concentrated. The crude product was purified by silica gel column chromatography to afford the desired compound. Isolated weight: 2.01 g, yield: 77% as a white solid.

Step 3

Diethyl malonate (6.3 g, 39.5 mmol) and ethyl 4-aminonicotinate (5 g, 30 mmol) were added to fresh EtONa (1.8 M, 73 mL, 131.6 mmol) solution. Then the mixture was stirred at 90° C. for overnight. Then the solvent was removed under reduce pressure in vacuum, the mixture was dissolved in 50 mL H$_2$O and adjusted to pH=5-6 with 1 M HCl. Extracted with EA (100 mL), filtered and the residue was used directly in the next step. A white solid (4.2 g), yield: 54.6%, as a white solid.

Step 4

To a solution of Ethyl 2,4-dihydroxy-1,6-naphthyridine-3-carboxylate (4.2 g, 17.9 mmol) in 27% HCl (50 mL). Then the mixture was stirred at 90° C. for overnight. Then the mixture was adjusted to pH=5-6 with 30% NaOH under ice-water bath. Filtered and the residue of the desired compound was used to next step directly. A white solid (2.6 g), yield: 89.6%, color: white, state: solid. LC-MS (ESI): 163 (M+1)$^+$.

Step 5

A mixture of 1,6-naphthyridine-2,4-diol (3.24 g, 20 mmol) and in POCl$_3$ (50 mL) was stirred at 110° C. for overnight. Then the solvent was removed under reduce pressure in vacuum, the mixture was dissolved in 100 mL DCM and adjusted to pH=5-6 with NaHCO$_3$ saturated aqueous solution. Extracted with EA (100 mL), washed with brine, dried over Na$_2$SO$_4$. Evaporation of the organic phase provides a yellow solid which was purified by flash column chromatography to afford the desired compound. Isolated weight: 2.8 g; Yield: 70%; Color: white; State: solid. LC-MS (ESI): 198, 200 (M+1)$^+$.

Step 6

A mixture of 2,4-dichloro-1,6-naphthyridine (1.0 g, 5 mmol), K$_2$CO$_3$ (1.38 g, 10 mmol) and 3-(piperidin-1-yl)propan-1-amine (0.71 g, 5 mmol) in CH$_3$CN (50 mL) and was stirred at 80° C. for overnight. 100 mL H$_2$O was added and extracted with EA (200 mL) washed with brine, dried over Na$_2$SO$_4$. Evaporated the solvent and the residue to afford the desired compound which used to next step directly. Isolated weight: 1.22 g, yield: 80%, color: white, state: solid. LC-MS (ESI): 305 (M+1)$^+$.

Step 7

The mixture of 2-chloro-N-(3-(piperidin-1-yl)propyl)-1,8-naphthyridin-4-amine (1.52 g, 5 mmol), methyl 4-(4,4,5,5-tetramethyl-1,3,2-dioxaborolan-2-yl)benzoate (1.305 g, 0.5 mmol), Pd(PPh$_3$)$_4$ (577 mg, 0.5 mmol) and NaHCO$_3$ saturated aqueous solution (3 ml) in dioxane (30 mL) was stirred at 100° C. for overnight. The mixture was diluted with EA, washed with water (30 mL×3) and brine (20 mL×1), dried over Na$_2$SO$_4$, filtered and concentrated. The crude product was purified by silica gel column chromatography to afford the desired compound (1.603 g, 80%) as a white solid. LC-MS (ESI): 405 (M+1)$^+$.

Step 8

To a solution of methyl 4-(4-(3-(piperidin-1-yl)propylamino)-1,6-naphthyridin-2-yl)benzoate (162 mg, 0.4 mmol) and LiOH·H$_2$O (41 mg, 1 mmol) in CH$_3$OH/H$_2$O (30 mL/3 mL). Then the mixture was stirred at 75° C. for 2 hours. 1 mL 1M HCl aq. was added and the mixture was adjusted to pH=5 and the residue was purified by Prep-HPLC to afford the desired compound. Isolated weight: 50 mg; Yield: 32%; Color: white; State: solid. LC-MS (ESI): 391 (M+1)$^+$. $^1$H NMR (DMSO-d$_6$) δ 9.96 (br. s., 1H), 9.06 (br. s., 1H), 8.24-8.34 (m, 2H), 8.06-8.15 (m, 2H), 7.98 (m, 1H), 7.29 (s, 1H), 3.84 (t, J=6.9 Hz, 2H), 3.58 (d, J=12.2 Hz, 2H), 3.27-3.30 (m, 2H), 2.88-2.99 (m, 2H), 2.21-2.36 (m, 2H), 1.95 (d, J=14.6 Hz, 2H), 1.69-1.89 (m, 3H), 1.40-1.59 (m, 1H).

Example 7: Synthesis of 4-(4-((3-(piperidin-1-yl)propyl)amino)-1,6-naphthyridin-2-yl)-N-(piperidin-4-yl)benzamide

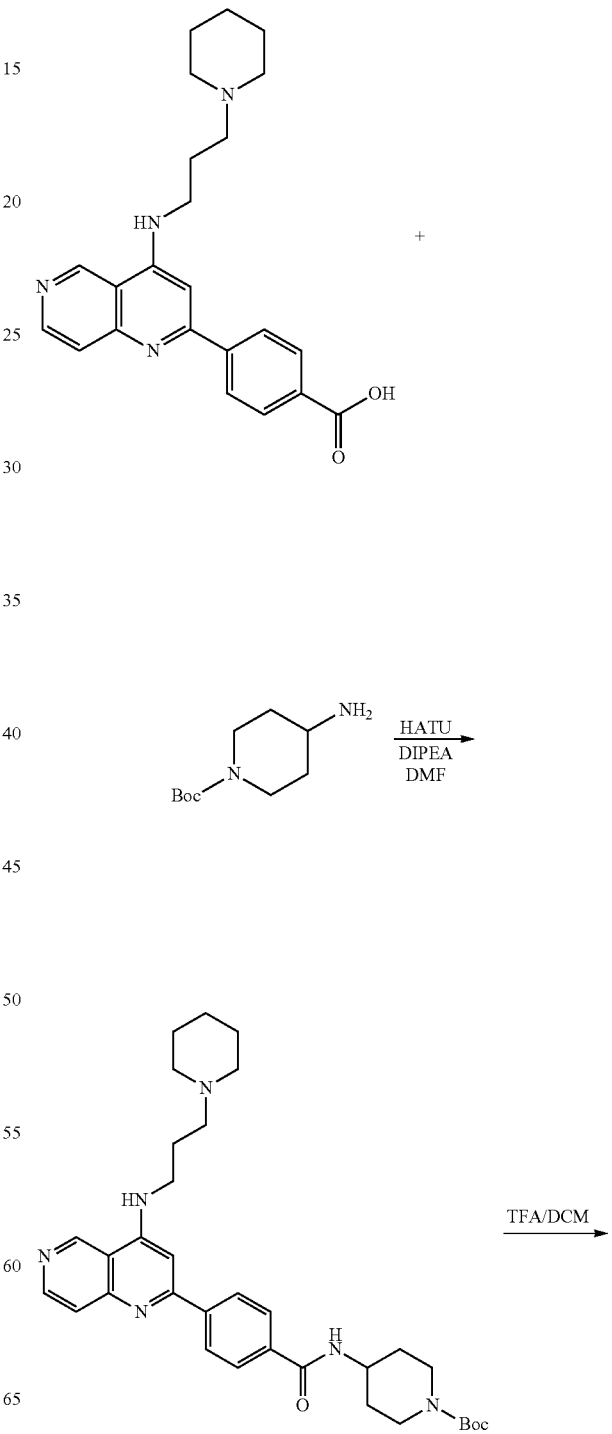

-continued

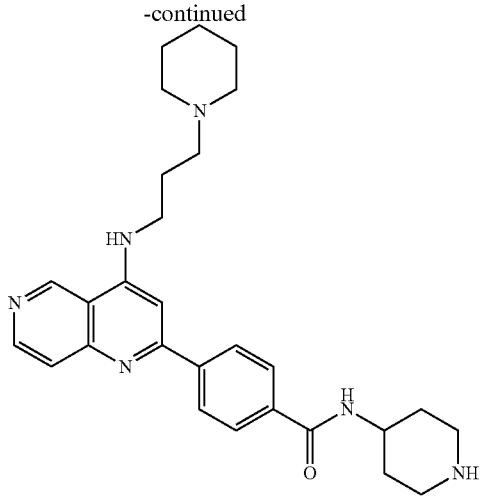

Step 1

To a solution of 4-(4-(3-(piperidin-1-yl)propylamino)-1,6-naphthyridin-2-yl)benzoic acid (117 mg, 0.3 mmol), tert-butyl 4-aminopiperidine-1-carboxylate (60 mg, 0.3 mmol), HATU (137 mg, 0.36 mmol) and DIPEA (129 mg, 1 mmol) in DMF (5 mL) and was stirred at r.t. for 2 hours. 100 mL H$_2$O was added and extracted with EA (100 mL) wash with brine, dried over Na$_2$SO$_4$. Evaporated the solvent and the residue to give desired compound which was purified by TLC to afford the desired compound. Isolated weight: 123 mg, yield: 71.5%, color: white, state: solid. LC-MS (ESI): 573 (M+1)$^+$.

Step 2

To a solution of tert-butyl 4-(4-(4-(3-(piperidin-1-yl)propylamino)-1,6-naphthyridin-2-yl)benzamido)piperidine-1-carboxylate (114 mg, 0.2 mmol) in TFA/DCM (1 mL/10 mL) and was stirred at r.t. for 2 hours. Evaporated the solvent and the residue to give desired compound which was purified by prep-HPLC to afford the desired compound. Isolated weight: 48 mg, yield: 50%, color: yellow, state: solid. LC-MS (ESI): 473 (M+1)$^+$. $^1$H NMR (CD$_3$OD) δ 9.83 (br. s., 1H), 8.93 (br. s., 1H), 8.14 (s, 4H), 7.96 (d, J=4.6 Hz, 1H), 7.30 (s, 1H), 4.25 (tt, J=11.0, 4.1 Hz, 1H), 3.86 (t, J=6.9 Hz, 2H), 3.47-3.66 (m, 4H), 3.33-3.36 (m, 2H), 3.20 (td, J=12.8, 3.0 Hz, 2H), 2.88-3.03 (m, 2H), 2.20-2.39 (m, 4H), 1.71-2.01 (m, 7H), 1.54 (qd, J=12.6, 3.9 Hz, 1H).

Example 8: Synthesis of 4-(4-((3-(piperidin-1-yl)propyl)amino)-1,6-naphthyridin-2-yl)-N-(2-(pyridin-4-yl)ethyl)benzamide

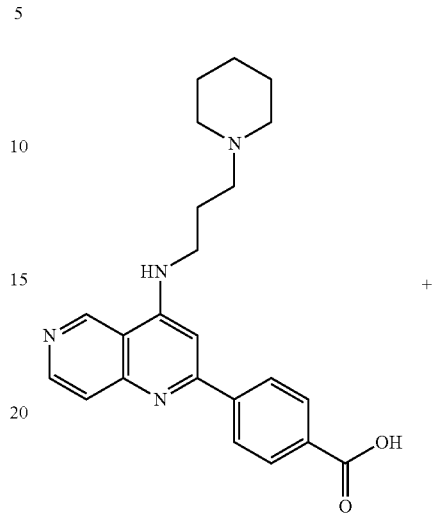

To a solution of 4-(4-(3-(piperidin-1-yl)propylamino)-1,6-naphthyridin-2-yl)benzoic acid (78 mg, 0.2 mmol), 2-(pyridin-4-yl)ethanamine (24.4 mg, 0.2 mmol), HATU (114 mg, 0.3 mmol) and DIPEA (65 mg, 0.5 mmol) in DMF (5 mL) and was stirred at r.t. for 2 hours. 100 mL H$_2$O was added and extracted with EA (100 mL) wash with brine, dried over Na$_2$SO$_4$. Evaporated the solvent and the residue to give desired compound which was purified by TLC to afford the desired compound. Isolated weight: 40 mg, yield: 40%, color: yellow, state: solid.

LC-MS (ESI): 495 (M+1)$^+$. $^1$H NMR (CD$_3$OD) δ 9.48 (s, 1H), 8.53 (d, J=6.1 Hz, 1H), 8.44 (d, J=5.8 Hz, 2H), 8.09-8.17 (m, J=8.5 Hz, 2H), 7.87-7.94 (m, J=8.2 Hz, 2H), 7.73 (d, J=5.8 Hz, 1H), 7.38 (d, J=6.1 Hz, 2H), 7.05 (s, 1H), 3.69 (t, J=7.2 Hz, 2H), 3.60 (t, J=6.7 Hz, 2H), 3.12-3.31 (m, 6H), 3.01 (t, J=7.0 Hz, 2H), 2.18-2.30 (m, 2H), 1.79-1.92 (m, 4H), 1.66 (m, 2H).

Example 9: Synthesis of N-(2-(dimethylamino)ethyl)-4-(4-((3-(piperidin-1-yl)propyl)amino)-1,6-naphthyridin-2-yl)benzamide

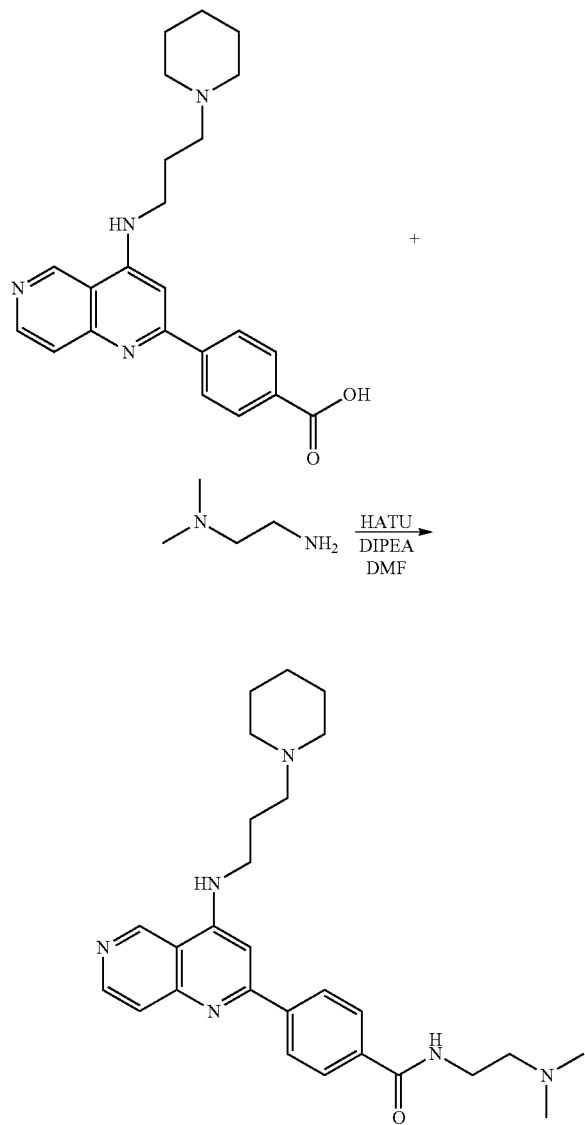

To a solution of 4-(4-(3-(piperidin-1-yl)propylamino)-1,6-naphthyridin-2-yl)benzoic acid (78 mg, 0.2 mmol), N1,N1-dimethylethane-1,2-diamine (17 mg, 0.2 mmol), HATU (114 mg, 0.3 mmol) and DIPEA (65 mg, 0.5 mmol) in DMF (5 mL) and was stirred at r.t. for 2 hours. 100 mL H$_2$O was added and extracted with EA (100 mL) wash with brine, dried over Na$_2$SO$_4$. Evaporated the solvent and the residue to give desired compound which was purified by Prep-TLC to afford the desired compound. Isolated weight: 40 mg, yield: 43%, color: white, state: solid. LC-MS (ESI): 461 (M+1)$^+$. $^1$H NMR (CD$_3$OD) δ 9.58 (s., 1H), 8.59 (d, J=6.0 Hz, 1H), 8.22 (d, J=8.8 Hz, 2H), 8.07 (d, J=8.4 Hz, 2H), 7.82 (d, J=6.0 Hz, 1H), 7.15 (s, 1H), 3.74-3.66 (m, 4H), 3.20-3.15 (m, 5H), 3.07-3.04 (m, 2H), 2.70 (s, 6H), 2.25-2.29 (m, 2H), 1.88-1.86 (m, 4H), 1.69-1.65 (m, 2H), 1.30 (s, 1H).

Example 10: Synthesis of 1-methyl-N-(3-(4-methylpiperazin-1-yl)propyl)-5-(4-((3-(piperidin-1-yl)propyl)amino)-1,6-naphthyridin-2-yl)-1H-indole-2-carboxamide

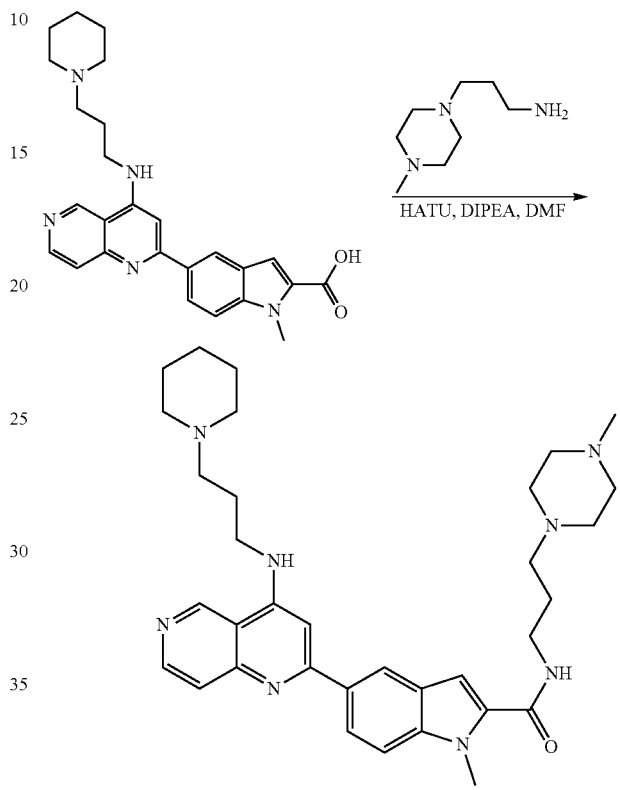

The mixture of 1-methyl-5-(4-((3-(piperidin-1-yl)propyl)amino)-1,6-naphthyridin-2-yl)-1H-indole-2-carboxylic acid (88 mg, 0.2 mmol), 3-(4-methylpiperazin-1-yl)propan-1-amine (47 mg, 0.3 mmol), HATU (91 mg, 0.24 mmol) and DIPEA (78 mg, 0.6 mmol) in DMF (3 mL) was stirred at room temperature overnight. Water (30 mL) was added, and then the mixture was extracted with EA three times. The combined organic layers were washed with water (20 mL×3) and brine (20 mL×1), dried over Na$_2$SO$_4$, filtered and concentrated. The residue was purified by the Prep-HPLC to afford 1-methyl-N-(3-(4-methylpiperazin-1-yl)propyl)-5-((3-(piperidin-1-yl)propyl)amino)-1,6-naphthyridin-2-yl)-1H-indole-2-carboxamide as a white solid (20 mg, 12% yield). LC-MS (ESI): 538.4 (M+1)$^+$; $^1$H NMR (CD$_3$OD) δ 9.83 (br, s, 1H), 8.97 (br, s, 1H), 8.38 (d, J=1.6 Hz, 1H), 7.91 (dd, J=8.8, 1.6 Hz, 2H), 7.76 (d, J=8.8 Hz, 1H), 7.24 (d, J=2.4 Hz, 2H), 4.09 (s, 3H), 3.82 (t, J=6.8 Hz, 2H), 3.56 (d, J=12.4 Hz, 2H), 3.46 (t, J=6.8 Hz, 2H), 3.32-3.39 (m, 6H), 2.86-3.13 (m, 8H), 2.83 (s, 3H), 2.28-2.35 (m, 2H), 1.93-2.00 (m, 4H), 1.74-1.87 (m, 3H), 1.50-1.56 (m, 1H).

Example 11: Synthesis of 1-methyl-5-(4-((3-(piperidin-1-yl)propyl)amino)-1,6-naphthyridin-2-yl)-N-(2-(pyridin-4-yl)ethyl)-1H-indole-2-carboxamide

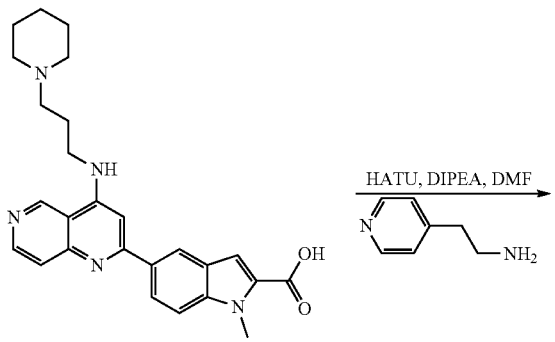

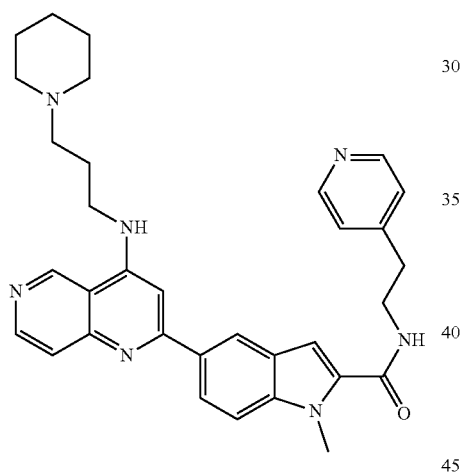

The mixture of 1-methyl-5-(4-((3-(piperidin-1-yl)propyl)amino)-1,6-naphthyridin-2-yl)-1H-indole-2-carboxylic acid (88 mg, 0.2 mmol), 2-(pyridin-4-yl)ethanamine (37 mg, 0.3 mmol), HATU (91 mg, 0.24 mmol) and DIPEA (78 mg, 0.6 mmol) in DMF (3 mL) was stirred at room temperature overnight. Water (30 mL) was added, and then the mixture was extracted with EA three times. The combined organic layers were washed with water (20 mL×3) and brine (20 mL×1), dried over Na$_2$SO$_4$, filtered and concentrated. The residue was purified by the Prep-HPLC to afford 1-methyl-5-(4-((3-(piperidin-1-yl)propyl)amino)-1,6-naphthyridin-2-yl)-N-(2-(pyridin-4-yl)ethyl)-1H-indole-2-carboxamide as a white solid (20 mg, 20% yield). LC-MS (ESI): 548.3 (M+1)$^+$; $^1$H NMR (CD$_3$OD) δ 9.79 (br, s, 1H), 8.93 (br, s, 3H), 8.38 (d, J=1.6 Hz, 1H), 8.08 (br, s, 2H), 7.91 (dd, J=8.8, 1.6 Hz, 2H), 7.74 (d, J=8.8 Hz, 1H), 7.24 (s, 1H), 7.19 (s, 1H), 4.05 (s, 3H), 3.79-3.87 (m, 4H), 3.56 (d, J=12 Hz, 2H), 3.24-3.27 (m, 4H), 2.92 (t, J=12.2 Hz, 2H), 2.28-2.35 (m, 2H), 1.94-1.97 (m, 2H), 1.74-1.86 (m, 3H), 1.50-1.57 (m, 1H).

Example 12: Synthesis of 1-methyl-5-(4-((3-(piperidin-1-yl)propyl)amino)-1,6-naphthyridin-2-yl)-N-(tetrahydro-2H-pyran-4-yl)-1H-indole-2-carboxamide

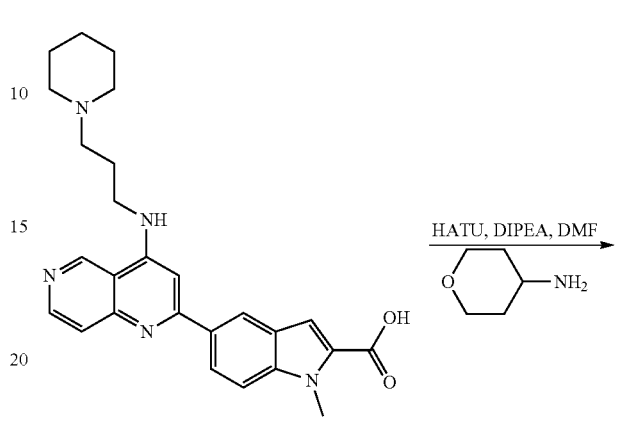

The mixture of 1-methyl-5-(4-((3-(piperidin-1-yl)propyl)amino)-1,6-naphthyridin-2-yl)-1H-indole-2-carboxylic acid (65 mg, 0.15 mmol), tetrahydro-2H-pyran-4-amine (20 mg, 0.19 mmol), HATU (87 mg, 0.26 mmol) and DIPEA (58 mg, 0.45 mmol) in DMF (3 mL) was stirred at room temperature overnight. Water (30 mL) was added, and then the mixture was extracted with EA three times. The combined organic layers were washed with water (20 mL×3) and brine (20 mL×1), dried over Na$_2$SO$_4$, filtered and concentrated. The residue was purified by the Prep-HPLC to afford 1-methyl-5-(4-((3-(piperidin-1-yl)propyl)amino)-1,6-naphthyridin-2-yl)-N-(tetrahydro-2H-pyran-4-yl)-1H-indole-2-carboxamide as a white solid (15 mg, 19% yield). LC-MS (ESI): 527.3 (M+1)$^+$; $^1$H NMR (CD$_3$OD) δ 9.47 (br, s, 1H), 8.58 (br, s, 1H), 8.34 (s, 1H), 8.00 (d, J=8.8 Hz, 1H), 7.79 (s, 1H), 7.60 (d, J=8.8 Hz, 1H), 7.17 (s, 1H), 7.08 (s, 1H), 4.09-4.17 (m, 1H), 4.05 (s, 3H), 4.00 (d, J=8.8 Hz, 2H), 3.52-3.62 (m, 4H), 2.95-3.11 (m, 6H), 2.11-2.19 (m, 2H), 1.92-1.96 (m, 2H), 1.70-1.79 (m, 6H), 1.60 (s, 2H).

Example 13: Synthesis of N-(1,1-dioxidotetrahydro-2H-thiopyran-4-yl)-1-methyl-5-(4-((3-(piperidin-1-yl)propyl)amino)-1,6-naphthyridin-2-yl)-1H-indole-2-carboxamide Example 14: Synthesis of N,N-diethyl-4-(4-((3-(piperidin-1-yl)propyl)amino)-1,6-naphthyridin-2-yl)-3-(trifluoromethyl)benzamide

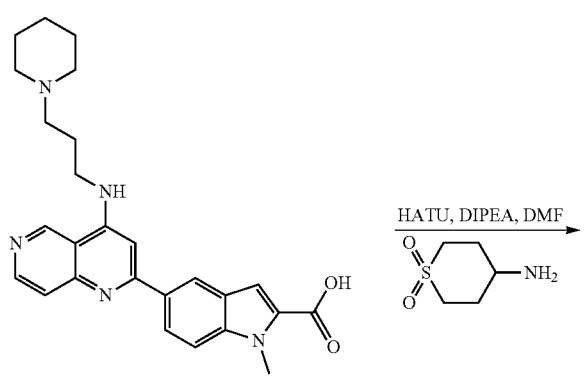

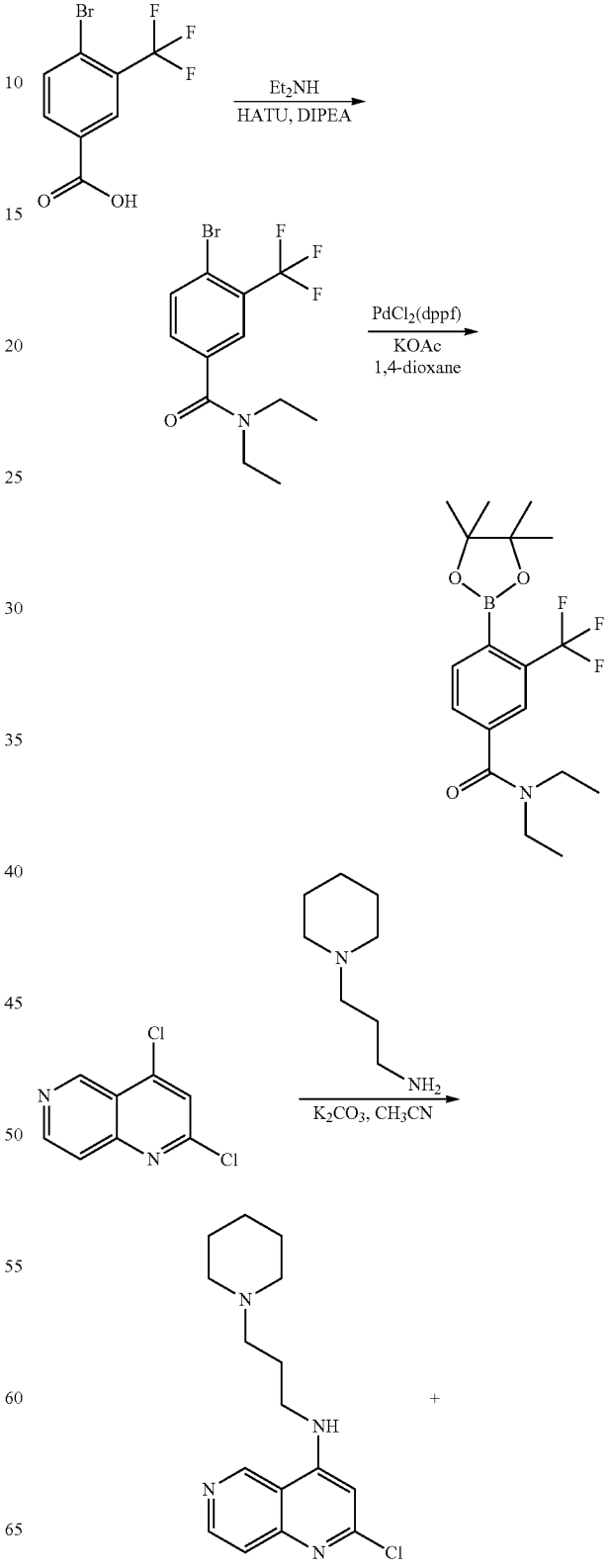

The mixture of 1-methyl-5-(4-((3-(piperidin-1-yl)propyl)amino)-1,6-naphthyridin-2-yl)-1H-indole-2-carboxylic acid (65 mg, 0.15 mmol), 4-aminotetrahydro-2H-thiopyran 1,1-dioxide (28 mg, 0.19 mmol), HATU (87 mg, 0.26 mmol) and DIPEA (58 mg, 0.45 mmol) in DMF (3 mL) was stirred at room temperature overnight. Water (30 mL) was added, and then the mixture was extracted with EA three times. The combined organic layers were washed with water (20 mL×3) and brine (20 mL×1), dried over $Na_2SO_4$, filtered and concentrated. The residue was purified by the Prep-HPLC to afford N-(1,1-dioxidotetrahydro-2H-thiopyran-4-yl)-1-methyl-5-(4-((3-(piperidin-1-yl)propyl)amino)-1,6-naphthyridin-2-yl)-1H-indole-2-carboxamide as a white solid (19 mg, 22% yield). LC-MS (ESI): 575.3 (M+1)$^+$; $^1$H NMR ($CD_3OD$) δ 8.89 (br, s, 1H), 8.03 (br, s, 1H), 7.03-7.05 (m, 2H), 6.87 (d, J=8.8 Hz, 1H), 6.36 (d, J=6.8 Hz, 2H), 3.34-3.40 (m, 1H), 3.19 (s, 3H), 2.94 (t, J=6.8 Hz, 2H), 2.67 (d, J=12.8 Hz, 2H), 2.46-2.49 (m, 4H), 2.23 (d, J=11.6 Hz, 3H), 2.06 (t, J=12.8 Hz, 2H), 1.37-1.45 (m, 7H), 1.04-1.15 (m, 2H), 0.91-0.94 (m, 3H).

-continued

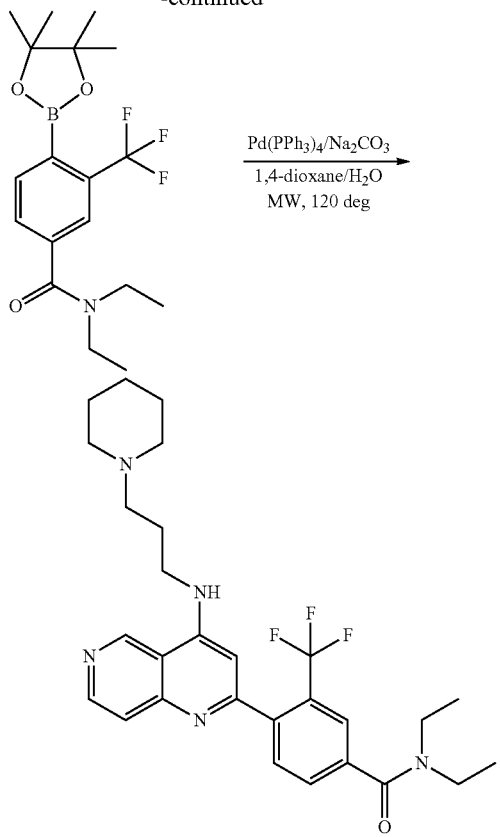

Step 1

To a mixture of 4-bromo-3-(trifluoromethyl)benzoic acid (1 g, 3.73 mmol) and HATU (1.7 g, 4.47 mmol) in DCM (20 mL) was added diethylamine (386 µl, 3.73 mmol) and DIPEA (2 ml, 11.2 mmol), then the mixture was stirred at rt overnight. The reaction mixture was poured into water (20 mL), extracted with DCM (10 mL×3), the combined organic layers was washed with water and brine, dried over $Na_2SO_4$, the drying agent was filtered off and the filtrate was concentrated in vacuo to get the residue which was purified with Combiflash (silica gel, eluting with 20% EA in PE) to afford 4-bromo-N,N-diethyl-3-(trifluoromethyl)benzamide (1.2 g, 99%) as a colorless oil. HPLC/UV purity: 92%; LC-MS (ESI): 324 (M+1)$^+$.

Step 2

The mixture of 4-bromo-N,N-diethyl-3-(trifluoromethyl) benzamide (1.2 g, 3.7 mmol), 4,4,4',4',5,5,5',5'-octamethyl-2,2'-bi(1,3,2-dioxaborolane)(1.13 g, 4.4 mmol), Pd(dppf)Cl$_2$ (302 mg, 0.37 mmol) and KOAc (710 mg, 16.2 mmol) in 1,4-Dioxane (20 mL) was heated to 100° C. and held for 18 hrs under N$_2$ atmosphere. The reaction mixture was cooled to rt and filtered by a pad of celite, the resulting filtrate was concentrated under the reduced pressure to get the residue which was purified with Combiflash ((silica gel, eluting with 25% EA in PE) to afford N,N-diethyl-4-(4,4,5,5-tetramethyl-1,3,2-dioxaborolan-2-yl)-3-(trifluoromethyl)benzamide (1.2 g, 87%) as an oil. HPLC/UV purity: 80%; LC-MS (ESI): 372 (M+1)$^+$.

Step 3

The mixture of 2,4-dichloro-1,6-naphthyridine (1 g, 5 mmol), 3-(piperidin-1-yl)propan-1-amine (710 mg, 5 mmol) and K$_2$CO$_3$ (1.38 g, 10 mmol) in CH$_3$CN (20 mL) was heated to 80° C. until TLC analysis indicated the total consumption of the starting material. The reaction mixture was filtered and the filtrate was concentrated to get the residue which was purified with Combiflash (silica gel, eluting with 10% methanol in DCM) to afford the mixture of 2-chloro-N-(3-(piperidin-1-yl)propyl)-1,6-naphthyridin-4-amine and 4-chloro-N-(3-(piperidin-1-yl)propyl)-1,6-naphthyridin-2-amine, the mixture was impossible to separate, so it was used to the next step without further purification.

Step 4

A 20-mL microwave vial was charged with 2-chloro-N-(3-(piperidin-1-yl)propyl)-1,6-naphthyridin-4-amine (200 mg, 0.655 mmol), N,N-diethyl-4-(4,4,5,5-tetramethyl-1,3,2-dioxaborolan-2-yl)-3-(trifluoromethyl)benzamide (365 mg, 0.983 mmol), Pd(PPh$_3$)$_4$ (75 mg, 0.0655 mmol) and Na$_2$CO$_3$ (138 mg, 1.31 mmol) dissolved 1,4-dioxane (3 mL) and H$_2$O (0.5 mL). A stir bar is added, the vial is sealed, and the resulting brown solution is heated for 2 h in a Biotage Initiator Eight Microwave Reactor held at a constant temperature of 120° C. The resulting solutions were concentrated by rotary evaporation (55° C., 20 mmHg). The adsorbed material was loaded onto a column and purified using Prep-TLC (silica gel, eluting with 10% methanol in DCM) to afford N,N-diethyl-4-(4-((3-(piperidin-1-yl)propyl)amino)-1,6-naphthyridin-2-yl)-3-(trifluoromethyl)benzamide (40 mg, 12%) as a yellow solid HPLC/UV purity: 94%; LC-MS (ESI): 514 (M+1)$^+$. $^1$H NMR (DMSO-d$_6$) δ 9.55 (s, 1H), 8.62 (d, J=5.8 Hz, 1H), 7.86 (s, 1H), 7.75-7.81 (m, 1H), 7.66-7.73 (m, 2H), 6.80 (s, 1H), 3.49-3.68 (m, 4H), 3.33 (d, J=1.8 Hz, 2H), 3.03-3.18 (m, 4H), 2.10-2.22 (m, 2H), 1.82 (m, 4H), 1.65 (m, 2H), 1.29 (d, J=5.2 Hz, 5H), 1.11-1.22 (m, 3H).

Example 15: Synthesis of 4-(4-((3-(piperidin-1-yl)propyl)amino)-1,6-naphthyridin-2-yl)-N-(piperidin-4-yl)-3-(trifluoromethyl)benzamide

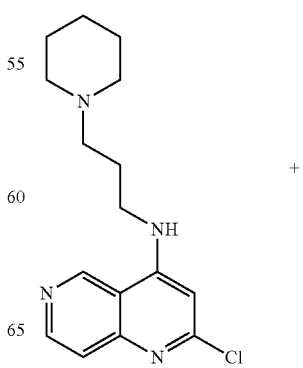

+

143

-continued

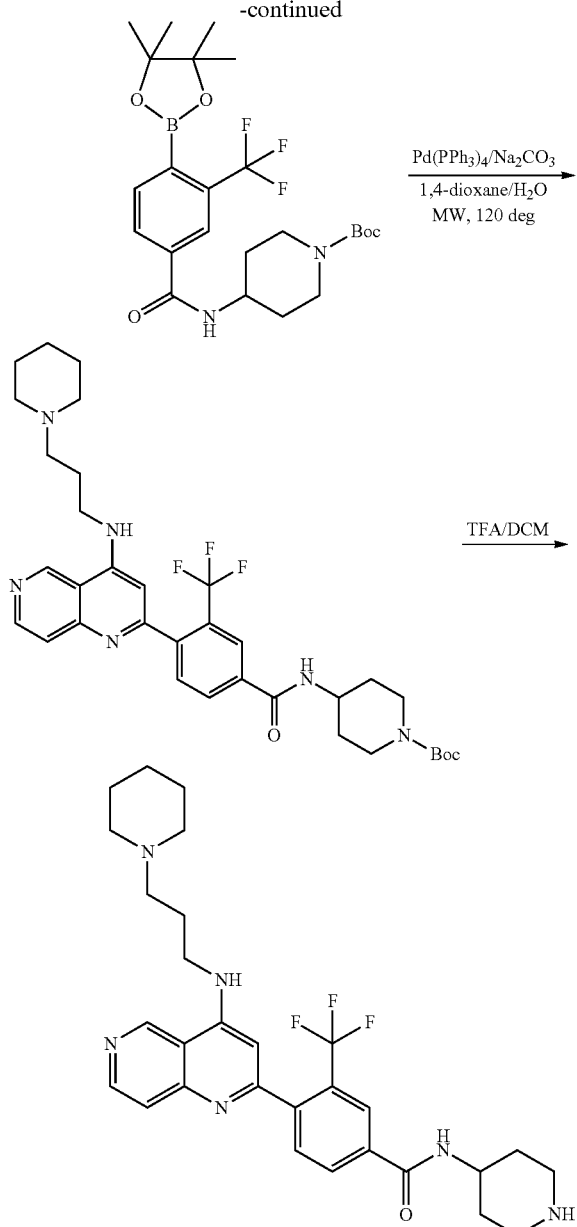

144

(trifluoromethyl)benzamide (40 mg, 11%) as a yellow solid HPLC/UV purity: 94%; LC-MS (ESI): 641 (M+1)⁺.

Step 2

To a solution of N,N-diethyl-4-(4-((3-(piperidin-1-yl)propyl)amino)-1,6-naphthyridin-2-yl)-3-(trifluoromethyl)benzamide (35 mg, 0.057 mmol) in DCM (1 mL) was added TFA (1 mL), then the reaction mixture was stirred at rt for 2 hrs. The solvent was removed under the reduced pressure to get the crude product which was purified with Prep-HPLC (Welch, XB-C18, 21.2 mm*250 mm, 10 um, eluting with 20% CH₃CN in 1‰ TFA in H₂O) to afford 4-(4-((3-(piperidin-1-yl)propyl)amino)-1,6-naphthyridin-2-yl)-N-(piperidin-4-yl)-3-(trifluoromethyl)benzamide (30 mg, 90%) as a TFA salt. HPLC/UV purity: 96%; LC-MS (ESI): 541 (M+1)⁺; $^1$H NMR (CD₃OD) δ 9.80 (s, 1H), 8.89 (d, J=6.1 Hz, 1H), 8.46 (s, 1H), 8.34 (d, J=7.9 Hz, 1H), 7.89 (d, J=7.9 Hz, 1H), 7.77 (d, J=6.1 Hz, 1H), 7.15 (s, 1H), 4.15-4.32 (m, 1H), 3.73 (t, J=7.0 Hz, 2H), 3.53 (t, J=14.0 Hz, 4H), 3.12-3.27 (m, 4H), 2.93 (t, J=12.4 Hz, 2H), 2.18-2.32 (m, 4H), 1.90-1.98 (m, 4H), 1.74-1.90 (m, 3H), 1.50 (d, J=12.2 Hz, 1H).

Example 16: Synthesis of 1-methyl-5-(4-(3-(piperidin-1-yl)propylamino)-1,6-naphthyridin-2-yl)-N-(tetrahydro-2H-thiopyran-4-yl)-1H-indole-2-carboxamide

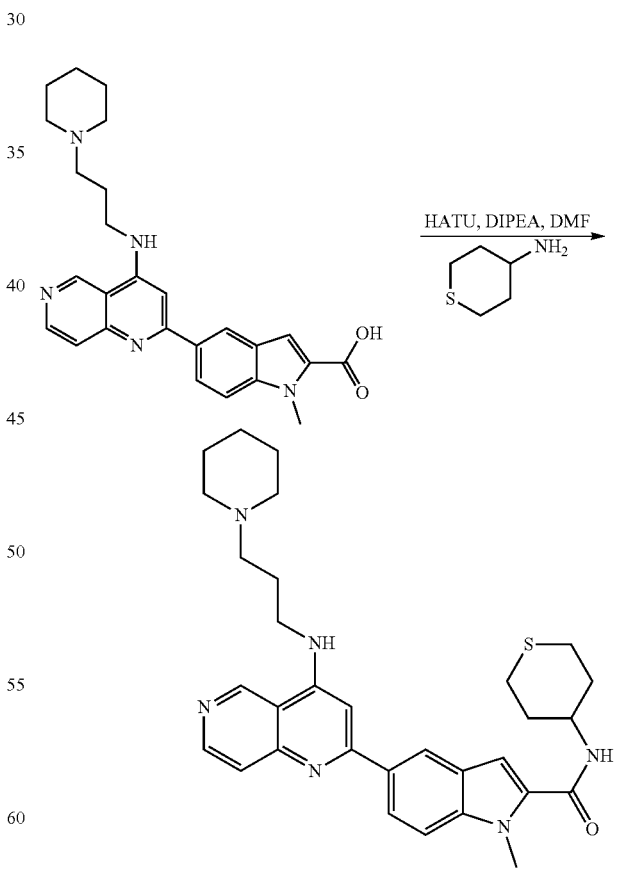

Step 1

A 20-mL microwave vial was charged with 2-chloro-N-(3-(piperidin-1-yl)propyl)-1,6-naphthyridin-4-amine (200 mg, 0.655 mmol), tert-butyl 4-(4-(4,4,5,5-tetramethyl-1,3,2-dioxaborolan-2-yl)-3-(trifluoromethyl)benzamido)piperidine-1-carboxylate (488 mg, 0.983 mmol), Pd(PPh₃)₄ (75 mg, 0.0655 mmol) and Na₂CO₃ (138 mg, 1.31 mmol) dissolved 1,4-dioxane (3 mL) and H₂O (0.5 mL). A stir bar is added, the vial is sealed, and the resulting brown solution is heated for 2 h in a Biotage Initiator Eight Microwave Reactor held at a constant temperature of 120° C. The resulting solutions were concentrated by rotary evaporation (55° C., 20 mmHg). The adsorbed material was loaded onto a column and purified using Prep-TLC (silica gel, eluting with 10% methanol in DCM) to afford N,N-diethyl-4-(4-((3-(piperidin-1-yl)propyl)amino)-1,6-naphthyridin-2-yl)-3-

The mixture of 1-methyl-5-(4-((3-(piperidin-1-yl)propyl)amino)-1,6-naphthyridin-2-yl)-1H-indole-2-carboxylic acid (35 mg, 0.08 mmol), tetrahydro-2H-thiopyran-4-amine (14 mg, 0.12 mmol), HATU (36 mg, 0.09 mmol) and DIPEA (31 mg, 0.24 mmol) in DMF (1 mL) was stirred at room temperature overnight. Water (30 mL) was added, and then the mixture was extracted with EA three times. The combined organic layers were washed with water (20 mL×3) and brine (20 mL×1), dried over Na$_2$SO$_4$, filtered and concentrated. The residue was purified by the Prep-HPLC to afford 1-methyl-5-(4-(3-(piperidin-1-yl)propylamino)-1,6-naphthyridin-2-yl)-N-(tetrahydro-2H-thiopyran-4-yl)-1H-indole-2-carboxamide as a yellow oil (14.7 mg, 35% yield). LC-MS (ESI): 543.2 (M+1)$^+$; 1H NMR (CD$_3$OD) δ 9.71 (s, 1H), 8.85 (d, J=5.8 Hz, 1H), 8.39 (d, J=1.6 Hz, 1H), 7.87-7.97 (m, 2H), 7.76 (d, J=8.9 Hz, 1H), 7.25 (s, 1H), 7.23 (s, 1H), 4.07 (s, 3H), 3.78-3.97 (m, 3H), 3.59 (d, J=12.2 Hz, 2H), 3.32-3.36 (m, 2H), 2.96 (t, J=12.5 Hz, 2H), 2.78-2.89 (m, 2H), 2.63-2.74 (m, 2H), 2.20-2.37 (m, 4H), 1.95 (d, J=14.3 Hz, 2H), 1.69-1.87 (m, 5H), 1.51 (d, J=12.2 Hz, 1H).

Example 17: Synthesis of 1-methyl-N-(1-methylpiperidin-4-yl)-5-(4-(propylamino)-1,6-naphthyridin-2-yl)-1H-indole-2-carboxamide

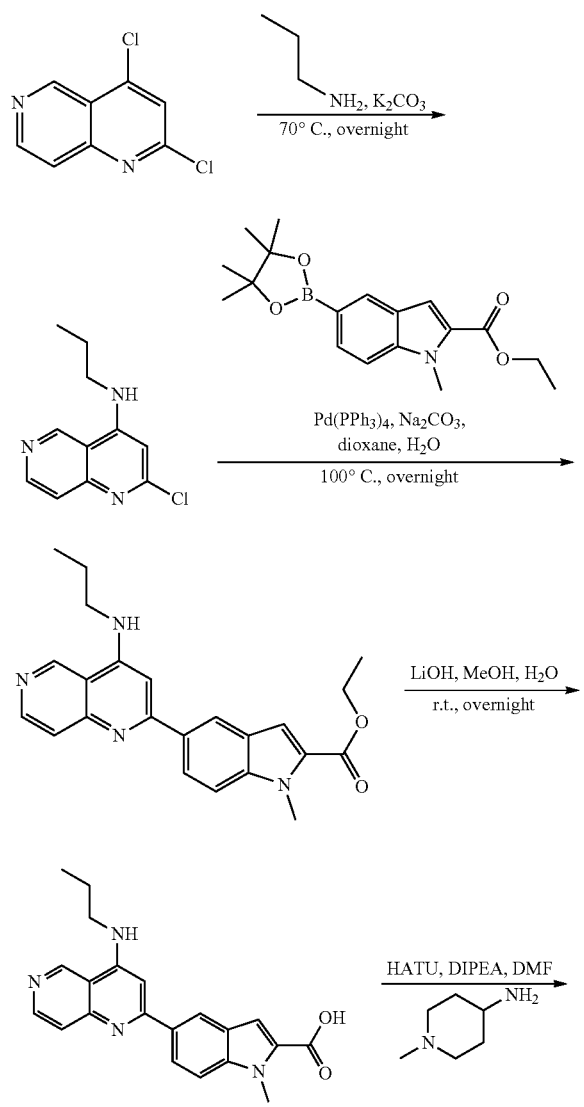

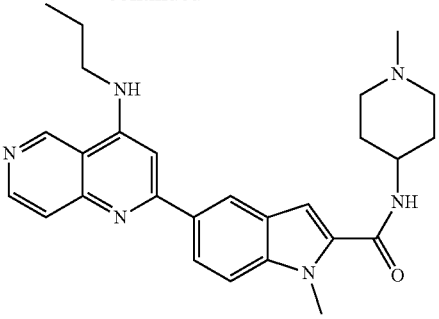

Step 1

The mixture of 2,4-dichloro-1,6-naphthyridine (1 g, 5.07 mmol), propan-1-amine (299 mg, 5.07 mmol) and K$_2$CO$_3$ (1.4 g, 10.14 mmol) in acetonitrile (30 ml) was heated to 90° C. overnight. After cooling to room temperature, water (40 mL) was added, and then the mixture was extracted with EA three times. The combined organic layers were washed with water (20 mL×1) and brine (15 mL×1), dried over Na$_2$SO$_4$, filtered and concentrated. The residue was purified by the flash column chromatography (silica gel, eluting with PE to EA) to afford 2-chloro-N-propyl-1,6-naphthyridin-4-amine as a yellow solid (0.33 g, 30% yield). LC-MS (ESI): 222.0 (M+1)$^+$.

Step 2

The mixture of 2-chloro-N-propyl-1,6-naphthyridin-4-amine (300 mg, 1.35 mmol, and ethyl 1-methyl-5-(4,4,5,5-tetramethyl-1,3,2-dioxaborolan-2-yl)-1H-indole-2-carboxylate (534 mg, 1.62 mmol), Na$_2$CO$_3$ (286 mg, 2.7 mmol) and Pd(PPh$_3$)$_4$ (312 mg, 0.27 mmol) in dioxane/H$_2$O (10 mL/2 mL) protected by N$_2$ atmosphere was heated to 100° C. overnight. After cooling to room temperature, water (30 mL) was added, and then the mixture was extracted with EA three times. The combined organic layers were washed with water (20 mL×3) and brine (15 mL×1), dried over Na$_2$SO$_4$, filtered and concentrated. The residue was purified by the flash column chromatography (silica gel, eluting with DCM to 10% MeOH in DCM) to afford ethyl 1-methyl-5-(4-(propylamino)-1,6-naphthyridin-2-yl)-1H-indole-2-carboxylate as a yellow solid (322 mg, 61% yield). LC-MS (ESI): 389.1 (M+1)$^+$; $^1$H NMR (DMSO-d$_6$) δ 9.60 (s, 1H), 8.51-8.62 (m, 2H), 8.28 (dd, J=8.9, 1.6 Hz, 1H), 7.79 (br. s., 1H), 7.73 (d, J=8.9 Hz, 1H), 7.67 (d, J=5.6 Hz, 1H), 7.43 (s, 1H), 7.13 (s, 1H), 4.37 (m, J=7.0 Hz, 2H), 4.01-4.13 (m, 3H), 3.39-3.50 (m, 2H), 1.70-1.85 (m, 2H), 1.37 (t, J=7.1 Hz, 3H), 1.05 (t, J=7.4 Hz, 3H).

Step 3

The mixture of Ethyl 1-methyl-5-(4-(propylamino)-1,6-naphthyridin-2-yl)-1H-indole-2-carboxylate (322 mg, 0.83 mmol) and LiOH·H$_2$O (348 mg, 8.3 mmol) in MeOH/H$_2$O (15 mL/3 mL) was stirred at room temperature overnight. The mixture was acidified with HCl aqueous solution (2 M) to pH=2, then concentrated to give the crude product that was used directly in the next step without further purification. LC-MS (ESI): 361.1 (M+1)$^+$.

Step 4

The mixture of 1-methyl-5-(4-(propylamino)-1,6-naphthyridin-2-yl)-1H-indole-2-carboxylic acid (100 mg, 0.28 mmol), 1-methylpiperidin-4-amine (0.05 ml, 0.41 mmol), HATU (128 mg, 0.34 mmol) and DIPEA (0.15 ml, 0.84 mmol) in DMF (2 mL) was stirred at room temperature overnight. Water (30 mL) was added, and then the mixture was extracted with EA three times. The combined organic layers were washed with water (20 mL×3) and brine (20 mL×1), dried over Na$_2$SO$_4$, filtered and concentrated. The residue was purified by the Prep-HPLC to afford 1-methyl-N-(1-methylpiperidin-4-yl)-5-(4-(propylamino)-1,6-naphthyridin-2-yl)-1H-indole-2-carboxamide as a yellow solid (8 mg, 6% yield). LC-MS (ESI): 457.2 (M+1)$^+$; $^1$H NMR (CD$_3$OD) δ 9.72 (s, 1H), 8.84 (d, J=5.8 Hz, 1H), 8.34-8.40 (d, J=1.6 Hz, 1H), 7.87-7.95 (m, 2H), 7.76 (d, J=8.9 Hz, 1H), 7.29 (s, 1H), 7.19 (s, 1H), 4.19 (s, 1H), 4.09 (s, 3H), 3.71 (t, J=7.3 Hz, 2H), 3.62 (d, J=12.5 Hz, 2H), 3.11-3.26 (m, 2H), 2.91 (s, 3H), 2.28 (d, J=14.3 Hz, 2H), 1.96-2.06 (m, 2H), 1.84-1.94 (m, 2H), 1.12 (t, J=7.5 Hz, 3H).

Example 18: Synthesis of 1-methyl-5-(4-(methylamino)-1,6-naphthyridin-2-yl)-N-(1-methylpiperidin-4-yl)-1H-indole-2-carboxamide

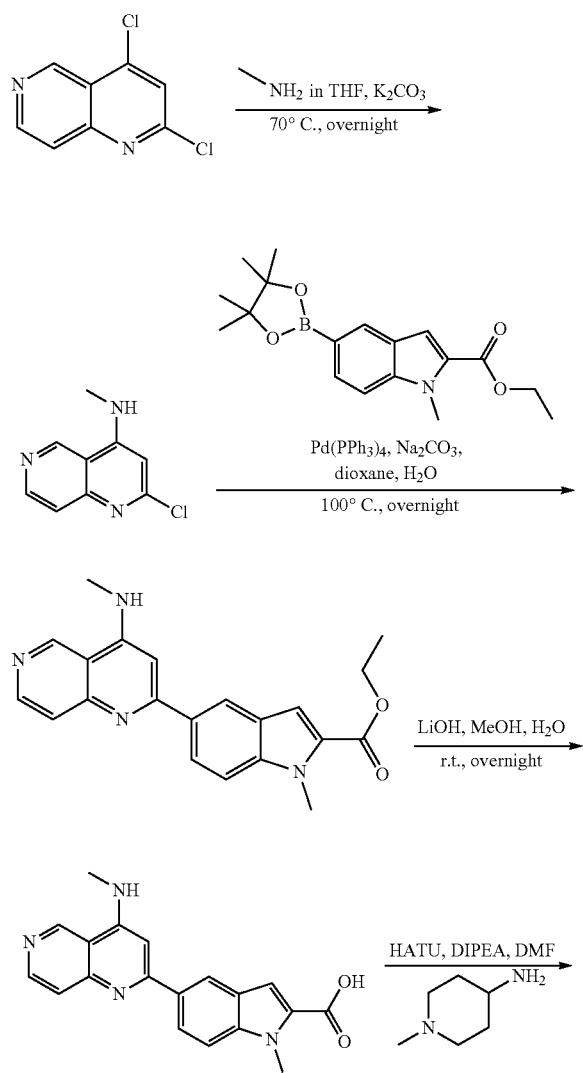

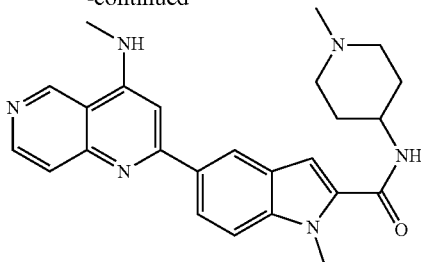

Step 1

The mixture of 2,4-dichloro-1,6-naphthyridine (1 g, 5.0 mmol), methanamine in THF (2.5 ml, 5.0 mmol) and K$_2$CO$_3$ (1.38 g, 10.0 mmol) in acetonitrile (30 ml) was heated to 90° C. overnight. After cooling to room temperature, water (40 mL) was added, and then the mixture was extracted with EA three times. The combined organic layers were washed with water (20 mL×1) and brine (20 mL×1), dried over Na$_2$SO$_4$, filtered and concentrated. The residue was purified by the flash column chromatography (silica gel, eluting with PE to EA) to afford 2-chloro-N-methyl-1,6-naphthyridin-4-amine as a yellow solid (0.16 g, 17% yield). LC-MS (ESI): 194.0 (M+1)$^+$.

Step 2

The mixture of 2-chloro-N-methyl-1,6-naphthyridin-4-amine (160 mg, 0.83 mmol, and ethyl 1-methyl-5-(4,4,5,5-tetramethyl-1,3,2-dioxaborolan-2-yl)-1H-indole-2-carboxylate (286 mg, 0.87 mmol), Na$_2$CO$_3$ (175 mg, 1.66 mmol) and Pd(PPh$_3$)$_4$ (191 mg, 0.16 mmol) in dioxane/H$_2$O (10 mL/2 mL) protected by N$_2$ atmosphere was heated to 100° C. overnight. After cooling to room temperature, water (30 mL) was added, and then the mixture was extracted with EA three times. The combined organic layers were washed with water (20 mL×3) and brine (20 mL×1), dried over Na$_2$SO$_4$, filtered and concentrated. The residue was purified by the flash column chromatography (silica gel, eluting with DCM to 10% MeOH in DCM) to afford ethyl 1-methyl-5-(4-(methylamino)-1,6-naphthyridin-2-yl)-1H-indole-2-carboxylate as a yellow solid (100 mg, 33% yield). LC-MS (ESI): 361.1 (M+1)$^+$.

Step 3

The mixture of ethyl 1-methyl-5-(4-(methylamino)-1,6-naphthyridin-2-yl)-1H-indole-2-carboxylate (100 mg, 0.27 mmol) and LiOH·H$_2$O (116 mg, 2.7 mmol) in MeOH/H$_2$O (5 mL/1 mL) was stirred at room temperature overnight. The mixture was acidified with HCl solution (2 M) to pH=2, then concentrated to give the crude product that was used directly in the next step without further purification. LC-MS (ESI): 333.1 (M+1)$^+$.

Step 4

The mixture of 1-methyl-5-(4-(methylamino)-1,6-naphthyridin-2-yl)-1H-indole-2-carboxylic acid (92 mg, 0.28 mmol), 1-methylpiperidin-4-amine (0.05 ml, 0.42 mmol), HATU (128 mg, 0.34 mmol) and DIPEA (0.15 ml, 0.87 mmol) in DMF (2 mL) was stirred at room temperature overnight. Water (30 mL) was added, and then the mixture was extracted with EA three times. The combined organic layers were washed with water (20 mL×3) and brine (20 mL×1), dried over Na₂SO₄, filtered and concentrated. The residue was purified by the Prep-HPLC to afford 1-methyl-5-(4-(methylamino)-1,6-naphthyridin-2-yl)-N-(1-methylpiperidin-4-yl)-1H-indole-2-carboxamide as a yellow oil (2.6 mg, 2% yield). LC-MS (ESI): 429.2 (M+1)⁺; 1H NMR (CD₃OD) δ 9.44 (s, 1H), 8.63 (d, J=6.1 Hz, 1H), 8.38 (d, J=1.6 Hz, 1H), 7.94-8.02 (m, 1H), 7.80 (d, J=5.8 Hz, 1H), 7.66 (d, J=8.9 Hz, 1H), 7.24 (s, 1H), 7.03 (s, 1H), 4.15 (t, J=10.8 Hz, 1H), 4.06 (s, 3H), 3.47 (d, J=12.5 Hz, 2H), 3.19 (s, 3H), 2.98-3.13 (m, 2H), 2.81 (s, 3H), 2.22 (d, J=11.3 Hz, 2H), 1.89-2.01 (m, 2H).

Example 19: Synthesis of 5-(4-(ethylamino)-1,6-naphthyridin-2-yl)-1-methyl-N-(1-methylpiperidin-4-yl)-1H-indole-2-carboxamide

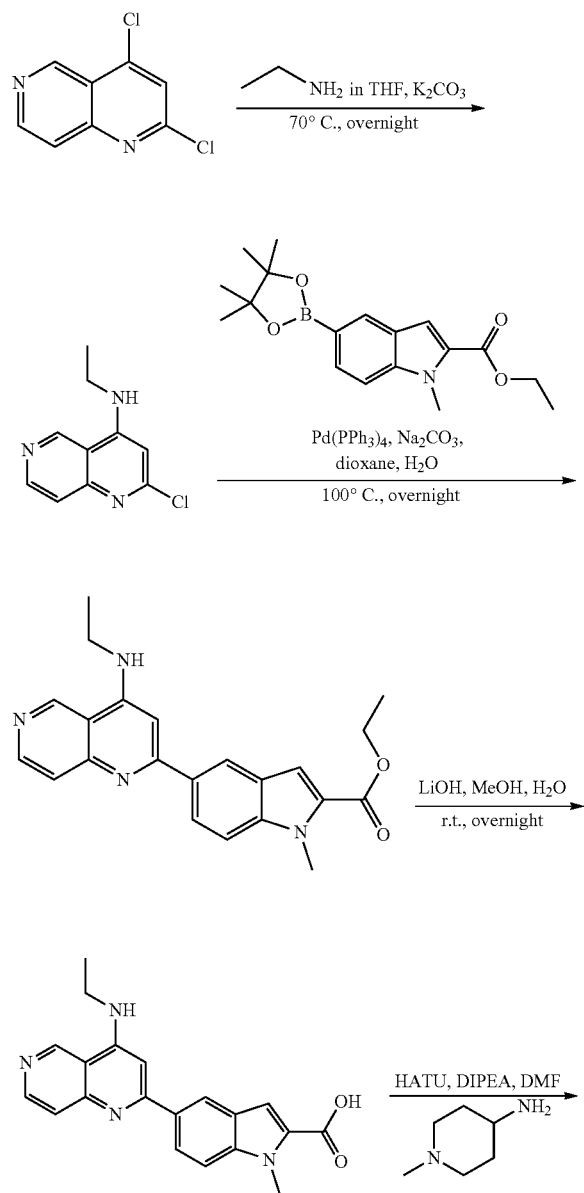

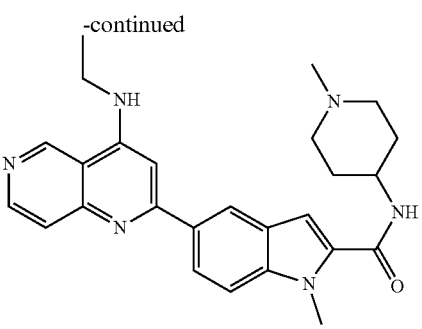

Step 1

The mixture of 2,4-dichloro-1,6-naphthyridine (1 g, 5.0 mmol), ethanamine in THF (2.5 ml, 5.0 mmol) and K₂CO₃ (1.38 g, 10.0 mmol) in acetonitrile (30 ml) was heated to 90° C. overnight. After cooling to room temperature, water (40 mL) was added, and then the mixture was extracted with EA three times. The combined organic layers were washed with water (20 mL×1) and brine (20 mL×1), dried over Na₂SO₄, filtered and concentrated. The residue was purified by the flash column chromatography (silica gel, eluting with PE to EA) to afford 2-chloro-N-ethyl-1,6-naphthyridin-4-amine as a yellow solid (0.24 g, 23% yield). LC-MS (ESI): 208.0 (M+1)⁺.

Step 2

The mixture of 2-chloro-N-ethyl-1,6-naphthyridin-4-amine (216 mg, 1.04 mmol, and ethyl 1-methyl-5-(4,4,5,5-tetramethyl-1,3,2-dioxaborolan-2-yl)-1H-indole-2-carboxylate (360 mg, 1.09 mmol), Na₂CO₃ (220 mg, 2.08 mmol) and Pd(PPh₃)₄ (240 mg, 0.21 mmol) in dioxane/H₂O (10 mL/2 mL) protected by N₂ atmosphere was heated to 100° C. overnight. After cooling to room temperature, water (30 mL) was added, and then the mixture was extracted with EA three times. The combined organic layers were washed with water (20 mL×3) and brine (20 mL×1), dried over Na₂SO₄, filtered and concentrated. The residue was purified by the flash column chromatography (silica gel, eluting with DCM to 10% MeOH in DCM) to afford ethyl 5-(4-(ethylamino)-1,6-naphthyridin-2-yl)-1-methyl-1H-indole-2-carboxylate as a yellow solid (135 mg, 34% yield). LC-MS (ESI): 375.1 (M+1)⁺.

Step 3

The mixture of ethyl 5-(4-(ethylamino)-1,6-naphthyridin-2-yl)-1-methyl-1H-indole-2-carboxylate (135 mg, 0.36 mmol) and LiOH·H₂O (151 mg, 3.6 mmol) in MeOH/H₂O (5 mL/1 mL) was stirred at room temperature overnight. The mixture was acidified with HCl solution (2 M) to pH=2, then concentrated to give the crude product that was used directly in the next step without further purification. LC-MS (ESI): 347.1 (M+1)⁺.

Step 4

The mixture of 5-(4-(ethylamino)-1,6-naphthyridin-2-yl)-1-methyl-1H-indole-2-carboxylic acid (125 mg, 0.36 mmol), 1-methylpiperidin-4-amine (0.06 ml, 0.54 mmol), HATU (164 mg, 0.43 mmol) and DIPEA (0.19 ml, 1.08 mmol) in DMF (2 mL) was stirred at room temperature overnight. Water (30 mL) was added, and then the mixture was extracted with EA three times. The combined organic layers were washed with water (20 mL×3) and brine (20 mL×1), dried over Na₂SO₄, filtered and concentrated. The residue was purified by the Prep-HPLC to afford 5-(4-(ethylamino)-1,6-naphthyridin-2-yl)-1-methyl-N-(1-methylpiperidin-4-yl)-1H-indole-2-carboxamide as a yellow solid (11.1 mg, 7% yield). LC-MS (ESI): 443.2 (M+1)⁺; ¹H NMR (DMSO-d₆) δ 9.78 (s, 1H), 9.46 (br. s., 1H), 8.84 (d, J=5.8 Hz, 1H), 8.59 (d, J=7.0 Hz, 1H), 8.40 (d, J=1.2 Hz, 1H), 7.98 (d, J=7.5 Hz, 1H), 7.92 (d, J=6.0 Hz, 1H), 7.81 (d, J=9.0 Hz, 1H), 7.31 (s, 1H), 7.18 (s, 1H), 4.06 (s, 5H), 3.74 (dt, J=13.1, 6.9 Hz, 3H), 3.12 (m, 2H), 2.80 (s, 3H), 2.00-2.18 (m, 2H), 1.85 (d, J=11.8 Hz, 2H), 1.38 (t, J=7.3 Hz, 3H).

Example 20: Synthesis of 1-methyl-N-(1-methylpiperidin-4-yl)-5-(4-((4-(pyrrolidin-1-ylmethyl)phenyl)amino)-1,6-naphthyridin-2-yl)-1H-indole-2-carboxamide

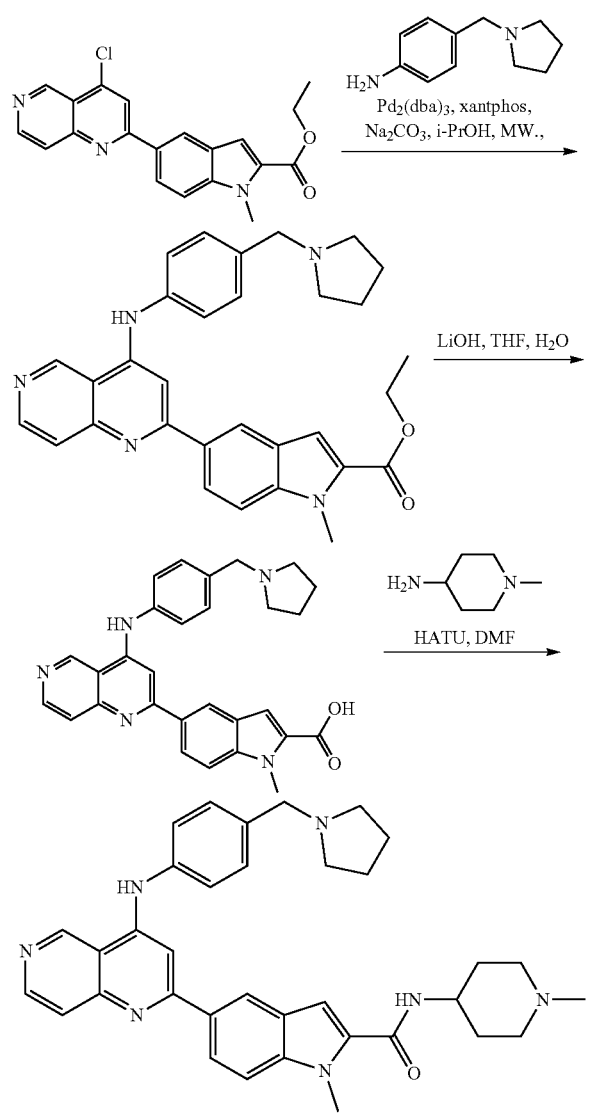

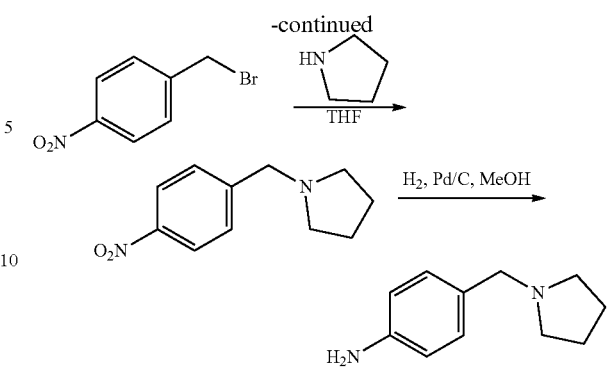

Step 1

The mixture of 1-(bromomethyl)-4-nitrobenzene (5.0 g, 23.1 mmol) and pyrrolidine (4.1 g, 57.8 mmol) in THF (50 mL) was stirred at room temperature overnight. Water (30 mL) was added, and then the mixture was extracted with EA three times. The combined organic layers were washed with water (50 mL×3) and brine (20 mL×1), dried over Na₂SO₄, filtered and concentrated. Purified by the flash column chromatography (silica gel, eluting with DCM to 10% MeOH in DCM) to afford 1-(4-nitrobenzyl)pyrrolidine as a yellow oil (4.5 g, 95% yield). LC-MS (ESI): 207 (M+1)⁺.

Step 2

The mixture of 1-(4-nitrobenzyl)pyrrolidine (3.5 g, 17.0 mmol) and Pd/C (350 mg, 10%) in MeOH (50 mL) under H2 atmosphere was stirred at room temperature overnight. The catalyst was removed by reduced pressure and the filtration was concentrated. The residue was purified by the flash column chromatography (silica gel, eluting with DCM to 30% MeOH in DCM) to afford 4-(pyrrolidin-1-ylmethyl)aniline as a yellow oil (1.0 g, 33% yield). LC-MS (ESI): 177 (M+1)⁺.

Step 3

The mixture of ethyl 5-(4-chloro-1,6-naphthyridin-2-yl)-1-methyl-1H-indole-2-carboxylate (73 mg, 0.20 mmol) and 4-(pyrrolidin-1-ylmethyl)aniline (46 mg, 0.26 mmol), Na₂CO₃ (43 mg, 0.40 mmol), xantphos (34 mg, 0.06 mmol) and Pd₂(dba)₃ (30 mg, 0.03 mmol) in i-PrOH (5 mL) protected by N₂ atmosphere was heated to 110° C. under microwave conditions for 1.5 hrs. After cooling to room temperature, water (60 mL) was added, and then the mixture was extracted with EA three times. The combined organic layers were washed with water (20 mL×3) and brine (20 mL×1), dried over Na₂SO₄, filtered and concentrated. The residue was purified by Prep-TLC (10% MeOH in DCM) to afford ethyl 1-methyl-5-(4-((4-(pyrrolidin-1-ylmethyl)phenyl)amino)-1,6-naphthyridin-2-yl)-1H-indole-2-carboxylate as a yellow solid (55 mg, 50% yield). LC-MS (ESI): 506 (M+1)⁺.

Step 4

The mixture of ethyl 1-methyl-5-(4-((4-(pyrrolidin-1-ylmethyl)phenyl)amino)-1,6-naphthyridin-2-yl)-1H-indole-2-carboxylate (60 mg, 0.12 mmol) and LiOH·H₂O (16 mg, 0.36 mmol) in THF/H₂O (6 mL/2 mL) was stirred at room temperature overnight. The mixture was acidified with HCl solution (2 M) to pH=2, then concentrated to give the crude product that was used directly in the next step without further purification. LC-MS (ESI): 478 (M+1)⁺.

Step 5

The mixture of 1-methyl-5-(4-((4-(pyrrolidin-1-ylmethyl) phenyl)amino)-1,6-naphthyridin-2-yl)-1H-indole-2-carboxylic acid (50 mg, 0.1 mmol), 1-methylpiperidin-4-amine (18 mg, 0.13 mmol), HATU (45 mg, 0.12 mmol) and DIPEA (40 mg, 0.3 mmol) in DMF (3 mL) was stirred at room temperature overnight. Water (30 mL) was added, and then the mixture was extracted with EA three times. The combined organic layers were washed with water (20 mL×3) and brine (20 mL×1), dried over Na₂SO₄, filtered and concentrated. Purification by Prep-HPLC to afford ethyl 1-methyl-5-(4-((4-(pyrrolidin-1-ylmethyl)phenyl)amino)-1,6-naphthyridin-2-yl)-1H-indole-2-carboxylate as a yellow solid (30 mg, 53% yield). LC-MS (ESI): 574 (M+1)⁺; ¹H NMR (CD₃OD) δ 9.51 (br, s, 1H), 8.41 (d, J=7.6 Hz, 1H), 8.29 (s, 1H), 7.99 (d, J=8.8 Hz, 1H), 7.88 (br, s, 1H), 7.62 (d, J=8.8 Hz, 1H), 7.55 (s, 1H), 7.46 (m, 4H), 7.21 (s, 1H), 4.13 (m, 1H), 3.99 (s, 3H), 3.73 (m, 4H), 2.93 (br, s, 2H), 2.60 (s, 3H), 2.31 (m, 4H), 1.82 (m, 2H), 1.76 (m, 4H), 1.67 (m, 2H).

Example 21: Synthesis of N-(3-(piperidin-1-yl)propyl)-5-(4-((3-(piperidin-1-yl)propyl)amino)-1,6-naphthyridin-2-yl)-1H-benzo[d]imidazole-2-carboxamide

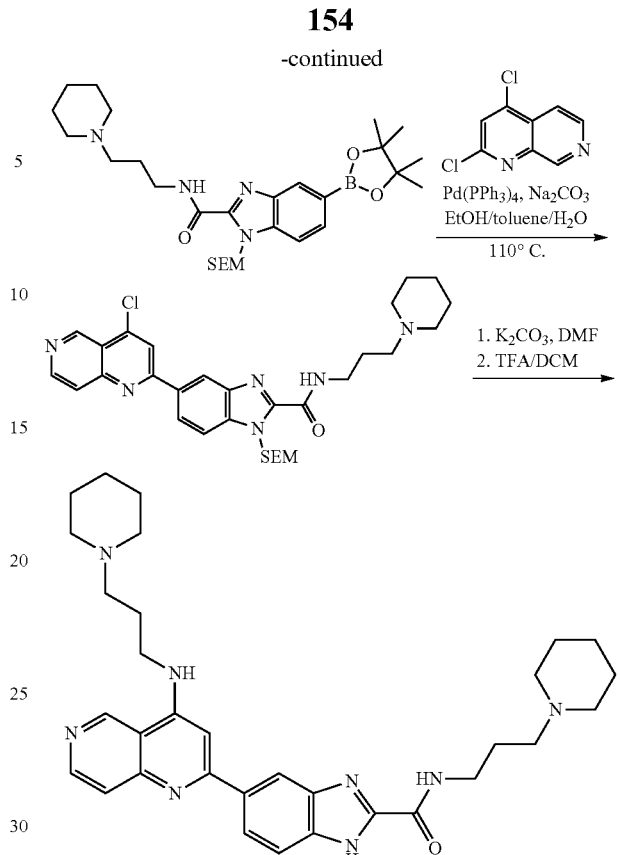

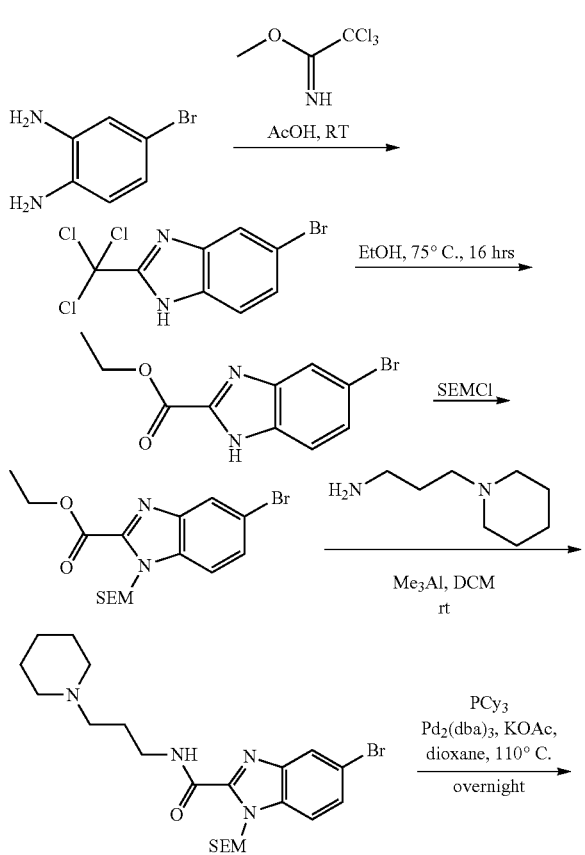

Step 1

To a solution of 4-bromobenzene-1,2-diamine (4.78 g, 25.5 mmol) in AcOH (50 mL) at 0° C. was added 5-bromo-2-(trichloromethyl)-1H-benzo[d]imidazole (5.0 g, 28.3 mmol), then the mixture was stirred at room temperature for 3 hrs. Water was added and the precipitate was collected by filtration. The solid was washed with water, then dried under vacuum to afford the crude product that was used directly in the next step without further purification. LC-MS (ESI): 312 (M+1)⁺.

Step 2

The mixture of 5-bromo-2-(trichloromethyl)-1H-benzo[d]imidazole (1.0 g, 3.18 mmol) and Na₂CO₃ (405 mg, 3.82 mmol) in EtOH (10 mL) was stirred at 75° C. overnight. The solvent was concentrated under reduced pressure and residue was poured into water, extracted with EA (50 mL). The organic layer was washed with water (30 mL) and brine (30 mL), dried over Na₂SO₄, filtered and concentrated. The residue was purified by the flash column chromatography (silica gel, eluting with PE to 20% EA in PE) to afford ethyl 5-bromo-1H-benzo[d]imidazole-2-carboxylate as a brown solid (731 mg, 85% yield). LC-MS (ESI): 270 (M+1)⁺.

Step 3

The mixture of ethyl 5-bromo-1H-benzo[d]imidazole-2-carboxylate (5.7 g, 21.1 mmol), SEMCl (5.3 g, 31.6 mmol) and Et₃N (6.4 g, 63.3 mmol) in DCM (40 mL) was stirred at room temperature overnight. The solvent was concentrated under reduced pressure and residue was poured into water, extracted with DCM (50 mL). The organic layer was washed with water (30 mL) and brine (30 mL), dried over Na$_2$SO$_4$, filtered and concentrated. The residue was purified by the flash column chromatography (silica gel, eluting with PE to 20% EA in PE) to afford ethyl 5-bromo-1-((2-(trimethylsilyl)ethoxy)methyl)-1H-benzo[d]imidazole-2-carboxylate as a brown oil (3.25 g, 39%). LC-MS (ESI): 400 (M+1)$^+$.

Step 4

To a solution of 3-(piperidin-1-yl)propan-1-amine (1.4 g, 10.0 mmol) in DCM (5 mL) was added Al(CH$_3$)$_3$ (10 mL, 10 mmol) dropwise at 0° C. under nitrogen, then the mixture was stirred at rt for 30 mins, the reaction mixture was cooled to 0° C. again. A solution of ethyl ethyl 5-bromo-1-((2-(trimethylsilyl)ethoxy)methyl)-1H-benzo[d]imidazole-2-carboxylate (400 mg, 1.0 mmol) in DCM (5 mL) was added dropwise, the resulting reaction mixture was stirred at rt for 18 hrs. The reaction mixture was quenched by water (10 mL), then extracted with DCM (10 mL×3), the combined organic layers were washed with water and brine, dried over Na$_2$SO$_4$, the drying agent was filtered off and the filtrate was concentrated in vacuo to get the residue which was purified with Combiflash (silica gel, eluting with 30% methanol in DCM) to afford 5-bromo-N-(3-(piperidin-1-yl)propyl)-1-((2-(trimethylsilyl)ethoxy)methyl)-1H-benzo[d]imidazole-2-carboxamide (454 mg, 91%) as a yellow oil. LC-MS (ESI): 495 (M+1)$^+$.

Step 5

The mixture of 5-bromo-N-(3-(piperidin-1-yl)propyl)-1-((2-(trimethylsilyl)ethoxy)methyl)-1H-benzo[d]imidazole-2-carboxamide (120 mg, 0.24 mmol), 4,4,4',4',5,5,5',5'-octamethyl-2,2'-bi(1,3,2-dioxaborolane) (80 mg, 0.29 mmol), Pd$_2$(dba)$_3$ (30 mg, 0.03 mmol), tricyclohexylphosphine (20 mg, 0.07 mmol) and KOAc (36 mg, 0.36 mmol) in 1,4-Dioxane (20 mL) was heated to 100° C. and held for 18 hrs under N$_2$ atmosphere. The reaction mixture was cooled to rt and filtered by a pad of celite, the resulting filtrate was concentrated under the reduced pressure to get the residue which was diluted with EA (30 mL), then washed by water and brine, dried over Na$_2$SO$_4$, the drying agent was filtered off and the filtrate was concentrated in vacuo to get a crude boric acid ester which was purified with Combiflash (silica gel, eluting with 10% methanol in DCM) to afford N-(3-(piperidin-1-yl)propyl)-5-(4,4,5,5-tetramethyl-1,3,2-dioxaborolan-2-yl)-1-((2-(trimethylsilyl)ethoxy)methyl)-1H-benzo[d]imidazole-2-carboxamide (100 mg, 77%) as a brown oil. LC-MS (ESI): 543 (M+1)$^+$.

Step 6

The mixture of 2,4-dichloro-1,7-naphthyridine (20 mg, 0.10 mmol), N-(3-(piperidin-1-yl)propyl)-5-(4,4,5,5-tetramethyl-1,3,2-dioxaborolan-2-yl)-1-((2-(trimethylsilyl)ethoxy)methyl)-1H-benzo[d]imidazole-2-carboxamide (60 mg, 0.11 mmol), Pd(PPh$_3$)$_4$ (29 mg, 0.025 mmol) and Na$_2$CO$_3$ (26 mg, 0.25 mmol) were dissolved in 1,4-dioxane (5 mL) and H$_2$O (1 mL). The resulting brown suspension was stirred at 110° C. overnight. The solvent was concentrated under reduced pressure and residue was poured into water, extracted with EA (50 mL). The organic layer was washed with water (30 mL) and brine (30 mL), dried over Na$_2$SO$_4$, filtered and concentrated. The residue was purified by Prep-TLC (eluting with DCM to 20% MeOH in DCM) to get 5-(4-chloro-1,6-naphthyridin-2-yl)-N-(3-(piperidin-1-yl)propyl)-1-((2-(trimethylsilyl)ethoxy)methyl)-1H-benzo[d]imidazole-2-carboxamide as a yellow solid (15 mg, 26% yield). LC-MS (ESI): 579 (M+1)$^+$.

Step 7

The mixture of 5-(4-chloro-1,6-naphthyridin-2-yl)-N-(3-(piperidin-1-yl)propyl)-1-((2-(trimethylsilyl)ethoxy)methyl)-1H-benzo[d]imidazole-2-carboxamide (29 mg, 0.05 mmol), 3-(piperidin-1-yl)propan-1-amine (13 mg, 0.10 mmol) and K$_2$CO$_3$ (13 mg, 0.10 mmol) in DMF (3 ml) was heated to 90° C. and held for 18 hrs. The reaction mixture was poured into water (20 mL), extracted with EA (10 mL×3), the combined organic layers were washed by water and brine, dried over Na$_2$SO$_4$. The drying agent was filtered off and the filtrate was concentrated under the reduced pressure to get the residue, which was dissolved in TFA (1 mL) and DCM (10 mL), then stirred at rt for 18 hrs. The solvent was removed under the reduced pressure to afford the residue which was purified with Prep-HPLC (Welch, XB-C18, 21.2 mm*250 mm, 10 um, eluting with 40% CH$_3$CN in 1‰ TFA in H$_2$O) to afford N-(3-(piperidin-1-yl)propyl)-5-(4-((3-(piperidin-1-yl)propyl)amino)-1,6-naphthyridin-2-yl)-1H-benzo[d]imidazole-2-carboxamide. (5 mg, 9% yield) as a TFA salt. LC-MS (ESI): 555 (M+1)$^+$. $^1$H NMR (DMSO-d$_6$) δ 10.09 (br, s, 1H), 9.92 (s, 1H), 9.71 (br, s, 1H), 9.26 (s, 1H), 8.88 (d, J=5.6 Hz, 1H), 8.40 (s, 1H), 7.98-8.03 (m, 2H), 7.86-7.89 (m, 1H), 7.30 (s, 1H), 3.82-3.84 (m, 2H), 3.42-3.48 (m, 6H), 3.23-3.25 (m, 2H), 3.12-3.16 (m, 2H), 2.87-2.92 (m, 4H), 2.15-2.20 (m, 2H), 1.97-2.02 (m, 2H), 1.80-1.83 (m, 4H), 1.63-1.69 (m, 6H), 1.37-1.41 (m, 2H).

Example 22: Synthesis of methyl 3-carbamoyl-4-(4-((3-(piperidin-1-yl)propyl)amino)-1,6-naphthyridin-2-yl)benzoate

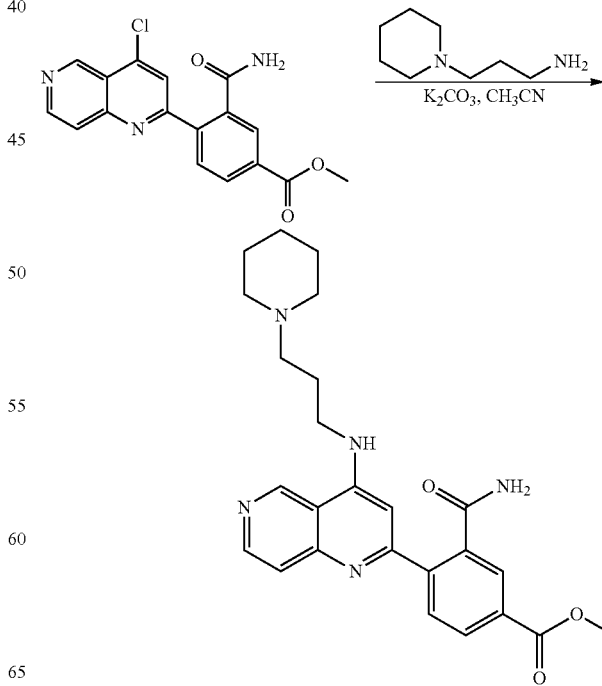

The mixture of methyl 3-carbamoyl-4-(4-chloro-1,6-naphthyridin-2-yl)benzoate (330 mg, 0.96 mmol), 3-(piperidin-1-yl)propan-1-amine (274 mg, 1.93 mmol) and K$_2$CO$_3$ (266 mg, 1.93 mmol) in DMF (5 mL) was heated to 80° C. and held for 18 hrs. The reaction mixture was poured into water (20 mL), extracted with EA (10 mL×3), the combined organic layers were washed by water and brine, dried over Na$_2$SO$_4$. The drying agent was filtered off and the filtrate was concentrated under the reduced pressure to get the residue which was purified with Combiflash (silica gel, eluting with 10% methanol in DCM) to afford methyl 3-carbamoyl-4-(4-((3-(piperidin-1-yl)propyl)amino)-1,6-naphthyridin-2-yl)benzoate (200 mg, 46%) as an orange solid. HPLC/UV purity: 94%; LC-MS (ESI): 448 (M+1)$^+$.

$^1$H NMR (DMSO-d$_6$) δ 9.58 (s, 1H), 8.58 (d, J=4.6 Hz, 1H), 8.10 (d, J=8.0 Hz, 1H), 7.97-8.06 (m, 3H), 7.87 (d, J=8.0 Hz, 1H), 7.60 (d, J=5.7 Hz, 1H), 7.49 (s, 1H), 6.80 (s, 1H), 3.92 (s, 3H), 3.33 (m, 4H), 2.39 (m, 4H), 1.87 (m, 2H), 1.52 (m, 4H), 1.39 (m, 2H).

Example 23: Synthesis of 5-(4-methoxy-1,6-naphthyridin-2-yl)-1-methyl-N-(1-methylpiperidin-4-yl)-1H-indole-2-carboxamide

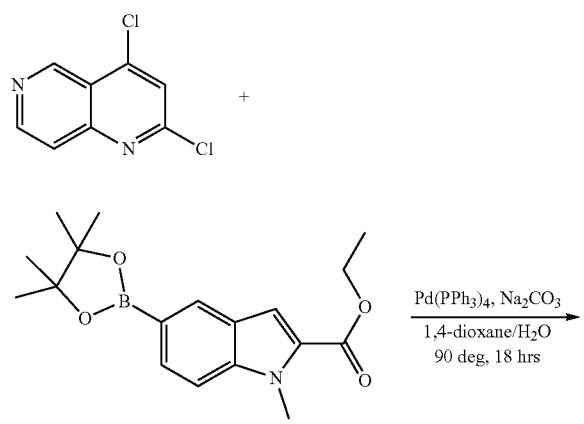

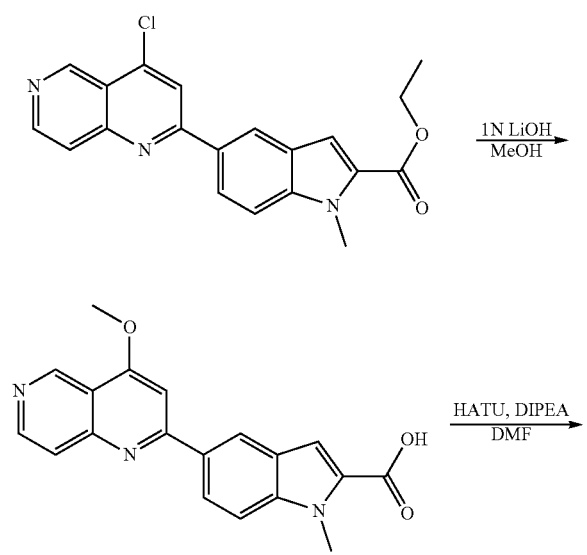

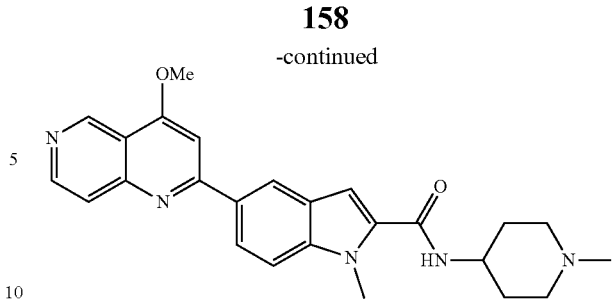

Step 1

The mixture of 2,4-dichloro-1,6-naphthyridine (1.5 g, 4.93 mmol), ethyl 1-methyl-5-(4,4,5,5-tetramethyl-1,3,2-dioxaborolan-2-yl)-1H-indole-2-carboxylate (1.94 g, 5.92 mmol), Pd(PPh$_3$)$_4$ (569 mg, 0.493 mmol) and Na$_2$CO$_3$ (1.04 g, 9.86 mmol) in 1,4-Dioxane (20 mL) and H$_2$O (4 mL) was heated to 90° C. and held for 18 hrs under nitrogen atmosphere. The reaction mixture was filtered by a pad of celite, the filtrate was concentrated to get the residue which was washed by water (30 mL) and EA (30 mL), ethyl 5-(4-chloro-1,6-naphthyridin-2-yl)-1-methyl-1H-indole-2-carboxylate (1.7 g, 94%) to afford a yellow solid. HPLC/UV purity: 90%; LC-MS (ESI): 366 (M+1)$^+$. $^1$H NMR (DMSO-d$_6$) δ 9.55 (s, 1H), 8.85 (d, J=5.8 Hz, 1H), 8.77 (s, 1H), 8.60 (s, 1H), 8.46 (d, J=8.0 Hz, 1H), 8.01 (d, J=6.1 Hz, 1H), 7.80 (d, J=9.2 Hz, 1H), 7.43 (s, 1H), 4.37 (q, J=7.2 Hz, 2H), 4.10 (s, 3H), 1.37 (t, J=7.0 Hz, 3H).

Step 2

To a mixture of ethyl 5-(4-chloro-1,6-naphthyridin-2-yl)-1-methyl-1H-indole-2-carboxylate (500 mg, 1.37 mmol) in Methanol (6 mL) was added 1N LiOH aqueous (4.1 mL), then the reaction mixture was heated to 50° C. and held for 2 hrs. LCMS analysis showed complete consumption of start materials. Methanol was removed under the reduced pressure to get a slurry. Water (5 mL) was added, then pH of the mixture was adjusted to 4 with 1N HCl aqueous. The solvent was removed under the reduced pressure to afford crude 5-(4-methoxy-1,6-naphthyridin-2-yl)-1-methyl-1H-indole-2-carboxylic acid (500 mg, 99%) which was used to the next step without further purification.

Step 3

To a mixture of 5-(4-methoxy-1,6-naphthyridin-2-yl)-1-methyl-1H-indole-2-carboxylic acid (495 mg, 1.37 mmol) and HATU (625 mg, 1.64 mmol) in DMF (4 mL) was added 1-methylpiperidin-4-amine (156 mg, 1.37 mmol) and DIPEA (530 mg, 4.11 mmol), then the resulting mixture was stirred at rt for 1 hr. The reaction mixture was poured into water (10 mL), extracted with EA (10 mL×3), the combined organic layers was washed with water and brine, dried over Na$_2$SO$_4$, the drying agent was filtered off and the filtrate was concentrated in vacuo to get the residue which was purified with Combiflash (silica gel, eluting with 5% methanol in DCM) to afford 5-(4-methoxy-1,6-naphthyridin-2-yl)-1-methyl-N-(1-methylpiperidin-4-yl)-1H-indole-2-carboxamide (200 mg, 34%) as a solid. HPLC/UV purity: 94%; LC-MS (ESI): 430 (M+1)$^+$ $^1$H NMR (DMSO-d$_6$) δ 9.44 (s, 1H), 8.71 (d, J=6.0 Hz, 1H), 8.65 (s, 1H), 8.43 (d, J=7.6 Hz, 1H), 8.31 (dd, J=8.9, 1.5 Hz, 1H), 7.85 (d, J=5.8 Hz, 1H), 7.74 (s, 1H), 7.70 (d, J=8.8 Hz, 1H), 7.23 (s, 1H), 4.25 (s, 3H), 4.03 (s, 3H), 3.70-3.81 (m, 1H), 2.80 (d, J=11.6 Hz, 2H), 2.18 (s, 3H), 1.97 (t, J=11.1 Hz, 2H), 1.80 (d, J=10.7 Hz, 2H), 1.52-1.69 (m, 2H).
Example 24: Synthesis of 3-cyano-N,N-diethyl-4-(4-((3-(piperidin-1-yl)propyl)amino)-1,6-naphthyridin-2-yl)benzamide
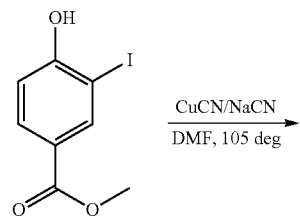
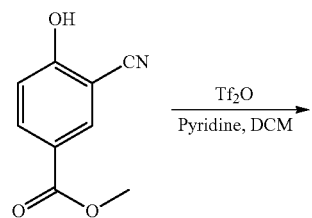
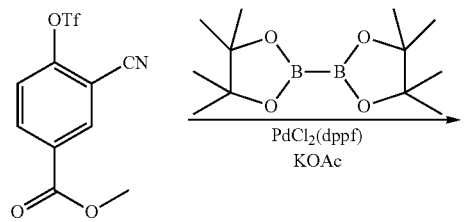
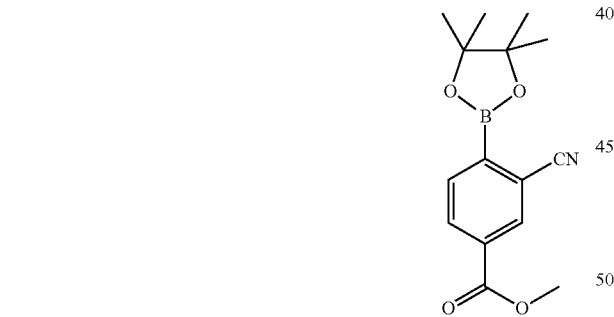
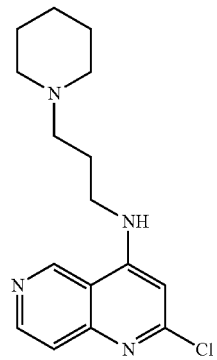

Step 1

To a solution of methyl 4-hydroxy-3-iodobenzoate (5 g, 18 mmol) in DMF (6 mL) was added cyanocopper (1.77 g, 19.8 mmol) and cyanosodium (97 mg, 1.98 mmol), the mixture was heated to 105° C. for 18 hrs. The reaction was cooled to rt and poured into water (50 mL), the gradual formation of a grey-green precipitate was observed, the precipitate was filtered and the filtrate was extracted with EA (50 mL) for three times, and the combined organic layers was washed by water and brine, dried over $Na_2SO_4$. The drying organic layers were filtered off and washed with additional ethyl acetate (20 mL). The combined filtrate is concentrated in vacuo to afford the crude product methyl 3-cyano-4-hydroxybenzoate (1.77 g, 55%) as a grey solid which was used to the next step without further purification. HPLC/UV purity: 90%; LC-MS (ESI): 178 $(M+1)^+$. $^1H$ NMR (DMSO-$d_6$) δ 12.11 (s, 1H), 8.16 (d, J=2.1 Hz, 1H), 8.06 (dd, J=8.7, 2.3 Hz, 1H), 7.12 (d, J=8.9 Hz, 1H), 3.84 (s, 3H).

Step 2

To a suspension of methyl 3-cyano-4-hydroxybenzoate (1.77 g, 10 mmol) in DCM (20 mL) was added pyridine (1.17 g, 15 mmol), then the mixture was cooled to 0° C., trifluoromethanesulfonic anhydride (3.38 g, 12 mmol) was dropwise added at 0° C. The mixture was stirred at rt overnight. Another 20 mL of DCM was added, the solution was washed with 1N HCl (15 mL) twice, washed with water and brine, and the organic layers were dried over $Na_2SO_4$. The drying agent was filtered off and the filtrate was concentrated under the reduced pressure to give the residue which was purified with Combiflash (silica gel, eluting with 10-20% PE in EA) to afford Methyl 3-cyano-4-(((trifluoromethyl)sulfonyl)oxy)benzoate (2.5 g, 81%) as a colorless oil. HPLC/UV purity: 90%; LC-MS (ESI): 309 $(M+1)^+$.

Step 3

The mixture of 3-cyano-4-(((trifluoromethyl)sulfonyl)oxy)benzoate (2.5 g, 8.1 mmol), 4,4,4',4',5,5,5',5'-octamethyl-2,2'-bi(1,3,2-dioxaborolane) (2.45 g, 9.7 mmol), Pd(dppf)Cl$_2$ (661 mg, 0.81 mmol) and KOAc (1.5 g, 16.2 mmol) in 1,4-Dioxane (20 mL) was heated to 100° C. and held for 18 hrs under $N_2$ atmosphere. The reaction mixture was cooled to rt and filtered by a pad of celite, the resulting filtrate was concentrated under the reduced pressure to get the residue which was diluted with EA (30 mL), then washed by water and brine, dried over $Na_2SO_4$, the drying agent was filtered off and the filtrate was concentrated in vacuo to afford a crude boric acid ester which was used to the next step without purification.

Step 4

A 20-mL microwave vial was charged with 2,4-dichloro-1,6-naphthyridine (500 mg, 2.5 mmol), methyl 3-cyano-4-(4,4,5,5-tetramethyl-1,3,2-dioxaborolan-2-yl)benzoate (1.16 mmol, 3 mmol), Pd(PPh$_3$)$_4$ (289 mg, 0.25 mmol) and NaHCO$_3$ (420 mg, 5 mmol) dissolved 1,4-dioxane (10 mL) and H$_2$O (1 mL). A stir bar is added, the vial is sealed, and the resulting brown solution is heated for 1 h in a Biotage Initiator Eight Microwave Reactor held at a constant temperature of 100° C. The resulting solutions were concentrated by rotary evaporation (55° C., 20 mmHg). The adsorbed material was loaded onto a column and purified using silica gel chromatography (silica gel, eluting with 2-5% methanol in DCM) to afford methyl 4-(4-chloro-1,6-naphthyridin-2-yl)-3-cyanobenzoate (400 mg, 50%) as a yellow solid HPLC/UV purity: 80%; LC-MS (ESI): 324 $(M+1)^+$ and methyl 3-carbamoyl-4-(4-chloro-1,6-naphthyridin-2-yl)benzoate (330 mg, 38%) as a brown solid. HPLC/UV purity: 95%; LC-MS (ESI): 342 $(M+1)^+$.

Step 5

The mixture of methyl 4-(4-chloro-1,6-naphthyridin-2-yl)-3-cyanobenzoate (400 mg, 1.27 mmol), 3-(piperidin-1-yl)propan-1-amine (368 mg, 2.59 mmol) and K$_2$CO$_3$ (357 mg, 2.59 mmol) in DMF (3 mL) was heated to 80° C. and held for 18 hrs. The reaction mixture was poured into water (10 mL), extracted with EA (10 mL×3), the combined organic layers were washed by water and brine, dried over $Na_2SO_4$. The drying agent was filtered off and the filtrate was concentrated under the reduced pressure to get the residue which was purified with Combiflash (silica gel, eluting with 10% methanol in DCM) to afford methyl 3-cyano-4-(4-((3-(piperidin-1-yl)propyl)amino)-1,6-naphthyridin-2-yl)benzoate (250 mg, 45%) as a yellow solid. HPLC/UV purity: 90%; LC-MS (ESI): 430 $(M+1)^+$.

Step 6

To a solution of methyl 3-cyano-4-(4-((3-(piperidin-1-yl)propyl)amino)-1,6-naphthyridin-2-yl)benzoate (200 mg, 0.465 mmol) in methanol (2 mL) and THF (2 mL) was added 1N LiOH aqueous (1.86 mL, 1.86 mmol), then the reaction mixture was stirred at rt overnight. The solvent was removed and water (5 mL) was added, then the pH of the water phase was adjusted with 1N HCl aqueous to 5, then it was cryodesiccated to afford a crude product (250 mg) as a yellow solid.

Step 7

To a mixture of 3-cyano-4-(4-((3-(piperidin-1-yl)propyl)amino)-1,6-naphthyridin-2-yl)benzoic acid (60 mg, 0.144 mmol) and HATU (65 mg, 0.17 mmol) in DMF (2 mL) was added diethylamine (13 mg, 0.17 mmol) and DIPEA (70 mg, 0.342 mmol), then the resulting mixture was stirred at rt for 1 hr. The reaction mixture was poured into water (10 mL), extracted with EA (10 mL×3), the combined organic layers was washed with water and brine, dried over $Na_2SO_4$, the drying agent was filtered off and the filtrate was concentrated in vacuo to get the residue which was purified with Prep-TLC (silica gel, eluting with 10% methanol in DCM) to afford 3-cyano-N,N-diethyl-4-(4-((3-(piperidin-1-yl)propyl)amino)-1,6-naphthyridin-2-yl)benzamide (15 mg, 22%) as a solid. HPLC/UV purity: 97%; LC-MS (ESI): 471 $(M+1)^+$. $^1H$ NMR (CDCl$_3$) δ 9.53 (s, 1H), 8.61 (d, J=6.4 Hz, 1H), 8.02 (d, J=8.0 Hz, 1H), 7.96 (s, 1H), 7.84 (d, J=8.0 Hz, 1H), 7.78 (d, J=6.0 Hz, 1H), 7.06 (s, 1H), 3.52-3.65 (m, 4H), 3.34 (d, J=8.2 Hz, 2H), 2.58-2.72 (m, 5H), 2.01-2.12 (m, 2H), 1.61-1.72 (m, 4H), 1.52 (m, 2H), 1.26-1.34 (m, 4H), 1.13-1.22 (m, 3H).

Example 25: Synthesis of N1,N1-diethyl-4-(4-((3-(piperidin-1-yl)propyl)amino)-1,6-naphthyridin-2-yl)isophthalamide

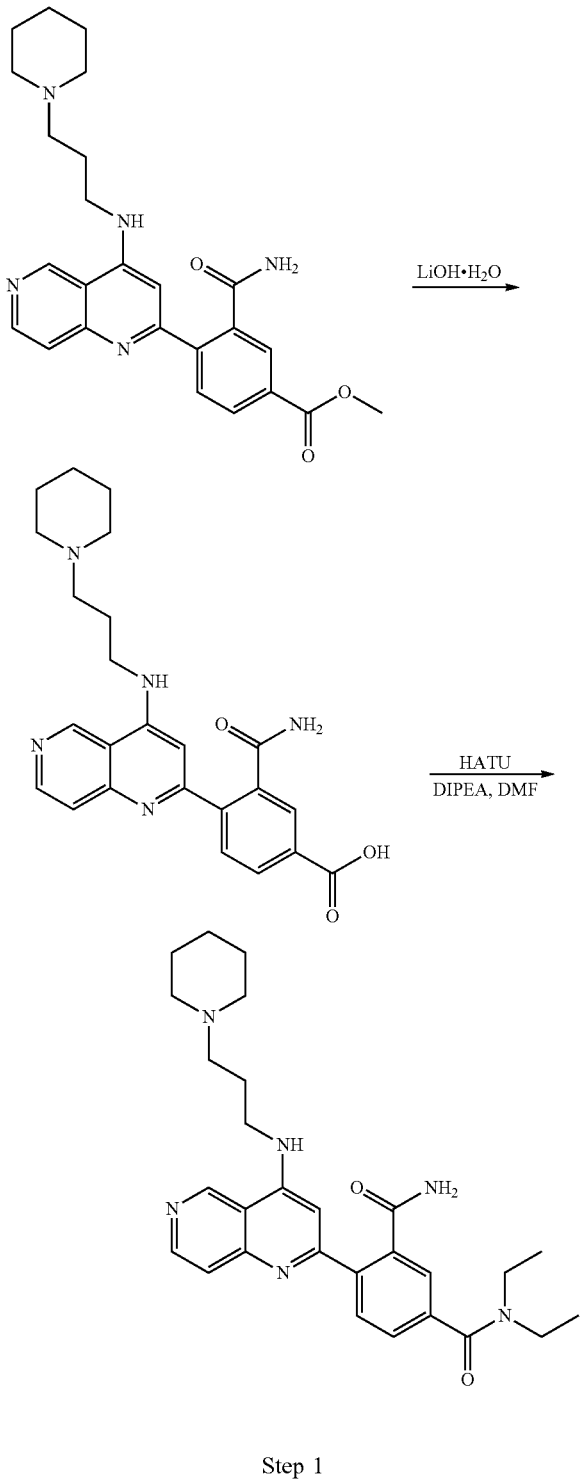

Step 1

To a solution of methyl 3-carbamoyl-4-(4-((3-(piperidin-1-yl)propyl)amino)-1,6-naphthyridin-2-yl)benzoate (200 mg, 0.446 mmol) in methanol (2 mL) and THF (2 mL) was added 1N LiOH aqueous (1.78 mL, 1.78 mmol), then the reaction mixture was stirred at 50° C. for 2 hrs. The solvent was removed and water (5 mL) was added, then the pH of the water phase was adjusted with 1N HCl aqueous to 4, then it was cryodesiccated to afford a crude product (200 mg) as a tan solid.

Step 2

To a mixture of 3-carbamoyl-4-(4-((3-(piperidin-1-yl)propyl)amino)-1,6-naphthyridin-2-yl)benzoic acid (100 mg, 0.23 mmol) and HATU (102 mg, 0.27 mmol) in DMF (2 mL) was added diethylamine (20 mg, 0.27 mmol) and DIPEA (89 mg, 0.69 mmol), then the resulting mixture was stirred at rt for 1 hr. The reaction mixture was poured into water (10 mL), extracted with EA (10 mL×3), the combined organic layers was washed with water and brine, dried over $Na_2SO_4$, the drying agent was filtered off and the filtrate was concentrated in vacuo to get the residue which was purified with Prep-TLC (silica gel, eluting with 10% methanol in DCM) to afford 3-carbamoyl-4-(4-((3-(piperidin-1-yl)propyl)amino)-1,6-naphthyridin-2-yl)benzoic acid (20 mg, 18%) as a solid. HPLC/UV purity: 92%; LC-MS (ESI): 489 (M+1)$^+$.

$^1$H NMR (CD$_3$OD) δ 9.50 (s, 1H), 8.59 (d, J=5.5 Hz, 1H), 7.83 (d, J=7.6 Hz, 1H), 7.74 (d, J=5.8 Hz, 1H), 7.60-7.67 (m, 2H), 6.89 (s, 1H), 3.54-3.62 (m, 4H), 3.32-3.46 (m, 6H), 3.19-3.26 (m, 2H), 2.13-2.26 (m, 2H), 1.86 (m, 4H), 1.27-1.33 (m, 5H), 1.17 (t, J=6.7 Hz, 3H).

Example 26: Synthesis of 1-methyl-5-(4-(methylamino)-1,6-naphthyridin-2-yl)-1H-indole-2-carboxamide

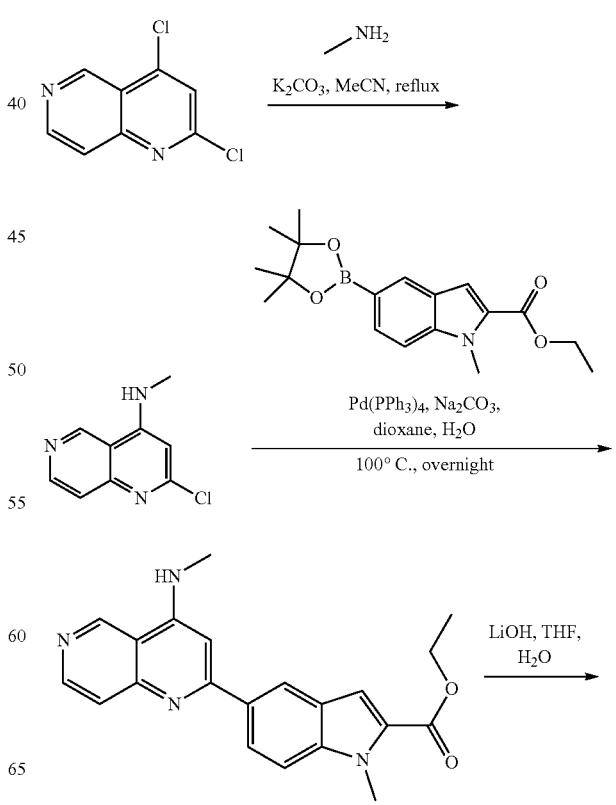

-continued

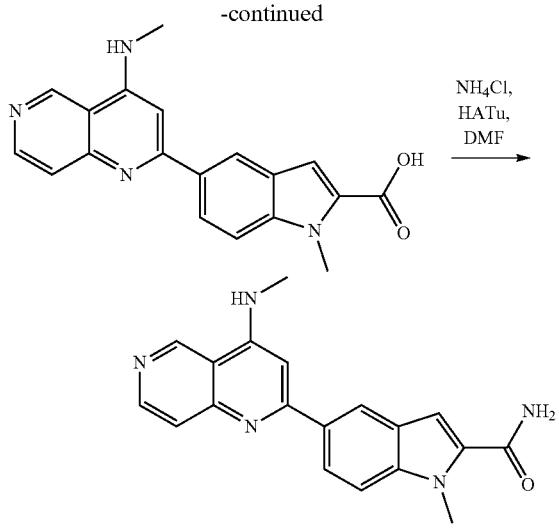

Step 1

The mixture of 2,4-dichloro-1,6-naphthyridine (1 g, 5.0 mmol), methanamine in THF (2.5 mL, 5.0 mmol) and K₂CO₃ (1.38 g, 10.0 mmol) in acetonitrile (30 ml) was heated to 90° C. overnight. After cooling to room temperature, water (40 mL) was added, and then the mixture was extracted with EA three times. The combined organic layers were washed with water (20 mL×3) and brine (20 mL×1), dried over Na₂SO₄, filtered and concentrated. The residue was purified by the flash column chromatography (silica gel, eluting with PE to EA) to afford 2-chloro-N-methyl-1,6-naphthyridin-4-amine as a yellow solid (0.16 g, 17% yield).

Step 2

The mixture of 2-chloro-N-methyl-1,6-naphthyridin-4-amine (160 mg, 0.83 mmol, and ethyl 1-methyl-5-(4,4,5,5-tetramethyl-1,3,2-dioxaborolan-2-yl)-1H-indole-2-carboxylate (286 mg, 0.87 mmol), Na₂CO₃ (175 mg, 1.66 mmol) and Pd(PPh₃)₄ (191 mg, 0.16 mmol) in dioxane/H₂O (10 mL/2 mL) protected by N₂ atmosphere was heated to 100° C. overnight. After cooling to room temperature, water (30 mL) was added, and then the mixture was extracted with EA three times. The combined organic layers were washed with water (20 mL×3) and brine (20 mL×1), dried over Na₂SO₄, filtered and concentrated. The residue was purified by the flash column chromatography (silica gel, eluting with DCM to 10% MeOH in DCM) to afford ethyl 1-methyl-5-(4-(methylamino)-1,6-naphthyridin-2-yl)-1H-indole-2-carboxylate as a yellow solid (100 mg, 33% yield).

Step 3

The mixture of ethyl 1-methyl-5-(4-(methylamino)-1,6-naphthyridin-2-yl)-1H-indole-2-carboxylate (100 mg, 0.27 mmol) and LiOH·H₂O (116 mg, 2.7 mmol) in MeOH/H₂O (5 mL/1 mL) was stirred at room temperature overnight. The mixture was acidified with HCl solution (2 M) to pH=2, then concentrated to give the crude product that was used directly in the next step without further purification. LC-MS (ESI): 333.1 (M+1)⁺.

Step 4

The mixture of 1-methyl-5-(4-(methylamino)-1,6-naphthyridin-2-yl)-1H-indole-2-carboxylic acid (50 mg, 0.15 mmol), NH₄Cl (40 mg, 0.75 mmol), HATU (87 mg, 0.23 mmol) and DIPEA (142 mg, 1.10 mmol) in DMF (3 mL) was stirred at room temperature overnight. Water (30 mL) was added, and then the mixture was extracted with EA three times. The combined organic layers were washed with water (20 mL×3) and brine (20 mL×1), dried over Na₂SO₄, filtered and concentrated. Purification by Prep-TLC and HPLC to afford 1-methyl-5-(4-(methylamino)-1,6-naphthyridin-2-yl)-1H-indole-2-carboxamide as a yellow solid (25 mg, 51% yield). LC-MS (ESI): 332 (M+1)⁺; ¹H NMR (CD₃OD) δ 9.59 (s, 1H), 8.85 (d, J=5.6 Hz, 1H), 8.39 (s, 1H), 7.93 (d, J=8.8 Hz, 1H), 7.88 (d, J=5.6 Hz, 1H), 7.78 (d, J=8.8 Hz, 1H), 7.31 (s, 1H), 7.15 (s, 1H), 4.12 (s, 3H), 3.31 (s, 3H).

Example 27: Synthesis of 3-cyano-N-(1-methylpiperidin-4-yl)-4-(4-((3-(piperidin-1-yl)propyl)amino)-1,6-naphthyridin-2-yl)benzamide

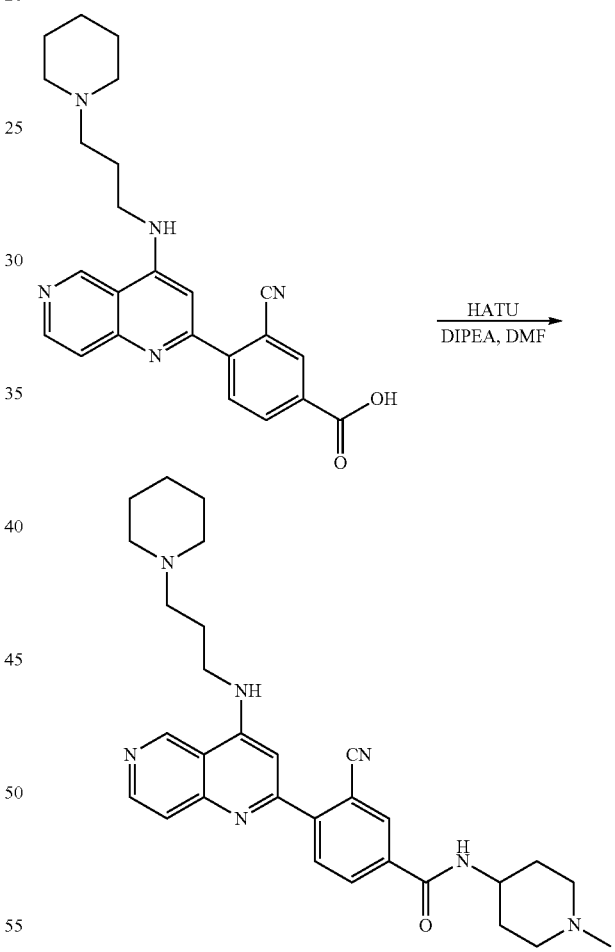

To a mixture of 3-cyano-4-(4-((3-(piperidin-1-yl)propyl)amino)-1,6-naphthyridin-2-yl)benzoic acid (60 mg, 0.144 mmol) and HATU (65 mg, 0.17 mmol) in DMF (2 mL) was added 1-methylpiperidin-4-amine (19 mg, 0.17 mmol) and DIPEA (70 mg, 0.342 mmol), then the resulting mixture was stirred at rt for 1 hr. The reaction mixture was poured into water (10 mL), extracted with EA (10 mL×3), the combined organic layers was washed with water and brine, dried over Na₂SO₄, the drying agent was filtered off and the filtrate was concentrated in vacuo to get the residue which was purified with Prep-TLC (silica gel, eluting with 10% methanol in DCM) to afford 3-cyano-N-(1-methylpiperidin-4-yl)-4-(4-((3-(piperidin-1-yl)propyl)amino)-1,6-naphthyridin-2-yl)benzamide (20 mg, 25%) as a solid. HPLC/UV purity: 97%; LC-MS (ESI): 512 (M+1)+. $^1$H NMR (CD$_3$OD) δ 9.54 (s, 1H), 8.63 (d, J=5.8 Hz, 1H), 8.37 (d, J=1.5 Hz, 1H), 8.26 (dd, J=8.2, 1.8 Hz, 1H), 8.04 (d, J=8.2 Hz, 1H), 7.79 (d, J=5.8 Hz, 1H), 7.09 (s, 1H), 3.94-4.06 (m, 1H), 3.10 (d, J=11.9 Hz, 2H), 2.84-3.02 (m, 5H), 2.40-2.55 (m, 5H), 2.13-2.23 (m, 2H), 2.07 (d, J=11.3 Hz, 2H), 1.72-1.83 (m, 6H), 1.59 (m, 2H), 1.27-1.37 (m, 3H).

Example 28: Synthesis of 1-methyl-N-(1-methylpiperidin-4-yl)-5-(4-(3-(piperidin-1-yl)propoxy)-1,6-naphthyridin-2-yl)-1H-indole-2-carboxamide

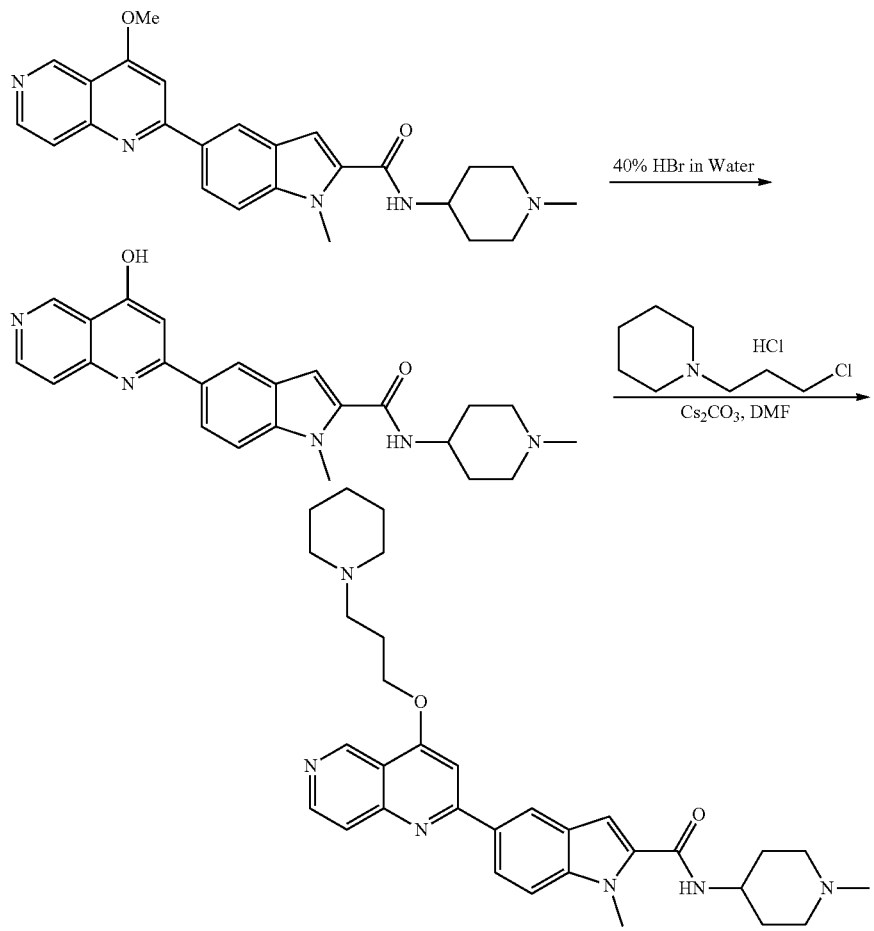

Step 1

The solution of 5-(4-methoxy-1,6-naphthyridin-2-yl)-1-methyl-N-(1-methylpiperidin-4-yl)-1H-indole-2-carboxamide (200 mg, 0.466 mmol) in 40% HBr in water was heated to 100° C. and held for 3 hrs. LCMS analysis showed complete consumption of start material. The water was removed under the reduced pressure to get the residue which was purified with Prep-HPLC (eluting with 30% methanol in water) to obtain 5-(4-hydroxy-1,6-naphthyridin-2-yl)-1-methyl-N-(1-methylpiperidin-4-yl)-1H-indole-2-carboxamide (190 mg, 95%) as a solid. HPLC/UV purity: 90%; LC-MS (ESI): 416 (M+1)+. $^1$H NMR (DMSO-d$_6$) δ 9.11 (s, 1H), 8.37 (d, J=7.6 Hz, 1H), 8.19-8.28 (m, 2H), 7.98 (d, J=9.2 Hz, 1H), 7.56 (d, J=9.2 Hz, 1H), 7.35 (d, J=6.4 Hz, 1H), 7.17 (s, 1H), 6.57 (s, 1H), 4.00 (s, 3H), 3.74 (d, J=8.2 Hz, 1H), 2.78 (d, J=11.0 Hz, 2H), 2.17 (s, 3H), 1.92-1.99 (m, 2H), 1.78 (d, J=10.7 Hz, 2H), 1.52-1.67 (m, 2H).

Step 2

The mixture of 5-(4-hydroxy-1,6-naphthyridin-2-yl)-1-methyl-N-(1-methylpiperidin-4-yl)-1H-indole-2-carboxamide (140 mg, 0.336 mmol) and Cs$_2$CO$_3$ (325 mg, 1 mmol) in DMF (2 mL) was heated to 70° C. and held for 2 hrs, then the mixture was cooled to 0° C., 1-(3-chloropropyl)piperidine hydrochloride (80 mg, 0.404 mmol) was added in one portion, then the resulting reaction mixture was heated to 70° C. and held for 1 hrs. The reaction mixture was poured into water (20 mL), extracted with EA (10 mL×3), the combined organic layers were washed by water and brine, dried over Na$_2$SO$_4$. The drying agent was filtered off and the filtrate was concentrated under the reduced pressure to get the residue which was purified with Prep-TLC (silica gel, DCM/Methanol/NH3·H$_2$O=10/1/0.1) to afford 1-methyl-N-(1-methylpiperidin-4-yl)-5-(4-(3-(piperidin-1-yl)propoxy)-1,6-naphthyridin-2-yl)-1H-indole-2-carboxamide (5 mg, 3%), HPLC/UV purity: 95%; LC-MS (ESI): 541 (M+1)+. $^1$H NMR (CD$_3$OD) δ 9.51 (s, 1H), 8.67 (d, J=6.1 Hz, 1H), 8.53 (s, 1H), 8.20 (d, J=8.9 Hz, 1H), 7.92 (d, J=6.1 Hz, 1H), 7.60-7.70 (m, 2H), 7.25 (s, 1H), 4.60 (t, J=5.6 Hz, 2H), 4.16 (m, 1H), 4.07 (s, 3H), 3.36-3.56 (m, 6H), 3.12 (d, J=11.3 Hz, 2H), 2.83 (s, 3H), 2.48 (dd, J=9.9, 6.0 Hz, 2H), 2.14-2.29 (m, 2H), 1.75-2.05 (m, 10H).

Example 29: Synthesis of 5-(4-((3-(piperidin-1-yl)propyl)amino)-1,6-naphthyridin-2-yl)-N-(piperidin-4-yl)-1H-benzo[d]imidazole-2-carboxamide

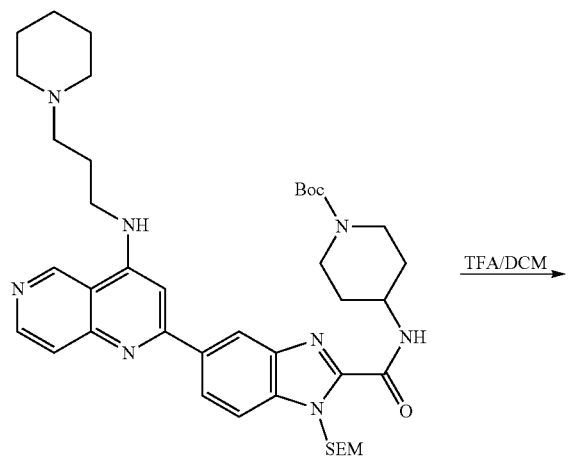

TFA/DCM

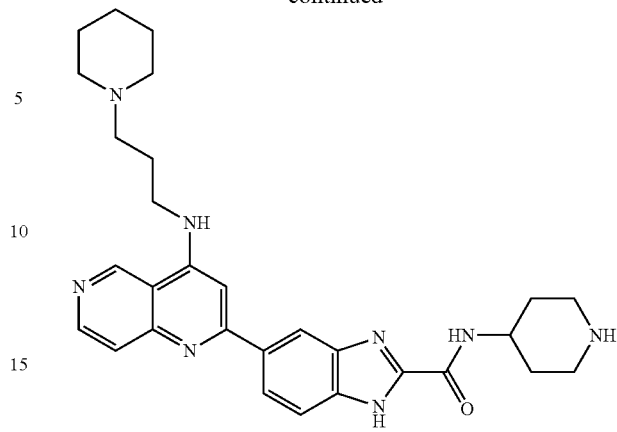

A mixture of tert-butyl 4-(5-(4-((3-(piperidin-1-yl)propyl)amino)-1,6-naphthyridin-2-yl)-1-((2-(trimethylsilyl)ethoxy)methyl)-1H-benzo[d]imidazole-2-carboxamido)piperidine-1-carboxylate (130 mg, 0.162 mmol) and TFA (2 mL) in DCM (4 mL) was heated to 40° C. and held for 2 hrs, the solvent was removed under the reduced pressure to get the residue which was purified with Prep-HPLC (Welch, XB-C18, 21.2 mm*250 mm, 10 um, eluting with 20% CH$_3$CN in 1‰ TFA in H$_2$O) to afford 5-(4-((3-(piperidin-1-yl)propyl)amino)-1,6-naphthyridin-2-yl)-N-(piperidin-4-yl)-1H-benzo[d]imidazole-2-carboxamide (30 mg, 33%) as a TFA salt. HPLC/UV purity: 93%; LC-MS (ESI): 513 (M+1)$^+$. $^1$H NMR (CD$_3$OD) δ 9.75 (s, 1H), 8.90 (d, J=6.0 Hz, 1H), 8.40 (s, 1H), 7.93-8.01 (m, 3H), 7.29 (s, 1H), 4.27 (m, 1H), 3.85-3.89 (t, J=6.8 Hz, 2H), 3.51-3.62 (m, 4H), 3.34 (m, 2H), 3.18-3.25 (t, J=12.8 Hz, 2H), 2.94-3.00 (m, 2H), 2.26-2.35 (m, 4H), 1.78-2.03 (m, 7H), 1.51-1.54 (m, 1H).

Example 30: Synthesis of 5-(4-(methylamino)-1,6-naphthyridin-2-yl)-N-(3-(piperidin-1-yl)propyl)-1H-benzo[d]imidazole-2-carboxamide

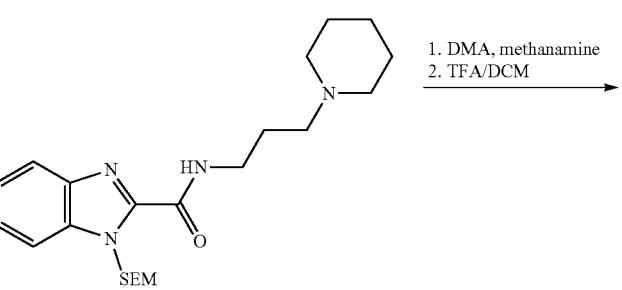

1. DMA, methanamine
2. TFA/DCM

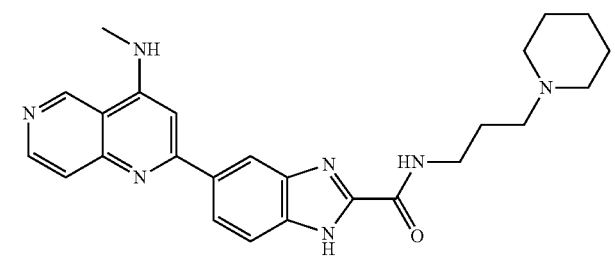

The mixture of 5-(4-chloro-1,6-naphthyridin-2-yl)-N-(3-(piperidin-1-yl)propyl)-1-((2-(trimethylsilyl)ethoxy)methyl)-1H-benzo[d]imidazole-2-carboxamide (120 mg, 0.2 mmol), and methyl amine (0.5 mL, 1.0 mmol, 2 M THF solution) in DMA (3 ml) was heated to 100° C. and held for 18 hrs. The reaction mixture was poured into water (20 mL), extracted with EA (10 mL×3), the combined organic layers were washed by water and brine, dried over Na$_2$SO$_4$. The drying agent was filtered off and the filtrate was concentrated under the reduced pressure to get the residue, which was dissolved in TFA (1 mL) and DCM (10 mL), then stirred at rt for 18 hrs. The solvent was removed under the reduced pressure to get the residue which was purified with Prep-HPLC (Welch, XB-C18, 21.2 mm*250 mm, 10 um, eluting with 40% CH$_3$CN in 1‰ TFA in H$_2$O) to afford 5-(4-(methylamino)-1,6-naphthyridin-2-yl)-N-(3-(piperidin-1-yl)propyl)-1H-benzo[d]imidazole-2-carboxamide. (30 mg, 39% yield) as a TFA salt. LC-MS (ESI): 444 (M+1)$^+$. $^1$H NMR (CD$_3$OD) δ 9.64 (s, 1H), 8.88 (d, J=6.0 Hz, 1H), 8.40 (s, 1H), 7.90-7.98 (m, 3H), 7.19 (s, 1H), 3.58-3.61 (m, 4H), 3.35 (s, 3H), 3.22-3.26 (m, 2H), 2.96-2.99 (m, 2H), 2.11-2.14 (m, 2H), 1.97-2.01 (m, 2H), 1.80-1.85 (m, 3H), 1.50-1.54 (m, 1H).

Example 31: Synthesis of 5-(4-(ethylamino)-1,6-naphthyridin-2-yl)-N-(3-(piperidin-1-yl)propyl)-1H-benzo[d]imidazole-2-carboxamide

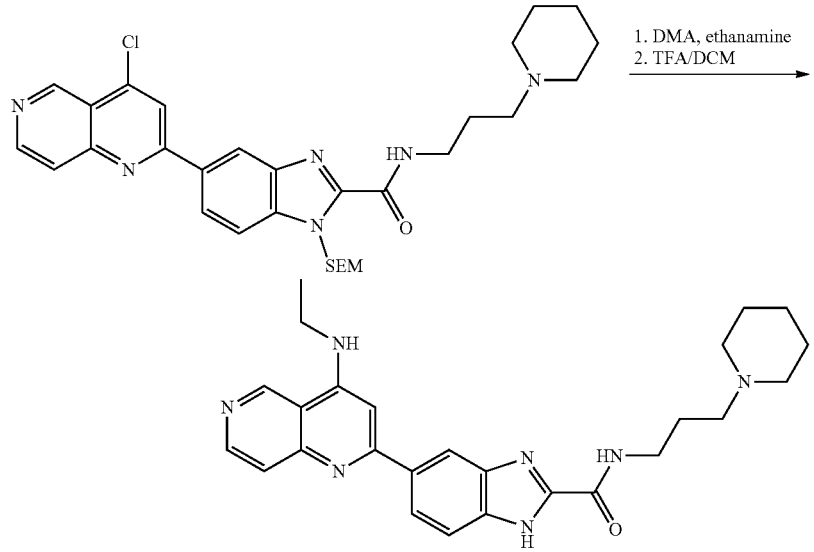

The mixture of 5-(4-chloro-1,6-naphthyridin-2-yl)-N-(3-(piperidin-1-yl)propyl)-1-((2-(trimethylsilyl)ethoxy)methyl)-1H-benzo[d]imidazole-2-carboxamide (100 mg, 0.17 mmol), and ethyl amine (0.5 mL, 1.0 mmol, 2 M THF solution) in DMA (3 ml) was heated to 100° C. and held for 18 hrs. The reaction mixture was poured into water (20 mL), extracted with EA (10 mL×3), the combined organic layers were washed by water and brine, dried over Na$_2$SO$_4$. The drying agent was filtered off and the filtrate was concentrated under the reduced pressure to get the residue, which was dissolved in TFA (1 mL) and DCM (10 mL), then stirred at rt for 18 hrs. The solvent was removed under the reduced pressure to get the residue which was purified with Prep-HPLC (Welch, XB-C18, 21.2 mm*250 mm, 10 um, eluting with 40% CH$_3$CN in 1‰ TFA in H$_2$O) to afford 5-(4-(ethylamino)-1,6-naphthyridin-2-yl)-N-(3-(piperidin-1-yl)propyl)-1H-benzo[d]imidazole-2-carboxamide. (25 mg, 32% yield) as a TFA salt. LC-MS (ESI): 458 (M+1)$^+$. $^1$H NMR (CD$_3$OD) δ 9.74 (s, 1H), 8.88 (d, J=6.0 Hz, 1H), 8.38 (s, 1H), 7.89-7.99 (m, 3H), 7.23 (s, 1H), 3.80 (q, J=7.2 Hz, 2H), 3.80 (t, J=6.8 Hz, 4H), 3.22-3.26 (m, 2H), 2.95-2.99 (m, 2H), 2.10-2.15 (m, 2H), 1.96-2.01 (m, 2H), 1.78-1.86 (m, 3H), 1.53-1.60 (m, 1H), 1.50 (t, J=7.2 Hz, 3H).

Example 32: Synthesis of N-(2-(dimethylamino)ethyl)-5-(4-(3-(piperidin-1-yl)propylamino)-1,6-naphthyridin-2-yl)-1H-benzo[d]imidazole-2-carboxamide

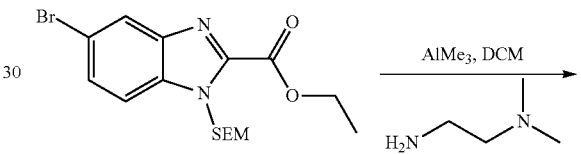

-continued

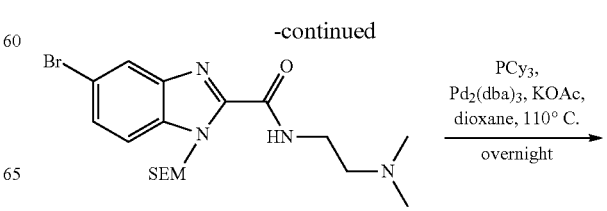

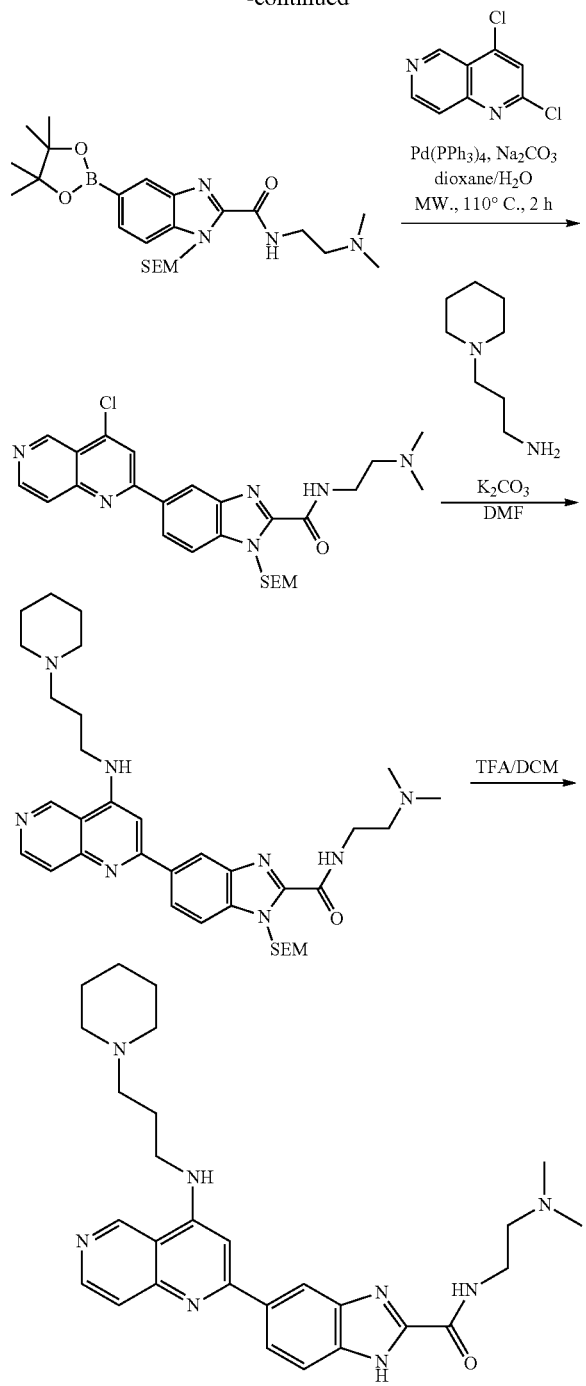

Step 1

To a solution of N1,N1-dimethylethane-1,2-diamine (880 mg, 10.0 mmol) in DCM (5 mL) was added Al(CH$_3$)$_3$ dropwise at 0° C. under nitrogen, then the mixture was stirred at rt for 30 mins, the reaction mixture was cooled to 0° C. again. A solution of ethyl ethyl 5-bromo-1-((2-(trimethylsilyl)ethoxy)methyl)-1H-benzo[d]imidazole-2-carboxylate (800 mg, 2.0 mmol) in DCM (5 mL) was added dropwise, the resulting reaction mixture was stirred at rt for 18 hrs. The reaction mixture was quenched by water (10 mL), then extracted with DCM (10 mL×3), the combined organic layers was washed with water and brine, dried over Na$_2$SO$_4$, the drying agent was filtered off and the filtrate was concentrated in vacuo to get the residue which was purified with Combiflash (silica gel, eluting with 30% methanol in DCM) to afford 5-bromo-N-(2-(dimethylamino)ethyl)-1-((2-(trimethylsilyl)ethoxy)methyl)-1H-benzo[d]imidazole-2-carboxamide (484 mg, 54%) as a yellow oil. LC-MS (ESI): 441.1 (M+1)$^+$.

Step 2

The mixture of 5-bromo-N-(2-(dimethylamino)ethyl)-1-((2-(trimethylsilyl)ethoxy)methyl)-1H-benzo[d]imidazole-2-carboxamide (484 mg, 1.06 mmol), 4,4,4',4',5,5,5',5'-octamethyl-2,2'-bi(1,3,2-dioxaborolane) (323 mg, 1.27 mmol), Pd$_2$(dba)$_3$ (97 mg, 0.106 mmol), tricyclohexylphosphine (60 mg, 0.21 mmol) and KOAc (311 mg, 3.18 mmol) in 1,4-Dioxane (20 mL) was heated to 100° C. and held for 18 hrs under N$_2$ atmosphere. The reaction mixture was cooled to rt and filtered by a pad of celite, the resulting filtrate was concentrated under the reduced pressure to get the residue which was diluted with EA (30 mL), then washed by water and brine, dried over Na$_2$SO$_4$, the drying agent was filtered off and the filtrate was concentrated in vacuo to get a crude boric acid ester which was purified with Combiflash (silica gel, eluting with 10% methanol in DCM) to afford N-(2-(dimethylamino)ethyl)-5-(4,4,5,5-tetramethyl-1,3,2-dioxaborolan-2-yl)-1-((2-(trimethylsilyl)ethoxy)methyl)-1H-benzo[d]imidazole-2-carboxamide (711 mg, 100%) as a brown oil. LC-MS (ESI): 489.3 (M+1)$^+$.

Step 3

A 10-mL microwave vial was charged with 2,4-dichloro-1,6-naphthyridine (100 mg, 0.5 mmol), N-(2-(dimethylamino)ethyl)-5-(4,4,5,5-tetramethyl-1,3,2-dioxaborolan-2-yl)-1-((2-(trimethylsilyl)ethoxy)methyl)-1H-benzo[d]imidazole-2-carboxamide (292 mg, 0.6 mmol), Pd(PPh$_3$)$_4$ (58 mg, 0.05 mmol) and Na$_2$CO$_3$ (106 mg, 1.0 mmol) dissolved 1,4-dioxane (3 mL) and H$_2$O (0.5 mL). A stir bar is added, the vial is sealed, and the resulting brown solution is heated for 2 h in a Biotage Initiator Eight Microwave Reactor held at a constant temperature of 110° C. The resulting solutions were concentrated by rotary evaporation (55° C., 20 mmHg). The adsorbed material was loaded onto a column and purified using silica gel chromatography (silica gel, eluting with 10% methanol in DCM) to afford 5-(4-chloro-1,6-naphthyridin-2-yl)-N-(2-(dimethylamino)ethyl)-1-((2-(trimethylsilyl)ethoxy)methyl)-1H-benzo[d]imidazole-2-carboxamide (75 mg, 28%) as a yellow oil LC-MS (ESI): 525.2 (M+1)$^+$.

Step 4

The mixture of 5-(4-chloro-1,6-naphthyridin-2-yl)-N-(2-(dimethylamino)ethyl)-1-((2-(trimethylsilyl)ethoxy) methyl)-1H-benzo[d]imidazole-2-carboxamide (75 mg, 0.14 mmol), 3-(piperidin-1-yl)propan-1-amine (40 mg, 0.28 mmol) and K$_2$CO$_3$ (38 mg, 0.28 mmol) in DMF (1 mL) was heated to 90° C. and held for 18 hrs. The reaction mixture was poured into water (20 mL), extracted with EA (10 mL×3), the combined organic layers were washed by water and brine, dried over Na$_2$SO$_4$. The drying agent was filtered off and the filtrate was concentrated under the reduced pressure to afford the residue which was purified with prep-TLC to afford N-(2-(dimethylamino)ethyl)-5-(4-(3-(piperidin-1-yl)propylamino)-1,6-naphthyridin-2-yl)-1-((2-

(trimethylsilyl)ethoxy)methyl)-1H-benzo[d]imidazole-2-carboxamide (50 mg, 55%) as a light yellow solid. LC-MS (ESI): 631.3 (M+1)$^+$.

Step 5

The mixture of N-(2-(dimethylamino)ethyl)-5-(4-(3-(piperidin-1-yl)propylamino)-1,6-naphthyridin-2-yl)-1-((2-(trimethylsilyl)ethoxy)methyl)-1H-benzo[d]imidazole-2-carboxamide (50 mg, 0.08 mmol) and TFA (1 mL) in DCM (1 mL) was stirred at rt for 18 hrs, then the solvent was removed under the reduced pressure to get the residue which was purified with Prep-HPLC (Welch, XB-C18, 21.2 mm*250 mm, 10 um, eluting with 40% CH$_3$CN in 1‰ TFA in H$_2$O) to afford N-(2-(dimethylamino)ethyl)-5-(4-(3-(piperidin-1-yl)propylamino)-1,6-naphthyridin-2-yl)-1H-benzo[d]imidazole-2-carboxamide (21.7 mg, 54%) as a TFA salt. HPLC/UV purity: 97%; LC-MS (ESI): 501.1 (M+1)$^+$. $^1$H NMR (DMSO-d$_6$) δ 9.80 (s, 1H), 9.54 (br. s., 2H), 9.30 (br. s., 1H), 8.89 (m, 1H), 8.41 (m, 1H), 8.01-7.94 (m, 3H), 7.29 (s, 1H), 3.79 (m, 2H), 3.71 (d, J=6.2 Hz, 2H), 3.46 (d, J=11.8 Hz, 2H), 3.35 (d, J=5.6 Hz, 2H), 3.22 (dd, J=10.3, 5.2 Hz, 2H), 2.89 (d, J=4.6 Hz, 6H), 2.13 (d, J=7.0 Hz, 2H), 1.95-2.08 (m, 1H), 1.82 (d, J=15.3 Hz, 2H), 1.51-1.74 (m, 4H), 1.38 (d, J=12.1 Hz, 1H).

Example 33: Synthesis of N-(3-(4-methylpiperazin-1-yl)propyl)-5-(4-((3-(piperidin-1-yl)propyl)amino)-1,6-naphthyridin-2-yl)-1H-benzo[d]imidazole-2-carboxamide A mixture of N-(3-(4-methylpiperazin-1-yl)propyl)-5-(4-((3-(piperidin-1-yl)propyl)amino)-1,6-naphthyridin-2-yl)-1-((2-(trimethylsilyl)ethoxy)methyl)-1H-benzo[d]imidazole-2-carboxamide (70 mg, 0.1 mmol) and TFA (1 mL) in DCM (1 mL) was heated to 40° C. and held for 2 hrs, the solvent was removed under the reduced pressure to afford the residue which was purified with Prep-HPLC (Welch, XB-C18, 21.2 mm*250 mm, 10 um, eluting with 20% CH$_3$CN in 1‰ TFA in H$_2$O) to afford N-(3-(4-methylpiperazin-1-yl)propyl)-5-(4-((3-(piperidin-1-yl)propyl)amino)-1,6-naphthyridin-2-yl)-1H-benzo[d]imidazole-2-carboxamide (50 mg, 65%) as a TFA salt. HPLC/UV purity: 100%; LC-MS (ESI): 570 (M+1)$^+$. $^1$H NMR (CD$_3$OD) δ 9.74 (s, 1H), 8.87 (d, J=6.1 Hz, 1H), 8.38 (s, 1H), 7.86-8.00 (m, 3H), 7.27 (s, 1H), 3.85 (t, J=6.9 Hz, 2H), 3.52-3.64 (m, 9H), 3.47 (m, 3H), 3.32-3.35 (m, 2H), 3.14-3.23 (m, 2H), 2.92-3.00 (m, 5H), 2.25-2.37 (m, 2H), 2.03-2.14 (m, 2H), 1.95 (d, J=14.3 Hz, 2H), 1.69-1.88 (m, 3H), 1.51 (d, J=12.5 Hz, 1H).

Example 34: Synthesis of piperazin-1-yl(5-(4-((3-(piperidin-1-yl)propyl)amino)-1,6-naphthyridin-2-yl)-1H-benzo[d]imidazol-2-yl)methanone

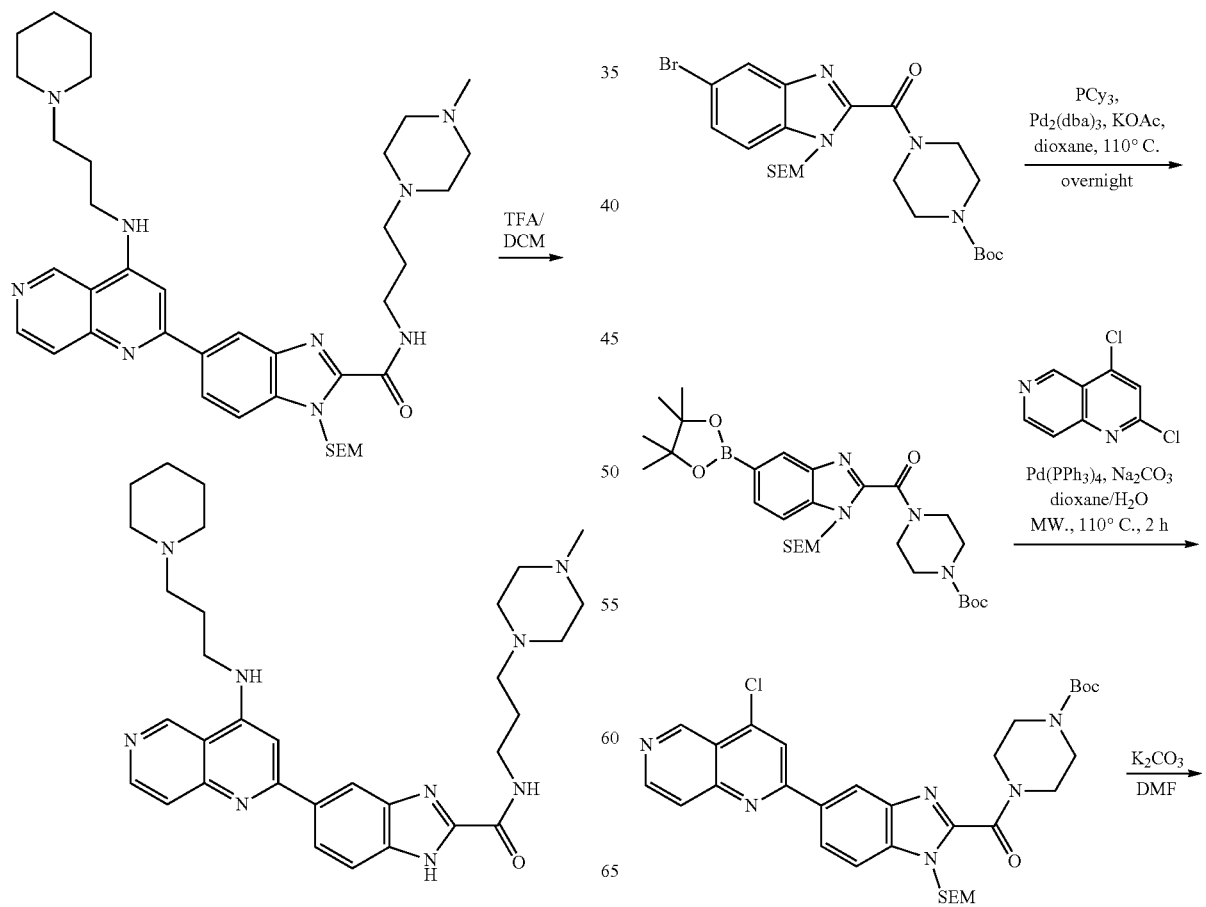

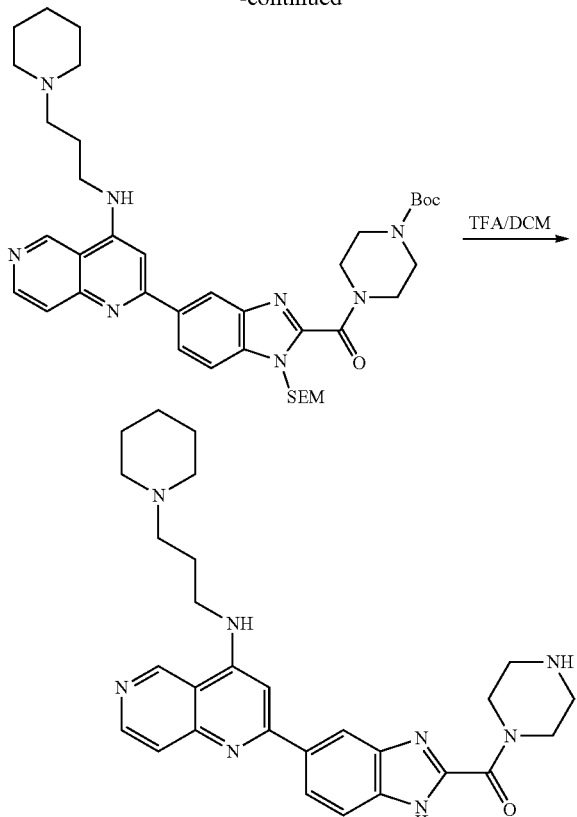

Step 1: tert-butyl 4-(5-bromo-1-((2-(trimethylsilyl)ethoxy)methyl)-1H-benzo[d]imidazole-2-carbonyl)piperazine-1-carboxylate To a solution of tert-butyl piperazine-1-carboxylate (2.09 g, 11.25 mmol) in DCM (10 mL) was added Al(CH$_3$)$_3$ dropwise at 0° C. under nitrogen, then the mixture was stirred at rt for 30 mins, the reaction mixture was cooled to 0° C. again. A solution of ethyl 5-bromo-1-((2-(trimethylsilyl)ethoxy)methyl)-1H-benzo[d]imidazole-2-carboxylate (900 mg, 2.25 mmol) in DCM (5 mL) was added dropwise, the resulting reaction mixture was stirred at rt for 18 hrs. The reaction mixture was quenched by water (10 mL), then extracted with DCM (10 mL×3), the combined organic layers was washed with water and brine, dried over Na$_2$SO$_4$, the drying agent was filtered off and the filtrate was concentrated in vacuo to get the residue which was purified with Combiflash (silica gel, eluting with 20% methanol in DCM) to afford tert-butyl 4-(5-bromo-1-((2-(trimethylsilyl)ethoxy)methyl)-1H-benzo[d]imidazole-2-carbonyl)piperazine-1-carboxylate (780 mg, 65%) as a white solid. HPLC/UV purity: 90%; LC-MS (ESI): 539 (M+1)$^+$.

Step 2

The mixture of tert-butyl 4-(5-bromo-1-((2-(trimethylsilyl)ethoxy)methyl)-1H-benzo[d]imidazole-2-carbonyl)piperazine-1-carboxylate (850 mg, 1.57 mmol), 4,4,4',4',5,5,5',5'-octamethyl-2,2'-bi(1,3,2-dioxaborolane)(480 g, 1.89 mmol), Pd$_2$(dba)$_3$ (144 mg, 0.157 mmol), tricyclohexylphosphine (90 mg, 0.32 mmol) and KOAc (308 g, 3.14 mmol) in 1,4-Dioxane (20 mL) was heated to 100° C. and held for 18 hrs under N$_2$ atmosphere. The reaction mixture was cooled to rt and filtered by a pad of celite, the resulting filtrate was concentrated under the reduced pressure to get the residue which was diluted with EA (30 mL), then washed by water and brine, dried over Na$_2$SO$_4$, the drying agent was filtered off and the filtrate was concentrated in vacuo to get a crude boric acid ester which was purified with Combiflash (silica gel, eluting with 20% methanol in DCM) to afford tert-butyl 4-(5-(4,4,5,5-tetramethyl-1,3,2-dioxaborolan-2-yl)-1-((2-(trimethylsilyl)ethoxy)methyl)-1H-benzo[d]imidazole-2-carbonyl)piperazine-1-carboxylate (1.5 g, 100%) as a white solid. HPLC/UV purity: 60%; LC-MS (ESI): 587 (M+1)$^+$.

Step 3

A 20-mL microwave vial was charged with 2,4-dichloro-1,6-naphthyridine (426 mg, 2.13 mmol), tert-butyl 4-(5-(4,4,5,5-tetramethyl-1,3,2-dioxaborolan-2-yl)-1-((2-(trimethylsilyl)ethoxy)methyl)-1H-benzo[d]imidazole-2-carbonyl)piperazine-1-carboxylate (1.5 g, 2.55 mmol), Pd(PPh$_3$)$_4$ (246 mg, 0.213 mmol) and Na$_2$CO$_3$ (451 mg, 4.26 mmol) dissolved 1,4-dioxane (10 mL) and H$_2$O (1 mL). A stir bar is added, the vial is sealed, and the resulting brown solution is heated for 2 h in a Biotage Initiator Eight Microwave Reactor held at a constant temperature of 110° C. The resulting solutions were concentrated by rotary evaporation (55° C., 20 mmHg). The adsorbed material was loaded onto a column and purified using silica gel chromatography (silica gel, eluting with 2-5% methanol in DCM) to afford tert-butyl 4-(5-(4-chloro-1,6-naphthyridin-2-yl)-1-((2-(trimethylsilyl)ethoxy)methyl)-1H-benzo[d]imidazole-2-carbonyl)piperazine-1-carboxylate (500 mg, 37%) as a yellow solid HPLC/UV purity: 80%; LC-MS (ESI): 623 (M+1)$^+$ Step 4

The mixture of tert-butyl 4-(5-(4-chloro-1,6-naphthyridin-2-yl)-1-((2-(trimethylsilyl)ethoxy)methyl)-1H-benzo[d]imidazole-2-carbonyl)piperazine-1-carboxylate (500 mg, 0.803 mmol), 3-(piperidin-1-yl)propan-1-amine (171 mg, 1.2 mmol) and K$_2$CO$_3$ (221 mg, 1.6 mmol) in DMF (2 mL) was heated to 80° C. and held for 18 hrs. The reaction mixture was poured into water (20 mL), extracted with EA (10 mL×3), the combined organic layers were washed by water and brine, dried over Na$_2$SO$_4$. The drying agent was filtered off and the filtrate was concentrated under the reduced pressure to get the residue which was purified with Combiflash (silica gel, eluting with 10% methanol and 1% NH3 in DCM) to afford tert-butyl 4-(5-(4-((3-(piperidin-1-yl)propyl)amino)-1,6-naphthyridin-2-yl)-1-((2-(trimethylsilyl)ethoxy)methyl)-1H-benzo[d]imidazole-2-carbonyl)piperazine-1-carboxylate (310 mg, 53%) as a yellow solid. HPLC/UV purity: 90%; LC-MS (ESI): 729 (M+1)$^+$.

Step 5

The mixture of tert-butyl 4-(5-(4-((3-(piperidin-1-yl)propyl)amino)-1,6-naphthyridin-2-yl)-1-((2-(trimethylsilyl)ethoxy)methyl)-1H-benzo[d]imidazole-2-carbonyl)piperazine-1-carboxylate (310 mg, 0.429 mmol) and TFA (1 mL) in DCM (1 mL) was stirred at rt for 18 hrs, then the solvent was removed under the reduced pressure to get the residue which was purified with Prep-HPLC (Welch, XB-C18, 21.2 mm*250 mm, 10 um, eluting with 20% CH$_3$CN in 1‰ TFA in H$_2$O) to afford piperazin-1-yl(5-(4-((3-(piperidin-1-yl)propyl)amino)-1,6-naphthyridin-2-yl)-1H-benzo[d]imidazol-2-yl)methanone (300 mg, 88%) as a TFA salt. HPLC/UV purity: 100%; LC-MS (ESI): 499 (M+1)+. ¹H NMR (CD₃OD) δ 9.73 (s, 1H), 8.87 (d, J=6.2 Hz, 1H), 8.40 (d, J=1.3 Hz, 1H), 7.95-8.01 (m, 1H), 7.88-7.94 (m, 2H), 7.28 (s, 1H), 4.08 (m, 2H), 3.85 (t, J=6.9 Hz, 2H), 3.58 (d, J=12.1 Hz, 2H), 3.42 (m, 4H), 3.31-3.35 (m, 4H), 2.95 (t, J=12.4 Hz, 2H), 2.25-2.36 (m, 2H), 1.94 (d, J=15.0 Hz, 2H), 1.71-1.88 (m, 3H), 1.51 (m, 1H).

Example 35: Synthesis of N,N-diethyl-5-(4-((3-(piperidin-1-yl)propyl)amino)-1,6-naphthyridin-2-yl)-1H-benzo[d]imidazole-2-carboxamide

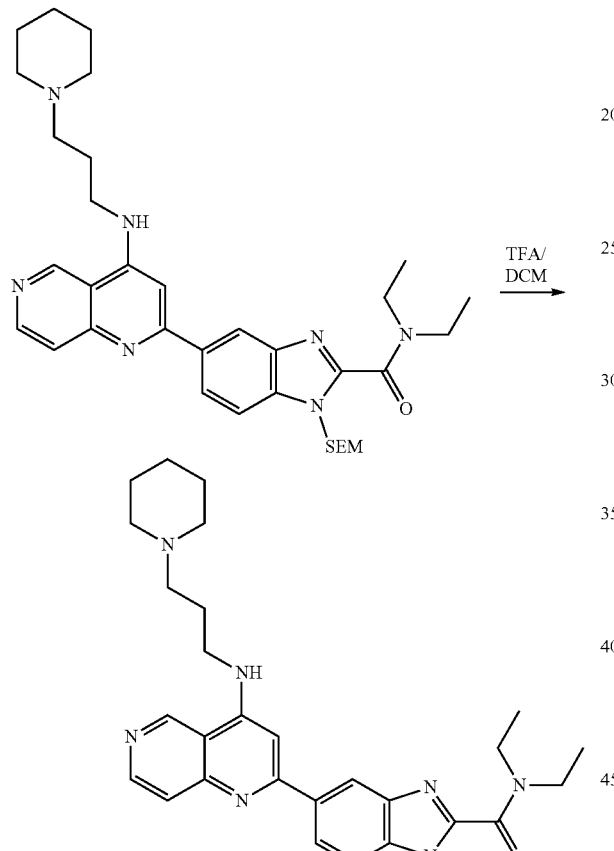

A mixture of N,N-diethyl-5-(4-((3-(piperidin-1-yl)propyl)amino)-1,6-naphthyridin-2-yl)-1-((2-(trimethylsilyl)ethoxy)methyl)-1H-benzo[d]imidazole-2-carboxamide (100 mg, 0.162 mmol) and TFA (1 mL) in DCM (1 mL) was heated to 40° C. and held for 2 hrs, the solvent was removed under the reduced pressure to get the residue which was purified with Prep-HPLC (Welch, XB-C18, 21.2 mm*250 mm, 10 um, eluting with 20% CH₃CN in 1‰ TFA in H₂O) to afford N,N-diethyl-5-(4-((3-(piperidin-1-yl)propyl)amino)-1,6-naphthyridin-2-yl)-1H-benzo[d]imidazole-2-carboxamide (80 mg, 80%) as a TFA salt. HPLC/UV purity: 100%; LC-MS (ESI): 486 (M+1)+. ¹H NMR (CD₃OD) δ 9.73 (s, 1H), 8.87 (d, J=6.1 Hz, 1H), 8.40 (s, 1H), 7.85-8.02 (m, 3H), 7.29 (s, 1H), 4.06 (q, J=7.0 Hz, 2H), 3.85 (t, J=6.9 Hz, 2H), 3.54-3.70 (m, 4H), 3.34 (d, J=3.4 Hz, 2H), 2.96 (t, J=12.4 Hz, 2H), 2.23-2.37 (m, 2H), 1.95 (d, J=14.3 Hz, 2H), 1.69-1.88 (m, 3H), 1.45-1.58 (m, 1H), 1.27-1.35 (m, 6H).

Example 36: Synthesis of (4-ethylpiperazin-1-yl)(5-(4-((3-(piperidin-1-yl)propyl)amino)-1,6-naphthyridin-2-yl)-1H-benzo[d]imidazol-2-yl)methanone and (1-ethyl-5-(4-((3-(piperidin-1-yl)propyl)amino)-1,6-naphthyridin-2-yl)-1H-benzo[d]imidazol-2-yl)(4-ethylpiperazin-1-yl)methanone

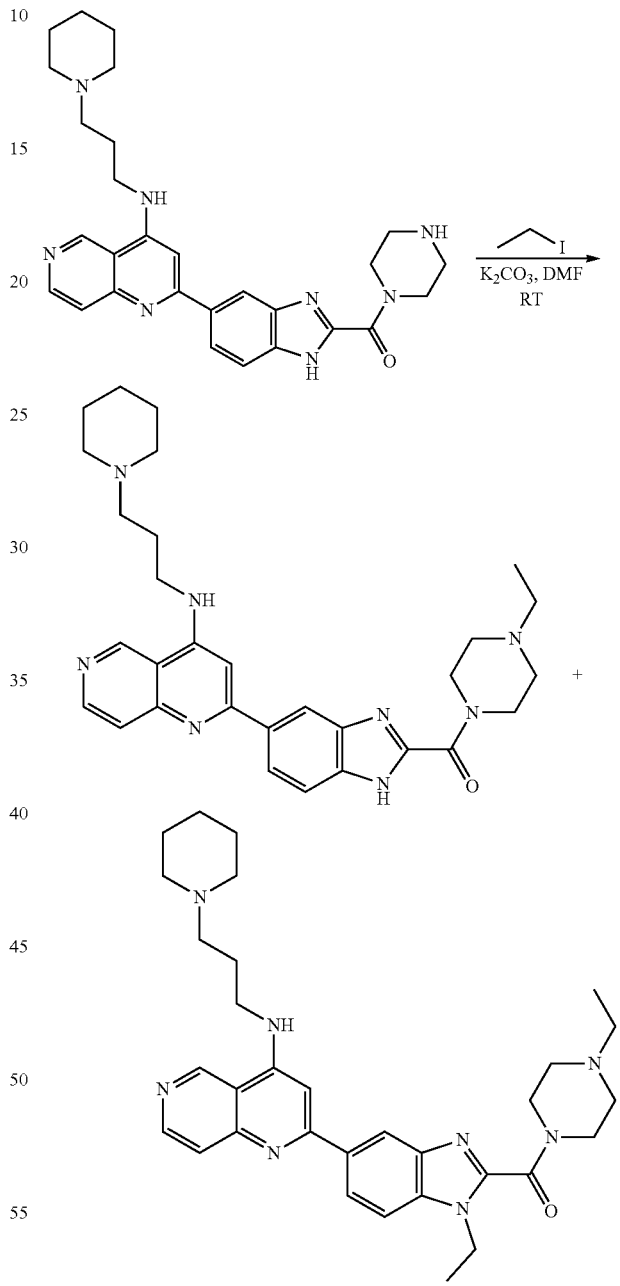

The mixture of piperazin-1-yl(5-(4-((3-(piperidin-1-yl)propyl)amino)-1,6-naphthyridin-2-yl)-1H-benzo[d]imidazol-2-yl)methanone (100 mg, 0.2 mmol) and K₂CO₃ (82 mg, 0.6 mmol) in DMF (1 mL) was stirred at rt for 30 min, then iodoethane (34 mg, 0.22 mmol) was added dropwise, the resulting reaction mixture was stirred at rt for 2 hrs. The reaction mixture was poured into water (20 mL), extracted with EA (10 mL×3), the combined organic layers were washed by water and brine, dried over Na₂SO₄. The drying agent was filtered off and the filtrate was concentrated under the reduced pressure to get the residue which was purified with Prep-TLC (silica gel, DCM/Methanol/NH₃·H₂O=10/1/0.1) to afford two products including (4-ethylpiperazin-1-yl)(5-(4-((3-(piperidin-1-yl)propyl)amino)-1,6-naphthyridin-2-yl)-1H-benzo[d]imidazol-2-yl)methanone (10 mg), HPLC/UV purity: 99%; LC-MS (ESI): 527 (M+1)⁺. ¹H NMR (CD₃OD) δ 9.49 (s, 1H), 8.59 (d, J=6.2 Hz, 1H), 8.38 (s, 1H), 8.09 (d, J=8.6 Hz, 1H), 7.82 (d, J=6.7 Hz, 2H), 7.14 (s, 1H), 4.44 (m, 2H), 3.90 (m, 2H), 3.66 (t, J=6.7 Hz, 2H), 3.04 (d, J=7.8 Hz, 6H), 2.67 (t, J=4.8 Hz, 4H), 2.56 (q, J=7.2 Hz, 2H), 2.16-2.26 (m, 2H), 1.75-1.86 (m, 4H), 1.63 (m, 2H), 1.19 (t, J=7.3 Hz, 3H).

And (1-ethyl-5-(4-((3-(piperidin-1-yl)propyl)amino)-1,6-naphthyridin-2-yl)-1H-benzo[d]imidazol-2-yl)(4-ethylpiperazin-1-yl)methanone (5 mg), HPLC/UV purity: 98%; LC-MS (ESI): 555 (M+1)⁺. ¹H NMR (CD₃OD) δ 9.37 (s, 1H), 8.47 (d, J=5.8 Hz, 1H), 8.31 (s, 1H), 8.07 (d, J=8.9 Hz, 1H), 7.64-7.73 (m, 2H), 7.03 (s, 1H), 4.35 (q, J=7.1 Hz, 2H), 3.80 (m, 2H), 3.58-3.68 (m, 2H), 3.53 (t, J=6.7 Hz, 2H), 2.87 (d, J=7.0 Hz, 6H), 2.56 (t, J=4.6 Hz, 2H), 2.35-2.50 (m, 4H), 2.00-2.12 (m, 2H), 1.61-1.72 (m, 4H), 1.50 (m, 2H), 1.41 (t, J=7.2 Hz, 3H), 1.05 (t, J=7.2 Hz, 3H).

Example 37: Synthesis of N-(3-(piperidin-1-yl)propyl)-5-(4-(3-(piperidin-1-yl)propylamino)-1,6-naphthyridin-2-yl)benzo[b]thiophene-2-carboxamide

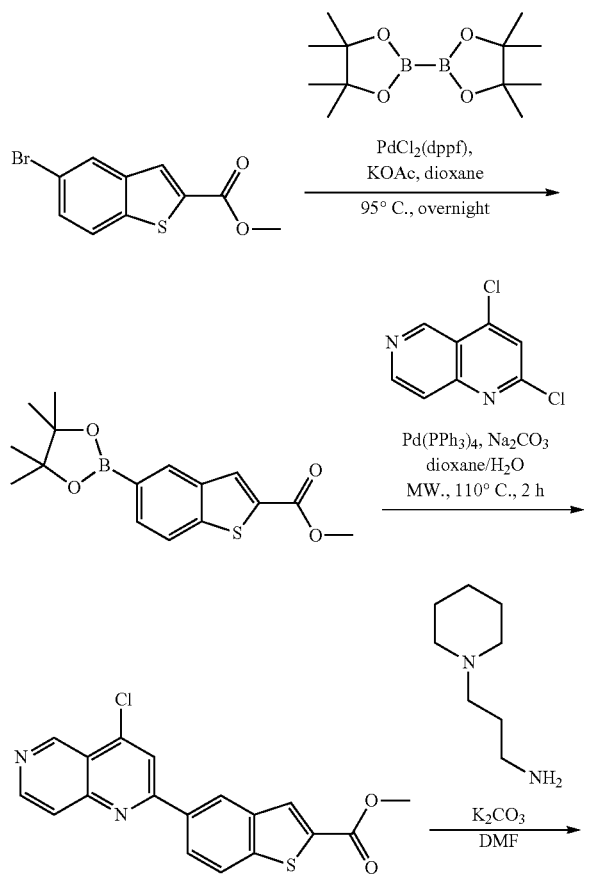

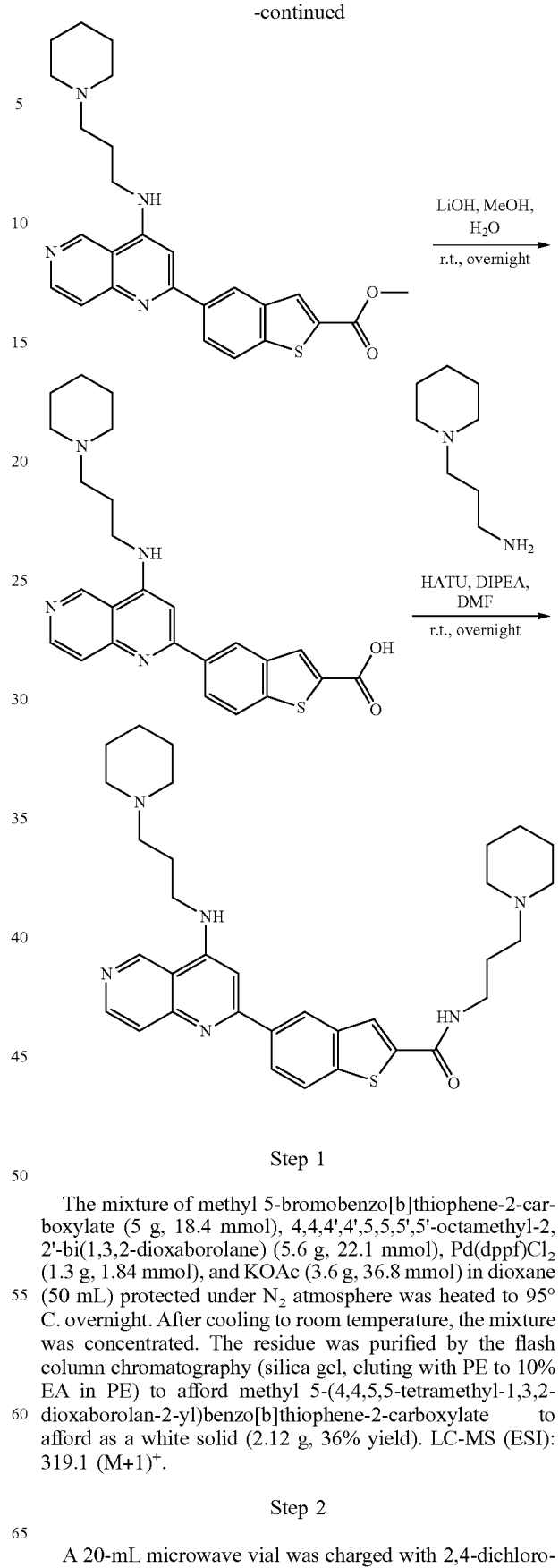

Step 1

The mixture of methyl 5-bromobenzo[b]thiophene-2-carboxylate (5 g, 18.4 mmol), 4,4,4',4',5,5,5',5'-octamethyl-2,2'-bi(1,3,2-dioxaborolane) (5.6 g, 22.1 mmol), Pd(dppf)Cl₂ (1.3 g, 1.84 mmol), and KOAc (3.6 g, 36.8 mmol) in dioxane (50 mL) protected under N₂ atmosphere was heated to 95° C. overnight. After cooling to room temperature, the mixture was concentrated. The residue was purified by the flash column chromatography (silica gel, eluting with PE to 10% EA in PE) to afford methyl 5-(4,4,5,5-tetramethyl-1,3,2-dioxaborolan-2-yl)benzo[b]thiophene-2-carboxylate to afford as a white solid (2.12 g, 36% yield). LC-MS (ESI): 319.1 (M+1)⁺.

Step 2

A 20-mL microwave vial was charged with 2,4-dichloro-1,6-naphthyridine (1.1 g, 5.5 mmol), methyl 5-(4,4,5,5- tetramethyl-1,3,2-dioxaborolan-2-yl)benzo[b]thiophene-2-carboxylate (2.12 g, 6.6 mmol), Pd(PPh₃)₄ (0.63 g, 0.1 mmol) and Na₂CO₃ (1.1 g, 11 mmol) dissolved 1,4-dioxane (10 mL) and H₂O (2 mL). A stir bar is added, the vial is sealed, and the resulting brown solution is heated for 2 h in a Biotage Initiator Eight Microwave Reactor held at a constant temperature of 110° C. The resulting solutions were concentrated by rotary evaporation (55° C., 20 mmHg). The adsorbed material was loaded onto a column and purified using silica gel chromatography (silica gel, eluting with PE to 50% EA in PE) to afford methyl 5-(4-chloro-1,6-naphthyridin-2-yl)benzo[b]thiophene-2-carboxylate (1.0 g, 52%) as a yellow oil, LC-MS (ESI): 355.0 (M+1)⁺.

Step 3

The mixture of methyl 5-(4-chloro-1,6-naphthyridin-2-yl)benzo[b]thiophene-2-carboxylate (1.0 g, 2.8 mmol), 3-(piperidin-1-yl)propan-1-amine (0.48 g, 3.36 mmol) and K₂CO₃ (0.78 g, 5.6 mmol) in DMF (1 ml) was heated to 90° C. and held for 18 hrs. The reaction mixture was poured into water (20 mL), extracted with EA (10 mL×3), the combined organic layers were washed by water and brine, dried over Na₂SO₄. The drying agent was filtered off and the filtrate was concentrated under the reduced pressure to afford the residue which was purified with prep-TLC to afford methyl 5-(4-(3-(piperidin-1-yl)propylamino)-1,6-naphthyridin-2-yl)benzo[b]thiophene-2-carboxylate (136 mg, 9%) as a yellow solid. LC-MS (ESI): 461.1 (M+1)⁺.

Step 4

The mixture of methyl 5-(4-(3-(piperidin-1-yl)propylamino)-1,6-naphthyridin-2-yl)benzo[b]thiophene-2-carboxylate (136 mg, 0.29 mmol) and LiOH·H₂O (124 mg, 2.95 mmol) in MeOH/H₂O (5 mL/1 mL) was stirred at room temperature overnight. The mixture was acidified with HCl solution (2 M) to pH=2, then concentrated to give the crude product that was used directly in the next step without further purification. LC-MS (ESI): 447.1 (M+1)⁺.

Step 5

The mixture of 5-(4-(3-(piperidin-1-yl)propylamino)-1,6-naphthyridin-2-yl)benzo[b]thiophene-2-carboxylic acid (100 mg, 0.22 mmol), 3-(piperidin-1-yl)propan-1-amine (63 mg, 0.45 mmol), HATU (125 mg, 0.33 mmol) and DIPEA (0.11 ml, 0.66 mmol) in DMF (2 mL) was stirred at room temperature overnight. Water (30 mL) was added, and then the mixture was extracted with EA three times. The combined organic layers were washed with water (20 mL×3) and brine (20 mL×1), dried over Na₂SO₄, filtered and concentrated. The residue was purified by the Prep-HPLC to afford N-(3-(piperidin-1-yl)propyl)-5-(4-(3-(piperidin-1-yl)propylamino)-1,6-naphthyridin-2-yl)benzo[b]thiophene-2-carboxamide as a yellow oil (2.6 mg, 2% yield). LC-MS (ESI): 571.3 (M+1)⁺; 1H NMR (CD₃OD) δ 9.66 (s, 1H), 8.79 (d, J=5.2 Hz, 1H), 8.53 (s, 1H), 8.16 (d, J=8.5 Hz, 1H), 8.10 (s, 1H), 7.96 (d, J=8.5 Hz, 1H), 7.83 (d, J=5.8 Hz, 1H), 7.23 (s, 1H), 3.77 (t, J=6.7 Hz, 2H), 3.39-3.54 (m, 6H), 3.25 (s, 2H), 3.06-3.14 (m, 2H), 2.76-2.92 (m, 4H), 2.15-2.29 (m, 2H), 1.96-2.07 (m, 2H), 1.80-1.92 (m, 4H), 1.62-1.79 (m, 6H), 1.34-1.50 (m, 2H).

Example 38: Synthesis of N,N-diethyl-4-(4-(3-(piperidin-1-yl)propylamino)-1,5-naphthyridin-2-yl)benzamide

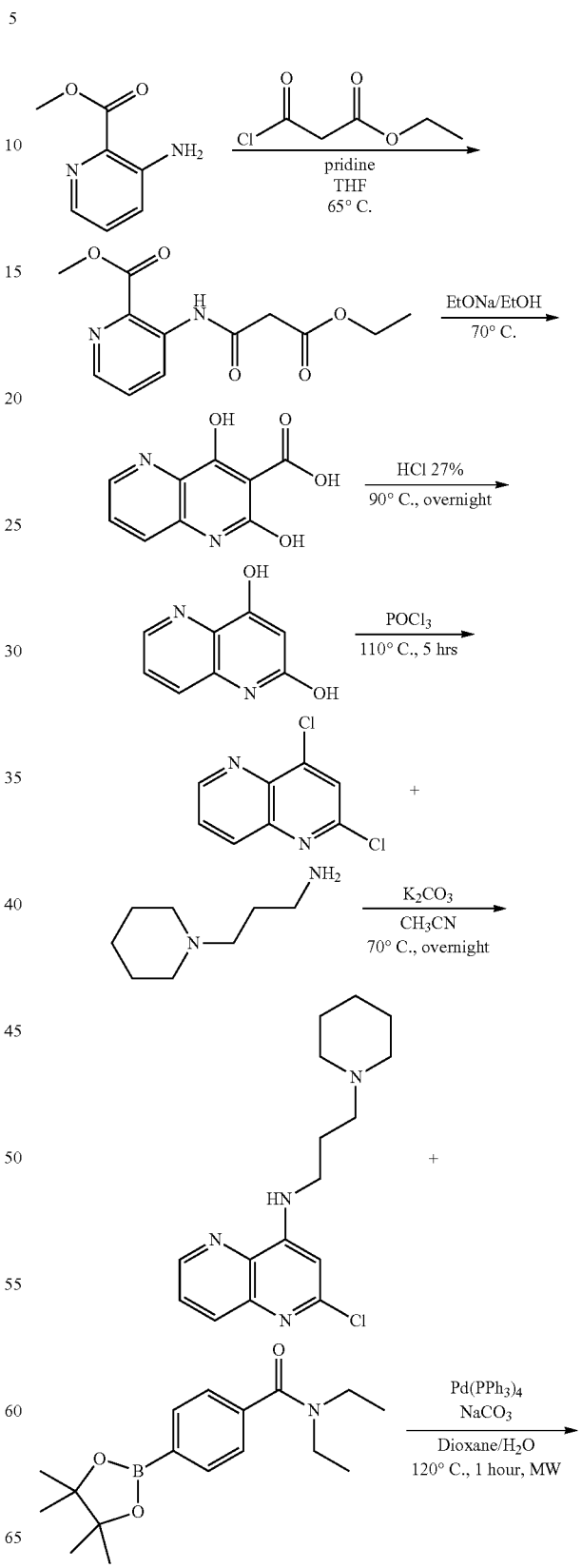

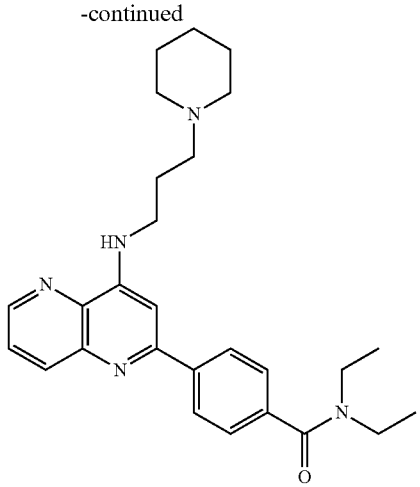

Step 1

To a solution of methyl 3-aminopicolinate (3.04 g, 20 mmol) and pyridine (4.74 g, 60 mmol) in THF (120 mL). Then ethyl 3-chloro-3-oxopropanoate (4.5 g, 30 mmol) was added dropwise under 65° C. Then the mixture was stirred at 65° C. for 2 hours. Then the solvent was removed under reduce and the residue was purified by flash column chromatography to afford desired compound. Isolated weight: 2.6 g, yield: 48.87%, as a yellow oil.

Step 2

To a solution of Na (345 mg, 15 mmol) in EtOH (30 mL) until the mixture was clear. Then methyl 3-(3-ethoxy-3-oxopropanamido)picolinate (2.6 g, 9.77 mmol) was added. Then the mixture was stirred at 70° C. for 2 hours. Then the solvent was removed under reduce to afford desired crude product which used to next step directly.

Step 3

To a solution of Ethyl 2,4-dihydroxy-1,5-naphthyridine-3-carboxylate (2.0 g, 9.75 mmol) in 27% HCl (30 mL). Then the mixture was stirred at 90° C. for 3 hours. Filtered and the residue was desired compound which used to next step directly. A white solid (1.2 g), yield: 76%. LC-MS (ESI): 163 (M+1)$^+$.

Step 4

A mixture of 1,5-naphthyridine-2,4-diol (648 mg, 4 mmol) and in POCl$_3$ (30 mL) was stirred at 120° C. for overnight. Then the solvent was removed under reduce pressure in vacuum, the mixture was dissolved in 100 mL DCM and adjusted to pH=8-9 with NaHCO$_3$ saturated aqueous solution. Extracted with DCM (100 mL), washed with brine, dried over Na$_2$SO$_4$. Evaporation of the organic phase and the residue was purified by flash column to afford a white solid (600 mg). Yield: 75%; LC-MS (ESI): 198, 200 (M+1)$^+$.

Step 5

A mixture of 2,4-dichloro-1,5-naphthyridine (400 mg, 2 mmol) and 3-(piperidin-1-yl)propan-1-amine (284 mg, 2.0 mmol) in CH$_3$CN (20 mL) and was stirred at 90° C. for 3 hours. Filtered and the mixture was evaporated and the residue was purified by Prep-TLC to give desired compound as a white solid (340 mg), yield: 56%. LC-MS (ESI): 305 (M+1)$^+$.

Step 6

The mixture of 2-chloro-N-(3-(piperidin-1-yl)propyl)-1,5-naphthyridin-4-amine (60.8 mg, 0.2 mmol), N,N-diethyl-4-(4,4,5,5-tetramethyl-1,3,2-dioxaborolan-2-yl)benzamide (121 mg, 0.4 mmol), Pd(PPh$_3$)$_4$ (24 mg, 0.02 mmol) and Na$_2$CO$_3$ (85 mg, 0.8 mmol) in Dioxane/H$_2$O (5 mL/0.5 mL) was stirred at for 120° C. 1 hour by MW. The mixture was diluted with DCM, washed with water (20 mL×3) and brine (20 mL×1), dried over Na$_2$SO$_4$, filtered and concentrated. The crude product was purified by Prep-TLC to afford N,N-diethyl-4-(4-(3-(piperidin-1-yl)propylamino)-1,5-naphthyridin-2-yl)benzamide (15 mg, 16.6%) as an white solid. HPLC/UV purity=92.5%; LC-MS (ESI): 446.2 (M+1)$^+$; $^1$H NMR (CD$_3$OD) δ 8.76 (dd, J=4.3, 1.1 Hz, 1H), 8.45 (m, 1H), 7.83-7.90 (m, 2H), 7.77-7.81 (m, 1H), 7.53-7.59 (m, 2H), 7.31-7.42 (m, 1H), 3.79 (t, J=6.9 Hz, 2H), 3.60 (d, J=7.6 Hz, 4H), 3.39 (d, J=6.4 Hz, 2H), 3.33 (m, 1H), 3.23-3.29 (m, 1H), 2.99 (t, J=12.4 Hz, 2H), 2.22-2.34 (m, 2H), 1.91-2.00 (m, 2H), 1.85 (m, 3H), 1.54 (d, J=12.4 Hz, 1H), 1.29 (t, J=6.5 Hz, 3H), 1.19 (t, J=6.5 Hz, 3H).

Example 39: Synthesis of N,N-diethyl-4-(4-(3-(piperidin-1-yl)propylamino)-1,7-naphthyridin-2-yl)benzamide

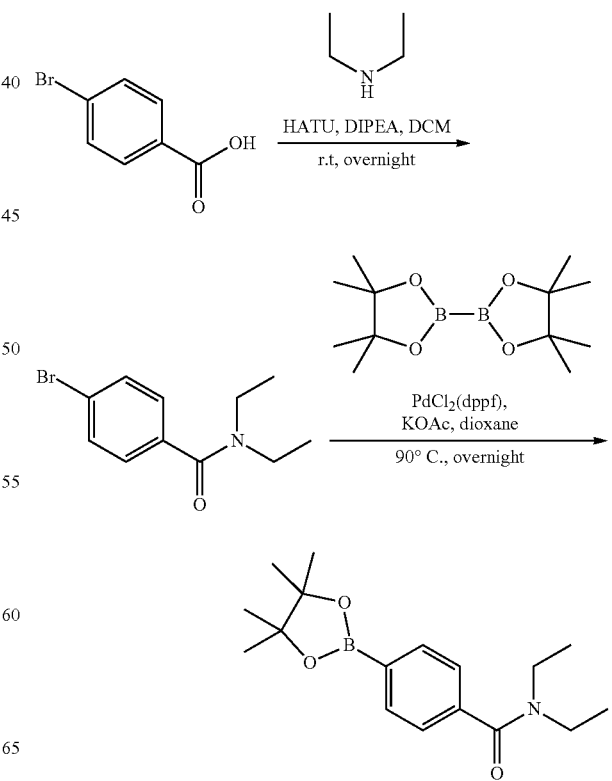

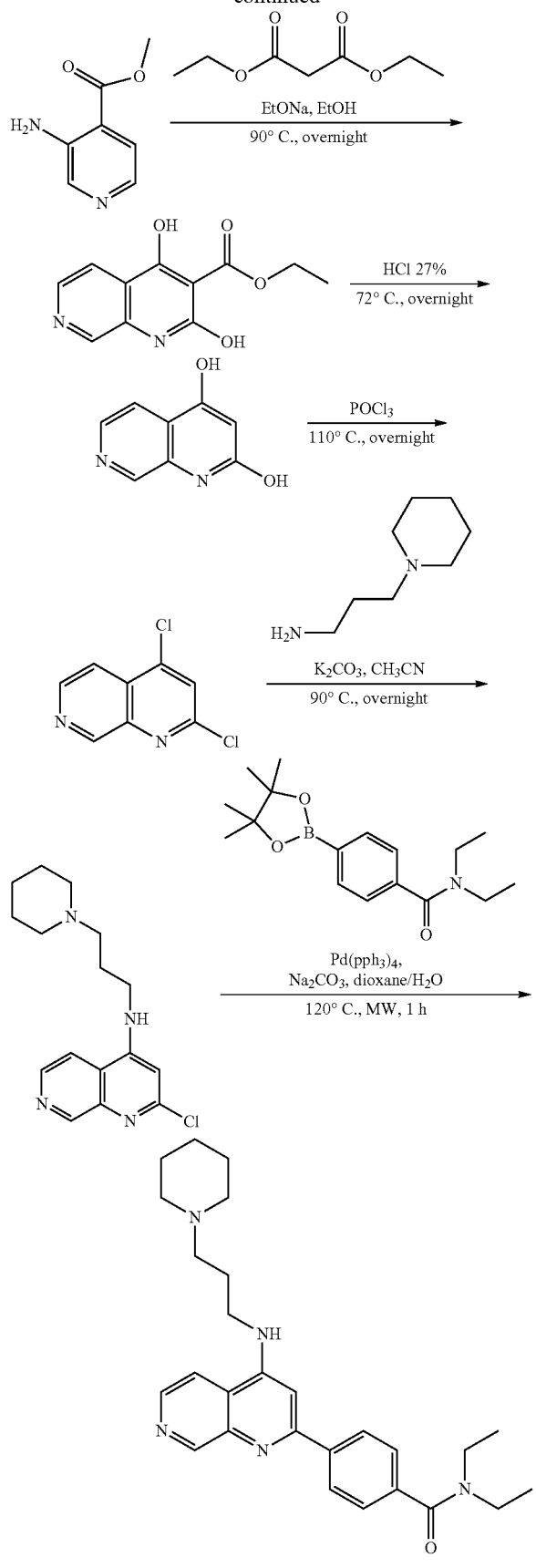

Step 1

To a solution of Na (1.0 g, 45.1 mmol) in EtOH (50 mL) was stirred at rt for 2 hrs, A solution of methyl 3-aminoisonicotinate (5.0 g, 30.1 mmol) and diethyl malonate (5.7 g, 36.1 mmol) in EtOH (30 mL) was added dropwise, the resulting reaction mixture was heated to 90° C. overnight. After cooling to room temperature, the mixture was concentrated. The residue was adjusted to PH=5-6 with 1N HCl, extracted with EtOAc (30 mL×3) dried over $Na_2SO_4$, filtered and concentrated to get crude ethyl 2,4-dihydroxy-1,7-naphthyridine-3-carboxylate (1.09 g, 15% yield) which was used to the next step without further purification. LC-MS (ESI): 235.0 $(M+1)^+$.

Step 2

The mixture of ethyl 2,4-dihydroxy-1,7-naphthyridine-3-carboxylate (1.09 g, 4.6 mmol) in 27% HCl (20 mL) was stirred at 72° C. overnight. After cooling to room temperature, the mixture was filtered to get 1,7-naphthyridine-2,4-diol (0.3 g, 40% yield) which was used to the next step without further purification. LC-MS (ESI): 163.0 $(M+1)^+$.

Step 3

A mixture of 1,7-naphthyridine-2,4-diol (250 mg, 1.5 mmol) and in $POCl_3$ (2 mL) was stirred at 120° C. overnight. After cooling to room temperature, the mixture was concentrated. The residue was dissolved in 10 mL DCM and adjusted to pH=8-9 with $NaHCO_3$ saturated aqueous solution. Extracted with EtOAc (10 mL×3), washed with brine, dried over $Na_2SO_4$. Filtered and concentrated. The residue was purified by the flash column chromatography (silica gel, eluting with PE to 20% EA in PE) to afford 2,4-dichloro-1,7-naphthyridine as a yellow oil (146 mg, 47% yield). LC-MS (ESI): 198.9 $(M+1)^+$.

Step 4

The mixture of 2,4-dichloro-1,7-naphthyridine (146 mg, 0.73 mmol), 3-(piperidin-1-yl)propan-1-amine (104 mg, 0.73 mmol) and $K_2CO_3$ (201 mg, 1.46 mmol) in $CH_3CN$ (5 mL) was heated to 90° C. and held for 18 hrs. The reaction mixture was poured into water (20 mL), extracted with EA (10 mL×3), the combined organic layers were washed by water and brine, dried over $Na_2SO_4$. The drying agent was filtered off and the filtrate was concentrated under the reduced pressure to get the residue which was purified Prep-TLC to afford 2-chloro-N-(3-(piperidin-1-yl)propyl)-1,7-naphthyridin-4-amine (76 mg, 34%) as a yellow solid. LC-MS (ESI): 305.1 $(M+1)^+$.

Step 5

The mixture of 4-bromobenzoic acid (3 g, 14.9 mmol), diethylamine (4.6 ml, 44.7 mmol), HATU (8.5 g, 22.3 mmol) and DIPEA (6.6 ml, 44.7 mmol) in DCM (30 mL) was stirred at room temperature overnight. Water (30 mL) was added, and then the mixture was extracted with EA three times. The combined organic layers were washed with water (20 mL×3) and brine (20 mL×1), dried over $Na_2SO_4$, filtered and concentrated. The residue was purified by the flash column chromatography (silica gel, eluting with PE to 20% EA in PE) to afford 4-bromo-N,N-diethylbenzamide as a brown oil (2.8 g, 73% yield). LC-MS (ESI): 256.9 $(M+1)^+$.

Step 6

The mixture of 4-bromo-N,N-diethylbenzamide (2.8 g, 11.2 mmol), 4,4,4',4',5,5,5',5'-octamethyl-2,2'-bi(1,3,2-dioxaborolane) (3.4 g, 13.4 mmol), PdCl$_2$(dppf) (0.8 g, 1.12 mmol), and KOAc (2.2 g, 22.4 mmol) in dioxane (50 mL) protected under N$_2$ atmosphere was heated to 90° C. overnight. After cooling to room temperature, the mixture was concentrated. The residue was purified by the flash column chromatography (silica gel, eluting with DCM to 3% MeOH in DCM) to afford N,N-diethyl-4-(4,4,5,5-tetramethyl-1,3,2-dioxaborolan-2-yl)benzamide as a brown solid (2.3 g, 69% yield). LC-MS (ESI): 303.9 (M+1)$^+$.

Step 7

A 10-mL microwave vial was charged with 2-chloro-N-(3-(piperidin-1-yl)propyl)-1,7-naphthyridin-4-amine (76 mg, 0.25 mmol), N,N-diethyl-4-(4,4,5,5-tetramethyl-1,3,2-dioxaborolan-2-yl)benzamide (151 mg, 0.5 mmol), Pd(PPh$_3$)$_4$ (58 mg, 0.05 mmol) and Na$_2$CO$_3$ (53 mg, 0.5 mmol) dissolved 1,4-dioxane (2.5 mL) and H$_2$O (0.5 mL). A stir bar is added, the vial is sealed, and the resulting brown solution is heated for 1 h in a Biotage Initiator Eight Microwave Reactor held at a constant temperature of 120° C. The resulting solutions were concentrated by rotary evaporation (55° C., 20 mmHg). The mixture was filtered off and the filtrate was concentrated under the reduced pressure to get the residue which was purified with Prep-TLC to afford N,N-diethyl-4-(4-(3-(piperidin-1-yl)propylamino)-1,7-naphthyridin-2-yl)benzamide (32 mg, 28%) as a yellow solid. LC-MS (ESI): 446.2 (M+1)$^+$. $^1$H NMR (CD$_3$OD) δ 8.94 (s, 1H), 8.18 (d, J=5.5 Hz, 1H), 7.55-7.62 (m, 4H), 7.52 (d, J=5.5 Hz, 1H), 7.00 (s, 1H), 3.66-3.71 (m, 2H), 3.52-3.63 (m, 2H), 3.39 (d, J=6.8 Hz, 2H), 3.29-3.32 (m, 2H), 3.09-3.28 (m, 4H), 2.13-2.24 (m, 2H), 1.87 (m, 4H), 1.68 (m, 2H), 1.25-1.33 (m, 3H), 1.19 (t, J=6.4 Hz, 3H).

Example 40: Synthesis of N,N-diethyl-4-(2-(3-(piperidin-1-yl)propylamino)-1,8-naphthyridin-4-yl)benzamide

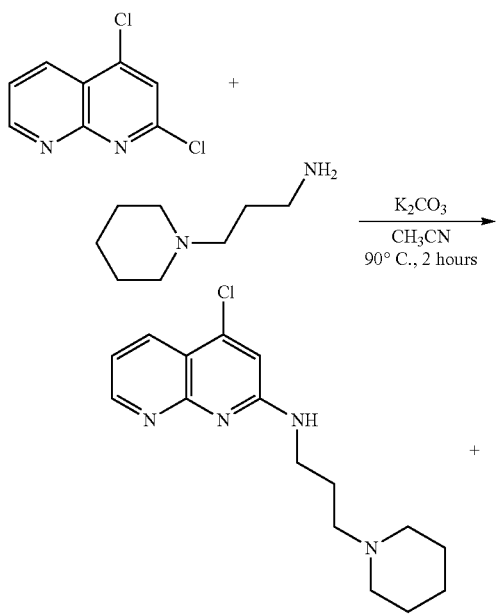

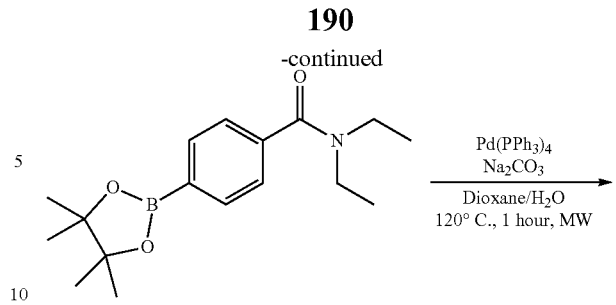

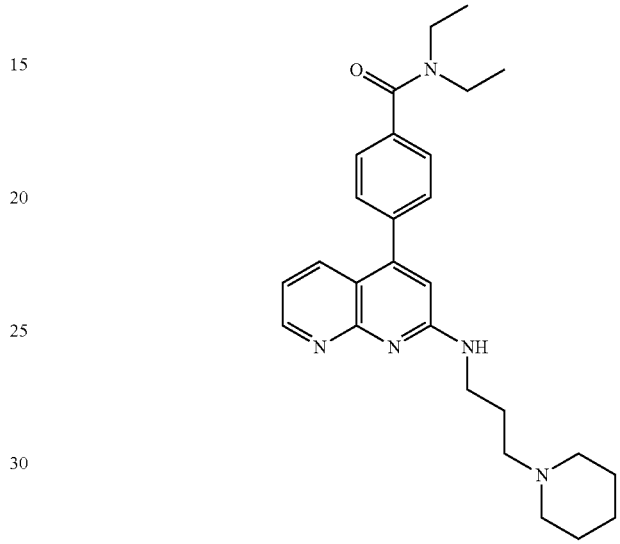

Step 1

A mixture of 2,4-dichloro-1,8-naphthyridine (1.0 g, 5 mmol) and 3-(piperidin-1-yl)propan-1-amine (0.71 g, 5 mmol) in CH$_3$CN (50 mL) and was stirred at 90° C. for 2 hours. Filtered and the mixture was evaporated and the residue was purified by Prep-TLC to give the desired compound (200 mg). LC-MS (ESI): 305 (M+1)$^+$.

Step 2

The mixture of 4-chloro-N-(3-(piperidin-1-yl)propyl)-1,8-naphthyridin-2-amine (61 mg, 0.205 mmol), N,N-diethyl-4-(4,4,5,5-tetramethyl-1,3,2-dioxaborolan-2-yl)benzamide (120 mg, 0.4 mmol), Pd(PPh$_3$)$_4$ (23 mg, 0.02 mmol) and Na$_2$CO$_3$ (43 mg, 0.4 mmol) in Dioxane/H$_2$O (2.5 mL/0.5 mL) was stirred at for 120° C. 1 hour under MW. The mixture was diluted with DCM, washed with water (10 mL×3) and brine (20 mL×1), dried over Na$_2$SO$_4$, filtered and concentrated. The crude product was purified by the Prep-HPLC to N,N-diethyl-4-(2-(3-(piperidin-1-yl)propylamino)-1,8-naphthyridin-4-yl)benzamide (43 mg, yield: 48%) as an white solid. HPLC/UV purity=95%; LC-MS (ESI): 446.2 (M+1)$^+$; $^1$H NMR (CD$_3$OD) δ 8.87 (br. s., 1H), 8.14 (d, J=7.3 Hz, 1H), 7.52-7.62 (m, 4H), 7.28-7.39 (m, 1H), 6.89 (s, 1H), 3.60 (d, J=6.9 Hz, 3H), 3.33-3.52 (m, 5H), 3.18-3.27 (m, 2H), 3.04 (m, 1H), 3.00 (m, 1H), 2.07-2.20 (m, 2H), 1.87-1.96 (m, 4H), 1.80 (m, 1H), 1.59 (m, 1H), 1.29 (t, J=6.6 Hz, 3H), 1.19 (t, J=6.6 Hz, 3H).

Example 41: Synthesis of N,N-diethyl-4-(4-(3-(piperidin-1-yl)propylamino)-1,8-naphthyridin-2-yl)benzamide

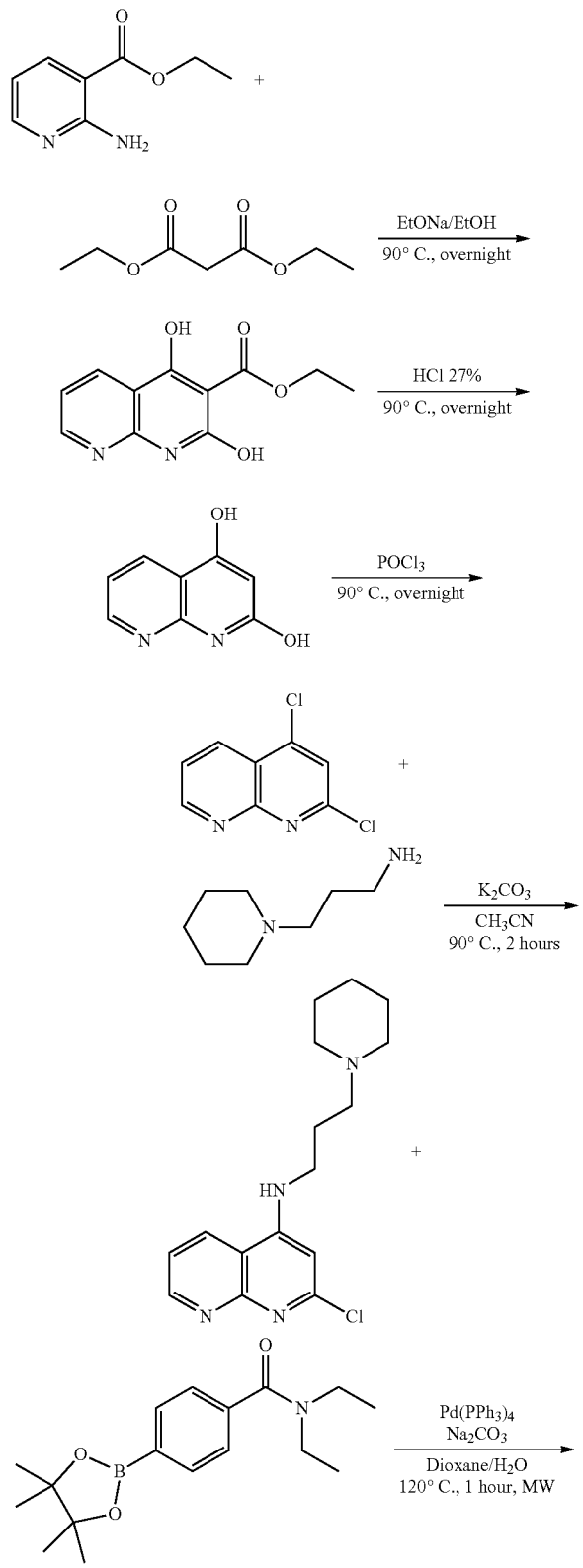

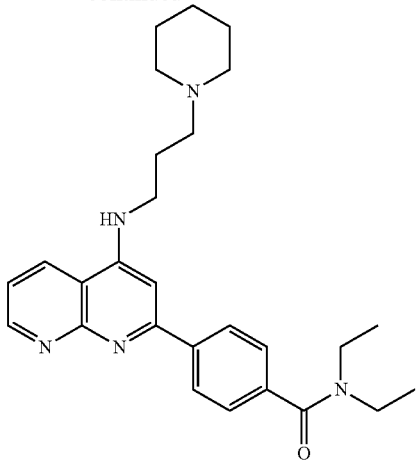 [SMILES: CCN(CC)C(=O)c1ccc(-c2cc(NCCCN3CCCCC3)c3cccnc3n2)cc1]

Step 1

To a solution of Na (1.035 g, 45 mmol) in EtOH (30 mL) until the mixture was clear. Then diethyl malonate (5.76 g, 36 mmol), EtOH (10 mL) and ethyl 2-aminonicotinate (5 g, 30 mmol) in EtONa (1.5 M, 30 mL). Then the mixture was stirred at 90° C. for overnight. Then the solvent was removed under reduce pressure in vacuum, the mixture was dissolved in 50 mL H$_2$O and adjusted to pH=5-6 with 1 M HCl. Extracted with EA (100 mL), filtered and the residue was used in next step directly. A white solid (3.5 g), yield: 49.6%.

Step 2

To a solution of Ethyl 2,4-dihydroxy-1,8-naphthyridine-3-carboxylate (3.5 g, 14.89 mmol) in 27% HCl (100 mL). Then the mixture was stirred at 90° C. for overnight. Then the mixture was adjusted to pH=5-6 with 30% NaOH under ice-water bath. Filtered and the residue was used in next step directly. A white solid (2.02 g), yield: 83.7%. LC-MS (ESI): 163 (M+1)$^+$.

Step 3

A mixture of 1,8-naphthyridine-2,4-diol (2.02 g, 12.47 mmol) and in POCl$_3$ (100 mL) was stirred at 90° C. for overnight. Then the solvent was removed under reduce pressure in vacuum, the mixture was dissolved in 100 mL DCM and adjusted to pH=5-6 with NaHCO$_3$ saturated aqueous solution. Extracted with DCM (100 mL), washed with brine, dried over Na$_2$SO$_4$. Evaporation of the organic phase provides a yellow solid (1.9 g) for use in the next step without further purification. Yield: 76%; LC-MS (ESI): 198, 200 (M+1)$^+$.

Step 4

A mixture of 2,4-dichloro-1,8-naphthyridine (1.0 g, 5 mmol) and 3-(piperidin-1-yl)propan-1-amine (0.71 g, 5 mmol) in CH$_3$CN (50 mL) and was stirred at 90° C. for 2 hours. Filtered and the mixture was evaporated and the residue was purified by-TLC to give desired compound (400 mg). LC-MS (ESI): 305 (M+1)$^+$.

Step 5

The mixture of 2-chloro-N-(3-(piperidin-1-yl)propyl)-1,8-naphthyridin-4-amine (63 mg, 0.205 mmol), N,N-diethyl-4-(4,4,5,5-tetramethyl-1,3,2-dioxaborolan-2-yl)benzamide (121 mg, 0.4 mmol), Pd(PPh$_3$)$_4$ (23.1 mg, 0.02 mmol) and Na$_2$CO$_3$ (42 mg, 0.4 mmol) in Dioxane/H$_2$O (2 mL/0.2 mL) was stirred at for 120° C. 1 hour by MW. The mixture was diluted with DCM, washed with water (20 mL×3) and brine (20 mL×1), dried over Na$_2$SO$_4$, filtered and concentrated. The crude product was purified by the Prep-HPLC to N,N-diethyl-4-(4-(3-(piperidin-1-yl)propylamino)-1,8-naphthyridin-2-yl)benzamide (7.5 mg, 8.2%) as an off-white solid. HPLC/UV purity=95%; LC-MS (ESI): 446 (M+1)$^+$; $^1$H NMR (CD$_3$OD) δ 8.96 (d, J=3.7 Hz, 1H), 8.69-8.76 (m, 1H), 8.17 (d, J=8.2 Hz, 2H), 7.44-7.62 (m, 3H), 7.03 (s, 1H), 3.56-3.73 (m, 4H), 3.31-3.41 (m, 6H), 3.28 (m, 2H), 2.17-2.35 (m, 2H), 1.86 (m, 4H), 1.68 (m, 2H), 1.29 (t, J=6.9 Hz, 3H), 1.17 (t, J=6.7 Hz, 3H).

Example 42: Synthesis of N,N-Diethyl-4-(4-((3-morpholinopropyl)amino)-1,6-naphthyridin-2-yl)benzamide

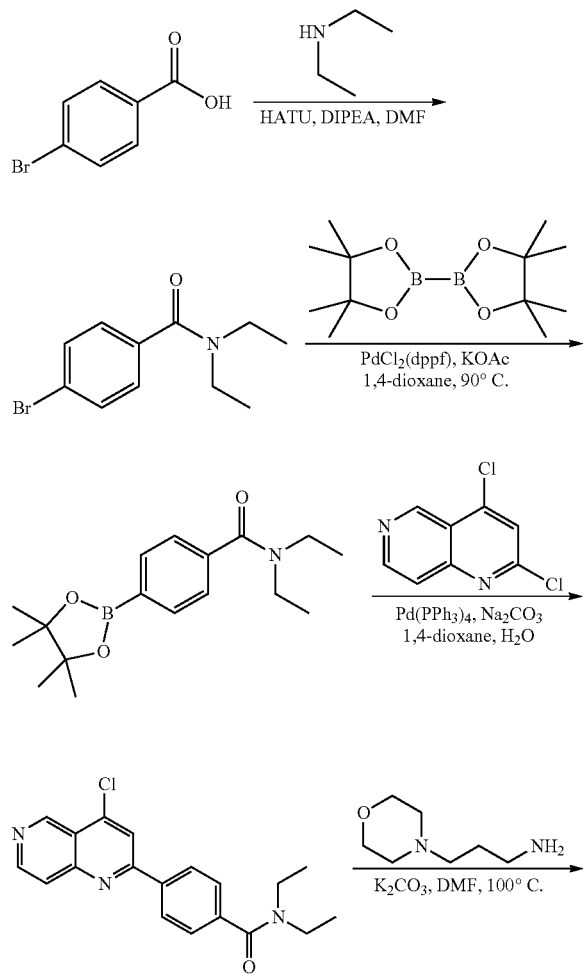

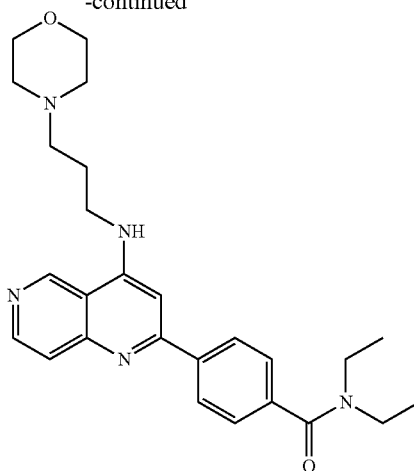

Step 1

The mixture of 4-bromobenzoic acid (5.0 g, 24.9 mmol), diethylamine (703 mg, 27.4 mmol), HATU (11.4 g, 29.9 mmol) and DIPEA (6.4 g, 49.8 mmol) in DMF (20 mL) was stirred at room temperature overnight. The reaction mixture was quenched with water (10 mL), and then extracted with EA (20 mL×3). The organic layer was washed with water (20 mL×3) and brine (30 mL), dried over Na$_2$SO$_4$, concentrated and purified by flash column chromatography (silica gel, eluting with 5% to 20% EA/PE) to afford 4-Bromo-N,N-diethylbenzamide (6.0 g, 94%) as oil. LC-MS (ESI): 256.9 (M+1)$^+$.

Step 2

The mixture of 4-bromo-N,N-diethylbenzamide (6.0 g, 23.4 mmol), bis(pinacolato)diboron (7.1 g, 27.4 mmol), Pd(dppf)Cl$_2$ (1.7 g, 2.34 mmol) and KOAc (4.6 g, 46.8 mmol) in 1,4-dioxane (20 mL) was stirred at 90° C. under N$_2$ for 18 hrs. The reaction mixture was diluted with DCM (20 mL), washed with water (20 mL×3) and brine (10 mL), dried over Na$_2$SO$_4$, concentrated and purified by flash column chromatography (silica gel, eluting with 10% to 50% EA/PE) to afford N,N-diethyl-4-(4,4,5,5-tetramethyl-1,3,2-dioxaborolan-2-yl)benzamide (1.8 g, 25%) as brown solid. LC-MS (ESI): 303.9 (M+1)$^+$.

Step 3: 4-(4-Chloro-1,6-naphthyridin-2-yl)-N,N-diethylbenzamide

The mixture of N,N-diethyl-4-(4,4,5,5-tetramethyl-1,3,2-dioxaborolan-2-yl)benzamide (1.8 g, 5.9 mmol), 2,4-dichloro-1,6-naphthyridine (7.1 g, 5.4 mmol), Pd(PPh$_3$)$_4$ (624 mg, 0.54 mmol) and Na$_2$CO$_3$ (1.1 g, 10.8 mmol) in 1,4-dioxane/H$_2$O (8 mL/2 mL) was stirred at 100° C. under N$_2$ for 16 hrs. The reaction mixture was concentrated and purified by flash column chromatography (silica gel, eluting with 1% to 3% MeOH/DCM) to afford 4-(4-chloro-1,6-naphthyridin-2-yl)-N,N-diethylbenzamide (1.8 g, 90%) as yellow solid. LC-MS (ESI): 339.9 (M+1)$^+$.

Step 4

To a solution of 4-(4-chloro-1,6-naphthyridin-2-yl)-N,N-diethylbenzamide (100 mg, 0.29 mmol) in DMF (5 mL)

were added 3-morpholinopropan-1-amine (62 mg, 0.44 mmol) and K$_2$CO$_3$ (80 mg, 0.58 mmol). After stirred at 100° C. overnight, the reaction mixture was quenched with water (5 mL), and extracted with DCM (10 mL×3). The organic layer was washed with water (10 mL×3) and brine (10 mL), dried over Na$_2$SO$_4$, concentrated and purified by prep-TLC to afford N,N-diethyl-4-(4-((3-morpholinopropyl)amino)-1,6-naphthyridin-2-yl)benzamide (10 mg, 8%) as yellow solid. HPLC/UV purity: 100%; LC-MS (ESI): 448.3 (M+1)$^+$. $^1$H NMR (METHANOL-d4) δ: 9.77 (s, 1H), 8.89 (d, J=6.4 Hz, 1H), 8.12 (d, J=8.4 Hz, 2H), 7.94 (d, J=6.4 Hz, 1H), 7.69 (d, J=8.4 Hz, 2H), 7.29 (s, 1H), 4.13-4.02 (m, 2H), 3.88 (t, J=6.8 Hz, 2H), 3.84-3.75 (m, 2H), 3.63 (q, J=7.2 Hz, 2H), 3.59-3.50 (m, 2H), 3.43-3.34 (m, 4H), 3.26-3.15 (m, 2H), 2.38-2.32 (m, 2H), 1.32 (t, J=7.2 Hz, 3H), 1.18 (t, J=7.2 Hz, 3H).

Example 43: Synthesis N,N-Diethyl-4-(4-((2-(piperidin-1-yl)ethyl)amino)-1,6-naphthyridin-2-yl)benzamide

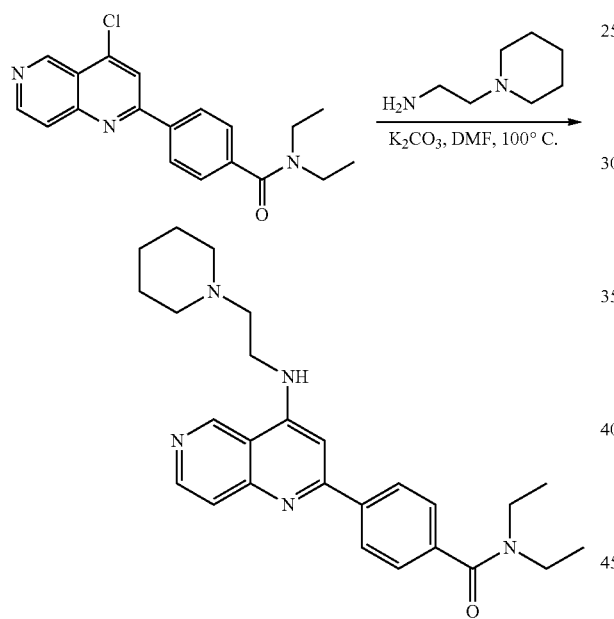

To a solution of 4-(4-chloro-1,6-naphthyridin-2-yl)-N,N-diethylbenzamide (100 mg, 0.29 mmol) in DMF (5 mL) were added 2-(piperidin-1-yl)ethan-1-amine (56 mg, 0.44 mmol) and K$_2$CO$_3$ (80 mg, 0.58 mmol). After stirred at 100° C. overnight, the reaction mixture was quenched with water (5 mL), and extracted with DCM (10 mL×3). The organic layer was washed with water (10 mL×3) and brine (10 mL), dried over Na$_2$SO$_4$, concentrated and purified by prep-HPLC to afford N,N-diethyl-4-(4-((2-(piperidin-1-yl)ethyl)amino)-1,6-naphthyridin-2-yl)benzamide (30 mg, 24%) as yellow solid. HPLC/UV purity: 100%; LC-MS (ESI): 432.2 (M+1)$^+$. $^1$H NMR (METHANOL-d4) δ: 9.73 (s, 1H), 8.87 (d, J=6.0 Hz, 1H), 8.15 (d, J=8.4 Hz, 2H), 7.95 (d, J=6.0 Hz, 1H), 7.67 (d, J=8.4 Hz, 2H), 7.36 (s, 1H), 4.21 (t, J=6.0 Hz, 2H), 3.73 (d, J=11.2 Hz, 2H), 3.64-3.58 (m, 4H), 3.36-3.30 (m, 2H), 3.05 (t, J=10.8 Hz, 2H), 1.95-1.84 (m, 5H), 1.55-1.59 (m, 1H), 1.30 (t, J=7.2 Hz, 3H), 1.18 (t, J=7.2 Hz, 3H).

Example 44: Synthesis of N,N-Diethyl-4-(4-((3-(piperazin-1-yl)propyl)amino)-1,6-naphthyridin-2-yl)benzamide

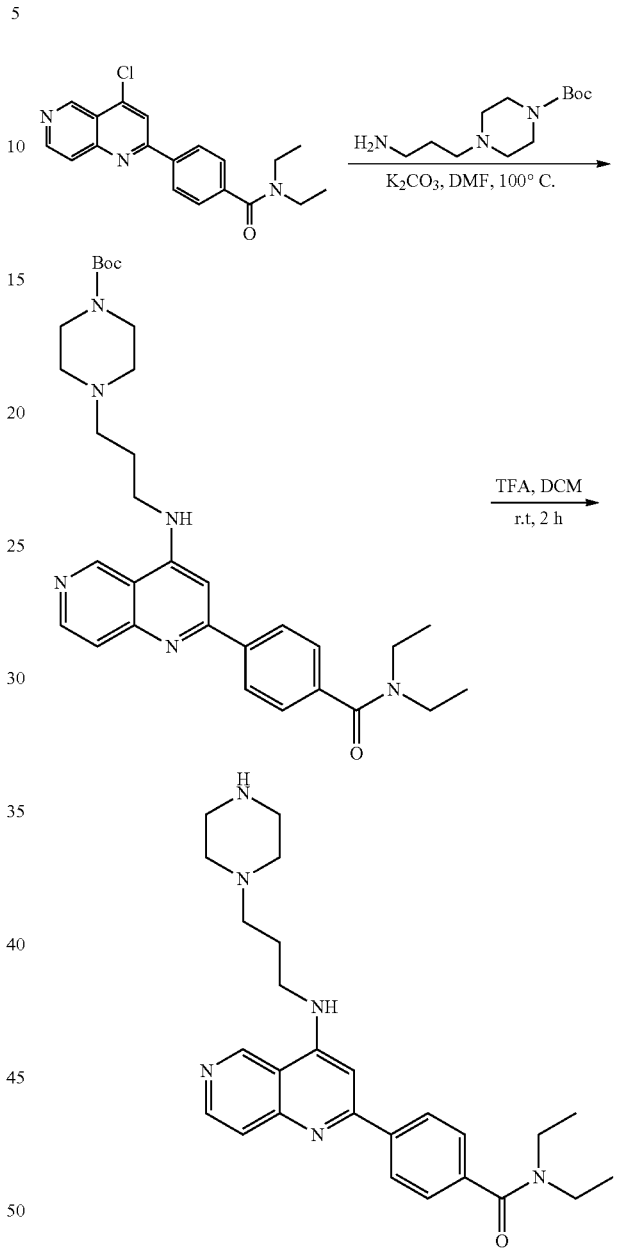

Step 1

To a solution of 4-(4-chloro-1,6-naphthyridin-2-yl)-N,N-diethylbenzamide (300 mg, 0.88 mmol) in DMF (5 mL) were added tert-butyl 4-(3-aminopropyl)piperazine-1-carboxylate (321 mg, 1.32 mmol) and K$_2$CO$_3$ (240 mg, 1.76 mmol). After stirred at 100° C. overnight, the reaction mixture was quenched with water (5 mL), and extracted with DCM (10 mL×3). The organic layer was washed with water (10 mL×3) and brine (10 mL), dried over Na$_2$SO$_4$, concentrated and purified by prep-HPLC to afford tert-butyl 4-(3-((2-(4-(diethylcarbamoyl)phenyl)-1,6-naphthyridin-4-yl)

amino)propyl)piperazine-1-carboxylate (300 mg, 62%) as yellow solid. HPLC/UV purity: 100%; LC-MS (ESI): 547.2 (M+1)$^+$.

Step 2

To a solution of tert-butyl 4-(3-((2-(4-(diethylcarbamoyl) phenyl)-1,6-naphthyridin-4-yl)amino)propyl)piperazine-1-carboxylate (300 mg, 0.55 mmol) in DCM was added TFA (125 mg, 1.10 mmol). After stirred at room temperature for 2 hrs, the reaction mixture was concentrated and purified by prep-HPLC to afford N,N-diethyl-4-(4-((3-(piperazin-1-yl) propyl)amino)-1,6-naphthyridin-2-yl)benzamide (200 mg, 82%) as yellow solid. HPLC/UV purity: 100%; LC-MS (ESI): 447.3 (M+1)$^+$. $^1$H NMR (METHANOL-d4) δ: 9.74 (s, 1H), 8.87 (d, J=6.4 Hz, 1H), 8.09 (d, J=8.4 Hz, 2H), 7.90 (d, J=6.0 Hz, 1H), 7.68 (d, J=8.8 Hz, 2H), 7.27 (s, 1H), 3.86 (t, J=6.8 Hz, 2H), 3.61 (q, J=6.8 Hz, 2H), 3.46-3.43 (m, 4H), 3.36-3.32 (m, 2H), 3.32-3.30 (m, 4H), 3.16 (t, J=7.6 Hz, 2H), 2.28-2.21 (m, 2H), 1.30 (t, J=7.2 Hz, 3H), 1.17 (t, J=7.2 Hz, 3H).

Example 45: Synthesis of N,N-Diethyl-4-(4-((3-(4-(methylsulfonyl)piperazin-1-yl)propyl)amino)-1,6-naphthyridin-2-yl)benzamide

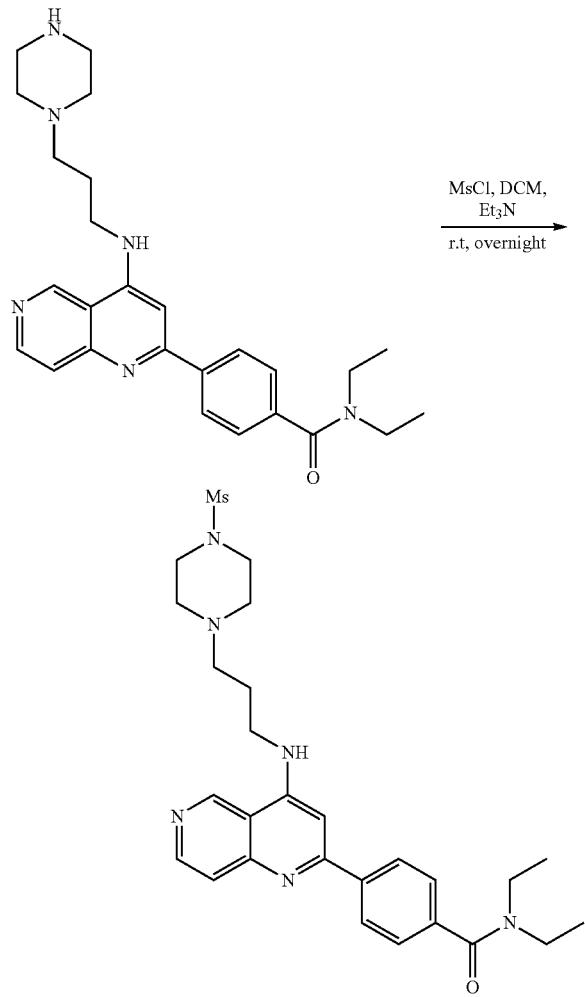

To a solution of N,N-diethyl-4-(4-((3-(piperazin-1-yl)propyl)amino)-1,6-naphthyridin-2-yl)benzamide (200 mg, 0.45 mmol) in DCM were added MsCl (57 mg, 0.50 mmol) and Et$_3$N (91 mg, 0.90 mmol). After stirred at room temperature overnight, the reaction mixture was quenched with water (5 mL), and extracted with DCM (10 mL×3). The organic layer was washed with water (10 mL×3) and brine (10 mL), dried over Na$_2$SO$_4$, concentrated and purified by prep-HPLC to afford N,N-diethyl-4-(4-((3-(4-(methylsulfonyl)piperazin-1-yl)propyl)amino)-1,6-naphthyridin-2-yl)benzamide (25 mg, 11%) as yellow solid. HPLC/UV purity: 99%; LC-MS (ESI): 525.2 (M+1)$^+$. $^1$H NMR (METHANOL-d4) δ: 9.48 (s, 1H), 8.57 (d, J=6.0 Hz, 1H), 8.13 (d, J=7.8 Hz, 2H), 7.78 (d, J=6.0 Hz, 1H), 7.56 (d, J=8.4 Hz, 2H), 7.08 (s, 1H), 3.60 (t, J=6.6 Hz, 4H), 3.35 (s, 2H), 3.21 (s, 4H), 2.83 (s, 3H), 2.63-2.60 (m, 6H), 2.02 (t, J=6.6 Hz, 2H), 1.29-1.27 (m, 3H), 1.16 (t, J=6.6 Hz, 3H).

Example 46: Synthesis of N,N-Diethyl-4-(4-((1-methylpiperidin-4-yl)amino)-1,6-naphthyridin-2-yl) benzamide

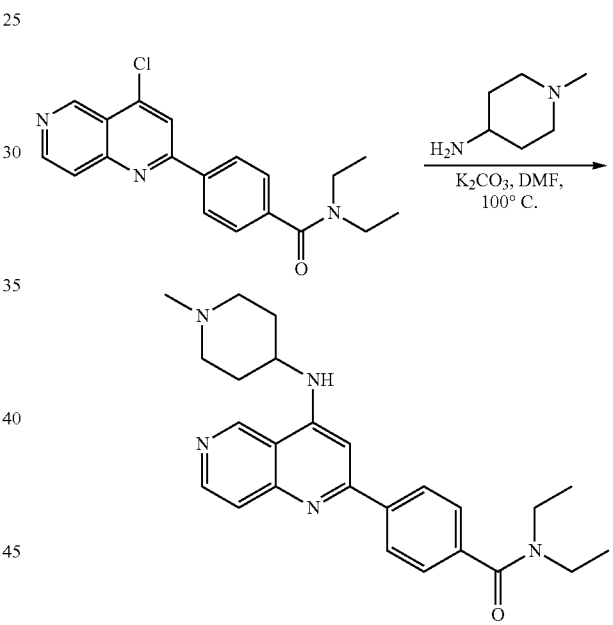

To a solution of 4-(4-chloro-1,6-naphthyridin-2-yl)-N,N-diethylbenzamide (100 mg, 0.29 mmol) in DMF (5 mL) were added 1-methylpiperidin-4-amine (50 mg, 0.44 mmol) and K$_2$CO$_3$ (80 mg, 0.58 mmol). After stirred at 100° C. overnight, the reaction mixture was quenched with water (5 mL), and extracted with DCM (10 mL×3). The organic layer was washed with water (10 mL×3) and brine (10 mL), dried over Na$_2$SO$_4$, concentrated and purified by prep-HPLC to afford N,N-diethyl-4-(4-((1-methylpiperidin-4-yl)amino)-1,6-naphthyridin-2-yl)benzamide (15 mg, 12%) as yellow solid. HPLC/UV purity: 100%; LC-MS (ESI): 418.3 (M+1)$^+$. $^1$H NMR (METHANOL-d4) δ 9.84 (s, 1H), 8.87 (d, J=6.0 Hz, 1H), 8.12 (d, J=8.0 Hz, 2H), 7.93 (d, J=6.0 Hz, 1H), 7.68 (d, J=8.0 Hz, 2H), 7.40 (s, 1H), 4.49 (m, 1H), 3.71 (d, J=12.4 Hz, 2H), 3.64-3.59 (m, 2H), 3.34-3.24 (m, 4H), 2.95 (s, 3H), 2.43 (d, J=13.2 Hz, 2H), 2.23-2.14 (m, 2H), 1.30 (t, J=7.2 Hz, 3H), 1.16 (t, J=7.2 Hz, 3H).

Example 47: Synthesis of 4-(4-((2-(Dimethylamino)ethyl)amino)-1,6-naphthyridin-2-yl)-N,N-diethylbenzamide

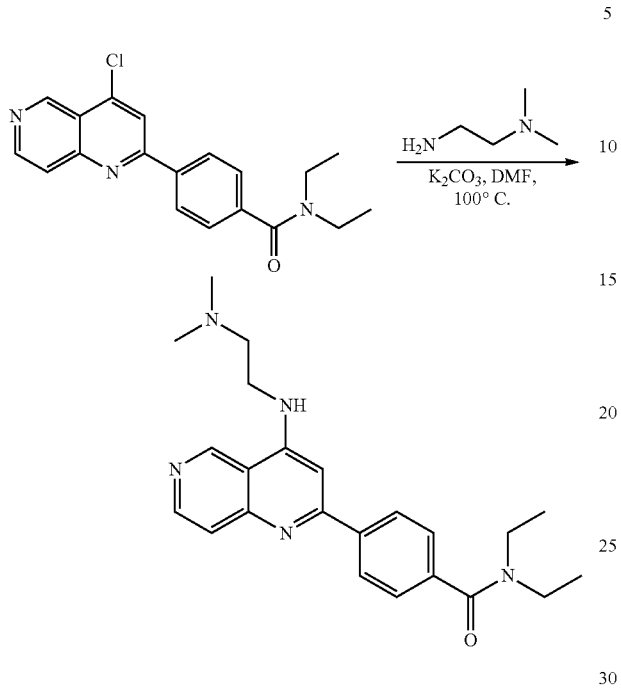

To a solution of 4-(4-chloro-1,6-naphthyridin-2-yl)-N,N-diethylbenzamide (50 mg, 0.15 mmol) in DMF (3 ml) were added $N^1,N^1$-dimethylethane-1,2-diamine (19 mg, 0.22 mmol) and $K_2CO_3$ (40 mg, 0.29 mmol). The reaction mixture was stirred at 100° C. overnight, then quenched with water (3 mL), and extracted with DCM (10 mL×3). The organic mixture was washed with water (10 mL×3) and brine (10 mL), dried over $Na_2SO_4$, concentrated and purified by prep-HPLC to afford 4-(4-((2-(dimethylamino)ethyl)amino)-1,6-naphthyridin-2-yl)-N,N-diethylbenzamide (20 mg, 58%) as yellow oil. HPLC/UV purity: 100%; LC-MS (ESI): 392.2 (M+1)$^+$. $^1$H NMR (METHANOL-d4) δ: 9.74 (s, 1H), 8.87 (d, J=6.0 Hz, 1H), 8.15 (d, J=7.8 Hz, 2H), 7.96 (d, J=6.0, 1H), 7.67 (d, J=8.4 Hz, 2H), 7.39 (s, 1H), 4.20 (t, J=6.0 Hz, 2H), 3.66-3.59 (m, 4H), 3.35-3.31 (m, 2H), 3.03 (s, 6H), 1.31 (t, J=7.2 Hz, 3H), 1.16 (t, J=7.2 Hz, 3H).

Example 48: Synthesis of N,N-diethyl-4-(4-(3-(4-methylpiperazin-1-yl)propylamino)-1,6-naphthyridin-2-yl)benzamide

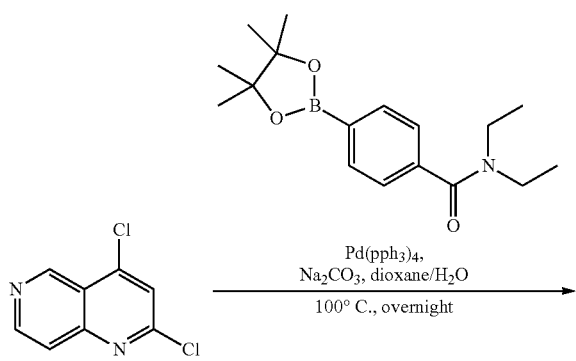

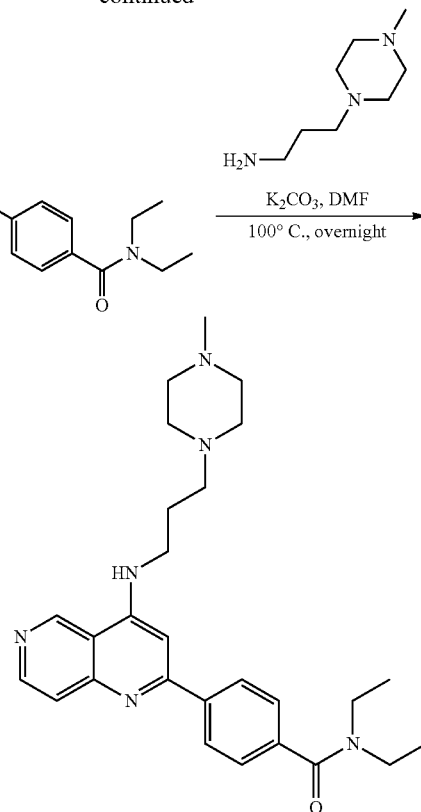

Step 1

The mixture of 2,4-dichloro-1,6-naphthyridine (345 mg, 1.72 mmol), N,N-diethyl-4-(4,4,5,5-tetramethyl-1,3,2-dioxaborolan-2-yl)benzamide (785 mg, 2.59 mmol), Pd(PPh$_3$)$_4$ (198 mg, 0.1 mmol) and Na$_2$CO$_3$ (365 mg, 2.0 mmol) in 1,4-dioxane (10 mL) and H$_2$O (2 mL) under N$_2$ atmosphere was heated to 100° C. overnight. After cooling to room temperature, the mixture was concentrated by rotary evaporation (55° C., 20 mmHg). The residue was purified by the flash column chromatography (silica gel, eluting with DCM to 3% MeOH in DCM) to afford 4-(4-chloro-1,6-naphthyridin-2-yl)-N,N-diethylbenzamide as a colorless oil (452 mg, 77%). LC-MS (ESI): 340.1 (M+1)$^+$.

Step 2

The mixture of 4-(4-chloro-1,6-naphthyridin-2-yl)-N,N-diethylbenzamide (100 mg, 0.29 mmol), 3-(4-methylpiperazin-1-yl)propan-1-amine (68 mg, 0.43 mmol) and K$_2$CO$_3$ (80 mg, 0.58 mmol) in DMF (1 mL) was heated at 100° C. for 18 hrs. The reaction mixture was poured into water (20 mL), extracted with EA (10 mL×3). The combined organic layers were washed by water (10 mL×3) and brine (10 mL), dried over Na$_2$SO$_4$, filtered and the filtrate was concentrated under the reduced pressure to give the residue which was purified prep-TLC to afford N,N-diethyl-4-(4-(3-(4-methylpiperazin-1-yl)propylamino)-1,6-naphthyridin-2-yl)benzamide (14.8 mg, 10%) as a yellow oil. HPLC/UV purity: 100%; LC-MS (ESI): 461.3 (M+1)$^+$. $^1$H NMR (METHANOL-d$_4$) δ: 9.74 (s, 1H), 8.90 (d, J=6.2 Hz, 1H), 8.04-8.16 (d, J=8.3 Hz, 2H), 7.91 (d, J=6.2 Hz, 1H), 7.62-7.75 (d, J=8.3 Hz, 2H), 7.28 (s, 1H), 3.86 (t, J=6.9 Hz, 2H), 3.63 (q, J=6.8 Hz, 2H), 3.34-3.44 (m, 6H), 2.99-3.15 (m, 4H), 2.96 (t, J=7.3 Hz, 2H), 2.91 (s, 3H), 2.10-2.24 (m, 2H), 1.32 (t, J=7.0 Hz, 3H), 1.19 (t, J=7.0 Hz, 3H).

Example 49: Synthesis of N,N-diethyl-4-(4-(2-morpholinoethylamino)-1,6-naphthyridin-2-yl)benzamide

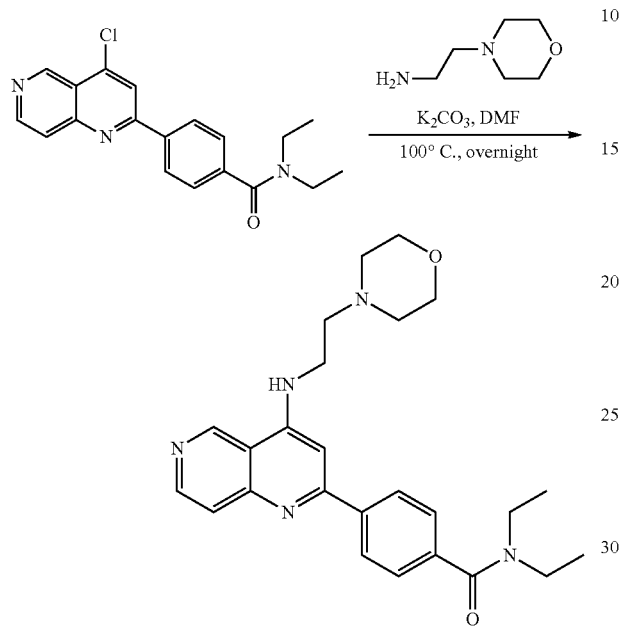

The mixture of 4-(4-chloro-1,6-naphthyridin-2-yl)-N,N-diethylbenzamide (150 mg, 0.44 mmol), 2-morpholinoethanamine (86 mg, 0.66 mmol) and K₂CO₃ (121 mg, 0.88 mmol) in DMF (1 mL) was heated at 100° C. for 18 hrs. The reaction mixture was poured into water (20 mL), extracted with EA (10 mL×3). The combined organic layers were washed by water (10 mL×3) and brine (10 mL), dried over Na₂SO₄ and filtered. The filtrate was concentrated under the reduced pressure to get the residue which was purified prep-TLC to afford N,N-diethyl-4-(4-(2-morpholinoethylamino)-1,6-naphthyridin-2-yl)benzamide (28 mg, 15%). HPLC/UV purity: 100%; LC-MS (ESI): 434.3 (M+1)⁺. ¹HNMR (METHANOL-d₄) δ: 9.72 (s, 1H), 8.88 (d, J=5.9 Hz, 1H), 8.09-8.19 (d, J=8.6 Hz, 2H), 7.95 (d, J=6.2 Hz, 1H), 7.60-7.71 (d, J=8.3 Hz, 2H), 7.38 (s, 1H), 4.23 (t, J=6.2 Hz, 2H), 3.91-3.93 (m, 4H), 3.67 (t, J=6.2 Hz, 2H), 3.56-3.63 (m, 2H), 3.31-3.38 (m, 4H), 1.30 (t, J=7.0 Hz, 3H), 1.16 (t, J=7.0 Hz, 3H).

Example 50: Synthesis of N,N-diethyl-4-(4-(2-(4-methylpiperazin-1-yl)ethylamino)-1,6-naphthyridin-2-yl)benzamide

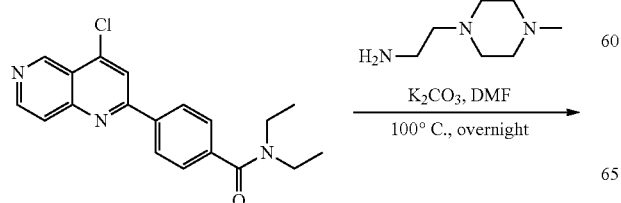

-continued

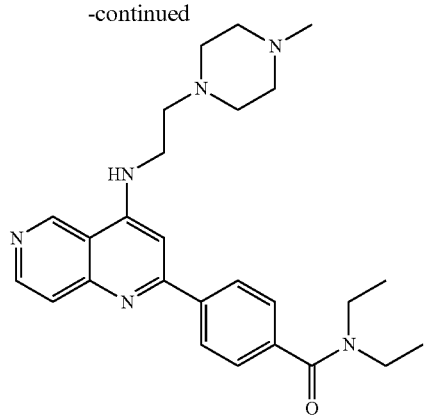

The mixture of 4-(4-chloro-1,6-naphthyridin-2-yl)-N,N-diethylbenzamide (150 mg, 0.44 mmol), 2-(4-methylpiperazin-1-yl)ethanamine (94 mg, 0.66 mmol) and K₂CO₃ (121 mg, 0.88 mmol) in DMF (1 mL) was heated at 100° C. for 18 hrs. The reaction mixture was poured into water (20 mL), extracted with EA (10 mL×3). The combined organic layers were washed by water (10 mL×3) and brine (10 mL), dried over Na₂SO₄. The drying agent was filtered off and the filtrate was concentrated under the reduced pressure to give the residue which was purified prep-TLC to afford N,N-diethyl-4-(4-(2-(4-methylpiperazin-1-yl)ethylamino)-1,6-naphthyridin-2-yl)benzamide. (8 mg, 4%). HPLC/UV purity: 100%; LC-MS (ESI): 447.2 (M+1)⁺. ¹H NMR (METHANOL-d₄) δ: 9.76 (s, 1H), 8.90 (d, J=6.2 Hz, 1H), 8.08-8.17 (d, J=8.3 Hz, 2H), 7.93 (d, J=6.2 Hz, 1H), 7.64-7.74 (d, J=8.3 Hz, 2H), 7.30 (s, 1H), 3.95 (t, J=6.2 Hz, 2H), 3.63 (q, J=6.8 Hz, 2H), 3.32-3.47 (m, 10H), 3.06 (t, J=6.2 Hz, 2H), 2.92 (s, 3H), 1.32 (t, J=7.0 Hz, 3H), 1.18 (t, J=7.0 Hz, 3H).

Example 51: Synthesis of N,N-diethyl-4-(4-(tetrahydro-2H-pyran-4-ylamino)-1,6-naphthyridin-2-yl)benzamide

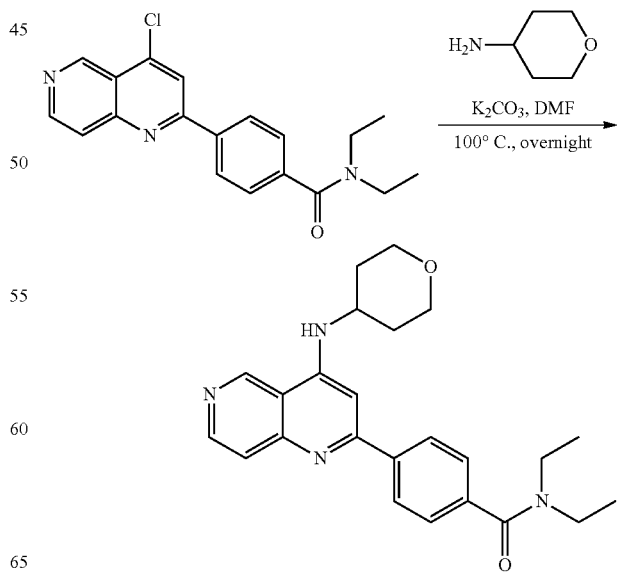

The mixture of 4-(4-chloro-1,6-naphthyridin-2-yl)-N,N-diethylbenzamide (100 mg, 0.29 mmol), tetrahydro-2H-pyran-4-amine (43 mg, 0.43 mmol) and K₂CO₃ (121 mg, 0.88 mmol) in DMF (1 mL) was heated at 100° C. for 18 hrs. The reaction mixture was poured into water (20 mL), extracted with EA (10 mL×3). The combined organic layers were washed by water (10 mL×3) and brine (10 mL), dried over Na₂SO₄. Filtered and the filtrate was concentrated under the reduced pressure to give the residue which was purified by prep-TLC to afford N,N-diethyl-4-(4-(tetrahydro-2H-pyran-4-ylamino)-1,6-naphthyridin-2-yl)benzamide (10 mg, 9%). HPLC/UV purity: 99%; LC-MS (ESI): 405.2 (M+1)⁺. ¹HNMR (METHANOL-d₄) δ: 9.62 (s, 1H), 8.62 (d, J=5.9 Hz, 1H), 8.13 (d, J=8.1 Hz, 2H), 7.80 (d, J=5.9 Hz, 1H), 7.58 (d, J=8.3 Hz, 2H), 7.19 (s, 1H), 4.00-4.22 (m, 4H), 3.55-3.72 (m, 4H), 3.34-3.36 (m, 1H), 2.11 (d, J=12.9 Hz, 2H), 1.79-1.89 (m, 2H), 1.32 (t, J=7.0 Hz, 3H), 1.17 (t, J=6.7 Hz, 3H).

Example 52: Synthesis of N,N-diethyl-4-(4-(2-(piperazin-1-yl)ethylamino)-1,6-naphthyridin-2-yl)benzamide

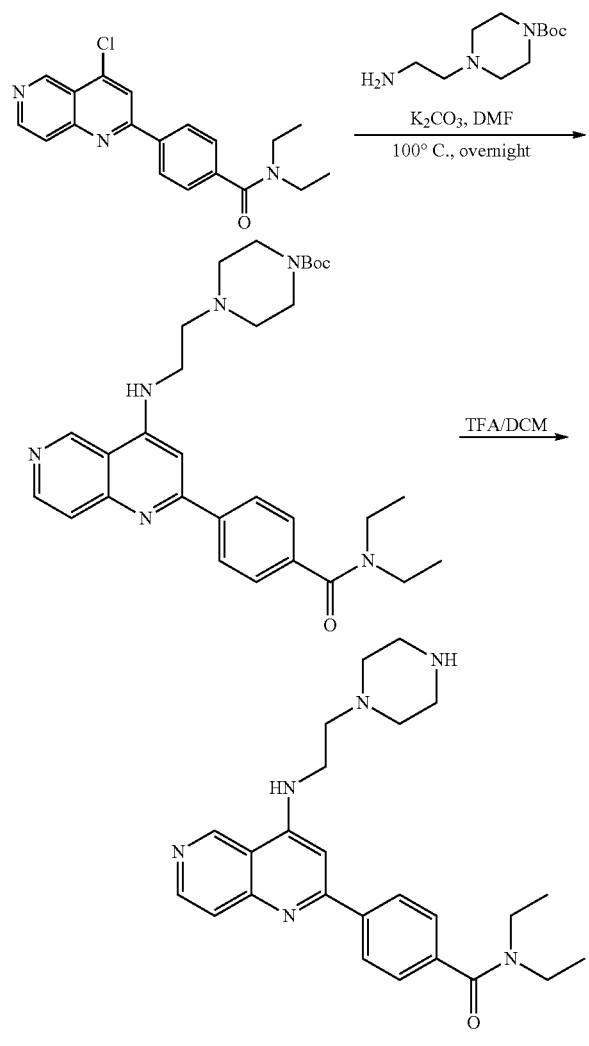

Step 1

The mixture of 4-(4-chloro-1,6-naphthyridin-2-yl)-N,N-diethylbenzamide (278 mg, 0.82 mmol), tert-butyl 4-(2-aminoethyl)piperazine-1-carboxylate (281 mg, 1.23 mmol) and K₂CO₃ (226 mg, 1.64 mmol) in DMF (1 mL) was heated at 100° C. for 18 hrs. The reaction mixture was poured into water (20 mL), extracted with EA (10 mL×3). The combined organic layers were washed by water (10 mL×3) and brine (10 mL), dried over Na₂SO₄. Filtered and the filtrate was concentrated under the reduced pressure to give the residue which was purified prep-TLC to afford tert-butyl 4-(2-(2-(4-(diethylcarbamoyl)phenyl)-1,6-naphthyridin-4-ylamino)ethyl)piperazine-1-carboxylate (90 mg, 20%). LC-MS (ESI): 533.3 (M+1)⁺.

Step 2

The mixture of tert-butyl 4-(2-(2-(4-(diethylcarbamoyl)phenyl)-1,6-naphthyridin-4-ylamino)ethyl)piperazine-1-carboxylate (90 mg, 0.16 mmol) and TFA (1 mL) in DCM (1 mL) was stirred at room temperature for 18 hrs. Then the solvent was removed under the reduced pressure to give the residue which was purified with Prep-HPLC (Welch, XB-C18, 21.2 mm×250 mm, 10 um, eluting with 40% CH₃CN in 1‰ TFA in H₂O) to afford N,N-diethyl-4-(4-(2-(piperazin-1-yl)ethylamino)-1,6-naphthyridin-2-yl)benzamide (13 mg, 18%) as a TFA salt. HPLC/UV purity: 99%; LC-MS (ESI): 433.3 (M+1)⁺. ¹H NMR (METHANOL-d₄) δ: 9.75 (s, 1H), 8.90 (d, J=6.1 Hz, 1H), 8.07-8.18 (d, J=8.2 Hz, 2H), 7.94 (d, J=5.8 Hz, 1H), 7.65-7.74 (d, J=8.5 Hz, 2H), 7.32 (s, 1H), 4.00 (t, J=6.1 Hz, 2H), 3.63 (d, J=7.3 Hz, 2H), 3.34-3.40 (m, 6H), 3.01-3.18 (m, 6H), 1.32 (t, J=7.0 Hz, 3H), 1.18 (t, J=7.0 Hz, 3H).

Example 53: Synthesis of N,N-diethyl-4-(4-(2-(4-(methylsulfonyl)piperazin-1-yl)ethylamino)-1,6-naphthyridin-2-yl)benzamide

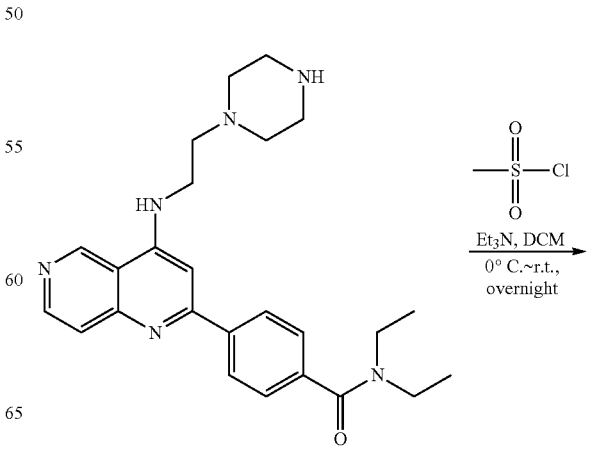

205

-continued

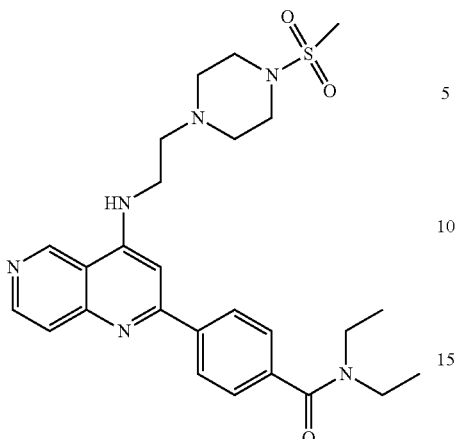

The mixture of N,N-diethyl-4-(4-(2-(piperazin-1-yl)eth-ylamino)-1,6-naphthyridin-2-yl)benzamide (50 mg, 0.11 mmol) and Et$_3$N (0.03 mL, 0.22 mmol) in DCM (5 mL) was cooled to 0° C. Then methanesulfonyl chloride (20 mg, 0.17 mmol) added. The mixture was stirred at room temperature for 18 hrs. The reaction mixture was poured into water (20 mL), extracted with EA (10 mL×3). The combined organic layers were washed by water (10 mL) and brine (10 mL), dried over Na$_2$SO$_4$. Filtered and the filtrate was concentrated under the reduced pressure to give the crude mixture which was purified by prep-TLC to afford N,N-diethyl-4-(4-(2-(4-(methylsulfonyl)piperazin-1-yl)ethylamino)-1,6-naphthyri-din-2-yl)benzamide (7 mg, 29%). HPLC/UV purity: 99%; LC-MS (ESI): 511.2 (M+1)$^+$. $^1$H NMR (METHANOL-d$_4$) δ: 9.52 (s, 1H), 8.62 (d, J=5.8 Hz, 1H), 8.10-8.20 (d, J=7.9 Hz, 2H), 7.82 (d, J=6.1 Hz, 1H), 7.53-7.63 (d, J=7.9 Hz, 2H), 7.16 (s, 1H), 3.72 (t, J=6.4 Hz, 2H), 3.61 (d, J=7.0 Hz, 2H), 3.35-3.41 (m, 2H), 3.22-3.30 (m, 4H), 2.82-2.92 (m, 5H), 2.68-2.77 (m, 4H), 1.31 (t, J=6.9 Hz, 3H), 1.19 (t, J=6.7 Hz, 3H).

Example 54: Synthesis of N,N-Diethyl-4-(4-(4-methoxyphenylamino)-1,6-naphthyridin-2-yl)benz-amide

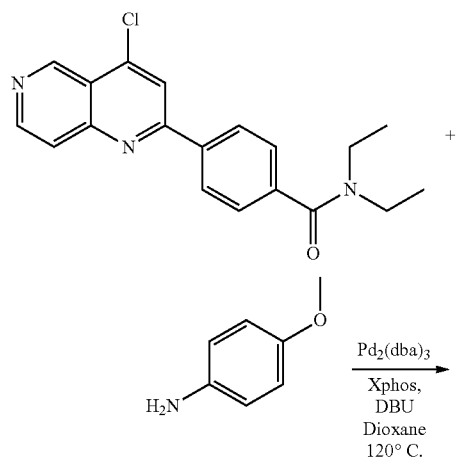

206

-continued

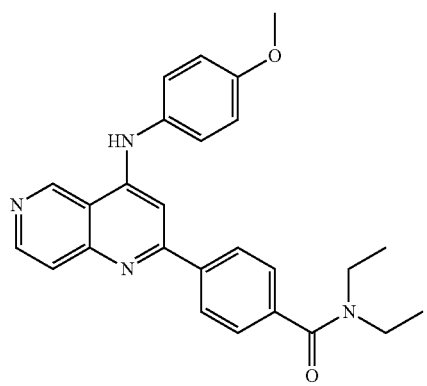

The mixture of 4-(4-chloro-1,6-naphthyridin-2-yl)-N,N-diethylbenzamide (67.6 mg, 0.2 mmol), 4-methoxyaniline (27 mg, 0.22 mmol), Pd$_2$(dba)$_3$ (18 mg, 0.02 mmol), Xphos (9.1 mg, 0.02 mmol) and Cs$_2$CO$_3$ (183 mg, 0.2 mmol) in 1,4-dioxane (5 mL) was stirred at 120° C. overnight. The reaction mixture was filtered, concentrated and purified by silica gel column chromatography to give N,N-diethyl-4-(4-(4-methoxyphenylamino)-1,6-naphthyridin-2-yl)benzamide (36 mg, 42%) as white solid. HPLC/UV purity: 100%; LC-MS (ESI): 427.3 (M+1)$^+$. $^1$H NMR (METHOL-d$_4$) δ: 9.53 (s, 1H), 8.51 (d, J=6.0 Hz, 1H), 7.85 (d, J=8.0 Hz, 2H), 7.73 (d, J=6.0 Hz, 1H), 7.39 (d, J=8.0 Hz, 2H), 7.28 (d, J=8.8 Hz, 2H), 7.03 (s, 1H), 6.98 (d, J=8.8 Hz, 2H), 3.76 (s, 3H), 3.48-3.44 (m, 2H), 3.21-3.19 (m, 2H), 1.17 (t, J=6.4 Hz, 3H), 1.03 (t, J=6.4 Hz, 3H).

Example 55: Synthesis of 4-(4-(4-(Dimethylamino) phenylamino)-1,6-naphthyridin-2-yl)-N,N-diethyl-benzamide

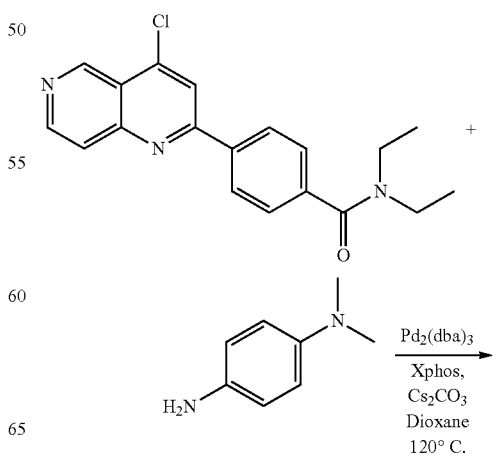

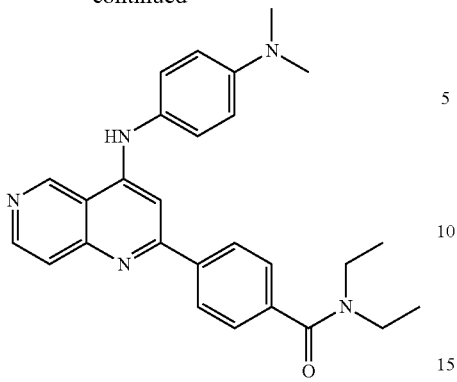

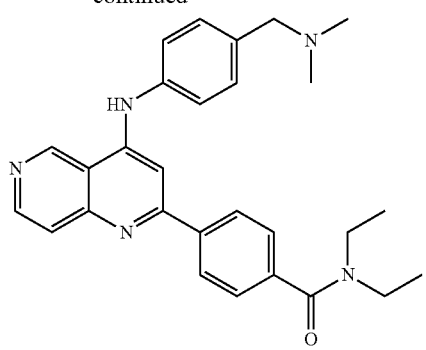

The mixture of 4-(4-chloro-1,6-naphthyridin-2-yl)-N,N-diethylbenzamide (68 mg, 0.2 mmol), N¹,N¹-dimethylbenzene-1,4-diamine (32 mg, 0.24 mmol), Pd₂(dba)₃ (19 mg, 0.02 mmol), Xphos (10 mg, 0.02 mmol), and Cs₂CO₃ (130 mg, 0.2 mmol) in 1,4-dioxane (5 mL) was stirred at 120° C. overnight. The reaction mixture was filtered, concentrated and purified by silica gel column chromatography (DCM/MeOH=10/1) to give 4-(4-(4-(dimethylamino)phenylamino)-1,6-naphthyridin-2-yl)-N,N-diethylbenzamide (40 mg, 45%) as white solid. HPLC/UV purity: 100%; LC-MS (ESI): 440.3 (M+1)⁺. ¹H NMR (METHOL-d₄) δ: 9.65 (s, 1H), 8.62 (d, J=6.0 Hz, 1H), 7.96 (d, J=8.4 Hz, 2H), 7.83 (d, J=6.4 Hz, 1H), 7.51 (d, J=8.0 Hz, 2H), 7.32-7.20 (m, 2H), 7.12 (s, 1H), 6.93 (m, 2H), 3.59 (q, J=6.8 Hz, 2H), 3.33-3.31 (m, 2H), 3.02 (s, 6H), 1.29 (t, J=7.2 Hz, 3H), 1.15 (t, J=7.2 Hz, 3H).

Example 56: Synthesis of 4-(4-(4-((Dimethylamino)methyl)phenylamino)-1,6-naphthyridin-2-yl)-N,N-diethylbenzamide The mixture of 4-(4-chloro-1,6-naphthyridin-2-yl)-N,N-diethylbenzamide (68 mg, 0.2 mmol), 4-((dimethylamino)methyl)iline (33 mg, 0.24 mmol), Pd₂(dba)₃ (18 mg, 0.02 mmol), Xphos (10 mg, 0.02 mmol), and Cs₂CO₃ (130 mg, 0.2 mmol) in 1,4-dioxane (5 mL) was stirred at 120° C. overnight. The reaction mixture was filtered, concentrated and purified by silica gel column chromatography to give 4-(4-(4-((dimethylamino)methyl)phenylamino)-1,6-naphthyridin-2-yl)-N,N-diethylbenzamide (40 mg, 44%) as yellow solid. HPLC/UV purity: 100%; LC-MS (ESI): 454.3 (M+1)⁺. ¹H NMR (METHOL-d₄) δ: 9.68 (s, 1H), 8.67 (d, J=6.0 Hz, 1H), 8.05 (d, J=8.4 Hz, 2H), 7.89 (d, J=6.0 Hz, 1H), 7.57-7.52 (m, 7H), 3.97 (s, 2H), 3.59 (q, J=6.4 Hz, 2H), 3.34-3.33 (m, 2H), 2.63 (s, 6H), 1.29 (t, J=6.8 Hz, 3H), 1.16 (t, J=6.8 Hz, 3H).

Example 57: Synthesis of N,N-Diethyl-4-(4-(4-(2-methoxyethylamino)phenylamino)-1,6-naphthyridin-2-yl)benzamide

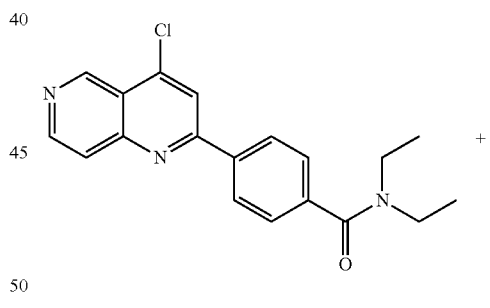

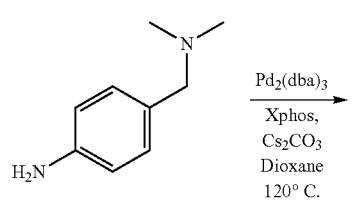

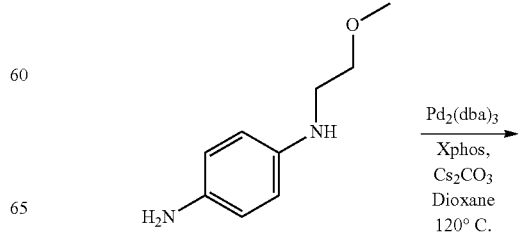

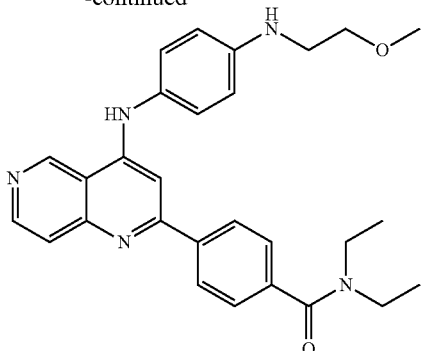

The mixture of 4-(4-chloro-1,6-naphthyridin-2-yl)-N,N-diethylbenzamide (102 mg, 0.3 mmol), N$^1$-(2-methoxyethyl)benzene-1,4-diamine (60 mg, 0.36 mmol), Pd$_2$(dba)$_3$ (19 mg, 0.02 mmol), Xphos (10 mg, 0.02 mmol), and Cs$_2$CO$_3$ (130 mg, 0.2 mmol) in 1,4-Dioxane (5 mL) was stirred at 120° C. overnight. The reaction mixture was filtered, concentrated and purified by silica gel column chromatography to give N,N-diethyl-4-(4-(4-(2-methoxyethylamino)phenylamino)-1,6-naphthyridin-2-yl)benzamide (70 mg, 50%) as white solid. HPLC/UV purity: 100%; LC-MS (ESI): 470.3 (M+1)$^+$. $^1$H NMR (METHOL-d$_4$) δ: 9.62 (s, 1H), 8.59 (t, J=6.0 Hz, 1H), 7.93 (d, J=7.6 Hz, 2H), 7.81 (d, J=6.0 Hz, 1H), 7.48 (d, J=7.6 Hz, 2H), 7.21 (d, J=8.0 Hz, 2H), 7.07 (s, 1H), 6.80 (d, J=8.4 Hz, 2H), 3.62 (t, J=5.2 Hz, 2H), 3.58-3.54 (m, 2H), 3.40 (s, 3H), 3.33-3.30 (m, 4H), 1.26 (t, J=6.8 Hz, 3H), 1.13 (t, J=6.8 Hz, 3H).

Example 58: Synthesis of 4-(4-((2-(1,1-Dioxidothiomorpholino)ethyl)amino)-1,6-naphthyridin-2-yl)-N,N-diethylbenzamide 4-(4-((2-(1,1-Dioxidothiomorpholino)ethyl)amino)-1,6-naphthyridin-2-yl)-N,N-diethylbenzamide was synthesized in a similar fashion as Example 52, Step 1. HPLC/UV purity: 100%; LC-MS (ESI): 482.2 (M+1)$^+$. $^1$H NMR (METHOL-d$_4$) δ: 9.74 (s, 1H), 8.89 (d, J=5.6 Hz, 1H), 8.12 (d, J=7.2 Hz, 2H), 7.91 (d, J=5.6 Hz, 1H), 7.70 (d, J=7.6 Hz, 2H), 7.32 (s, 1H), 3.93 (t, J=5.2 Hz, 2H), 3.61-3.63 (m, 2H), 3.34-3.36 (m, 2H), 3.22-3.24 (m, 4H), 3.15-3.17 (m, 4H), 3.10 (t, J=5.2 Hz, 2H), 1.31 (t, J=6.4 Hz, 3H), 1.18 (t, J=6.4 Hz, 3H).

Example 59: Synthesis of 4-(4-((3-(1,1-Dioxidothiomorpholino)propyl)amino)-1,6-naphthyridin-2-yl)-N',N-diethylbenzamide

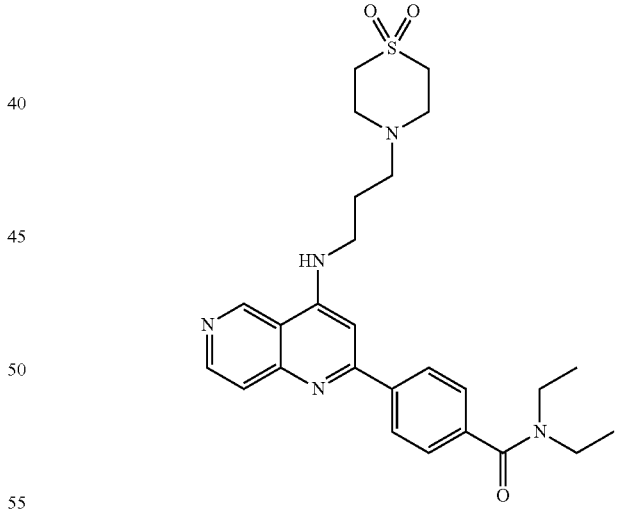

4-(4-((3-(1,1-Dioxidothiomorpholino)propyl)amino)-1,6-naphthyridin-2-yl)-N,N-diethylbenzamide was synthesized in a similar fashion as Example 52, Step 1. HPLC/UV purity: 100%; LC-MS (ESI): 496.2 (M+1)$^+$. $^1$H NMR (METHOL-d$_4$) δ: 9.78 (s, 1H), 8.89 (d, J=5.6 Hz, 1H), 8.12 (d, J=7.2 Hz, 2H), 7.93 (d, J=5.6 Hz, 1H), 7.69 (d, J=7.6 Hz, 2H), 7.30 (s, 1H), 3.88 (t, J=6.4 Hz, 2H), 3.68-3.72 (m, 4H), 3.61-3.63 (m, 2H), 3.48-3.52 (m, 4H), 3.32-3.37 (m, 4H), 2.31 (t, J=7.2 Hz, 2H), 1.31 (t, J=6.4 Hz, 3H), 1.18 (t, J=6.8 Hz, 3H).

Example 60: Synthesis of N,N-Diethyl-4-(4-(1-methylpyrrolidin-3-ylamino)-1,6-naphthyridin-2-yl)benzamide

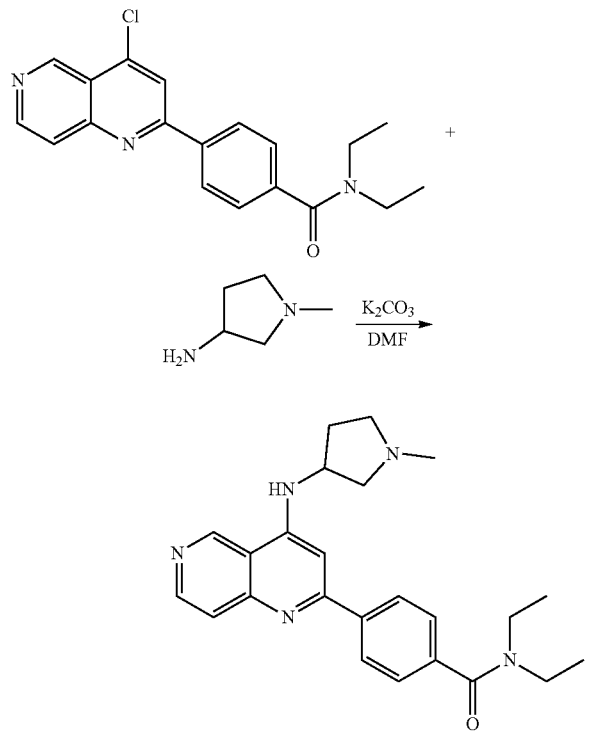

The mixture of 4-(4-chloro-1,6-naphthyridin-2-yl)-N,N-diethylbenzamide (135 mg, 0.4 mmol), 1-methylpyrrolidin-3-amine (60 mg, 0.7 mmol) and K₂CO₃ (138 mg, 1 mmol) in DMF (5 mL) was stirred at 115° C. overnight. After adding 200 mL water, the mixture was extracted with EA (100 mL), washed with brine, concentrated and purified by flash column chromatography to give N,N-diethyl-4-(4-(1-methylpyrrolidin-3-ylamino)-1,6-naphthyridin-2-yl)benzamide (20 mg, 12.4%) as white solid. HPLC/UV purity: 100%; LC-MS (ESI): 404.2 (M+1)⁺. ¹H NMR (METHOL-d₄) δ: 9.94 (s, 1H), 8.92 (s, 1H), 8.15 (d, J=8.4 Hz, 2H), 7.98 (s, 1H), 7.67 (d, J=8.0 Hz, 2H), 7.32 (s, 1H), 4.37-4.35 (m, 1H), 4.05-3.91 (m, 2H), 3.62-3.58 (m, 2H), 3.35-3.30 (m, 4H), 3.06 (s, 3H), 2.96-2.80 (m, 1H), 2.51-2.46 (m, 1H), 1.29 (t, J=6.8 Hz, 3H), 1.16 (t, J=6.8 Hz, 3H).

Example 61: Synthesis of N,N-Diethyl-4-(4-(piperidin-4-ylamino)-1,6-naphthyridin-2-yl)benzamide

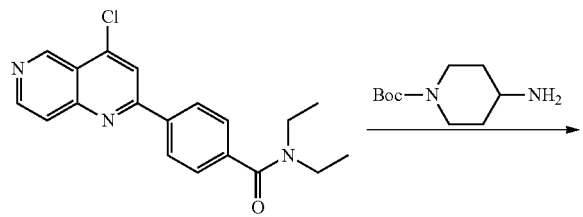

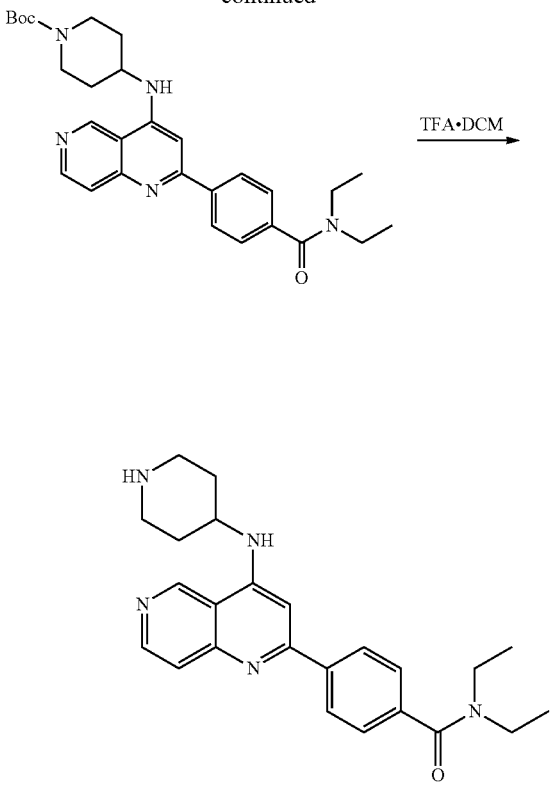

Step 1

The mixture of 4-(4-chloro-1,6-naphthyridin-2-yl)-N,N-diethylbenzamide (100 mg, 0.29 mmol), tert-butyl 4-aminopiperidine-1-carboxylate (118 mg, 0.59 mmol), and K₂CO₃ (122 mg, 0.88 mmol) in DMF (2 mL) was stirred at 80° C. overnight. The reaction mixture was quenched with water (5 mL), extracted with EA (5 mL×3), washed with water (10 mL) and brine (20 mL), and dried over Na₂SO₄. After filtration, the filtrate was concentrated and purified by prep-TLC (DCM/MeOH=10/1) to afford tert-butyl 4-(2-(4-(diethylcarbamoyl)phenyl)-1,6-naphthyridin-4-ylamino)piperidine-1-carboxylate (30 mg, 21.7%) as yellow solid. LC-MS (ESI): 504.6 (M+1)⁺.

Step 2

Tert-butyl 4-(2-(4-(diethylcarbamoyl)phenyl)-1,6-naphthyridin-4-ylamino)piperidine-1-carboxylate (30 mg, 0.05 mmol) in DCM was added TFA (0.5 mL). After stirred at room temperature for 2 hrs, the reaction mixture was concentrated and purified by prep-TLC to afford N,N-diethyl-4-(4-(piperidin-4-ylamino)-1,6-naphthyridin-2-yl)benzamide (1.6 mg, 6.6%) as yellow solid. HPLC/UV purity: 100%; LC-MS (ESI): 404.2 (M+1)⁺. ¹H NMR (DMSO-d₆) δ: 9.92 (s, 1H), 8.87 (d, J=6.4 Hz, 1H), 8.80 (d, J=9.6 Hz, 1H), 8.61 (d, J=9.6 Hz, 1H), 8.15 (d, J=7.6 Hz, 2H), 7.94 (d, J=6.0 Hz, 1H), 7.66 (d, J=8.4 Hz, 2H), 7.39 (s, 1H), 4.43-4.41 (m, 1H), 3.49-3.46 (m, 4H), 3.23-3.22 (m, 2H), 3.15-3.06 (m, 2H), 2.20-2.17 (m, 2H), 1.99-1.89 (m, 2H), 1.24 (t, J=6.8 Hz, 3H), 1.10 (t, J=6.8 Hz, 3H).

Example 62: Synthesis of N-(1-Methylpiperidin-4-yl)-4-(4-((1-methylpyrrolidin-3-yl)amino)-1,6-naphthyridin-2-yl)benzamide

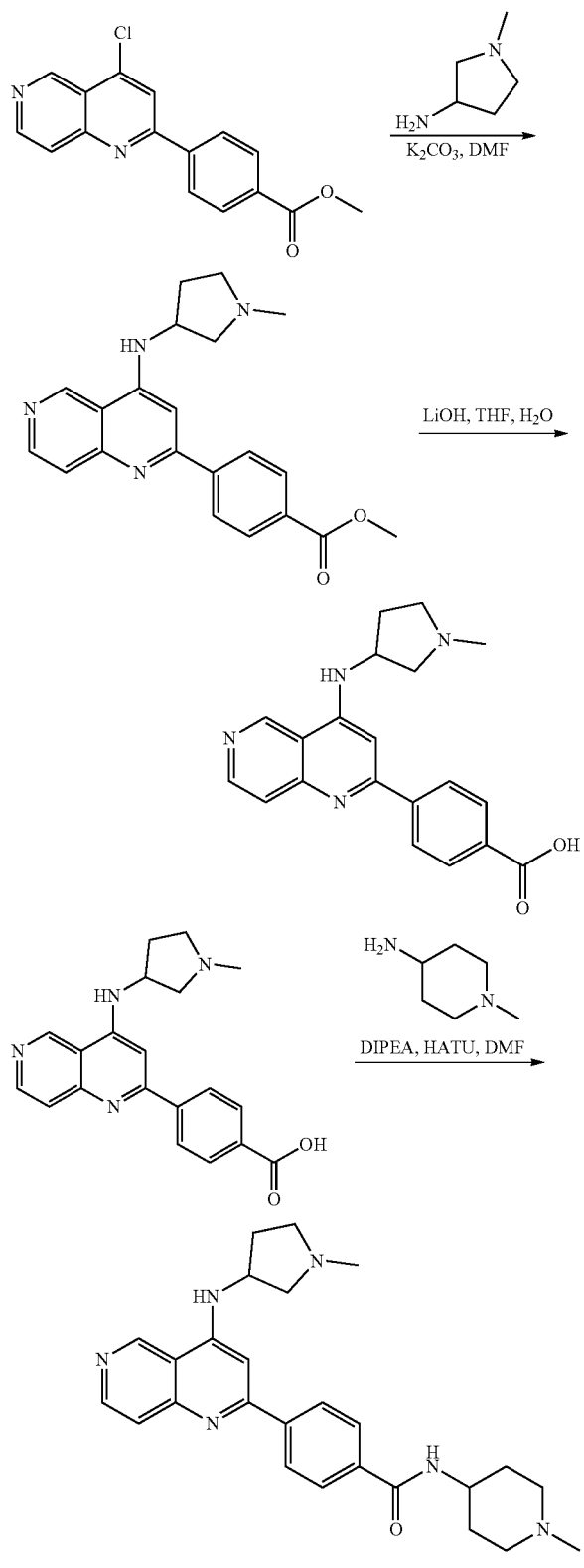

Step 1

The mixture of methyl 4-(4-chloro-1,6-naphthyridin-2-yl)benzoate (100 mg, 0.33 mmol), 1-methylpyrrolidin-3-amine (60 mg, 0.6 mmol) and $K_2CO_3$ (138 mg, 1.0 mmol) in DMF (10 mL) was stirred at 75° C. overnight. After completion, water (10 mL) was added, and then the mixture was extracted with EA (20 mL) three times. The combined organic layers were washed with water (10 mL) and brine (10 mL), dried over $Na_2SO_4$, filtered, concentrated and purified by prep-TLC to give methyl 4-(4-((1-methylpyrrolidin-3-yl)amino)-1,6-naphthyridin-2-yl)benzoate (60 mg, 50%) as brown solid. LC-MS (ESI): 362.1 $(M+1)^+$.

Step 2

The solution of methyl 4-(4-((1-methylpyrrolidin-3-yl)amino)-1,6-naphthyridin-2-yl)benzoate (110 mg, 0.3 mmol) and $LiOH \cdot H_2O$ (38 mg, 0.9 mmol) in $THF/H_2O$ (10 mL/3 mL) was stirred at room temperature overnight. The mixture was acidified with 2 N aq. HCl solution to pH=2, then concentrated to give the crude product as white solid that was used directly in the next step without further purification. LC-MS (ESI): 349.1 $(M+1)^+$.

Step 3

The mixture of 4-(4-((1-methylpyrrolidin-3-yl)amino)-1,6-naphthyridin-2-yl)benzoic acid (72 mg, 0.2 mmol), 1-methylpiperidin-4-amine (35 mg, 0.3 mmol), HATU (114 mg, 0.3 mmol) and DIPEA (52 mg, 0.4 mmol) in DMF (5 mL) was stirred at room temperature overnight. After completion, water (30 mL) was added, and then the mixture was extracted with EA three times. The combined organic layers were washed with water (10 mL) and brine (10 mL), dried over $Na_2SO_4$, filtered, concentrated and purified by pre-HPLC to give N-(1-methylpiperidin-4-yl)-4-(4-((1-methylpyrrolidin-3-yl)amino)-1,6-naphthyridin-2-yl)benzamide (10 mg, 11%. HPLC/UV purity: 100%; LC-MS (ESI): 445.1 $(M+1)^+$. $^1H$ NMR (METHOL-$d_4$) δ: 9.80 (s, 1H), 8.77 (d, J=8.4 Hz, 1H), 8.22 (d, J=8.4 Hz, 2H), 8.09 (d, J=8.4 Hz, 2H), 7.94 (d, J=8.4 Hz, 1H), 7.27 (s, 1H), 4.20-4.23 (m, 2H), 3.61-3.66 (m, 4H), 3.46-3.50 (m, 2H), 3.20-3.25 (m, 2H), 3.08 (s, 3H), 2.93 (s, 3H), 2.44-2.50 (m, 1H), 2.26-2.35 (m, 2H), 1.94-2.05 (m, 3H).

Example 63: Synthesis of 4-(4-((1-Methylpyrrolidin-3-yl)amino)-1,6-naphthyridin-2-yl)-N-(3-(piperidin-1-yl)propyl)benzamide

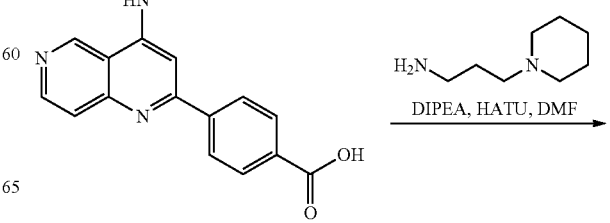

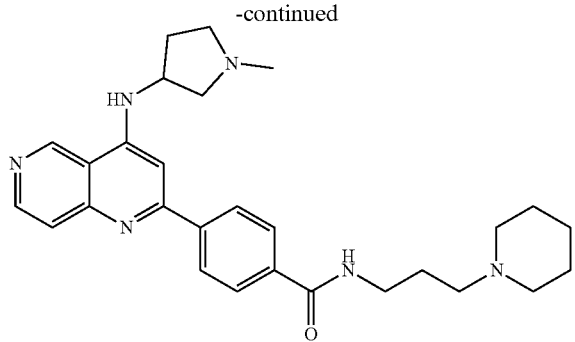

4-(4-((1-Methylpyrrolidin-3-yl)amino)-1,6-naphthyridin-2-yl)-N-(3-(piperidin-1-yl)propyl)benzamide was synthesized in a similar fashion as Example 62, Step 3. HPLC/UV purity: 100%; LC-MS (ESI): 473.3 (M+1)⁺. 1H NMR (METHOL-d4) δ: 9.54 (s, 1H), 8.77 (d, J=6.0 Hz, 1H), 8.14 (d, J=8.4 Hz, 2H), 7.98 (d, J=8.4 Hz, 2H), 7.78 (d, J=6.0 Hz, 1H), 7.02 (s, 1H), 4.45-4.47 (m, 1H), 3.48 (t, J=8.4 Hz, 2H), 3.00-3.05 (m, 1H), 2.89-2.95 (m, 1H), 2.82-2.86 (m, 1H), 2.68-2.74 (m, 5H), 2.61-2.65 (m, 1H), 2.52-2.57 (m, 1H), 2.46-2.52 (m, 3H), 1.92-2.03 (m, 4H), 1.70-1.74 (m, 4H), 1.55-1.57 (m, 2H).

Example 64: Synthesis of N-(3-(Piperidin-1-yl)propyl)-4-(4-(piperidin-4-ylamino)-1,6-naphthyridin-2-yl)benzamide Step 1

The mixture of 4-(4-chloro-1,6-naphthyridin-2-yl)-N-(3-(piperidin-1-yl)propyl)benzamide (150 mg, 0.367 mmol), tert-butyl 4-aminopiperidine-1-carboxylate (147 mg, 0.733 mmol) and K₂CO₃ (152 mg, 1.1 mmol) in DMF (10 mL) was stirred at 100° C. overnight. Then 100 mL water was added and the mixture was extracted with EA (100 mL×2), washed with brine, dried over Na₂SO₄, concentrated and purified with silica gel column chromatography to give tert-butyl 4-(2-(4-(3-(piperidin-1-yl)propylcarbamoyl)phenyl)-1,6-naphthyridin-4-ylamino)piperidine-1-carboxylate (100 mg, 46%) as white solid. HPLC/UV purity: 100%; LC-MS (ESI): 573.3 (M+1)⁺.

Step 2

The solution of tert-butyl 4-(2-(4-(3-(piperidin-1-yl)propylcarbamoyl)phenyl)-1,6-naphthyridin-4-ylamino)piperidine-1-carboxylate (57 mg, 0.1 mmol) in TFA/DCM (1 mL/5 mL) was stirred at room temperature for 2 hours. The reaction mixture was concentrated and purified by Prep-HPLC (Welch, XB-C18, 21.2 mm×250 mm, 10 um, eluting with 20% CH₃CN in 1‰ TFA in H₂O) to give N-(3-(piperidin-1-yl)propyl)-4-(4-(piperidin-4-ylamino)-1,6-naphthyridin-2-yl)benzamide (8 mg, 16.8%) as white solid. HPLC/UV purity: 100%; LC-MS (ESI): 473.3 (M+1)⁺. ¹H NMR (METHANOL-d₄) δ: 9.84 (s, 1H), 8.86 (d, J=6.0 Hz, 1H), 8.17-8.11 (m, 4H), 7.93 (d, J=6.0 Hz, 1H), 7.42 (s, 1H), 4.51-4.46 (m, 1H), 3.59-3.52 (m, 6H), 3.31-3.23 (m, 2H), 3.23-3.18 (m, 2H), 2.96 (t, J=12.0 Hz, 2H), 2.39 (d, J=13.2 Hz, 2H), 2.14-2.04 (m, 4H), 1.98 (d, J=14.8 Hz, 2H), 1.88-1.74 (m, 3H), 1.55-1.51 (m, 1H).

Example 65: Synthesis of N-(1-Methylpiperidin-4-yl)-4-(4-(piperidin-4-ylamino)-1,6-naphthyridin-2-yl)benzamide

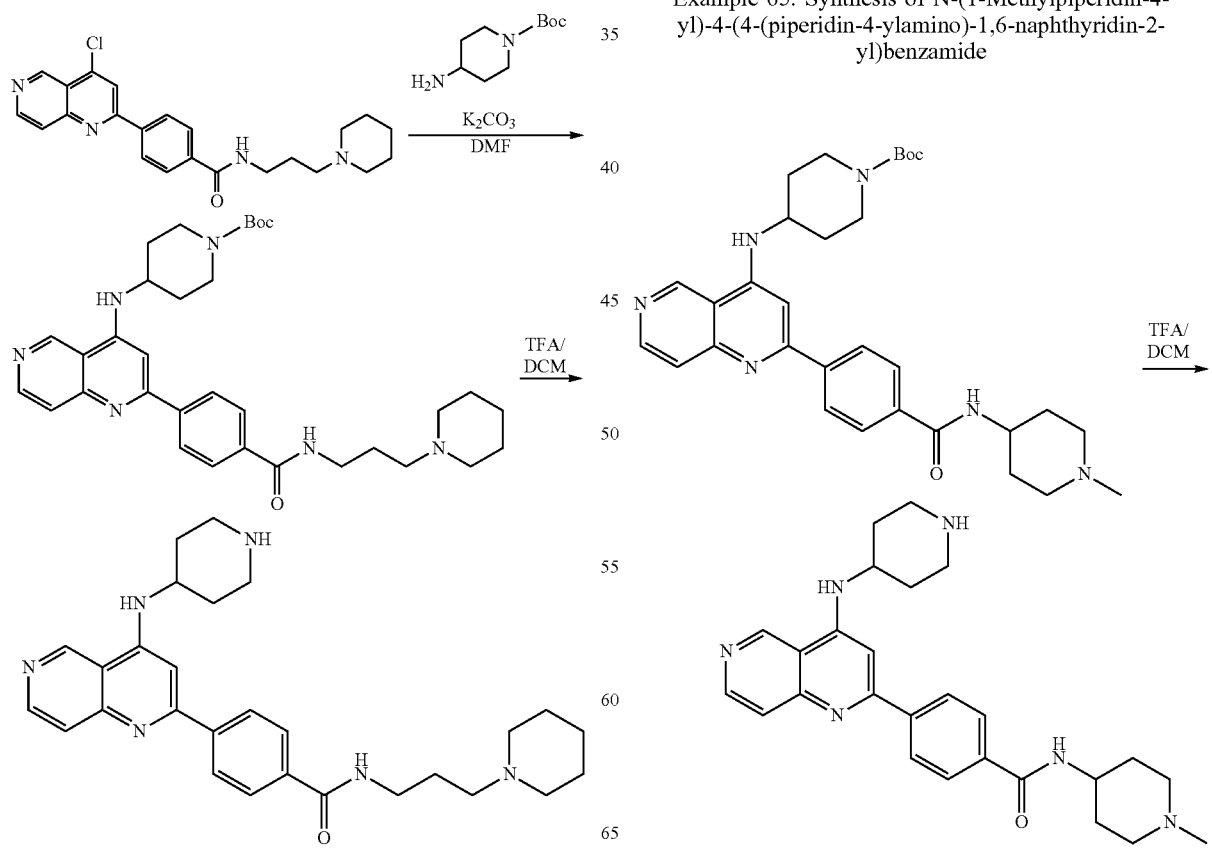

The solution of tert-butyl 4-(2-(4-(1-methylpiperidin-4-ylcarbamoyl)phenyl)-1,6-naphthyridin-4-ylamino)piperidine-1-carboxylate (16.3 mg, 0.03 mmol) in TFA/DCM (1 mL/5 mL) was stirred at room temperature for 2 hrs. The solution was concentrated and purified by Prep-HPLC (Welch, XB-C18, 21.2 mm×250 mm, 10 um, eluting with 20% CH$_3$CN in 1‰ TFA in H$_2$O) to give N-(1-methylpiperidin-4-yl)-4-(4-(piperidin-4-ylamino)-1,6-naphthyridin-2-yl)benzamide (7 mg, 52.5%) as white solid. HPLC/UV purity: 100%; LC-MS (ESI): 445.2 (M+1). $^1$H NMR (METHANOL-d$_4$) δ: 9.58 (s, 1H), 8.58 (d, J=6.0 Hz, 1H), 8.15 (d, J=8.4 Hz, 2H), 8.00 (d, J=8.8 Hz, 2H), 7.80 (d, J=6.0 Hz, 1H), 7.14 (s, 1H), 4.63-4.60 (m, 1H), 3.99-3.95 (m, 1H), 3.30-3.15 (m, 2H), 2.99-2.87 (m, 4H), 2.35 (s, 3H), 2.22 (t, J=12.4 Hz, 4H), 2.06-1.96 (m, 2H), 1.78-1.69 (m, 4H).

Example 66: Synthesis of N,N-diethyl-4-(4-(pyrrolidin-3-ylamino)-1,6-naphthyridin-2-yl)benzamide

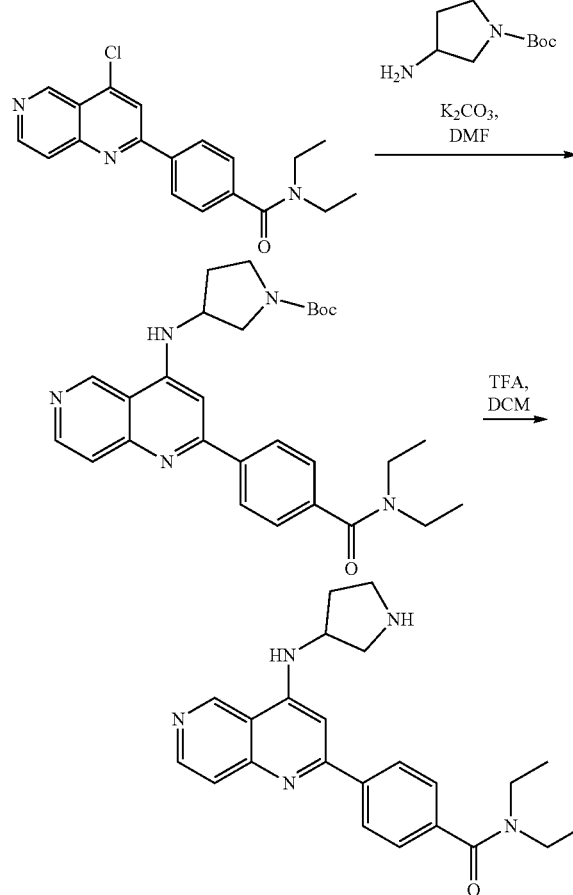

N,N-diethyl-4-(4-(pyrrolidin-3-ylamino)-1,6-naphthyridin-2-yl)benzamide was synthesized in a similar fashion as Example 64. HPLC/UV purity: 100%; LC-MS (ESI): 390.2 (M+1)$^+$. $^1$H NMR (METHANOL-d$_4$) δ: 9.89 (s, 1H), 8.85 (d, J=6.0 Hz, 1H), 8.15 (d, J=8.0 Hz, 2H), 7.97 (d, J=6.0 Hz, 1H), 7.66 (d, J=8.0 Hz, 2H), 7.35 (s, 1H), 3.82-3.87 (m, 1H), 3.50-3.68 (m, 5H), 3.30-3.34 (m, 3H), 2.60-2.66 (m, 1H), 2.41-2.44 (m, 1H), 1.29 (t, J=6.4 Hz, 3H), 1.16 (t, J=6.8 Hz, 3H).

Example 67: Synthesis of N-(3-(Piperidin-1-yl)propyl)-4-(4-(pyrrolidin-3-ylamino)-1,6-naphthyridin-2-yl)benzamide

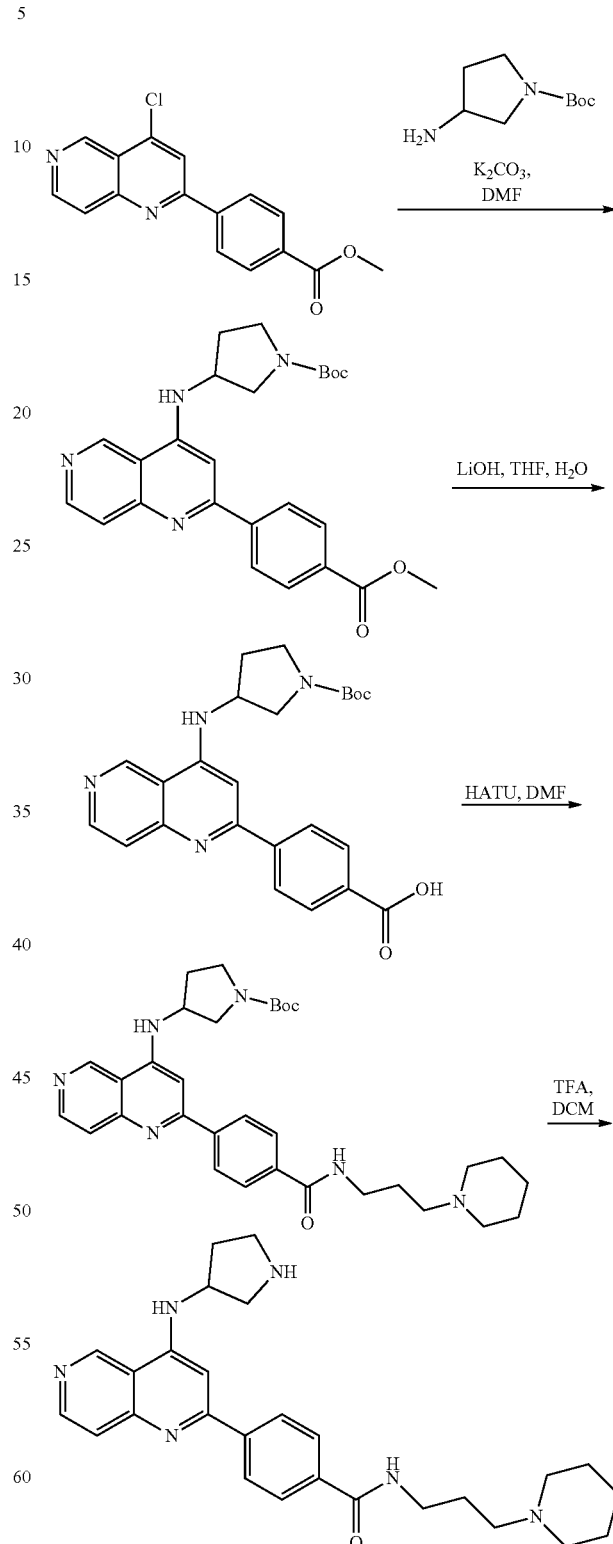

N-(3-(Piperidin-1-yl)propyl)-4-(4-(pyrrolidin-3-ylamino)-1,6-naphthyridin-2-yl)benzamide was synthesized in a similar fashion as Examples 62 and 64. HPLC/UV purity: 100%; LC-MS (ESI): 459.2 (M+1)⁺. ¹H NMR (METHANOL-d₄) δ: 9.96 (s, 1H), 8.86 (d, J=6.0 Hz, 1H), 8.22 (d, J=8.0 Hz, 2H), 8.15 (d, J=8.0 Hz, 2H), 8.01 (d, J=6.0 Hz, 1H), 7.39 (s, 1H), 3.81-3.86 (m, 1H), 3.68-3.71 (m, 2H), 3.56-3.61 (m, 6H), 3.22 (d, J=6.0 Hz, 2H), 2.98 (d, J=12.4 Hz, 2H), 2.63-2.67 (m, 1H), 2.42-2.48 (m, 1H), 2.11-2.15 (m, 2H), 1.97-2.01 (m, 2H), 1.81-1.88 (m, 3H), 1.56-1.58 (m, 1H).

Example 68: Synthesis of N-(1-Methylpiperidin-4-yl)-4-(4-(pyrrolidin-3-ylamino)-1,6-naphthyridin-2-yl)benzamide

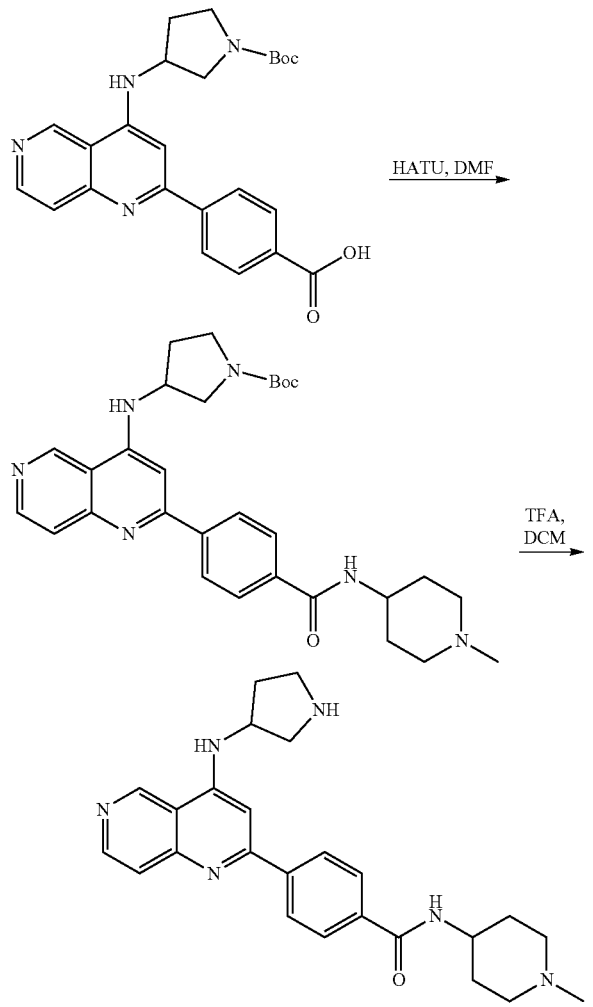

N-(1-Methylpiperidin-4-yl)-4-(4-(pyrrolidin-3-ylamino)-1,6-naphthyridin-2-yl)benzamide was synthesized in a similar fashion as Examples 62 and 64. HPLC/UV purity: 100%; LC-MS (ESI): 431.2 (M+1)⁺. ¹H NMR (METHANOL-d₄) δ: 9.90 (s, 1H), 8.84 (d, J=6.4 Hz, 1H), 8.20 (d, J=8.4 Hz, 2H), 8.12 (d, J=8.0 Hz, 2H), 7.99 (d, J=6.4 Hz, 1H), 7.36 (s, 1H), 4.20-4.25 (m, 1H), 3.83-3.86 (m, 1H), 3.45-3.72 (m, 6H), 3.22 (d, J=12.4 Hz, 2H), 2.92 (s, 3H), 2.62-2.66 (m, 1H), 2.42-2.48 (m, 1H), 2.27-2.31 (m, 2H), 1.97-2.05 (m, 2H).

Example 69: Synthesis of N-(1-Methylpiperidin-4-yl)-4-(4-((1-methylpiperidin-4-yl)amino)-1,6-naphthyridin-2-yl)benzamide

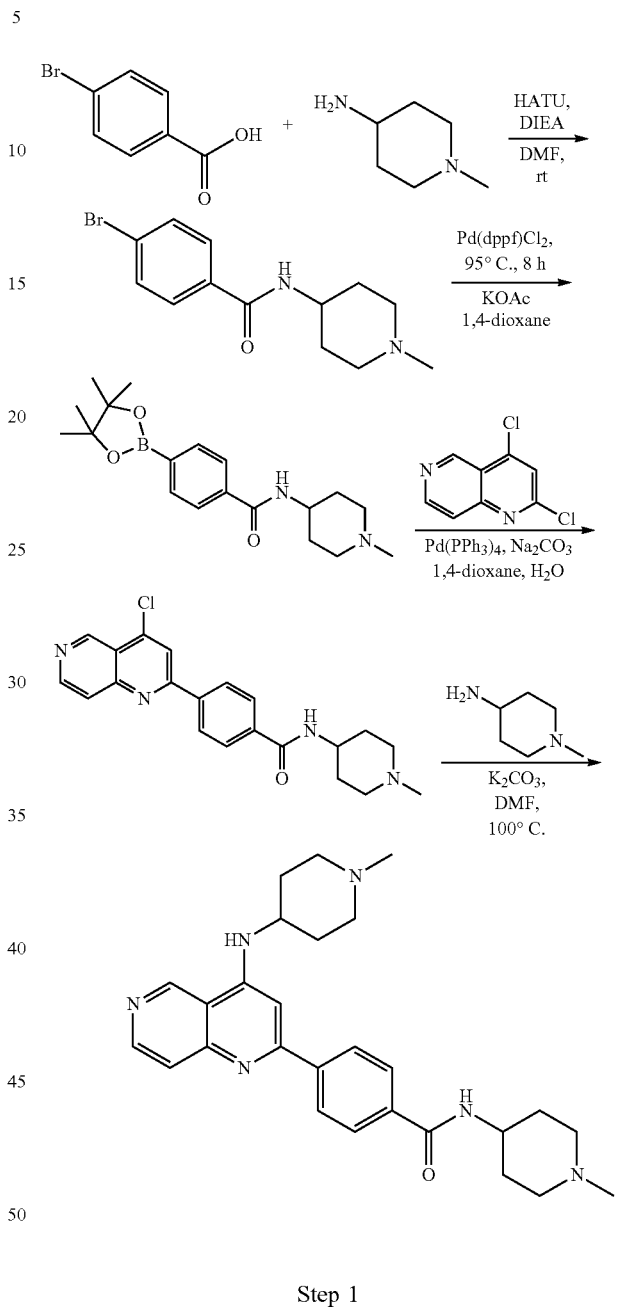

Step 1

The mixture of 4-Bromobenzoic acid (2.0 g, 9.9 mmol), 1-methylpiperidin-4-amine (2.3 g, 19.8 mmol), HATU (5.7 g, 14.9 mmol) and DIPEA (2.6 g, 19.8 mmol) in DMF (30 mL) was stirred at room temperature overnight. The reaction mixture was quenched with water (20 mL), extracted with DCM (20 mL×3). The combined organic layer was washed with water (20 mL×3) and brine (30 mL), dried over Na₂SO₄, concentrated and purified by flash column chromatography (silica gel, eluting with DCM to 10% MeOH/DCM) to afford 4-bromo-N-(1-methylpiperidin-4-yl)benzamide (2.4 g, 81%) as yellow solid. LC-MS (ESI): 297.1 (M+1)⁺.

Step 2

The mixture of 4-bromo-N-(1-methylpiperidin-4-yl)benzamide (500 mg, 1.68 mmol), bis(pinacolato)diboron (1.3 g, 5.04 mmol), Pd(dppf)Cl$_2$ (123 mg, 0.168 mmol) and KOAc (330 g, 3.36 mmol) in 1,4-dioxane (15 mL) was stirred at 95° C. under N$_2$ for 8 hrs. The reaction mixture was concentrated and purified by flash column chromatography (silica gel, eluting with DCM to 10% MeOH/DCM) to afford N-(1-methylpiperidin-4-yl)-4-(4,4,5,5-tetramethyl-1,3,2-dioxaborolan-2-yl)benzamide (300 mg, 52%) as brown solid. LC-MS (ESI): 345.1 (M+1)$^+$.

Step 3

The mixture of N-(1-methylpiperidin-4-yl)-4-(4,4,5,5-tetramethyl-1,3,2-dioxaborolan-2-yl)benzamide (300 mg, 0.87 mmol), 2,4-dichloro-1,6-naphthyridine (143 mg, 0.72 mmol), Pd(PPh$_3$)$_4$ (83 mg, 0.072 mmol) and Na$_2$CO$_3$ (153 mg, 1.44 mmol) in 1,4-dioxane/H$_2$O (12 mL/3 mL) was stirred at 100° C. under N$_2$ for 16 hrs. The reaction mixture was concentrated and purified by flash column chromatography (silica gel, eluting with 1% to 3% MeOH/DCM) to afford 4-(4-chloro-1,6-naphthyridin-2-yl)-N-(1-methylpiperidin-4-yl)benzamide (30 mg, 9%) as oil. LC-MS (ESI): 381.1 (M+1)$^+$.

Step 4

To a solution of 4-(4-chloro-1,6-naphthyridin-2-yl)-N-(1-methylpiperidin-4-yl)benzamide (30 mg, 0.08 mmol) in DMF (2 mL) were added 1-methylpiperidin-4-amine (18 mg, 0.16 mmol) and K$_2$CO$_3$ (22 mg, 0.16 mmol). The reaction mixture was stirred at 100° C. overnight, then quenched with water (5 mL), and extracted with DCM (5 mL×3). The organic layer was washed by water (10 mL×3) and brine (20 mL), dried over Na$_2$SO$_4$, concentrated and purified by prep-TLC to afford N-(1-methylpiperidin-4-yl)-4-(4-((1-methylpiperidin-4-yl)amino)-1,6-naphthyridin-2-yl)benzamide (5 mg, 14%) as yellow oil. HPLC/UV purity: 100%; LC-MS (ESI): 459.2 (M+1)$^+$. $^1$H NMR (METHANOL-d$_4$) δ: 9.83 (s, 1H), 8.86 (d, J=6.0 Hz, 1H), 8.13 (m, 4H), 7.92 (d, J=6.0 Hz, 1H), 7.40 (s, 1H), 4.42-4.49 (m, 1H), 4.24-4.18 (m, 1H), 3.70 (d, J=12.8 Hz, 2H), 3.62 (d, J=12.4 Hz, 2H), 3.27-3.18 (m, 4H), 2.93 (d, J=13.6 Hz, 6H), 2.42 (d, J=13.6 Hz, 2H), 2.29 (d, J=13.6 Hz, 2H), 2.21-2.13 (m, 2H), 2.04-1.92 (m, 2H).

Example 70: Synthesis of N-(3-(Piperidin-1-yl)propyl)-4-(4-((tetrahydro-2H-pyran-4-yl)amino)-1,6-naphthyridin-2-yl)benzamide

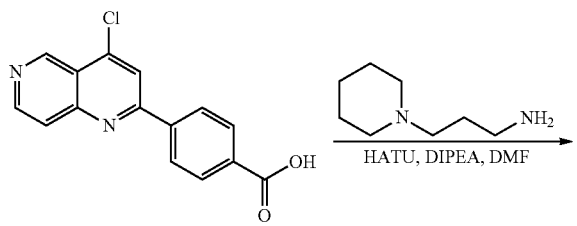

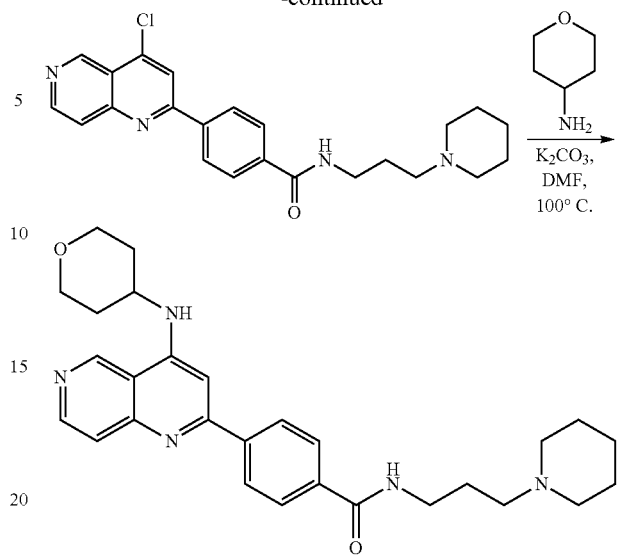

Step 1

The mixture of 4-(4-chloro-1,6-naphthyridin-2-yl)benzoic acid (250 mg, 0.88 mmol), 3-(piperidin-1-yl)propan-1-amine (151 mg, 1.06 mmol), HATU (403 mg, 1.06 mmol) and DIPEA (227 g, 1.76 mmol) in DMF (8 mL) was stirred at room temperature overnight. The reaction mixture was quenched with water (5 mL), extracted with DCM (10 mL×3), washed with water (10 mL×3) and brine (20 mL), dried over Na$_2$SO$_4$, concentrated and purified by prep-TLC (MeOH/DCM=10/1) to afford 4-(4-chloro-1,6-naphthyridin-2-yl)-N-(3-(piperidin-1-yl)propyl)benzamide (300 mg, 83%) as yellow oil. LC-MS (ESI): 409.1 (M+1)$^+$.

Step 2

To a solution of 4-(4-chloro-1,6-naphthyridin-2-yl)-N-(3-(piperidin-1-yl)propyl)benzamide (100 mg, 0.24 mmol) in DMF (5 mL) were added tetrahydro-2H-pyran-4-amine (36 mg, 0.36 mmol) and K$_2$CO$_3$ (66 mg, 0.48 mmol). The reaction mixture was stirred at 100° C. overnight, then quenched with water (5 mL), and extracted with DCM (5 mL×3). The organic layer was washed with water (10 mL×3) and brine (20 mL), dried over Na$_2$SO$_4$, concentrated and purified by prep-PLC to afford N-(3-(piperidin-1-yl)propyl)-4-(4-((tetrahydro-2H-pyran-4-yl)amino)-1,6-naphthyridin-2-yl)benzamide (10 mg, 9%) as yellow solid. HPLC/UV purity: 100%; LC-MS (ESI): 474.2 (M+1)$^+$. $^1$H NMR (METHANOL-d$_4$) δ: 9.83 (s, 1H), 8.85 (d, J=6.0 Hz, 1H), 8.13 (s, 4H), 7.90 (d, J=6.0 Hz, 1H), 7.36 (s, 1H), 4.44-4.36 (m, 1H), 4.07 (d, J=11.6, 4.0 Hz, 2H), 3.68-3.53 (m, 6H), 3.20 (t, J=7.6 Hz, 2H), 2.96 (t, J=11.6 Hz, 2H), 2.14-2.09 (m, 4H), 1.99-1.75 (m, 7H), 1.59-1.50 (m, 1H).

Example 71: Synthesis of N-(3-(Piperidin-1-yl)propyl)-4-(4-((pyridin-4-ylmethyl)amino)-1,6-naphthyridin-2-yl)benzamide

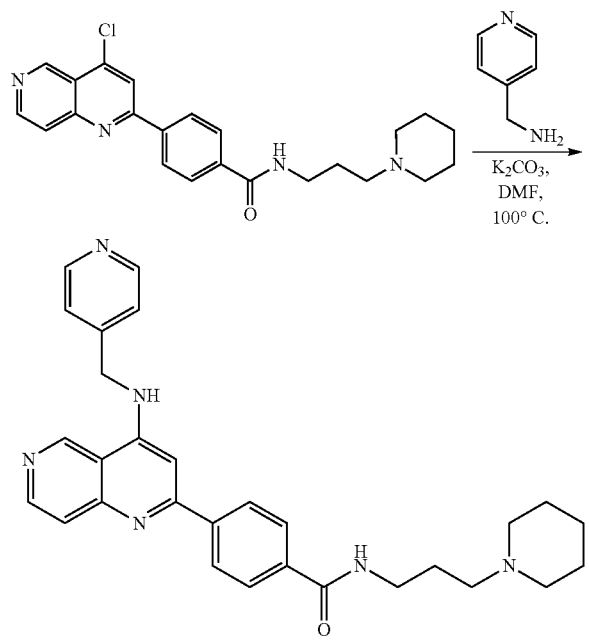

To a solution of 4-(4-chloro-1,6-naphthyridin-2-yl)-N-(3-(piperidin-1-yl)propyl)benzamide (100 mg, 0.24 mmol) in DMF (5 mL) were added pyridin-4-ylmethanamine (52 mg, 0.48 mmol) and K$_2$CO$_3$ (66 mg, 0.48 mmol). The reaction mixture was stirred at 80° C. overnight, then quenched with water (5 mL), and extracted with DCM (5 mL×3). The organic layer was washed with water (10 mL×3) and brine (20 mL), dried over Na$_2$SO$_4$, concentrated and purified by prep-PLC to afford N-(3-(piperidin-1-yl)propyl)-4-(4-((pyridin-4-ylmethyl)amino)-1,6-naphthyridin-2-yl)benzamide (1.6 mg, 1%) as yellow oil. HPLC/UV purity: 100%; LC-MS (ESI): 481.3 (M+1)$^+$. $^1$H NMR (METHANOL-d$_4$) δ: 9.82 (s, 1H), 8.90 (d, J=6.0 Hz, 1H), 8.72 (s, 2H), 8.08-8.01 (m, 5H), 7.90 (d, J=5.6 Hz, 2H), 7.17 (s, 1H), 5.22 (d, J=7.6 Hz, 2H), 3.58-3.50 (m, 4H), 3.18 (t, J=7.6 Hz, 2H), 2.95 (t, J=11.2 Hz, 2H), 2.12-2.06 (m, 2H), 1.97 (d, J=15.2 Hz, 2H), 1.87-1.73 (m, 3H), 1.60-1.51 (m, 1H).

Example 72: Synthesis of N-(1-Methylpiperidin-4-yl)-4-(4-((tetrahydro-2H-pyran-4-yl)amino)-1,6-naphthyridin-2-yl)benzamide

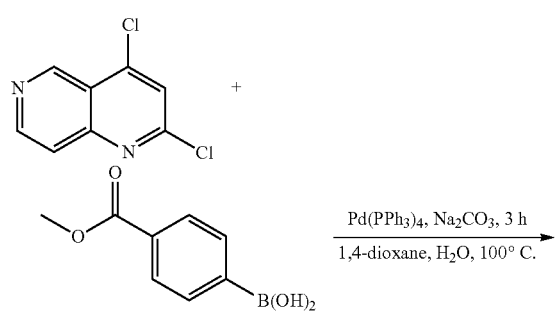

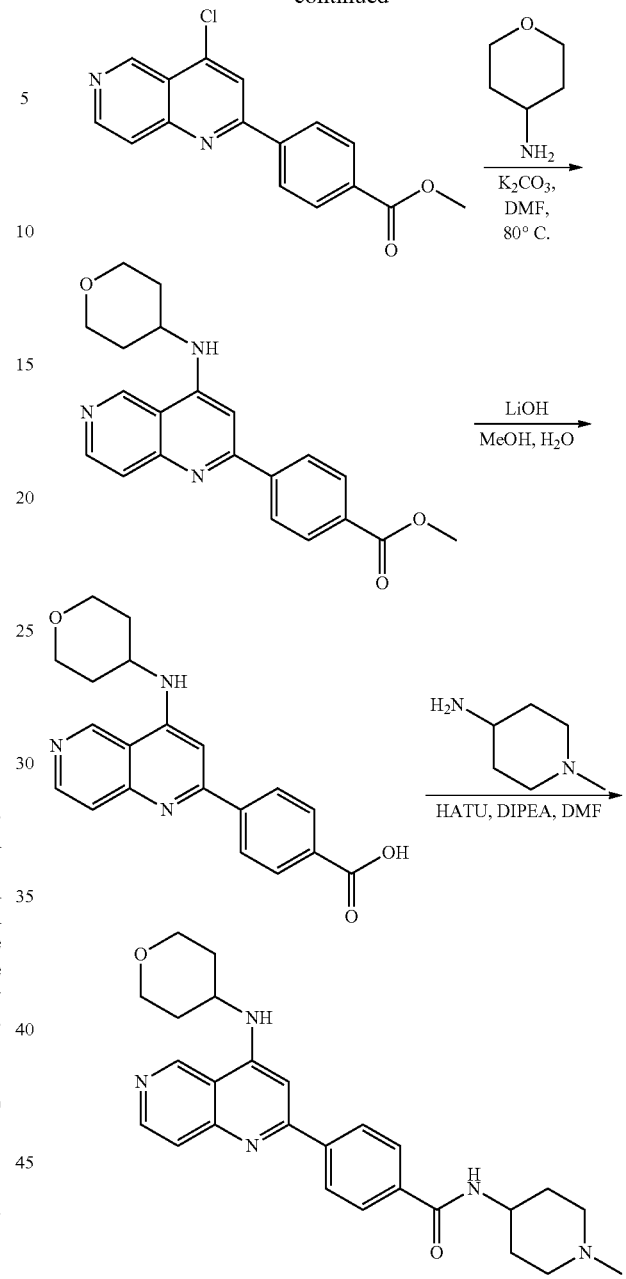

Step 1

The mixture of 2,4-dichloro-1,6-naphthyridine (1.0 g, 5.0 mmol), (4-(methoxycarbonyl)phenyl)boronic acid (1.1 g, 6.0 mmol), Pd(PPh$_3$)$_4$ (578 mg, 0.5 mmol) and Na$_2$CO$_3$ (1.06 g, 10.0 mmol) in 1,4-dioxane/H$_2$O (20/5 mL) was stirred at 100° C. under N$_2$ for 3 hrs. The reaction mixture was concentrated, diluted with DCM (30 mL), washed with water (10 mL×3) and brine (20 mL), and dried over Na$_2$SO$_4$. After filtration, the filtrate was concentrated and purified by flash column chromatography (silica gel, eluting with 10% to 20% EA/PE) to afford methyl 4-(4-chloro-1,6-naphthyridin-2-yl)benzoate (1.0 g, 67%) as white solid. LC-MS(ESI): 299.0 (M+1)$^+$.

Step 2

To a solution of methyl 4-(4-chloro-1,6-naphthyridin-2-yl)benzoate (200 mg, 0.67 mmol) in DMF (5 mL) were added tetrahydro-2H-pyran-4-amine (102 mg, 1.01 mmol) and K₂CO₃ (185 mg, 1.34 mmol). The reaction mixture was stirred at 80° C. overnight, then quenched with water (5 mL), and extracted with DCM (10 mL×3). The organic layer was washed with water (10 mL×3) and brine (20 mL), dried over Na₂SO₄, concentrated and purified by flash column chromatography (silica gel, eluting with 10% to 50% EA/PE) to afford methyl 4-(4-((tetrahydro-2H-pyran-4-yl)amino)-1,6-naphthyridin-2-yl)benzoate (150 mg, 8%) as yellow solid. LC-MS (ESI): 364.1 (M+1);

Step 3

To a solution of methyl 4-(4-((tetrahydro-2H-pyran-4-yl)amino)-1,6-naphthyridin-2-yl)benzoate (150 mg, 0.42 mmol) in MeOH (5 ml) was added 1N aq. LiOH solution (1.68 mL). The reaction mixture was stirred at room temperature overnight. The reaction mixture was concentrated acidified with 1N aq. HCl solution to pH=2, and then lyophilized to afford 4-(4-((tetrahydro-2H-pyran-4-yl)amino)-1,6-naphthyridin-2-yl)benzoic acid as brown solid. The crude product was used in the next step without further purification. LC-MS (ESI): 350.1 (M+1)⁺.

Step 4

The mixture of 4-(4-((tetrahydro-2H-pyran-4-yl)amino)-1,6-naphthyridin-2-yl)benzoic acid (50 mg, 0.14 mmol), 1-methylpiperidin-4-amine (19 mg, 0.17 mmol), HATU (65 mg, 0.17 mmol) and DIPEA (36 mg, 0.28 mmol) in DMF (5 mL) was stirred at room temperature for 2 h. The reaction mixture was quenched with water (5 mL), extracted with DCM (10 mL×3), washed with water (10 mL×3) and brine (20 mL), dried over Na₂SO₄, concentrated and purified by prep-TLC to afford N-(1-methylpiperidin-4-yl)-4-(4-((tetrahydro-2H-pyran-4-yl)amino)-1,6-naphthyridin-2-yl)benzamide as yellow solid (60 mg, 94%). LC-MS (ESI): 446.2 (M+1)⁺. ¹H NMR (METHANOL-d₄) δ: 9.83 (s, 1H), 8.85 (d, J=6.0 Hz, 1H), 8.18-8.10 (m, 4H), 7.89 (d, J=6.0 Hz, 1H), 7.36 (s, 1H), 4.43-4.37 (m, 1H), 4.24-4.18 (m, 1H), 4.07 (dd, J=11.6, 4.0 Hz, 2H), 3.68-3.62 (m, 4H), 3.20 (t, J=11.6 Hz, 2H), 2.91 (s, 3H), 2.28 (d, J=12.0 Hz, 2H), 2.09 (d, J=10.4 Hz, 2H), 2.02-1.87 (m, 4H).

Example 73: Synthesis of 4-(8-Bromo-4-((3-(piperidin-1-yl)propyl)amino)-1,6-naphthyridin-2-yl)-N,N-diethylbenzamide

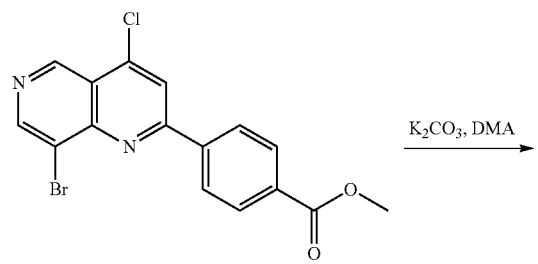

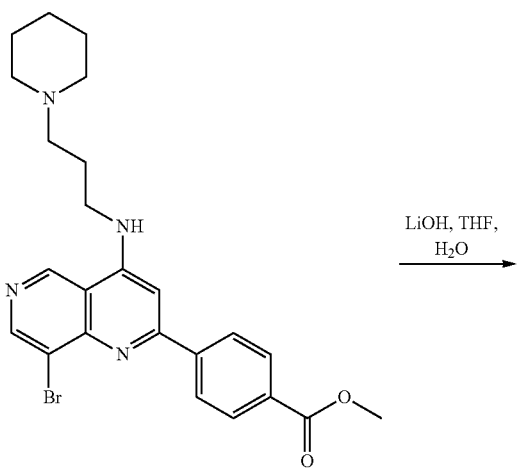

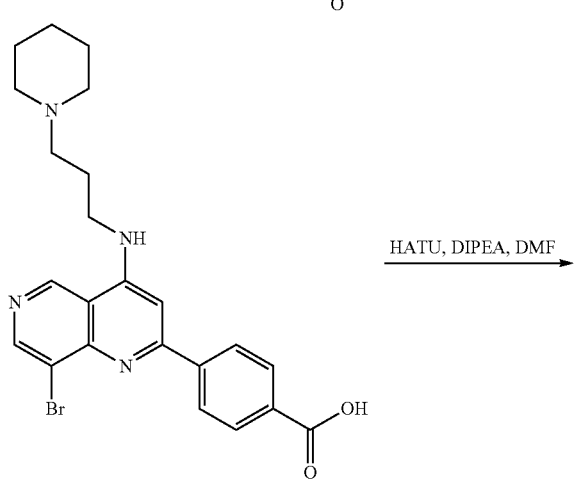

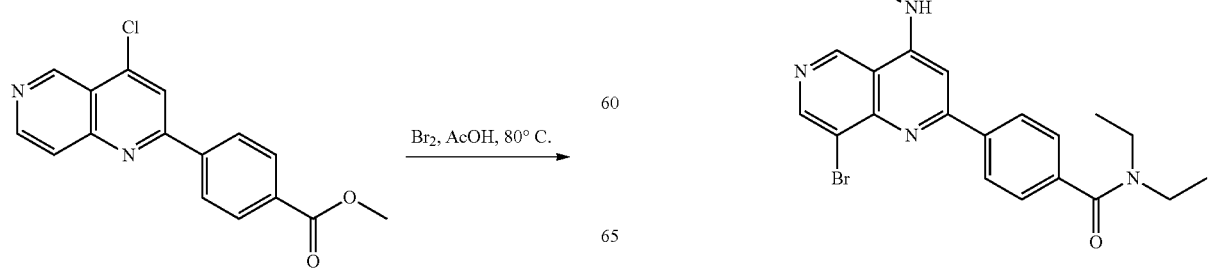

Step 1

The mixture of methyl 4-(4-chloro-1,6-naphthyridin-2-yl)benzoate (90 mg, 0.30 mmol) and Br$_2$ (53 mg, 0.33 mmol) in acetic acid (10 mL) was stirred at 70° C. overnight. The solvent was removed under reduced pressure and the residue was poured into saturated NaHCO$_3$ solution (10 mL). The mixture was extracted with EA (20 mL) three times. The combined organic layers were washed with water (10 mL×3) and brine (10 mL), dried over Na$_2$SO$_4$, filtered, concentrated, and purified by prep-TLC to give methyl 4-(8-bromo-4-chloro-1,6-naphthyridin-2-yl)benzoate (80 mg, 72%) as brown solid. LC-MS (ESI): 376.9 (M+1)$^+$.

Step 2

The mixture of methyl 4-(8-bromo-4-chloro-1,6-naphthyridin-2-yl)benzoate (50 mg, 0.13 mmol), 3-(piperidin-1-yl)propan-1-amine (22 mg, 0.16 mmol) and K$_2$CO$_3$ (36 mg, 0.26 mmol) in DMA (2 mL) was stirred at 70° C. overnight. Then water (10 mL) was added, and the mixture was extracted with EA (20 mL) three times. The combined organic layers were washed with water (10 mL×3) and brine (10 mL×1), dried over Na$_2$SO$_4$, filtered, concentrated and purified by prep-TLC to give methyl 4-(8-bromo-4-((3-(piperidin-1-yl)propyl)amino)-1,6-naphthyridin-2-yl)benzoate (48 mg, 77%) as brown oil. LC-MS (ESI): 482.8 (M+1)$^+$.

Step 3

The mixture of methyl 4-(8-bromo-4-((3-(piperidin-1-yl)propyl)amino)-1,6-naphthyridin-2-yl)benzoate (48 mg, 0.10 mmol) and LiOH·H$_2$O (12 mg, 0.30 mmol) in THF/H$_2$O (3 mL/1.5 mL) was stirred at room temperature overnight. The mixture was acidified with 2N aq. HCl solution to pH=4, and then concentrated to give the crude product as brown solid that was used directly in the next step without further purification. LC-MS (ESI): 468.8 (M+1)$^+$.

Step 4

Step 4 to synthesize 4-(8-Bromo-4-((3-(piperidin-1-yl)propyl)amino)-1,6-naphthyridin-2-yl)-N,N-diethylbenzamide was completed in a similar fashion as Example 72, Step 4. LC-MS (ESI): 523.8 (M+1)$^+$. $^1$H NMR (METHANOL-d$_4$) δ: 9.59 (s, 1H), 8.97 (s, 1H), 8.33 (d, J=8.0 Hz, 2H), 7.61 (d, J=8.0 Hz, 2H), 7.33 (s, 1H), 3.75 (t, J=6.8 Hz, 2H), 3.58-3.64 (m, 4H), 3.33-3.39 (m, 2H), 3.29-3.31 (m, 2H), 2.98 (t, J=12.4 Hz, 2H), 2.25-2.30 (m, 2H), 1.95-1.99 (m, 2H), 1.77-1.84 (m, 3H), 1.51-1.58 (m, 1H), 1.32 (t, J=6.8 Hz, 3H), 1.19 (t, J=6.8 Hz, 3H).

Example 74: Synthesis of 4-(8-Bromo-4-((3-(piperidin-1-yl)propyl)amino)-1,6-naphthyridin-2-yl)-N-(1-methylpiperidin-4-yl)benzamide

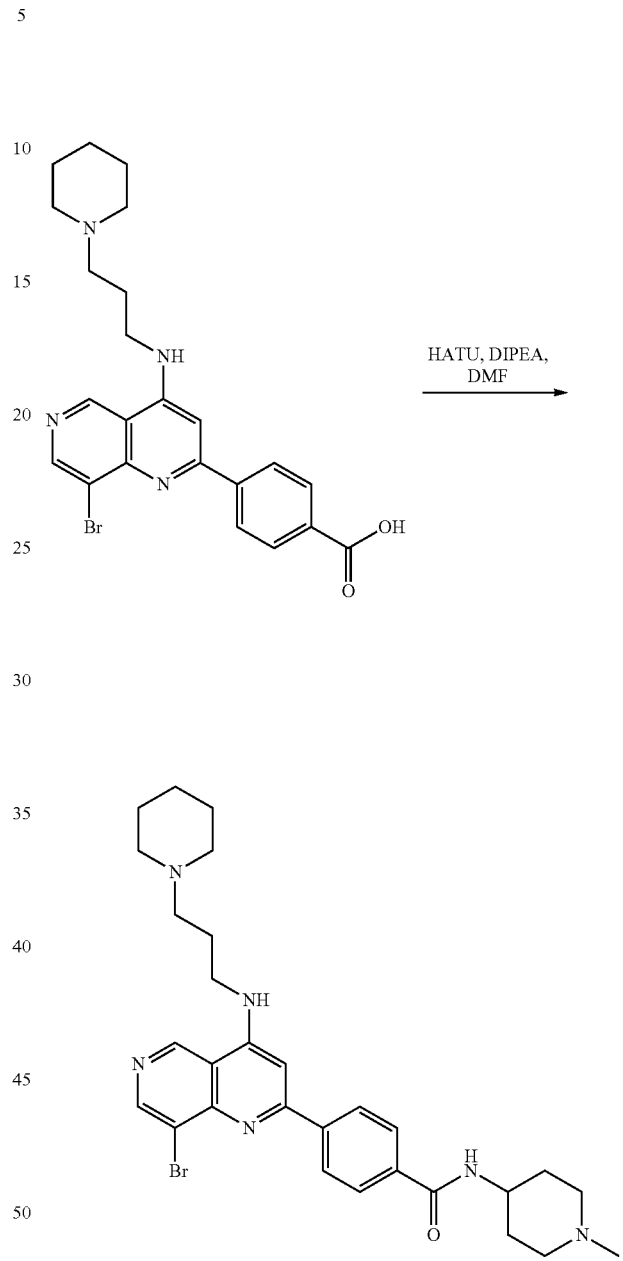

4-(8-Bromo-4-((3-(piperidin-1-yl)propyl)amino)-1,6-naphthyridin-2-yl)-N-(1-methylpiperidin-4-yl)benzamide was synthesized in a similar fashion as Example 73. LC-MS (ESI): 565.3 (M+1)$^+$. $^1$H NMR (METHANOL-d$_4$) δ: 9.39 (s, 1H), 8.79 (s, 1H), 8.29 (d, J=8.0 Hz, 2H), 7.92 (d, J=8.0 Hz, 2H), 7.22 (s, 1H), 4.08-4.12 (m, 1H), 3.60 (t, J=6.8 Hz, 2H), 3.45-3.52 (m, 4H), 3.15-3.19 (m, 2H), 3.11 (t, J=12.8 Hz, 2H), 2.81-2.89 (m, 5H), 2.13-2.21 (m, 4H), 1.80-1.86 (m, 4H), 1.34-1.75 (m, 3H), 1.40-1.46 (m, 1H).

Example 75: Synthesis of N,N-Diethyl-4-(8-methyl-4-((3-(piperidin-1-yl)propyl)amino)-1,6-naphthyridin-2-yl)benzamide

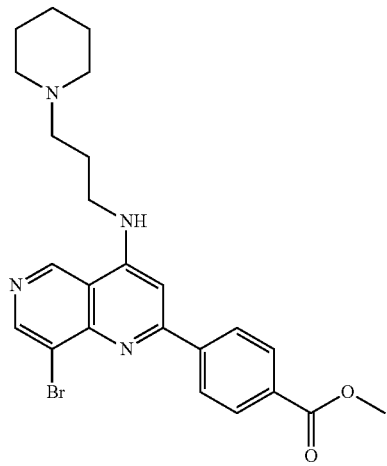

Me₂Zn, dioxane →

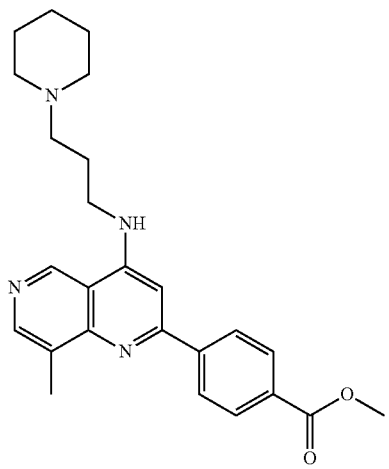

LiOH, THF, H₂O →

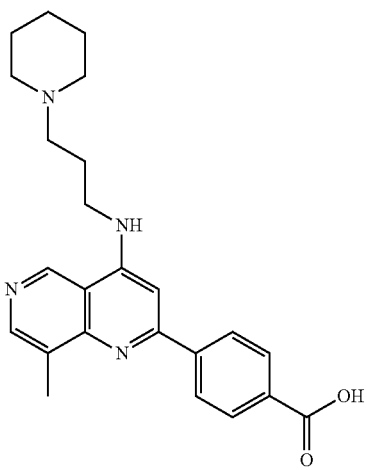

HATU, DIPEA, DMF →

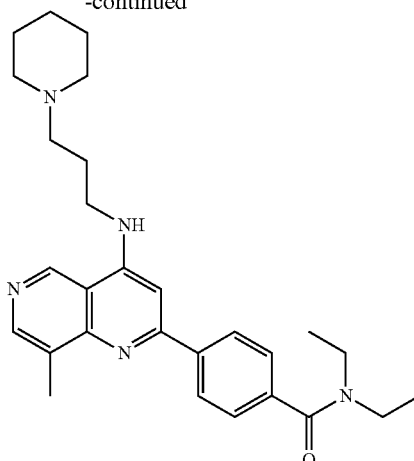

Step 1

The mixture of methyl 4-(8-bromo-4-((3-(piperidin-1-yl)propyl)amino)-1,6-naphthyridin-2-yl)benzoate (48 mg, 0.10 mmol), dimethylzinc solution in THF (0.2 mL, 0.20 mmol) and Pd(t-Bu₃P)₂ (10 mg, 0.02 mmol) in dioxane (8 mL) was stirred at 80° C. under N₂ atmosphere for 3 hours. Then water (10 mL) was added, and the mixture was extracted with EA (20 mL). The organic layer was washed with water (10 mL) and brine (10 mL), dried over Na₂SO₄, filtered, concentrated and purified by flash chromatography to give methyl 4-(8-methyl-4-((3-(piperidin-1-yl)propyl)amino)-1,6-naphthyridin-2-yl)benzoate (32 mg, 78%) as yellow oil. LC-MS (ESI): 418.8 (M+1)⁺.

Step 2

The mixture of 4-(8-Methyl-4-((3-(piperidin-1-yl)propyl)amino)-1,6-naphthyridin-2-yl)benzoate (140 mg, 0.33 mmol) and LiOH·H₂O (42 mg, 1.0 mmol) in THF/H₂O (10 mL/5 mL) was stirred at room temperature overnight. Then the mixture was acidified with 1N aq. HCl solution to pH=2, and concentrated to give the crude product as brown solid that was used directly in the next step without further purification. LC-MS (ESI): 404.8 (M+1)⁺.

Step 3

Step 3 to synthesize N,N-Diethyl-4-(8-methyl-4-((3-(piperidin-1-yl)propyl)amino)-1,6-naphthyridin-2-yl)benzamide was completed in a similar fashion as Example 72, Step 4. LC-MS (ESI): 459.8 (M+1)⁺. ¹H NMR (METHANOL-d₄) δ: 9.49 (s, 1H), 8.46 (s, 1H), 8.24 (d, J=8.4 Hz, 2H), 7.49 (d, J=8.4 Hz, 2H), 7.25 (s, 1H), 3.63 (t, J=6.8 Hz, 2H), 3.46-3.51 (m, 4H), 3.21-3.26 (m, 2H), 3.18-3.23 (m, 2H), 2.86 (t, J=12.0 Hz, 2H), 2.69 (s, 3H), 2.13-2.20 (m, 2H), 1.84-1.93 (m, 2H), 1.65-1.76 (m, 3H), 1.38-1.50 (m, 1H), 1.23 (t, J=6.8 Hz, 3H), 1.07 (t, J=6.8 Hz, 3H).

Example 76: Synthesis of 4-(8-Methyl-4-((3-(piperidin-1-yl)propyl)amino)-1,6-naphthyridin-2-yl)-N-(1-methylpiperidin-4-yl)benzamide

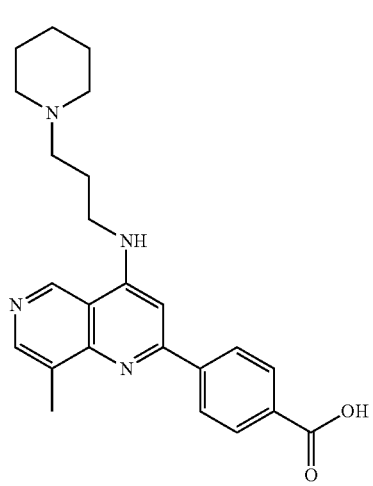

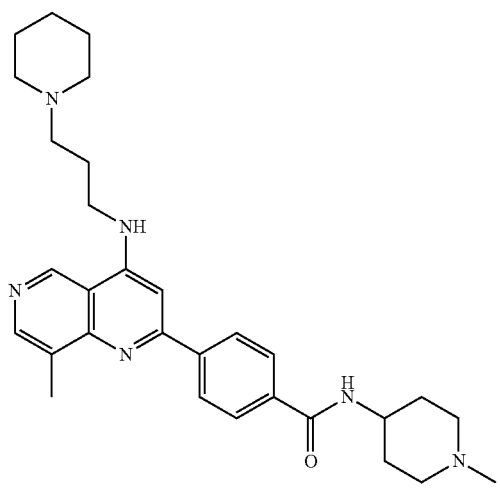

4-(8-Methyl-4-((3-(piperidin-1-yl)propyl)amino)-1,6-naphthyridin-2-yl)-N-(1-methylpiperidin-4-yl)benzamide was synthesized in a similar fashion as Example 72, Step 4. LC-MS (ESI): 501.4 (M+1)+. 1H NMR (METHANOL-d4) δ: 9.68 (s, 1H), 8.55 (s, 1H), 8.36 (d, J=8.0 Hz, 2H), 8.01 (d, J=8.0 Hz, 2H), 7.37 (s, 1H), 4.17-4.24 (m, 1H), 3.72 (t, J=6.0 Hz, 2H), 3.60 (t, J=14.6 Hz, 4H), 3.30-3.34 (m, 2H), 3.20 (t, J=12.0 Hz, 2H), 2.90-2.98 (m, 5H), 2.79 (s, 3H), 2.26-2.29 (m, 4H), 1.92-1.98 (m, 4H), 1.73-1.84 (m, 3H), 1.50-1.56 (m, 1H).

Example 77: Synthesis of 4-(8-Methyl-4-((3-(piperidin-1-yl)propyl)amino)-1,6-naphthyridin-2-yl)-N-(3-(piperidin-1-yl)propyl)benzamide

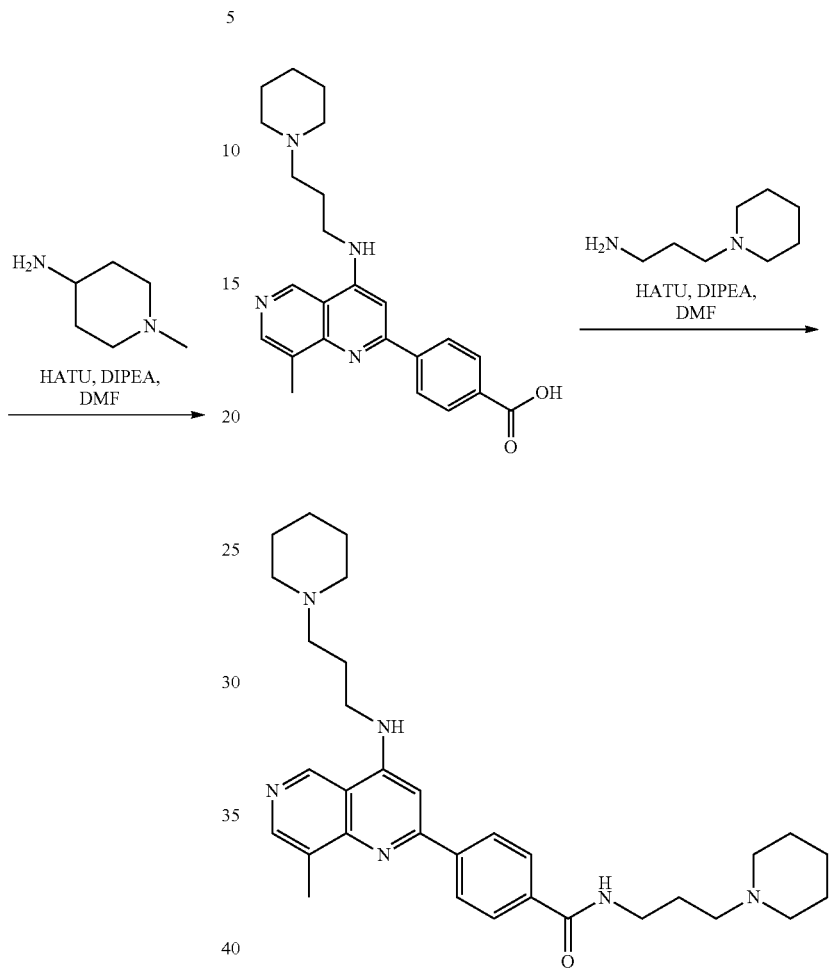

Synthesis of 4-(8-Methyl-4-((3-(piperidin-1-yl)propyl)amino)-1,6-naphthyridin-2-yl)-N-(3-(piperidin-1-yl)propyl)benzamide was synthesized in a similar fashion as Example 72, Step 4. LC-MS (ESI): 529.4 (M+1)+. 1H NMR (METHANOL-d4) δ: 9.58 (s, 1H), 8.44 (s, 1H), 8.29 (d, J=8.4 Hz, 2H), 7.95 (d, J=8.4 Hz, 2H), 7.29 (s, 1H), 3.63 (t, J=6.8 Hz, 2H), 3.42-3.49 (m, 6H), 3.23-3.26 (m, 2H), 3.09 (t, J=8.0 Hz, 2H), 2.85 (t, J=8.4 Hz, 4H), 2.70 (s, 3H), 2.16-2.21 (m, 2H), 1.96-2.01 (m, 2H), 1.83-1.90 (m, 4H), 1.68-1.75 (m, 6H), 1.37-1.45 (m, 2H).

Example 78: Synthesis of N-(3-(piperidin-1-yl)propyl)-5-(4-((3-(piperidin-1-yl)propyl)amino)-1,6-naphthyridin-2-yl)picolinamide

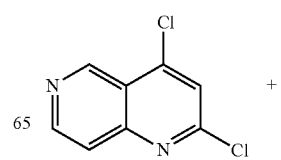

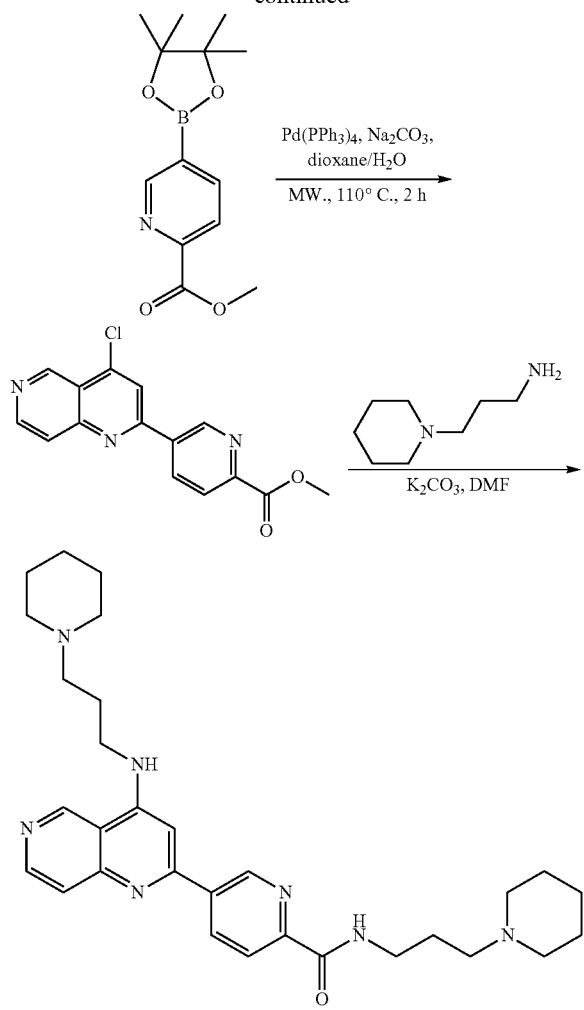

Step 1

A 20-mL microwave vial was charged with 2,4-dichloro-1,6-naphthyridine (633 mg, 3.2 mmol), methyl 5-(4,4,5,5-tetramethyl-1,3,2-dioxaborolan-2-yl)picolinate (1 g, 3.8 mmol), Pd(PPh₃)₄ (364 mg, 0.32 mmol), Na₂CO₃ (670 mg, 6.32 mmol), 1,4-dioxane (10 mL) and H₂O (1 mL). The vial is sealed, and the resulting brown solution was heated for 2 hrs in a Biotage Initiator Eight Microwave Reactor at a constant temperature of 110° C. The resulting solution was concentrated by rotary evaporation (55° C., 20 mmHg). The residue was purified by Prep-TLC (silica gel, eluting with 5% methanol in DCM) to give methyl 5-(4-chloro-1,6-naphthyridin-2-yl)picolinate (900 mg, 95%) as a yellow solid. HPLC/UV purity: 94%; LC-MS (ESI): 300.1 (M+1)⁺.

Step 2

The mixture of methyl 5-(4-chloro-1,6-naphthyridin-2-yl)picolinate (600 mg, 2 mmol), 3-(piperidin-1-yl)propan-1-amine (569 mg, 2.4 mmol) and K₂CO₃ (552 mg, 4 mmol) in DMF (3 mL) was heated at 80° C. for 18 hrs. The reaction mixture was poured into water (20 mL), extracted with EA (10 mL×3). The combined organic layers were washed by water and brine, dried over Na₂SO₄. The drying agent was filtered off and the filtrate was concentrated under the reduced pressure to give the crude product, which was purified by Prep-TLC (silica gel, eluting with 10% methanol and 1% NH₃·H₂O in DCM) to afford N-(3-(piperidin-1-yl)propyl)-5-(4-((3-(piperidin-1-yl)propyl)amino)-1,6-naphthyridin-2-yl)picolinamide (400 mg, 39%) as a yellow solid. HPLC/UV purity: 100%; LC-MS (ESI): 516.3 (M+1)⁺. ¹H NMR (METHANOL-d₄) δ: 9.49 (s, 1H), 9.30 (d, J=2.1 Hz, 1H), 8.55-8.65 (m, 2H), 8.24 (d, J=8.1 Hz, 1H), 7.80 (d, J=6.2 Hz, 1H), 7.11 (s, 1H), 3.50-3.58 (m, J=17.9, 6.8 Hz, 4H), 2.41-2.63 (m, 12H), 1.97-2.08 (m, 2H), 1.83-1.95 (m, 2H), 1.60-1.74 (m, 8H), 1.47-1.59 (m, 4H).

Example 79: Synthesis of N-(1-methylpiperidin-4-yl)-5-(4-((3-(piperidin-1-yl)propyl)amino)-1,6-naphthyridin-2-yl)picolinamide

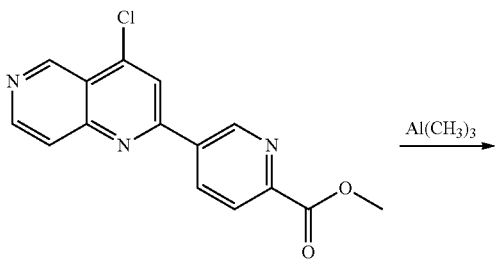

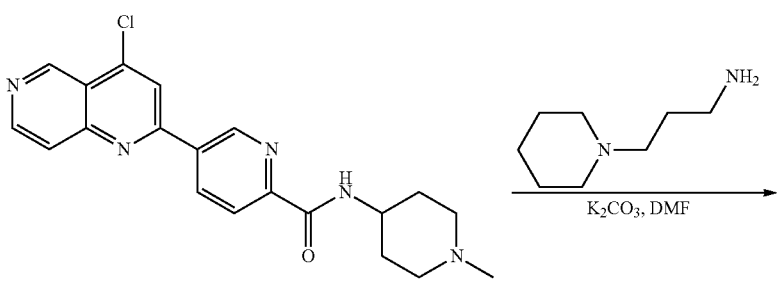

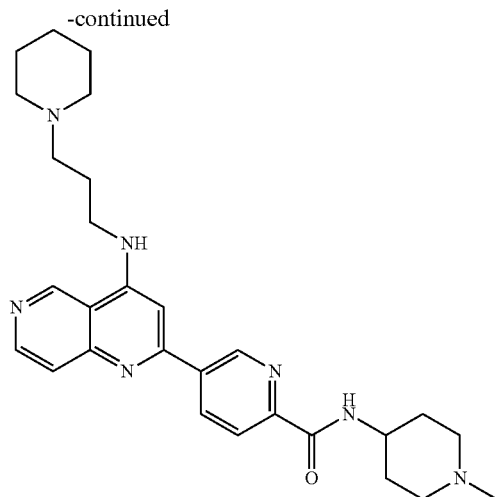

Step 1

To a solution of 1-methylpiperidin-4-amine (301 mg, 2.64 mmol) in DCM (10 mL) was added Al(CH$_3$)$_3$ (2.6 mL, 2.64 mmol) drop wise at 0° C. under nitrogen. The mixture was stirred at room temperature for 30 mins, and then was cooled to 0° C. again. A solution of methyl 5-(4-chloro-1,6-naphthyridin-2-yl)picolinate (158 mg, 0.53 mmol) in DCM (5 mL) was added drop wise, and the resulting reaction mixture was stirred at room temperature for 18 hrs. The reaction mixture was quenched by water (10 mL), then extracted with DCM (10 mL×3). The combined organic layers were washed with water and brine, dried over Na$_2$SO$_4$. The drying agent was filtered off and the filtrate was concentrated in vacuo to give the crude mixture, which was purified with Prep-TLC (silica gel, eluting with 10% methanol and 1% NH$_3$·H$_2$O in DCM) to afford 5-(4-chloro-1,6-naphthyridin-2-yl)-N-(1-methylpiperidin-4-yl)picolinamide (120 mg, 60%) as a white solid. HPLC/UV purity: 90%; LC-MS (ESI): 382.3 (M+1)$^+$.

Step 2

The mixture of 5-(4-chloro-1,6-naphthyridin-2-yl)-N-(1-methylpiperidin-4-yl)picolinamide (120 mg, 0.3 mmol), 3-(piperidin-1-yl)propan-1-amine (65 mg, 0.45 mmol) and K$_2$CO$_3$ (83 mg, 0.6 mmol) in DMF (2 mL) was heated at 70° C. for 18 hrs. The reaction mixture was poured into water (20 mL), extracted with EA (10 mL×3). The combined organic layers were washed by water and brine, dried over Na$_2$SO$_4$. The drying agent was filtered off and the filtrate was concentrated under the reduced pressure to give the crude product, which was purified by Prep-TLC (silica gel, eluting with 10% methanol and 1% NH$_3$·H$_2$O in DCM) to afford N-(1-methylpiperidin-4-yl)-5-(4-((3-(piperidin-1-yl)propyl)amino)-1,6-naphthyridin-2-yl)picolinamide (20 mg, 14%) as a yellow solid. HPLC/UV purity: 100%; LC-MS (ESI): 488.2 (M+1)$^+$. $^1$H NMR (METHANOL-d$_4$) δ: 9.48 (s, 1H), 9.29 (d, J=1.8 Hz, 1H), 8.53-8.64 (m, 2H), 8.22 (d, J=8.2 Hz, 1H), 7.79 (d, J=6.1 Hz, 1H), 7.10 (s, 1H), 3.91-3.96 (m, 1H), 3.56 (t, J=6.9 Hz, 2H), 2.95 (d, J=11.6 Hz, 2H), 2.47-2.68 (m, 6H), 2.35 (s, 3H), 2.28 (t, J=11.4 Hz, 2H), 1.95-2.11 (m, 4H), 1.77 (d, J=9.8 Hz, 2H), 1.64-1.67 (m, 4H), 1.49-1.52 (m, 2H).

Example 80: Synthesis of 1-methyl-5-(4-(4-(piperidin-1-ylmethyl)benzylamino)-1,6-naphthyridin-2-yl)-N-(piperidin-4-yl)-1H-indole-2-carboxamide

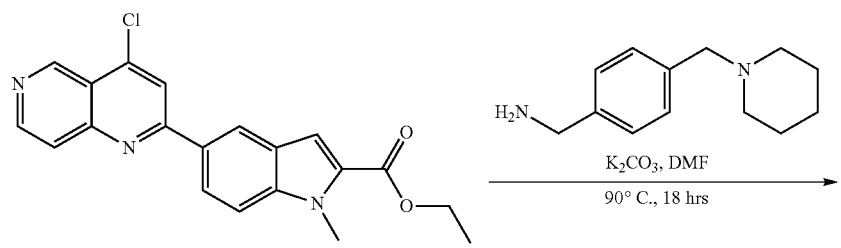

-continued
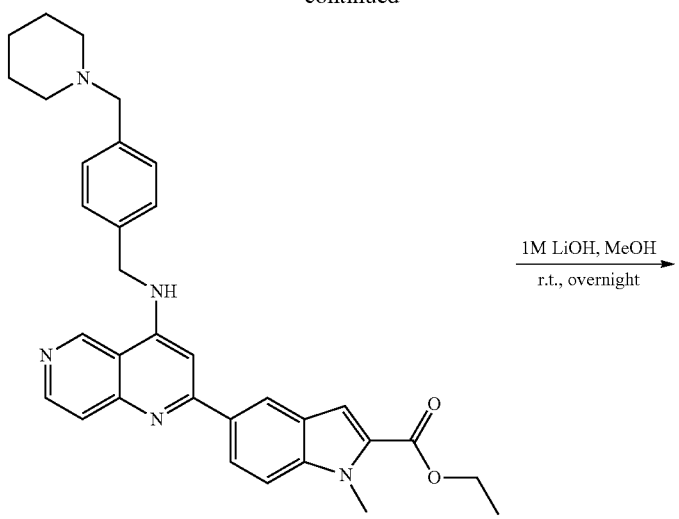
1M LiOH, MeOH
r.t., overnight
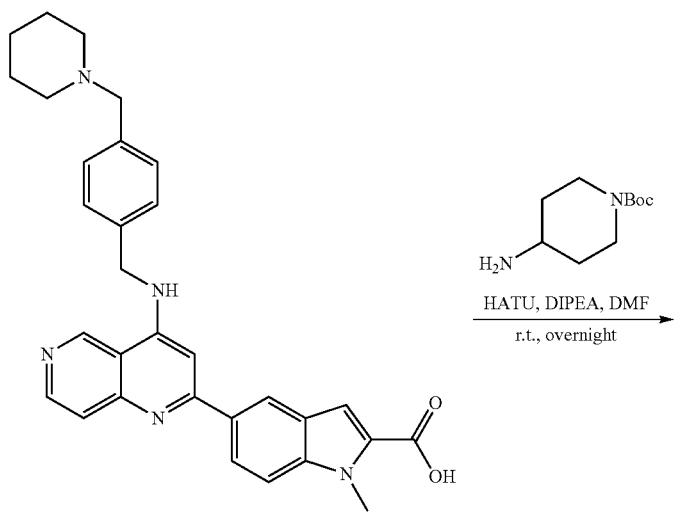
HATU, DIPEA, DMF
r.t., overnight
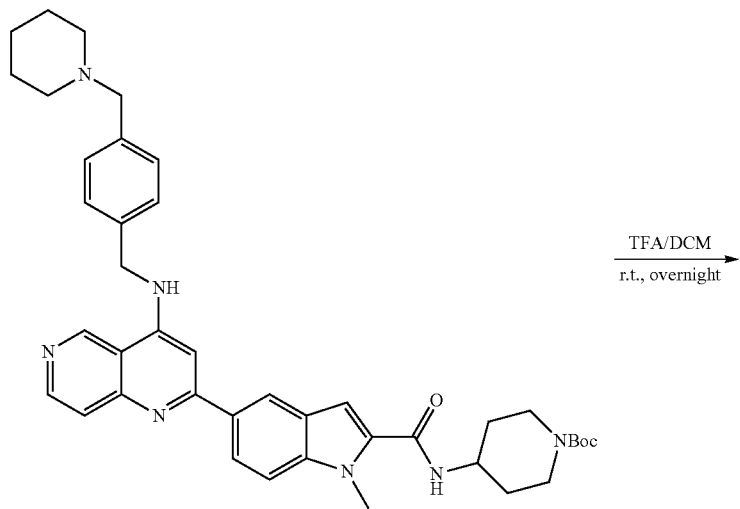
TFA/DCM
r.t., overnight

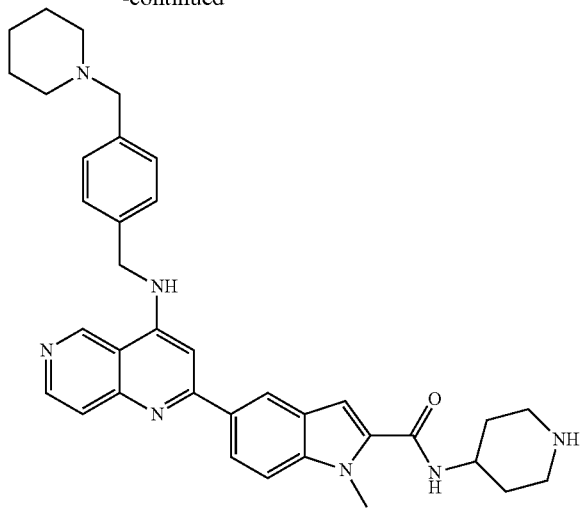

Step 1

The mixture of ethyl 5-(4-chloro-1,6-naphthyridin-2-yl)-1-methyl-1H-indole-2-carboxylate (400 mg, 1.09 mmol), (4-(piperidin-1-ylmethyl)phenyl)methanamine (447 mg, 2.19 mmol) and $K_2CO_3$ (302 mg, 2.19 mmol) in DMF (1 mL) was heated at 90° C. for 18 hrs. The reaction mixture was poured into water (20 mL), extracted with EA (10 mL×3). The combined organic layers were washed by water (10 mL×3) and brine (10 mL), dried over $Na_2SO_4$. The drying agent was filtered off and the filtrate was concentrated under the reduced pressure to give the residue which was purified by silica gel flash column chromatography to afford ethyl 1-methyl-5-(4-(4-(piperidin-1-ylmethyl)benzylamino)-1,6-naphthyridin-2-yl)-1H-indole-2-carboxylate (163 mg, 28%). LC-MS (ESI): 534.1 $(M+1)^+$.

Step 2

The mixture of ethyl 1-methyl-5-(4-(4-(piperidin-1-ylmethyl)benzylamino)-1,6-naphthyridin-2-yl)-1H-indole-2-carboxylate (163 mg, 0.30 mmol) and 1N aq. LiOH solution (1.2 mL, 1.22 mmol) in MeOH (5 mL) was stirred at room temperature overnight. The mixture was acidified with 1N aq. HCl solution (3 mL) to pH=2. The water phase was concentrated to give the crude product which was used directly in the next step without further purification. LC-MS (ESI): 506.3 $(M+1)^+$.

Step 3

The mixture of 1-methyl-5-(4-(4-(piperidin-1-ylmethyl)benzylamino)-1,6-naphthyridin-2-yl)-1H-indole-2-carboxylic acid (40 mg, 0.08 mmol), tert-butyl 4-aminopiperidine-1-carboxylate (32 mg, 0.16 mmol), HATU (45 mg, 0.12 mmol) and DIPEA (30 mg, 0.24 mmol) in DMF (1 mL) was stirred at room temperature overnight. Water (30 mL) was added, and then the mixture was extracted with EA (20 mL×3). The combined organic layers were washed with water (20 mL×3) and brine (20 mL×1), dried over $Na_2SO_4$, filtered and concentrated. The residue was purified by the Prep-TLC to obtain tert-butyl 4-(1-methyl-5-(4-(4-(piperidin-1-ylmethyl)benzylamino)-1,6-naphthyridin-2-yl)-1H-indole-2-carboxamido)piperidine-1-carboxylate (36 mg, 66%). LC-MS (ESI): 688.4 $(M+1)^+$.

Step 4

The mixture of tert-butyl 4-(1-methyl-5-(4-(4-(piperidin-1-ylmethyl)benzylamino)-1,6-naphthyridin-2-yl)-1H-indole-2-carboxamido)piperidine-1-carboxylate (36 mg, 0.05 mmol) and TFA (1 mL) in DCM (1 mL) was stirred at room temperature for 2 hrs. The reaction mixture was removed under the reduced pressure to give the residue which was purified with Prep-HPLC (Welch, XB-C18, 21.2 mm×250 mm, 10 um, eluting with 40% $CH_3CN$ in 1‰ TFA in $H_2O$) to afford 1-methyl-5-(4-(4-(piperidin-1-ylmethyl)benzylamino)-1,6-naphthyridin-2-yl)-N-(piperidin-4-yl)-1H-indole-2-carboxamide (30 mg, 90%) as a TFA salt. HPLC/UV purity: 100%; LC-MS (ESI): 588.2 $(M+1)^+$. $^1$H NMR (METHANOL-$d_4$) δ: 9.74 (s, 1H), 8.88 (d, J=6.1 Hz, 1H), 8.30 (s, 1H), 7.92 (d, J=6.1 Hz, 1H), 7.70-7.82 (m, 2H), 7.60-7.67 (d, J=7.9 Hz, 2H), 7.50-7.58 (d, J=8.2 Hz, 2H), 7.27 (s, 1H), 7.13 (s, 1H), 5.04 (s, 2H), 4.27 (s, 2H), 4.15-4.23 (m, 1H), 4.08 (s, 3H), 3.50 (d, J=13.4 Hz, 2H), 3.40 (d, J=12.8 Hz, 2H), 3.11-3.23 (m, 2H), 2.92 (t, J=11.4 Hz, 2H), 2.23 (d, J=11.6 Hz, 2H), 1.82-1.96 (m, 4H), 1.61-1.82 (m, 3H), 1.45-1.50 (m, 1H).

Example 81: Synthesis of 1-methyl-N-(1-methylpiperidin-4-yl)-5-(4-(4-(piperidin-1-ylmethyl)benzylamino)-1,6-naphthyridin-2-yl)-1H-indole-2-carboxamide

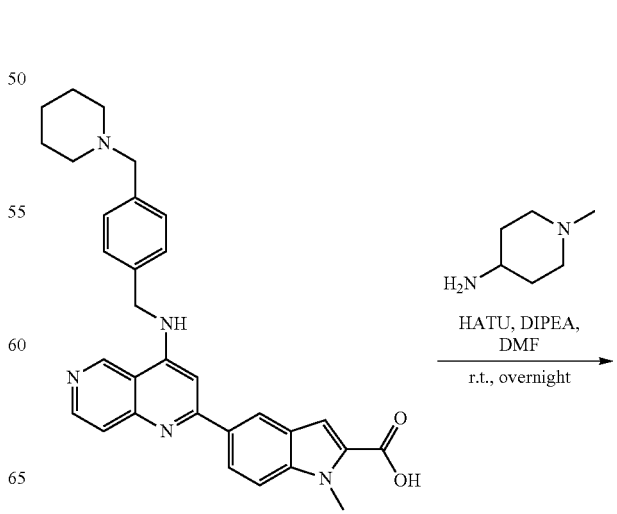

241
-continued

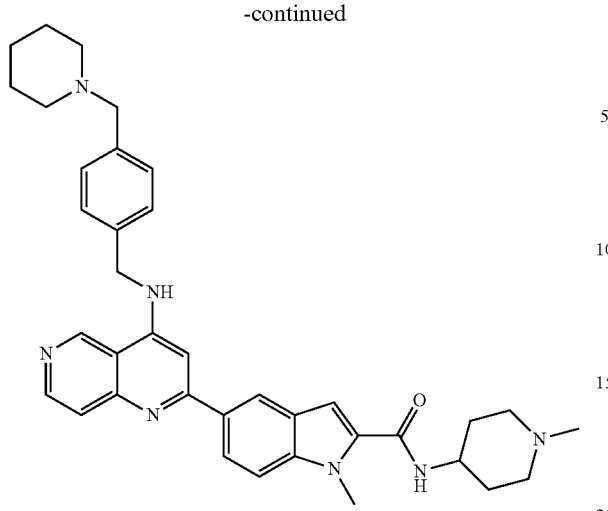

The mixture of 1-methyl-5-(4-(4-(piperidin-1-ylmethyl) benzylamino)-1,6-naphthyridin-2-yl)-1H-indole-2-carboxylic acid (56 mg, 0.11 mmol), 1-methylpiperidin-4-amine (25 mg, 0.22 mmol), HATU (62 mg, 0.16 mmol) and DIPEA (42 mg 0.33 mmol) in DMF (1 mL) was stirred at room temperature overnight. Water (30 mL) was added, and then the mixture was extracted with EA (20 mL×3). The combined organic layers were washed with water (20 mL×3) and brine (20 mL×1), dried over $Na_2SO_4$, filtered and concentrated. The residue was purified by Prep-HPLC (Welch, XB-C18, 21.2 mm×250 mm, 10 um, eluting with 40% $CH_3CN$ in 1‰ TFA in $H_2O$) to afford 1-methyl-5-(4-(4-(piperidin-1-ylmethyl)benzylamino)-1,6-naphthyridin-2-yl)-N-(piperidin-4-yl)-1H-indole-2-carboxamide (30 mg, 90%) as a TFA salt. HPLC/UV purity: 100%; LC-MS (ESI): 602.3 (M+1)+. 1H NMR (METHANOL-$d_4$) δ: 9.79 (s, 1H), 8.90 (d, J=4.8 Hz, 1H), 8.31 (s, 1H), 7.96 (d, J=5.7 Hz, 1H), 7.78-7.83 (d, 1H), 7.72-7.77 (d, 1H), 7.63-7.68 (d, J=8.0 Hz, 2H), 7.54-7.60 (d, J=7.8 Hz, 2H), 7.28 (s, 1H), 7.15 (s, 1H), 5.06 (s, 2H), 4.29 (s, 2H), 4.20-4.22 (m, 1H), 4.09 (s, 3H), 3.64 (d, J=12.4 Hz, 2H), 3.42 (d, J=12.1 Hz, 2H), 3.22 (t, J=12.5 Hz, 2H), 2.88-2.99 (m, 5H), 2.29 (d, J=13.5 Hz, 2H), 1.93-2.03 (m, 2H), 1.81-1.89 (m, 2H), 1.81 (d, J=13.0 Hz, 1H), 1.64-1.76 (m, 2H), 1.42-1.52 (m, 1H).

Example 82: Synthesis of (1-methyl-5-(4-(4-(piperidin-1-ylmethyl)benzylamino)-1,6-naphthyridin-2-yl)-1H-indol-2-yl)(4-methylpiperazin-1-yl)methanone

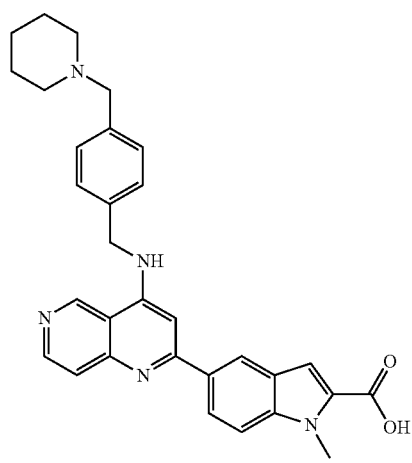

242
-continued

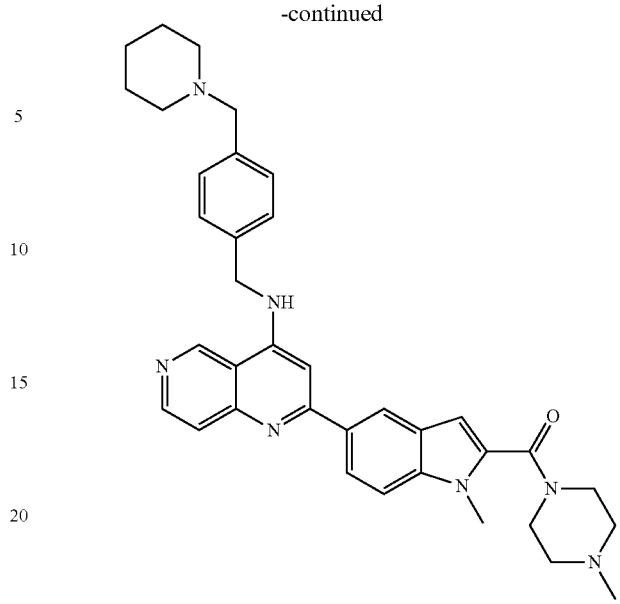

The mixture of 1-methyl-5-(4-(4-(piperidin-1-ylmethyl) benzylamino)-1,6-naphthyridin-2-yl)-1H-indole-2-carboxylic acid (56 mg, 0.11 mmol), 1-methylpiperazine (22 mg, 0.22 mmol), HATU (62 mg, 0.16 mmol) and DIPEA (42 mg 0.33 mmol) in DMF (1 mL) was stirred at room temperature overnight. Water (30 mL) was added, and then the mixture was extracted with EA (20 mL×3). The combined organic layers were washed with water (20 mL×3) and brine (20 mL×1), dried over $Na_2SO_4$, filtered and concentrated. The residue was purified with Prep-HPLC (Welch, XB-C18, 21.2 mm×250 mm, 10 um, eluting with 40% $CH_3CN$ in 1‰ TFA in $H_2O$) to afford (1-methyl-5-(4-(4-(piperidin-1-ylmethyl) benzylamino)-1,6-naphthyridin-2-yl)-1H-indol-2-yl)(4-methylpiperazin-1-yl)methanone (9 mg, 14%) as a TFA salt. HPLC/UV purity: 98%; LC-MS (ESI): 588.3 (M+1)+. 1H NMR (METHANOL-$d_4$) δ: 9.78 (s, 1H), 8.90 (d, J=5.7 Hz, 1H), 8.31 (s, 1H), 7.96 (d, J=6.0 Hz, 1H), 7.81 (d, J=8.9 Hz, 1H), 7.77 (d, J=8.7 Hz, 1H), 7.62-7.68 (d, J=7.8 Hz, 2H), 7.53-7.60 (d, J=7.8 Hz, 2H), 7.15 (s, 1H), 7.02 (s, 1H), 5.06 (s, 2H), 4.29 (s, 2H), 3.94 (s, 3H), 3.53-3.71 (m, 2H), 3.35-3.52 (m, 4H), 3.33-3.34 (m, 4H), 3.00 (s, 3H), 2.94 (t, J=11.7 Hz, 2H), 1.90 (d, J=14.4 Hz, 2H), 1.81 (d, J=12.8 Hz, 1H), 1.65-1.77 (m, 2H), 1.41-1.54 (m, 1H).

Example 83: Synthesis of 1-methyl-N-((1-methylpiperidin-4-yl)methyl)-5-(4-(4-(piperidin-1-ylmethyl) benzylamino)-1,6-naphthyridin-2-yl)-1H-indole-2-carboxamide

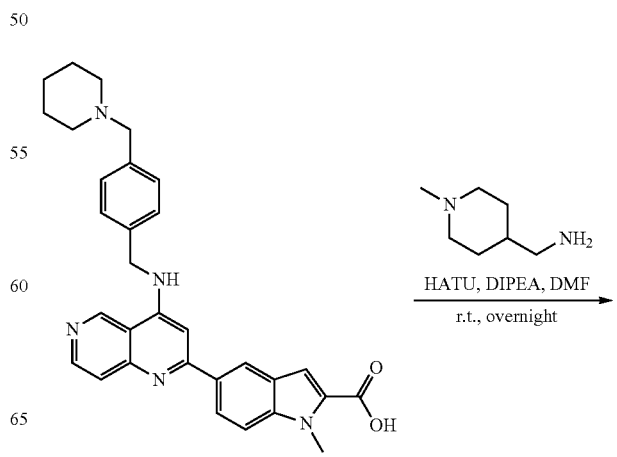

-continued

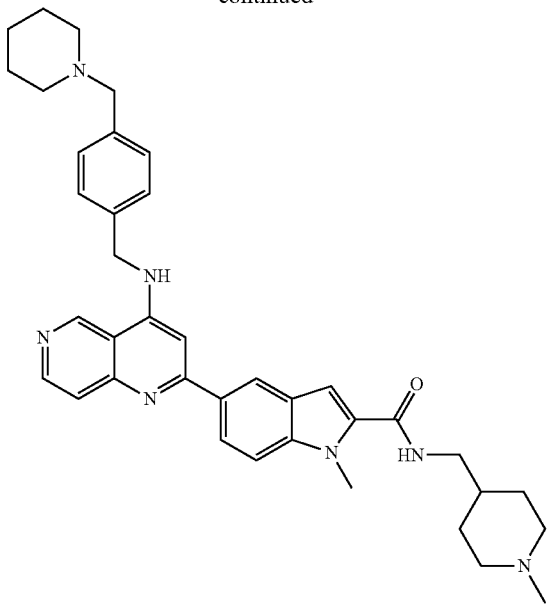

The mixture of 1-methyl-5-(4-(4-(piperidin-1-ylmethyl)benzylamino)-1,6-naphthyridin-2-yl)-1H-indole-2-carbox-ylic acid (30 mg, 0.06 mmol), (1-methylpiperidin-4-yl)methanamine (15 mg, 0.12 mmol), HATU (34 mg, 0.09 mmol) and DIPEA (23 mg 0.18 mmol) in DMF (1 mL) was stirred at room temperature overnight. Water (30 mL) was added, and then the mixture was extracted with EA (20 mL×3). The combined organic layers were washed with water (20 mL×3) and brine (20 mL×1), dried over $Na_2SO_4$, filtered and concentrated. The residue was purified with Prep-HPLC (Welch, XB-C18, 21.2 mm×250 mm, 10 um, eluting with 40% $CH_3CN$ in 1‰ TFA in $H_2O$) to afford 1-methyl-N-((1-methylpiperidin-4-yl)methyl)-5-(4-(4-(piperidin-1-ylmethyl)benzylamino)-1,6-naphthyridin-2-yl)-1H-indole-2-carboxamide (10 mg, 27%) as a yellow oil. HPLC/UV purity: 99%; LC-MS (ESI): 616.2 $(M+1)^+$. $^1H$ NMR (METHANOL-d4) δ: 9.78 (s, 1H), 8.90 (d, J=5.2 Hz, 1H), 8.32 (s, 1H), 7.95 (d, J=5.8 Hz, 1H), 7.72-7.84 (m, 2H), 7.66 (d, J=7.9 Hz, 2H), 7.52-7.61 (m, 2H), 7.26 (s, 1H), 7.16 (s, 1H), 5.06 (s, 2H), 4.29 (s, 2H), 4.10 (s, 3H), 3.58 (d, J=11.0 Hz, 2H), 3.36-3.46 (m, 4H), 2.88-3.08 (m, 7H), 2.10 (d, J=14.6 Hz, 2H), 1.90-1.99 (m, 3H), 1.81 (d, J=12.5 Hz, 1H), 1.70 (d, J=12.2 Hz, 2H), 1.42-1.65 (m, 3H).

Example 84: Synthesis of 1-methyl-5-(4-(methyl(3-(piperidin-1-yl)propyl)amino)-1,6-naphthyridin-2-yl)-N-(1-methylpiperidin-4-yl)-1H-indole-2-carboxamide

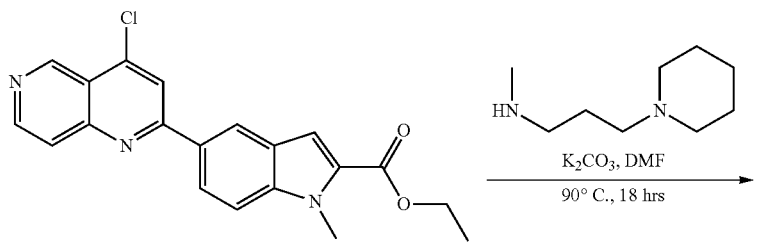

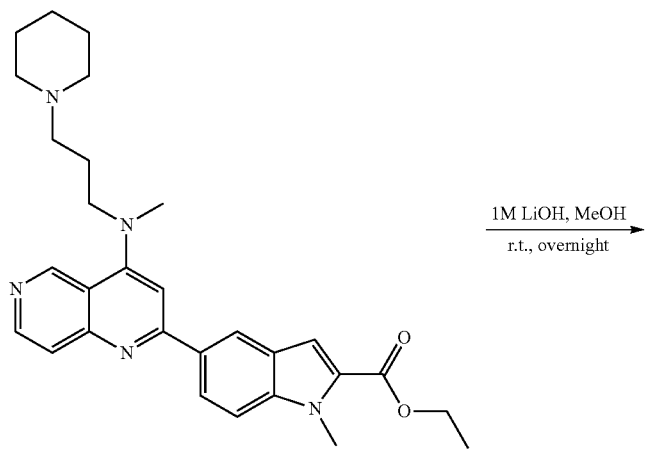

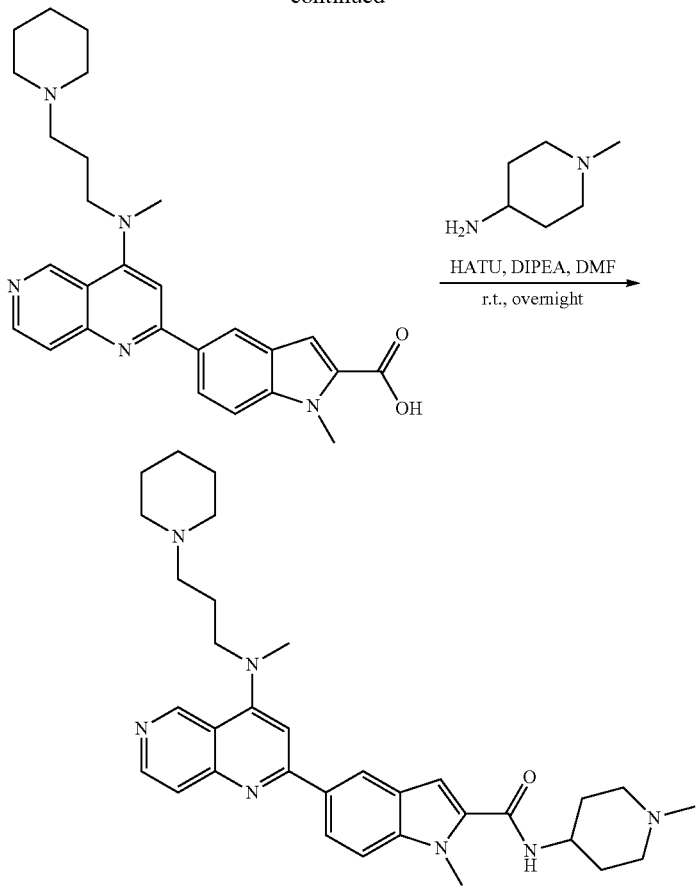

Step 1

The mixture of ethyl 5-(4-chloro-1,6-naphthyridin-2-yl)-1-methyl-1H-indole-2-carboxylate (150 mg, 0.41 mmol), N-methyl-3-(piperidin-1-yl)propan-1-amine (128 mg, 0.82 mmol) and $K_2CO_3$ (113 mg, 0.82 mmol) in DMF (1 mL) was heated at 90° C. for 18 hrs. The reaction mixture was poured into water (20 mL), extracted with EA (10 mL×3). The combined organic layers were washed by water (10 mL×3) and brine (10 mL), dried over $Na_2SO_4$. The drying agent was filtered off and the filtrate was concentrated under the reduced pressure to give the residue which was purified by silica gel flash column chromatography to afford ethyl 1-methyl-5-(4-(methyl(3-(piperidin-1-yl)propyl)amino)-1,6-naphthyridin-2-yl)-1H-indole-2-carboxylate (102 mg, 51%). LC-MS (ESI): 486.3 $(M+1)^+$.

Step 2

The mixture of ethyl 1-methyl-5-(4-(methyl(3-(piperidin-1-yl)propyl)amino)-1,6-naphthyridin-2-yl)-1H-indole-2-carboxylate (102 mg, 0.21 mmol) and 1N aq. LiOH solution (0.84 ml, 0.84 mmol) in MeOH (5 mL) was stirred at room temperature overnight. The mixture was acidified with 1N aq. HCl solution (10 mL) to pH=2. The water phase was concentrated to give the crude product that was used directly in the next step without further purification. LC-MS (ESI): 458.3 $(M+1)^+$.

Step 3

The mixture of 1-methyl-5-(4-(methyl(3-(piperidin-1-yl)propyl)amino)-1,6-naphthyridin-2-yl)-1H-indole-2-carboxylic acid (48 mg, 0.11 mmol), (1-methylpiperidin-4-yl)methanamine (24 mg, 0.21 mmol), HATU (60 mg, 0.16 mmol) and DIPEA (40 mg 0.32 mmol) in DMF (1 mL) was stirred at room temperature overnight. Water (30 mL) was added, and then the mixture was extracted with EA (20 mL×3). The combined organic layers were washed with water (20 mL×3) and brine (20 mL×1), dried over $Na_2SO_4$, filtered and concentrated. The residue was purified with Prep-HPLC (Welch, XB-C18, 21.2 mm×250 mm, 10 um, eluting with 40% $CH_3CN$ in 1‰ TFA in $H_2O$) to afford 1-methyl-5-(4-(methyl(3-(piperidin-1-yl)propyl)amino)-1,6-naphthyridin-2-yl)-N-(1-methylpiperidin-4-yl)-1H-indole-2-carboxamide (6 mg, 10%) as a yellow oil. HPLC/UV purity: 100%; LC-MS (ESI): 554.3 $(M+1)^+$. $^1H$ NMR (METHANOL-$d_4$) δ: 9.63 (s, 1H), 8.83 (d, J=5.9 Hz, 1H), 8.42 (d, J=1.6 Hz, 1H), 7.92-8.01 (m, 2H), 7.80 (d, J=8.9 Hz, 1H), 7.39 (s, 1H), 7.30 (s, 1H), 4.16-4.27 (m, 1H), 4.09 (s, 3H), 4.05 (t, J=7.5 Hz, 2H), 3.72 (s, 3H), 3.57-3.67 (m, 4H), 3.14-3.30 (m, 4H), 2.88-3.03 (m, 5H), 2.36-2.46 (m, 2H), 2.31 (d, J=13.2 Hz, 2H), 1.73-2.03 (m, 7H), 1.44-1.54 (m, 1H).

247
Example 85: Synthesis of 1-Methyl-N-(1-methylpiperidin-4-yl)-5-(4-(4-(piperidin-1-yl)butan-2-ylamino)-1,6-naphthyridin-2-yl)-1H-indole-2-carboxamide
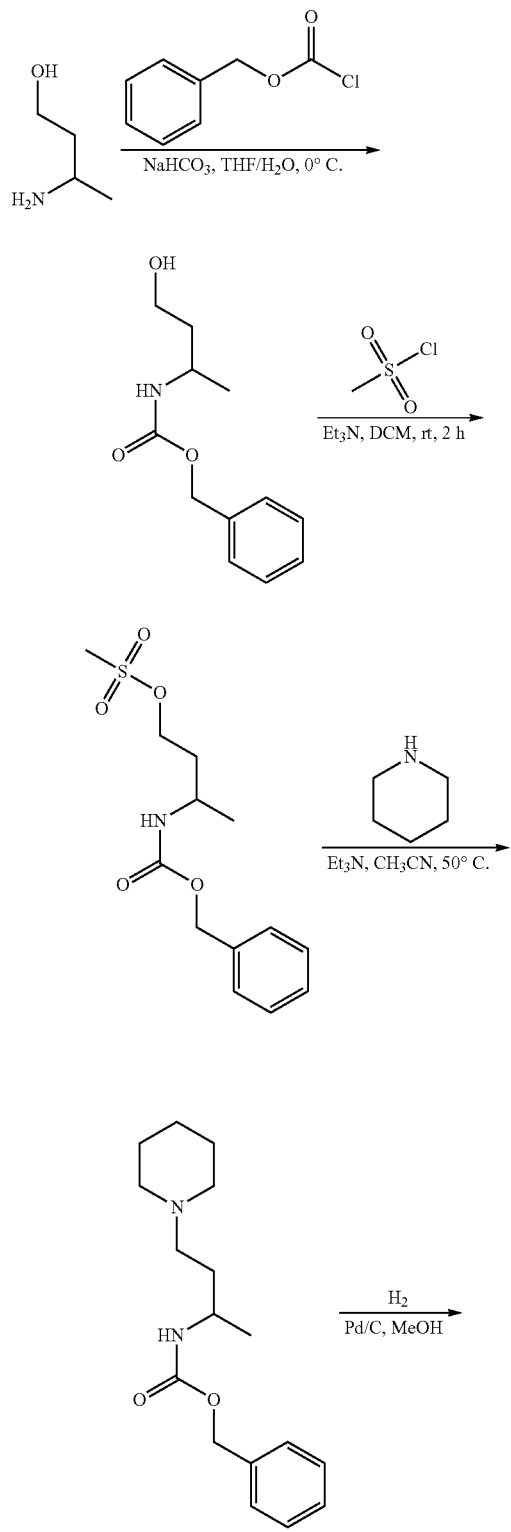
248
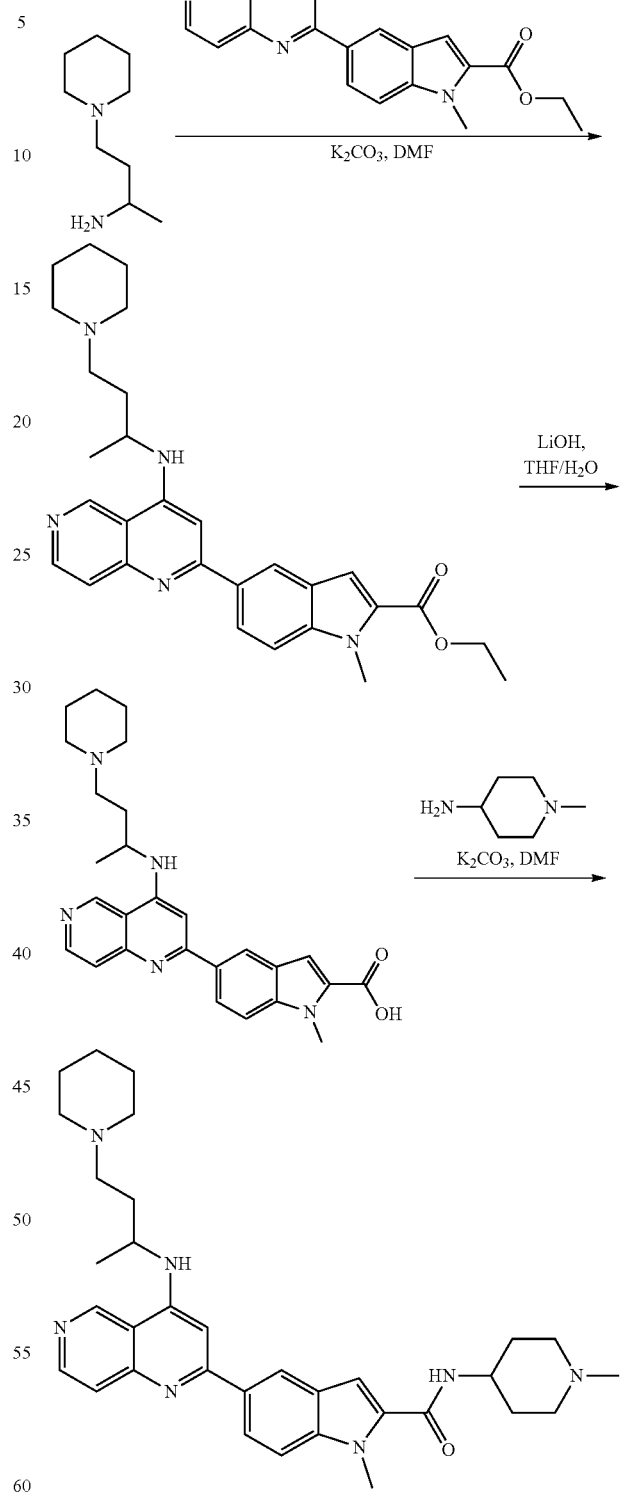
Step 1
To a solution of 3-aminobutan-1-ol (2 g, 22.4 mmol) and NaHCO$_3$ (2.8 g 33.3 mmol) in THF (30 mL) and H$_2$O (5 mL) was added benzyl carbonochloridate (4.6 g 27.0 mmol)

at 0° C. After stirred at room temperature overnight, the mixture was extracted with EA (30 mL). The organic layer was washed with brine, dried over anhydrous Na₂SO₄, concentrated and purified by flash chromatography to give crude benzyl 4-hydroxybutan-2-ylcarbamate as yellow oil (3 g, 60%) LC-MS (ESI): 223.7 (M+1)⁺.

Step 2

To a stirred and cooled (0° C.) solution of benzyl 4-hydroxybutan-2-ylcarbamate (3 g, 13.5 mmol) and Et₃N (2 g, 19.8 mmol) in dry DCM (20 mL) was added the solution of MsCl (1.7 g, 14.9 mmol) in dry DCM (10 mL) within 10 min. After addition, the mixture was stirring for 1 hr at 0° C. and 2 hrs at room temperature. The reaction mixture was poured into 1N aq. NaHCO₃ solution (50 mL) and extracted with EA (10 mL×3). The organic phase layer was separated, washed with brine, dried over Na₂SO₄, and concentrated to give 3-(benzyloxycarbonylamino)butyl methanesulfonate (4 g, crude) as yellow oil. LC-MS (ESI): 301.8 (M+1)⁺.

Step 3

A solution of 3-(benzyloxycarbonylamino)butyl methanesulfonate (4 g, crude), piperidine (1.3 g, 15.2 mmol) and Et₃N (1.6 g, 15.8 mmol) in CH₃CN was stirred at 50° C. for 3 hrs. The solvent was evaporated under reduce pressure. The residue was diluted with EA, washed with water, dried over anhydrous Na₂SO₄, concentrated and purified by flash column chromatography to give benzyl 4-(piperidin-1-yl)butan-2-ylcarbamate (2.5 g, 65%) as yellow solid. LC-MS (ESI): 290.7 (M+1)⁺; ¹H NMR (METHANOL-d4) δ: 10.92 (s, 1H), 7.41-7.28 (m, 5H), 5.53 (s, 2H), 5.10-5.12 (m, 3H), 3.80-3.65 (m, 1H), 3.56 (t, J=12.1 Hz, 2H), 3.03 (d, J=34.4 Hz, 2H), 2.59 (d, J=8.8 Hz, 2H), 2.05-1.79 (m, 7H), 1.39 (d, J=12.3 Hz, 1H), 1.21 (d, J=6.6 Hz, 3H).

Step 4

To a solution of benzyl 4-(piperidin-1-yl)butan-2-ylcarbamate (1 g, 3.4 mmol) in MeOH (20 mL) was added Pd/C (0.2 g). Then the mixture was stirred at room temperature under H₂ overnight. The reaction mixture was filtered. The pH was adjusted by NaOH solid to pH=13, concentrated and purified by Prep-HPLC to give 4-(piperidin-1-yl)butan-2-amine (410 mg, 76.3%) as yellow oil. LC-MS (ESI): 158.2 (M+1)⁺.

Step 5 and Step 6

Steps 5 and 6 were completed in a similar fashion as Example 84, Steps 1 and 2.

Step 7

The mixture of 1-methyl-5-(4-(4-(piperidin-1-yl)butan-2-ylamino)-1,6-naphthyridin-2-yl)-1H-indole-2-carboxylic acid (30 mg, 0.06 mmol), 1-methylpiperidin-4-amine (26 mg, 0.23 mmol), HATU (59 mg, 0.15 mmol) and DIPEA (40 mg, 0.3 mmol) in DMF (2 mL) was stirred at 50° C. for 5 hrs. The reaction mixture was poured into water (20 mL), extracted with EA (10 mL×3). The combined organic layers were washed with water and brine, dried over Na₂SO₄, concentrated and purified by Prep-TLC (silica gel, eluting with 10% methanol and 1% NH₃·H₂O in DCM) to afford 1-methyl-N-(1-methylpiperidin-4-yl)-5-(4-(4-(piperidin-1-yl)butan-2-ylamino)-1,6-naphthyridin-2-yl)-1H-indole-2-carboxamide (4.7 mg, 12.9%) as yellow solid. HPLC/UV purity: 99%; LC-MS (ESI): 554.3 (M+1)⁺. ¹H NMR (METHANOL-d4) δ: 9.88 (s, 1H), 8.87 (d, J=5.8 Hz, 1H), 8.52 (s, 1H), 8.01 (d, J=8.9, 1.8 Hz, 1H), 7.95 (d, J=6.0 Hz, 1H), 7.80 (d, J=8.9 Hz, 1H), 7.36 (d, J=6.6 Hz, 2H), 4.61-4.52 (m, 1H), 4.24-4.19 (m, 1H), 4.12 (s, 3H), 3.65-3.57 (m, 4H), 3.51-3.45 (m, 2H), 3.23 (t, J=12.6 Hz, 2H), 3.04-2.93 (m, 6H), 2.49-2.39 (m, 1H), 2.32-2.26 (m, 3H), 2.10-1.79 (m, 7H), 1.55 (d, J=6.4 Hz, 3H).

Example 86: Synthesis of 1-Methyl-N-(1-methylpiperidin-4-yl)-5-(4-((1-methylpiperidin-4-yl)amino)-1,6-naphthyridin-2-yl)-1H-indole-2-carboxamide

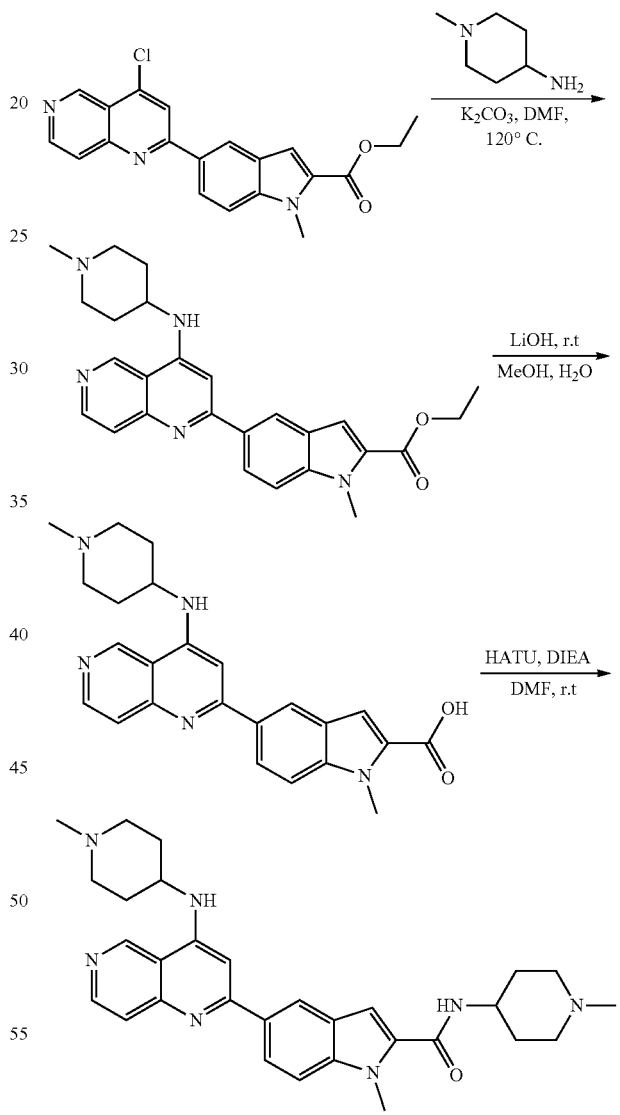

Step 1

To a solution of ethyl 5-(4-chloro-1,6-naphthyridin-2-yl)-1-methyl-1H-indole-2-carboxylate (500 mg, 1.37 mmol) in DMF (10 mL) were added 1-methylpiperidin-4-amine (313 mg, 2.74 mmol) and K₂CO₃ (379 mg, 2.74 mmol). The reaction mixture was stirred at 120° C. overnight, then quenched with water (5 mL), and extracted with DCM (10 mL×3). The organic layer was washed with water (20 mL×3) and brine (20 mL), dried over Na$_2$SO$_4$, concentrated and purified by flash column chromatography (silica gel, eluting with DCM to 10% MeOH/DCM) to afford ethyl 1-methyl-5-(4-((1-methylpiperidin-4-yl)amino)-1,6-naphthyridin-2-yl)-1H-indole-2-carboxylate (250 mg, 40%) as yellow solid. HPLC/UV purity: 99%; LC-MS (ESI): 443.9 (M+1)$^+$. $^1$H NMR (METHANOL-d4) δ: 9.78 (s, 1H), 8.87 (d, J=6.0 Hz, 1H), 8.45 (d, J=1.6 Hz, 1H), 7.99 (d, J=8.8, 1.6 Hz, 1H), 7.92 (d, J=6.4 Hz, 1H), 7.83 (d, J=8.8 Hz, 1H), 7.50 (s, 1H), 7.38 (s, 1H), 4.48-4.40 (m, 3H), 4.18 (s, 3H), 3.72 (d, J=12.0 Hz, 2H), 3.27 (d, J=12.0 Hz, 2H), 2.96 (s, 3H), 2.45 (d, J=15.2 Hz, 2H), 2.18 (d, J=14.0 Hz, 2H), 1.45 (t, J=7.2 Hz, 3H).

Step 2

To a solution of 1-methyl-5-(4-((1-methylpiperidin-4-yl)amino)-1,6-naphthyridin-2-yl)-1H-indole-2-carboxylate (250 mg, 0.56 mmol) in MeOH (5 ml) was added 1N aq. LiOH solution (2.24 mL). The reaction mixture was stirred at room temperature for 8 h. The reaction mixture was concentrated acidified with 1N aq. HCl solution to PH=4, and lyophilized to afford 1-methyl-5-(4-((1-methylpiperidin-4-yl)amino)-1,6-naphthyridin-2-yl)-1H-indole-2-carboxylic acid as brown solid. The crude product was used in the next step without further purification. LC-MS (ESI): 415.8 (M+1)$^+$.

Step 3

The mixture of 1-methyl-5-(4-((1-methylpiperidin-4-yl)amino)-1,6-naphthyridin-2-yl)-1H-indole-2-carboxylic acid (20 mg, 0.048 mmol), 1-methylpiperidin-4-amine (11 mg, 0.096 mmol), HATU (27 mg, 0.072 mmol) and DIPEA (13 mg, 0.096 mmol) in DMF (5 mL) was stirred at room temperature overnight. The reaction mixture was quenched with water (5 mL), extracted with DCM (5 mL×3), washed with water (10 mL×3) and brine (10 mL), dried over Na$_2$SO$_4$, concentrated and purified by prep-PLC to afford 1-methyl-N-(1-methylpiperidin-4-yl)-5-(4-((1-methylpiperidin-4-yl)amino)-1,6-naphthyridin-2-yl)-1H-indole-2-carboxamide as yellow solid (15 mg, 60%). LC-MS (ESI): 512.3 (M+1)$^+$. $^1$H NMR (METHANOL-d4) δ: 9.79 (s, 1H), 8.87 (d, J=6.4 Hz, 1H), 8.42 (s, 1H), 7.96 (d, J=22.0, 9.2 Hz, 2H), 7.80 (d, J=9.2 Hz, 1H), 7.39 (s, 1H), 7.29 (s, 1H), 4.53-4.47 (m, 1H), 4.22-4.15 (m, 1H), 4.11 (s, 3H), 3.71 (d, J=11.6 Hz, 2H), 3.63 (d, J=12.4 Hz, 2H), 3.26-3.13 (m, 4H), 2.94 (d, J=15.6 Hz, 6H), 2.45 (d, J=13.6 Hz, 2H), 2.30 (d, J=13.6 Hz, 2H), 2.25-2.12 (m, 2H), 2.03-1.90 (m, 2H).

Example 87: Synthesis of (1-Methyl-5-(4-((1-methylpiperidin-4-yl)amino)-1,6-naphthyridin-2-yl)-1H-indol-2-yl)(4-methylpiperazin-1-yl)methanone

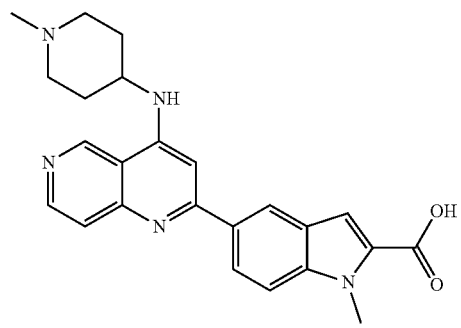

+

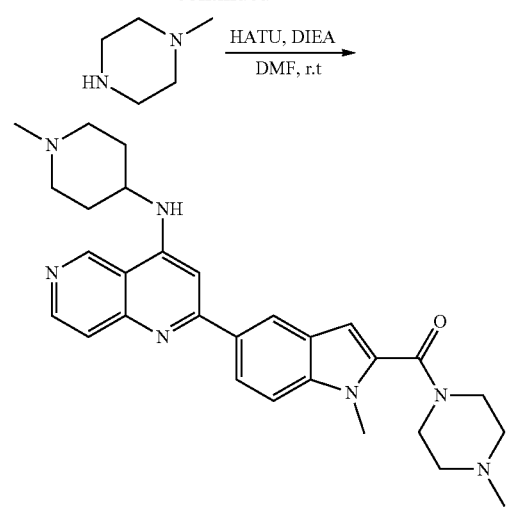

The mixture of 1-methyl-5-(4-((1-methylpiperidin-4-yl)amino)-1,6-naphthyridin-2-yl)-1H-indole-2-carboxylic acid (65 mg, 0.16 mmol), 1-methylpiperazine (32 mg, 0.32 mmol), HATU (93 mg, 0.24 mmol) and DIPEA (42 mg, 0.32 mmol) in DMF (5 mL) was stirred at room temperature overnight. The reaction mixture was quenched with water (5 mL), extracted with DCM (5 mL×3), washed with water (10 mL×3) and brine (10 mL), dried over Na$_2$SO$_4$, concentrated and purified by prep-TLC to afford (1-methyl-5-(4-((1-methylpiperidin-4-yl)amino)-1,6-naphthyridin-2-yl)-1H-indol-2-yl)(4-methylpiperazin-1-yl)methanone as yellow solid (30 mg, 38%). LC-MS (ESI): 498.3 (M+1)$^+$. $^1$H NMR (METHANOL-d4) δ: 9.79 (s, 1H), 8.86 (d, J=6.0 Hz, 1H), 8.43 (d, J=1.6 Hz, 1H), 7.98-7.92 (m, 2H), 7.79 (d, J=8.8 Hz, 1H), 7.40 (s, 1H), 7.03 (s, 1H), 4.51-1.53 (m, 1H), 3.95 (s, 3H), 3.71 (d, J=12.8 Hz, 2H), 3.67-3.27 (m, 10H), 2.99 (s, 3H), 2.95 (s, 3H), 2.44 (d, J=13.2 Hz, 2H), 2.20 (t, J=11.2 Hz, 2H).

Example 88: Synthesis of 1-Methyl-5-(4-((1-methylpiperidin-4-yl)amino)-1,6-naphthyridin-2-yl)-N-((1-methylpiperidin-4-yl)methyl)-1H-indole-2-carboxamide

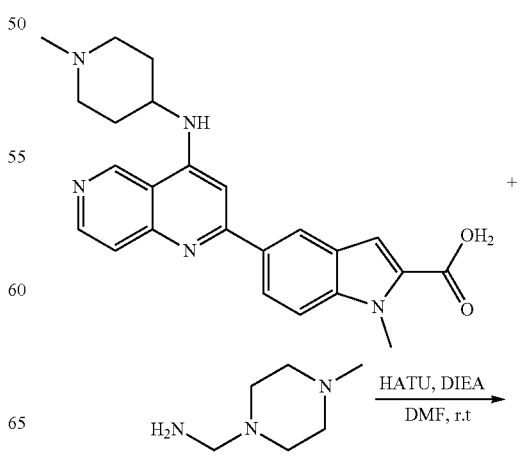

253

-continued

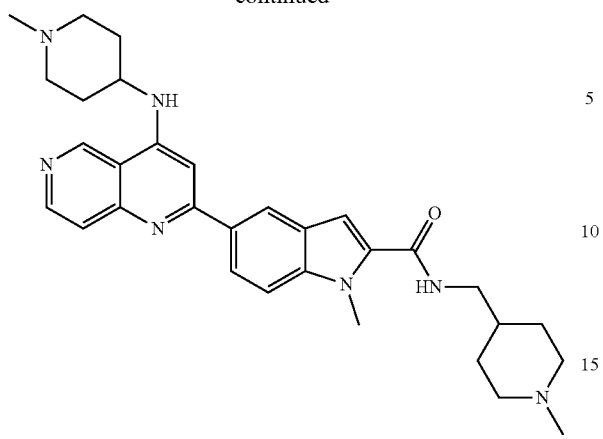

254

-continued

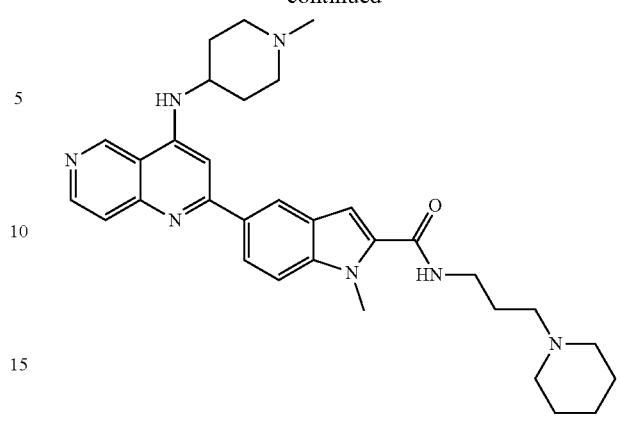

The mixture of 1-methyl-5-(4-((1-methylpiperidin-4-yl)amino)-1,6-naphthyridin-2-yl)-1H-indole-2-carboxylic acid (65 mg, 0.16 mmol), (4-methylpiperazin-1-yl)methanamine (41 mg, 0.32 mmol), HATU (91 mg, 0.24 mmol) and DIPEA (42 mg, 0.32 mmol) in DMF (5 mL) was stirred at room temperature overnight. The reaction mixture was quenched with water (5 mL), extracted with DCM (5 mL×3), washed with water (10 mL×3) and brine (10 mL), dried over $Na_2SO_4$, concentrated and purified by prep-TLC to afford 1-methyl-5-(4-((1-methylpiperidin-4-yl)amino)-1,6-naphthyridin-2-yl)-N-((1-methylpiperidin-4-yl)methyl)-1H-indole-2-carboxamide (30 mg, 37%) as yellow solid. LC-MS (ESI): 526.3 (M+1)$^+$. $^1$H NMR (METHANOL-d4) δ: 9.79 (s, 1H), 8.87 (d, J=6.0 Hz, 1H), 8.42 (s, 1H), 7.96 (d, J=9.0 Hz, 1.8 Hz, 1H), 7.92 (d, J=6.0 Hz, 1H), 7.79 (d, J=8.4 Hz, 1H), 7.39 (s, 1H), 7.27 (s, 1H), 4.49-4.52 (m, 1H), 4.10 (s, 3H), 3.71 (d, J=12.6 Hz, 2H), 3.57 (d, J=13.2 Hz, 2H), 3.37 (d, J=6.6 Hz, 2H), 3.33-3.29 (m, 2H), 3.02 (t, J=12.6 Hz, 2H), 2.95 (s, 3H), 2.88 (s, 3H), 2.44 (d, J=13.2 Hz, 2H), 2.18 (q, J=13.2 Hz, 2H), 2.09 (d, J=14.4 Hz, 2H), 1.99-1.97 (m, 1H), 1.60-1.53 (m, 2H).

The mixture of 1-methyl-5-(4-((1-methylpiperidin-4-yl)amino)-1,6-naphthyridin-2-yl)-1H-indole-2-carboxylic acid (50 mg, 0.12 mmol), 3-(piperidin-1-yl)propan-1-amine (34 mg, 0.24 mmol), HATU (68 mg, 0.18 mmol) and DIPEA (31 mg, 0.24 mmol) in DMF (5 mL) was stirred at room temperature overnight. The reaction mixture was quenched with water (5 mL), extracted with DCM (5 mL×3), washed with water (10 mL×3) and brine (10 mL), dried over $Na_2SO_4$, concentrated and purified by prep-PLC to afford 1-methyl-5-(4-((1-methylpiperidin-4-yl)amino)-1,6-naphthyridin-2-yl)-N-(3-(piperidin-1-yl)propyl)-1H-indole-2-carboxamide (20 mg, 31%) as yellow solid. LC-MS (ESI): 540.3 (M+1)$^+$. $^1$H NMR (METHANOL-d4) δ: 9.77 (s, 1H), 8.86 (d, J=6.0 Hz, 1H), 8.46 (d, J=1.6 Hz, 1H), 7.98-7.86 (m, 2H), 7.78 (d, J=8.8 Hz, 1H), 7.33 (d, J=14.8 Hz, 2H), 4.53-4.47 (m, 1H), 4.11 (s, 3H), 3.70 (d, J=13.2 Hz, 2H), 3.59 (d, J=12.4 Hz, 2H), 3.53 (t, J=6.4 Hz, 2H), 3.38-3.32 (m, 2H), 3.22 (t, J=7.6 Hz, 2H), 3.01-2.95 (m, 5H), 2.45 (d, J=14.0 Hz, 2H), 2.16-2.08 (m, 4H), 1.99 (d, J=14.0 Hz, 2H), 1.88-1.75 (m, 3H), 1.59-1.51 (m, 1H).

Example 89: Synthesis of 1-Methyl-5-(4-((1-methylpiperidin-4-yl)amino)-1,6-naphthyridin-2-yl)-N-(3-(piperidin-1-yl)propyl)-1H-indole-2-carboxamide Example 90: Synthesis of N-(1-Methylpiperidin-4-yl)-6-(4-(3-(piperidin-1-yl)propylamino)-1,6-naphthyridin-2-yl)-1H-indole-2-carboxamide

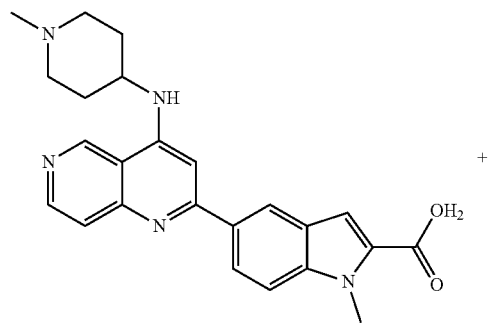

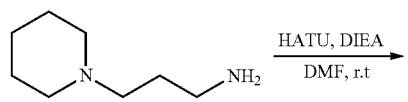

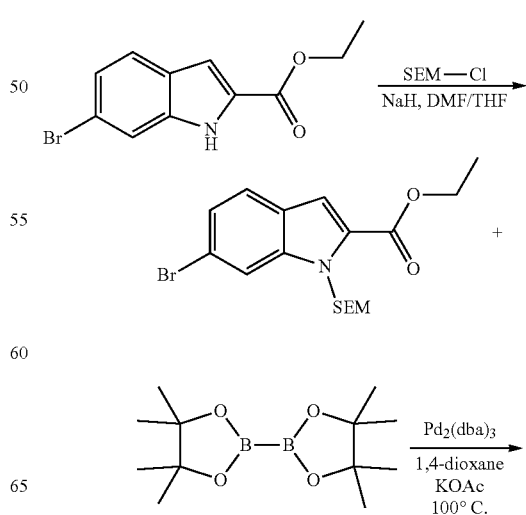

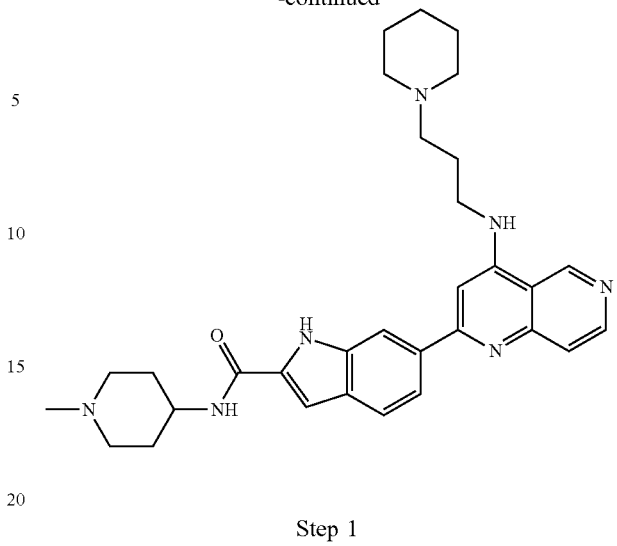

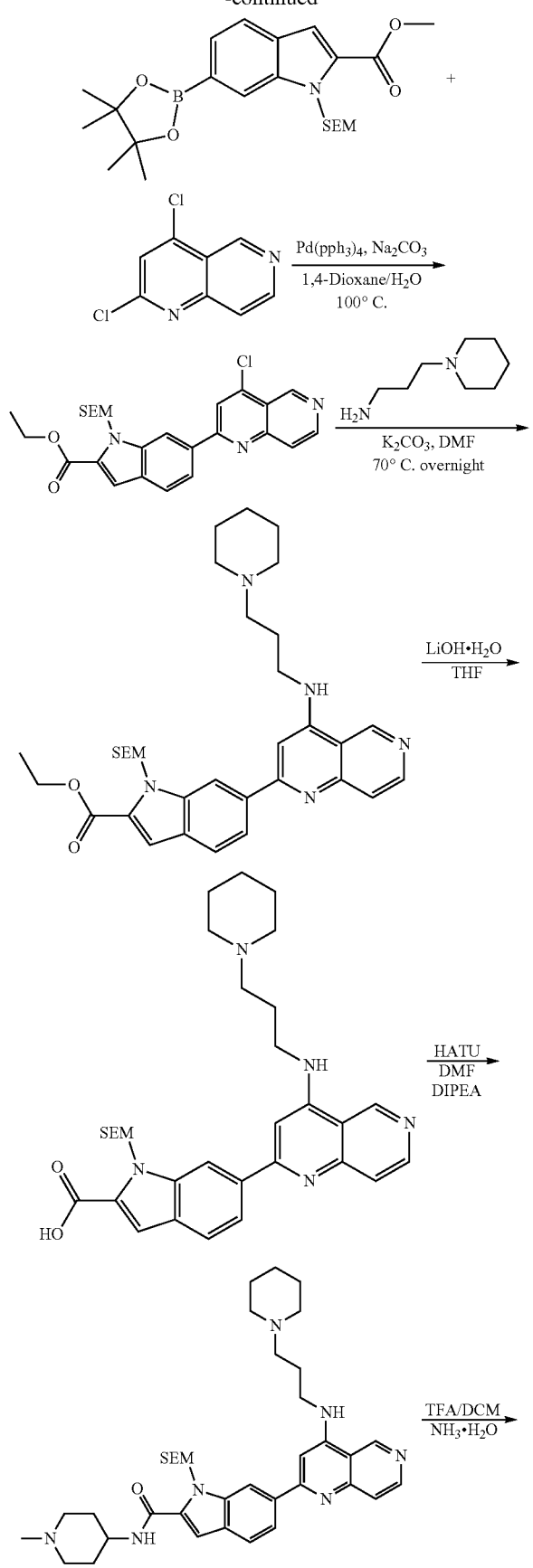

Step 1

NaH (240 mg, 6 mmol) was added to a solution of ethyl 6-bromo-1H-indole-2-carboxylate (1.34 g, 5 mmol) in DMF/THF (20 mL/40 mL). After SEMCl (913 mg, 5.5 mmol) was added drop wise, the mixture was stirred at room temperature overnight. Then the reaction was quenched by adding water (100 mL). The mixture was extracted with EA (20 mL×3), washed with brine, dried over $Na_2SO_4$, concentrated and purified by silica gel column chromatography to give ethyl 6-bromo-1-((2-(trimethylsilyl)ethoxy)methyl)-1H-indole-2-carboxylate (1.92 g, 96%) as colorless oil. HPLC/UV purity: 90%; LC-MS (ESI): 400.1 (M+1)$^+$.

Step 2

The mixture of ethyl 6-bromo-1-((2-(trimethylsilyl)ethoxy)methyl)-1H-indole-2-carboxylate (199 mg, 0.5 mmol), 4,4,4',4',5,5,5',5'-octamethyl-2,2'-bi(1,3,2-dioxaborolane) (152 mg, 0.6 mmol), KOAc (98 mg, 1 mmol) and Pd (dppf)Cl$_2$ (41 mg, 0.05 mmol) in 1,4-dioxane (20 mL) was stirred at 100° C. overnight. The reaction mixture was filtered, concentrated and purified by silica gel column chromatography to give methyl 6-(4,4,5,5-tetramethyl-1,3,2-dioxaborolan-2-yl)-1-((2-(trimethylsilyl)ethoxy)methyl)-1H-indole-2-carboxylate (100 mg, 45%) as yellow oil. HPLC/UV purity: 90%; LC-MS (ESI): 431.9 (M+1)$^+$.

Step 3

The solution of methyl 6-(4,4,5,5-tetramethyl-1,3,2-dioxaborolan-2-yl)-1-((2-(trimethylsilyl)ethoxy)methyl)-1H-indole-2-carboxylate (431 mg, 1 mmol), 2,4-dichloro-1,6-naphthyridine (198 mg, 1 mmol), $Na_2CO_3$ (212 mg, 2 mmol) and Pd(PPh$_3$)$_4$ (115 mg, 0.1 mmol) in Dioxane/H$_2$O (10 mL/1 mL) was stirred at 100° C. in Biotage Initiator Eight Microwave Reactor for 2 hrs. Then the solvent was removed and the residue was purified by silica gel column chromatography to give ethyl 6-(4-chloro-1,6-naphthyridin-2-yl)-1-((2-(trimethylsilyl)ethoxy)methyl)-1H-indole-2-carboxylate (220 mg, 45.7%) as white solid. HPLC/UV purity: 90%; LC-MS (ESI): 481.7 (M+1)$^+$.

Step 4

The mixture of ethyl 6-(4-chloro-1,6-naphthyridin-2-yl)-1-((2-(trimethylsilyl)ethoxy)methyl)-1H-indole-2-carboxylate (48.1 mg, 0.1 mmol), 3-(piperidin-1-yl)propan-1-amine (28 mg, 0.2 mmol) and K₂CO₃ (27 mg, 0.2 mmol) in DMF (3 mL) was stirred at 70° C. overnight. The reaction mixture was filtered, concentrated and purified by silica gel column chromatography to give Ethyl 6-(4-(3-(piperidin-1-yl)propylamino)-1,6-naphthyridin-2-yl)-1-((2-(trimethylsilyl)ethoxy)methyl)-1H-indole-2-carboxylate (40 mg, 68%) as white solid. HPLC/UV purity: 90%; LC-MS (ESI): 587.9 (M+1)⁺.

Step 5

The solution of ethyl 6-(4-(3-(piperidin-1-yl)propylamino)-1,6-naphthyridin-2-yl)-1-((2-(trimethylsilyl)ethoxy)methyl)-1H-indole-2-carboxylate (2.93 g, 5 mmol) and LiOH·H₂O (410 mg, 10 mmol) in CH₃OH/H₂O (100 mL/10 mL) was stirred at room temperature overnight. After adding 1N aq. HCl solution (11 mL), the solvent was removed to give crude 6-(4-(3-(piperidin-1-yl)propylamino)-1,6-naphthyridin-2-yl)-1-((2-(trimethylsilyl)ethoxy)methyl)-1H-indole-2-carboxylic acid (2.43 g, 87%) as yellow solid. HPLC/UV purity: 90%; LC-MS (ESI): 559.8 (M+1)⁺.

Step 6

The mixture of 6-(4-(3-(piperidin-1-yl)propylamino)-1,6-naphthyridin-2-yl)-1-((2-(trimethylsilyl)ethoxy)methyl)-1H-indole-2-carboxylic acid (112 mg, 0.2 mmol), 1-methylpiperidin-4-amine (23 mg, 0.2 mmol), HATU (114 mg, 0.3 mmol) and DIPEA (65 mg, 0.5 mmol) in DMF (5 mL) was stirred at room temperature overnight. After adding 50 mL water, the mixture was extracted with EA (100 mL), washed with brine, dried over Na₂SO₄, concentrated and purified by flash column chromatography to give N-(1-methylpiperidin-4-yl)-6-(4-(3-(piperidin-1-yl)propylamino)-1,6-naphthyridin-2-yl)-1-((2-(trimethylsilyl)ethoxy)methyl)-1H-indole-2-carboxamide (105 mg, 80%), as white solid. HPLC/UV purity: 90%; LC-MS (ESI): 655.9 (M+1)⁺.

Step 7

The solution of N-(1-methylpiperidin-4-yl)-6-(4-(3-(piperidin-1-yl)propylamino)-1,6-naphthyridin-2-yl)-1-((2-(trimethylsilyl)ethoxy)methyl)-1H-indole-2-carboxamide (105 mg, 0.16 mmol) in TFA/DCM (5 mL/5 mL) was stirred at room temperature overnight. Then the solvent was removed. The residue was dissolved in NH₃·H₂O (10 mL) and stirred at room temperature overnight. The reaction mixture was concentrated and purified by Prep-HPLC (Welch, XB-C18, 21.2 mm×250 mm, 10 um, eluting with 20% CH₃CN in 1‰ TFA in H₂O) to give N-(1-Methylpiperidin-4-yl)-6-(4-(3-(piperidin-1-yl)propylamino)-1,6-naphthyridin-2-yl)-1H-indole-2-carboxamide (50 mg, 47.6%) as white solid. HPLC/UV purity: 100%; LC-MS (ESI): 525.8 (M+1)⁺. ¹H NMR (METHANOL-d₄) δ: 9.61 (s, 1H), 8.76 (d, J=6.0 Hz, 1H), 8.03 (s, 1H), 7.93-7.77 (m, 2H), 7.59 (d, J=8.4 Hz, 1H), 7.15 (d, J=14.4 Hz, 2H), 4.13-4.09 (m, 1H), 3.75 (t, J=6.8 Hz, 2H), 3.54-3.48 (m, 4H), 3.24-3.20 (m, 2H), 3.11 (t, J=12.2 Hz, 2H), 2.89-2.85 (m, 2H), 2.75 (s, 3H), 2.25-2.14 (m, 4H), 1.98-1.69 (m, 4H), 1.69-1.32 (m, 3H), 1.43-1.39 (m, 1H).

Example 91: Synthesis of N-(3-(Piperidin-1-yl)propyl)-6-(4-(3-(piperidin-1-yl)propylamino)-1,6-naphthyridin-2-yl)-1H-indole-2-carboxamide

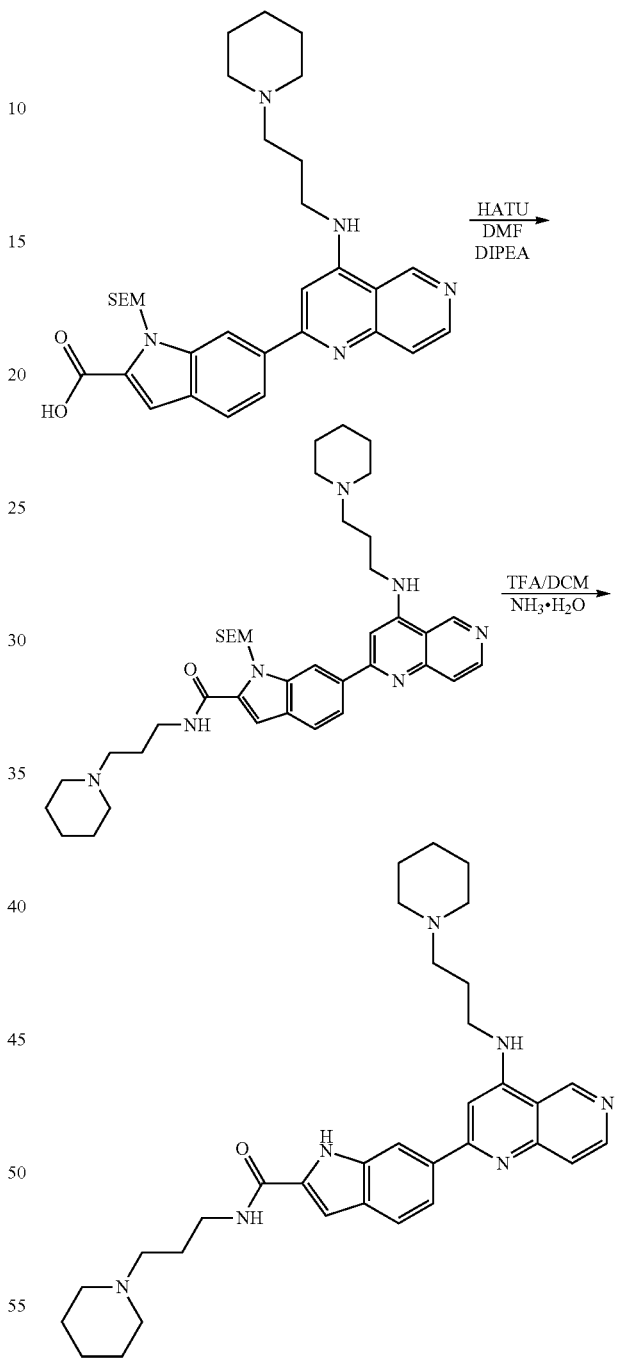

Step 1

The mixture of 6-(4-(3-(piperidin-1-yl)propylamino)-1,6-naphthyridin-2-yl)-1-((2-(trimethylsilyl)ethoxy)methyl)-1H-indole-2-carboxylic acid (112 mg, 0.2 mmol), 3-(piperidin-1-yl)propan-1-amine (28 mg, 0.2 mmol), HATU (114 mg, 0.3 mmol) and DIPEA (65 mg, 0.5 mmol) in DMF (5 mL) was stirred at room temperature overnight. After adding 50 mL water, the reaction mixture was extracted with EA (100 mL), washed with brine, dried over Na₂SO₄, concentrated and purified by flash column chromatography to give N-(3-(piperidin-1-yl)propyl)-6-(4-(3-(piperidin-1-yl)propylamino)-1,6-naphthyridin-2-yl)-1-((2-(trimethylsilyl)ethoxy)methyl)-1H-indole-2-carboxamide (120 mg, 87.6%), as white solid. HPLC/UV purity: 90%; LC-MS (ESI): 683.9 (M+1)⁺.

Step 2

The solution of N-(3-(piperidin-1-yl)propyl)-6-(4-(3-(piperidin-1-yl)propylamino)-1,6-naphthyridin-2-yl)-1-((2-(trimethylsilyl)ethoxy)methyl)-1H-indole-2-carboxamide (120 mg, 0.175 mmol) in TFA/DCM (1 mL/10 mL) was stirred at room temperature overnight. The solvent was removed. The residue was dissolved in NH₃·H₂O/DCM/CH₃OH (1 mL/10 mL/10 mL) and stirred at room temperature overnight. After removing the solvent, the residue was purified by Prep-HPLC (Welch, XB-C18, 21.2 mm×250 mm, 10 um, eluting with 20% CH₃CN in 1‰ TFA in H₂O) to give N-(3-(piperidin-1-yl)propyl)-6-(4-(3-(piperidin-1-yl)propylamino)-1,6-naphthyridin-2-yl)-1H-indole-2-carboxamide (40 mg, 41%) as white solid.

HPLC/UV purity: 100%; LC-MS (ESI): 553.9 (M+1)⁺. ¹H NMR (METHANOL-d₄) δ: 9.73 (s, 1H), 8.87 (d, J=6.0 Hz, 1H), 8.15 (s, 1H), 7.93-7.91 (m, 2H), 7.70 (d, J=8.4, 1.6 Hz, 1H), 7.22 (s, 2H), 3.86 (t, J=6.8 Hz, 2H), 3.72-3.50 (m, 6H), 3.29-3.16 (m, 2H), 3.02-2.90 (m, 4H), 2.34-2.22 (m, 2H), 2.22-2.04 (m, 2H), 2.01-1.95 (m, 4H), 1.87-1.84 (m, 6H), 1.57-1.30 (m, 2H).

Example 92: Synthesis of N-(2-(Dimethylamino)ethyl)-6-(4-(3-(piperidin-1-yl)propylamino)-1,6-naphthyridin-2-yl)-1H-indole-2-carboxamide

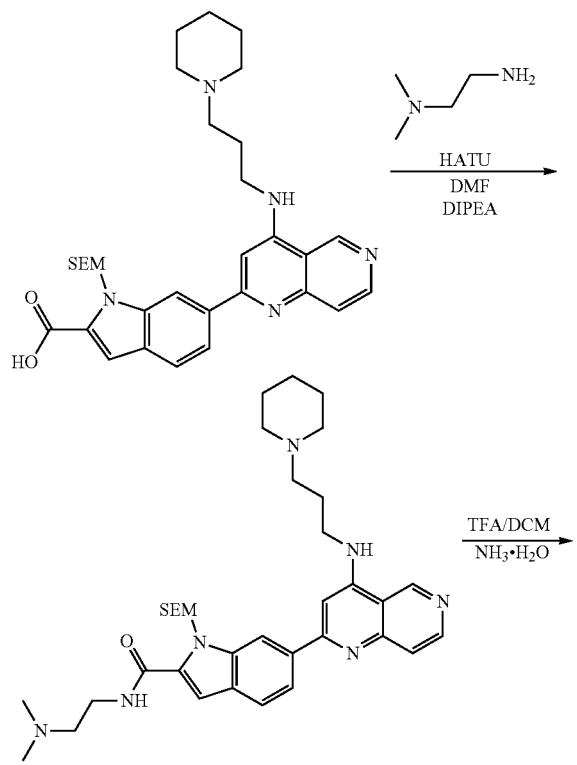

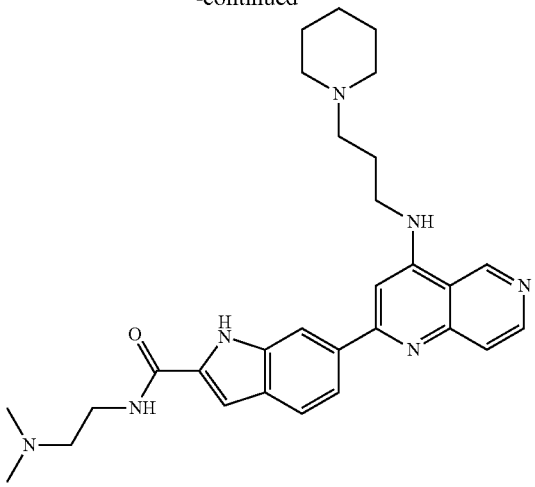

Step 1

The mixture of 6-(4-(3-(piperidin-1-yl)propylamino)-1,6-naphthyridin-2-yl)-1-((2-(trimethylsilyl)ethoxy)methyl)-1H-indole-2-carboxylic acid (112 mg, 0.2 mmol), N¹,N¹-dimethylethane-1,2-diamine (18 mg, 0.2 mmol), HATU (114 mg, 0.3 mmol) and DIPEA (65 mg, 0.5 mmol) in DMF (5 mL) was stirred at room temperature overnight. After adding 50 mL water, the reaction mixture was extracted with EA (100 mL), washed with brine, dried over Na₂SO₄, concentrated and purified by flash column chromatography to give N-(2-(dimethylamino)ethyl)-6-(4-(3-(piperidin-1-yl)propylamino)-1,6-naphthyridin-2-yl)-1-((2-(trimethylsilyl)ethoxy)methyl)-1H-indole-2-carboxamide (120 mg, 95%) as white solid. HPLC/UV purity: 95%; LC-MS (ESI): 629.8 (M+1)⁺.

Step 2

The solution of N-(2-(dimethylamino)ethyl)-6-(4-(3-(piperidin-1-yl)propylamino)-1,6-naphthyridin-2-yl)-1-((2-(trimethylsilyl)ethoxy)methyl)-1H-indole-2-carboxamide (113 mg, 0.2 mmol) in TFA/DCM (1 mL/10 mL) was stirred at room temperature overnight. Then the solvent was removed. The residue was dissolved in NH₃·H₂O/DCM/CH₃OH (1 mL/10 mL/10 mL) and stirred at room temperature overnight. After removing the solvent, the residue was purified by Prep-HPLC (Welch, XB-C18, 21.2 mm×250 mm, 10 um, eluting with 20% CH₃CN in 1‰ TFA in H₂O) to give N-(2-(dimethylamino)ethyl)-6-(4-(3-(piperidin-1-yl)propylamino)-1,6-naphthyridin-2-yl)-1H-indole-2-carboxamide (50 mg, 47.6%) as white solid. HPLC/UV purity: 100%; LC-MS (ESI): 499.8 (M+1)⁺. ¹H NMR (METHANOL-d₄) δ: 9.60 (s, 1H), 8.75 (d, J=6.0 Hz, 1H), 8.03 (s, 1H), 7.82-7.78 (m, 2H), 7.59 (d, J=8.8 Hz, 1H), 7.10 (d, J=8.8 Hz, 2H), 3.76-3.71 (m, 4H), 3.50 (d, J=12.0 Hz, 2H), 3.36-3.32 (m, 2H), 3.24-3.22 (m, 2H), 2.96 (s, 6H), 2.92-2.83 (m, 2H), 2.25-2.18 (m, 2H), 1.87-1.84 (m, 2H), 1.76-1.63 (m, 3H), 1.43-1.40 (m, 1H).

Example 93: Synthesis of 6-(4-(3-(Piperidin-1-yl)propylamino)-1,6-naphthyridin-2-yl)-N-(2-(pyridin-4-yl)ethyl)-1H-indole-2-carboxamide

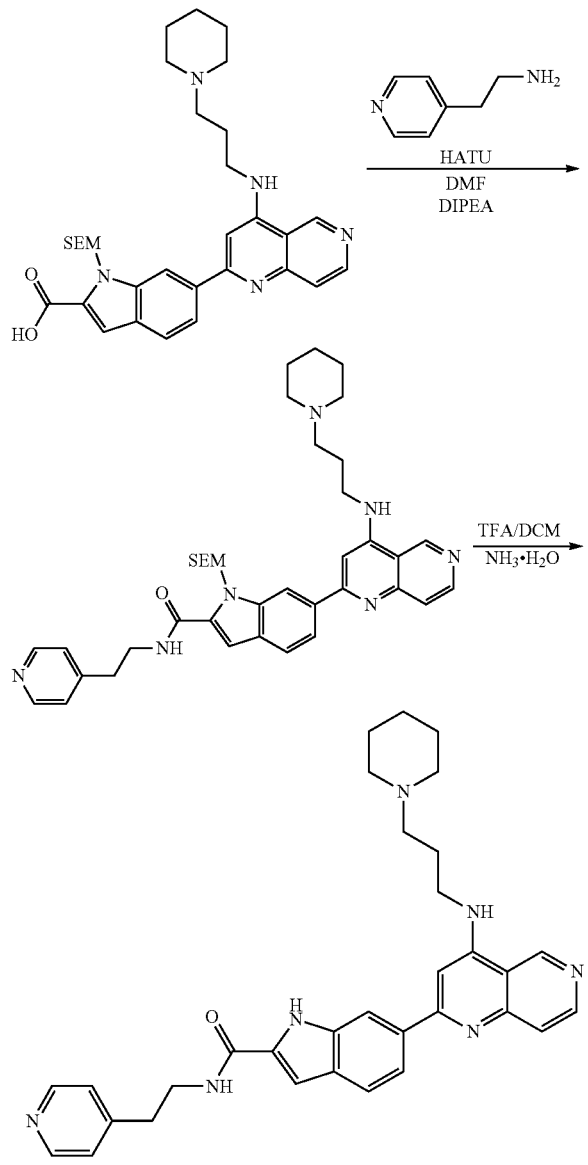

Step 1

The mixture of 6-(4-(3-(piperidin-1-yl)propylamino)-1,6-naphthyridin-2-yl)-1-((2-(trimethylsilyl)ethoxy)methyl)-1H-indole-2-carboxylic acid (112 mg, 0.2 mmol), 2-(pyridin-4-yl)ethanamine (24 mg, 0.2 mmol), HATU (114 mg, 0.3 mmol) and DIPEA (65 mg, 0.5 mmol) in DMF (5 mL) was stirred at room temperature overnight. After adding 50 mL water, the reaction mixture was extracted with EA (100 mL), washed with brine, dried over Na$_2$SO$_4$, concentrated and purified by flash column chromatography to give 6-(4-(3-(piperidin-1-yl)propylamino)-1,6-naphthyridin-2-yl)-N-(2-(pyridin-4-yl)ethyl)-1-((2-(trimethylsilyl)ethoxy)methyl)-1H-indole-2-carboxamide (126 mg, 95%) as white solid. HPLC/UV purity: 90%; LC-MS (ESI): 663.9 (M+1)$^+$.

Step 2

The solution of 6-(4-(3-(piperidin-1-yl)propylamino)-1,6-naphthyridin-2-yl)-N-(2-(pyridin-4-yl)ethyl)-1-((2-(trimethylsilyl)ethoxy)methyl)-1H-indole-2-carboxamide (120 mg, 0.18 mmol) in TFA/DCM (1 mL/10 mL) was stirred at room temperature overnight. Then the solvent was removed. The residue was dissolved in NH$_3$·H$_2$O/DCM/CH$_3$OH (1 mL/10 mL/10 mL) and stirred at room temperature overnight. After removing the solvent, the residue was purified by Prep-HPLC (Welch, XB-C18, 21.2 mm×250 mm, 10 um, eluting with 20% CH$_3$CN in 1‰ TFA in H$_2$O) to give 6-(4-(3-(piperidin-1-yl)propylamino)-1,6-naphthyridin-2-yl)-N-(2-(pyridin-4-yl)ethyl)-1H-indole-2-carboxamide (60 mg, 62.5%) as white solid. HPLC/UV purity: 90%; LC-MS (ESI): 533.8 (M+1)$^+$. $^1$H NMR (METHANOL-d$_4$) δ: 9.61 (s, 1H), 8.76 (d, J=6.0 Hz, 1H), 8.64 (d, J=6.4 Hz, 2H), 8.02 (s, 1H), 7.90 (d, J=6.4 Hz, 2H), 7.80 (d, J=7.2 Hz, 2H), 7.58 (d, J=8.4 Hz, 1H), 7.12 (s, 1H), 7.05 (s, 1H), 3.75-3.72 (m, 4H), 3.51-3.47 (m, 2H), 3.24-3.17 (m, 4H), 2.86 (t, J=12.4 Hz, 2H), 2.25-2.17 (m, 2H), 1.87-1.83 (m, 2H), 1.76-1.64 (m, 3H), 1.47-1.39 (m, 1H).

Example 94: Synthesis of 6-(4-(3-(Piperidin-1-yl)propylamino)-1,6-naphthyridin-2-yl)-N-(piperidin-4-yl)-1H-indole-2-carboxamide

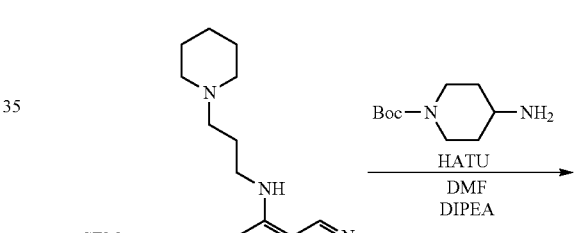

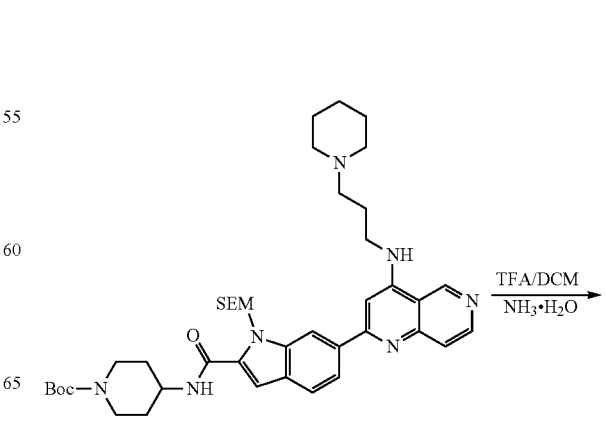

263
-continued

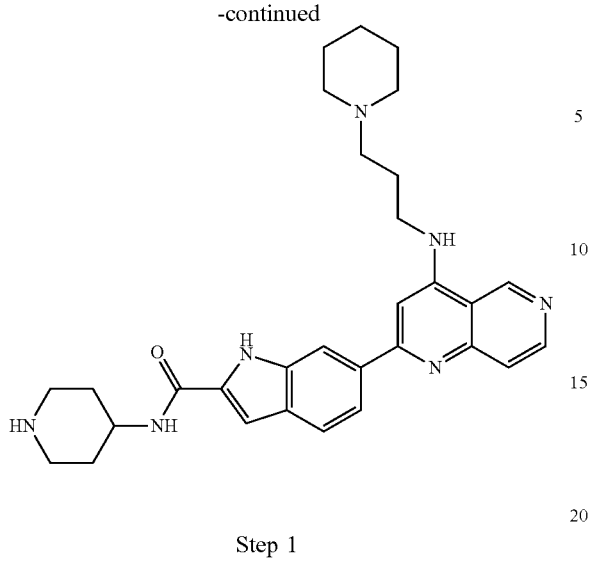

Step 1

The mixture of 6-(4-(3-(piperidin-1-yl)propylamino)-1,6-naphthyridin-2-yl)-1-((2-(trimethylsilyl)ethoxy)methyl)-1H-indole-2-carboxylic acid (112 mg, 0.2 mmol), tert-butyl 4-aminopiperidine-1-carboxylate (24 mg, 0.2 mmol), HATU (114 mg, 0.3 mmol) and DIPEA (65 mg, 0.5 mmol) in DMF (5 mL) was stirred at room temperature overnight. After adding 50 mL water, the reaction mixture was extracted with EA (100 mL), washed with brine, dried over $Na_2SO_4$, concentrated and purified by flash column chromatography to give tert-butyl 4-(6-(4-(3-(piperidin-1-yl)propylamino)-1,6-naphthyridin-2-yl)-1-((2-(trimethylsilyl)ethoxy)methyl)-1H-indole-2-carboxamido)piperidine-1-carboxylate (126 mg, 95%) as white solid. HPLC/UV purity: 90%; LC-MS (ESI): 741.9 $(M+1)^+$.

Step 2

The solution of tert-butyl 4-(6-(4-(3-(piperidin-1-yl)propylamino)-1,6-naphthyridin-2-yl)-1-((2-(trimethylsilyl)ethoxy)methyl)-1H-indole-2-carboxamido)piperidine-1-carboxylate (130 mg, 0.18 mmol) in TFA/DCM (1 mL/10 mL) was stirred at room temperature overnight. Then the solvent was removed. The residue was dissolved in $NH_3 \cdot H_2O$/DCM/$CH_3OH$ (1 mL/10 mL/10 mL) and stirred at room temperature overnight. After removing the solvent, the residue was purified by Prep-HPLC (Welch, XB-C18, 21.2 mm×250 mm, 10 um, eluting with 20% $CH_3CN$ in 1‰ TFA in $H_2O$) to give 6-(4-(3-(piperidin-1-yl)propylamino)-1,6-naphthyridin-2-yl)-N-(piperidin-4-yl)-1H-indole-2-carboxamide (50 mg, 56%) as white solid. HPLC/UV purity: 100%; LC-MS (ESI): 511.8 $(M+1)^+$. $^1$H NMR (METHANOL-$d_4$) δ: 9.72 (s, 1H), 8.87 (d, J=6.0 Hz, 1H), 8.14 (s, 1H), 7.97-7.87 (m, 2H), 7.70 (d, J=8.4 Hz, 1H), 7.27 (s, 1H), 7.22 (s, 1H), 4.26-4.21 (m, 1H), 3.86 (t, J=6.7 Hz, 2H), 3.63-3.60 (m, 2H), 3.55-3.52 (m, 2H), 3.36-3.33 (m, 2H), 3.23-3.17 (m, 2H), 3.01-2.94 (t, J=12.4 Hz, 2H), 2.37-2.25 (m, 4H), 2.0-1.71 (m, 7H), 1.57-1.49 (m, 1H).

264

Example 95: Synthesis of (4-Ethylpiperazin-1-yl)(6-(4-(3-(piperidin-1-yl)propylamino)-1,6-naphthyridin-2-yl)-1H-indol-2-yl)methanone

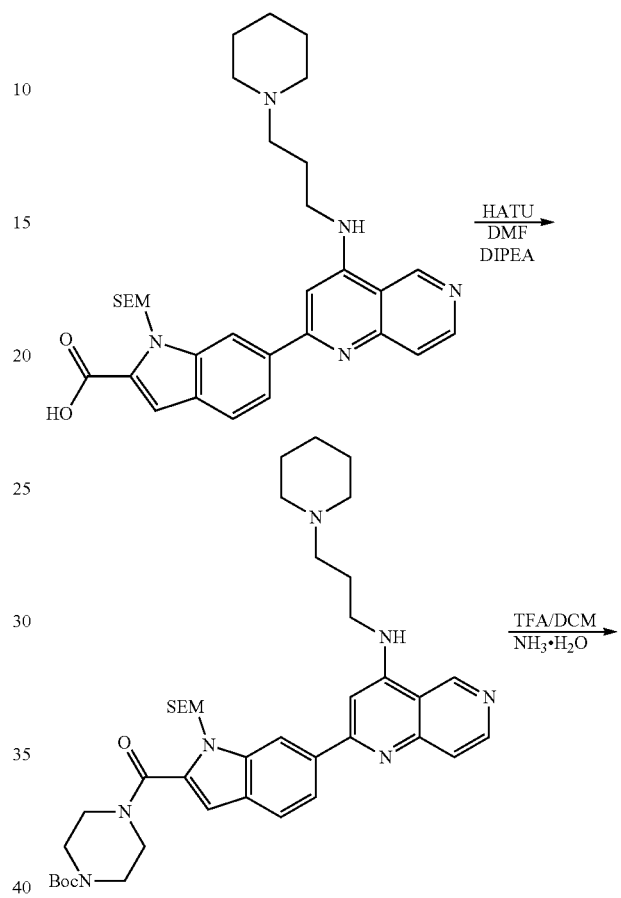

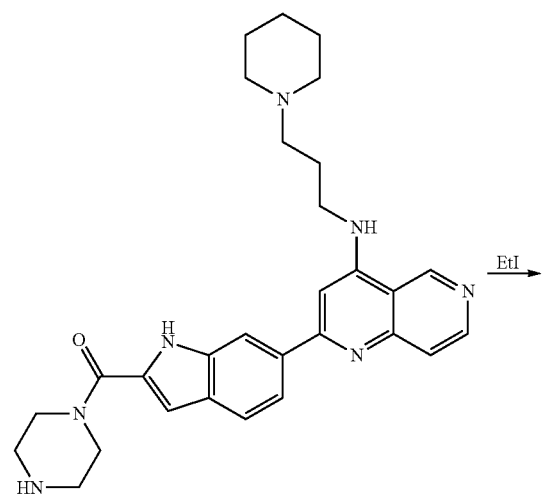

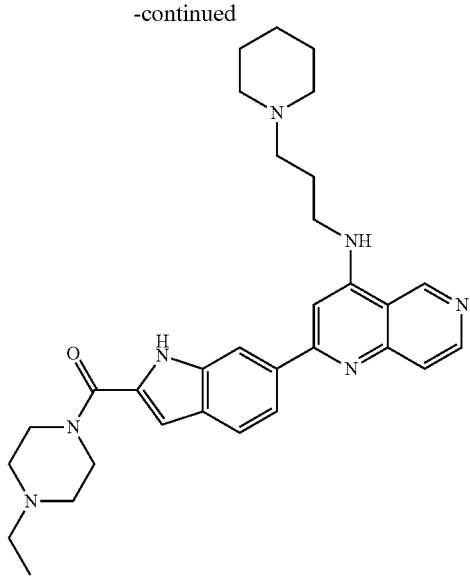

Step 1

The mixture of 6-(4-(3-(piperidin-1-yl)propylamino)-1,6-naphthyridin-2-yl)-1-((2-(trimethylsilyl)ethoxy)methyl)-1H-indole-2-carboxylic acid (279 mg, 0.5 mmol), tert-butyl piperazine-1-carboxylate (93 mg, 0.5 mmol), HATU (380 mg, 1 mmol) and DIPEA (258 mg, 2 mmol) in DMF (10 mL) was stirred at room temperature for 3 hours. After adding 50 mL water, the reaction mixture was extracted with EA (100 mL), washed with brine, dried over $Na_2SO_4$, concentrated and purified by flash column chromatography to give tert-butyl 4-(6-(4-(3-(piperidin-1-yl)propylamino)-1,6-naphthyridin-2-yl)-1-((2-(trimethylsilyl)ethoxy)methyl)-1H-indole-2-carbonyl)piperazine-1-carboxylate (290 mg, 80%) as white solid. HPLC/UV purity: 90%; LC-MS (ESI): 727.9 $(M+1)^+$.

Step 2

The solution of tert-butyl 4-(6-(4-(3-(piperidin-1-yl)propylamino)-1,6-naphthyridin-2-yl)-1-((2-(trimethylsilyl)ethoxy)methyl)-1H-indole-2-carbonyl)piperazine-1-carboxylate (290 mg, 0.4 mmol) in TFA/DCM (1 mL/10 mL) was stirred at room temperature for 2 hrs. Then the solvent was removed. The residue was dissolved in $NH_3 \cdot H_2O$/DCM/$CH_3OH$ (1 mL/10 mL/10 mL) and stirred at room temperature overnight. After removing the solvent, the residue was purified by Prep-HPLC (Welch, XB-C18, 21.2 mm×250 mm, 10 um, eluting with 20% $CH_3CN$ in 1‰ TFA in $H_2O$) to give piperazin-1-yl(6-(4-(3-(piperidin-1-yl)propylamino)-1,6-naphthyridin-2-yl)-1H-indol-2-yl)methanone (120 mg, 61%) as white solid. HPLC/UV purity: 100%; LC-MS (ESI): 497.9 $(M+1)^+$. $^1H$ NMR (METHANOL-$d_4$) δ: 9.73 (s, 1H), 8.88 (d, J=6.4 Hz, 1H), 8.16 (s, 1H), 7.94 (m, 2H), 7.72 (d, J=8.4, 1.6 Hz, 1H), 7.25 (d, J=10.8 Hz, 1H), 7.07 (s, 1H), 4.17-4.15 (m, 4H), 3.87 (t, J=6.8 Hz, 2H), 3.61 (d, J=12.0 Hz, 2H), 3.42-3.40 (m, 4H), 3.36-3.32 (m, 2H), 2.98 (t, J=12.4 Hz, 2H), 2.37-2.30 (m, 2H), 1.97 (d, J=15.2 Hz, 2H), 1.88-1.75 (m, 3H), 1.56-1.52 (m, 1H).

Step 3

The mixture of piperazin-1-yl(6-(4-(3-(piperidin-1-yl)propylamino)-1,6-naphthyridin-2-yl)-1H-indol-2-yl)methanone (50 mg, 0.1 mmol) and $K_2CO_3$ in DMF (5 mL) was stirred at room temperature for 3 h. After adding 50 mL water, the reaction mixture was extracted with EA (100 mL), washed with brine, dried over $Na_2SO_4$, concentrated and purified by Prep-HPLC (Welch, XB-C18, 21.2 mm×250 mm, 10 um, eluting with 20% $CH_3CN$ in 1‰ TFA in $H_2O$) to give (4-ethylpiperazin-1-yl)(6-(4-(3-(piperidin-1-yl)propylamino)-1,6-naphthyridin-2-yl)-1H-indol-2-yl)methanone (10 mg, 20%) as yellow solid. HPLC/UV purity: 100%; LC-MS (ESI): 525.9 $(M+1)^+$. $^1H$ NMR (METHANOL-$d_4$) δ: 9.72 (s, 1H), 8.87 (d, J=6.0 Hz, 1H), 8.15 (s, 1H), 7.92 (d, J=7.6 Hz, 2H), 7.71 (d, J=8.8 Hz, 1.6 Hz, 1H), 7.23 (s, 1H), 7.04 (s, 1H), 4.80 (m, 2H), 3.86 (t, J=7.2 Hz, 2H), 3.63-3.60 (m, 6H), 3.37-3.34 (m, 3H), 3.33-3.30 (m, 3H), 2.98 (t, J=12.4 Hz, 2H), 2.38-2.30 (m, 2H), 1.97 (d, J=14.8 Hz, 2H), 1.86-1.76 (m, 3H), 1.56-1.52 (m, 1H), 1.43 (t, J=7.6 Hz, 3H).

Example 96: Synthesis of N,N-diethyl-3-(4-(4-((3-(piperidin-1-yl)propyl)amino)-1,6-naphthyridin-2-yl)phenoxy)propanamide

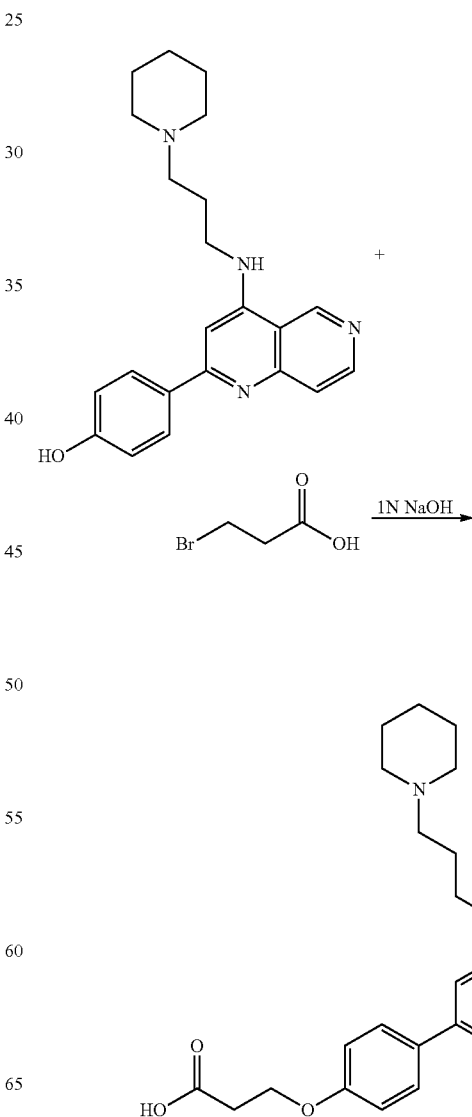

-continued

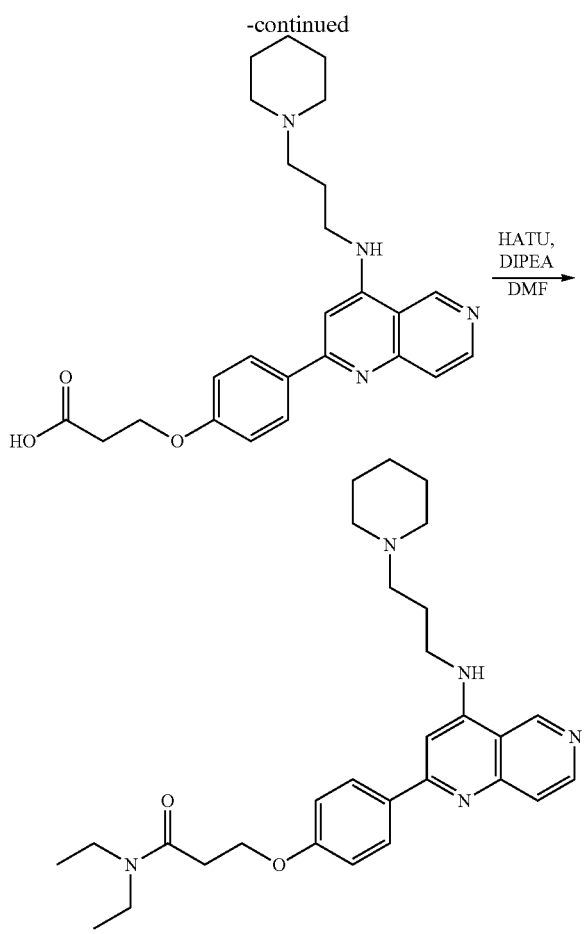

Step 1

The mixture of 4-(4-((3-(piperidin-1-yl)propyl)amino)-1,6-naphthyridin-2-yl)phenol (320 mg, 0.88 mmol) in 1N aq. NaOH solution (0.88 mL) was heated to 100° C., then a solution of 3-bromopropanoic acid (135 mg, 0.88 mmol) in 1N aq. NaOH solution (0.88 mL) was added. The resulting mixture was stirred at 100° C. and held for 2 hrs. The reaction mixture was cooled to room temperature and quenched with water (5 mL), then extracted with EA (10 mL×3). The combined organic layer was discarded and pH of the water phase was adjusted with 1N aq. HCl solution to pH=1. The acidified water phase was lyophilized to get a crude product, which was purified with Prep-HPLC (eluting with 20% $CH_3CN$ and 0.1% TFA in $H_2O$) to afford 3-(4-(4-((3-(piperidin-1-yl)propyl)amino)-1,6-naphthyridin-2-yl)phenoxy)propanoic acid as a yellow solid (80 mg, 20%). HPLC/UV purity: 100%; LC-MS (ESI): 435.3 (M+1)$^+$; $^1$H NMR (METHANOL-$d_4$) δ: 9.97-10.05 (m, 1H), 8.76 (d, J=7.1, 1H), 8.03-8.21 (m, 3H), 7.29 (s, 1H), 6.93-7.05 (m, 2H), 3.76 (t, J=6.9 Hz, 2H), 3.61 (d, J=12.1 Hz, 2H), 3.33-3.38 (m, 4H), 3.22 (t, J=6.3 Hz, 2H), 2.91-3.06 (m, 2H), 2.24-2.38 (m, 2H), 1.92-2.05 (m, 2H), 1.72-1.92 (m, 3H), 1.48-1.53 (m, 1H).

Step 2

To a mixture of 3-(4-(4-((3-(piperidin-1-yl)propyl) amino)-1,6-naphthyridin-2-yl)phenoxy)propanoic acid (20 mg, 0.045 mmol) and HATU (21 mg, 0.055 mmol) in DMF (1 mL) was added diethylamide (4 mg, 0.055 mmol) and DIPEA (11 mg, 0.09 mmol). The resulting mixture was stirred at room temperature for 1 hr. The reaction mixture was poured into water (10 mL), extracted with EA (10 mL×3). The combined organic layers were washed with water and brine, dried over $Na_2SO_4$. The drying agent was filtered off and the filtrate was concentrated in vacuo to get the residue, which was purified with Prep-TLC (silica gel, eluting with 15% methanol in DCM) to afford N,N-diethyl-3-(4-(4-((3-(piperidin-1-yl)propyl)amino)-1,6-naphthyridin-2-yl)phenoxy)propanamide (2 mg, 10%) as a solid. HPLC/UV purity: 100%; LC-MS (ESI): 490.2 (M+1)$^+$. $^1$H NMR (METHANOL-$d_4$) δ: 10.01 (s, 1H), 8.76 (d, J=7.0 Hz, 1H), 8.04-8.23 (m, 3H), 7.29 (s, 1H), 7.00 (d, J=8.9 Hz, 2H), 3.76 (t, J=6.7 Hz, 2H), 3.61 (d, J=13.2 Hz, 2H), 3.34-3.44 (m, 8H), 3.28-3.32 (m, 2H), 2.91-3.06 (m, 2H), 2.25-2.41 (m, 2H), 1.99 (d, J=15.3 Hz, 2H), 1.72-1.93 (m, 3H), 1.51-1.54 (m, 1H), 1.21 (t, J=7.1 Hz, 3H), 1.08 (t, J=7.1 Hz, 3H).

Example 97: Synthesis of N-(1-methylpiperidin-4-yl)-3-(4-(4-((3-(piperidin-1-yl)propyl)amino)-1,6-naphthyridin-2-yl)phenoxy)propanamide

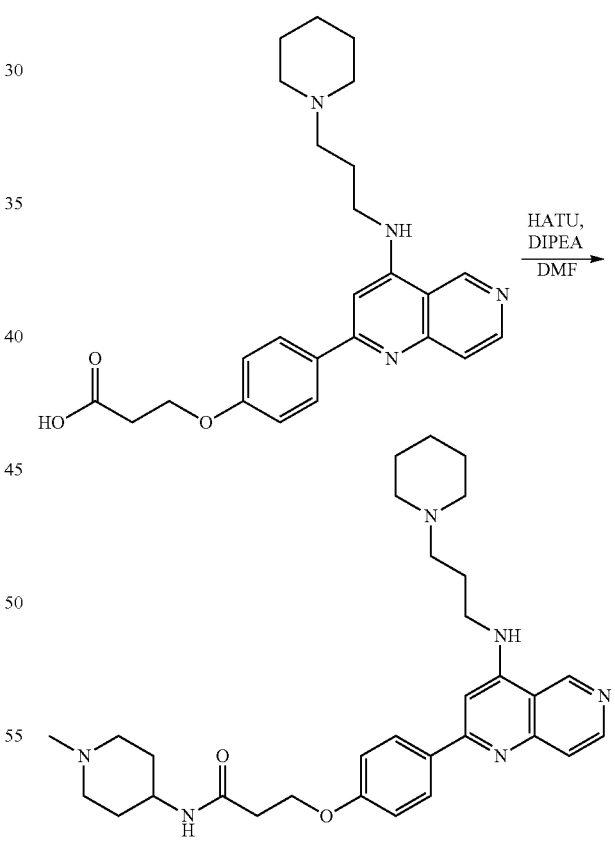

N-(1-methylpiperidin-4-yl)-3-(4-(4-((3-(piperidin-1-yl) propyl)amino)-1,6-naphthyridin-2-yl)phenoxy)propanamide was synthesized in a similar fashion as Example 96. HPLC/UV purity: 95%; LC-MS (ESI): 531.2 (M+1)$^+$. $^1$H NMR (METHANOL-$d_4$) δ: 9.98 (s, 1H), 8.65-8.67 (d, J=7.3 Hz, 1H), 8.15-8.17 (d, J=8.9 Hz, 2H), 8.06-8.08 (d, J=7.1 Hz, 1H), 7.29 (s, 1H), 6.98-7.01 (d, J=9.2 Hz, 2H), 3.88 (br.

s., 1H), 3.74 (t, J=6.7 Hz, 2H), 3.48-3.64 (m, 4H), 2.94-3.18 (m, 6H), 2.90 (s, 3H), 2.35-2.38 (m, 2H), 1.52-2.21 (m, 12H).

Example 98: Synthesis of N-((1-ethylpiperidin-4-yl)methyl)-3-(4-(4-((3-(piperidin-1-yl)propyl)amino)-1,6-naphthyridin-2-yl)phenoxy)propanamide and 3-(4-(4-(ethyl(3-(piperidin-1-yl)propyl)amino)-1,6-naphthyridin-2-yl)phenoxy)-N-((1-ethylpiperidin-4-yl)methyl)propanamide

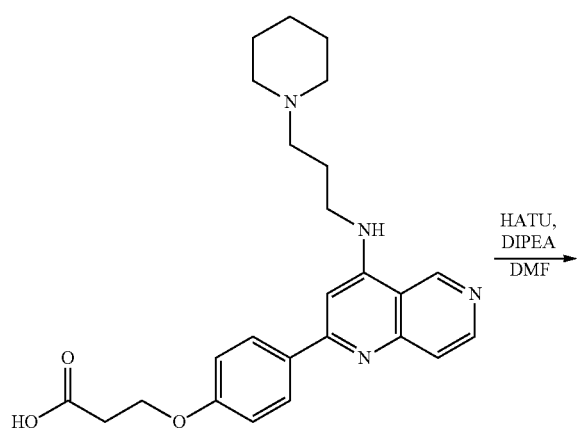

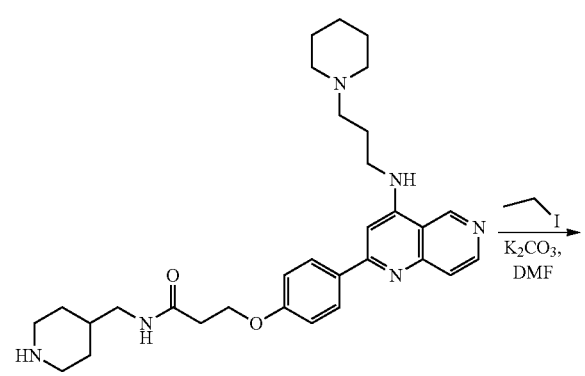

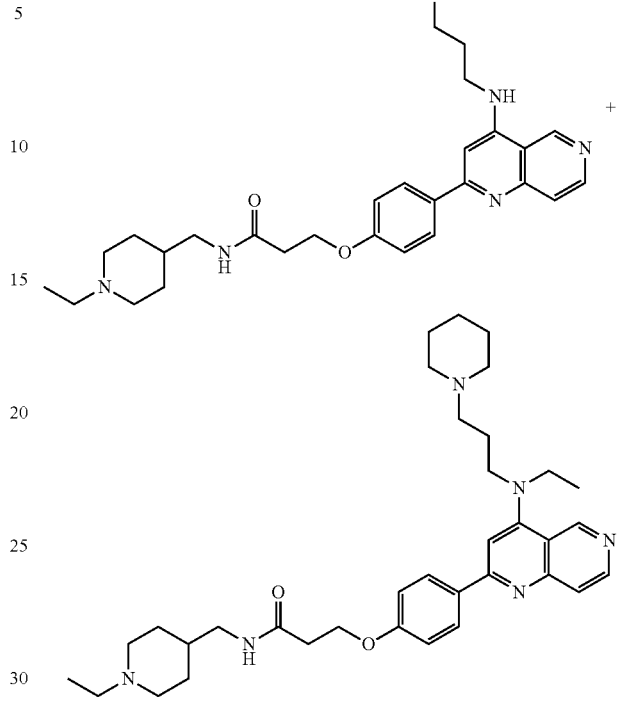

Step 1

To a mixture of 3-(4-(4-((3-(piperidin-1-yl)propyl)amino)-1,6-naphthyridin-2-yl)phenoxy)propanoic acid (100 mg, 0.23 mmol) and HATU (91 mg, 0.24 mmol) in DMF (1 mL) were added tert-butyl 4-(aminomethyl)piperidine-1-carboxylate (51 mg, 0.24 mmol) and DIPEA (60 mg, 0.46 mmol). The resulting mixture was stirred at room temperature for 1 hr. The reaction mixture was poured into water (10 mL), extracted with EA (10 mL×3). The combined organic layers were washed with water and brine, dried over $Na_2SO_4$. The drying agent was filtered off and the filtrate was concentrated in vacuo to give the residue, which was purified with Prep-HPLC (eluting with 20% CH3CN and 0.1% TFA in $H_2O$) to get tert-butyl 4-((3-(4-(4-((3-(piperidin-1-yl)propyl)amino)-1,6-naphthyridin-2-yl)phenoxy)propanamido)methyl)piperidine-1-carboxylate (80 mg, 55%) as a solid. HPLC/UV purity: 100%; LC-MS (ESI): 631.3 $(M+1)^+$.

Step 2

To a solution of tert-butyl 4-((3-(4-(4-((3-(piperidin-1-yl)propyl)amino)-1,6-naphthyridin-2-yl)phenoxy)propanamido)methyl)piperidine-1-carboxylate (80 mg, 0.126 mmol) in DCM (1 mL) was added TFA (1 mL). The reaction mixture was stirred at room temperature for 2 hrs. The solvent was removed under the reduced pressure to give the crude product, which was purified with Prep-HPLC (Welch, XB-C18, 21.2 mm×250 mm, 10 um, eluting with 20% CH3CN in 1‰ TFA in $H_2O$) to afford 3-(4-(4-((3-(piperidin-1-yl)propyl)amino)-1,6-naphthyridin-2-yl)phenoxy)-N-(piperidin-4-ylmethyl)propanamide (65 mg, 98%) as a TFA salt. HPLC/UV purity: 100%; LC-MS (ESI): 531.2 $(M+1)^+$.

$^1$H NMR (METHANOL-d$_4$) δ: 10.03 (s, 1H), 8.70 (d, J=7.1 Hz, 1H), 8.02-8.18 (m, 3H), 7.27 (s, 1H), 6.98 (d, J=8.7 Hz, 2H), 3.74 (t, J=6.6 Hz, 2H), 3.58 (d, J=12.2 Hz, 2H), 3.31-3.33 (m, 2H), 3.04-3.14 (m, 4H), 2.82-3.03 (m, 4H), 2.23-2.37 (m, 2H), 1.95 (d, J=15.3 Hz, 2H), 1.68-1.89 (m, 7H), 1.52 (d, J=12.2 Hz, 1H), 1.24-1.40 (m, 3H).

Step 3: N-((1-ethylpiperidin-4-yl)methyl)-3-(4-(4-((3-(piperidin-1-yl)propyl)amino)-1,6-naphthyridin-2-yl)phenoxy)propanamide The mixture of 3-(4-(4-((3-(piperidin-1-yl)propyl)amino)-1,6-naphthyridin-2-yl)phenoxy)-N-(piperidin-4-ylmethyl)propanamide (30 mg, 0.056 mmol) and K$_2$CO$_3$ (15 mg, 0.067 mmol) in DMF (1 mL) was stirred at room temperature for 30 min, followed by dropwise addition of iodoethane (10 mg, 0.22 mmol). The resulting reaction mixture was stirred at room temperature for 2 hrs. The reaction mixture was poured into water (20 mL), extracted with EA (10 mL×3). The combined organic layers were discarded and the water phase was lyophilized to give a crude product which was purified with Prep-HPLC to generate N-((1-ethylpiperidin-4-yl)methyl)-3-(4-(4-((3-(piperidin-1-yl)propyl)amino)-1,6-naphthyridin-2-yl)phenoxy)propanamide (20 mg, 64%) as a yellow solid. HPLC/UV purity: 100%; LC-MS (ESI): 559.1 (M+1)$^+$. $^1$H NMR (METHANOL-d$_4$) δ: 10.02 (s, 1H), 8.69 (d, J=7.0 Hz, 1H), 8.13-8.22 (d, J=8.9 Hz, 2H), 8.10 (d, J=7.3 Hz, 1H), 7.30 (s, 1H), 6.94-7.10 (d, J=8.6 Hz, 2H), 3.75 (t, J=6.7 Hz, 2H), 3.61 (d, J=12.4 Hz, 2H), 3.53 (d, J=12.6 Hz, 2H), 3.36 (d, J=8.6 Hz, 4H), 3.07-3.15 (m, 5H), 2.93-3.04 (m, 2H), 2.78-2.90 (m, 2H), 2.26-2.38 (m, 2H), 1.98 (d, J=15.0 Hz, 2H), 1.70-1.94 (m, 6H), 1.55 (d, J=12.4 Hz, 1H), 1.26-1.49 (m, 7H).

Step 4: 3-(4-(4-(ethyl(3-(piperidin-1-yl)propyl)amino)-1,6-naphthyridin-2-yl)phenoxy)-N-((1-ethylpiperidin-4-yl)methyl)propanamide The mixture of 3-(4-(4-((3-(piperidin-1-yl)propyl)amino)-1,6-naphthyridin-2-yl)phenoxy)-N-(piperidin-4-ylmethyl)propanamide (30 mg, 0.056 mmol) and K$_2$CO$_3$ (15 mg, 0.11 mmol) in DMF (1 mL) was stirred at room temperature for 30 min, followed by the drop wise addition of iodoethane (10 mg, 0.22 mmol). The resulting reaction mixture was stirred at room temperature for 2 hrs. The reaction mixture was poured into water (20 mL), extracted with EA (10 mL×3). The water phase was lyophilized to give a crude product, which was purified with Prep-HPLC to afford N-((1-ethylpiperidin-4-yl)methyl)-3-(4-(4-((3-(piperidin-1-yl)propyl)amino)-1,6-naphthyridin-2-yl)phenoxy)propanamide (15 mg, 48%) as a yellow solid. purity: 100%; LC-MS (ESI): 587.2 (M+1)$^+$. $^1$H NMR (METHANOL-d$_4$) δ: 10.04 (s, 1H), 8.66 (dd, J=7.3, 1.3 Hz, 1H), 8.21-8.30 (d, J=8.9 Hz, 2H), 8.09 (d, J=7.0 Hz, 1H), 7.32 (s, 1H), 7.04-7.19 (d, J=8.9 Hz, 2H), 4.18 (q, J=7.0 Hz, 2H), 3.74 (t, J=6.7 Hz, 2H), 3.61 (d, J=12.4 Hz, 2H), 3.48-3.57 (m, 2H), 3.34-3.41 (m, 4H), 3.10-3.12 (m, 5H), 2.99 (t, J=12.4 Hz 2H), 2.76-2.90 (m, 2H), 2.25-2.37 (m, 2H), 1.96-2.01 (m, 2H), 1.86 (t, J=13.4 Hz, 6H), 1.49-1.52 (m, 1H), 1.47 (t, J=7.0 Hz, 3H), 1.37-1.42 (m, 2H), 1.25-1.34 (m, 4H).

Example 99: Synthesis of 4-cyano-5-(4-((3-(piperidin-1-yl)propyl)amino)-1,6-naphthyridin-2-yl)-N-(piperidin-4-yl)-1H-benzo[d]imidazole-2-carboxamide

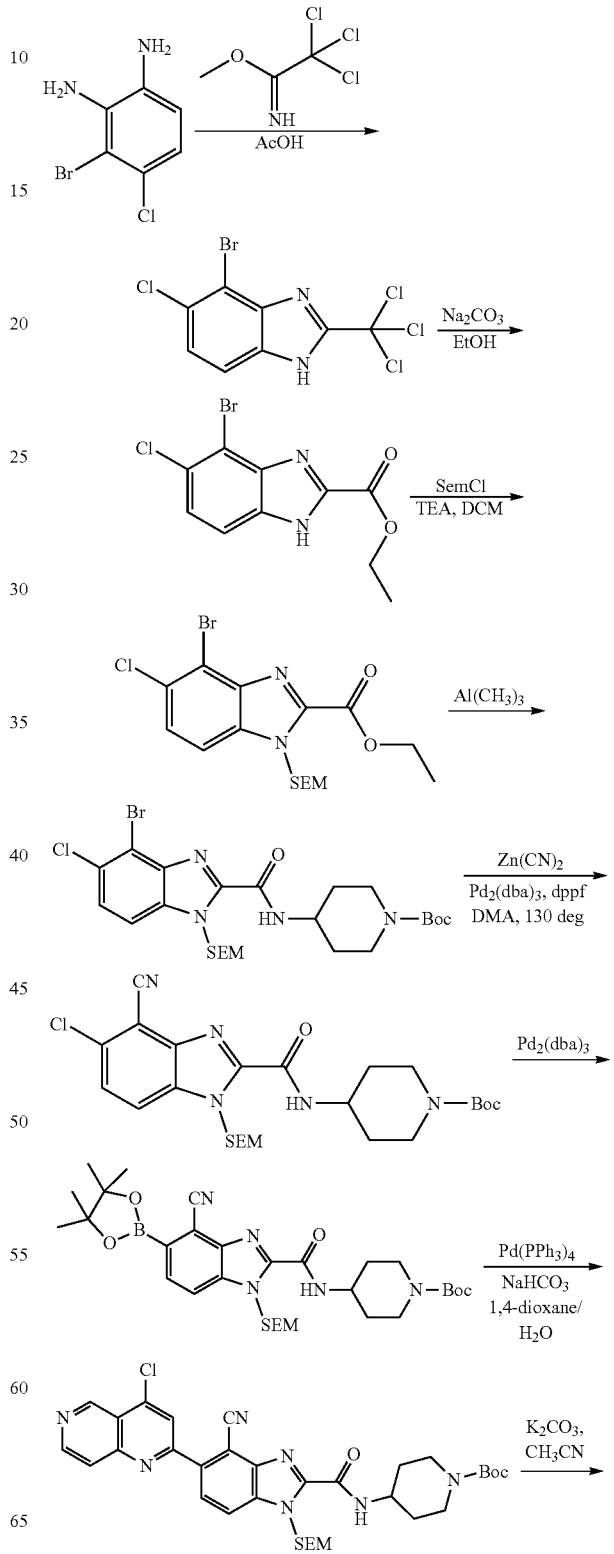

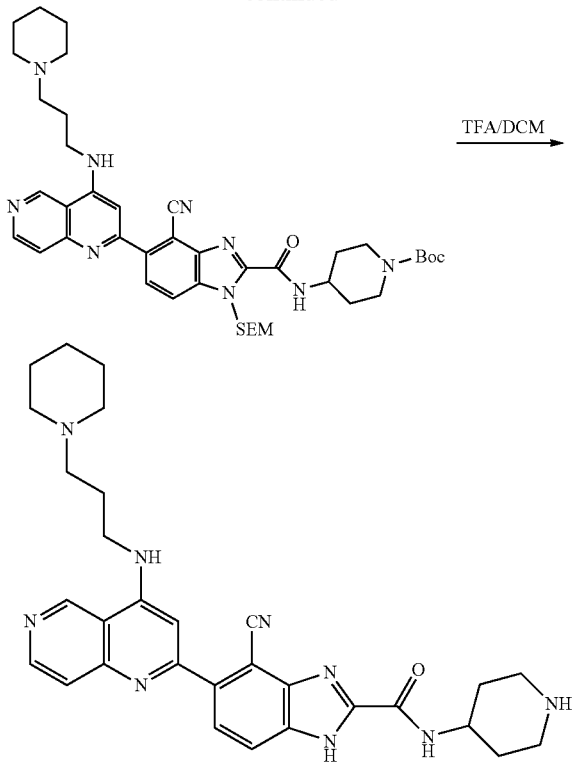

Step 1

To a solution of 3-bromo-4-chlorobenzene-1,2-diamine (4 g, 18 mmol) in AcOH (30 mL) was added methyl 2,2,2-trichloroacetimidate (3.5 g, 20 mmol) drop wise at 0° C. Then the reaction mixture was stirred at room temperature overnight. The mixture was poured into water (200 mL), and precipitate was collected and dried to give 4-bromo-5-chloro-2-(trichloromethyl)-1H-benzo[d]imidazole (5.5 g, 80%) as a white solid. HPLC/UV purity: 95%; LC-MS (ESI): 349.1 (M+1)$^+$.

Step 2

To the solution of 4-bromo-5-chloro-2-(trichloromethyl)-1H-benzo[d]imidazole (7.5 g, 21.5 mmol) in EtOH (100 mL) was added Na$_2$CO$_3$ (2.74 g, 25.8 mmol). The resulting mixture was heated at 90° C. for 18 hrs. The reaction mixture was cooled to room temperature and the solvent was removed under the reduced pressure to give slurry, which was diluted with water, and extracted with EA (20 mL×3). The combined organic layers were dried over Na$_2$SO$_4$, filtered, and the filtrate was concentrated in vacuo to give the residue, which was purified by flash column chromatography (silica gel, eluting with PE to 30% EA/PE) to afford ethyl 4-bromo-5-chloro-1H-benzo[d]imidazole-2-carboxylate (6.5 g, 98%) as a solid. HPLC/UV purity: 90%; LC-MS (ESI): 304.3 (M+1)$^+$.

Step 3

To a solution of ethyl 4-bromo-5-chloro-1h-benzo[d]imidazole-2-carboxylate (7 g, 22.8 mmol) in dcm (50 mL) was added triethylamine (6.9 g, 68.4 mmol). Then the mixture was cooled to 0° C., and 2-(trimethylsilyl)ethoxymethyl chloride (5.7 g, 34.3 mmol) was added drop wise. The resulting mixture was stirred at room temperature overnight. The solvent was removed, and the resulting crude mixture was diluted by water (30 mL), extracted with ea (20 mL×3). The combined organic layers were dried over Na$_2$SO$_4$, filtered, and the filtrate was concentrated in vacuo to give the crude mixture, which was purified by flash column chromatography (silica gel, eluting with pe to 10% EA/PE) to afford ethyl 4-bromo-5-chloro-1-((2-(trimethylsilyl)ethoxy)methyl)-1H-benzo[d]imidazole-2-carboxylate (4.9 g, 62%) as a solid. HPLC/UV purity: 90%; LC-MS (ESI): 434.1 (M+1)$^+$.

Step 4

To a solution of tert-butyl 4-aminopiperidine-1-carboxylate (4.62 g, 23 mmol) in DCM (20 mL) was added Al(CH$_3$)$_3$ (1N in toluene, 23 mL, 23 mmol) drop wise at 0° C. under nitrogen. The mixture was stirred at room temperature for 30 mins, and then the reaction mixture was cooled to 0° C. A solution of ethyl 4-bromo-5-chloro-1-((2-(trimethylsilyl)ethoxy)methyl)-1H-benzo[d]imidazole-2-carboxylate (2 g, 4.61 mmol) in DCM (5 mL) was added drop wise. The resulting reaction mixture was stirred at room temperature for 18 hrs. The reaction mixture was quenched by water (10 mL), extracted with DCM (10 mL×3). The combined organic layers were washed with water and brine, dried over Na$_2$SO$_4$, and the drying agent was filtered off. The filtrate was concentrated in vacuo to give the crude mixture, which was purified by flash column chromatography (silica gel, eluting with PE to 30% EA/PE) to afford tert-butyl 4-(4-bromo-5-chloro-1-((2-(trimethylsilyl)ethoxy)methyl)-1H-benzo[d]imidazole-2-carboxamido)piperidine-1-carboxylate (2.5 g, 92%) as a white solid. HPLC/UV purity: 90%; LC-MS (ESI): 589.3 (M+1)$^+$.

Step 5

The mixture of tert-butyl 4-(4-bromo-5-chloro-1-((2-(trimethylsilyl)ethoxy)methyl)-1H-benzo[d]imidazole-2-carboxamido)piperidine-1-carboxylate (2.15 g, 3.66 mmol), Zn(CN)$_2$ (1.28 g, 11 mmol), Pd$_2$(dba)$_3$ (335 mg, 0.366 mmol) and dppf (405 mg, 0.732 mmol) in DMA (8 mL) was heated at 130° C. for 18 hrs under N$_2$ atmosphere. The reaction mixture was concentrated by rotary evaporation (55° C., 20 mmHg). The residue was purified by silica gel chromatography (silica gel, eluting with PE to 30% EtOAc/PE) to give tert-butyl 4-(5-chloro-4-cyano-1-((2-(trimethylsilyl)ethoxy)methyl)-1H-benzo[d]imidazole-2-carboxamido)piperidine-1-carboxylate (1 g, 51%) as a brown solid HPLC/UV purity: 90%; LC-MS (ESI): 535.2 (M+1)$^+$.

Step 6

The mixture of tert-butyl 4-(4-cyano-5-(4,4,5,5-tetramethyl-1,3,2-dioxaborolan-2-yl)-1-((2-(trimethylsilyl)ethoxy)methyl)-1H-benzo[d]imidazole-2-carboxamido)piperidine-1-carboxylate (400 mg, 0.75 mmol), 4,4,4',4',5,5,5',5'-octamethyl-2,2'-bi(1,3,2-dioxaborolane) (286 mg, 1.13 mmol), Pd$_2$(dba)$_3$ (68.7 mg, 0.075 mmol), XPhos (72 mg, 0.15 mmol) and NaOAc (123 mg, 1.5 mmol) in 1,4-dioxane (20 mL) was heated at 110° C. for 18 hrs under N$_2$ atmosphere. The mixture was cooled to room temperature and the solvent was removed under reduced pressure to give the crude mixture, which was purified by flash column chromatography (silica gel, eluting with CH$_2$Cl$_2$ to 2% MeOH/CH$_2$Cl$_2$) to afford tert-butyl 4-(4-cyano-5-(4,4,5,5- tetramethyl-1,3,2-dioxaborolan-2-yl)-1-((2-(trimethylsilyl)ethoxy)methyl)-1H-benzo[d]imidazole-2-carboxamido)piperidine-1-carboxylate (400 mg, 86%) as a brown oil.

Step 7

A 20-mL microwave vial was charged with 2,4-dichloro-1,6-naphthyridine (60 mg, 0.93 mmol), tert-butyl 4-(4-cyano-5-(4,4,5,5-tetramethyl-1,3,2-dioxaborolan-2-yl)-1-((2-(trimethylsilyl)ethoxy)methyl)-1H-benzo[d]imidazole-2-carboxamido)piperidine-1-carboxylate (280 mg, 0.45 mmol), Pd(PPh₃)₄ (34 mg, 0.03 mmol), NaHCO₃ (50 mg, 0.6 mmol), 1,4-dioxane (4 mL) and H₂O (0.5 mL). The sealed vial with the resulting brown solution was heated for 2 hrs in a Biotage Initiator Eight Microwave Reactor at a constant temperature of 100° C. The resulting solution was concentrated by rotary evaporation (55° C., 20 mmHg). The residue was purified by silica gel chromatography (silica gel, eluting with 2-5% methanol in DCM) to give tert-butyl 4-(5-(4-chloro-1,6-naphthyridin-2-yl)-4-cyano-1-((2-(trimethylsilyl)ethoxy)methyl)-1H-benzo[d]imidazole-2-carboxamido)piperidine-1-carboxylate (90 mg, 45%) as a yellow solid. HPLC/UV purity: 70%; LC-MS (ESI): 662.2 (M+1)⁺

Step 8

The mixture of tert-butyl 4-(5-(4-chloro-1,6-naphthyridin-2-yl)-4-cyano-1-((2-(trimethylsilyl)ethoxy)methyl)-1H-benzo[d]imidazole-2-carboxamido)piperidine-1-carboxylate (90 mg, 0.147 mmol), 3-(piperidin-1-yl)propan-1-amine (42 mg, 0.294 mmol) and K₂CO₃ (40 mg, 0.294 mmol) in DMF (2 mL) was heated at 80° C. for 18 hrs. The reaction mixture was poured into water (10 mL), extracted with EA (10 mL×3). The combined organic layers were washed by water and brine, dried over Na₂SO₄. The drying agent was filtered off and the filtrate was concentrated under the reduced pressure to give the residue, which was purified with Prep-TLC (silica gel, eluting with 10% methanol and 1% NH3 in DCM) to afford tert-butyl 4-(4-cyano-5-(4-((3-(piperidin-1-yl)propyl)amino)-1,6-naphthyridin-2-yl)-1-((2-(trimethylsilyl)ethoxy)methyl)-1H-benzo[d]imidazole-2-carboxamido)piperidine-1-carboxylate (15 mg, 13%) as a yellow solid. HPLC/UV purity: 90%; LC-MS (ESI): 768.1 (M+1)⁺.

Step 9

The mixture of tert-butyl 4-(4-cyano-5-(4-((3-(piperidin-1-yl)propyl)amino)-1,6-naphthyridin-2-yl)-1-((2-(trimethylsilyl)ethoxy)methyl)-1H-benzo[d]imidazole-2-carboxamido)piperidine-1-carboxylate (15 mg, 0.019 mmol) and TFA (1 mL) in DCM (1 mL) was stirred at room temperature for 18 hrs. The solvent was removed under reduced pressure to give the crude mixture, which was purified with Prep-HPLC (Welch, XB-C18, 21.2 mm×250 mm, 10 um, eluting with 20% CH3CN in 1‰ TFA in H₂O) to afford 4-cyano-5-(4-((3-(piperidin-1-yl)propyl)amino)-1,6-naphthyridin-2-yl)-N-(piperidin-4-yl)-1H-benzo[d]imidazole-2-carboxamide (5 mg, 50%) as a TFA salt. HPLC/UV purity: 100%; LC-MS (ESI): 538.3 (M+1)⁺. ¹H NMR (METHANOL-d₄) δ: 9.64 (s, 1H), 8.74 (d, J=6.1 Hz, 1H), 8.52 (s, 1H), 8.36 (d, J=1.5 Hz, 1H), 7.83 (d, J=6.1 Hz, 1H), 7.24 (s, 1H), 4.10-4.25 (m, 1H), 3.74 (t, J=6.9 Hz, 2H), 3.36-3.55 (m, 4H), 3.24-3.28 (m, 2H), 3.10 (t, J=12.5, 2.7 Hz, 2H), 2.86 (t, J=12.5 Hz, 2H), 2.10-2.28 (m, 4H), 1.81-1.95 (m, 4H), 1.62-1.80 (m, 3H), 1.42-1.50 (m, 1H).

Example 100: Synthesis of (4-ethylpiperazin-1-yl)(5-(4-((4-(pyrrolidin-1-ylmethyl)phenyl)amino)-1,6-naphthyridin-2-yl)-1H-benzo[d]imidazol-2-yl)methanone

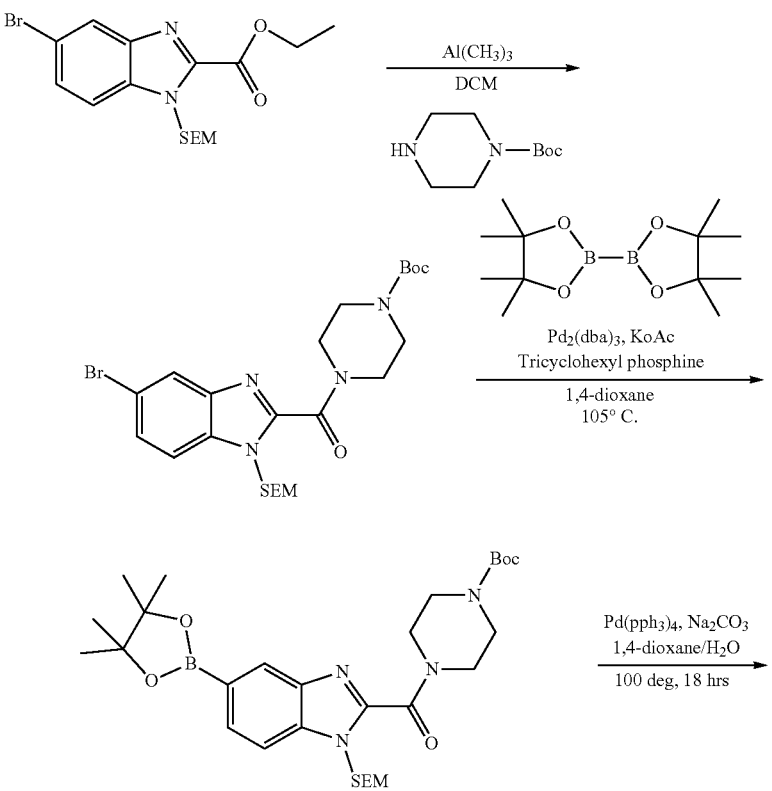

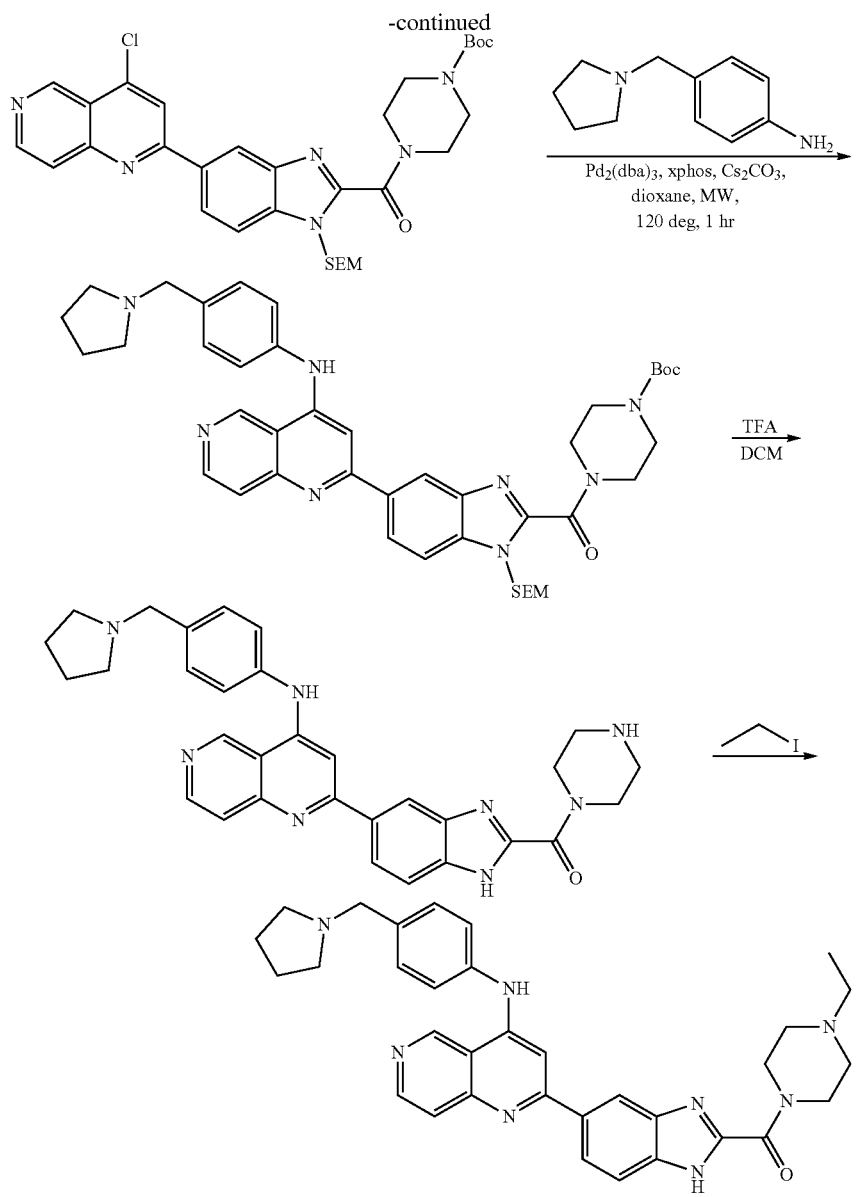

Step 1

To a solution of tert-butyl piperazine-1-carboxylate (2.2 g, 12 mmol) in DCM (10 mL) was added Al(CH₃)₃ (1N in toluene, 12 mL, 12 mmol) dropwise at 0° C. under nitrogen. The mixture was stirred at room temperature for 30 mins, and then it was cooled to 0° C. again. A solution of ethyl 5-bromo-1-((2-(trimethylsilyl)ethoxy)methyl)-1H-benzo[d]imidazole-2-carboxylate (950 mg, 2.31 mmol) in DCM (5 mL) was added drop wise. The resulting reaction mixture was stirred at room temperature for 18 hrs. The reaction mixture was quenched by water (10 mL), extracted with DCM (10 mL×3). The combined organic layers were washed with water and brine, dried over Na₂SO₄, filtered. The filtrate was concentrated in vacuo to give the residue which was purified by flash column chromatography (silica gel, eluting with PE to 30% EA/PE) to afford tert-butyl 4-(5-bromo-1-((2-(trimethylsilyl)ethoxy)methyl)-1H-benzo[d]imidazole-2-carbonyl)piperazine-1-carboxylate (1.2 g, 95%) as a white solid. HPLC/UV purity: 90%; LC-MS (ESI): 539.3 (M+1)⁺.

Step 2

The mixture of tert-butyl 4-(5-bromo-1-((2-(trimethylsilyl)ethoxy)methyl)-1H-benzo[d]imidazole-2-carbonyl)piperazine-1-carboxylate (1.5 g, 2.64 mmol), 4,4,4',4',5,5,5',5'-octamethyl-2,2'-bi(1,3,2-dioxaborolane) (804 mg, 3.17 mmol), Pd₂(dba)₃ (241 mg, 0.264 mmol), tricyclohexylphosphine (147 mg, 0.53 mmol) and KOAc (517 mg, 5.28 mmol) in 1,4-Dioxane (20 mL) was heated at 100° C. for 18 hrs under N₂ atmosphere. The reaction mixture was cooled to room temperature and filtered by a pad of celite. The resulting filtrate was concentrated under reduced pressure to give the crude mixture, which was diluted with EA (30 mL), washed by water and brine, dried over Na₂SO₄, and filtered. The filtrate was concentrated in vacuo to give a crude boric acid ester, which was purified by flash column chromatography (silica gel, eluting with 30% EA in PE) to afford tert-butyl 4-(5-(4,4,5,5-tetramethyl-1,3,2-dioxaborolan-2-yl)-1-((2-(trimethylsilyl)ethoxy)methyl)-1H-benzo[d]imidazole-2-carbonyl)piperazine-1-carboxylate (1.3 g, 83%) as a oil. HPLC/UV purity: 60%; LC-MS (ESI): 587.2 (M+1)⁺.

Step 3

The mixture of 2,4-dichloro-1,6-naphthyridine (340 mg, 1.7 mmol), tert-butyl 4-(5-(4,4,5,5-tetramethyl-1,3,2-dioxaborolan-2-yl)-1-((2-(trimethylsilyl)ethoxy)methyl)-1H-benzo[d]imidazole-2-carbonyl)piperazine-1-carboxylate (1.3 mg, 2.21 mmol), Pd(PPh₃)₄ (196 mg, 0.17 mmol), and Na₂CO₃ (360 mg, 3.4 mmol) in 1,4-Dioxane (10 mL) and H₂O (2 mL) was heated at 100° C. for 18 hrs under N₂ atmosphere. The reaction mixture was cooled to room temperature and filtered by a pad of celite. The resulting filtrate was concentrated under reduced pressure to give the residue, which was diluted with EA (30 mL), then washed by water and brine, dried over Na₂SO₄, filtered. The filtrate was concentrated in vacuo to give a crude boric acid ester, which was purified with Combiflash (silica gel, eluting with 5% MeOH in DCM) to afford tert-butyl 4-(5-(4-chloro-1,6-naphthyridin-2-yl)-1-((2-(trimethylsilyl)ethoxy)methyl)-1H-benzo[d]imidazole-2-carbonyl)piperazine-1-carboxylate (500 mg, 50%) as a oil. HPLC/UV purity: 60%; LC-MS (ESI): 623.1 (M+1)⁺.

Step 4

A 20-mL microwave vial was charged with tert-butyl 4-(5-(4-chloro-1,6-naphthyridin-2-yl)-1-((2-(trimethylsilyl)ethoxy)methyl)-1H-benzo[d]imidazole-2-carbonyl)piperazine-1-carboxylate (170 mg, 0.273 mmol), 4-(pyrrolidin-1-ylmethyl)aniline (53 mg, 0.3 mmol), Pd₂(dba)₃ (25 mg, 0.027 mmol), Xphos (31 mg, 0.054 mmol), Cs₂CO₃ (138 mg, 1.31 mmol) and 1,4-dioxane (10 mL). The sealed vial with the resulting brown solution was heated for 1 hr in a Biotage Initiator Eight Microwave Reactor at a constant temperature of 120° C. The resulting solutions were concentrated by rotary evaporation (55° C., 20 mmHg). The crude mixture was purified by Prep-TLC (silica gel, eluting with 10% methanol in DCM) to give tert-butyl 4-(5-(4-((4-(pyrrolidin-1-ylmethyl)phenyl)amino)-1,6-naphthyridin-2-yl)-1-((2-(trimethylsilyl)ethoxy)methyl)-1H-benzo[d]imidazole-2-carbonyl)piperazine-1-carboxylate (90 mg, 43%) as a oil. HPLC/UV purity: 90%; LC-MS (ESI): 763.2 (M+1)⁺.

Step 5

The mixture of tert-butyl 4-(5-(4-((4-(pyrrolidin-1-ylmethyl)phenyl)amino)-1,6-naphthyridin-2-yl)-1-((2-(trimethylsilyl)ethoxy)methyl)-1H-benzo[d]imidazole-2-carbonyl)piperazine-1-carboxylate (15 mg, 0.019 mmol) and TFA (1 mL) in DCM (1 mL) was stirred at room temperature for 18 hrs. The solvent was removed under reduced pressure to give the crude mixture, which was purified with Prep-HPLC (Welch, XB-C18, 21.2 mm×250 mm, 10 um, eluting with 20% CH3CN in 1‰ TFA in H₂O) to afford piperazin-1-yl (5-(4-((4-(pyrrolidin-1-ylmethyl)phenyl)amino)-1,6-naphthyridin-2-yl)-1H-benzo[d]imidazol-2-yl)methanone (5 mg, 50%) as a TFA salt. HPLC/UV purity: 100%; LC-MS (ESI): 538.2 (M+1)⁺. ¹H NMR (METHANOL-d₄) δ: 9.91 (s, 1H), 8.94 (d, J=5.5 Hz, 1H), 8.30 (s, 1H), 8.03 (d, J=5.8 Hz, 1H), 7.87 (s, 2H), 7.71-7.84 (m, 4H), 7.37 (s, 1H), 4.50 (s, 2H), 4.06-4.09 (m, 2H), 3.55-3.60 (m, 2H), 3.36-3.43 (m, 4H), 3.263.29 (m, 4H), 2.19-2.23 (m, 2H), 2.05-2.06 (m, 2H).

Step 6

The mixture of piperazin-1-yl(5-(4-((4-(pyrrolidin-1-ylmethyl)phenyl)amino)-1,6-naphthyridin-2-yl)-1H-benzo[d]imidazol-2-yl)methanone (30 mg, 0.059 mmol) and K₂CO₃ (33 mg, 0.24 mmol) in DMF (1 mL) was stirred at room temperature for 30 min, and then iodoethane (10 mg, 0.064 mmol) was added drop wise. The resulting reaction mixture was stirred at room temperature for 2 hrs. The reaction mixture was poured into water (20 mL), extracted with EA (10 mL×3). The combined organic layers were washed by water and brine, dried over Na₂SO₄. The drying agent was filtered off and the filtrate was concentrated under reduced pressure to give the crude mixture, which was purified with Prep-HPLC to give (4-ethylpiperazin-1-yl)(5-(4-((4-(pyrrolidin-1-ylmethyl)phenyl)amino)-1,6-naphthyridin-2-yl)-1H-benzo[d]imidazol-2-yl)methanone (5 mg, 15%), HPLC/UV purity: 100%; LC-MS (ESI): 561.2 (M+1)⁺. ¹H NMR (METHANOL-d₄) δ: 9.80 (s, 1H), 8.83 (d, J=6.1 Hz, 1H), 8.18 (s, 1H), 7.91 (d, J=6.1 Hz, 1H), 7.70-7.80 (m, 2H), 7.58-7.70 (m, 4H), 7.25 (s, 1H), 4.38 (s, 2H), 3.59-3.62 (m, 2H), 3.36-3.58 (m, 4H), 3.10-3.20 (m, 8H), 2.06-2.16 (m, 2H), 1.92-1.95 (m, 2H), 1.31 (t, J=7.3 Hz, 3H).

Example 101: Synthesis of N-(3-(piperidin-1-yl)propyl)-5-(4-((4-(pyrrolidin-1-ylmethyl)phenyl)amino)-1,6-naphthyridin-2-yl)-1H-benzo[d]imidazole-2-carboxamide

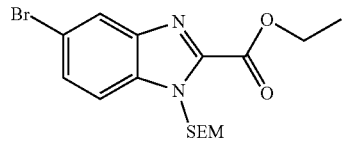
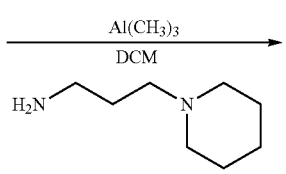

-continued
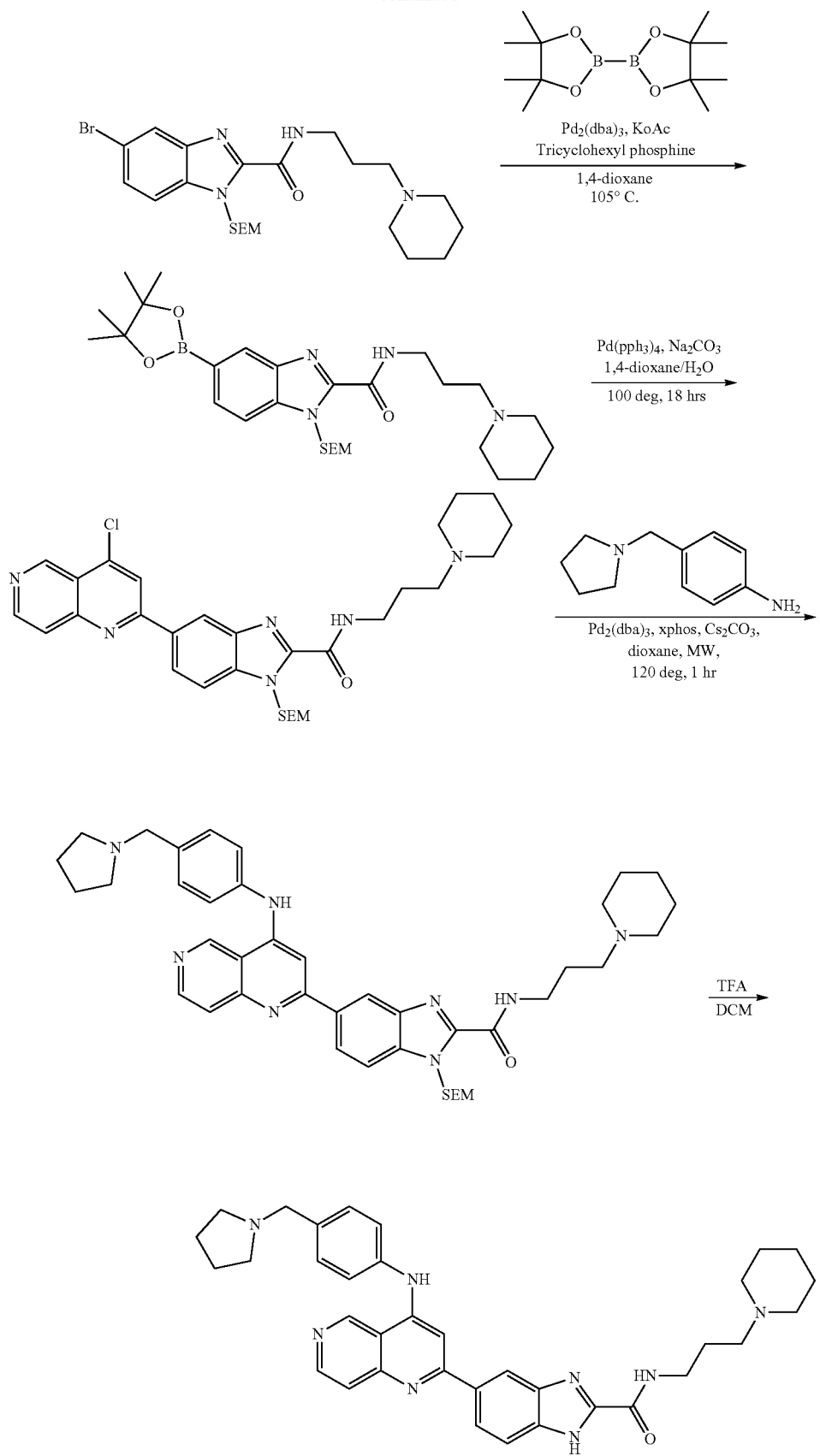

Steps 1-4

Steps 1-4 were completed in a similar fashion as Example 100, Steps 1-4.

Step 5

The mixture of N-(3-(piperidin-1-yl)propyl)-5-(4-((4-(pyrrolidin-1-ylmethyl)phenyl)amino)-1,6-naphthyridin-2-yl)-1-((2-(trimethylsilyl)ethoxy)methyl)-1H-benzo[d]imidazole-2-carboxamide (100 mg, 0.139 mmol) and TFA (1 mL) in DCM (1 mL) was stirred at rt for 2 hrs. The solvent was removed under reduced pressure to give the crude mixture, which was purified with Prep-HPLC (Welch, XB-C18, 21.2 mm×250 mm, 10 um, eluting with 20% CH₃CN in 1‰ TFA in H₂O) to afford N-(3-(piperidin-1-yl)propyl)-5-(4-((4-(pyrrolidin-1-ylmethyl)phenyl)amino)-1,6-naphthyridin-2-yl)-1H-benzo[d]imidazole-2-carboxamide (75 mg, 92%) as a TFA salt. HPLC/UV purity: 100%; LC-MS (ESI): 589.2 (M+1)⁺. ¹H NMR (METHANOL-d₄) δ: 9.92 (s, 1H), 8.95 (d, J=6.1 Hz, 1H), 8.30 (s, 1H), 8.03 (d, J=6.1 Hz, 1H), 7.70-7.92 (m, 6H), 7.35 (s, 1H), 4.50 (s, 2H), 3.53-3.67 (m, 6H), 3.18-3.30 (m, 4H), 2.90-3.05 (m, 2H), 2.14-2.24 (m, 2H), 2.04-1.99 (m, 6H), 1.73-1.92 (m, 3H), 1.50-1.54 (m, 1H).

Example 102: Synthesis of N-(2-(dimethylamino)ethyl)-5-(4-((4-(pyrrolidin-1-ylmethyl)phenyl)amino)-1,6-naphthyridin-2-yl)-1H-benzo[d]imidazole-2-carboxamide

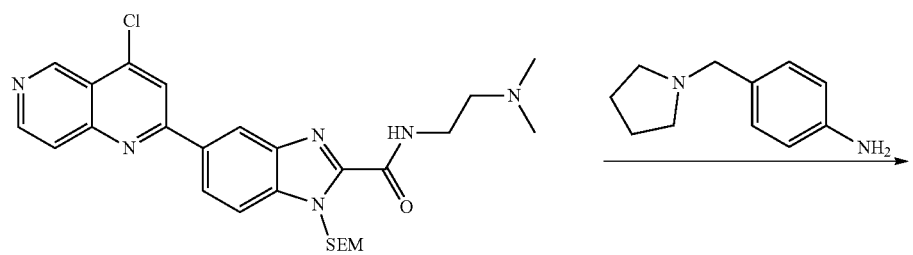

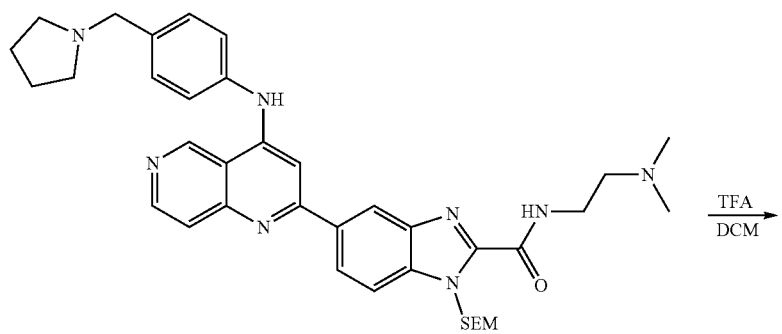

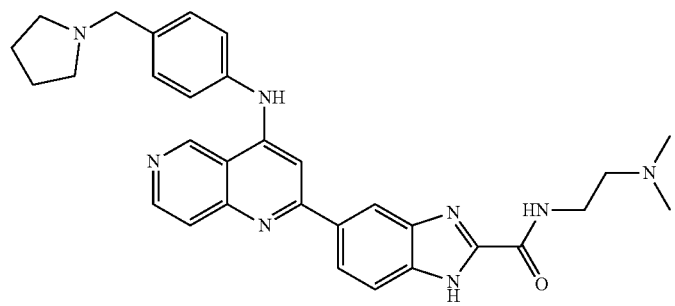

Step 1

Step 1 was completed in a similar fashion as Example 100, Step 4.

Step 2

The mixture of N-(2-(dimethylamino)ethyl)-5-(4-((4-(pyrrolidin-1-ylmethyl)phenyl)amino)-1,6-naphthyridin-2-yl)-1-((2-(trimethylsilyl)ethoxy)methyl)-1H-benzo[d]imidazole-2-carboxamide (15 mg, 0.022 mmol) and TFA (1 mL) in DCM (1 mL) was stirred at room temperature for 2 hrs. The solvent was removed under reduced pressure to give the crude mixture, which was purified with Prep-HPLC (Welch, XB-C18, 21.2 mm×250 mm, 10 um, eluting with 20% CH$_3$CN in 1‰ TFA in H$_2$O) to afford N-(2-(dimethylamino)ethyl)-5-(4-((4-(pyrrolidin-1-ylmethyl)phenyl)amino)-1,6-naphthyridin-2-yl)-1H-benzo[d]imidazole-2-carboxamide (6 mg, 54%) as a TFA salt. HPLC/UV purity: 100%; LC-MS (ESI): 535.3 (M+1)$^+$. $^1$H NMR (METHANOL-d$_4$) δ: 9.76 (s, 1H), 8.80 (d, J=6.1 Hz, 1H), 8.20 (s, 1H), 7.90 (d, J=6.1 Hz, 1H), 7.71-7.78 (m, 2H), 7.58-7.69 (m, 4H), 7.28 (s, 1H), 4.38 (s, 2H), 3.75 (t, J=5.8 Hz, 2H), 3.48 (br. s., 2H), 3.34 (t, J=6.0 Hz, 2H), 3.16-3.20 (m, 2H), 2.90 (s, 6H), 2.05-2.12 (m, 2H), 1.95-1.95 (m, 2H).

Example 103: Synthesis of N-(3-(4-methylpiperazin-1-yl)propyl)-5-(4-((4-(pyrrolidin-1-ylmethyl)phenyl)amino)-1,6-naphthyridin-2-yl)-1H-benzo[d]imidazole-2-carboxamide

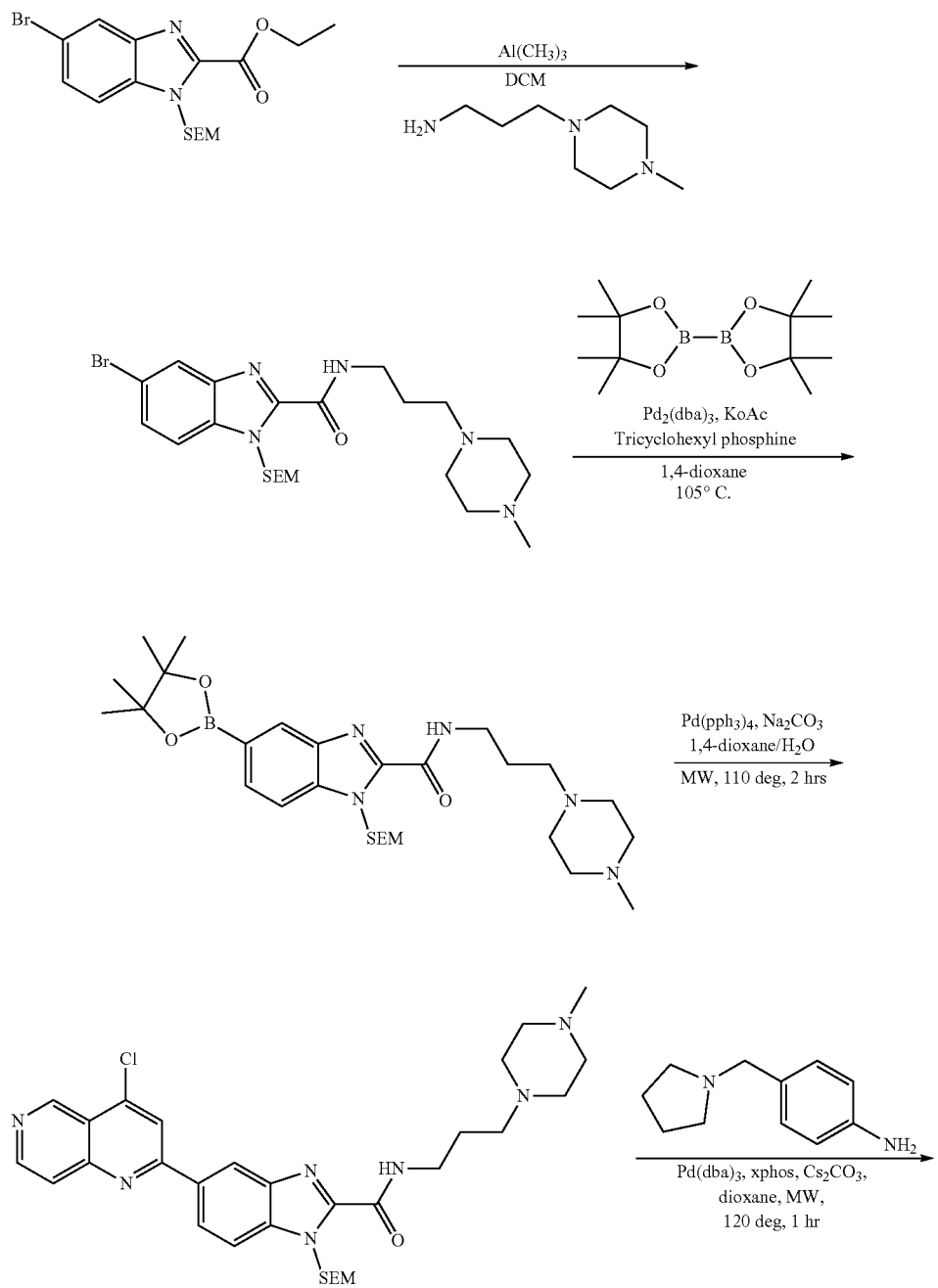

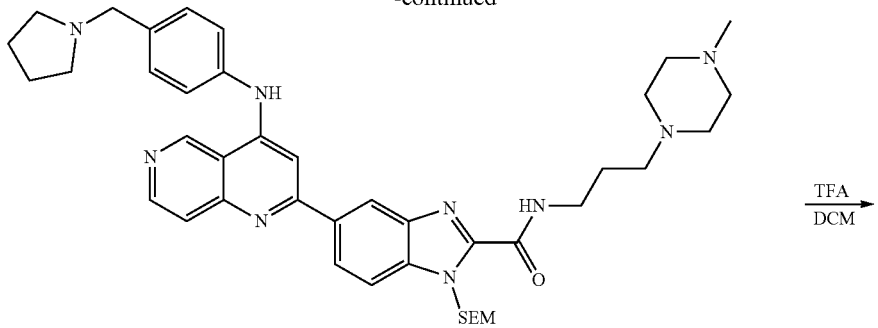

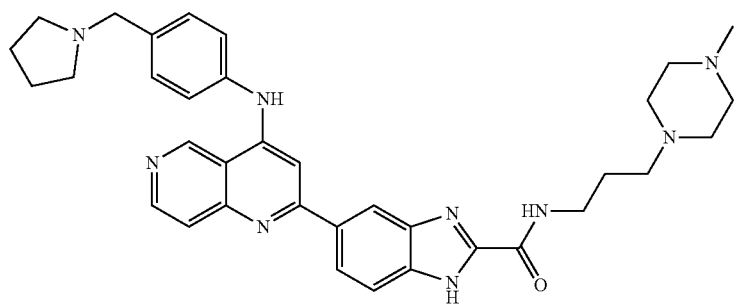

Steps 1-4

Steps 1-4 were completed in a similar fashion as Example 100, Steps 1-4.

Step 5

The mixture of N-(3-(4-methylpiperazin-1-yl)propyl)-5-(4-((4-(pyrrolidin-1-ylmethyl)phenyl)amino)-1,6-naphthyridin-2-yl)-1-((2-(trimethylsilyl)ethoxy)methyl)-1H-benzo[d]imidazole-2-carboxamide (90 mg, 0.12 mmol) and TFA (1 mL) in DCM (1 mL) was stirred at room temperature for 2 hrs. The solvent was removed under reduced pressure to give the crude mixture, which was purified with Prep-HPLC (Welch, XB-C18, 21.2 mm×250 mm, 10 um, eluting with 20% CH$_3$CN in 1‰ TFA in H$_2$O) to afford N-(3-(4-methylpiperazin-1-yl)propyl)-5-(4-((4-(pyrrolidin-1-ylmethyl)phenyl)amino)-1,6-naphthyridin-2-yl)-1H-benzo[d]imidazole-2-carboxamide (70 mg, 97%) as a TFA salt. HPLC/UV purity: 100%; LC-MS (ESI): 604.2 (M+1)$^+$. $^1$H NMR (METHANOL-d$_4$) δ: 9.92 (s, 1H), 8.95 (d, J=6.1 Hz, 1H), 8.29 (s, 1H), 8.03 (d, J=6.1 Hz, 1H), 7.70-7.91 (m, 6H), 7.35 (s, 1H), 4.50 (s, 2H), 3.58 (t, J=6.7 Hz, 4H), 3.46-3.49 (m, 4H), 3.16-3.32 (m, 6H), 3.01 (t, J=7.3 Hz, 2H), 2.93 (s, 3H), 2.05-2.24 (m, 2H), 2.03-2.16 (m, 4H).

Example 104: Synthesis of 5-(4-((3-(piperidin-1-yl)propyl)amino)-1,6-naphthyridin-2-yl)-N-(2-(pyridin-4-yl)ethyl)-1H-benzo[d]imidazole-2-carboxamide

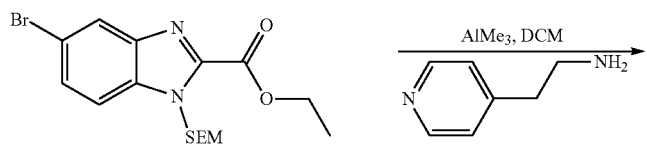

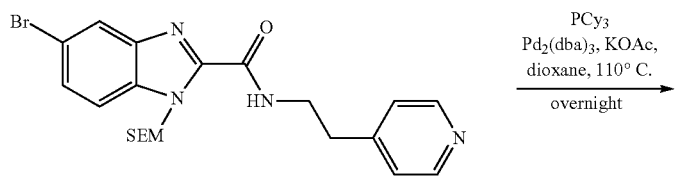

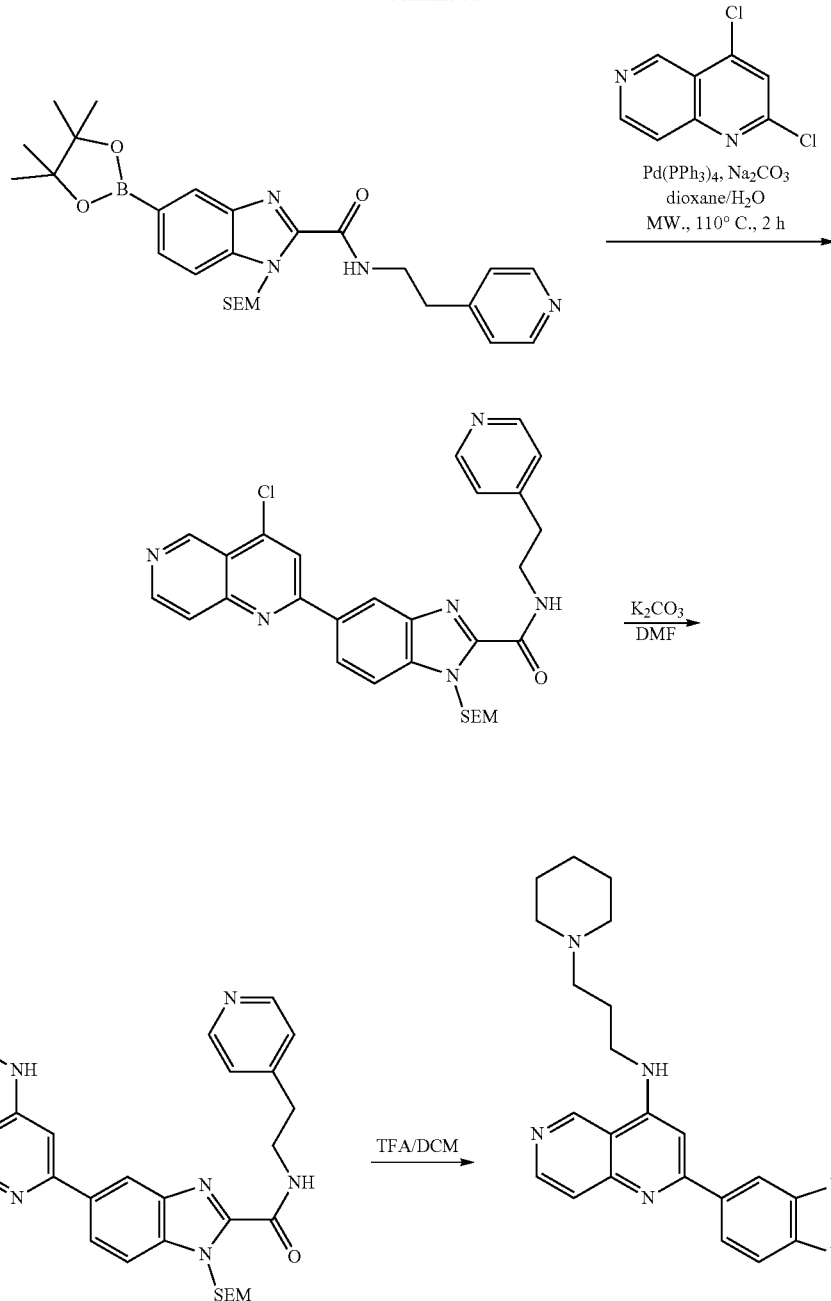

Steps 1-3

Steps 1-3 were completed in a similar fashion as Example 100, Steps 1-3.

Step 4

Step 4 was completed in a similar fashion as Example 99, Step 8.

Step 5

The mixture of 5-(4-((3-(piperidin-1-yl)propyl)amino)-1,6-naphthyridin-2-yl)-N-(2-(pyridin-4-yl)ethyl)-1-((2-(trimethylsilyl)ethoxy)methyl)-1H-benzo[d]imidazole-2-carboxamide (50 mg, 0.075 mmol) and TFA (1 mL) in DCM (1 mL) was heated at 40° C. for 2 hrs., The solvent was removed under reduced pressure to give the crude product, which was purified with Prep-HPLC (Welch, XB-C18, 21.2 mm×250 mm, 10 um, eluting with 20% CH$_3$CN in 1‰ TFA in H$_2$O) to afford 5-(4-((3-(piperidin-1-yl)propyl)amino)-1,6-naphthyridin-2-yl)-N-(2-(pyridin-4-yl)ethyl)-1H-benzo[d]imidazole-2-carboxamide (40 mg, 95%) as a TFA salt. HPLC/UV purity: 100%; LC-MS (ESI): 535.3 (M+1)$^+$. $^1$H NMR (METHANOL-d$_4$) δ: 9.75 (s, 1H), 8.89 (d, J=5.8 Hz, 1H), 8.77 (d, J=6.1 Hz, 2H), 8.38 (s, 1H), 8.06 (d, J=6.1 Hz, 2H), 7.96-8.02 (m, 1H), 7.89-7.96 (m, 2H), 7.29 (s, 1H), 3.83-3.95 (m, 4H), 3.61 (d, J=12.5 Hz, 2H), 2.97 (t, J=11.9 Hz, 2H), 2.26-2.40 (m, 2H), 1.97 (d, J=14.3 Hz, 2H), 1.71-1.90 (m, 3H), 1.48-1.53 (m, 1H).

Example 105: Synthesis of N-(1-Methylpiperidin-4-yl)-6-(4-(3-(piperidin-1-yl)propylamino)-1,6-naphthyridin-2-yl)-3H-imidazo[4,5-b]pyridine-2-carboxamide
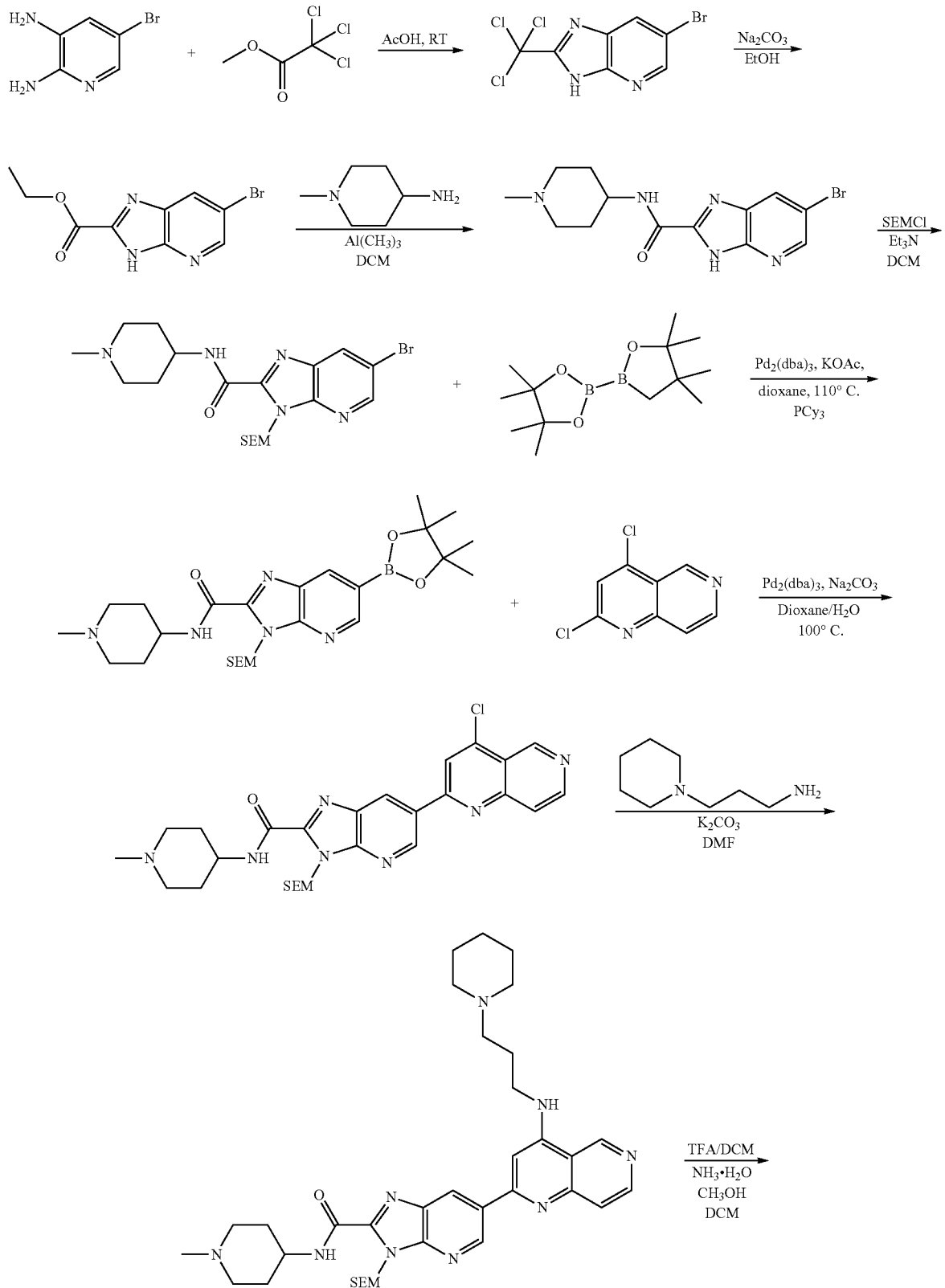

-continued

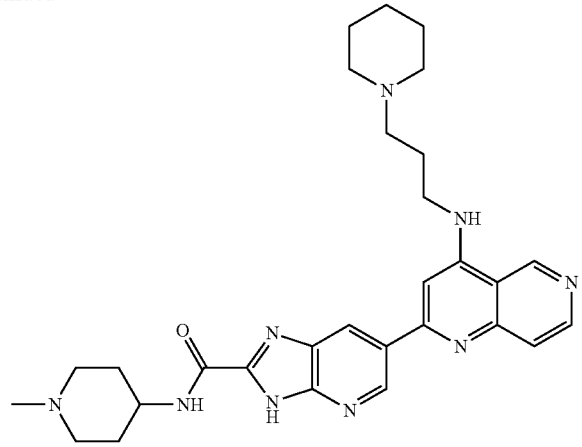

Step 1

The solution of 5-bromopyridine-2,3-diamine (5.64 g, 30 mmol) in AcOH (30 mL) was cooled to 0° C. Then methyl 2,2,2-trichloroacetate (6.336 g, 36 mmol) was added drop wise. The reaction mixture was stirred at room temperature overnight. After adding water (1000 mL), the mixture was filtered to give 6-bromo-2-(trichloromethyl)-3H-imidazo[4,5-b]pyridine (4.52 g, 85.9%) as white solid. HPLC/UV purity: 95%; LCMS (ESI): 315.8 (M+1)$^+$.

Step 2

The mixture of 6-bromo-2-(trichloromethyl)-3H-imidazo[4,5-b]pyridine (4.53 g, 14.38 mmol) and $Na_2CO_3$ (2.28 g, 21.5 mmol) in EtOH (100 mL) was stirred at 70° C. for 3 hours. Then the mixture was diluted with water (200 mL), extracted with EA (100 mL×2). The combined organic layer was washed with brine, dried over $Na_2SO_4$ and concentrated. The crude product was purified by silica gel column chromatography to give ethyl-6-bromo-3H-imidazo[4,5-b]pyridine-2-carboxylate (2.83 g, 73.5%) as white solid. HPLC/UV purity: 90%; LCMS (ESI): 269.8 (M+1)$^+$.

Step 3

To the solution of ethyl-6-bromo-3H-imidazo[4,5-b]pyridine-2-carboxylate (2.7 g, 10 mmol) in DCM (50 mL) was added $Al(CH_3)_3$ (50 mL, 1M) drop wise at 0° C. The mixture was warmed to room temperature and stirred 30 min. Then 1-methylpiperidin-4-amine (5.7 g, 50 mmol) was added at 0° C. and the mixture was stirred at room temperature overnight. The mixture was diluted with DCM, washed with water 200 mL, dried over $Na_2SO_4$, filtered and concentrated. The crude product was purified by silica gel column chromatography to give 6-bromo-N-(1-methylpiperidin-4-yl)-3H-imidazo[4,5-b]pyridine-2-carboxamide (2.06 g, 61%) as white solid. HPLC/UV purity: 95%; LCMS (ESI): 340.8 (M+1)$^+$.

Step 4

The solution of 6-bromo-N-(1-methylpiperidin-4-yl)-3H-imidazo[4,5-b]pyridine-2-carboxamide (1.011 g, 3 mmol) and $Et_3N$ (606 mg, 6 mmol) in DCM (120 mL) was added SEMCl (664 mg, 4 mmol) drop wise. Then the mixture was stirred at room temperature overnight. The solvent was removed and the crude product was purified by silica gel column chromatography to give 6-bromo-N-(1-methylpiperidin-4-yl)-3-((2-(trimethylsilyl)ethoxy)methyl)-3H-imidazo[4,5-b]pyridine-2-carboxamide (960 mg, 68%) as dark solid. HPLC/UV purity: 95%; LCMS (ESI): 469.9 (M+1)$^+$.

Step 5

The mixture of 6-bromo-N-(1-methylpiperidin-4-yl)-3-((2-(trimethylsilyl)ethoxy)methyl)-3H-imidazo[4,5-b]pyridine-2-carboxamide (910 mg, 1.94 mmol), 4,4,4',4',5,5,5',5'-octamethyl-2,2'-bi(1,3,2-dioxaborolane) (741 mg, 2.91 mmol), KOAc (490 mg, 5 mmol), $PCy_3$ (112 mg, 0.4 mmol) and $Pd_2(dba)_3$ (183 mg, 0.2 mmol) in 1,4-dioxane (20 mL) was stirred at 110° C. overnight. The reaction mixture was filtered, concentrated and purified by silica gel column chromatography to give N-(1-methylpiperidin-4-yl)-6-(4,4,5,5-tetramethyl-1,3,2-dioxaborolan-2-yl)-3-((2-(trimethylsilyl)ethoxy)methyl)-3H-imidazo[4,5-b]pyridine-2-carboxamide (800 mg, 80%) as white solid. HPLC/UV purity: 90%; LCMS (ESI): 515.8 (M+1)$^+$.

Step 6

The mixture of N-(1-methylpiperidin-4-yl)-6-(4,4,5,5-tetramethyl-1,3,2-dioxaborolan-2-yl)-3-((2-(trimethylsilyl)ethoxy)methyl)-3H-imidazo[4,5-b]pyridine-2-carboxamide (515 mg, 1 mmol), 2,4-dichloro-1,6-naphthyridine (198 mg, 1 mmol), $Na_2CO_3$ (212 mg, 2 mmol), Pd $(PPh_3)_4$ (115 mg, 0.1 mmol) in 1,4-Dioxane (12 mL) and $H_2O$ (2 mL) was stirred in a Biotage Initiator Eight Microwave Reactor at 100° C. for 2 hrs. Then the mixture was extracted with EA (100 mL×2), washed with $H_2O$ (100 mL) and brine, dried over $Na_2SO_4$, concentrated and purified by silica gel chromatography to give 6-(4-chloro-1,6-naphthyridin-2-yl)-N-(1-methylpiperidin-4-yl)-3-((2-(trimethylsilyl)ethoxy)methyl)-3H-imidazo[4,5-b]pyridine-2-carboxamide (300 mg, 54.3%) as white solid. HPLC/UV purity: 90%; LCMS (ESI): 551.7 (M+1)$^+$.

Step 7

The mixture of 6-(4-chloro-1,6-naphthyridin-2-yl)-N-(1-methylpiperidin-4-yl)-3-((2-(trimethylsilyl)ethoxy)methyl)-3H-imidazo[4,5-b]pyridine-2-carboxamide (300 mg, 0.54 mmol), 3-(piperidin-1-yl)propan-1-amine (142 mg, 1.0 mmol) and $K_2CO_3$ (138 mg, 1 mmol) in DMF (10 mL) was stirred at 70° C. overnight. The mixture was filtered, concentrated and purified by silica gel chromatography to give N-(1-methylpiperidin-4-yl)-6-(4-(3-(piperidin-1-yl)propylamino)-1,6-naphthyridin-2-yl)-3-((2-(trimethylsilyl)ethoxy)methyl)-3H-imidazo[4,5-b]pyridine-2-carboxamide (135 mg, 38%) as white solid. HPLC/UV purity: 90%; LCMS (ESI): 657.9 (M+1)$^+$.

Step 8

The solution of N-(1-methylpiperidin-4-yl)-6-(4-(3-(piperidin-1-yl)propylamino)-1,6-naphthyridin-2-yl)-3-((2-(trimethylsilyl)ethoxy)methyl)-3H-imidazo[4,5-b]pyridine-2-carboxamide (132 mg, 0.2 mmol) in TFA/DCM (1 mL/10 mL) was stirred at room temperature overnight. Then the solvent was removed. The residue was dissolved in DCM/CH$_3$OH/NH$_3$·H$_2$O (10 mL/1 mL/1 mL) and stirred at room temperature overnight. The reaction mixture was concentrated and purified by Prep-HPLC (Welch, XB-C18, 21.2 mm×250 mm, 10 um, eluting with 20% CH$_3$CN in 1‰ TFA in H$_2$O) to give N-(1-methylpiperidin-4-yl)-6-(4-(3-(piperidin-1-yl)propylamino)-1,6-naphthyridin-2-yl)-3H-imidazo[4,5-b]pyridine-2-carboxamide (50 mg, 47.6%) as TFA solid. HPLC/UV purity: 100%; LCMS (ESI): 527.8 (M+1)$^+$. $^1$H NMR (METHANOL-d$_4$) δ: 9.79 (s, 1H), 9.15 (s, 1H), 8.87 (d, J=6.0 Hz, 1H), 8.80 (s, 1H), 7.95 (d, J=5.4 Hz, 1H), 7.37 (s, 1H), 4.28-4.24 (m, 1H), 3.87 (t, J=6.0 Hz, 2H), 3.67-3.60 (m, 4H), 3.35-3.33 (m, 2H), 3.24 (t, J=12.0 Hz, 2H), 2.99-2.97 (m, 2H), 2.94 (s, 3H), 2.36-2.31 (m, 4H), 2.08-2.0 (m, 2H), 1.98-1.96 (m, 2H), 1.87-1.82 (m, 3H), 1.6-1.51 (m, 1H).

Example 106: Synthesis of N-(1-methylpiperidin-4-yl)-2-(4-(4-(3-(piperidin-1-yl)propylamino)-1,6-naphthyridin-2-yl)phenoxy)acetamide

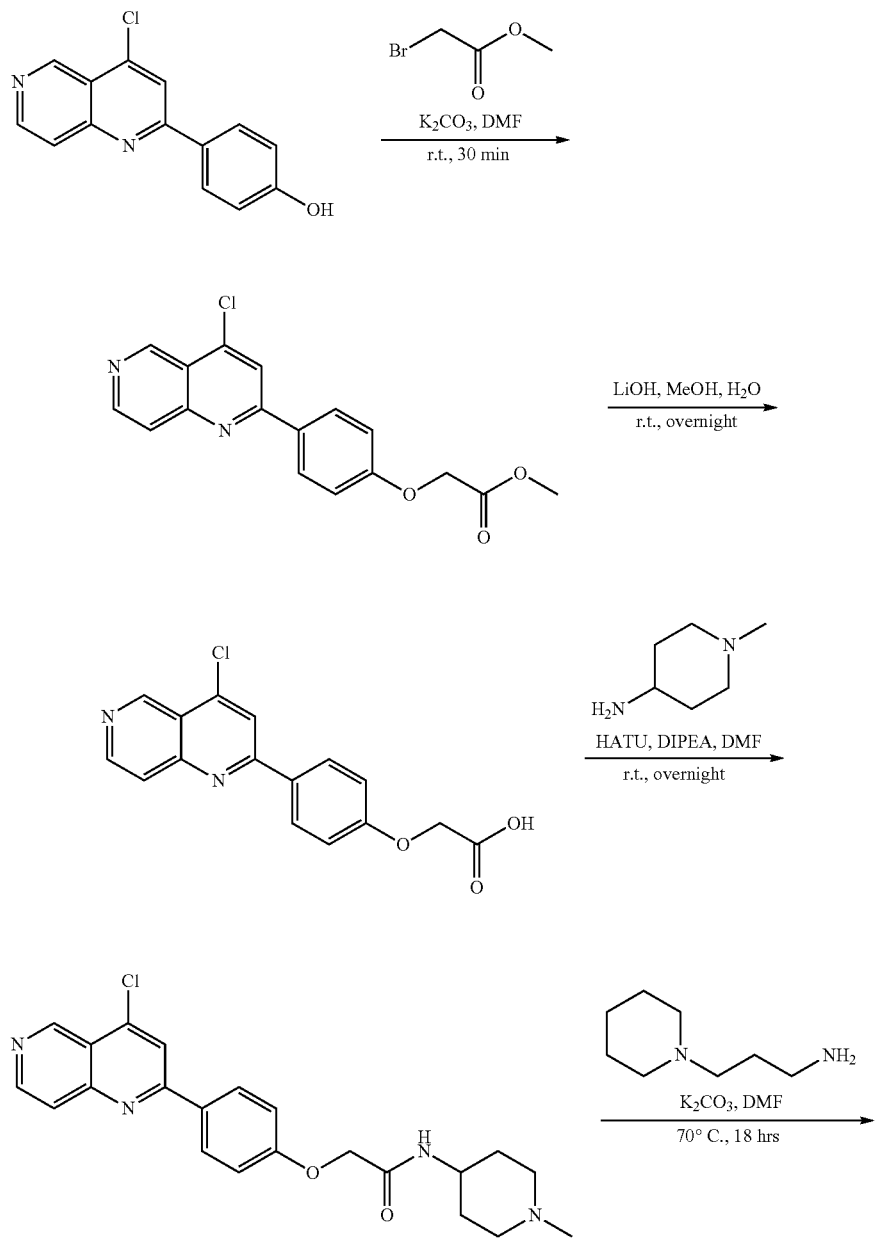

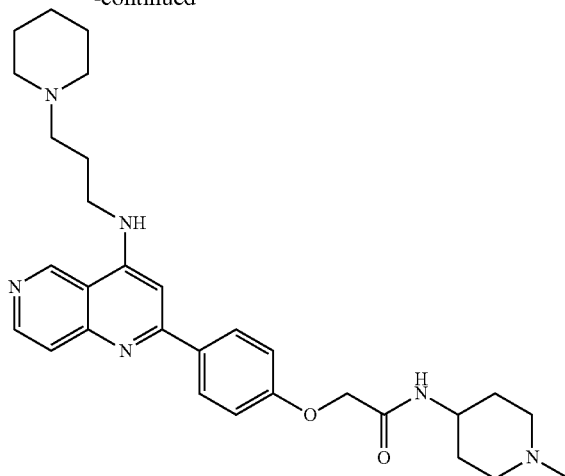

Step 1

The mixture of 4-(4-chloro-1,6-naphthyridin-2-yl)phenol (1 g, 3.89 mmol), methyl 2-bromoacetate (591 mg, 3.89 mmol) and $K_2CO_3$ (1.07 g, 7.78 mmol) in DMF (1 mL) was stirred at room temperature for 30 min. The reaction mixture was poured into water (20 mL), extracted with EA (20 mL×3). The combined organic layers were washed by water (10 mL×3) and brine (10 mL), dried over $Na_2SO_4$. Filtered and the filtrate was concentrated under the reduced pressure to give the residue which was purified by silica gel flash column chromatography to afford methyl 2-(4-(4-chloro-1, 6-naphthyridin-2-yl)phenoxy)acetate (500 mg, 38%). LC-MS (ESI): 329.3 (M+1)+.

Step 2

The mixture of methyl 2-(4-(4-chloro-1,6-naphthyridin-2-yl)phenoxy)acetate (500 mg, 1.51 mmol) and 1N aq. LiOH solution (6 ml, 6.07 mmol) in MeOH (5 mL) was stirred at room temperature overnight. The mixture was acidified with 1N aq. HCl solution to pH=2, then concentrated to give the crude product which was used directly in the next step without further purification. LC-MS (ESI): 315.2 (M+1)+.

Step 3

The mixture of 2-(4-(4-chloro-1,6-naphthyridin-2-yl)phenoxy)acetic acid (100 mg, 0.32 mmol), 1-methylpiperidin-4-amine (72 mg, 0.63 mmol), HATU (145 mg, 0.38 mmol) and DIPEA (82 mg 0.64 mmol) in DMF (1 mL) was stirred at room temperature overnight. Water (30 mL) was added, and then the mixture was extracted with EA (20 mL×3). The combined organic layers were washed with water (20 mL×3) and brine (20 mL×1), dried over $Na_2SO_4$, filtered and concentrated. The residue was purified by Prep-TLC to obtain 2-(4-(4-chloro-1, 6-naphthyridin-2-yl)phenoxy)-N-(1-methylpiperidin-4-yl)acetamide (46 mg, 37%). LC-MS (ESI): 411.3 (M+1)+.

Step 4

The mixture of 2-(4-(4-chloro-1,6-naphthyridin-2-yl)phenoxy)-N-(1-methylpiperidin-4-yl)acetamide (46 mg, 0.11 mmol), 3-(piperidin-1-yl)propan-1-amine (23 mg, 0.16 mmol) and $K_2CO_3$ (30 mg, 0.22 mmol) in DMF (1 mL) was heated at 70° C. for 18 hrs. The reaction mixture was poured into water (20 mL), extracted with EA (10 mL×3). The combined organic layers were washed by water and brine, dried over Na2SO4. The drying agent was filtered off and the filtrate was concentrated under the reduced pressure to give the residue which was purified with prep-TLC to afford N-(1-methylpiperidin-4-yl)-2-(4-(4-(3-(piperidin-1-yl)propylamino)-1,6-naphthyridin-2-yl)phenoxy)acetamide (10 mg, 17%) as a yellow oil. HPLC/UV purity: 99%; LC-MS (ESI): 517.2 (M+1)+. $^1$H NMR (METHANOL-$d_4$) δ: 9.46 (s, 1H), 8.55 (d, J=6.1 Hz, 1H), 7.93-8.04 (d, J=8.9 Hz, 2H), 7.70 (d, J=5.8 Hz, 1H), 7.07-7.16 (d, J=8.9 Hz, 2H), 7.01 (s, 1H), 4.56 (s, 2H), 3.96-4.01 (m, 1H), 3.62 (t, J=6.9 Hz, 2H), 3.36-3.45 (m, 2H), 3.15-3.20 (m, 4H), 3.04 (d, J=7.9 Hz, 4H), 2.76 (s, 3H), 2.13-2.25 (m, 2H), 2.00-2.07 (m, 2H), 1.84-1.97 (m, 2H), 1.56-1.83 (m, 6H). 4H), 1.96-1.85 (m, 2H).

Example 107: Synthesis of N-(3-(piperidin-1-yl)propyl)-2-((4-(4-((3-(piperidin-1-yl)propyl)amino)-1,6-naphthyridin-2-yl)benzyl)oxy)acetamide

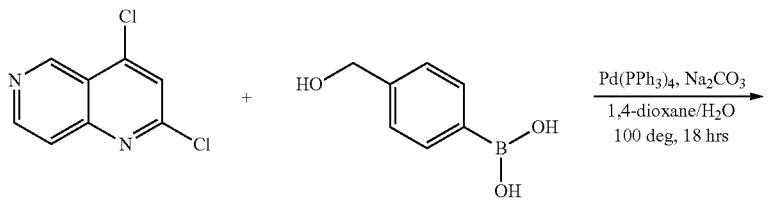

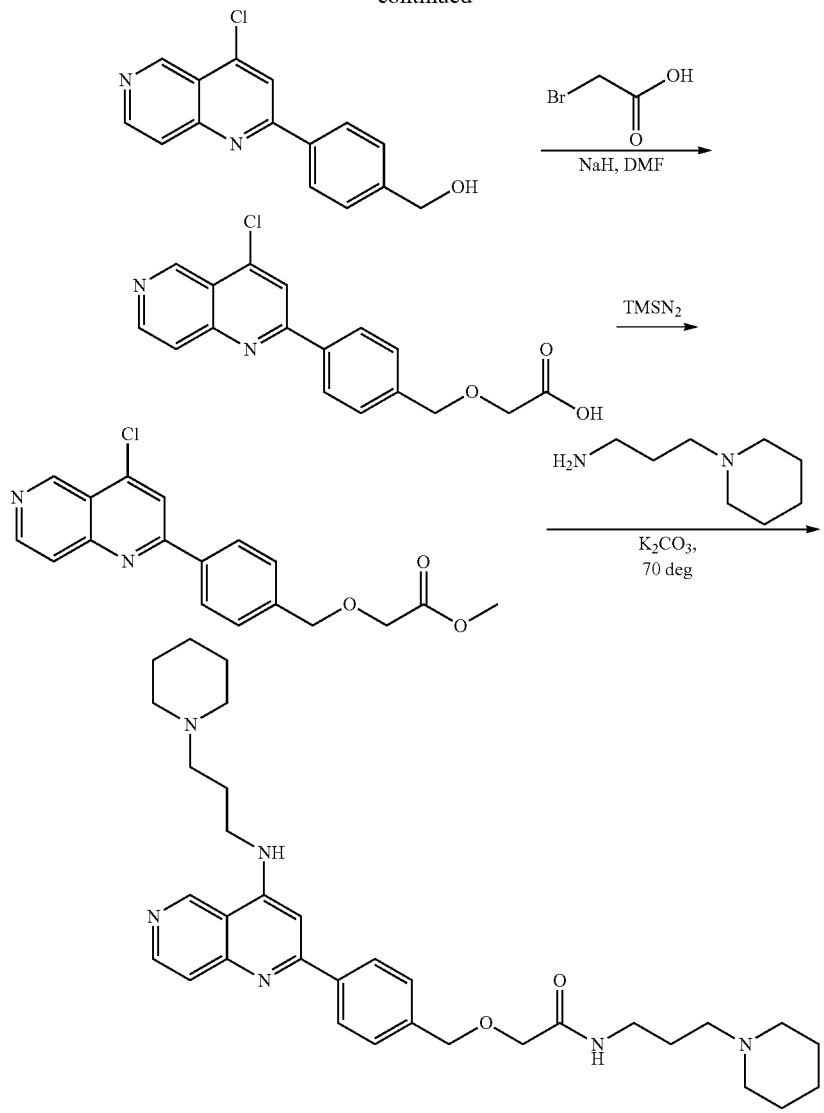

Step 1

The mixture of 2,4-dichloro-1,6-naphthyridine (1.89 g, 9.44 mmol), (4-(hydroxymethyl)phenyl)boronic acid (1.58 g, 10.4 mmol), Pd(PPh$_3$)$_4$ (545 mg, 0.47 mmol) and Na$_2$CO$_3$ (2 g, 18.9 mmol) in 1,4-dioxane (40 mL) and H$_2$O (8 mL) was heated at 100° C. for 18 hrs under N$_2$ atmosphere. The mixture was cooled to room temperature, and then was concentrated under reduced pressure to give the crude mixture, which was purified by flash column chromatography (silica gel, eluting with CH$_2$Cl$_2$ to 10% Methanol/CH$_2$Cl$_2$) to afford (4-(4-chloro-1,6-naphthyridin-2-yl)phenyl)methanol as a white solid (1.9 g, 76%). HPLC/UV purity: 95%; LC-MS (ESI): 271.4 (M+1)$^+$.

Step 2

To a mixture of (4-(4-chloro-1,6-naphthyridin-2-yl)phenyl)methanol (500 mg, 1.85 mmol) and 2-bromoacetic acid (283 mg, 2.03 mmol) in DMF (5 mL) was added NaH (148 mg, 3.7 mmol) at 0° C. under N$_2$ atmosphere in one portion. The resulting mixture was stirred at room temperature for 24 hrs. The mixture was quenched by water (10 mL). The pH of the resulting mixture was adjusted with 1N aq. HCl solution (30 mL) to pH 1. The resulting precipitate was filtered off and the filtrate was extracted with EA (10 mL×3). The combined organic layers were washed by water and brine, dried over Na$_2$SO$_4$. The drying agent was filtered off and the EA phase was used to the next step without further purification.

Step 3

To a solution of 2-((4-(4-chloro-1,6-naphthyridin-2-yl)benzyl)oxy)acetic acid (400 mg, 1.21 mmol) in EA (10 mL) and Methanol (4 mL) was added (Trimethylsilyl)diazomethane (2 N in THF, 1.42 mL, 2.42 mmol) drop wise at 0° C. The reaction mixture was stirred at room temperature for 2 hrs, and then was quenched by water (10 mL). The organic layer was separated from the aqueous phase, and concentrated to give a crude product, which was purified by flash column chromatography (silica gel, eluting with Methanol/CH$_2$Cl$_2$=1/30) to afford methyl 2-((4-(4-chloro-1,6-naphthyridin-2-yl)benzyl)oxy)acetate (90 mg, 22%). HPLC/UV purity: 95%; LC-MS (ESI): 343.4 (M+1)+. $^1$H NMR (DMSO-d$_6$) δ: 9.59 (s, 1H), 8.88 (d, J=5.9 Hz, 1H), 8.58 (s, 1H), 8.34-8.42 (d, J=8.3 Hz, 2H), 8.03 (d, J=5.9 Hz, 1H), 7.54-7.61 (d, J=8.1 Hz, 2H), 4.68 (s, 2H), 4.27 (s, 2H), 3.70 (s, 3H).

Step 4

The mixture of methyl 2-((4-(4-chloro-1,6-naphthyridin-2-yl)benzyl)oxy)acetate (90 mg, 0.26 mmol), 3-(piperidin-1-yl)propan-1-amine (74 mg, 0.52 mmol) and K$_2$CO$_3$ (72 mg, 0.52 mmol) in DMF (2 mL) was heated at 70° C. for 18 hrs. The reaction mixture was poured into water (20 mL), extracted with EA (10 mL×3). The combined organic layers were washed by water and brine, dried over Na$_2$SO$_4$. The drying agent was filtered off and the filtrate was concentrated under reduced pressure to give the crude product, which was purified with Prep-TLC (silica gel, DCM/Methanol/NH$_3$·H$_2$O=10/1/0.1) to afford N-(3-(piperidin-1-yl)propyl)-2-((4-(4-((3-(piperidin-1-yl)propyl)amino)-1,6-naphthyridin-2-yl)benzyl)oxy)acetamide (40 mg, 27%) as a yellow solid. HPLC/UV purity: %; LC-MS (ESI): 559.1 (M+1)+. $^1$H NMR (METHANOL-d$_4$) δ: 9.75 (s, 1H), 8.89 (d, J=5.9 Hz, 1H), 8.01-8.11 (d, J=8.3 Hz, 2H), 7.93 (d, J=5.9 Hz, 1H), 7.69-7.77 (d, J=8.3 Hz, 2H), 7.25 (s, 1H), 4.80 (s, 2H), 4.09 (s, 2H), 3.86 (t, J=6.9 Hz, 2H), 3.50-3.66 (m, 4H), 3.40 (t, J=6.7 Hz, 2H), 3.30-3.32 (m, 2H), 3.10-3.19 (m, 2H), 2.89-3.02 (m, 4H), 2.28-2.39 (m, 2H), 1.92-2.07 (m, 6H), 1.73-1.91 (m, 6H), 1.48-1.54 (m, 2H).

Example 108: Synthesis of N,N-diethyl-2-((4-(4-((3-(piperidin-1-yl)propyl)amino)-1,6-naphthyridin-2-yl)benzyl)oxy)acetamide

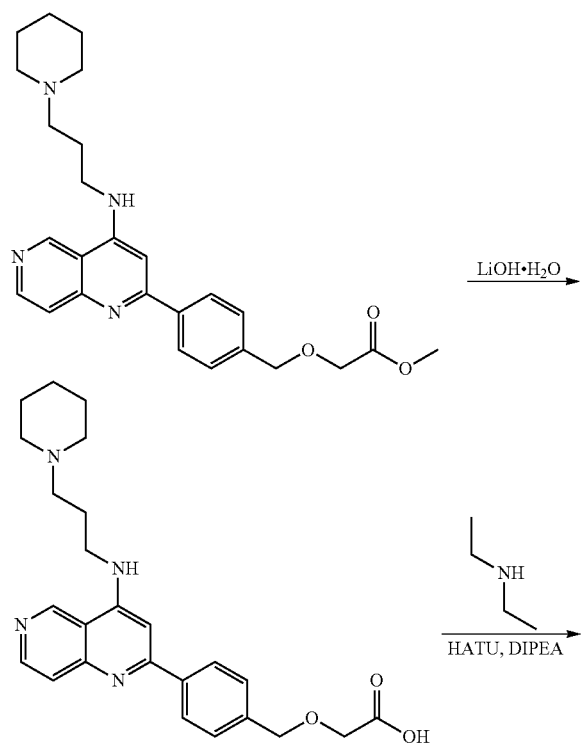

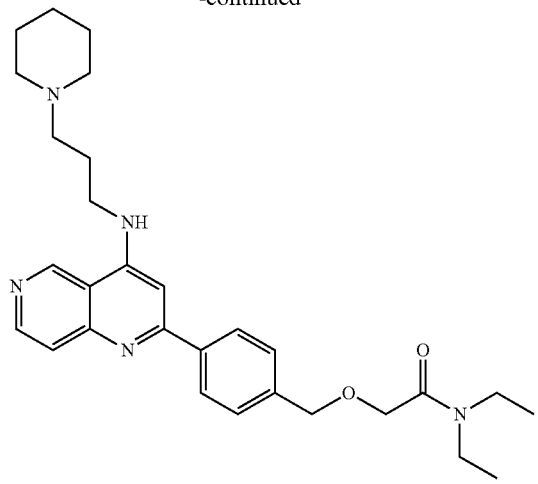

Step 1

To a solution of methyl 2-((4-(4-((3-(piperidin-1-yl)propyl)amino)-1,6-naphthyridin-2-yl)benzyl)oxy)acetate (90 mg, 0.2 mmol) in methanol (4 mL) was added 1N aq. LiOH solution (0.6 mL, 0.6 mmol). The reaction mixture was stirred at 50° C. for 2 hrs. The solvent was removed and water (5 mL) was added. The pH of the water phase was adjusted with 1N aq. HCl solution to pH 4. It was lyophilized to give crude product (90 mg) as a white solid.

Step 2

To a mixture of 2-((4-(4-((3-(piperidin-1-yl)propyl)amino)-1,6-naphthyridin-2-yl)benzyl)oxy)acetic acid (45 mg, 0.1 mmol) and HATU (47 mg, 0.12 mmol) in DMF (1 mL) was added diethylamide (15 mg, 0.2 mmol) and DIPEA (27 mg, 0.2 mmol). The resulting mixture was stirred at room temperature for 1 hr. The reaction mixture was poured into water (10 mL), extracted with EA (10 mL×3). The combined organic layers were washed with water and brine, dried over Na$_2$SO$_4$. The drying agent was filtered off and the filtrate was concentrated in vacuo to generate the crude product, which was purified with Prep-TLC (silica gel, DCM/Methanol=10/1, uv) to give N,N-diethyl-2-((4-(4-((3-(piperidin-1-yl)propyl)amino)-1,6-naphthyridin-2-yl)benzyl)oxy)acetamide (10 mg, 20%) as a solid. HPLC/UV purity: 100%; LC-MS (ESI): 490.1 (M+1)+. $^1$H NMR (METHANOL-d$_4$) δ: 9.57 (s, 1H), 8.68 (d, J=5.8 Hz, 1H), 8.00-8.10 (d, J=7.8 Hz, 2H), 7.83 (d, J=6.0 Hz, 1H), 7.58-7.68 (d, J=7.9 Hz, 2H), 7.14 (s, 1H), 4.71 (s, 2H), 4.31 (s, 2H), 3.73 (t, J=6.8 Hz, 2H), 3.55-3.57 (m, 2H), 3.33-3.45 (m, 6H), 2.93-2.98 (m, 2H), 2.20-2.34 (m, 2H), 1.68-1.85 (m, 6H), 1.09-1.23 (m, 6H)

Example 109: Synthesis of N-(1-methylpiperidin-4-yl)-2-((4-(4-((3-(piperidin-1-yl)propyl)amino)-1,6-naphthyridin-2-yl)benzyl)oxy)acetamide

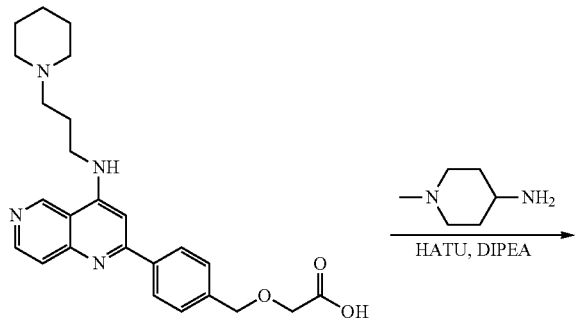

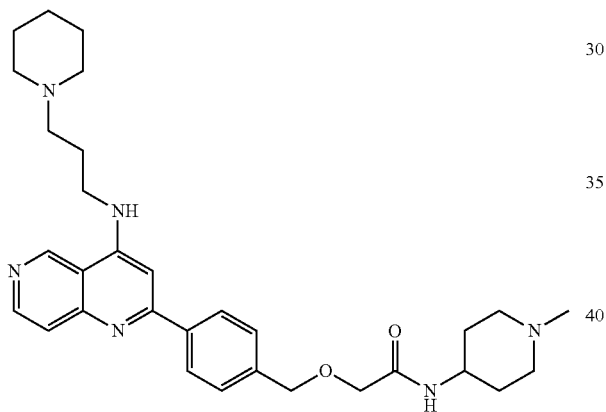

To a mixture of 2-((4-(4-((3-(piperidin-1-yl)propyl)amino)-1,6-naphthyridin-2-yl)benzyl)oxy)acetic acid (45 mg, 0.1 mmol) and HATU (47 mg, 0.12 mmol) in DMF (1 mL) was added 1-methylpiperidin-4-amine (17 mg, 0.2 mmol) and DIPEA (27 mg, 0.2 mmol). The resulting mixture was stirred at room temperature for 1 hr. The reaction mixture was poured into water (10 mL), extracted with EA (10 mL×3). The combined organic layers were washed with water and brine, dried over $Na_2SO_4$. The drying agent was filtered off and the filtrate was concentrated in vacuo to generate the crude product, which was purified with Prep-HPLC to give N-(1-methylpiperidin-4-yl)-2-((4-(4-((3-(piperidin-1-yl)propyl)amino)-1,6-naphthyridin-2-yl)benzyl)oxy)acetamide (15 mg, 28%) as a solid. HPLC/UV purity: 100%; LC-MS (ESI): 531.3 $(M+1)^+$. $^1$H NMR (METHANOL-$d_4$) δ: 9.74 (s, 1H), 8.89 (d, J=5.9 Hz, 1H), 8.01-8.09 (d, J=8.1 Hz, 2H), 7.92 (d, J=5.9 Hz, 1H), 7.68-7.77 (d, J=8.1 Hz, 2H), 7.24 (s, 1H), 4.79 (s, 2H), 4.04-4.07 (m, 3H), 3.86 (t, J=7.0 Hz, 2H), 3.53-3.69 (m, 4H), 3.27-3.30 (m, 2H), 3.10-3.21 (m, 2H), 2.96 (d, J=13.7 Hz, 2H), 2.90 (s, 3H), 2.26-2.40 (m, 2H), 2.17 (d, J=14.0 Hz, 2H), 1.97 (d, J=15.6 Hz, 2H), 1.71-1.93 (m, 5H), 1.48-1.53 (m, 1H).

Example 110: Synthesis of N-((1-ethylpiperidin-4-yl)methyl)-2-(4-(4-(3-(piperidin-1-yl)propylamino)-1,6-naphthyridin-2-yl)benzyloxy)acetamide

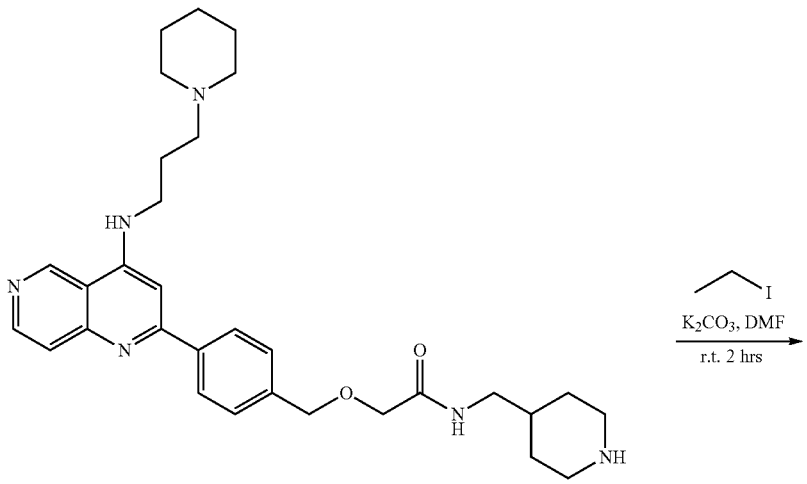

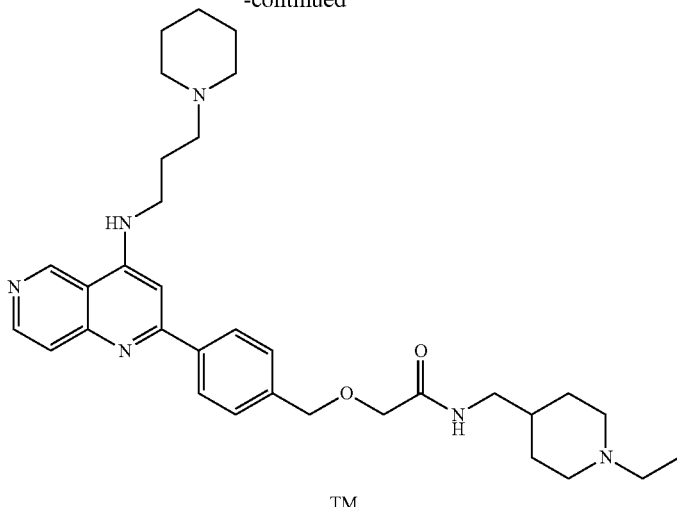

TM

The mixture of 2-(4-(4-(3-(piperidin-1-yl)propylamino)-1,6-naphthyridin-2-yl)benzyloxy)-N-(piperidin-4-ylmethyl)acetamide (28 mg, 0.05 mmol), iodoethane (8 mg, 0.05 mmol) and K$_2$CO$_3$ (14 mg, 0.1 mmol) in DMF (1 mL) was stirred at room temperature for 2 hrs. The reaction mixture was poured into water (20 mL), extracted with EA (10 mL×3), the combined organic layers were washed by water (10 mL×3) and brine (10 mL), dried over Na$_2$SO$_4$. The drying agent was filtered off and the filtrate was concentrated under the reduced pressure to give the crude product which was purified prep-TLC to afford N-((1-ethylpiperidin-4-yl)methyl)-2-(4-(4-(3-(piperidin-1-yl)propylamino)-1,6-naphthyridin-2-yl)benzyloxy)acetamide (4 mg, 14%). HPLC/UV purity: 96%; LC-MS (ESI): 559.4 (M+1)$^+$. $^1$H NMR (METHANOL-d$_4$) δ: 9.74 (s, 1H), 8.89 (d, J=5.9 Hz, 1H), 8.01-8.09 (d, J=8.3 Hz, 2H), 7.93 (d, J=5.9 Hz, 1H), 7.69-7.77 (m, J=8.3 Hz, 2H), 7.25 (s, 1H), 4.80 (s, 2H), 4.03-4.10 (m, 2H), 3.86 (t, J=6.9 Hz, 2H), 3.54-3.67 (m, 4H), 3.34-3.37 (m, 2H), 3.25 (d, J=6.7 Hz, 2H), 3.18 (q, J=7.3 Hz, 2H), 2.88-3.02 (m, 4H), 2.26-2.38 (m, 2H), 1.77-2.07 (m, 8H), 1.44-1.59 (m, 3H), 1.27-1.35 (m, 3H).

Example 111: Synthesis of N-((1-methylpiperidin-4-yl)methyl)-2-(4-(4-(3-(piperidin-1-yl)propylamino)-1,6-naphthyridin-2-yl)benzyloxy)acetamide

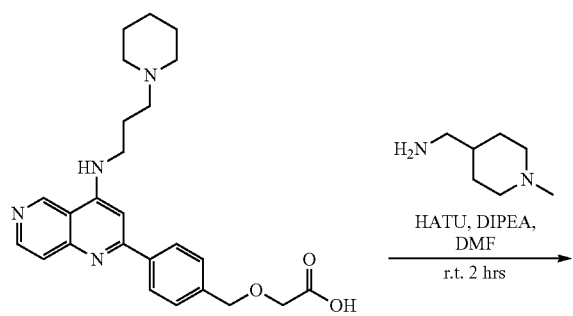

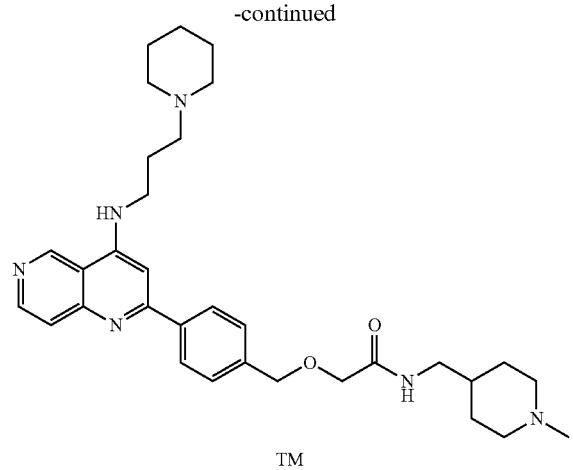

TM

The mixture of 2-(4-(4-(3-(piperidin-1-yl)propylamino)-1,6-naphthyridin-2-yl)benzyloxy)acetic acid (45 mg, 0.10 mmol), (1-methylpiperidin-4-yl)methanamine (14 mg, 0.11 mmol), HATU (45 mg, 0.12 mmol) and DIPEA (25 mg, 0.20 mmol) in DMF (1 mL) was stirred at room temperature for 2 hrs. Water (30 mL) was added, and then the mixture was extracted with EA (20 mL×3). The combined organic layers were washed with water (20 mL×3) and brine (20 mL×1), dried over Na$_2$SO$_4$, filtered and concentrated. The residue was purified by the Prep-TLC to obtain N-((1-methylpiperidin-4-yl)methyl)-2-(4-(4-(3-(piperidin-1-yl)propylamino)-1,6-naphthyridin-2-yl)benzyloxy)acetamide as a yellow oil (17 mg, 30%). HPLC/UV purity: 100%; LC-MS (ESI): 545.3 (M+1)$^+$; $^1$H NMR (METHANOL-d$_4$) δ: 9.53 (s, 1H), 8.59 (d, J=6.0 Hz, 1H), 8.07-8.14 (d, J=8.3 Hz, 2H), 7.80 (d, J=6.0 Hz, 1H), 7.56-7.64 (d, J=8.2 Hz, 2H), 7.11 (s, 1H), 4.74 (s, 2H), 4.05 (s, 2H), 3.68 (t, J=6.8 Hz, 2H), 3.47 (d, J=12.6 Hz, 2H), 3.33-3.34 (m, 2H), 3.16-3.29 (m, 7H), 2.90-3.02 (m, 2H), 2.82 (s, 3H), 2.20-2.34 (m, 2H), 1.92-2.01 (m, 2H), 1.85-1.90 (m, 4H), 1.63-1.75 (m, 2H), 1.50-1.53 (m, 2H).

307

Example 112: Synthesis of N-(2-(4-methyl-1,4-diazepan-1-yl)ethyl)-2-(4-(4-(3-(piperidin-1-yl)propylamino)-1,6-naphthyridin-2-yl)benzyloxy)acetamide

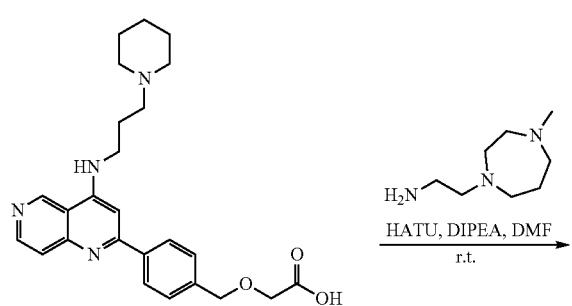

TM

The mixture of 2-(4-(4-(3-(piperidin-1-yl)propylamino)-1,6-naphthyridin-2-yl)benzyloxy)acetic acid (31 mg, 0.07 mmol), 2-(4-methyl-1,4-diazepan-1-yl)ethanamine (11 mg, 0.07 mmol), HATU (32 mg, 0.08 mmol) and DIPEA (18 mg 0.14 mmol) in DMF (1 mL) was stirred at room temperature for 2 hrs. Water (30 mL) was added, and then the mixture was extracted with EA (20 mL×3). The combined organic layers were washed with water (20 mL×3) and brine (20 mL×1), dried over $Na_2SO_4$, filtered and concentrated. The residue was purified by the Prep-TLC to obtain N-(2-(4-methyl-1,4-diazepan-1-yl)ethyl)-2-(4-(4-(3-(piperidin-1-yl)propylamino)-1,6-naphthyridin-2-yl)benzyloxy)acetamide as a yellow oil (12 mg, 30%). HPLC/UV purity: 100%; LC-MS (ESI): 574.3 (M+1)$^+$; $^1$H NMR (METHANOL-$d_4$) δ: 9.81 (s, 1H), 8.84 (d, J=6.1 Hz, 1H), 8.08-8.14 (d, J=8.5 Hz, 2H), 7.95 (d, J=6.1 Hz, 1H), 7.68-7.76 (d, J=8.2 Hz, 2H), 7.27 (s, 1H), 4.78 (s, 2H), 4.06-4.13 (m, 2H), 3.88 (t, J=6.9 Hz, 2H), 3.59 (d, J=11.3 Hz, 2H), 3.39-3.52 (m, 6H), 3.32-3.36 (m, 2H), 3.26 (d, J=16.2 Hz, 2H), 2.96-3.13 (m, 4H), 2.91-2.96 (m, 2H), 2.89 (s, 3H), 2.35 (q, J=7.6 Hz, 2H), 2.09-2.21 (m, 2H), 1.82-1.96 (m, 5H), 1.51-1.54 (m, 1H).

308

Example 113: Synthesis of 2-(4-(4-(3-(piperidin-1-yl)propylamino)-1,6-naphthyridin-2-yl)benzyloxy)-N-(piperidin-4-ylmethyl)acetamide

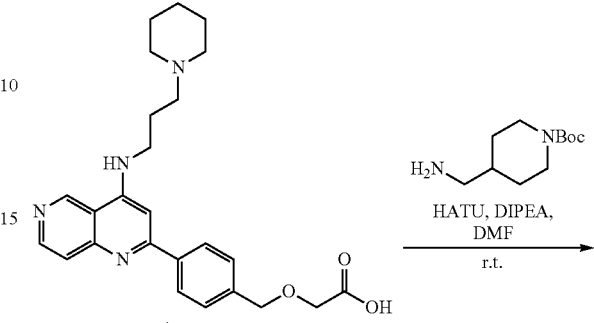

Step 1

The mixture of 2-(4-(4-(3-(piperidin-1-yl)propylamino)-1,6-naphthyridin-2-yl)benzyloxy)acetic acid (31 mg, 0.07 mmol), tert-butyl 4-(aminomethyl)piperidine-1-carboxylate (15 mg, 0.07 mmol), HATU (32 mg, 0.08 mmol) and DIPEA (18 mg 0.14 mmol) in DMF (1 mL) was stirred at room temperature for 2 hrs. Water (30 mL) was added, and then the mixture was extracted with EA (20 mL×3). The combined organic layers were washed with water (20 mL×3) and brine (20 mL×1), dried over $Na_2SO_4$, filtered and concentrated. The residue was purified by the Prep-TLC to obtain tert-butyl 4-((2-(4-(4-(3-(piperidin-1-yl)propylamino)-1,6-naphthyridin-2-yl)benzyloxy)acetamido)methyl)piperidine-1-carboxylate as a yellow oil (40 mg, 90%). LC-MS (ESI): 631 (M+1)$^+$.

Step 2

The mixture of tert-butyl 4-((2-(4-(4-(3-(piperidin-1-yl)propylamino)-1,6-naphthyridin-2-yl)benzyloxy)acetamido)methyl)piperidine-1-carboxylate (40 mg, 0.06 mmol) and TFA (1 mL) in DCM (1 mL) was stirred at room temperature for 18 hrs, then the solvent was removed under the reduced pressure to get the residue which was purified with Prep-HPLC (Welch, XB-C18, 21.2 mm×250 mm, 10 um, eluting with 40% CH₃CN in 1‰ TFA in H₂O) to afford 2-(4-(4-(3-(piperidin-1-yl)propylamino)-1,6-naphthyridin-2-yl)benzyloxy)-N-(piperidin-4-ylmethyl)acetamide (30 mg, 90%) as a TFA salt. HPLC/UV purity: 100%; LC-MS (ESI): 531.3 (M+1)⁺.¹H NMR (METHANOL-d₄) δ: 9.76 (s, 1H), 8.88 (d, J=6.2 Hz, 1H), 8.02-8.09 (d, J=8.3 Hz, 2H), 7.94 (d, J=5.9 Hz, 1H), 7.68-7.78 (d, J=8.3 Hz, 2H), 7.25 (s, 1H), 4.80 (s, 2H), 4.07 (s, 2H), 3.86 (t, J=6.9 Hz, 2H), 3.60 (d, J=11.8 Hz, 2H), 3.43 (d, J=12.6 Hz, 2H), 3.33-3.35 (m, 2H), 3.25 (d, J=6.4 Hz, 2H), 2.97-3.02 (m, 4H), 2.26-2.39 (m, 2H), 1.75-2.00 (m, 8H), 1.41-1.59 (m, 3H).

Example 114: Synthesis of N-(2-(1-methylpiperidin-4-yl)ethyl)-2-(4-(4-(3-(piperidin-1-yl)propylamino)-1,6-naphthyridin-2-yl)benzyloxy)acetamide

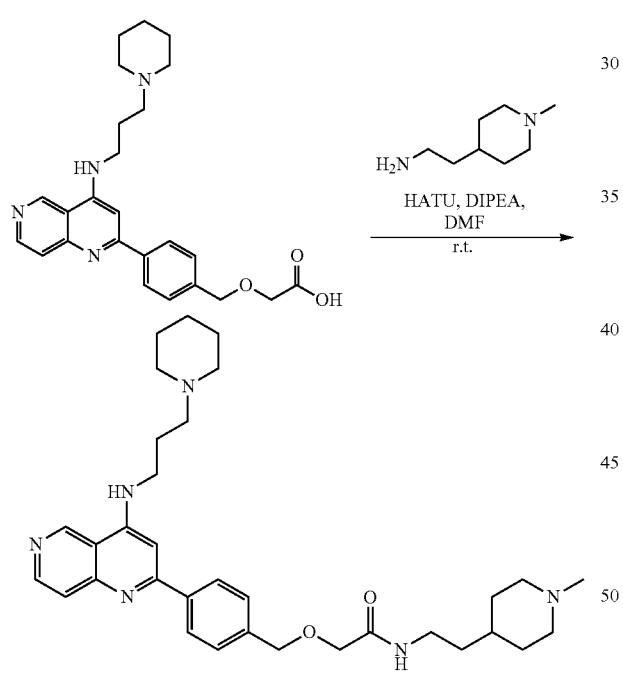

The mixture of 2-(4-(4-(3-(piperidin-1-yl)propylamino)-1,6-naphthyridin-2-yl)benzyloxy)acetic acid (31 mg, 0.07 mmol), 2-(1-methylpiperidin-4-yl)ethanamine (10 mg, 0.07 mmol), HATU (32 mg, 0.08 mmol) and DIPEA (18 mg 0.14 mmol) in DMF (1 mL) was stirred at room temperature for 2 hrs. Water (30 mL) was added, and then the mixture was extracted with EA (20 mL×3). The combined organic layers were washed with water (20 mL×3) and brine (20 mL×1), dried over Na₂SO₄, filtered and concentrated. The residue was purified by the Prep-TLC to obtain N-(2-(1-methylpiperidin-4-yl)ethyl)-2-(4-(4-(3-(piperidin-1-yl)propylamino)-1,6-naphthyridin-2-yl)benzyloxy)acetamide as a yellow oil (14 mg, 35%). HPLC/UV purity: 100%; LC-MS (ESI): 559 (M+1)⁺; ¹H NMR (METHANOL-d₄) δ: 9.75 (s, 1H), 8.89 (d, J=5.9 Hz, 1H), 8.05 (d, J=8.3 Hz, 2H), 7.93 (d, J=5.9 Hz, 1H), 7.72-7.74 (d, J=8.3 Hz, 2H), 7.25 (s, 1H), 4.79 (s, 2H), 4.04 (s, 2H), 3.86 (t, J=6.9 Hz, 2H), 3.47-3.65 (m, 4H), 3.34-3.41 (m, 4H), 2.92-3.05 (m, 4H), 2.87 (s, 3H), 2.26-2.39 (m, 2H), 2.07 (d, J=14.2 Hz, 2H), 1.97 (d, J=14.5 Hz, 2H), 1.74-1.90 (m, 3H), 1.41-1.61 (m, 4H).

Example 115: Synthesis of N-(1-Methylpiperidin-4-yl)-3-(4-(4-(3-(piperidin-1-yl)propylamino)-1,6-naphthyridin-2-yl)benzyloxy)propanamide

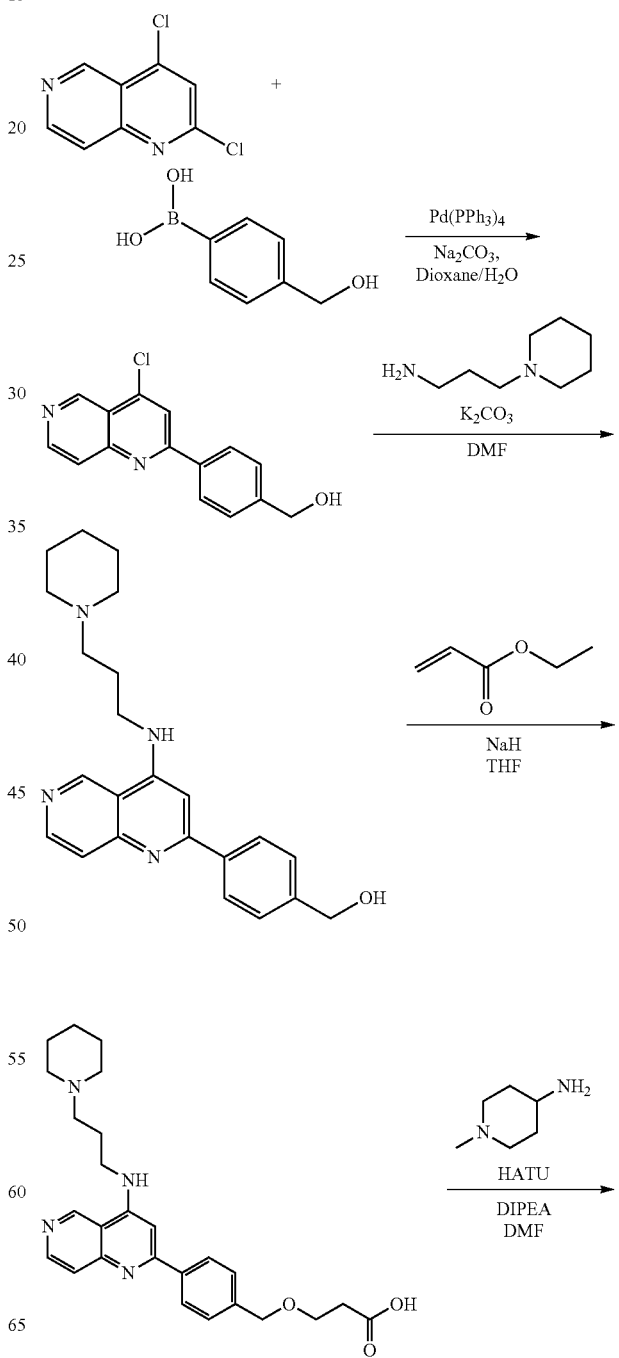

-continued

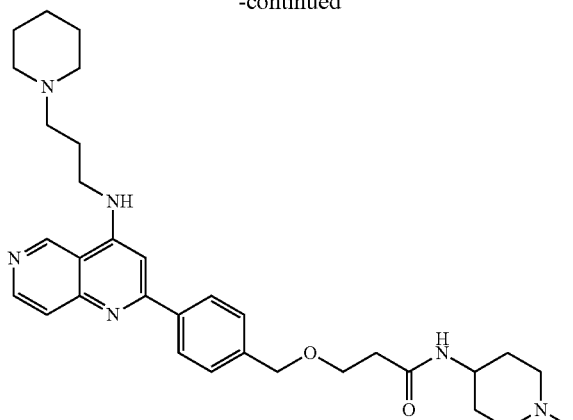

Step 1

The mixture of 4-(hydroxymethyl)phenylboronic acid (3.8 g, 25 mmol), 2,4-dichloro-1,6-naphthyridine (5 g, 25 mmol), $Na_2CO_3$ (5.3 g, 50 mmol) and $Pd(PPh_3)_4$ (1.155 g, 1 mmol) in 1,4-Dioxane (50 mL) and $H_2O$ (5 mL) was stirred at 95° C. for 4 hrs. The mixture was filtered, concentrated and purified by silica gel column chromatography to give (4-(4-chloro-1,6-naphthyridin-2-yl)phenyl)methanol (4.9 g, 72%) as white solid. HPLC/UV purity: 95%; LC-MS (ESI): 271.2 $(M+1)^+$.

Step 2

The mixture of (4-(4-chloro-1,6-naphthyridin-2-yl)phenyl)methanol (1.355 g, 5 mmol) and 3-(piperidin-1-yl)propan-1-amine (710 mg, 5 mmol) and $K_2CO_3$ (1.38 g, 10 mmol) in DMF (10 mL) was stirred at 90° C. overnight. Then water (50 mL) was added and the mixture was extracted with EA (30 mL×3). The combined organic layer was washed with brine, dried over $Na_2SO_4$, concentrated and purified by flash column chromatography to give (4-(4-(3-(piperidin-1-yl)propylamino)-1,6-naphthyridin-2-yl)phenyl)methanol (1.138 g, 82%) as white solid. HPLC/UV purity: 95%; LC-MS (ESI): 377.2 $(M+1)^+$.

Step 3

The solution of (4-(4-(3-(piperidin-1-yl)propylamino)-1,6-naphthyridin-2-yl)phenyl)methanol (752 mg, 2 mmol) in THF (40 mL) was cooled to 0° C., and NaH (120 mg, 60%, 3.0 mmol) was added. After stirred at 0° C. for 30 min, ethyl acrylate (200 mg, 2 mmol) was added and the resulting mixture was stirred at room temperature for another 3 hrs. Then water (50 mL) was added and the mixture was extracted with EA (30 mL×3), washed with brine, dried over $Na_2SO_4$, concentrated and purified by flash column chromatography to give 3-(4-(4-(3-(piperidin-1-yl)propylamino)-1,6-naphthyridin-2-yl)benzyloxy)propanoic acid (200 mg, 22%) as white solid. HPLC/UV purity: 95%; LC-MS (ESI): 449.3 $(M+1)^+$.

Step 4

The mixture of 3-(4-(4-(3-(piperidin-1-yl)propylamino)-1,6-naphthyridin-2-yl)benzyloxy)propanoic acid (45 mg, 0.1 mmol), 1-methylpiperidin-4-amine (23 mg, 0.2 mmol), HATU (76 mg, 0.2 mmol) and DIPEA (40 mg, 0.3 mmol) in DMF (2.0 mL) was stirred at room temperature overnight. Then water (50 mL) was added and the mixture was extracted with EA (30 mL×3), washed with brine, dried over $Na_2SO_4$, concentrated and purified by flash column chromatography to give N-(1-methylpiperidin-4-yl)-3-(4-(4-(3-(piperidin-1-yl)propylamino)-1,6-naphthyridin-2-yl)benzyloxy)propanamide (10 mg, 18.2%) as yellow solid. HPLC/UV purity: 100%; LC-MS (ESI): 545.3 $(M+1)^+$. $^1H$ NMR (METHANOL-$d_4$) δ: 9.72 (s, 1H), 8.88 (d, J=6.0 Hz, 1H), 8.02 (d, J=8.4 Hz, 2H), 7.92 (d, J=5.6 Hz, 1H), 7.65 (d, J=8.0 Hz, 2H), 7.22 (s, 1H), 4.69 (s, 2H), 4.00-3.94 (m, 1H), 3.87-3.82 (m, 4H), 3.61-3.55 (m, 4H), 3.32-3.31 (m, 1H), 3.14 (t, J=12.8 Hz, 2H), 2.98 (t, J=13.2 Hz, 2H), 2.88 (s, 3H), 2.55 (t, J=5.6 Hz, 2H), 2.33-2.29 (m, 2H), 2.19 (d, J=14.8 Hz, 2H), 2.06-1.96 (m, 3H), 1.84-1.75 (m, 5H), 1.61-1.50 (m, 1H).

Example 116: Synthesis of methyl-N-(1-methylpiperidin-4-yl)-5-(4-((3-(piperidin-1-yl)propyl)amino)-1,6-naphthyridin-2-yl)-1H-pyrrolo[3,2-b]pyridine-2-carboxamide

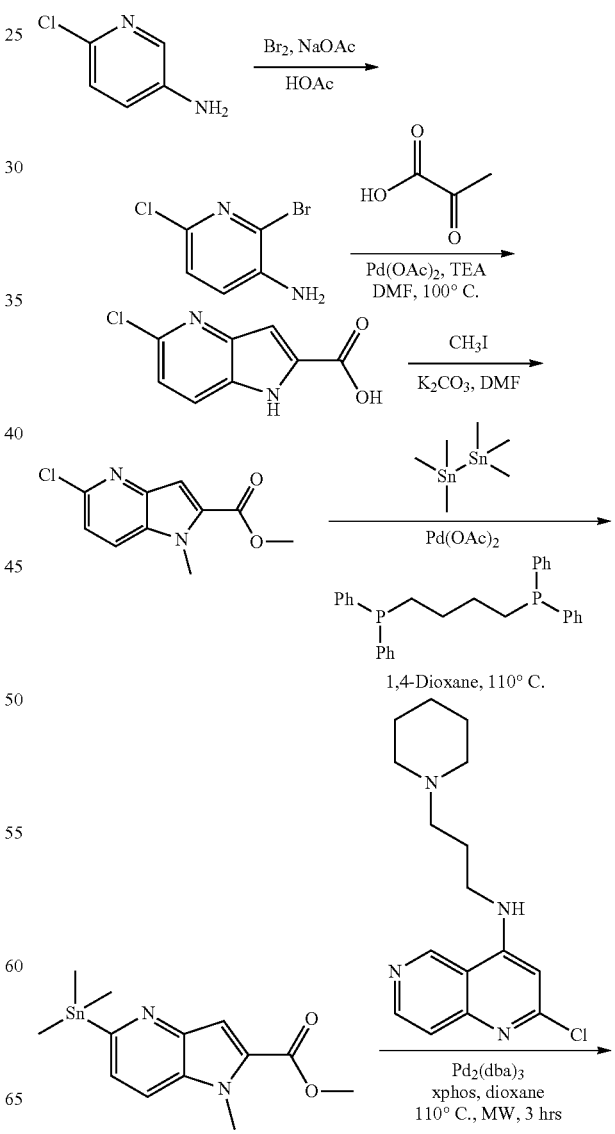

-continued

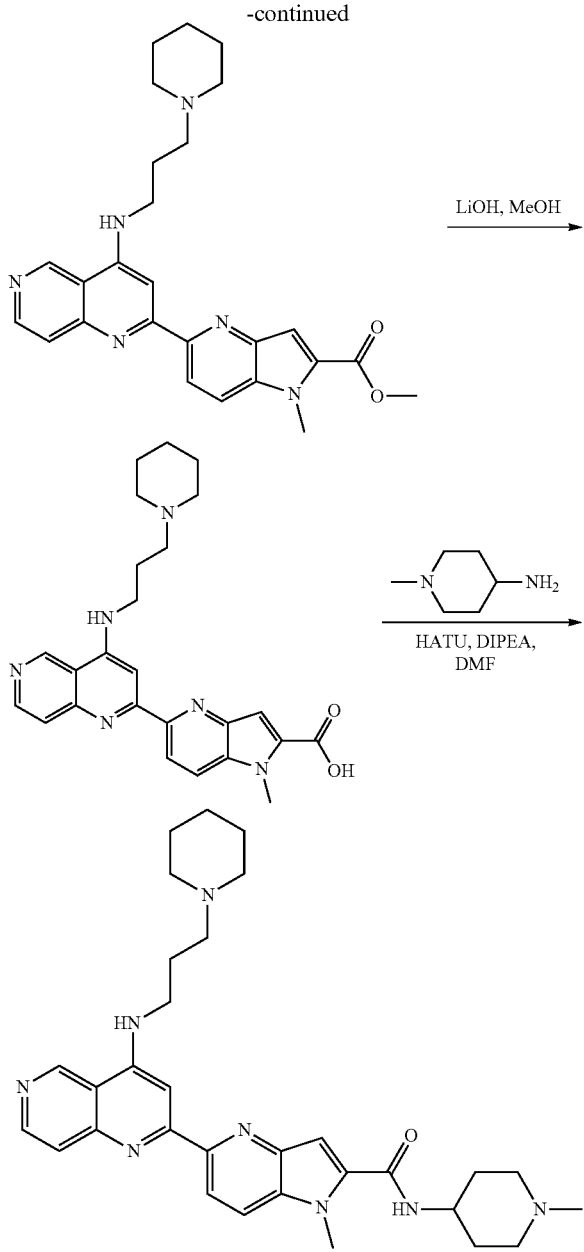

Step 1

To a mixture of 6-chloropyridin-3-amine (5 g, 38.9 mmol) and NaOAc (6.37 g, 77.8 mmol) in AcOH (30 mL) was added a solution of bromine (6.8 g, 42.8 mmol) in AcOH (5 mL). The resulting reaction mixture was stirred at room temperature for 18 hrs. Acetic acid was removed under reduced pressure to give the residue, which was dissolved into EA (50 mL), washed by NaHCO$_3$ aqueous (20 mL×5), water and brine. The organic layers was dried over Na$_2$SO$_4$, and the drying agent was filtered off. The filtrate was concentrated in vacuo to give the crude product, which was purified by silica gel chromatography (silica gel, eluting with 5% methanol in DCM) to give 2-bromo-6-chloropyridin-3-amine (5 g, 62%) as an orange solid. HPLC/UV purity: 90%; LC-MS (ESI): 207.3 (M+1)$^+$.

Step 2

To the mixture of 2-bromo-6-chloropyridin-3-amine (5 g, 24.4 mmol), Pd(OAc)$_2$ (1.09 g, 4.88 mmol), PPh$_3$ (1.91 g, 7.32 mmol) and triethylamine (10.8 g, 107.3 mmol) in DMF (30 mL) in N$_2$ atmosphere, was added 2-oxopropanoic acid (5.69 g, 64.6 mmol) by a syringe. The resulting mixture was heated at 115° C. for 18 hrs under N$_2$. The reaction mixture was cooled to room temperature and poured into water (200 mL) The resulting precipitate was filtered and the filtrate was washed with EA (30 mL×3). The pH of aqueous phase was adjusted with 1N aq. HCl solution to pH 4, and the resulting precipitate was collected by filtration and dried by reduced pressure to give 5-chloro-1H-pyrrolo[3,2-b]pyridine-2-carboxylic acid (2.44 g, 51%) as a solid. HPLC/UV purity: 90%; LC-MS (ESI): 197.1 (M+1)$^+$.

Step 3

To a mixture of 5-chloro-1H-pyrrolo[3,2-b]pyridine-2-carboxylic acid (2.44 g, 12.44 mmol) and Cs$_2$CO$_3$ (8 g, 24.9 mmol) in DMF (10 mL) was added CH$_3$I (3.85 g, 27.3 mmol) at room temperature. The mixture was heated at 70° C. for 18 hrs. The reaction mixture was cooled to room temperature and quenched by water (50 mL), extracted with EA (20 mL×3). The combined organic layers were washed by water and brine, dried over Na$_2$SO$_4$. The drying agent was filtered off and the filtrate was concentrated under the reduced pressure to give the crude product, which was purified by silica gel chromatography (silica gel, eluting with 20% EA in PE) to give methyl 5-chloro-1-methyl-1H-pyrrolo[3,2-b]pyridine-2-carboxylate (1.8 g, 64%) as a yellow solid. HPLC/UV purity: 90%; LC-MS (ESI): 225 (M+1)$^+$.

Step 4

To the mixture of methyl 5-chloro-1-methyl-1H-pyrrolo [3,2-b]pyridine-2-carboxylate (1.6 g, 7.14 mmol), Pd(OAc)$_2$ (160 mg, 0.714 mmol) and 1,4-bis(diphenylphosphino)butane (608 mg, 1.43 mmol) in 1,4-dioxane (20 mL) in N$_2$ atmosphere, was added a solution of 1,1,1,2,2,2-hexamethyldistannane (2.8 g, 8.57 mmol) in 1,4-dioxane (2 mL) by a syringe. The resulting mixture was heated at 100° C. for 18 hrs under N$_2$. The reaction mixture was concentrated to give the residue, which was diluted with EA (50 mL), extracted with EA (20 mL×3). The combined organic layers were washed by water and brine, dried over Na$_2$SO$_4$. The drying agent was filtered off and the filtrate was concentrated under reduced pressure to give methyl 1-methyl-5-(trimethylstannyl)-1H-pyrrolo[3,2-b]pyridine-2-carboxylate (1.5 g, 59%) as a crude product which was used to the next step without further purification.

Step 5

A 20-mL microwave vial was charged with 2-chloro-N-(3-(piperidin-1-yl)propyl)-1,6-naphthyridin-4-amine (235 mg, 0.78 mmol), methyl 1-methyl-5-(trimethylstannyl)-1H-pyrrolo[3,2-b]pyridine-2-carboxylate (330 mg, 0.93 mmol), Pd$_2$(dba)$_3$ (71 mg, 0.078 mmol), Xphos (90 mg, 0.156 mmol) and 1,4-Dioxane (10 mL). The sealed vial with the resulting brown solution was heated for 2 hrs in a Biotage Initiator Eight Microwave Reactor at a constant temperature of 120° C. The resulting solutions were concentrated by rotary evaporation (55° C., 20 mmHg). The resulting crude mixture was purified using Prep-TLC (silica gel, eluting with 10% methanol in DCM) to give methyl1-methyl-5-(4-((3-(piperidin-1-yl)propyl)amino)-1,6-naphthyridin-2-yl)-1H-pyrrolo[3,2-b]pyridine-2-carboxylate (40 mg, 22%) as a white solid. HPLC/UV purity: 95%; LC-MS (ESI): 459.4 (M+1)⁺. ¹H NMR (METHANOL-d₄) δ: 9.37 (s, 1H), 8.48 (d, J=5.8 Hz, 1H), 8.41 (d, J=8.9 Hz, 1H), 8.07 (d, J=8.8 Hz, 1H), 7.73 (d, J=5.8 Hz, 1H), 7.59 (s, 1H), 7.36 (s, 1H), 4.07 (s, 3H), 3.88 (s, 3H), 3.52-3.60 (m, 2H), 2.83-2.99 (m, 6H), 2.05-2.15 (m, 2H), 1.61-1.78 (m, 4H), 1.48-1.51 (m, 2H).

Step 6

To a solution of methyl 1-methyl-5-(4-((3-(piperidin-1-yl)propyl)amino)-1,6-naphthyridin-2-yl)-1H-pyrrolo[3,2-b]pyridine-2-carboxylate (30 mg, 0.065 mmol) in methanol (1 mL) was added 1N aq. LiOH solution (0.26 mL, 0.26 mmol). The reaction mixture was stirred at 40° C. for 2 hrs. The solvent was removed and water (5 mL) was added. The pH of the water phase was adjusted with 1N aq. HCl solution to pH 4. Then it was lyophilized to give a crude product (40 mg) as a white solid. The crude product was used to the next step without purification.

Step 7

To a mixture of 1-methyl-5-(4-((3-(piperidin-1-yl)propyl)amino)-1,6-naphthyridin-2-yl)-1H-pyrrolo[3,2-b]pyridine-2-carboxylic acid (30 mg, 0.065 mmol) and HATU (38 mg, 0.101 mmol) in DMF (2 mL) was added 1-methylpiperidin-4-amine (11 mg, 0.101 mmol) and DIPEA (26 mg, 0.203 mmol). Then the resulting mixture was stirred at rt for 1 hr. The reaction mixture was poured into water (10 mL), extracted with EA (10 mL×3). The combined organic layers were washed with water and brine, dried over Na₂SO₄. The drying agent was filtered off and the filtrate was concentrated in vacuo to give the crude product, which was purified with Prep-TLC (silica gel, DCM/Methanol/NH₃·H₂O=10/1/0.1) to give 1-methyl-N-(1-methylpiperidin-4-yl)-5-(4-((3-(piperidin-1-yl)propyl)amino)-1,6-naphthyridin-2-yl)-1H-pyrrolo[3,2-b]pyridine-2-carboxamide (15 mg, 43%) as a solid. HPLC/UV purity: 100%; LC-MS (ESI): 541 (M+1)⁺. ¹H NMR (METHANOL-d₄) δ: 9.36 (s, 1H), 8.46 (d, J=6.1 Hz, 1H), 8.30 (d, J=8.8 Hz, 1H), 7.99 (d, J=8.9 Hz, 1H), 7.71 (d, J=5.8 Hz, 1H), 7.52 (s, 1H), 7.14 (s, 1H), 3.97 (s, 3H), 3.85-3.92 (m, 1H), 3.50 (t, J=6.7 Hz, 2H), 2.85-2.96 (m, 2H), 2.49-2.66 (m, 6H), 2.26 (s, 3H), 2.17 (t, J=11.6 Hz, 2H), 1.88-2.05 (m, 4H), 1.54-1.72 (m, 6H), 1.41-1.43 (m, 2H).

Example 117: Synthesis of 1-methyl-5-(4-((3-(piperidin-1-yl)propyl)amino)-1,6-naphthyridin-2-yl)-1H-pyrrolo[3,2-b]pyridine-2-carboxamide

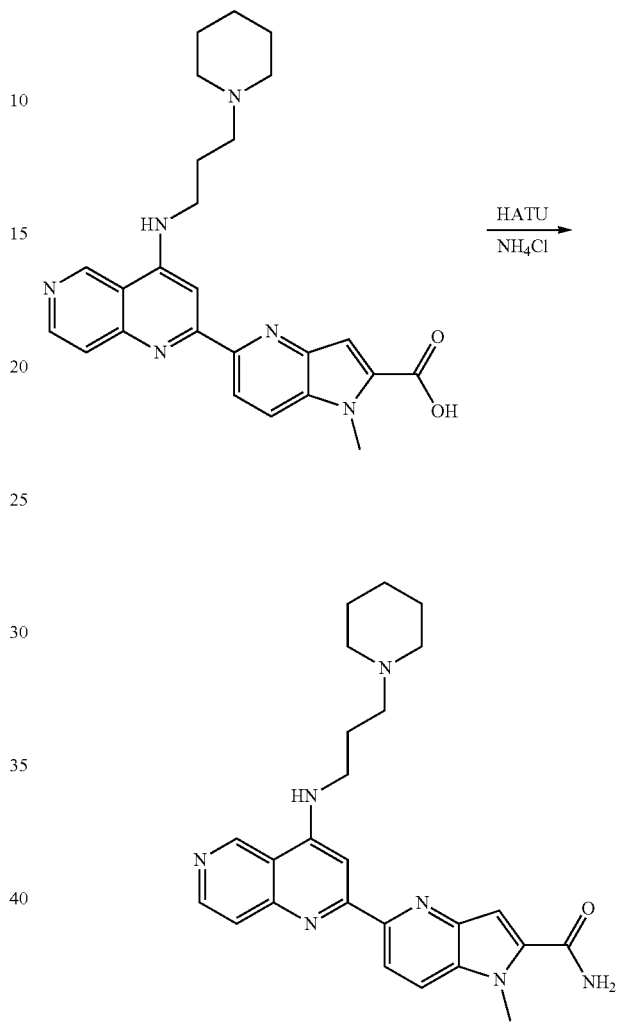

To a mixture of 1-methyl-5-(4-((3-(piperidin-1-yl)propyl)amino)-1,6-naphthyridin-2-yl)-1H-pyrrolo[3,2-b]pyridine-2-carboxylic acid (10 mg, 0.023 mmol) and HATU (10 mg, 0.027 mmol) in DMF (1 mL) was added ammonium chloride (2.4 mg, 0.045 mmol) and DIPEA (8.7 mg, 0.067 mmol). Then the resulting mixture was stirred at rt for 1 hr. The reaction mixture was poured into water (10 mL), extracted with EA (10 mL×3). The combined organic layers were washed with water and brine, dried over Na₂SO₄. The drying agent was filtered off and the filtrate was concentrated in vacuo to give the residue, which was purified with Prep-TLC (silica gel, DCM/Methanol/NH₃·H₂O=10/1/0.1) to give 1-methyl-5-(4-((3-(piperidin-1-yl)propyl)amino)-1,6-naphthyridin-2-yl)-1H-pyrrolo[3,2-b]pyridine-2-carboxamide (6 mg, 60%) as a solid. HPLC/UV purity: 100%; LC-MS (ESI): 444.3 (M+1)⁺. ¹H NMR (METHANOL-d₄) δ: 9.50 (s, 1H), 8.61 (d, J=5.9 Hz, 1H), 8.47 (d, J=8.9 Hz, 1H), 8.16 (d, J=8.9 Hz, 1H), 7.86 (d, J=5.9 Hz, 1H), 7.70 (s, 1H), 7.33 (s, 1H), 4.14 (s, 3H), 3.69 (t, J=6.7 Hz, 2H), 3.01-3.27 (m, 6H), 2.17-2.32 (m, 2H), 1.71-1.92 (m, 4H), 1.64-1.69 (m, 2H).

Example 118: Synthesis of (E)-N-(1-Methylpiperidin-4-yl)-3-(4-(4-(3-(piperidin-1-yl)propylamino)-1,6-naphthyridin-2-yl)phenyl)acrylamide & (Z)—N-(1-Methylpiperidin-4-yl)-3-(4-(4-(3-(piperidin-1-yl)propylamino)-1,6-naphthyridin-2-yl)phenyl)acrylamide
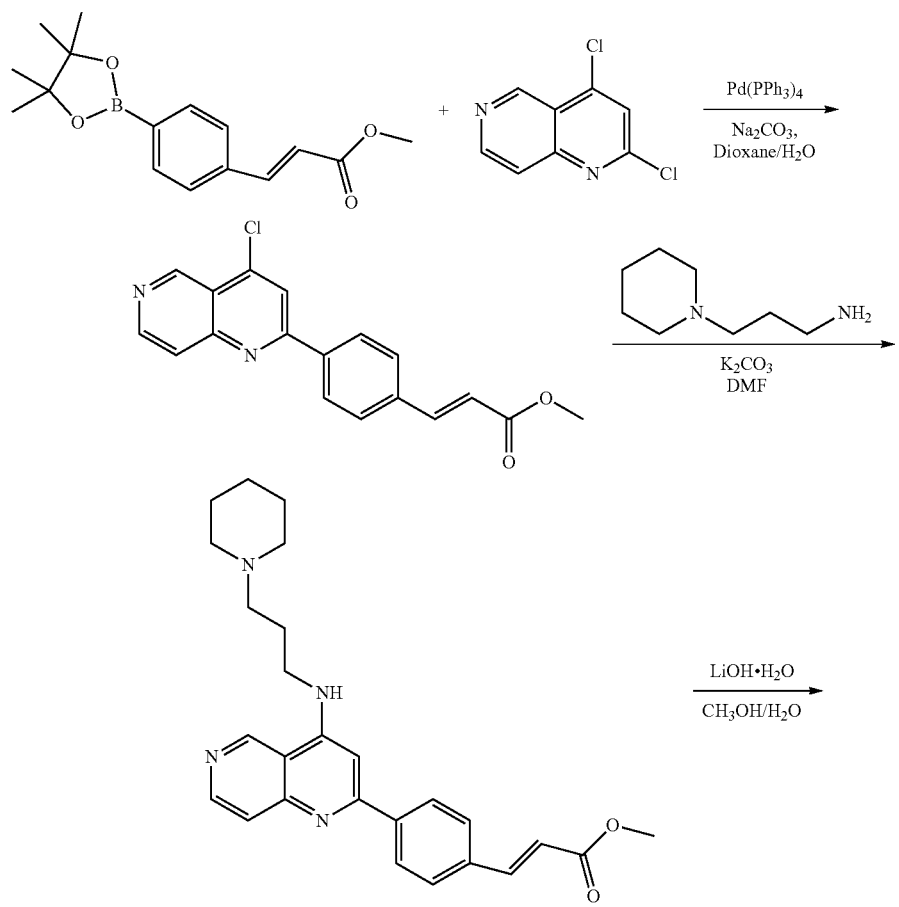
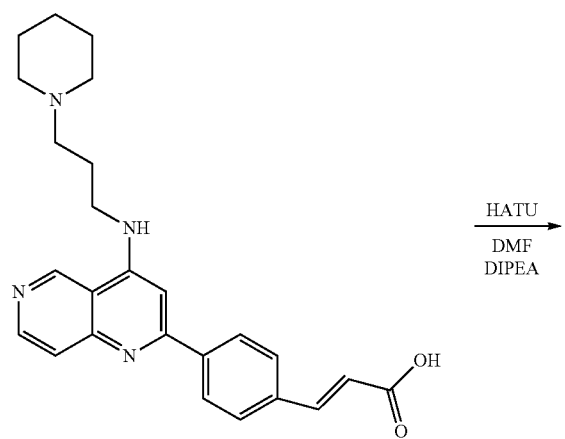

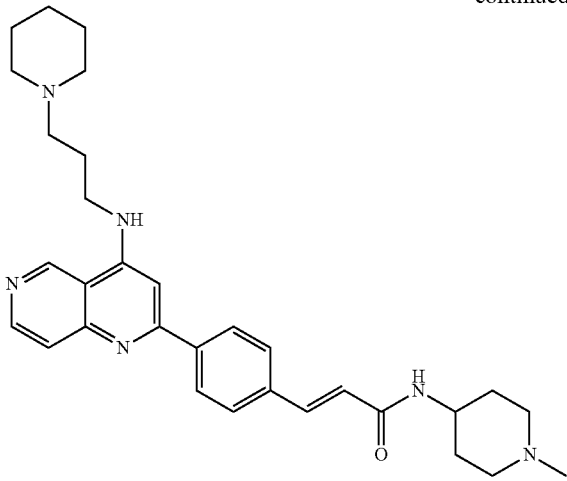

Step 1

The mixture of methyl 3-(4-(4,4,5,5-tetramethyl-1,3,2-dioxaborolan-2-yl)phenyl)acrylate (198 mg, 1 mmol), 2,4-dichloro-1,6-naphthyridine (206 mg, 1 mmol), Pd(PPh₃)₄ (115 mg, 0.1 mmol) and Na₂CO₃ (212 mg, 2 mmol) in Dioxane/H₂O (20 mL/2 mL) was stirred at 100° C. overnight. The mixture was diluted with EA, washed with water (100 mL×3) and brine (100 mL×1), dried over Na₂SO₄, filtered, concentrated to give crude methyl 3-(4-(4-chloro-1,6-naphthyridin-2-yl)phenyl)acrylate (230 mg, 71%) as white solid which was used directly in the next step. HPLC/UV purity: 95%; LC-MS (ESI): 324.8 (M+1)⁺.

Step 2

The mixture of methyl 3-(4-(4-chloro-1,6-naphthyridin-2-yl)phenyl)acrylate (230 mg, 0.7 mmol), K₂CO₃ (290 mg, 2.1 mmol) and 3-(piperidin-1-yl)propan-1-amine (149 mg, 1.05 mmol) in DMF (10 mL) was stirred at 70° C. overnight. The mixture was filtered, concentrated and purified by silica gel chromatography to give methyl 3-(4-(4-(3-(piperidin-1-yl)propylamino)-1,6-naphthyridin-2-yl)phenyl)acrylate (240 mg, 80%) as white solid. HPLC/UV purity: 100%; LC-MS (ESI): 430.8 (M+1)⁺.

Step 3

The solution of methyl 3-(4-(4-(3-(piperidin-1-yl)propylamino)-1,6-naphthyridin-2-yl)phenyl)acrylate (129 mg, 0.3 mmol) and LiOH·H₂O (25 mg, 0.6 mmol) in CH₃OH/H₂O (10 mL/1 mL) was stirred at 65° C. for 3 hours. Then the mixture was cooled to room temperature and 0.7 mL 1N aq. HCl solution was added. The solvent was removed to give crude 3-(4-(4-(3-(piperidin-1-yl)propylamino)-1,6-naphthyridin-2-yl)phenyl)acrylic acid which was used in next step directly. HPLC/UV purity: 95%; LC-MS (ESI): 416.7 (M+1)⁺.

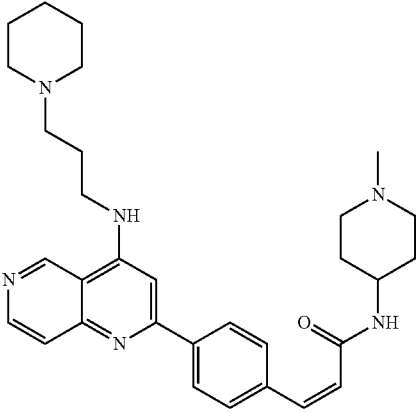

Step 4

The solution of 3-(4-(4-(3-(piperidin-1-yl)propylamino)-1,6-naphthyridin-2-yl)phenyl)acrylic acid (42 mg, 0.1 mmol), 1-methylpiperidin-4-amine (23 mg, 0.2 mmol), HATU (76 mg, 0.2 mmol) and DIPEA (39 mg, 0.3 mmol) in DMF (3 mL) was stirred at room temperature overnight. Then 50 mL water was added and the mixture was extracted with EA (100 mL), washed with brine, dried over Na₂SO₄, concentrated and purified by Prep-HPLC (Welch, XB-C18, 21.2 mm×250 mm, 10 um, eluting with 20% CH₃CN in 1‰ TFA in H₂O) to give the desired products.

(E)-N-(1-methylpiperidin-4-yl)-3-(4-(4-(3-(piperidin-1-yl)propylamino)-1,6-naphthyridin-2-yl)phenyl)acrylamide (6 mg, 10.5%). HPLC/UV purity: 100%; LC-MS (ESI): 512.9 (M+1)⁺. ¹H NMR (METHANOL-d₄) δ: 9.63 (s, 1H), 8.77 (d, J=6.4 Hz, 1H), 7.95 (d, J=8.4 Hz, 2H), 7.81 (d, J=6.0 Hz, 1H), 7.76 (d, J=8.4 Hz, 2H), 7.57 (d, J=15.6 Hz, 1H), 7.15 (s, 1H), 6.69 (d, J=15.6 Hz, 1H), 4.00-3.95 (m, 1H), 3.74 (t, J=6.8 Hz, 2H), 3.53-3.47 (m, 4H), 3.23-3.18 (m, 2H), 3.22-3.10 (m, 2H), 2.88-2.77 (m, 5H), 2.21-2.12 (m, 4H), 1.76-1.86 (m, 2H), 1.73-1.67 (m, 5H), 1.43-1.40 (m, 1H).

(Z)—N-(1-methylpiperidin-4-yl)-3-(4-(4-(3-(piperidin-1-yl)propylamino)-1,6-naphthyridin-2-yl)phenyl)acrylamide (18 mg, 31.5%) as white solid. HPLC/UV purity: 100%; LC-MS (ESI): 512.9 (M+1)⁺. ¹H NMR (METHANOL-d₄) δ: 9.63 (s, 1H), 8.77 (d, J=5.6 Hz, 1H), 7.90 (d, J=8.8 Hz, 2H), 7.81 (d, J=5.6 Hz, 1H), 7.56 (d, J=8.4 Hz, 2H), 7.13 (s, 1H), 6.82 (d, J=12.4 Hz, 1H), 6.10 (d, J=12.4 Hz, 1H), 3.95-3.88 (m, 1H), 3.74 (t, J=7.2 Hz, 2H), 3.50-3.43 (m, 4H), 3.23-3.18 (m, 2H), 3.19-3.16 (m 2H), 2.88 (t, J=12 Hz, 2H), 2.76 (s, 3H), 2.21-2.10 (m, 2H), 2.10-2.06 (m, 2H), 1.97-1.86 (m, 2H), 1.75-1.55 (m, 5H), 1.49-1.37 (m, 1H).

Example 119: Synthesis of (E)-N-(2-(Dimethyl-amino)ethyl)-3-(4-(4-(3-(piperidin-1-yl)propy-lamino)-1,6-naphthyridin-2-yl)phenyl)acrylamide Example 120: Synthesis of (E)-N-(3-(Piperidin-1-yl)propyl)-3-(4-(4-(3-(piperidin-1-yl)propylamino)-1,6-naphthyridin-2-yl)phenyl)acrylamide

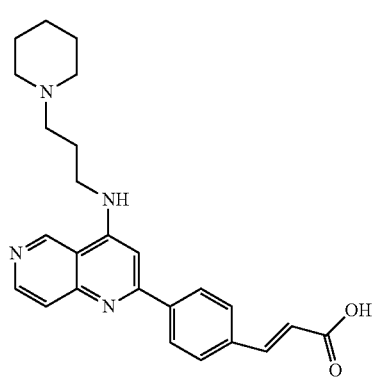

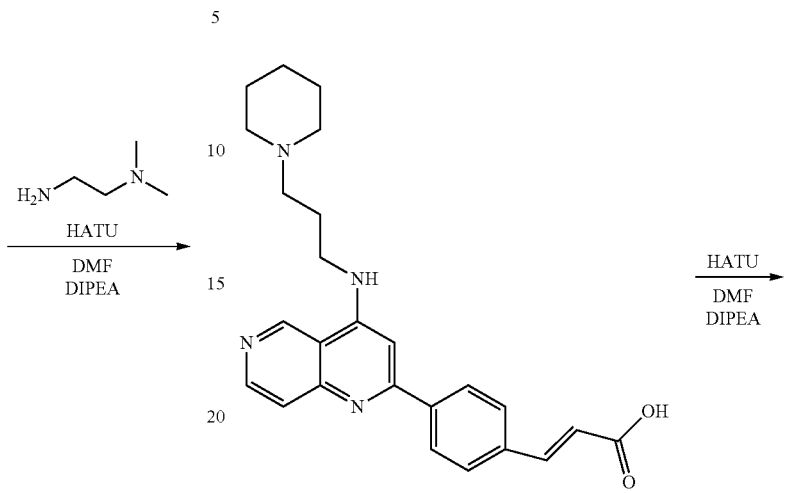

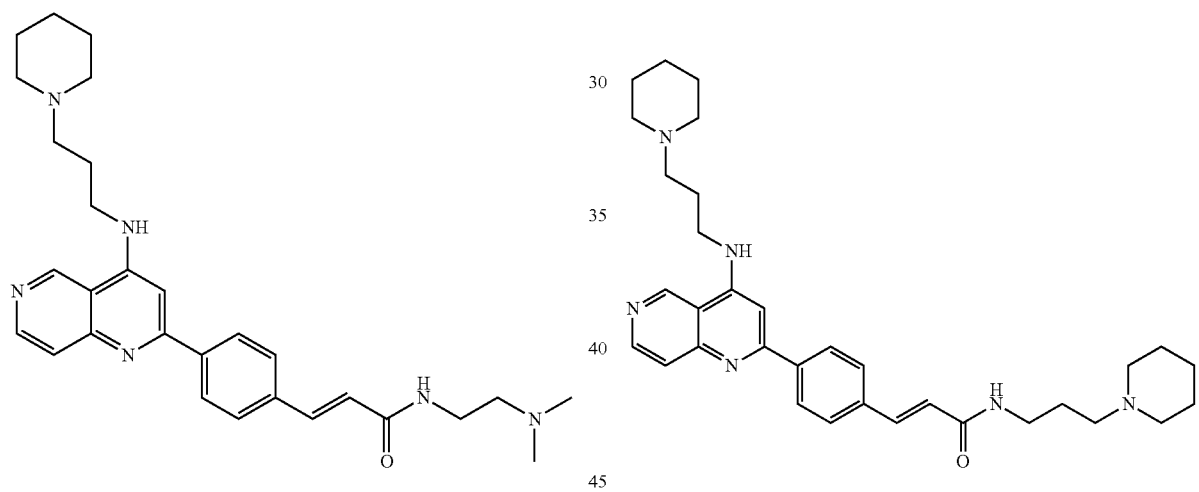

The solution of 3-(4-(4-(3-(piperidin-1-yl)propylamino)-1,6-naphthyridin-2-yl)phenyl)acrylic acid (62 mg, 0.1 mmol), N',N¹-dimethylethane-1,2-diamine (18 mg, 0.3 mmol), HATU (114 mg, 0.3 mmol) and DIPEA (58 mg, 0.45 mmol) in DMF (3 mL) was stirred at room temperature overnight. Then 100 mL water was added and the mixture was extracted with EA (100 mL), washed with brine, dried over $Na_2SO_4$, concentrated and purified by Prep-HPLC (Welch, XB-C18, 21.2 mm×250 mm, 10 um, eluting with 20% $CH_3CN$ in 1‰ TFA in $H_2O$) to give (E)-N-(2-(dimethylamino)ethyl)-3-(4-(4-(3-(piperidin-1-yl)propylamino)-1,6-naphthyridin-2-yl)phenyl)acrylamide (40 mg, 41.9%) as white solid. HPLC/UV purity: 100%; LC-MS (ESI): 486.8 $(M+1)^+$. ¹H NMR (METHANOL-$d_4$) δ: 9.74 (s, 1H), 8.89-8.89 (m, 1H), 8.10 (d, J=8.4 Hz, 2H), 7.93-7.85 (m, 3H), 7.70 (d, J=15.6 Hz, 1H), 7.27 (s, 1H), 6.84 (d, J=16 Hz, 1H), 3.86 (t, J=6.8 Hz, 2H), 3.74 (t, J=6.8 Hz, 2H), 3.62-3.58 (m, 2H), 3.40-3.36 (m, 2H), 3.36-3.30 (m, 2H), 3.00 (s, 6H), 2.97-2.94 (m, 2H), 2.34-2.30 (m, 2H), 1.99-1.95 (m, 2H), 1.87-1.78 (m, 3H), 1.59-1.49 (m, 1H).

The mixture of (E)-3-(4-(4-(3-(piperidin-1-yl)propy-lamino)-1,6-naphthyridin-2-yl)phenyl)acrylic acid (84 mg, 0.2 mmol), (1-methylpiperidin-4-yl)methanamine (28 mg, 0.2 mmol), HATU (76 mg, 0.2 mmol) and DIPEA (52 mg, 0.4 mmol) in DMF (4.0 mL) was stirred at room temperature overnight. Then 100 mL water was added and the mixture was extracted with EA (100 mL), washed with brine, dried over $Na_2SO_4$, concentrated and purified by Prep-HPLC (Welch, XB-C18, 21.2 mm×250 mm, 10 um, eluting with 20% $CH_3CN$ in 1‰ TFA in $H_2O$) to give (E)-N-(3-(piperidin-1-yl)propyl)-3-(4-(4-(3-(piperidin-1-yl)propylamino)-1,6-naphthyridin-2-yl)phenyl)acrylamide (60 mg, 55%) as yellow solid. HPLC/UV purity: 100%; LC-MS (ESI): 540.9 $(M+1)^+$. ¹H NMR (METHANOL-$d_4$) δ: 9.84 (s, 1H), 8.95 (s, 1H), 8.09 (d, J=8.4 Hz, 2H), 7.95 (d, J=4.0 Hz, 1H), 7.89 (d, J=8.0 Hz, 2H), 7.69 (d, J=15.2 Hz, 1H), 7.28 (s, 1H), 6.85 (d, J=15.6 Hz, 1H), 3.86 (t, J=6.8 Hz, 2H), 3.62-3.59 (m, 4H), 3.46 (t, J=6.4 Hz, 2H), 3.35-3.31 (m, 2H), 3.20-3.15 (m, 2H), 3.01-2.90 (m, 4H), 2.34-2.30 (m, 2H), 2.07-1.95 (m, 6H), 1.87-1.77 (m, 6H), 1.57-1.54 (m, 2H).

Example 121: Synthesis of (E)-N-((1-Methylpiperidin-4-yl)methyl)-3-(4-(4-(3-(piperidin-1-yl)propylamino)-1,6-naphthyridin-2-yl)phenyl)acrylamide

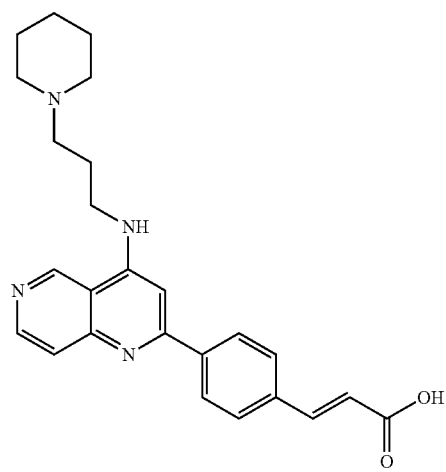

The mixture of (E)-3-(4-(4-(3-(piperidin-1-yl)propylamino)-1,6-naphthyridin-2-yl)phenyl)acrylic acid (84 mg, 0.2 mmol), (1-methylpiperidin-4-yl)methanamine (26 mg, 0.2 mmol), HATU (76 mg, 0.2 mmol) and DIPEA (52 mg, 0.4 mmol) in DMF (5.0 mL) was stirred at room temperature overnight. Then 100 mL water was added and the mixture was extracted with EA (100 mL×2), washed with brine, dried over $Na_2SO_4$, concentrated and purified by Prep-HPLC (Welch, XB-C18, 21.2 mm×250 mm, 10 um, eluting with 20% $CH_3CN$ in 1‰ TFA in $H_2O$) to give (E)-N-((1-methylpiperidin-4-yl)methyl)-3-(4-(4-(3-(piperidin-1-yl)propylamino)-1,6-naphthyridin-2-yl)phenyl)acrylamide (60 mg, 57%) as yellow solid. HPLC/UV purity: 100%; LC-MS (ESI): 526.9 (M+1)$^+$. $^1$H NMR (METHANOL-$d_4$) δ: 9.75 (s, 1H), 8.88 (d, J=6.0 Hz, 1H), 8.08 (d, J=8.4 Hz, 2H), 7.93 (d, J=5.6 Hz, 1H), 7.89 (d, J=8.0 Hz, 2H), 7.67 (d, J=16.0 Hz, 1H), 7.27 (s, 1H), 6.85 (d, J=15.6 Hz, 1H), 3.86 (t, J=6.4 Hz, 2H), 3.62-3.55 (m, 4H), 3.55-3.31 (m, 4H), 3.04-2.94 (m, 2H), 2.93-3.00 (m, 4H), 2.88 (s, 3H), 2.34-2.30 (m, 2H), 2.08-1.79 (m, 7H), 1.58-1.52 (m, 2H).

Example 122: Synthesis of (E)-N-(2-(1-Methylpiperidin-4-yl)ethyl)-3-(4-(4-(3-(piperidin-1-yl)propylamino)-1,6-naphthyridin-2-yl)phenyl)acrylamide

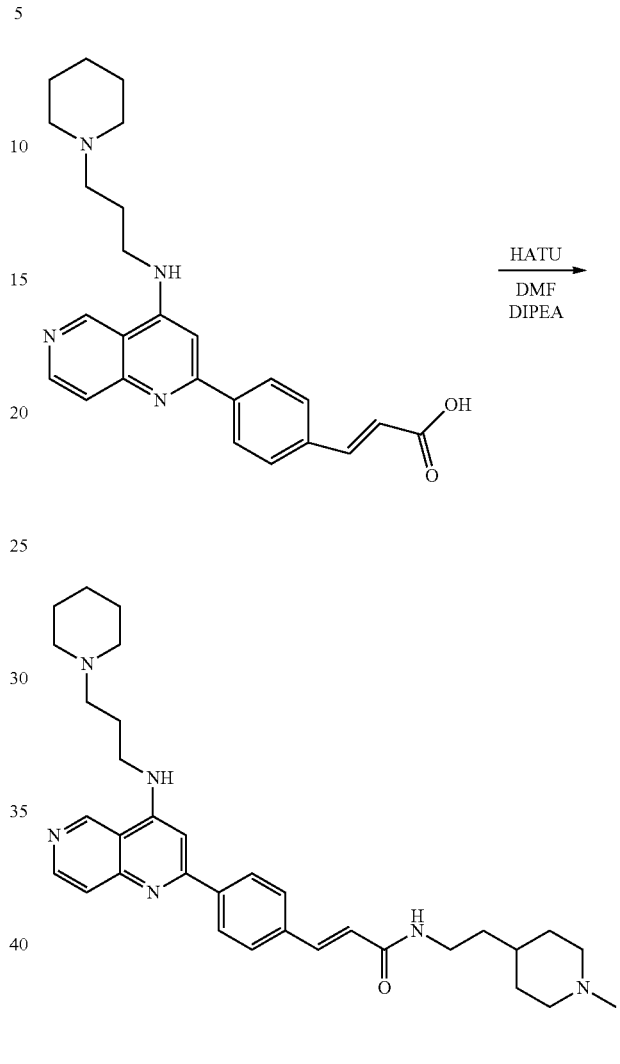

The mixture of (E)-3-(4-(4-(3-(piperidin-1-yl)propylamino)-1,6-naphthyridin-2-yl)phenyl)acrylic acid (84 mg, 0.2 mmol), 2-(1-methylpiperidin-4-yl)ethanamine (29 mg, 0.2 mmol), HATU (76 mg, 0.2 mmol) and DIPEA (52 mg, 0.4 mmol) in DMF (10.0 mL) was stirred at room temperature for 3 hours. Then 100 mL water was added and the mixture was extracted with EA (100 mL), washed with brine, dried over $Na_2SO_4$, concentrated and purified by Prep-HPLC (Welch, XB-C18, 21.2 mm×250 mm, 10 um, eluting with 20% $CH_3CN$ in 1‰ TFA in $H_2O$) to give (E)-N-(2-(1-methylpiperidin-4-yl)ethyl)-3-(4-(4-(3-(piperidin-1-yl)propylamino)-1,6-naphthyridin-2-yl)phenyl)acrylamide (60 mg, 55%) as yellow solid. HPLC/UV purity: 100%; LC-MS (ESI): 540.9 (M+1)$^+$. $^1$H NMR (METHANOL-$d_4$) δ: 9.75 (s, 1H), 8.88 (d, J=6.0 Hz, 1H), 8.08 (d, J=8.4 Hz, 2H), 7.93 (d, J=6.0 Hz, 1H), 7.88 (d, J=8.8 Hz, 2H), 7.65 (d, J=15.6 Hz, 1H), 7.26 (d, J=7.6 Hz, 1H), 6.82 (d, J=15.6 Hz, 1H), 3.86 (t, J=6.8 Hz, 2H), 3.63-3.50 (m, 4H), 3.43 (t, J=6.8 Hz, 2H), 3.35-3.31 (m, 2H), 3.03-2.92 (m, 4H), 2.87 (s, 3H), 2.36-2.28 (m, 2H), 2.09 (d, J=14.0 Hz, 2H), 1.97 (d, J=15.6 Hz, 2H), 1.88-1.76 (m, 3H), 1.70-1.66 (m, 1H), 1.64-1.40 (m, 5H).

Example 123: Synthesis of (E)-N-((1-Ethylpiperidin-4-yl)methyl)-3-(4-(4-(3-(piperidin-1-yl)propylamino)-1,6-naphthyridin-2-yl)phenyl)acrylamide

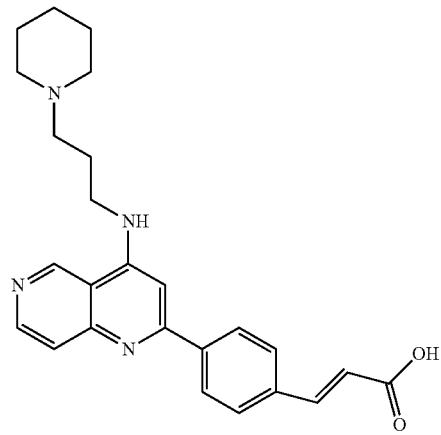

HATU
DMF
DIPEA

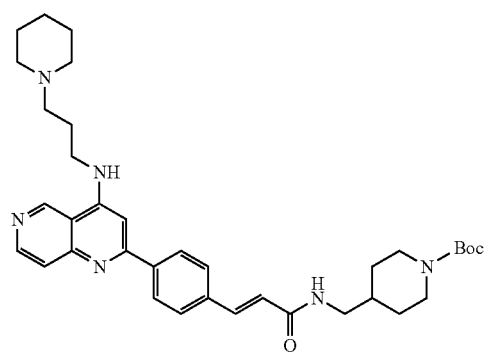

TFA
DCM

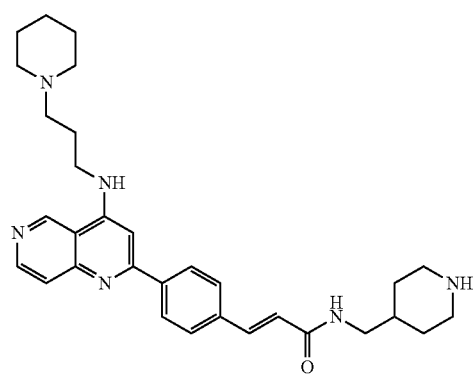

EtI
DMF
K₂CO₃

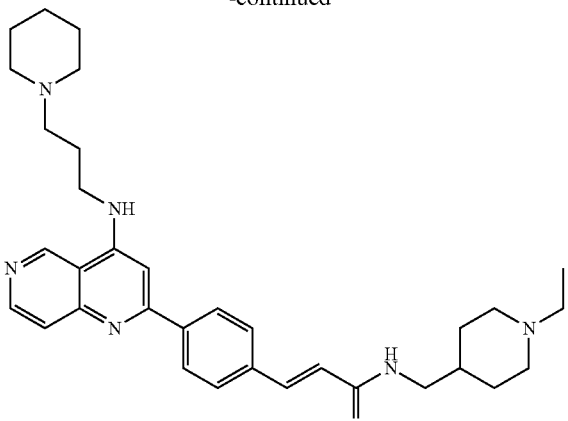

Step 1

The mixture of (E)-3-(4-(4-(3-(piperidin-1-yl)propylamino)-1,6-naphthyridin-2-yl)phenyl)acrylic acid (83 mg, 0.2 mmol), tert-butyl 4-(aminomethyl)piperidine-1-carboxylate (43 mg, 0.3 mmol), HATU (115 mg, 0.3 mmol) and DIPEA (65 mg, 0.5 mmol) in DMF (5.0 mL) was stirred at room temperature overnight. Then 100 mL water was added and the mixture was extracted with EA (50 mL×2), washed with brine, dried over $Na_2SO_4$, concentrated and purified by Prep-HPLC (Welch, XB-C18, 21.2 mm×250 mm, 10 um, eluting with 20% $CH_3CN$ in 1‰ TFA in $H_2O$) to give (E)-tert-butyl 4-((3-(4-(4-(3-(piperidin-1-yl)propylamino)-1,6-naphthyridin-2-yl)phenyl)acrylamido)methyl)piperidine-1-carboxylate (80 mg, 65.6%) as yellow solid. HPLC/UV purity: 90%; LC-MS (ESI): 612.9 (M+1)⁺.

Step 2

The solution of (E)-tert-butyl 4-((3-(4-(4-(3-(piperidin-1-yl)propylamino)-1,6-naphthyridin-2-yl)phenyl)acrylamido)methyl)piperidine-1-carboxylate (80 mg, 0.13 mmol) in TFA/DCM (1 mL/5 mL) was stirred at room temperature for 1 hour. The mixture was concentrated and purified by Prep-HPLC (Welch, XB-C18, 21.2 mm×250 mm, 10 um, eluting with 20% $CH_3CN$ in 1‰ TFA in $H_2O$) to give (E)-3-(4-(4-(3-(piperidin-1-yl)propylamino)-1,6-naphthyridin-2-yl)phenyl)-N-(piperidin-4-ylmethyl)acrylamide (40 mg, 60%) as yellow solid. HPLC/UV purity: 100%; LC-MS (ESI): 513.3 (M+1)⁺. ¹H NMR (METHANOL-d₄) δ: 9.63 (s, 1H), 8.76 (d, J=6.0 Hz, 1H), 8.01-7.95 (m, 2H), 7.81-7.75 (m, 3H), 7.55 (d, J=16.0 Hz, 1H), 7.15 (s, 1H), 6.73 (d, J=16.0 Hz, 1H), 3.78-3.72 (m, 2H), 3.49 (d, J=11.2 Hz, 2H), 3.33 (d, J=12.8 Hz, 2H), 3.23-3.20 (m, 4H), 2.98-2.79 (m, 4H), 2.22-2.18 (m, 2H), 2.01-1.80 (m, 5H), 1.76-1.67 (m, 3H), 1.42-1.36 (m, 3H).

Step 3

The mixture of (E)-3-(4-(4-(3-(piperidin-1-yl)propylamino)-1,6-naphthyridin-2-yl)phenyl)-N-(piperidin-4-ylmethyl)acrylamide (31 mg, 0.06 mmol), EtI (15.6 mg, 0.1 mmol) and $K_2CO_3$ (28 mg, 0.2 mmol) in DMF (5 mL) was stirred at room temperature for 2 hours. Then 100 mL water was added and the mixture was extracted with EA (100 mL), washed with brine, dried over $Na_2SO_4$, concentrated and purified by Prep-HPLC (Welch, XB-C18, 21.2 mm×250 mm, 10 um, eluting with 20% CH$_3$CN in 1‰ TFA in H$_2$O) to give (E)-N-((1-ethylpiperidin-4-yl)methyl)-3-(4-(4-(3-(piperidin-1-yl)propylamino)-1,6-naphthyridin-2-yl)phenyl)acrylamide (5 mg, 17%) as white solid. HPLC/UV purity: 100%; LC-MS (ESI): 541.3 (M+1)$^+$. $^1$H NMR (METHANOL-d$_4$) δ: 9.45 (s, 1H), 8.50 (d, J=5.6 Hz, 1H), 8.04 (d, J=8.4 Hz, 2H), 7.71-7.66 (m, 3H), 7.53 (d, J=16.0 Hz, 1H), 7.04 (s, 1H), 6.68 (d, J=15.6 Hz, 1H), 3.61-3.57 (m, 2H), 3.53-3.47 (m, 2H), 3.21-3.17 (m, 2H), 3.10-3.07 (m, 2H), 2.86-2.82 (m, 2H), 2.20-2.16 (m, 2H), 1.99-1.92 (m, 2H), 1.90-1.70 (m, 6H), 1.52-1.40 (m, 4H), 1.26 (t, J=7.6 Hz, 3H), 1.23-1.18 (m, 5H).

Example 124: Synthesis of (E)-N-(2-(4-Methyl-1,4-diazepan-1-yl)ethyl)-3-(4-(4-(3-(piperidin-1-yl)propylamino)-1,6-naphthyridin-2-yl)phenyl)acrylamide

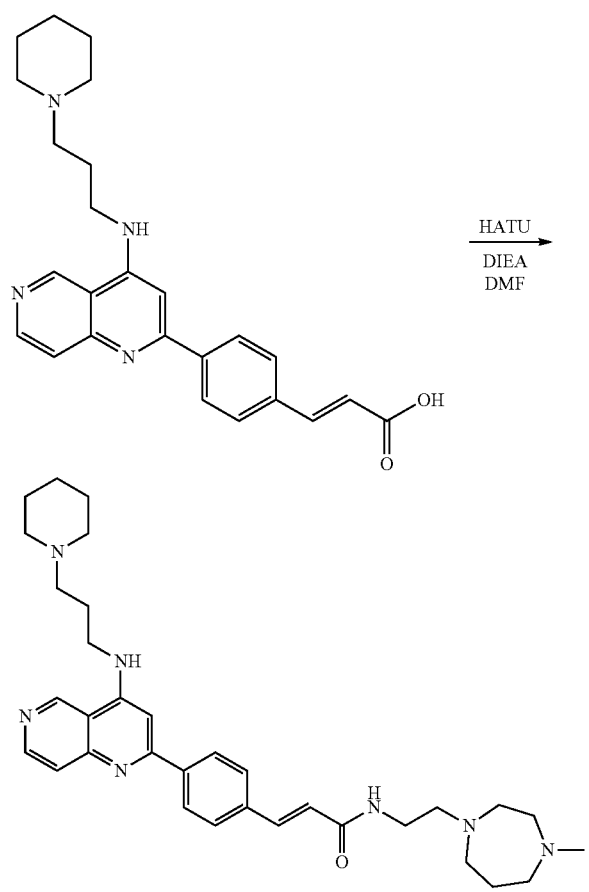

The mixture of (E)-3-(4-(4-(3-(piperidin-1-yl)propylamino)-1,6-naphthyridin-2-yl)phenyl)acrylic acid (205 mg, 0.5 mmol), 2-(4-methyl-1,4-diazepan-1-yl)ethanamine (78 mg, 0.5 mmol), HATU (380 mg, 1 mmol) and DIPEA (129 mg, 1 mmol) in DMF (5.0 mL) was stirred at room temperature overnight. Then 50 mL water was added and the mixture was extracted with EA (200 mL), washed with water (100 mL×2) and brine (100 mL×1), dried over Na$_2$SO$_4$, filtered, concentrated and purified by Prep-HPLC (Welch, XB-C18, 21.2 mm×250 mm, 10 um, eluting with 20% CH$_3$CN in 1‰ TFA in H$_2$O) to give (E)-N-(2-(4-methyl-1,4-diazepan-1-yl)ethyl)-3-(4-(4-(3-(piperidin-1-yl)propylamino)-1,6-naphthyridin-2-yl)phenyl)acrylamide (100 mg, 36%) as white solid. HPLC/UV purity: 100%; LC-MS (ESI): 556.3 (M+1)$^+$. $^1$H NMR (METHANOL-d$_4$) δ: 9.75 (s, 1H), 8.89 (d, J=6.0 Hz, 1H), 8.09 (d, J=8.4 Hz, 2H), 7.93 (d, J=6.0 Hz, 1H), 7.89 (d, J=8.0 Hz, 2H), 7.70 (d, J=16.0 Hz, 1H), 7.28 (s, 1H), 6.84 (d, J=16.0 Hz, 1H), 3.88-3.74 (m, 6H), 3.76 (t, J=5.6 Hz, 2H), 3.66-3.59 (m, 6H), 3.44 (t, J=5.6 Hz, 2H), 3.32-3.30 (m, 2H), 3.01-2.94 (m, 5H), 2.37-2.30 (m, 4H), 1.99-1.95 (m, 2H), 1.88-1.79 (m, 3H), 1.59-1.50 (m, 1H).

Example 125: Synthesis of (E)-N,N-Diethyl-3-(4-(4-((4-(pyrrolidin-1-ylmethyl)phenyl)amino)-1,6-naphthyridin-2-yl)phenyl)acrylamide

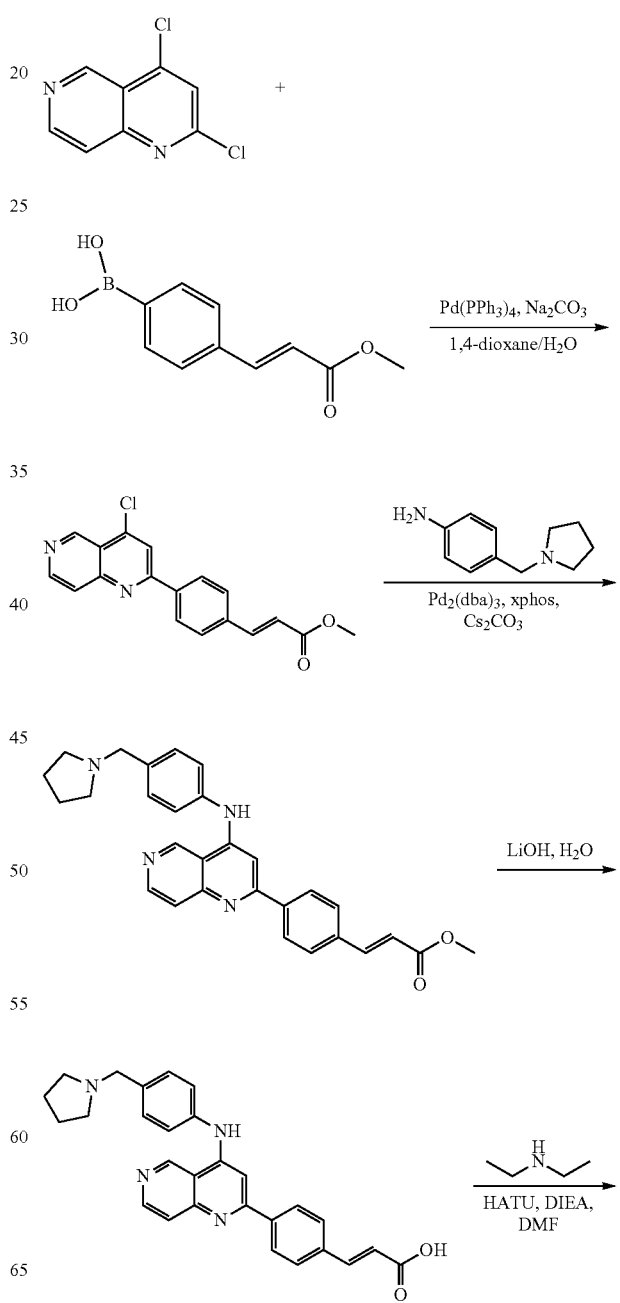

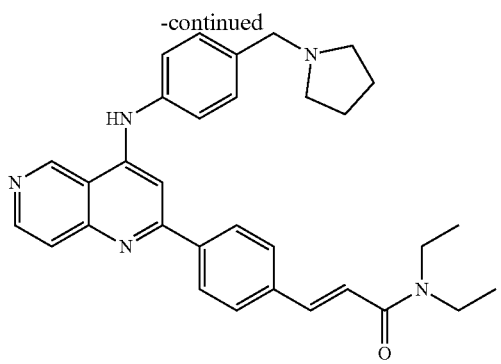

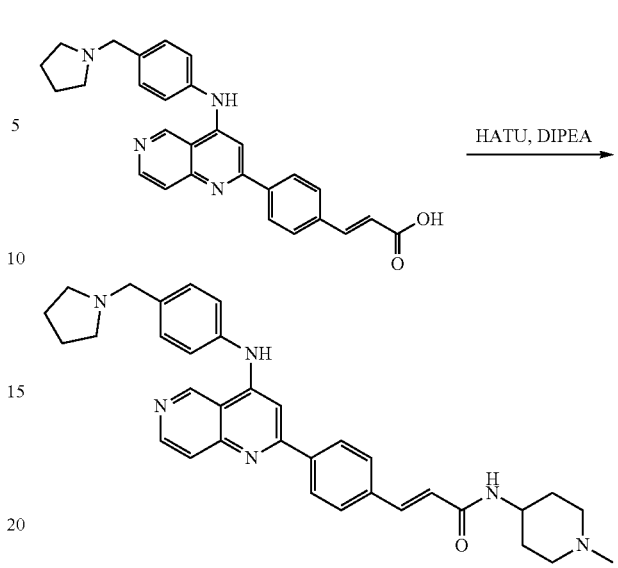

Step 1

The mixture of 2,4-dichloro-1,6-naphthyridine (2 g, 10 mmol), (E)-(4-(3-methoxy-3-oxoprop-1-en-1-yl)phenyl)boronic acid (2.47 g, 12 mmol), Pd(PPh$_3$)$_4$ (575 mg, 0.5 mmol) and Na$_2$CO$_3$ (2.12 g, 20 mmol) in 1,4-dioxane (40 mL) and H$_2$O (5 mL) was heated at 100° C. for 18 hrs under N$_2$ atmosphere. The resulting solutions were concentrated by rotary evaporation (55° C., 20 mmHg). The crude mixture was purified by silica gel chromatography (silica gel, eluting with 10% methanol in DCM) to give (E)-methyl 3-(4-(4-chloro-1,6-naphthyridin-2-yl)phenyl)acrylate (2.87 g, 88%) as a yellow solid HPLC/UV purity: 90%; LC-MS (ESI): 325.3 (M+1)$^+$.

Step 2

To a 20-mL microwave vial was charged with (E)-methyl 3-(4-(4-chloro-1,6-naphthyridin-2-yl)phenyl)acrylate (500 mg, 1.54 mmol), 4-(pyrrolidin-1-ylmethyl)aniline (298 mg, 1.69 mmol), Pd$_2$(dba)$_3$ (141 mg, 0.154 mmol), Xphos (177 mg, 0.308 mmol), Cs$_2$CO$_3$ (1 g, 3.08 mmol) and, 1,4-dioxane (10 mL). The sealed vial with the resulting mixture was heated for 1 hrs in a Biotage Initiator Eight Microwave Reactor at a constant temperature of 120° C. The resulting solutions were concentrated by rotary evaporation (55° C., 20 mmHg). The crude mixture was purified using silica gel chromatography (silica gel, eluting with 10% methanol in DCM) to give (E)-methyl 3-(4-(4-((4-(pyrrolidin-1-ylmethyl)phenyl)amino)-1,6-naphthyridin-2-yl)phenyl)acrylate (380 mg, 53%) as a yellow solid. HPLC/UV purity: 95%; LC-MS (ESI): 465.3 (M+1)$^+$

Step 3

To a solution of (E)-methyl 3-(4-(4-((4-(pyrrolidin-1-ylmethyl)phenyl)amino)-1,6-naphthyridin-2-yl)phenyl)acrylate (380 mg, 0.818 mmol) in methanol (2 mL) and THF (2 mL) was added 1N aqueous LiOH solution (3.27 mL, 3.27 mmol). The reaction mixture was stirred at room temperature overnight. The solvent was removed and water (5 mL) was added. The pH of the water phase was adjusted with 1N aq. HCl solution to pH 4. It was lyophilized to give crude product (500 mg) as a yellow solid.

Step 4

The mixture of (E)-3-(4-(4-((4-(pyrrolidin-1-ylmethyl)phenyl)amino)-1,6-naphthyridin-2-yl)phenyl)acrylic acid (100 mg, 0.22 mmol), diethylamine (32 mg, 0.44 mmol), HATU (380.23 g, 0.33 mmol) and DIPEA (57 mg, 0.44 mmol) in DMF (3 mL) was stirred at room temperature overnight. The reaction mixture was quenched with water (3 mL), extracted with EtOAc (5 mL×3), washed with water (5 mL×3) and brine (10 mL), dried over Na$_2$SO$_4$, concentrated and purified by prep-PLC to afford (E)-N,N-diethyl-3-(4-(4-((4-(pyrrolidin-1-ylmethyl)phenyl)amino)-1,6-naphthyridin-2-yl)phenyl)acrylamide (40 mg, 36%) as yellow solid. LC-MS (ESI): 506.3 (M+1)$^+$. $^1$H NMR (400 MHz, CD$_3$OD) δ 9.89 (s, 1H), 8.92 (d, J=6.0 Hz, 1H), 8.01 (d, J=6.0 Hz, 1H), 7.94-7.86 (m, 4H), 7.78-7.71 (m, 4H), 7.64 (d, J=15.6 Hz, 1H), 7.30 (s, 1H), 7.22 (d, J=15.6 Hz, 1H), 4.48 (s, 2H), 3.64-3.58 (m, 4H), 3.52 (q, J=15.6 Hz, 2H), 3.31-3.26 (m, 2H), 2.14 (d, J=67.2 Hz, 4H), 1.28 (t, J=7.2 Hz, 3H), 1.20 (t, J=7.2 Hz, 3H).

Example 126: Synthesis of N-(1-Methylpiperidin-4-yl)-3-(4-(4-(1-methylpiperidin-4-ylamino)-1,6-naphthyridin-2-yl)phenyl)propanamide

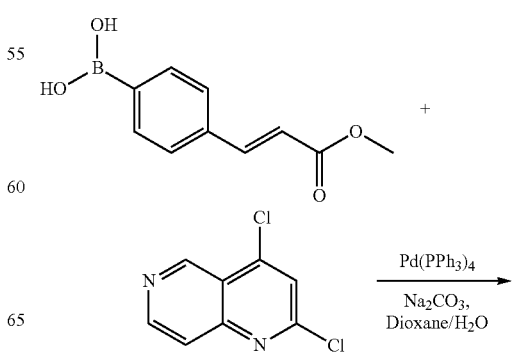

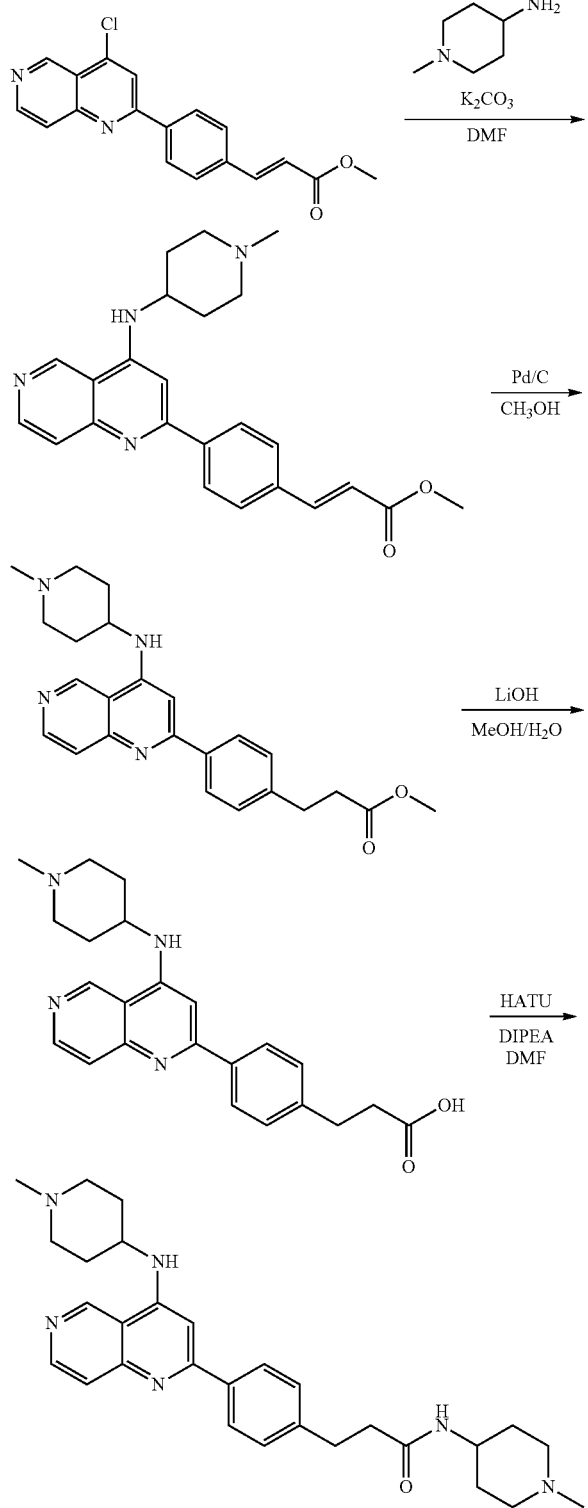

Step 1

The mixture of 4-(3-methoxy-3-oxoprop-1-enyl)phenylboronic acid (412 mg, 2 mmol), 2,4-dichloro-1,6-naphthyridine (400 mg, 2 mmol), $Na_2CO_3$ (424 mg, 4 mmol) and $Pd(PPh_3)_4$ (230 mg, 0.2 mmol) in 1,4-dioxane/$H_2O$ (50 mL/5 mL) was stirred at 100° C. overnight. The mixture was diluted with EA, washed with water (100 mL×3) and brine (100 mL×1), dried over $Na_2SO_4$, filtered, concentrated and purified by silica gel column chromatography to give methyl 3-(4-(4-chloro-1,6-naphthyridin-2-yl)phenyl)acrylate (420 mg, 65%) as white solid which was used in next step directly. HPLC/UV purity: 100%; LC-MS (ESI): 325.2 $(M+1)^+$.

Step 2

The mixture of (E)-methyl 3-(4-(4-chloro-1,6-naphthyridin-2-yl)phenyl)acrylate (324 mg, 1 mmol), 1-methylpiperidin-4-amine (230 mg, 2.0 mmol) and $K_2CO_3$ (280 mg, 2 mmol) in DMF (20 mL) was stirred at 100° C. for 2 hrs. Then 100 mL water was added and the mixture was extracted with EA (100 mL), washed with brine, dried over $Na_2SO_4$, concentrated and purified by silica gel column chromatography to give (E)-methyl 3-(4-(4-(1-methylpiperidin-4-ylamino)-1,6-naphthyridin-2-yl)phenyl)acrylate (200 mg, 50%) as white solid. HPLC/UV purity: 100%; LC-MS (ESI): 403.2 $(M+1)^+$.

Step 3

The mixture of (E)-methyl 3-(4-(4-(1-methylpiperidin-4-ylamino)-1,6-naphthyridin-2-yl)phenyl)acrylate (200 mg, 0.5 mmol), Pd/C (10%, 30 mg) in MeOH (40 mL) was stirred under $H_2$ atmosphere at room temperature overnight. The mixture was filtered and concentrated to give crude methyl 3-(4-(4-(1-methylpiperidin-4-ylamino)-1,6-naphthyridin-2-yl)phenyl)propanoate (200 mg, 99%) as white solid. HPLC/UV purity: 100%; LC-MS (ESI): 405.2 $(M+1)^+$.

Step 4

The solution of methyl 3-(4-(4-(1-methylpiperidin-4-ylamino)-1,6-naphthyridin-2-yl)phenyl)propanoate (200 mg, 0.5 mmol) and LiOH·$H_2O$ (41 mg, 1 mmol) in MeOH (10 mL) and $H_2O$ (1 mL) was stirred at 80° C. for 6 hrs. Then the mixture was cooled to room temperature and 1.1 mL 1N aq. HCl solution was added. The solvent was removed to give crude 3-(4-(4-(1-Methylpiperidin-4-ylamino)-1,6-naphthyridin-2-yl)phenyl)propanoic acid which was used in next step directly. HPLC/UV purity: 100%; LC-MS (ESI): 391.2 $(M+1)^+$.

Step 5

The mixture of 3-(4-(4-(1-methylpiperidin-4-ylamino)-1,6-naphthyridin-2-yl)phenyl)propanoic acid (78 mg, 0.2 mmol), 1-methylpiperidin-4-amine (34 mg, 0.3 mmol), HATU (114 mg, 0.3 mmol) and DIPEA (65 mg, 0.5 mmol) in DMF (5.0 mL) was stirred at room temperature for 2 hours. Then 100 mL water was added and the mixture was extracted with EA (100 mL×2), washed with brine, dried over $Na_2SO_4$, concentrated and purified by silica gel column chromatography to give N-(1-methylpiperidin-4-yl)-3-(4-(4-(1-methylpiperidin-4-ylamino)-1,6-naphthyridin-2-yl)phenyl)propanamide (5 mg, 5.2%) as white solid. HPLC/UV purity: 90%; LC-MS (ESI): 487.3 $(M+1)^+$. $^1H$ NMR (METHANOL-$d_4$) δ: 9.80 (s, 1H), 8.86 (d, J=6.0 Hz, 1H), 7.97 (d, J=8.0 Hz, 2H), 7.90 (d, J=6.0 Hz, 1H), 7.55 (d, J=8.0 Hz, 2H), 7.32 (s, 1H), 4.50-4.43 (m, 1H), 3.97-3.85 (m, 1H), 3.70 (d, J=12.8 Hz, 2H), 3.53 (d, J=11.6 Hz, 2H), 3.30-3.20

(m, 2H), 3.13-3.04 (m, 4H), 2.94 (s, 3H), 2.85 (s, 3H), 2.57 (t, J=8.0 Hz, 2H), 2.41 (d, J=14.0 Hz, 2H), 2.18-2.00 (m, 4H), 1.83-1.62 (m, 2H).

Example 127: Synthesis of N,N-Diethyl-3-(4-(4-(1-methylpiperidin-4-ylamino)-1,6-naphthyridin-2-yl)phenyl)propanamide

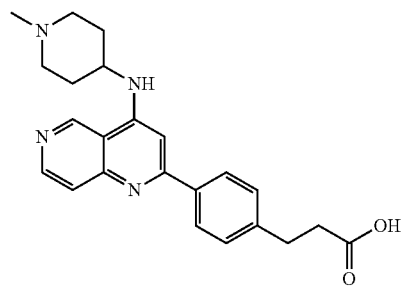

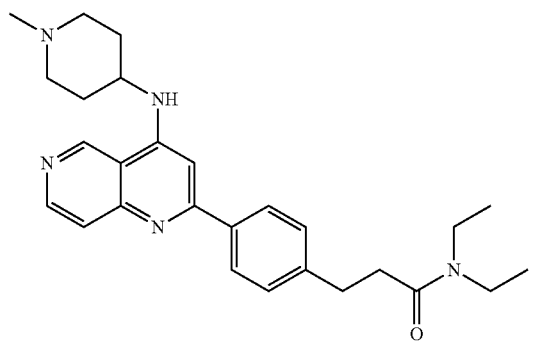

The solution of 3-(4-(4-(1-methylpiperidin-4-ylamino)-1,6-naphthyridin-2-yl)phenyl)propanoic acid (78 mg, 0.2 mmol), diethylamine (22 mg, 0.3 mmol), HATU (114 mg, 0.3 mmol) and DIPEA (65 mg, 0.3 mmol) in DMF (5.0 mL) was stirred at room temperature for 3 hours. Then 100 mL water was added and the mixture was extracted with EA (100 mL×2), washed with brine, dried over $Na_2SO_4$, concentrated and purified by silica gel column chromatography to give N,N-diethyl-3-(4-(4-(1-methylpiperidin-4-ylamino)-1,6-naphthyridin-2-yl)phenyl)propanamide (30 mg, 33%) as white solid. HPLC/UV purity: 100%; LC-MS (ESI): 446.3 $(M+1)^+$. $^1H$ NMR (METHANOL-$d_4$) δ: 9.82 (s, 1H), 8.89 (d, J=6.0 Hz, 1H), 7.98 (d, J=8.0 Hz, 2H), 7.93 (d, J=6.0 Hz, 1H), 7.60 (d, J=8.0 Hz, 2H), 7.34 (s, 1H), 4.50-4.45 (m, 1H), 3.72 (d, J=12.8 Hz, 2H), 3.42-3.32 (m, 4H), 3.30-3.26 (m, 2H), 3.13 (t, J=7.2 Hz, 2H), 2.97 (s, 3H), 2.79 (t, J=7.2 Hz, 2H), 2.44 (d, J=14.4 Hz, 2H), 2.25-2.15 (m, 2H), 1.19-1.11 (m, 6H).

Example 128: Synthesis of N-((1-Methylpiperidin-4-yl)methyl)-3-(4-(4-(3-(piperidin-1-yl)propylamino)-1,6-naphthyridin-2-yl)phenyl)propanamide

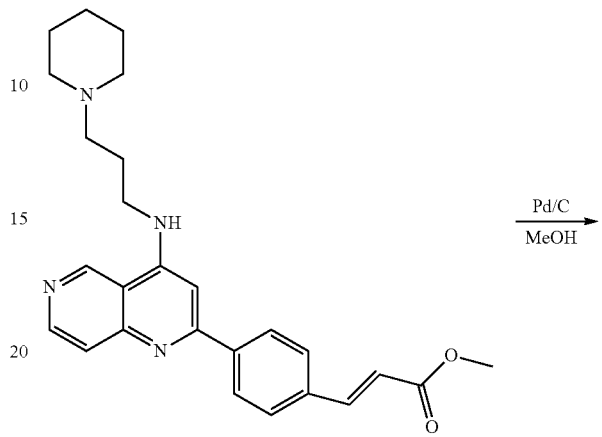

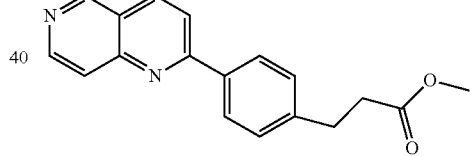

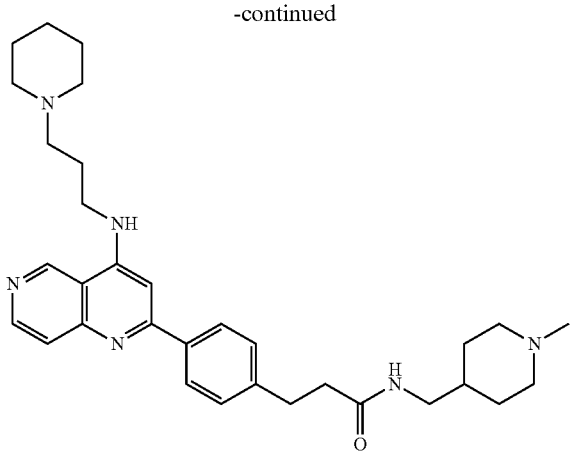

Step 1

The mixture of (E)-methyl 3-(4-(4-(3-(piperidin-1-yl)propylamino)-1,6-naphthyridin-2-yl)phenyl)acrylate (430 mg, 1 mmol) and Pd/C (80 mg) in MeOH (50 mL) was stirred at 35° C. for 3 hours under $H_2$ balloon protection. The mixture was filtered, concentrated to give crude methyl 3-(4-(4-(3-(piperidin-1-yl)propylamino)-1,6-naphthyridin-2-yl)phenyl)propanoate (430 mg, 99%) as yellow solid which was used in next step directly. HPLC/UV purity: 95%; LC-MS (ESI): 432.8 (M+1)$^+$.

Step 2

The solution of methyl 3-(4-(4-(3-(piperidin-1-yl)propylamino)-1,6-naphthyridin-2-yl)phenyl)propanoate (430 mg, 0.99 mmol) and LiOH·$H_2$O (82 mg, 2 mmol) in MeOH/$H_2$O (20 mL/2 mL) was stirred at 65° C. for 3 hours. Then the mixture was cooled to room temperature and 2.3 mL 1N aq. HCl solution was added. The solvent was removed to give crude 3-(4-(4-(3-(piperidin-1-yl)propylamino)-1,6-naphthyridin-2-yl)phenyl)propanoic acid (400 mg, 95%) as white solid which was used in next step directly. HPLC/UV purity: 90%; LC-MS (ESI): 418.8 (M+1)$^+$.

Step 3

The mixture of 3-(4-(4-(3-(piperidin-1-yl)propylamino)-1,6-naphthyridin-2-yl)phenyl)propanoic acid (84 mg, 0.2 mmol), (1-methylpiperidin-4-yl)methanamine (26 mg, 0.2 mmol), HATU (76 mg, 0.2 mmol) and DIPEA (52 mg, 0.4 mmol) in DMF (3.0 mL) was stirred at room temperature overnight. Then 50 mL water was added and the mixture was extracted with EA (100 mL), washed with brine, dried over $Na_2SO_4$, concentrated and purified by Prep-HPLC (Welch, XB-C18, 21.2 mm×250 mm, 10 um, eluting with 20% $CH_3CN$ in 1‰ TFA in $H_2O$) to give N-((1-methylpiperidin-4-yl)methyl)-3-(4-(4-(3-(piperidin-1-yl)propylamino)-1,6-naphthyridin-2-yl)phenyl)propanamide (53 mg, 50%) as yellow solid. HPLC/UV purity: 100%; LC-MS (ESI): 528.8 (M+1)$^+$. $^1$H NMR (METHANOL-$d_4$): 9.73 (s, 1H), 8.88 (d, J=6.4 Hz, 1H), 7.97 (d, J=8.4 Hz, 2H), 7.92 (d, J=5.6 Hz, 2H), 7.57 (d, J=8.4 Hz, 2H), 7.21 (s, 1H), 3.85 (t, J=6.4 Hz, 2H), 3.60 (d, J=12.4 Hz, 2H), 3.53 (d, J=12.4 Hz, 2H), 3.32-3.29 (m, 2H), 3.14 (d, J=6.8 Hz, 2H), 3.12-3.07 (m, 2H), 3.0-2.90 (m, 4H), 2.86 (s, 3H), 2.62 (t, J=8.4 Hz, 2H), 2.33-2.29 (m, 2H), 2.01-1.92 (m, 4H), 1.85-1.79 (m, 4H), 1.47-1.40 (m, 3H).

Example 129: Synthesis of N-(2-(1-Methylpiperidin-4-yl)ethyl)-3-(4-(4-(3-(piperidin-1-yl)propylamino)-1,6-naphthyridin-2-yl)phenyl)propanamide

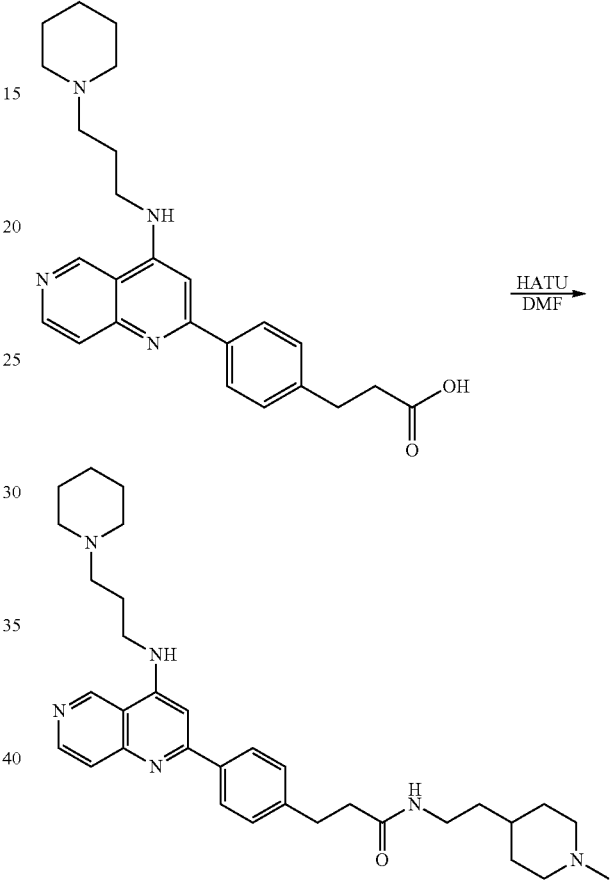

The mixture of 3-(4-(4-(3-(piperidin-1-yl)propylamino)-1,6-naphthyridin-2-yl)phenyl)propanoic acid (125 mg, 0.3 mmol), 2-(1-methylpiperidin-4-yl)ethanamine (43 mg, 0.3 mmol), HATU (190 mg, 0.5 mmol) and DIPEA (129 mg, 1 mmol) in DMF (5.0 mL) was stirred at room temperature overnight. Then 50 mL water was added and the mixture was extracted with EA (50 mL×2), washed with brine, dried over $Na_2SO_4$, concentrated and purified by Prep-HPLC (Welch, XB-C18, 21.2 mm×250 mm, 10 um, eluting with 20% $CH_3CN$ in 1‰ TFA in $H_2O$) to give N-(2-(1-methylpiperidin-4-yl)ethyl)-3-(4-(4-(3-(piperidin-1-yl)propylamino)-1,6-naphthyridin-2-yl)phenyl)propanamide (81 mg, 50%) as yellow solid. HPLC/UV purity: 100%; LC-MS (ESI): 542.9 (M+1)$^+$. $^1$H NMR (METHANOL-$d_4$) δ: 9.74 (s, 1H), 8.88 (d, J=6.0 Hz, 1H), 7.97 (d, J=8.4 Hz, 2H), 7.93 (d, J=6.0 Hz, 1H), 7.57 (d, J=8.4 Hz, 2H), 7.22 (s, 1H), 3.85 (t, J=6.8 Hz, 2H), 3.61 (d, J=12.4 Hz, 2H), 3.52 (d, J=12.8 Hz, 2H), 3.34-3.30 (m, 2H), 3.25 (t, J=7.2 Hz, 2H), 3.08 (t, J=7.2 Hz, 2H), 3.01-2.90 (m, 4H), 2.86 (s, 3H), 2.59 (t, J=7.2 Hz, 2H), 2.34-2.29 (m, 2H), 2.06-1.95 (m, 4H), 1.88-1.39 (m, 9H).

Example 130: Synthesis of 3-(4-(4-(3-(Piperidin-1-yl)propylamino)-1,6-naphthyridin-2-1)phenyl)-N-(piperidin-4-yl)propanamide

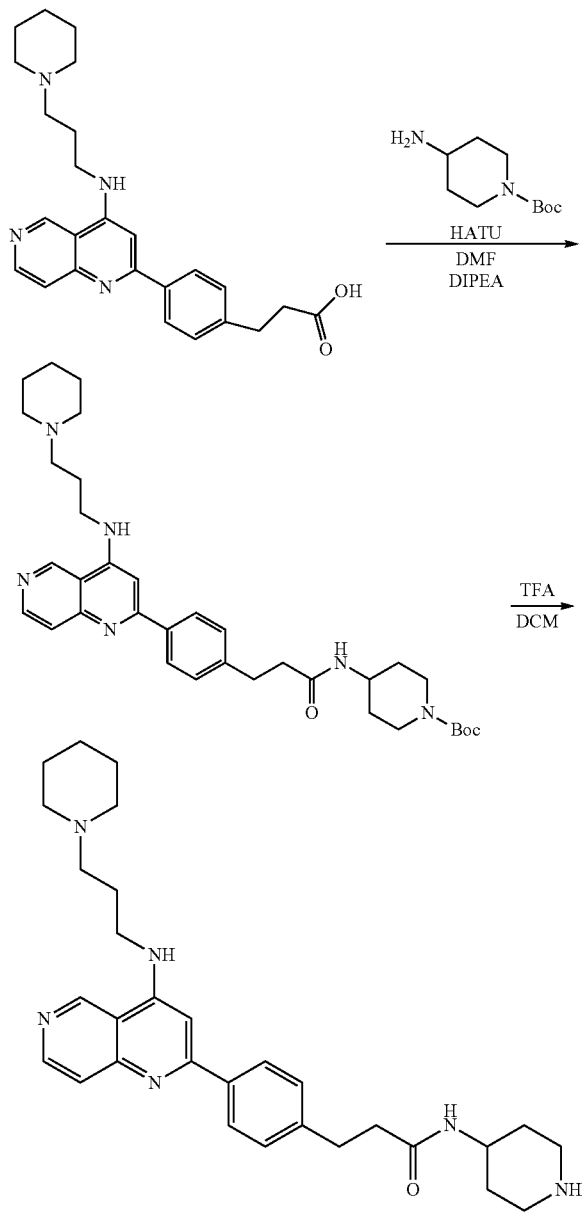

Step 1

The mixture of 3-(4-(4-(3-(piperidin-1-yl)propylamino)-1,6-naphthyridin-2-yl)phenyl)propanoic acid (125 mg, 0.3 mmol), tert-butyl 4-aminopiperidine-1-carboxylate (60 mg, 0.3 mmol), HATU (190 mg, 0.5 mmol) and DIPEA (129 mg, 1 mmol) in DMF (10.0 mL) was stirred at room temperature overnight. Then 100 mL water was added and the mixture was extracted with EA (50 mL×2), washed with brine, dried over $Na_2SO_4$, concentrated and purified by Prep-HPLC (Welch, XB-C18, 21.2 mm×250 mm, 10 um, eluting with 20% $CH_3CN$ in 1‰ TFA in $H_2O$) to give tert-butyl 4-(3-(4-(4-(3-(piperidin-1-yl)propylamino)-1,6-naphthyridin-2-yl)phenyl)propanamido)piperidine-1-carboxylate (100 mg, 55%) as yellow solid. HPLC/UV purity: 100%; LC-MS (ESI): 601.3 $(M+1)^+$.

Step 2

The solution of tert-butyl 4-(3-(4-(4-(3-(piperidin-1-yl)propylamino)-1,6-naphthyridin-2-yl)phenyl)propanamido)piperidine-1-carboxylate (100 mg, 0.136 mmol) in TFA/DCM (1 mL/5 mL) was stirred at room temperature for 2 hour. Then the solution was concentrated and purified by Prep-HPLC (Welch, XB-C18, 21.2 mm×250 mm, 10 um, eluting with 20% $CH_3CN$ in 1‰ TFA in $H_2O$) to give 3-(4-(4-(3-(piperidin-1-yl)propylamino)-1,6-naphthyridin-2-yl)phenyl)-N-(piperidin-4-yl)propanamide (40 mg, 47.9%) as white solid. HPLC/UV purity: 100%; LC-MS (ESI): 502.3 $(M+1)^+$. $^1$H NMR (METHANOL-$d_4$) δ: 9.73 (s, 1H), 8.88 (d, J=6.4 Hz, 1H), 7.97 (d, J=8.0 Hz, 2H), 7.92 (d, J=6.4 Hz, 1H), 7.60 (d, J=8.0 Hz, 2H), 7.22 (s, 1H), 4.64 (d, J=13.6 Hz, 1H), 4.12 (d, J=13.6 Hz, 1H), 3.85 (t, J=7.2 Hz, 2H), 3.60 (d, J=12.0 Hz, 2H), 3.39-3.34 (m, 1H), 3.32-3.30 (m, 2H), 3.22-3.18 (m, 1H), 3.10-3.07 (m, 2H), 2.99-2.92 (m, 2H), 2.88-2.83 (m, 2H), 2.78-2.70 (m, 1H), 2.33-2.29 (m, 2H), 2.12-2.01 (m, 2H), 2.01-1.95 (m, 2H), 1.85-1.75 (m, 3H), 1.58-1.45 (m, 3H).

Example 131: Synthesis of N-(2-(Diethylamino)-2-oxoethyl)-3-(4-(4-(3-(piperidin-1-yl)propylamino)-1,6-naphthyridin-2-yl)phenyl)propenamide

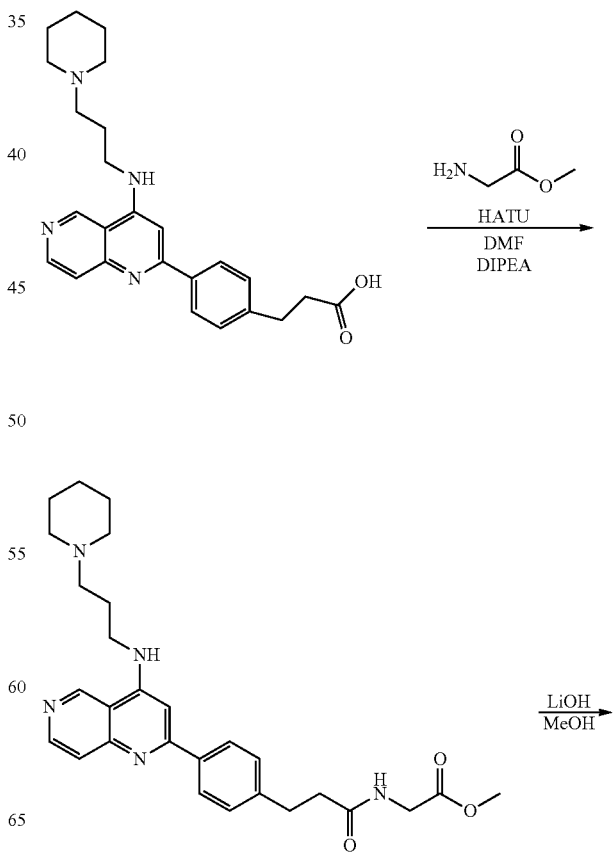

-continued

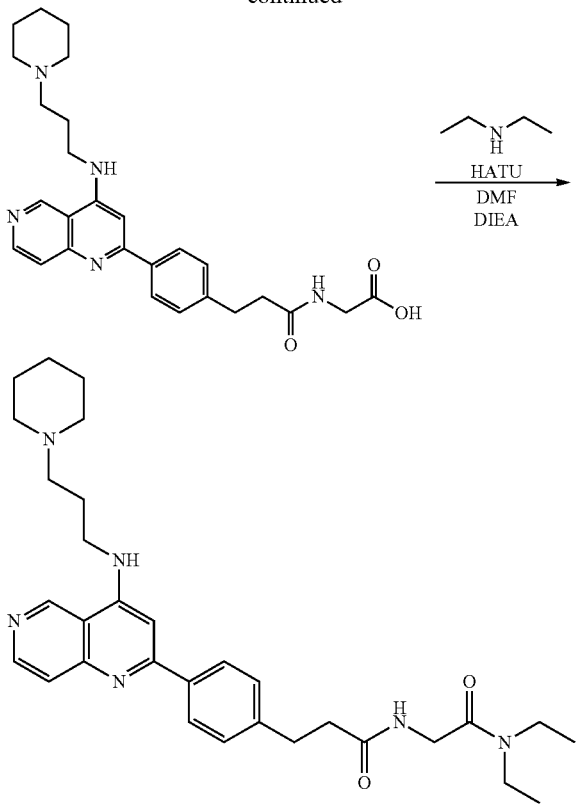

Step 1

The mixture of 3-(4-(4-(3-(piperidin-1-yl)propylamino)-1,6-naphthyridin-2-yl)phenyl)propanoic acid (410 mg, 0.98 mmol), methyl 2-aminoacetate.HCl (250 mg, 2 mmol), HATU (380 mg, 1 mmol) and DIPEA (516 mg, 4 mmol) in DMF (5.0 mL) was stirred at room temperature for 3 hours. Then 100 mL water was added and the mixture was extracted with EA (100 mL), washed with brine, dried over $Na_2SO_4$, concentrated and purified by flash column chromatography to give Methyl 2-(3-(4-(4-(3-(piperidin-1-yl)propylamino)-1,6-naphthyridin-2-yl)phenyl)propanamido)acetate (320 mg, 67%) as yellow solid. HPLC/UV purity: 100%; LC-MS (ESI): 490.3 $(M+1)^+$. $^1$H NMR (METHANOL-$d_4$) δ: 9.45 (s, 1H), 8.57-8.55 (m, 1H), 7.98 (d, J=8.0 Hz, 2H), 7.78 (d, J=6.0 Hz, 1H), 7.43 (d, J=8.0 Hz, 2H), 7.01 (s, 1H), 3.95 (s, 2H), 3.74 (s, 3H), 3.57 (t, J=6.8 Hz, 2H), 3.05 (t, J=8.0 Hz, 2H), 2.73-2.62 (m, 8H), 2.10-2.06 (m, 2H), 1.74-1.68 (m, 4H), 1.58-1.55 (m, 2H).

Step 2

The solution of methyl 2-(3-(4-(4-(3-(piperidin-1-yl)propylamino)-1,6-naphthyridin-2-yl)phenyl)propanamido)acetate (98 mg, 0.2 mmol) and LiOH·$H_2O$ (20 mg, 0.5 mmol) in MeOH/$H_2O$ (10 mL/1 mL) was stirred at 65° C. for 2 hrs. Then the mixture was cooled to room temperature and 0.7 mL 1N aq. HCl solution was added. The solvent was removed to give 2-(3-(4-(4-(3-(piperidin-1-yl)propylamino)-1,6-naphthyridin-2-yl)phenyl)propanamido)acetic acid (410 mg, 98%) as white solid which was used to in next step directly. HPLC/UV purity: 100%; LC-MS (ESI): 476.3 $(M+1)^+$.

Step 3

The mixture of 2-(3-(4-(4-(3-(piperidin-1-yl)propylamino)-1,6-naphthyridin-2-yl)phenyl)propanamido)acetic acid (90 mg, 0.189 mmol), diethylamine (22 mg, 0.3 mmol), HATU (114 mg, 0.3 mmol) and DIPEA (77 mg, 4 mmol) in DMF (5.0 mL) was stirred at room temperature for 3 hours. Then 50 mL water was added and the mixture was extracted with DCM/MeOH (100 mL/10 mL), dried over $Na_2SO_4$, concentrated and purified by flash column chromatography to give N-(2-(diethylamino)-2-oxoethyl)-3-(4-(4-(3-(piperidin-1-yl)propylamino)-1,6-naphthyridin-2-yl)phenyl)propanamide (320 mg, 67%) as yellow solid. HPLC/UV purity: 100%; LC-MS (ESI): 531.3 $(M+1)^+$. $^1$H NMR (METHANOL-$d_4$) δ: 9.72 (s, 1H), 8.71 (d, J=6.0 Hz, 1H), 8.03 (d, J=8.4 Hz, 2H), 7.87 (d, J=6.0 Hz, 1H), 7.52 (d, J=7.6 Hz, 2H), 7.17 (s, 1H), 4.07 (s, 2H), 3.79 (t, J=6.8 Hz, 2H), 3.77-3.50 (m, 2H), 3.43-3.37 (m, 2H), 3.09 (t, J=7.6 Hz, 2H), 2.99-2.95 (m, 4H), 2.70-2.67 (m, 2H), 2.36-2.34 (m, 2H), 1.95-1.90 (m, 4H), 1.88-1.50 (m, 2H), 1.25-1.20 (m, 5H), 1.14 (t, J=7.2 Hz, 3H).

Example 132: Synthesis of N-(1-Ethylpiperidin-4-yl)-3-(4-(4-(3-(piperidin-1-yl)propylamino)-1,6-naphthyridin-2-yl)phenyl)propanamide

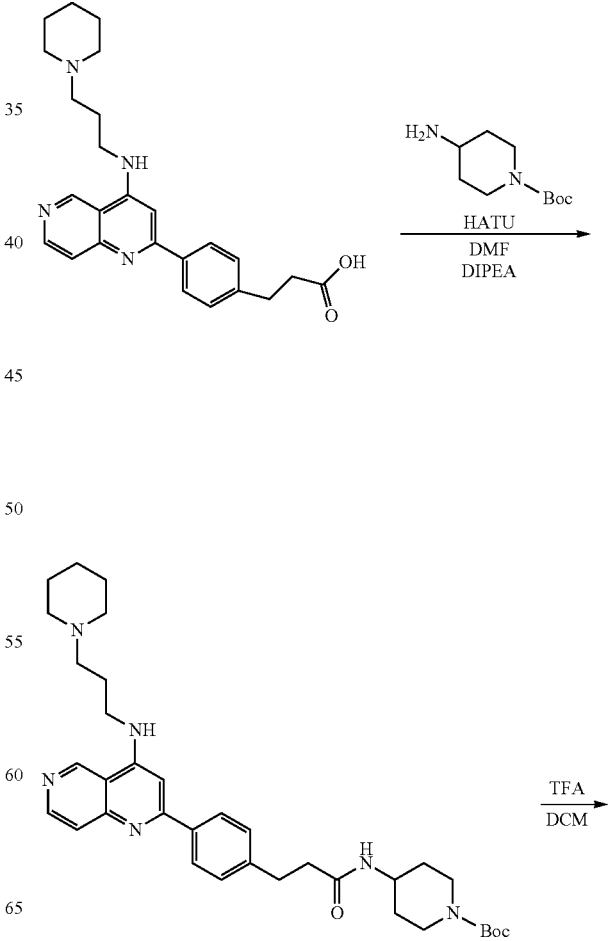

341

-continued

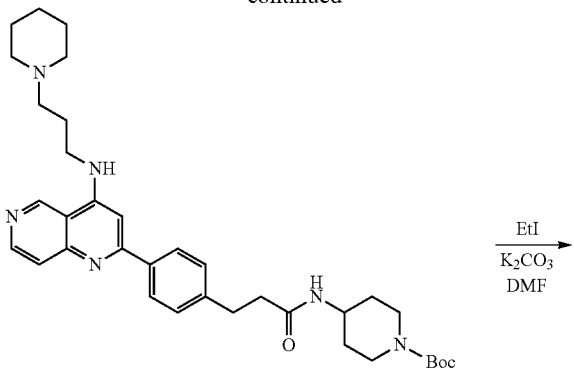

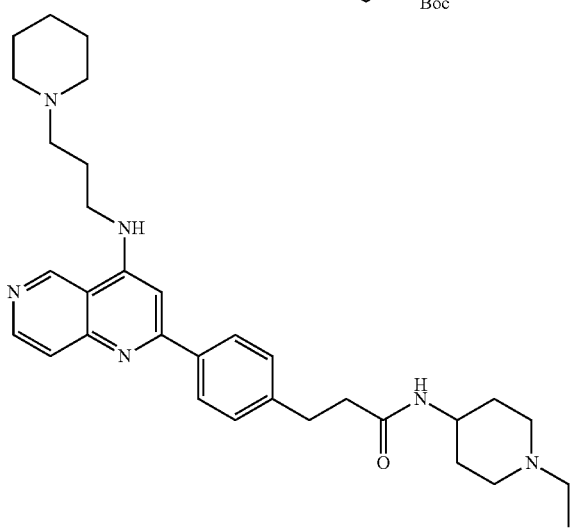

Step 1

The mixture of 3-(4-(4-(3-(piperidin-1-yl)propylamino)-1,6-naphthyridin-2-yl)phenyl)propanoic acid (400 mg, 0.956 mmol), tert-butyl 4-aminopiperidine-1-carboxylate (200 mg, 1 mmol), HATU (380 mg, 1 mmol) and DIPEA (258 mg, 2 mmol) in DMF (15.0 mL) was stirred at room temperature for 3 hours. Then 200 mL water was added and the mixture was extracted with EA (200 mL), washed with brine, dried over Na₂SO₄, concentrated and purified by flash column chromatography to give tert-butyl 4-(3-(4-(4-(3-(piperidin-1-yl)propylamino)-1,6-naphthyridin-2-yl)phenyl)propanamido)piperidine-1-carboxylate (500 mg, 83.3%) as white solid. HPLC/UV purity: 90%; LC-MS (ESI): 601.3 (M+1)⁺.

Step 2

The solution of tert-butyl 4-(3-(4-(4-(3-(piperidin-1-yl)propylamino)-1,6-naphthyridin-2-yl)phenyl)propanamido)piperidine-1-carboxylate (480 mg, 0.8 mmol) in TFA/DCM (1 mL/5 mL) was stirred at room temperature for 2 hours. Then the solution was concentrated and purified by silica gel column chromatography to give 3-(4-(4-(3-(piperidin-1-yl)propylamino)-1,6-naphthyridin-2-yl)phenyl)-N-(piperidin-4-yl)propanamide (390 mg, 98%) as white solid which was used in next step directly. HPLC/UV purity: 95%; LC-MS (ESI): 501.3 (M+1)⁺.

Step 3

The mixture of 3-(4-(4-(3-(piperidin-1-yl)propylamino)-1,6-naphthyridin-2-yl)phenyl)-N-(piperidin-4-yl)propana-

342 mide (100 mg, 0.2 mmol), EtI (31 mg, 0.2 mmol) and K₂CO₃ (69 mg, 0.5 mmol) in DMF (5 mL) was stirred at room temperature overnight. The mixture was filtered, concentrated and purified by Prep-HPLC (Welch, XB-C18, 21.2 mm×250 mm, 10 um, eluting with 20% CH₃CN in 1%0 TFA in H₂O) and TLC to give N-(1-ethylpiperidin-4-yl)-3-(4-(4-(3-(piperidin-1-yl)propylamino)-1,6-naphthyridin-2-yl)phenyl)propanamide (60 mg, 57%) as white solid. HPLC/UV purity: 100%; LC-MS (ESI): 530.4 (M+1)⁺. ¹H NMR (METHANOL-d₄) δ: 9.76 (s, 1H), 8.78 (d, J=5.6 Hz, 1H), 8.05 (d, J=8.4 Hz, 2H), 7.93 (d, J=6.0 Hz, 1H), 7.56 (d, J=8.4 Hz, 2H), 7.23 (s, 1H), 4.68 (d, J=14.0 Hz, 1H), 4.12 (d, J=12.8 Hz, 1H), 3.84 (t, J=6.8 Hz, 2H), 3.65-3.58 (m, 2H), 3.39-3.35 (m, 2H), 3.15-3.07 (m, 6H), 2.89-2.84 (m, 2H), 2.73-2.68 (m, 1H), 2.37-2.33 (m, 2H), 2.16-2.14 (m, 2H), 2.01-1.85 (m, 6H), 1.52-1.48 (m, 4H), 1.36-1.31 (m, 3H).

Example 133: Synthesis of N-(2-(4-Methyl-1,4-diazepan-1-yl)ethyl)-3-(4-(4-(3-(piperidin-1-yl)propylamino)-1,6-naphthyridin-2-yl)phenyl)propanamide

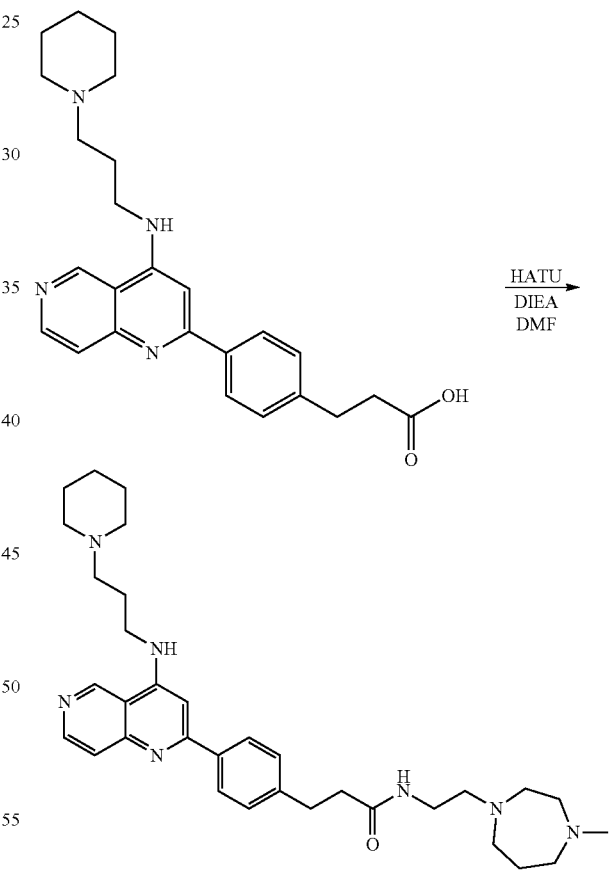

The mixture of 3-(4-(4-(3-(piperidin-1-yl)propylamino)-1,6-naphthyridin-2-yl)phenyl)propanoic acid (104 mg, 0.25 mmol), 2-(4-methyl-1,4-diazepan-1-yl)ethanamine (40 mg, 0.25 mmol), HATU (190 mg, 0.5 mmol) and DIPEA (65 mg, 0.5 mmol) in DMF (5.0 mL) was stirred at room temperature for 3 hours. Then 50 mL water was added and the mixture was extracted with EA (100 mL), washed with brine, dried over Na₂SO₄, concentrated and purified by Prep-HPLC (Welch, XB-C18, 21.2 mm×250 mm, 10 um, eluting with 20% CH$_3$CN in 1‰ TFA in H$_2$O) to give N-(2-(4-methyl-1,4-diazepan-1-yl)ethyl)-3-(4-(4-(3-(piperidin-1-yl)propylamino)-1,6-naphthyridin-2-yl)phenyl)propanamide (40 mg, 28.7%) as yellow solid. HPLC/UV purity: 100%; LC-MS (ESI): 558.4 (M+1)$^+$. $^1$H NMR (METHANOL-d$_4$) δ: 9.81 (s, 1H), 8.82 (d, J=6.0 Hz, 1H), 8.04 (d, J=8.4 Hz, 2H), 7.95 (d, J=6.0 Hz, 1H), 7.58 (d, J=8.4 Hz, 2H), 7.24 (s, 1H), 3.87 (t, J=6.8 Hz, 2H), 3.63-3.58 (m, 2H), 3.42-3.35 (m, 6H), 3.11-3.05 (m, 6H), 2.95-2.88 (m, 6H), 2.76-2.73 (m, 2H), 2.67 (t, J=7.2 Hz, 2H), 2.39-2.33 (m, 2H), 2.11-2.05 (m, 2H), 1.98-1.80 (m, 5H), 1.62-1.50 (m, 2H).

Example 134: Synthesis of N-(2-(1-methylpiperidin-4-yl)ethyl)-3-(4-(4-((3-(piperidin-1-yl)propyl)amino)-1,6-naphthyridin-2-yl)phenyl)propiolamide

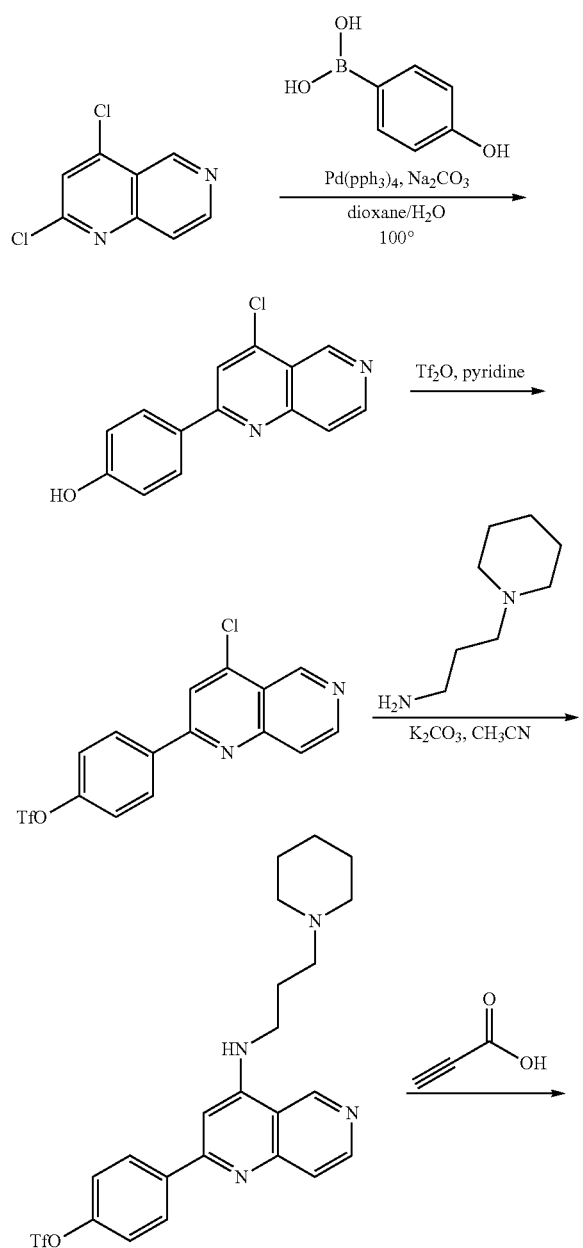

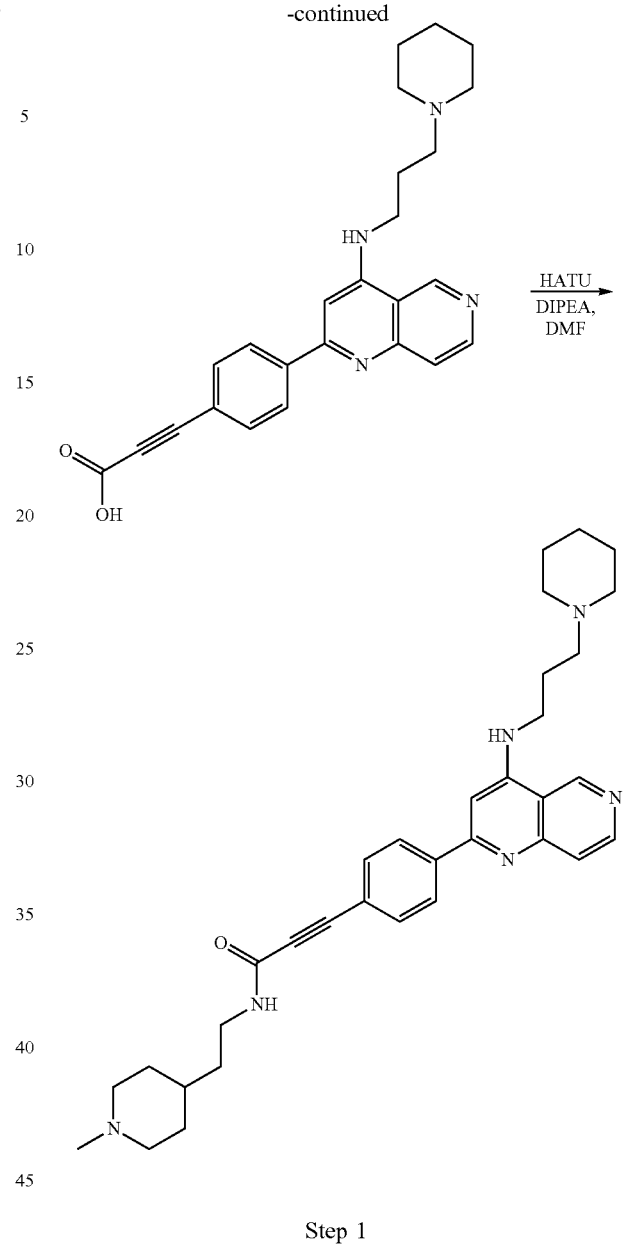

Step 1

The mixture of 2,4-dichloro-1,6-naphthyridine (1 g, 5.0 mmol), (4-hydroxyphenyl)boronic acid (1.1 g, 5.25 mmol), Pd(PPh$_3$)$_4$ (577 mg, 0.5 mmol) and Na$_2$CO$_3$ (1.06 g, 10 mmol) in 1,4-dioxane (20 mL) and H$_2$O (4 mL) was heated at 100° C. for 18 hrs under N$_2$ atmosphere. The mixture was cooled to room temperature, and then the mixture was concentrated under reduced pressure to give the crude mixture, which was purified by flash column chromatography (silica gel, eluting with CH$_2$Cl$_2$ to 10% Methanol/CH$_2$Cl$_2$) to afford 4-(4-chloro-1,6-naphthyridin-2-yl)phenol as a yellow solid (680 mg, 53%). HPLC/UV purity: 85%; LC-MS (ESI): 257.1 (M+1)$^+$.

Step 2

To a mixture of 4-(4-chloro-1,6-naphthyridin-2-yl)phenol (680 mg, 2.66 mmol) and pyridine (311 mg, 3.99 mmol) in DCM (30 mL) was added trifluoromethanesulfonic anhydride (898 mg, 3.18 mmol) drop wise at 0° C., and then the reaction mixture was stirred at room temperature for 1 hr. DCM was removed under reduced pressure to give the slurry, which was dissolved into EA (30 mL), washed by water and brine. The organic layers was dried over Na₂SO₄, filtered and the filtrate was concentrated to give the crude product, which was purified by flash column chromatography (silica gel, eluting with PE to 30% EA/PE) to afford 4-(4-chloro-1,6-naphthyridin-2-yl)phenyl trifluoromethanesulfonate (266 mg, 26%) as a white solid. HPLC/UV purity: 90%; LC-MS (ESI): 389.2 (M+1)⁺.

Step 3

The mixture of 4-(4-chloro-1,6-naphthyridin-2-yl)phenyl trifluoromethanesulfonate (180 mg, 0.66 mmol), 3-(piperidin-1-yl)propan-1-amine (113 mg, 0.79 mmol) and K₂CO₃ (182 mg, 1.32 mmol) in CH₃CN (10 mL) was heated at 100° C. for 18 hrs. The reaction mixture was poured into water (20 mL), extracted with EA (10 mL×3). The combined organic layers were washed by water and brine, dried over Na₂SO₄. The drying agent was filtered off and the filtrate was concentrated under the reduced pressure to give the crude product, which was purified by flash column chromatography (silica gel, eluting with 10% methanol in DCM) to afford 4-(4-((3-(piperidin-1-yl)propyl)amino)-1,6-naphthyridin-2-yl)phenyl trifluoromethanesulfonate (170 mg, 52%) as a yellow solid. HPLC/UV purity: 90%; LC-MS (ESI): 495.3 (M+1)⁺.

Step 4

A 10-mL sealed tube, charged with 4-(4-((3-(piperidin-1-yl)propyl)amino)-1,6-naphthyridin-2-yl)phenyl trifluoromethanesulfonate (170 mg, 0.34 mmol), propiolic acid (48 mg, 0.69 mmol), Pd(PPh₃)₄ (39 mg, 0.03 mmol), DBU (104 mg, 0.69 mmol) and DMSO (2 mL). The mixture was heated at 35° C. for 18 hrs. The resulting solution was poured into sat. NaHCO₃ aqueous (20 mL), then washed with EA (10 mL×3). The pH of the water phase was adjusted to pH 1 with 1N aq. HCl solution. The acidified water phase was lyophilized to give a solid. The solid was dissolved into DCM/Methanol=5/1 (30 mL), then filtered by a pad of celite and the filtrate was concentrated to give the crude acid (300 mg). The crude acid was used to the next step without further purification.

Step 5

To a mixture of 3-(4-(4-((3-(piperidin-1-yl)propyl)amino)-1,6-naphthyridin-2-yl)phenyl)propiolic acid (40 mg, 0.1 mmol) and HATU (45 mg, 0.12 mmol) in DMF (2 mL) were added 2-(1-methylpiperidin-4-yl)ethanamine (17 mg, 0.17 mmol) and DIPEA (38 mg, 0.3 mmol). The resulting mixture was stirred at rt for 1 hr. The reaction mixture was poured into water (10 mL), extracted with EA (10 mL×3). The combined organic layers were washed with water and brine, dried over Na₂SO₄. The drying agent was filtered off and the filtrate was concentrated in vacuo to give the crude product, which was purified by Prep-TLC (silica gel, eluting with 10% methanol and 1% NH₃·H₂O in DCM) to afford N-(2-(1-methylpiperidin-4-yl)ethyl)-3-(4-(4-((3-(piperidin-1-yl)propyl)amino)-1,6-naphthyridin-2-yl)phenyl)propiolamide (5 mg, 10%) as a yellow solid. HPLC/UV purity: 100%; LC-MS (ESI): 540.2 (M+1)⁺. H NMR (METHANOL-d₄) δ: 9.49 (s, 1H), 8.58 (d, J=6.1 Hz, 1H), 8.05 (d, J=8.5 Hz, 2H), 7.63-7.80 (m, 3H), 7.08 (s, 1H), 3.60-3.70 (m, 2H), 3.42-3.51 (m, 4H), 2.89-2.95 (m, 4H), 2.76 (s, 3H), 2.13-2.24 (m, 2H), 2.08 (d, J=14.5, 6.6 Hz, 1H), 1.73-2.04 (m, 10H), 1.44-1.54 (m, 4H), 1.31-1.44 (m, 2H).

Example 135: Synthesis of N-((1-methylpiperidin-4-yl)methyl)-3-(4-(4-((3-(piperidin-1-yl)propyl)amino)-1,6-naphthyridin-2-yl)phenyl)propiolamide

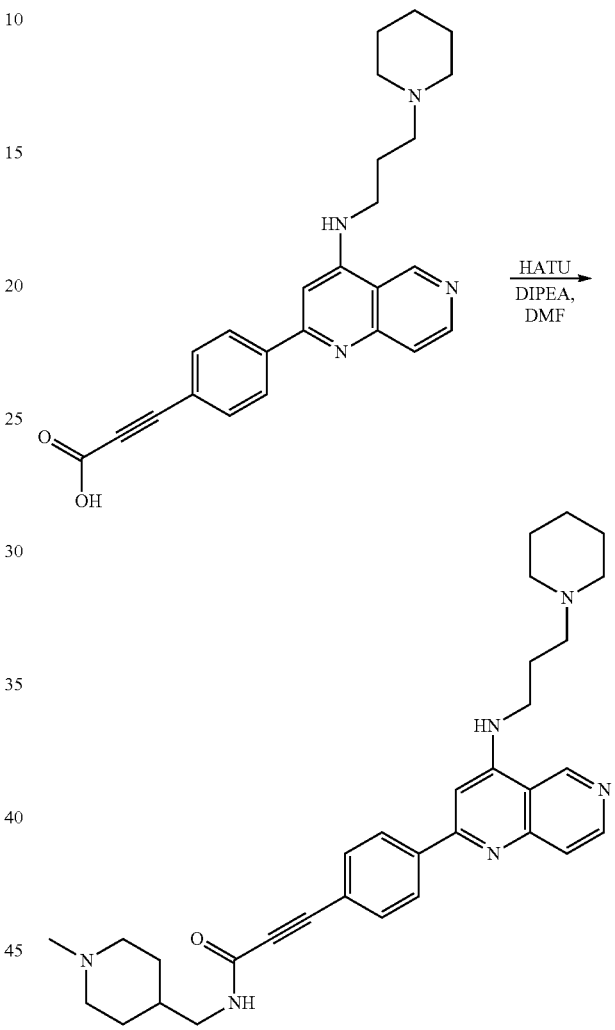

To a mixture of 3-(4-(4-((3-(piperidin-1-yl)propyl)amino)-1,6-naphthyridin-2-yl)phenyl)propiolic acid (40 mg, 0.1 mmol) and HATU (45 mg, 0.12 mmol) in DMF (2 mL) were added (1-methylpiperidin-4-yl)methanamine (15 mg, 0.17 mmol) and DIPEA (38 mg, 0.3 mmol). The resulting mixture was stirred at room temperature for 1 hr. The reaction mixture was poured into water (10 mL), extracted with EA (10 mL×3). The combined organic layers were washed with water and brine, dried over Na₂SO₄. The drying agent was filtered off and the filtrate was concentrated in vacuo to give the crude product, which was purified by Prep-TLC (silica gel, eluting with 10% methanol and 1% NH₃·H₂O in DCM) to afford N-((1-methylpiperidin-4-yl)methyl)-3-(4-(4-((3-(piperidin-1-yl)propyl)amino)-1,6-naphthyridin-2-yl)phenyl)propiolamide (5 mg, 10%) as a yellow solid. HPLC/UV purity: 100%; LC-MS (ESI): 525.3 (M+1)⁺. ¹H NMR (METHANOL-d₄) δ: 9.38 (s, 1H), 8.47 (d, J=6.1 Hz, 1H), 8.03 (d, J=8.2 Hz, 2H), 7.61-7.73 (m, 3H), 6.98 (s, 1H), 3.49 (t, J=6.9 Hz, 2H), 3.05-3.16 (m, 4H), 2.71-2.81 (m, 4H), 2.46 (s, 3H), 2.41-2.45 (m, 2H), 1.97-2.05 (m, 2H), 2.01-2.03 (m, 1H), 1.80 (d, J=15.6 Hz, 2H), 1.56-1.70 (m, 5H), 1.45-1.50 (m, 3H), 1.32 (t, J=12.2 Hz, 2H).

Example 136: Synthesis of N-(2-(1-methylazepan-4-yl)ethyl)-3-(4-(4-((3-(piperidin-1-yl)propyl)amino)-1,6-naphthyridin-2-yl)phenyl)propiolamide

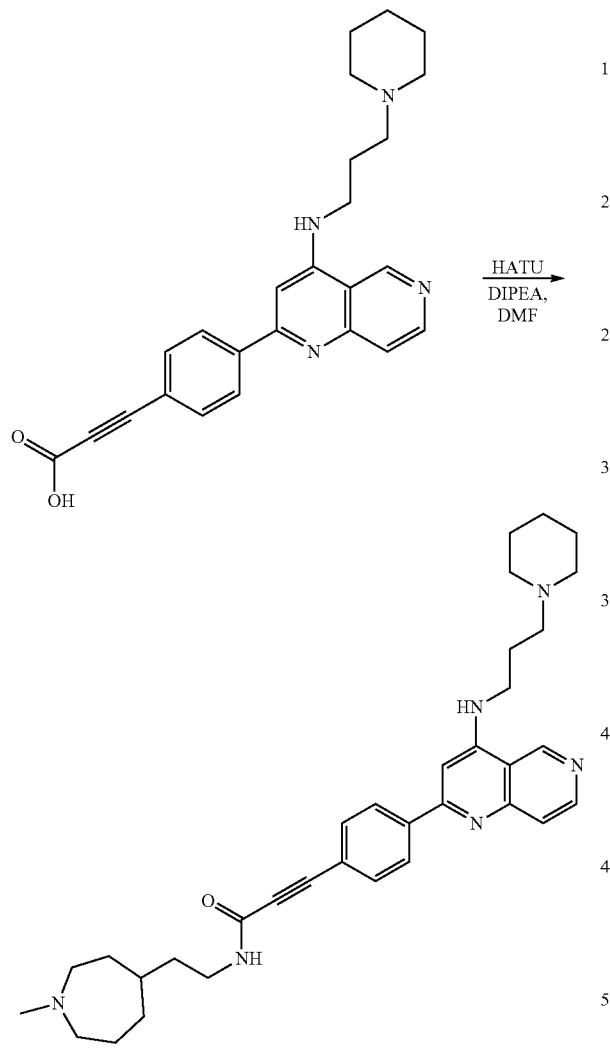

To a mixture of 3-(4-(4-((3-(piperidin-1-yl)propyl)amino)-1,6-naphthyridin-2-yl)phenyl)propiolic acid (80 mg, 0.19 mmol) and HATU (87 mg, 0.23 mmol) in DMF (2 mL) were added 2-(1-methylazepan-4-yl)ethanamine (36 mg, 0.17 mmol) and DIPEA (74 mg, 0.58 mmol). The resulting mixture was stirred at rt for 1 hr. The reaction mixture was poured into water (10 mL), extracted with EA (10 mL×3). The combined organic layers were washed with water and brine, dried over Na$_2$SO$_4$. The drying agent was filtered off and the filtrate was concentrated in vacuo to give the crude product, which was purified by Prep-HPLC to afford N-(2-(1-methylazepan-4-yl)ethyl)-3-(4-(4-((3-(piperidin-1-yl)propyl)amino)-1,6-naphthyridin-2-yl)phenyl)propiolamide (5 mg, 5%) as a yellow solid. HPLC/UV purity: 100%; LC-MS (ESI): 553.3 (M+1)$^+$. $^1$H NMR (METHANOL-d$_4$) δ: 9.75 (s, 1H), 8.88 (d, J=6.1 Hz, 1H), 8.11 (d, J=8.5 Hz, 2H), 7.82-7.97 (m, 3H), 7.28 (s, 1H), 3.85 (t, J=6.9 Hz, 2H), 3.57-3.68 (m, 6H), 3.52-3.55 (m, 4H), 3.29-3.32 (m, 4H), 3.17 (t, J=6.0 Hz, 2H), 2.92-3.03 (m, 5H), 2.19-2.36 (m, 4H), 1.97 (d, J=14.3 Hz, 2H), 1.73-1.91 (m, 3H), 1.53-1.56 (m, 1H).

Example 137: Synthesis of (Z)—N'-hydroxy-N-(1-methylpiperidin-4-yl)-4-(4-((3-(piperidin-1-yl)propyl)amino)-1,6-naphthyridin-2-yl)benzimidamide

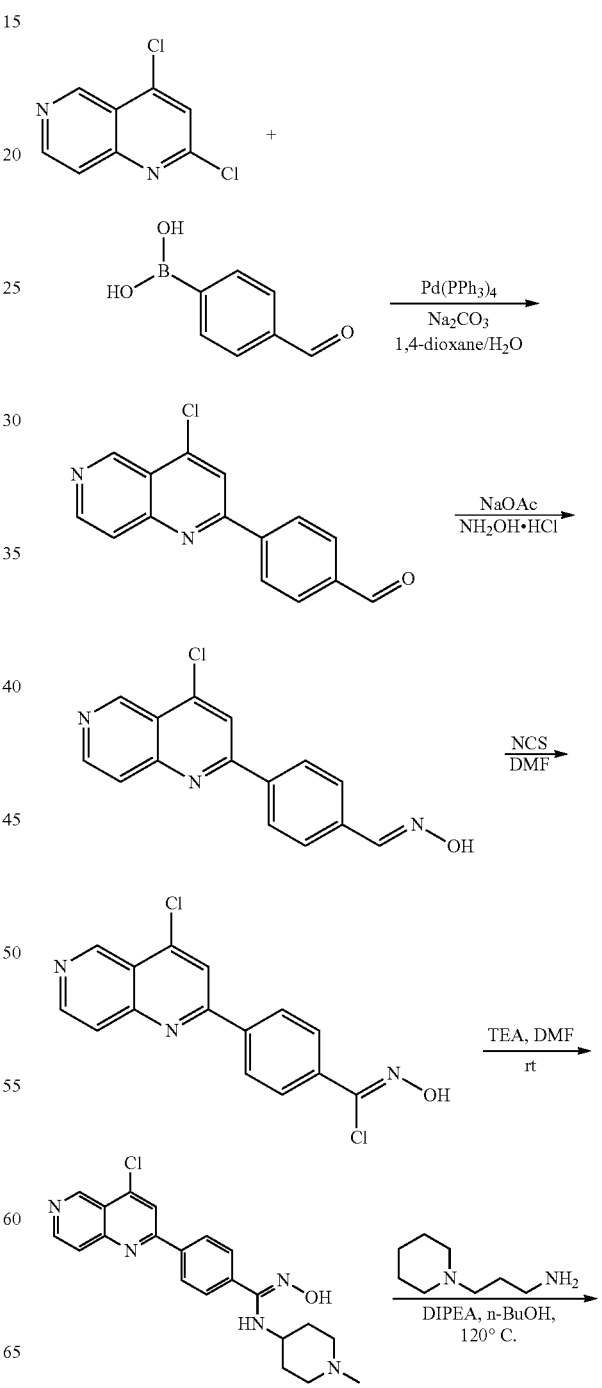

-continued

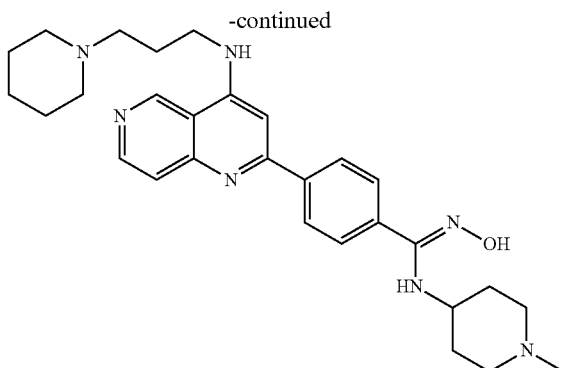

Step 1

The mixture of 2,4-dichloro-1,6-naphthyridine (2 g, 10 mmol), (4-formylphenyl)boronic acid (1.65 g, 11 mmol), Pd(PPh$_3$)$_4$ (577 mg, 0.5 mmol) and Na$_2$CO$_3$ (2.12 g, 20 mmol) in 1,4-dioxane (40 mL) and H$_2$O (8 mL) was heated at 90° C. for 2 hrs under N$_2$ atmosphere. The mixture was cooled to room temperature, and was concentrated under reduced pressure to give the crude product, which was purified by flash column chromatography (silica gel, eluting with 5% methanol/DCM) to afford 4-(4-chloro-1,6-naphthyridin-2-yl)benzaldehyde (2 g, 74%) as a white solid. HPLC/UV purity: 90%; LC-MS (ESI): 269.3 (M+1)$^+$.

Step 2

To a suspension of 4-(4-chloro-1,6-naphthyridin-2-yl)benzaldehyde (2 g, 7.43 mmol) in methanol (40 mL) were added NaOAc (1.03 g, 12.6 mmol) and hydroxylamine hydrochloride (545 mg, 7.8 mmol). The resulting mixture was stirred at room temperature for 1 hrs, and then the solvent was removed under the reduced pressure to give a slurry, to which water (20 mL) was added, followed by the addition of 10% aq. K$_2$CO$_3$ solution until pH=10. The resulting precipitate was collected and dried to give (E)-4-(4-chloroquinolin-2-yl)benzaldehyde oxime (2.1 g, 100%) as a white solid. HPLC/UV purity: 95%; LC-MS (ESI): 284.3 (M+1)$^+$.

Step 3

To a mixture of (E)-4-(4-chloroquinolin-2-yl)benzaldehyde oxime (2.3 g, 8.12 mmol) in DMF (15 mL) was added NCS (1.62 g, 12.2 mmol) portion wise at 0° C. The resulting reaction mixture was stirred at room temperature overnight. The mixture was quenched by water (30 mL). The resulting precipitate was collected to give the crude product, a 1:1 mixture of (Z)-4-(4-chloro-1,6-naphthyridin-2-yl)-N-hydroxybenzimidoyl chloride and (Z)-4-(4,8-dichloro-1,6-naphthyridin-2-yl)-N-hydroxybenzimidoyl chloride, which was used to the next step without purification

Step 4

To a mixture of (Z)-4-(4-chloro-1,6-naphthyridin-2-yl)-N-hydroxybenzimidoyl chloride (1.7 g, 4.8 mmol) in DMF (6 mL) were added 1-methylpiperidin-4-amine (820 mg, 7.2 mmol) and Et$_3$N (1.33 ml, 9.6 mmol) and the reaction mixture was stirred at room temperature for 1 hrs. The reaction mixture was poured into water (10 mL), extracted with EA (10 mL×3). The combined organic layers were washed with water and brine, dried over Na$_2$SO$_4$. The drying agent was filtered off and the filtrate was concentrated in vacuo to give the crude product, which was purified by flash column chromatography (silica gel, eluting with 10% Methanol/DCM) to afford a mixture of (Z)-4-(4-chloro-1,6-naphthyridin-2-yl)-N'-hydroxy-N-(1-methylpiperidin-4-yl)benzimidamide and (Z)-4-(4,8-dichloro-1,6-naphthyridin-2-yl)-N'-hydroxy-N-(1-methylpiperidin-4-yl)benzimidamide (500 mg, 26%) as a white solid. HPLC/UV purity: 48%; LC-MS (ESI): 396.3 (M+1)$^+$.

Step 5

To a mixture of (Z)-4-(4-chloro-1,6-naphthyridin-2-yl)-N'-hydroxy-N-(1-methylpiperidin-4-yl)benzimidamide (55 mg, 0.14 mmol) and 3-(piperidin-1-yl)propan-1-amine (39 mg, 0.28 mmol) in n-BuOH (1 mL) was added DIPEA (36 mg, 0.28 mmol). The reaction vessel was sealed, and the reaction mixture was heated at 120° C. for 4 hrs. The reaction mixture was poured into water (10 mL), extracted with EA (10 mL×3). The combined organic layers were washed with water and brine, dried over Na$_2$SO$_4$. The drying agent was filtered off and the filtrate was concentrated in vacuo to give the crude mixture, which was purified by Prep-TLC (silica gel, eluting with 10% methanol and 1% NH$_3$·H$_2$O in DCM) to afford (Z)—N'-hydroxy-N-(1-methylpiperidin-4-yl)-4-(4-((3-(piperidin-1-yl)propyl)amino)-1,6-naphthyridin-2-yl)benzimidamide (5 mg, 13%) as a yellow solid. HPLC/UV purity: 100%; LC-MS (ESI): 502.3 (M+1)$^+$. $^1$H NMR (METHANOL-d$_4$) δ: 9.75 (s, 1H), 8.86 (d, J=6.2 Hz, 1H), 8.22 (d, J=8.1 Hz, 2H), 7.96 (d, J=6.2 Hz, 1H), 7.86 (d, J=8.3 Hz, 2H), 7.32 (s, 1H), 3.84 (t, J=6.9 Hz, 2H), 3.48-3.68 (m, 5H), 3.32-3.35 (m, 2H), 2.97 (t, J=12.5 Hz, 4H), 2.82 (s, 3H), 2.27-2.39 (m, 2H), 2.18 (d, J=12.6 Hz, 2H), 1.93-2.09 (m, 4H), 1.74-1.91 (m, 3H), 1.50-1.53 (m, 1H).

Example 138: Synthesis of (Z)-4-(8-chloro-4-((3-(piperidin-1-yl)propyl)amino)-1,6-naphthyridin-2-yl)-N'-hydroxy-N-(1-methylpiperidin-4-yl)benzimidamide

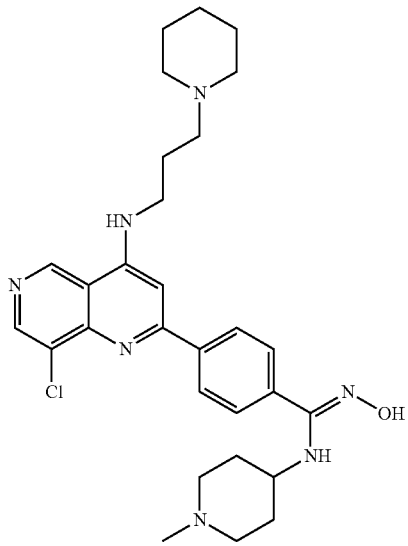 [SMILES: CN1CCC(N/C(=N\O)c2ccc(-c3cc(NCCCN4CCCCC4)c4cncc(Cl)c4n3)cc2)CC1]

(Z)-4-(8-chloro-4-((3-(piperidin-1-yl)propyl)amino)-1,6-naphthyridin-2-yl)-N'-hydroxy-N-(1-methylpiperidin-4-yl)benzimidamide was synthesized in a similar fashion as Example 137. HPLC/UV purity: 100%; LC-MS (ESI): 536.3 (M+1)⁺. ¹H NMR (METHANOL-d₄) δ: ¹H NMR (METHANOL-d₄) δ: 9.48 (s, 1H), 8.74 (s, 1H), 8.54 (d, J=8.3 Hz, 2H), 7.82 (d, J=8.3 Hz, 2H), 7.31 (s, 1H), 3.68 (t, J=6.7 Hz, 3H), 3.45-3.62 (m, 4H), 3.30-3.33 (m, 2H), 2.87-3.04 (m, 4H), 2.78 (s, 3H), 2.02-2.32 (m, 6H), 1.93 (d, J=14.5 Hz, 2H), 1.67-1.88 (m, 3H), 1.44-1.57 (m, 1H).

Example 139: Synthesis of (Z)—N'-methoxy-N-(1-methylpiperidin-4-yl)-4-(4-(3-(piperidin-1-yl)propylamino)-1,6-naphthyridin-2-yl)benzimidamide

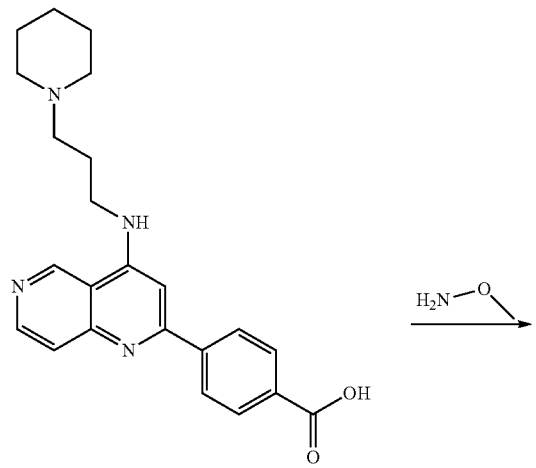

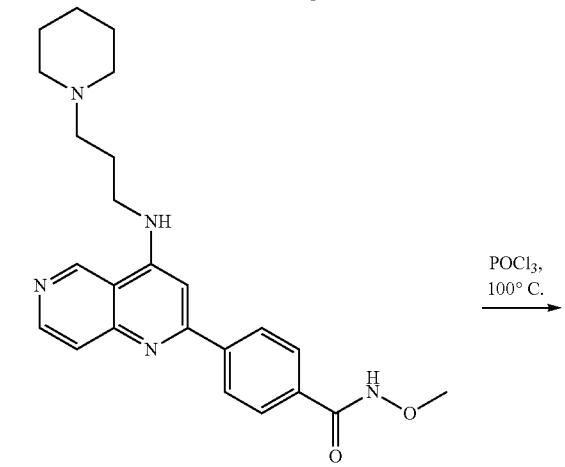

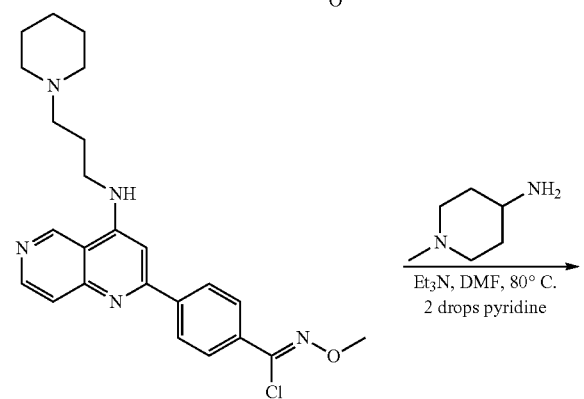

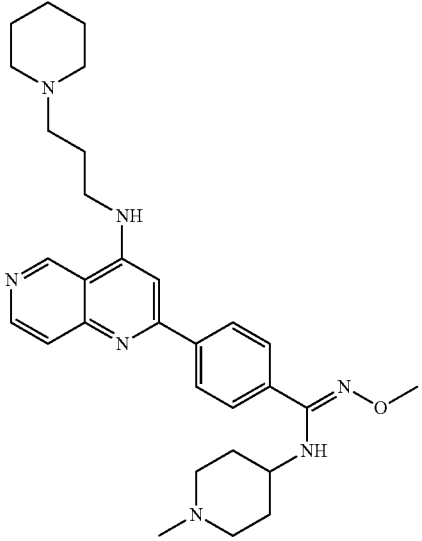

Step 1

The mixture of 4-(4-(3-(piperidin-1-yl)propylamino)-1,6-naphthyridin-2-yl)benzoic acid (300 mg, 0.77 mmol), O-methylhydroxylamine (361 mg, 7.7 mmol), HATU (351 mg, 0.92 mmol) and DIPEA (165 mg, 1.54 mmol) in DMF (2 mL) was stirred at room temperature overnight. The reaction mixture was quenched with water (5 mL), extracted with EtOAc (5 mL×3), washed with water (10 mL×3) and brine (20 mL), dried over Na₂SO₄, concentrated and purified by prep-TLC (DCM:MeOH=10:1) to afford N-methoxy-4-(4-(3-(piperidin-1-yl)propylamino)-1,6-naphthyridin-2-yl)benzamide (140 mg, 43.3%) as yellow solid. LC-MS (ESI): 420.2 (M+1)⁺.

Step 2

A solution of N-methoxy-4-(4-(3-(piperidin-1-yl)propylamino)-1,6-naphthyridin-2-yl)benzamide (142 mg, 0.338 mmol) in POCl₃ (5 mL) was stirred at 100° C. for 5 h. The reaction was cooled to room temperature. Then the mixture was washed with 30 mL saturated NaHCO₃ solution, extracted with DCM (20 mL×3 times), dried over Na₂SO₄, concentrated and purified by flash column chromatography to give (Z)—N-methoxy-4-(4-(3-(piperidin-1-yl)propylamino)-1,6-naphthyridin-2-yl)benzimidoyl chloride (39 mg, 26.3%) as yellow solid. LC-MS (ESI): 439.6 (M+1)⁺.

Step 3

A solution of (Z)—N-methoxy-4-(4-(3-(piperidin-1-yl)propylamino)-1,6-naphthyridin-2-yl)benzimidoyl chloride (39 mg, 0.089 mmol), 1-methylpiperidin-4-amine (31 mg, 0.27 mmol) and pyridine (0.3 mL) in DMF (2 mL) was stirred at 80° C. overnight. The reaction was cooled to room temperature, quenched with water (10 mL), and extracted with DCM (10 mL×3). The organic phase was concentrated and purified by Prep-HPLC to give (Z)—N'-methoxy-N-(1-methylpiperidin-4-yl)-4-(4-(3-(piperidin-1-yl)propylamino)-1,6-naphthyridin-2-yl)benzimidamide (21.5 mg, 46.8%) as white solid. LC-MS (ESI): 516.7 (M+1)⁺. ¹H NMR (METHANOL-d4) δ 9.64 (s, 1H), 8.69 (d, J=5.8 Hz, 1H), 8.21 (d, J=8.4 Hz, 2H), 7.86 (d, J=6.0 Hz, 1H), 7.73 (d, J=8.3 Hz, 2H), 7.22 (s, 1H), 3.88 (s, 3H), 3.76 (t, J=6.8 Hz, 2H), 3.69-3.58 (m, 1H), 3.54-3.36 (m, 4H), 3.36-3.32 (m, 2H), 3.05-2.91 (m, 4H), 2.82 (s, 3H), 2.38-2.27 (m, 2H), 2.12-2.05 (m, 2H), 1.97-1.85 (m, 7H), 1.62-1.58 (m, 1H).

Example 140: Synthesis of N-(3-(piperidin-1-yl)propyl)-6-(4-(3-(piperidin-1-yl)propylamino)-1,6-naphthyridin-2-yl)benzo[b]thiophene-2-carboxamide

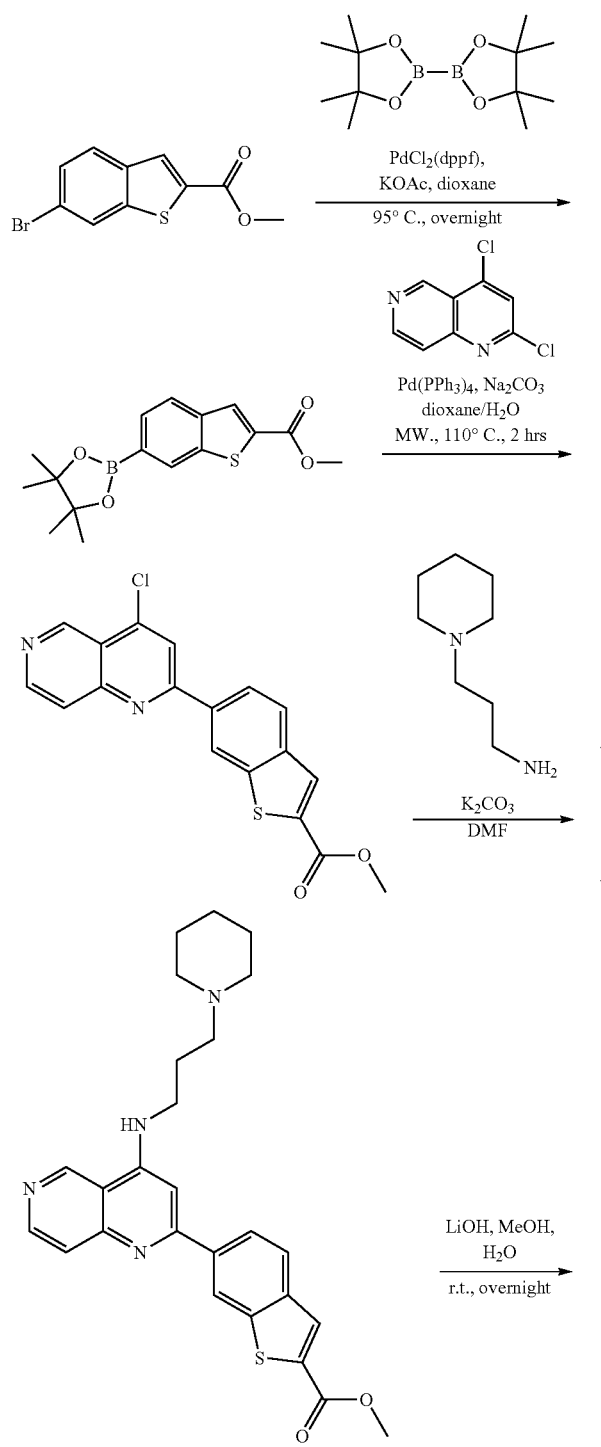

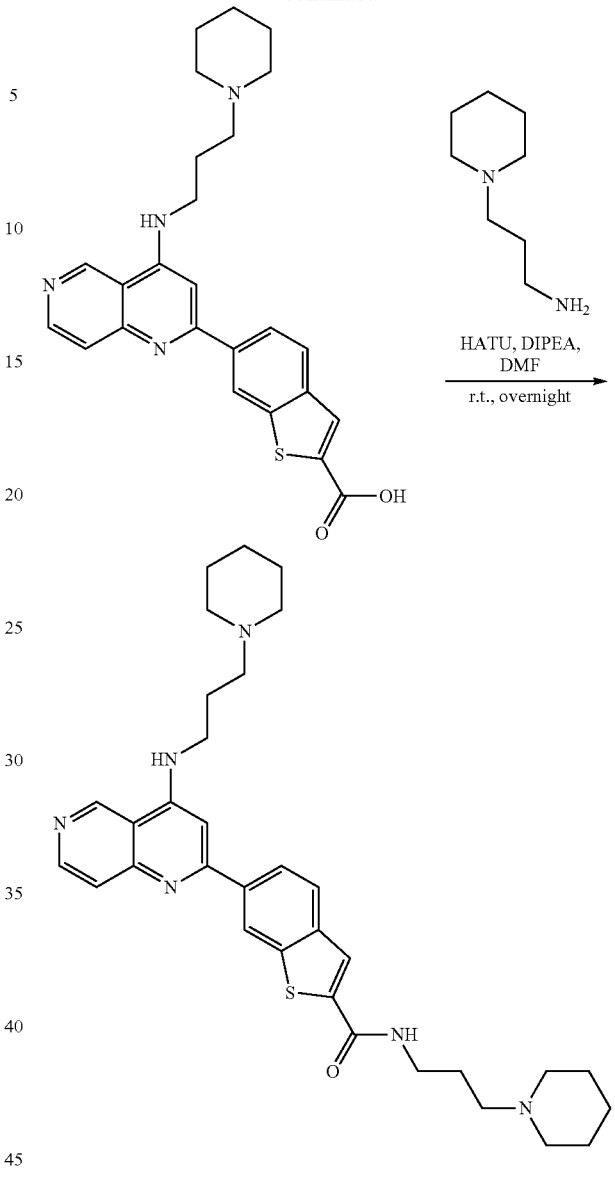

Step 1

The mixture of methyl 6-bromobenzo[b]thiophene-2-carboxylate (5 g, 18.4 mmol), 4,4,4',4',5,5,5',5'-octamethyl-2,2'-bi(1,3,2-dioxaborolane) (5.6 g, 22.1 mmol), PdCl$_2$(dppf) (1.3 g, 1.84 mmol), and KOAc (3.6 g, 36.8 mmol) in 1,4-dioxane (50 mL) under N$_2$ atmosphere was heated at 95° C. overnight. After cooling to room temperature, the mixture was concentrated. The residue was purified by the flash column chromatography (silica gel, eluting with PE to 10% EA in PE) to methyl 6-(4,4,5,5-tetramethyl-1,3,2-dioxaborolan-2-yl)benzo[b]thiophene-2-carboxylate as a white solid (3.36 g, 57%). LC-MS (ESI): 319.3 (M+1)$^+$.

Step 2

A 20-mL microwave vial was charged with 2,4-dichloro-1,6-naphthyridine (500 mg, 2.5 mmol), methyl 6-(4,4,5,5-tetramethyl-1,3,2-dioxaborolan-2-yl)benzo[b]thiophene-2-carboxylate (834 mg, 2.62 mmol), Pd(PPh$_3$)$_4$ (288 mg, 0.25 mmol), Na₂CO₃ (530 mg, 5 mmol), 1,4-dioxane (10 mL) and H₂O (2 mL). The sealed vial with the resulting brown solution is heated for 2 hrs in a Biotage Initiator Eight Microwave Reactor at a constant temperature of 110° C. The resulting solutions were concentrated by rotary evaporation (55° C., 20 mmHg). The adsorbed material was purified by silica gel chromatography (silica gel, eluting with PE to 50% EA in PE) to give methyl 6-(4-chloro-1,6-naphthyridin-2-yl)benzo[b]thiophene-2-carboxylate (705 mg, 80%) as a yellow oil. LC-MS (ESI): 355.0 (M+1)⁺

Step 3

The mixture of methyl 6-(4-chloro-1,6-naphthyridin-2-yl)benzo[b]thiophene-2-carboxylate (505 mg, 1.43 mmol), 3-(piperidin-1-yl)propan-1-amine (406 mg, 2.86 mmol) and K₂CO₃ (395 mg, 2.86 mmol) in DMF (1 mL) was heated at 80° C. for 18 hrs. The reaction mixture was poured into water (20 mL), extracted with EA (10 mL×3). The combined organic layers were washed by water and brine, dried over Na₂SO₄. Filtered and the filtrate was concentrated under the reduced pressure to give the residue which was purified by prep-TLC to afford methyl 6-(4-(3-(piperidin-1-yl)propylamino)-1,6-naphthyridin-2-yl)benzo[b]thiophene-2-carboxylate (310 mg, 47%) as a white solid. LC-MS (ESI): 461.3 (M+1)⁺.

Step 4

The mixture of methyl 6-(4-(3-(piperidin-1-yl)propylamino)-1,6-naphthyridin-2-yl)benzo[b]thiophene-2-carboxylate (310 mg, 0.67 mmol) and LiOH (282 mg, 6.7 mmol) in MeOH (5 mL) and H₂O (1 mL) was stirred at room temperature overnight. The mixture was acidified with 1N aq. HCl solution to pH=2. The mixture was concentrated to give the crude product that was used directly in the next step without further purification. LC-MS (ESI): 447.3 (M+1)⁺.

Step 5

The mixture of 6-(4-(3-(piperidin-1-yl)propylamino)-1,6-naphthyridin-2-yl)benzo[b]thiophene-2-carboxylic acid (70 mg, 0.15 mmol), 3-(piperidin-1-yl)propan-1-amine (44 mg, 0.31 mmol), HATU (87 mg, 0.23 mmol) and DIPEA (58 mg, 0.45 mmol) in DMF (1 mL) was stirred at room temperature overnight. Water (30 mL) was added, and then the mixture was extracted with EA three times. The combined organic layers were washed with water (20 mL×3) and brine (20 mL×1), dried over Na₂SO₄, filtered and concentrated. The residue was purified by the Prep-HPLC to obtain N-(3-(piperidin-1-yl)propyl)-6-(4-(3-(piperidin-1-yl)propylamino)-1,6-naphthyridin-2-yl)benzo[b]thiophene-2-carboxamide (6.5 mg, 7%). HPLC/UV purity: 100%; LC-MS (ESI): 571.3 (M+1)⁺; ¹H NMR (METHANOL-d₄) δ: 9.71 (s, 1H), 8.78 (d, J=5.8 Hz, 1H), 8.72 (s, 1H), 8.06-8.16 (m, 3H), 7.89 (d, J=6.1 Hz, 1H), 7.28 (s, 1H), 3.83 (t, J=7.0 Hz, 2H), 3.48-3.68 (m, 6H), 3.17-3.29 (m, 4H), 2.91-3.05 (m, 4H), 2.29-2.40 (m, 2H), 2.08-2.21 (m, 2H), 1.90-2.00 (m, 4H), 1.78-1.90 (m, 6H), 1.46-1.64 (m, 2H).

Example 141: Synthesis of N-(2-(dimethylamino)ethyl)-6-(4-(3-(piperidin-1-yl)propylamino)-1,6-naphthyridin-2-yl)benzo[b]thiophene-2-carboxamide

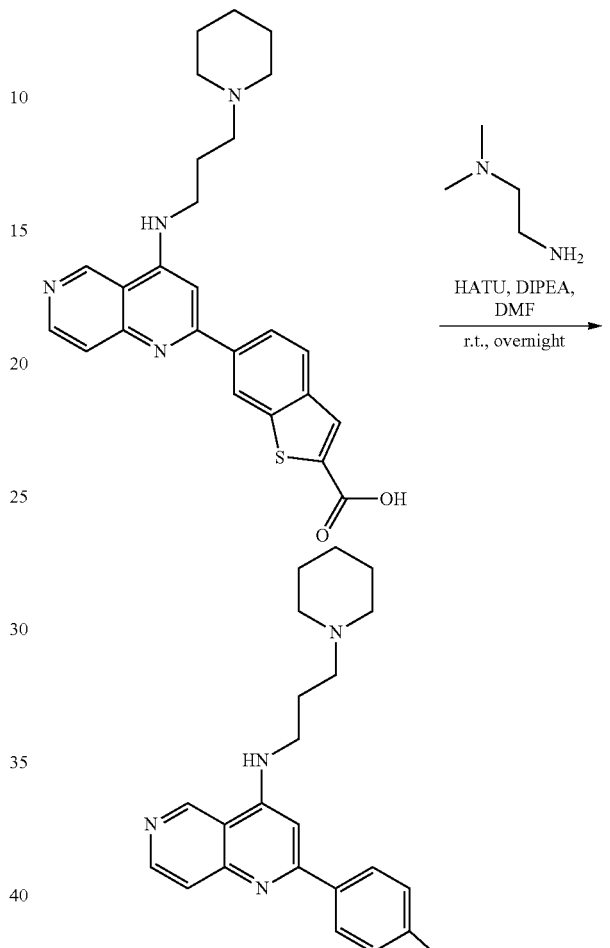

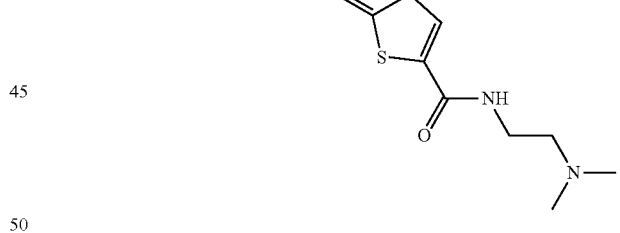

The mixture of 6-(4-(3-(piperidin-1-yl)propylamino)-1,6-naphthyridin-2-yl)benzo[b]thiophene-2-carboxylic acid (70 mg, 0.15 mmol), N,N-dimethylethane-1,2-diamine (27 mg, 0.31 mmol), HATU (87 mg, 0.23 mmol) and DIPEA (58 mg, 0.45 mmol) in DMF (1 mL) was stirred at room temperature overnight. Water (30 mL) was added, and then the mixture was extracted with EA three times. The combined organic layers were washed with water (20 mL×3) and brine (20 mL×1), dried over Na₂SO₄, filtered and concentrated. The residue was purified by the Prep-HPLC to obtain N-(2-(dimethylamino)ethyl)-6-(4-(3-(piperidin-1-yl)propylamino)-1,6-naphthyridin-2-yl)benzo[b]thiophene-2-carboxamide (4.7 mg, 6%). HPLC/UV purity: 100%; LC-MS (ESI): 517.2 (M+1)⁺; ¹H NMR (METHANOL-d4) δ: 9.64 (s, 1H), 8.78 (d, J=5.8 Hz, 1H), 8.58 (s, 1H), 8.10 (d, J=8.2 Hz, 1H), 8.02 (s, 1H), 7.91-7.97 (m, 1H), 7.82 (d, J=6.1 Hz, 1H), 7.23 (s, 1H), 3.69-3.80 (m, 4H), 3.49 (d, J=12.5 Hz, 2H), 3.34 (t, J=5.8 Hz, 2H), 2.75-2.98 (m, 10H), 2.14-2.25 (m, 2H), 1.85 (d, J=14.0 Hz, 2H), 1.59-1.80 (m, 3H), 1.41-1.48 (m, 1H).

Example 142: Synthesis of N-(1-methylpiperidin-4-yl)-6-(4-(3-(piperidin-1-yl)propylamino)-1,6-naphthyridin-2-yl)benzo[b]thiophene-2-carboxamide lamino)-1,6-naphthyridin-2-yl)benzo[b]thiophene-2-carboxamide (10 mg, 8%). HPLC/UV purity: 100%; LC-MS (ESI): 542.3 (M+1)+; 1H NMR (METHANOL-d4) δ: 9.37 (s, 1H), 8.54 (s, 1H), 8.47 (d, J=6.1 Hz, 1H), 8.05 (d, J=8.5 Hz, 1H), 7.90-7.99 (m, 2H), 7.70 (d, J=5.8 Hz, 1H), 7.06 (s, 1H), 3.84-4.00 (m, 1H), 3.55 (t, J=6.7 Hz, 2H), 3.11 (d, J=11.9 Hz, 2H), 2.93-3.03 (m, 4H), 2.83-2.93 (m, 2H), 2.42-2.58 (m, 5H), 2.05-2.17 (m, 2H), 2.00 (d, J=11.9 Hz, 2H), 1.64-1.81 (m, 6H), 1.41-1.60 (m, 2H).

Example 143: Synthesis of 6-(4-(3-(piperidin-1-yl)propylamino)-1,6-naphthyridin-2-yl)-N-(piperidin-4-yl)benzo[b]thiophene-2-carboxamide

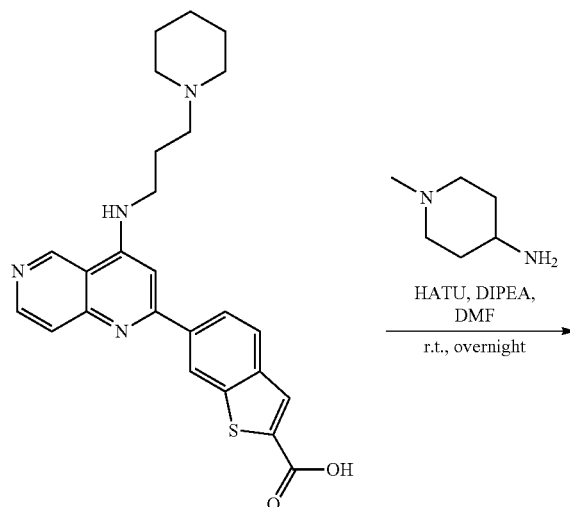

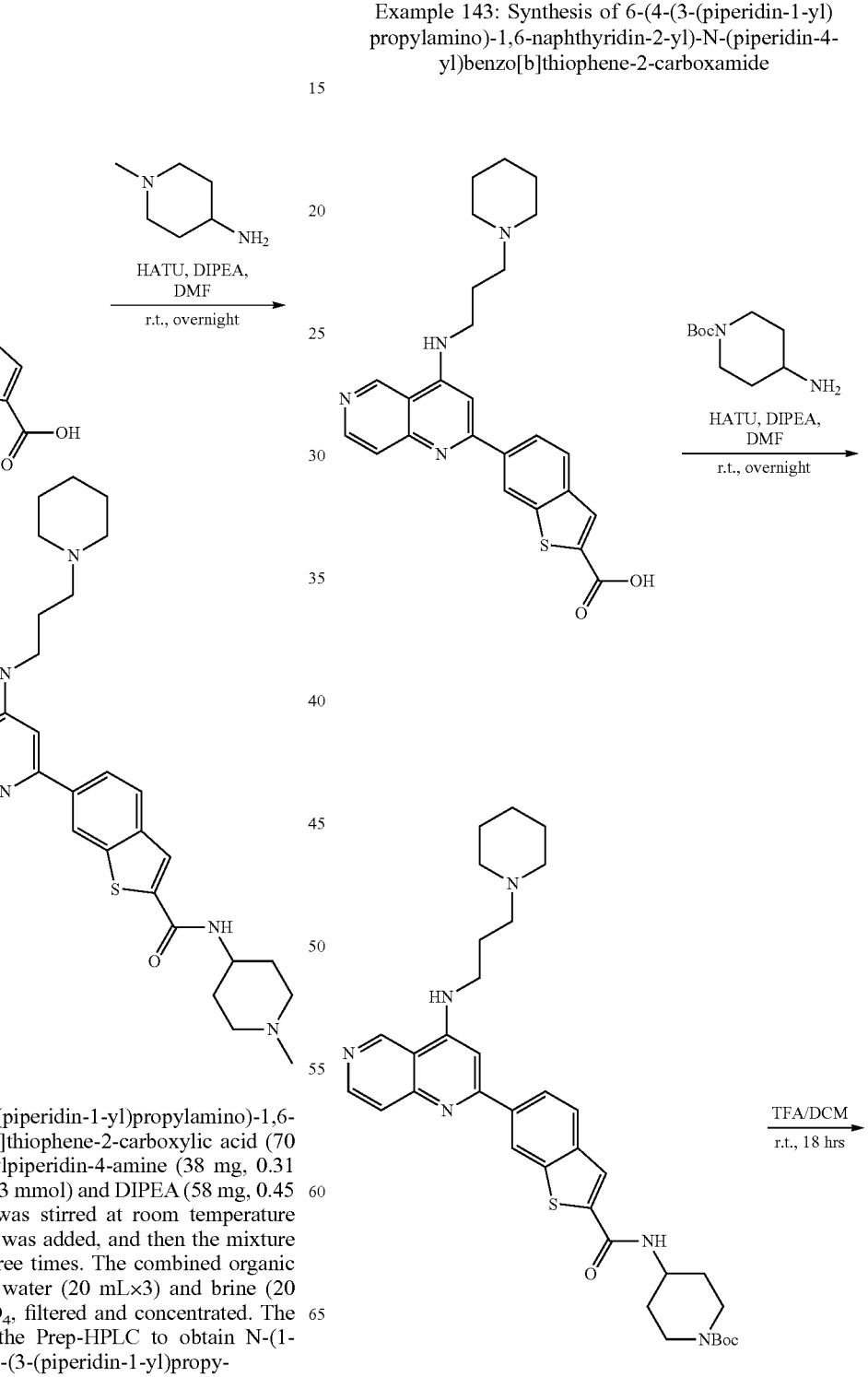

The mixture of 6-(4-(3-(piperidin-1-yl)propylamino)-1,6-naphthyridin-2-yl)benzo[b]thiophene-2-carboxylic acid (70 mg, 0.15 mmol), 1-methylpiperidin-4-amine (38 mg, 0.31 mmol), HATU (87 mg, 0.23 mmol) and DIPEA (58 mg, 0.45 mmol) in DMF (1 mL) was stirred at room temperature overnight. Water (30 mL) was added, and then the mixture was extracted with EA three times. The combined organic layers were washed with water (20 mL×3) and brine (20 mL×1), dried over Na2SO4, filtered and concentrated. The residue was purified by the Prep-HPLC to obtain N-(1-methylpiperidin-4-yl)-6-(4-(3-(piperidin-1-yl)propy-

Example 144: Synthesis of N,N-diethyl-6-(4-(3-(piperidin-1-yl)propylamino)-1,6-naphthyridin-2-yl)benzo[b]thiophene-2-carboxamide

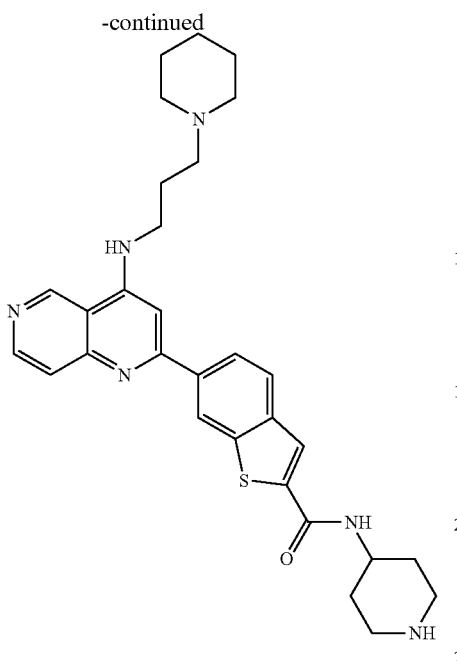

Step 1

The mixture of 6-(4-(3-(piperidin-1-yl)propylamino)-1,6-naphthyridin-2-yl)benzo[b]thiophene-2-carboxylic acid (70 mg, 0.15 mmol), tert-butyl 4-aminopiperidine-1-carboxylate (62 mg, 0.31 mmol), HATU (87 mg, 0.23 mmol) and DIPEA (58 mg, 0.45 mmol) in DMF (1 mL) was stirred at room temperature overnight. Water (30 mL) was added, and then the mixture was extracted with EA three times. The combined organic layers were washed with water (20 mL×3) and brine (20 mL×1), dried over Na$_2$SO$_4$, filtered and concentrated. The residue was purified by the Prep-TLC to afford tert-butyl 4-(6-(4-(3-(piperidin-1-yl)propylamino)-1,6-naphthyridin-2-yl)benzo[b]thiophene-2-carboxamido)piperidine-1-carboxylate (90 mg, 95%). LC-MS (ESI): 629.3 (M+1)$^+$.

Step 2

The mixture of tert-butyl 4-(6-(4-(3-(piperidin-1-yl)propylamino)-1,6-naphthyridin-2-yl)benzo[b]thiophene-2-carboxamido)piperidine-1-carboxylate (90 mg, 0.14 mmol) and TFA (1 mL) in DCM (1 mL) was stirred at room temperature for 18 hrs. Then the solvent was removed under the reduced pressure to give the residue which was purified with Prep-HPLC (Welch, XB-C18, 21.2 mm×250 mm, 10 um, eluting with 40% CH$_3$CN in 1‰ TFA in H$_2$O) to afford 6-(4-(3-(piperidin-1-yl)propylamino)-1,6-naphthyridin-2-yl)-N-(piperidin-4-yl)benzo[b]thiophene-2-carboxamide (15 mg, 20%) as a TFA salt. HPLC/UV purity: 100%; LC-MS (ESI): 529.3 (M+1)$^+$; $^1$H NMR (METHANOL-d4) δ: 9.75 (s, 1H), 8.88 (d, J=5.7 Hz, 1H), 8.60-8.69 (m, 1H), 8.10-8.18 (m, 1H), 8.06-8.10 (m, 1H), 8.03 (d, J=7.8 Hz, 1H), 7.94 (d, J=6.0 Hz, 1H), 7.20-7.34 (m, 1H), 4.16-4.27 (m, 1H), 3.88 (t, J=6.6 Hz, 2H), 3.63 (d, J=11.7 Hz, 2H), 3.54 (d, J=12.8 Hz, 2H), 3.34-3.42 (m, 2H), 3.16-3.25 (m, 2H), 2.99 (t, J=12.2 Hz, 2H), 2.32-2.41 (m, 2H), 2.27 (d, J=11.9 Hz, 2H), 1.91-2.02 (m, 4H), 1.76-1.90 (m, 3H), 1.41-1.45 (m, 1H).

The mixture of 6-(4-(3-(piperidin-1-yl)propylamino)-1,6-naphthyridin-2-yl)benzo[b]thiophene-2-carboxylic acid (70 mg, 0.15 mmol), diethylamine (23 mg, 0.31 mmol), HATU (87 mg, 0.23 mmol) and DIPEA (58 mg, 0.45 mmol) in DMF (1 mL) was stirred at room temperature overnight. Water (30 mL) was added, and then the mixture was extracted with EA three times. The combined organic layers were washed with water (20 mL×3) and brine (20 mL×1), dried over Na$_2$SO$_4$, filtered and concentrated. The residue was purified by the Prep-HPLC to afford N,N-diethyl-6-(4-(3-(piperidin-1-yl)propylamino)-1,6-naphthyridin-2-yl)benzo[b]thiophene-2-carboxamide (6.8 mg, 8%). HPLC/UV purity: 100%; LC-MS (ESI): 502.3 (M+1)$^+$; $^1$H NMR (METHANOL-d4) δ: 9.76 (s, 1H), 8.89 (t, J=5.4 Hz, 1H), 8.68 (d, J=5.0 Hz, 1H), 8.19 (d, J=8.5 Hz, 1H), 8.05 (t, J=8.4 Hz, 1H), 7.96 (d, J=6.0 Hz, 1H), 7.67-7.81 (m, 1H), 7.33 (d, J=9.8 Hz, 1H), 3.89 (t, J=6.8 Hz, 2H), 3.54-3.70 (m, 6H), 3.36 (d, J=7.6 Hz, 2H), 2.99 (t, J=12.2 Hz, 2H), 2.25-2.45

(m, 2H), 1.98 (d, J=14.9 Hz, 2H), 1.72-1.91 (m, 3H), 1.54 (d, J=12.6 Hz, 1H), 1.24-1.40 (m, 6H).

Example 145: Synthesis of N-(1-ethylpiperidin-4-yl)-6-(4-(3-(piperidin-1-yl)propylamino)-1,6-naphthyridin-2-yl)benzo[b]thiophene-2-carboxamide

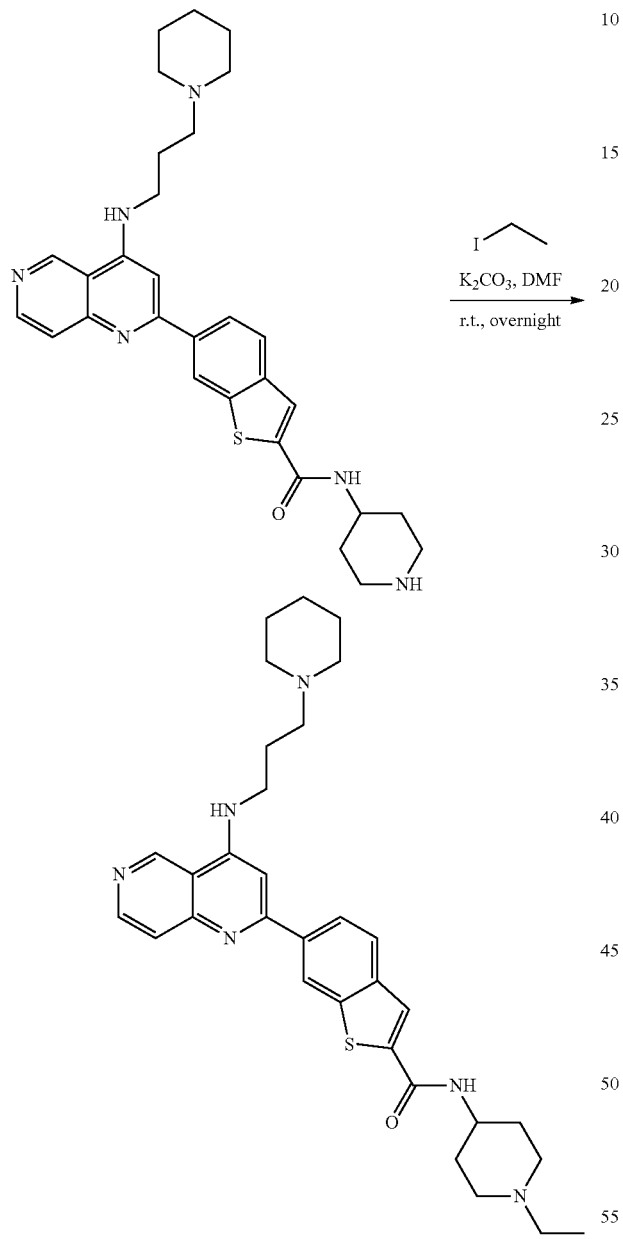

The mixture of 6-(4-(3-(piperidin-1-yl)propylamino)-1,6-naphthyridin-2-yl)-N-(piperidin-4-yl)benzo[b]thiophene-2-carboxamide (156 mg, 0.19 mmol), iodoethane (29 mg, 0.19 mmol) and $K_2CO_3$ (79 mg, 0.57 mmol) in DMF (1 mL) was stirred at room temperature for 2 hrs. The reaction mixture was poured into water (20 mL), extracted with EA (10 mL×3). The combined organic layers were washed by water (10 mL×3) and brine (10 mL), dried over $Na_2SO_4$. The drying agent was filtered off and the filtrate was concentrated under the reduced pressure to obtain the residue which was purified by prep-TLC to afford N-(1-ethylpiperidin-4-yl)-6-(4-(3-(piperidin-1-yl) propylamino)-1,6-naphthyridin-2-yl)benzo[b]thiophene-2-carboxamide (14 mg, 13%). HPLC/UV purity: 100%; LC-MS (ESI): 557.3 $(M+1)^+$; $^1$H NMR (METHANOL-$d_4$) δ: 9.40 (s, 1H), 8.53 (s, 1H), 8.46 (d, J=5.7 Hz, 1H), 8.04 (d, J=8.2 Hz, 1H), 7.99 (s, 1H), 7.92 (d, J=8.0 Hz, 1H), 7.67 (d, J=5.7 Hz, 1H), 6.99-7.08 (d, 1H), 4.07 (t, J=10.8 Hz, 1H), 3.56 (t, J=6.6 Hz, 2H), 3.48 (d, J=11.7 Hz, 2H), 3.09-3.20 (m, 4H), 3.05 (q, J=6.9 Hz, 3H), 2.91-2.99 (m, 2H), 2.10-2.21 (m, 4H), 1.87-1.99 (m, 2H), 1.71-1.80 (m, 4H), 1.46-1.63 (m, 2H), 1.26 (t, J=7.3 Hz, 3H).

Example 146: Synthesis of (4-methylpiperazin-1-yl)(6-(4-(3-(piperidin-1-yl)propylamino)-1,6-naphthyridin-2-yl)benzo[b]thiophen-2-yl)methanone

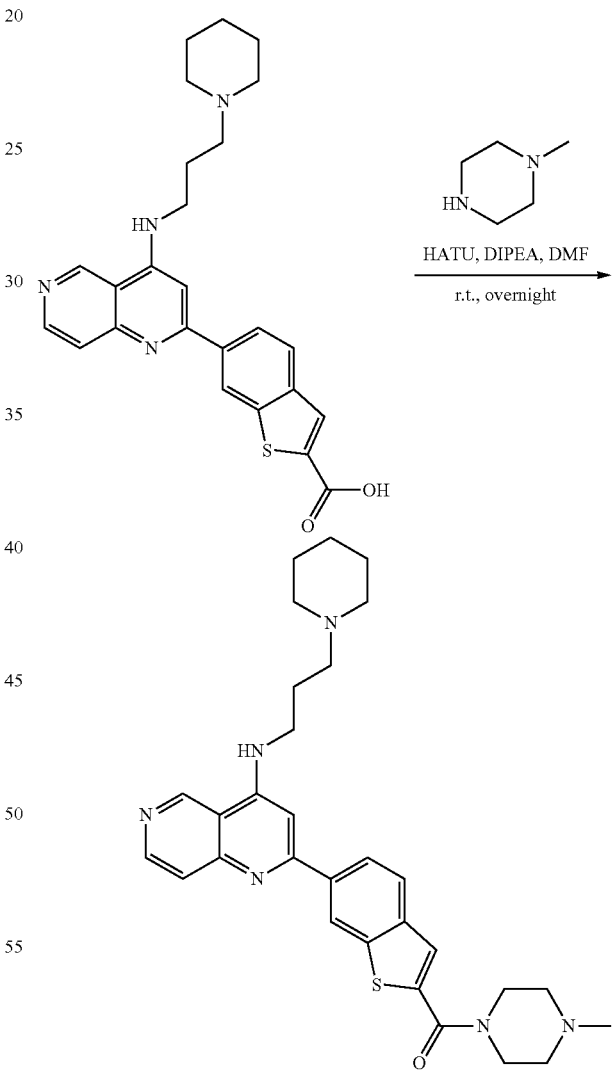

The mixture of 6-(4-(3-(piperidin-1-yl)propylamino)-1,6-naphthyridin-2-yl)benzo[b]thiophene-2-carboxylic acid (70 mg, 0.15 mmol), 1-methylpiperazine (31 mg, 0.31 mmol), HATU (87 mg, 0.23 mmol) and DIPEA (58 mg, 0.45 mmol) in DMF (1 mL) was stirred at room temperature overnight. Water (30 mL) was added, and then the mixture was extracted with EA three times. The combined organic layers were washed with water (20 mL×3) and brine (20 mL×1), dried over Na$_2$SO$_4$, filtered and concentrated. The residue was purified by the Prep-HPLC to afford (4-methylpiperazin-1-yl)(6-(4-(3-(piperidin-1-yl)propylamino)-1,6-naphthyridin-2-yl)benzo[b]thiophen-2-yl)methanone (12.8 mg, 16%). HPLC/UV purity: 94%; LC-MS (ESI): 529.2 (M+1)$^+$; $^1$H NMR (METHANOL-d$_4$) δ: 9.30 (s, 1H), 8.47 (s, 1H), 8.42 (d, J=6.1 Hz, 1H), 7.98 (d, J=8.5 Hz, 1H), 7.88 (d, J=8.5 Hz, 1H), 7.65 (d, J=5.8 Hz, 1H), 7.58 (s, 1H), 6.94 (s, 1H), 3.67-3.78 (m, 4H), 3.41 (t, J=6.9 Hz, 2H), 3.16-3.24 (m, 2H), 2.49-2.59 (m, 4H), 2.39-2.46 (m, 4H), 2.25 (s, 3H), 1.87-1.98 (m, 2H), 1.50-1.62 (m, 4H), 1.35-1.48 (m, 2H).

Example 147: Synthesis of Piperazin-1-yl(6-(4-(3-(piperidin-1-yl)propylamino)-1,6-naphthyridin-2-yl)benzo[b]thiophen-2-yl)methanone

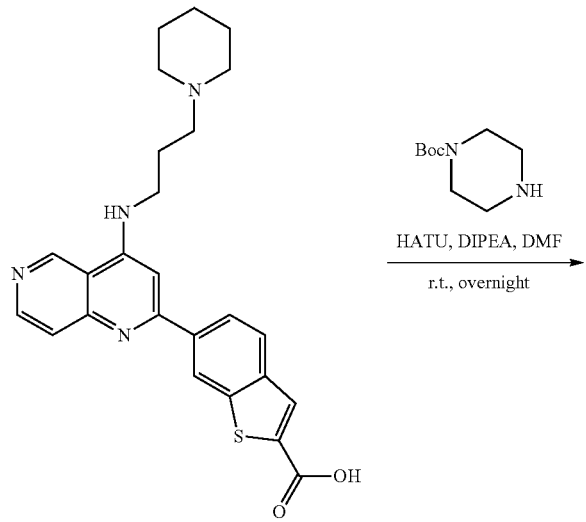

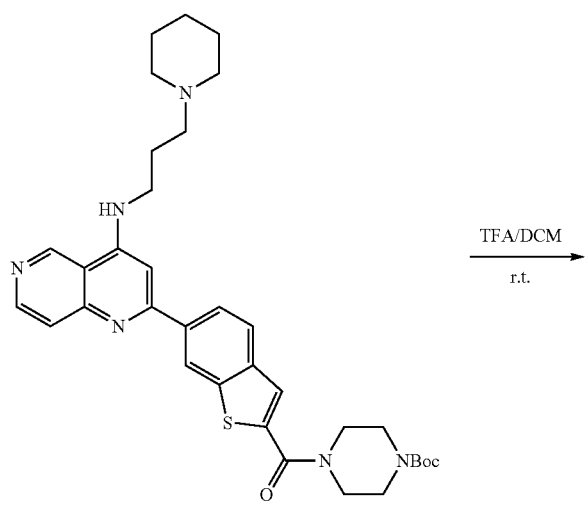

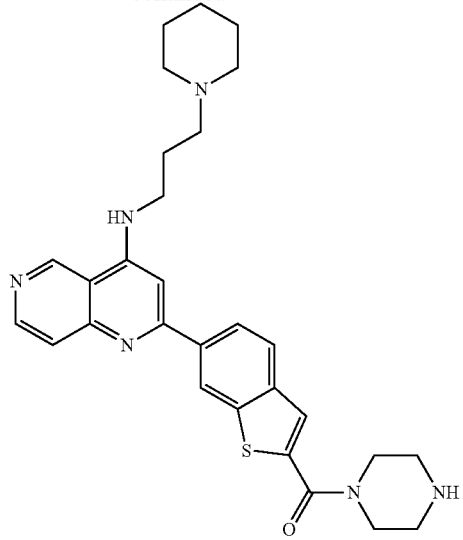

Step 1

The mixture of 6-(4-(3-(piperidin-1-yl)propylamino)-1,6-naphthyridin-2-yl)benzo[b]thiophene-2-carboxylic acid (117 mg, 0.26 mmol), tert-butyl piperazine-1-carboxylate (96 mg, 0.52 mmol), HATU (148 mg, 0.39 mmol) and DIPEA (100 mg, 0.78 mmol) in DMF (1 mL) was stirred at room temperature overnight. Water (30 mL) was added, and then the mixture was extracted with EA three times. The combined organic layers were washed with water (20 mL×3) and brine (20 mL×1), dried over Na$_2$SO$_4$, filtered and concentrated. The residue was purified by the Prep-TLC to afford tert-butyl 4-(6-(4-(3-(piperidin-1-yl)propylamino)-1,6-naphthyridin-2-yl)benzo[b]thiophene-2-carbonyl)piperazine-1-carboxylate (42 mg, 26%). LC-MS (ESI): 615.3 (M+1)$^+$;

Step 2

The mixture of tert-butyl 4-(6-(4-(3-(piperidin-1-yl)propylamino)-1,6-naphthyridin-2-yl)benzo[b]thiophene-2-carbonyl)piperazine-1-carboxylate (42 mg, 0.06 mmol) and TFA (1 mL) in DCM (1 mL) was stirred at room temperature for 18 hrs. Then the solvent was removed under the reduced pressure to give the residue which was purified with Prep-HPLC (Welch, XB-C18, 21.2 mm×250 mm, 10 um, eluting with 40% CH$_3$CN in 1‰ TFA in H$_2$O) to afford piperazin-1-yl(6-(4-(3-(piperidin-1-yl)propylamino)-1,6-naphthyridin-2-yl)benzo[b]thiophen-2-yl)methanone (35 mg, 100%) as a TFA salt. HPLC/UV purity: 99%; LC-MS (ESI): 515.3 (M+1)$^+$; $^1$H NMR (METHANOL-d$_4$) D: 9.75 (s, 1H), 8.88 (d, J=6.1 Hz, 1H), 8.70 (s, 1H), 8.20 (d, J=8.5 Hz, 1H), 8.07 (d, J=8.4 Hz, 1H), 7.95 (d, J=6.1 Hz, 1H), 7.87 (s, 1H), 7.34 (s, 1H), 4.06-4.13 (m, 4H), 3.88 (t, J=6.7 Hz, 2H), 3.61 (d, J=11.9 Hz, 2H), 3.39-3.43 (m, 4H), 3.29-3.31 (m, 2H), 2.98 (t, J=12.4 Hz, 2H), 2.27-2.41 (m, 2H), 1.97 (d, J=15.0 Hz, 2H), 1.74-1.89 (m, 3H), 1.48-1.54 (m, 1H).

Example 148: Synthesis of (4-ethylpiperazin-1-yl)(6-(4-(3-(piperidin-1-yl)propylamino)-1,6-naphthyridin-2-yl)benzo[b]thiophen-2-yl)methanone

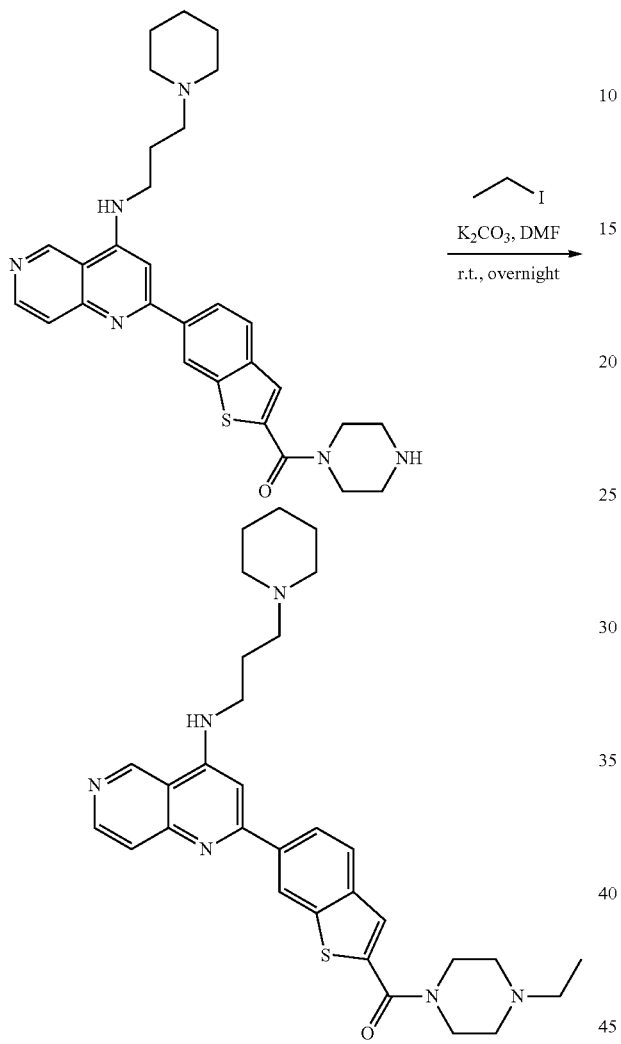

The mixture of piperazin-1-yl(6-(4-(3-(piperidin-1-yl)propylamino)-1,6-naphthyridin-2-yl)benzo[b]thiophen-2-yl)methanone (20 mg, 0.02 mmol), iodoethane (4 mg, 0.02 mmol) and K$_2$CO$_3$ (8 mg, 0.06 mmol) in DMF (1 mL) was stirred at room temperature for 2 hrs. The reaction mixture was poured into water (20 mL), extracted with EA (10 mL×3). The combined organic layers were washed by water (10 mL×3) and brine (10 mL), dried over Na$_2$SO$_4$. The drying agent was filtered off and the filtrate was concentrated under the reduced pressure to get the residue which was purified prep-TLC to afford (4-ethylpiperazin-1-yl)(6-(4-(3-(piperidin-1-yl)propylamino)-1,6-naphthyridin-2-yl)benzo[b]thiophen-2-yl)methanone (5.3 mg, 49%). HPLC/UV purity: 94%; LC-MS (ESI): 543.2 (M+1)$^+$; $^1$H NMR (METHANOL-d$_4$) δ: 9.66 (s, 1H), 8.79 (s, 1H), 8.61 (d, J=4.0 Hz, 1H), 8.11 (d, J=8.5 Hz, 1H), 7.94-8.01 (d, 1H), 7.84 (d, J=5.8 Hz, 1H), 7.80 (s, 1H), 7.25 (s, 1H), 3.77 (t, J=6.9 Hz, 2H), 3.48-3.60 (m, 6H), 3.22-3.29 (m, 4H), 2.96-3.20 (m, 4H), 2.86 (t, J=11.3 Hz, 2H), 2.16-2.29 (m, 2H), 1.85 (d, J=14.6 Hz, 2H), 1.70 (d, J=15.3 Hz, 3H), 1.42 (d, J=12.2 Hz, 1H), 1.30 (t, J=7.3 Hz, 3H).

Example 149: Synthesis of (E)-N,N-Diethyl-3-(5-(4-((3-(piperidin-1-yl)propyl)amino)-1,6-naphthyridin-2-yl)furan-2-yl)acrylamide

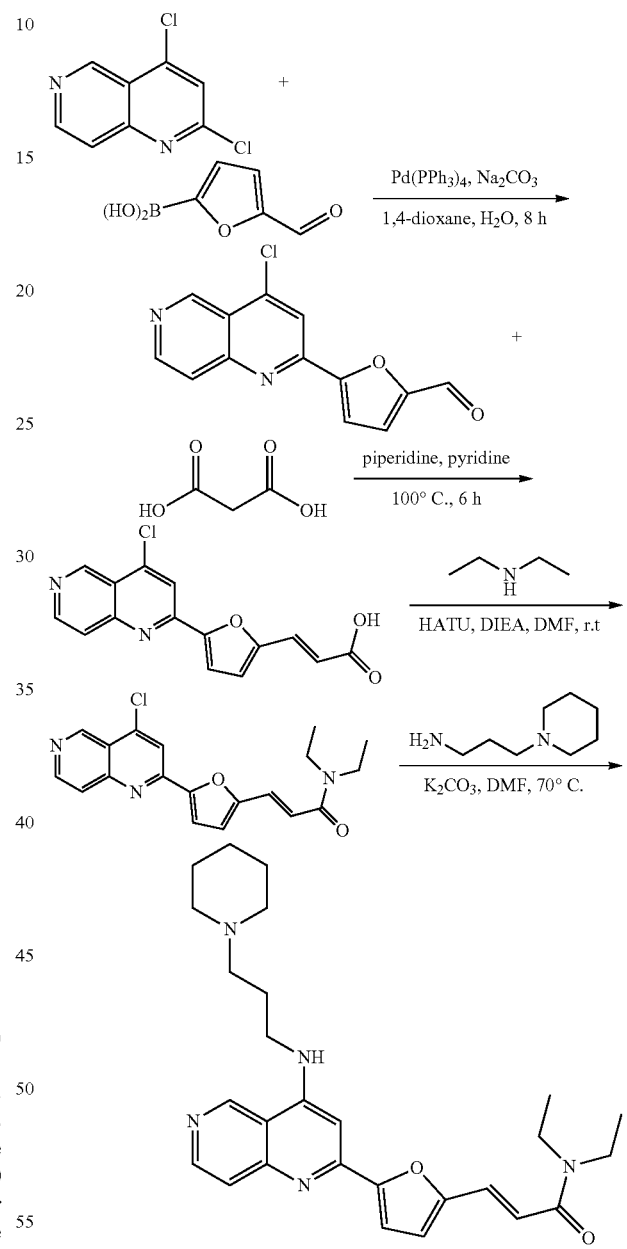

Step 1

The mixture of (5-formylfuran-2-yl)boronic acid (1.0 g, 7.15 mmol), 2,4-dichloro-1,6-naphthyridine (1.2 g, 5.96 mmol), Pd(PPh$_3$)$_4$ (689 mg, 0.596 mmol) and Na$_2$CO$_3$ (1.26 g, 11.92 mmol) in 1,4-dioxane/H$_2$O (20 mL/5 mL) was stirred at 100° C. under N$_2$ for 8 hrs. The reaction mixture was concentrated and purified by flash column chromatography (silica gel, eluting with 9% to 33% EA/PE) to afford 5-(4-chloro-1,6-naphthyridin-2-yl)furan-2-carbaldehyde (900 mg, 69%) as yellow solid. LC-MS (ESI): 259.1 (M+1)+.

Step 2

Malonic acid (258 mg, 2.48 mmol) was added to the mixture of 5-(4-chloro-1,6-naphthyridin-2-yl)furan-2-carbaldehyde (400 mg, 1.55 mmol), piperidine (0.04 mL) and pyridine (3 mL). After heated at 80° C. for 1 h and at 100° C. for 4.5 h, the reaction mixture was diluted with EtOAc (10 mL×3) and washed with water (10 mL×3). The water layer was acidified to pH=2 with 2N aq. HCl solution and extracted with EA (10 mL×3). The organic layer was dried over Na$_2$SO$_4$ and concentrated to afford crude (E)-3-(5-(4-chloro-1,6-naphthyridin-2-yl)furan-2-yl)acrylic acid (90 mg, 19%) as brown solid. LC-MS (ESI): 301.0 (M+1)+.

Step 3

The mixture of (E)-3-(5-(4-chloro-1,6-naphthyridin-2-yl)furan-2-yl)acrylic acid (90 mg, 0.30 mmol), diethylamine (44 mg, 0.60 mmol), HATU (171 mg, 0.45 mmol) and DIPEA (78 mg, 0.60 mmol) in DMF (3 mL) was stirred at room temperature overnight. The reaction mixture was quenched with water (5 mL), extracted with EA (5 mL×3), washed with water (10 mL×3) and brine (20 mL), and dried over Na$_2$SO$_4$, concentrated and purified by prep-TLC (EA/ PE=1/1) to afford (E)-3-(5-(4-chloro-1,6-naphthyridin-2-yl)furan-2-yl)-N,N-diethylacrylamide (20 mg, 19%) as yellow solid. LC-MS (ESI): 356.1 (M+1)+.

Step 4

To a solution of (E)-3-(5-(4-chloro-1,6-naphthyridin-2-yl)furan-2-yl)-N,N-diethylacrylamide (20 mg, 0.056 mmol) in DMF (2 mL) were added 3-(piperidin-1-yl)propan-1-amine (12 mg, 0.084 mmol) and K$_2$CO$_3$ (15 mg, 0.11 mmol). The reaction mixture was stirred at 70° C. overnight. The reaction mixture was quenched with water (2 mL), and extracted with DCM (5 mL×3). The organic layer was washed with water (10 mL×3) and brine (10 mL), dried over Na$_2$SO$_4$, concentrated and purified by prep-HPLC to afford (E)-N,N-diethyl-3-(5-(4-((3-(piperidin-1-yl)propyl)amino)-1,6-naphthyridin-2-yl)furan-2-yl)acrylamide (5 mg, 19%) as yellow oil. HPLC/UV purity: 100%; LC-MS (ESI): 462.2 (M+1)+. $^1$H NMR (METHANOL-d$_4$) δ: 9.66 (s, 1H), 8.81 (d, J=6.0 Hz, 1H), 7.93 (d, J=6.4, 1H), 7.87 (d, J=3.6 Hz, 1H), 7.53 (d, J=15.2 Hz, 1H), 7.35 (d, J=12.8 Hz, 2H), 7.16 (d, J=4.0 Hz, 1H), 3.82 (t, J=6.8 Hz, 2H), 3.68-3.51 (m, 6H), 2.96 (t, J=12.8 Hz, 2H), 2.32-2.28 (m, 2H), 1.96 (d, J=14.8 Hz, 2H), 1.87-1.77 (m, 3H), 1.56-1.50 (m, 1H), 1.31 (t, J=6.8 Hz, 5H), 1.21 (t, J=7.2 Hz, 3H).

Example 150: Synthesis of (E)-N-(2-(1-Methylpiperidin-4-yl)ethyl)-3-(5-(4-((3-(piperidin-1-yl)propyl)amino)-1,6-naphthyridin-2-yl)furan-2-yl)acrylamide

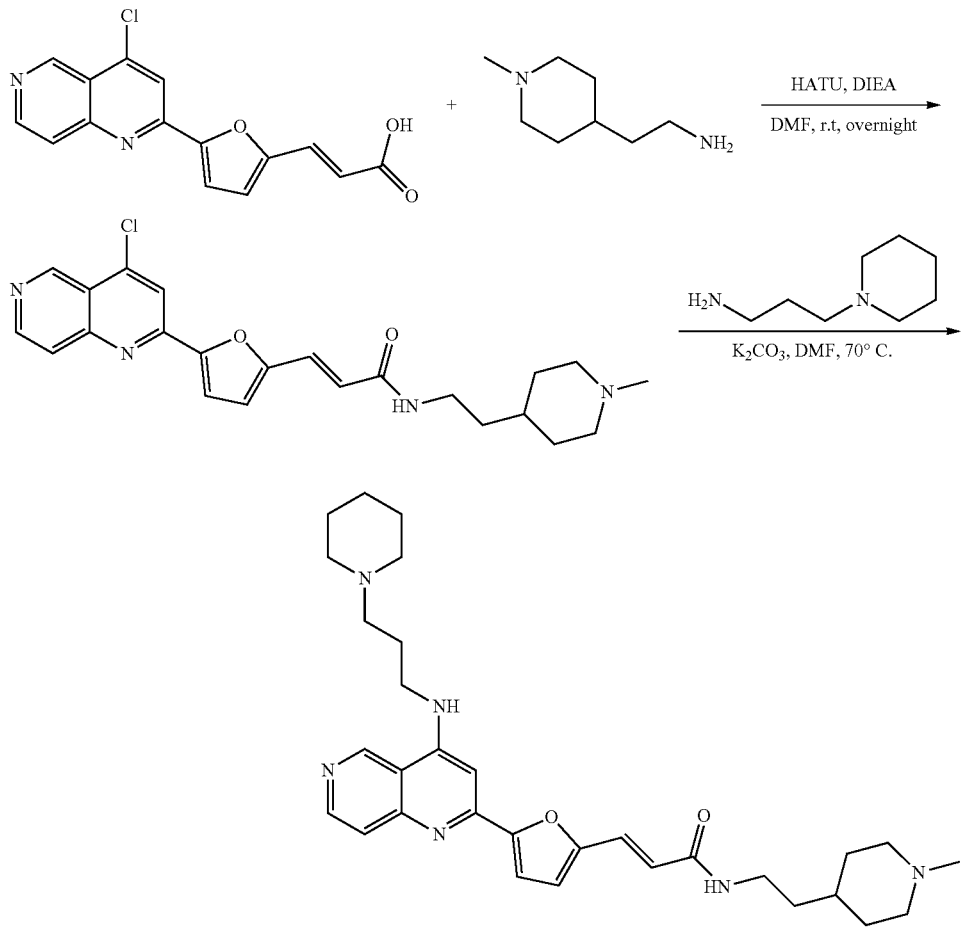

Step 1

The mixture of (E)-3-(5-(4-chloro-1,6-naphthyridin-2-yl)furan-2-yl)acrylic acid (60 mg, 0.20 mmol), 2-(1-methylpiperidin-4-yl)ethan-1-amine (57 mg, 0.40 mmol), HATU (114 mg, 0.30 mmol) and DIPEA (52 mg, 0.40 mmol) in DMF (5 mL) was stirred at room temperature overnight. The reaction mixture was quenched with water (5 mL), extracted with DCM (5 mL×3), washed with water (10 mL×3) and brine (20 mL), dried over Na$_2$SO$_4$, concentrated and purified by prep-TLC (DCM/MeOH=10/1) to afford (E)-3-(5-(4-chloro-1,6-naphthyridin-2-yl)furan-2-yl)-N-(2-(1-methylpiperidin-4-yl)ethyl)acrylamide (20 mg, 24%) as oil. LC-MS (ESI): 425.1 (M+1)$^+$.

Step 2

To a solution of (E)-3-(5-(4-chloro-1,6-naphthyridin-2-yl)furan-2-yl)-N-(2-(1-methylpiperidin-4-yl)ethyl)acrylamide (20 mg, 0.047 mmol) in DMF (3 mL) were added 3-(piperidin-1-yl)propan-1-amine (10 mg, 0.071 mmol) and K$_2$CO$_3$ (13 mg, 0.094 mmol). The reaction mixture was stirred at 70° C. overnight, then quenched with water (3 mL). The mixture was extracted with DCM (5 mL×3). The organic layer was washed with water (10 mL×3) and brine (10 mL), dried over Na$_2$SO$_4$, concentrated and purified by prep-HPLC to afford (E)-N-(2-(1-methylpiperidin-4-yl)ethyl)-3-(5-(4-((3-(piperidin-1-yl)propyl)amino)-1,6-naphthyridin-2-yl)furan-2-yl)acrylamide (8 mg, 32%) as yellow solid. LC-MS (ESI): 531.3 (M+1)$^+$. $^1$H NMR (METHANOL-d$_4$) δ: 9.67 (s, 1H), 8.79 (d, J=6.0 Hz, 1H), 7.96 (d, J=6.0 Hz, 1H), 7.84 (d, J=3.6 Hz, 1H), 7.45 (d, J=15.6 Hz, 1H), 7.31 (s, 1H), 7.06 (d, J=3.6 Hz, 1H), 6.89 (d, J=15.6 Hz, 1H), 3.82 (t, J=6.8 Hz, 2H), 3.59 (d, J=11.6 Hz, 2H), 3.55 (d, J=12.4 Hz, 2H), 3.41 (t, J=6.8 Hz, 2H), 3.01-2.93 (m, 4H), 2.85 (s, 3H), 2.33-2.27 (m, 2H), 2.06 (d, J=14.0 Hz, 2H), 1.95 (d, J=13.6 Hz, 2H), 1.82-1.62 (m, 6H), 1.57 (q, J=6.8 Hz, 2H), 1.53-1.41 (m, 3H), 1.31 (d, J=17.2 Hz, 1H).

Example 151: Synthesis of (E)-N-(1-Methylpiperidin-4-yl)-3-(5-(4-((3-(piperidin-1-yl)propyl)amino)-1,6-naphthyridin-2-yl)furan-2-yl)acrylamide

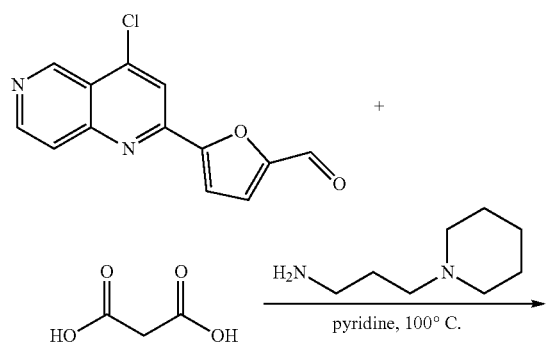

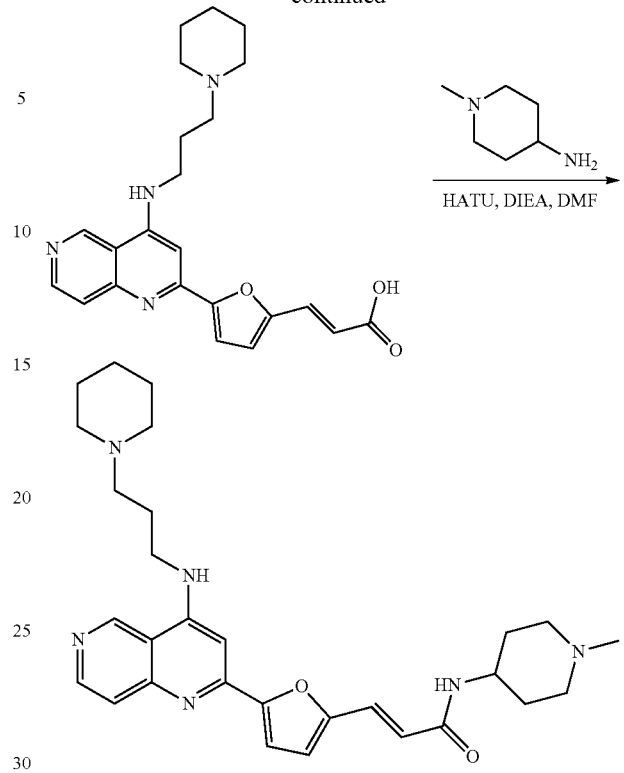

Step 1

Malonic acid (302 mg, 2.90 mmol) was added to the mixture of 5-(4-chloro-1,6-naphthyridin-2-yl)furan-2-carbaldehyde (500 mg, 1.93 mmol), 3-(piperidin-1-yl)propan-1-amine (0.05 mL) and pyridine (5 mL). The mixture was heated at 80° C. for 1 hr and then at 100° C. overnight. The solvent was removed and acidified to pH=2 with 2N aq. HCl solution. Then the mixture was concentrated and purified by prep-TLC to afford (E)-3-(5-(4-((3-(piperidin-1-yl)propyl)amino)-1,6-naphthyridin-2-yl)furan-2-yl)acrylic acid (35 mg, 4%) as brown solid. LC-MS (ESI): 407.0 (M+1)$^+$.

Step 2

The mixture of (E)-3-(5-(4-((3-(piperidin-1-yl)propyl)amino)-1,6-naphthyridin-2-yl)furan-2-yl)acrylic acid (25 mg, 0.06 mmol), 1-methylpiperidin-4-amine (10 mg, 0.09 mmol), HATU (34 mg, 0.09 mmol) and DIPEA (16 mg, 0.12 mmol) in DMF (2 mL) was stirred at room temperature overnight. The reaction mixture was quenched with water (2 mL), extracted with DCM (5 mL×3), washed with water (10 mL×3) and brine (20 mL), dried over Na$_2$SO$_4$, concentrated and purified by prep-TLC to afford (E)-N-(1-methylpiperidin-4-yl)-3-(5-(4-((3-(piperidin-1-yl)propyl)amino)-1,6-naphthyridin-2-yl)furan-2-yl)acrylamide (5 mg, 16%) as yellow oil. LC-MS (ESI): 503.3 (M+1)$^+$. $^1$H NMR (METHANOL-d$_4$) δ: 9.66 (s, 1H), 8.79 (d, J=6.0 Hz, 1H), 7.95 (d, J=6.0 Hz, 1H), 7.82 (d, J=3.6 Hz, 1H), 7.48 (d, J=16.0 Hz, 1H), 7.31 (s, 1H), 7.09 (d, J=4.0 Hz, 1H), 6.86 (d, J=15.6 Hz, 1H), 4.14-4.04 (m, 1H), 3.81 (t, J=6.8 Hz, 2H), 3.59 (d, J=12.4 Hz, 2H), 3.48-3.31 (m, 4H), 3.17 (t, J=11.2 Hz, 2H), 2.96 (t, J=11.2 Hz, 2H), 2.90 (s, 3H), 2.32-1.53 (m, 12H).

Example 152: Synthesis of (E)-3-(5-(4-(3-(Piperidin-1-yl)propylamino)-1,6-naphthyridin-2-yl)thiophen-2-yl)acrylic acid

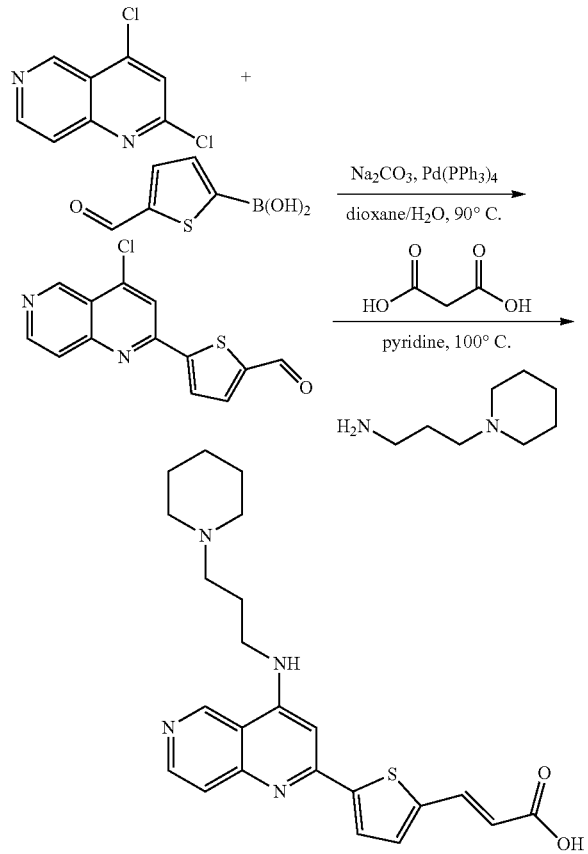

Step 1

The mixture of 5-formylthiophen-2-ylboronic acid (1.0 g, 6.41 mmol), 2,4-dichloro-1,6-naphthyridine (1.15 g, 5.78 mmol), Pd(PPh$_3$)$_4$ (689 mg, 0.596 mmol) and Na$_2$CO$_3$ (1.26 g, 11.92 mmol) in 1,4-dioxane (20 mL) and H$_2$O (5 mL) was stirred at 100° C. under N$_2$ for 8 hrs. The reaction mixture was concentrated and purified by flash column chromatography (silica gel, eluting with 9% to 33% EA/PE) to afford 5-(4-chloro-1,6-naphthyridin-2-yl)thiophene-2-carbaldehyde (900 mg, 51%) as yellow solid. LC-MS (ESI): 275.3 (M+1)$^+$.

Step 2

Malonic acid (425 mg, 4.08 mmol) was added to the mixture of 5-(4-chloro-1,6-naphthyridin-2-yl)thiophene-2-carbaldehyde (560 mg, 2.04 mmol), 3-(piperidin-1-yl)propan-1-amine (0.05 mL) and pyridine (5 mL). The mixture was heated at 80° C. for 1 hr and then at 120° C. overnight. The mixture was concentrated and acidified with 1N aq. HCl solution to pH=2. Then the solvent was removed and the residue was purified by prep-PLC to afford (E)-3-(5-(4-(3-(piperidin-1-yl)propylamino)-1,6-naphthyridin-2-yl)thiophen-2-yl)acrylic acid (12 mg, 1.4%) as yellow solid. LC-MS (ESI): 423.1 (M+1)$^+$. $^1$H NMR (METHANOL-d4) δ: 9.36 (s, 1H), 8.51 (d, J=6.0 Hz, 1H), 7.79 (d, J=3.9 Hz, 1H), 7.71 (d, J=6.0 Hz, 1H), 7.46 (d, J=15.6 Hz, 1H), 7.20 (d, J=3.9 Hz, 1H), 7.04 (s, 1H), 6.34 (d, J=15.7 Hz, 1H), 3.61 (t, J=6.8 Hz, 2H), 3.15-3.09 (m, 6H), 2.26-2.20 (m, 2H), 1.89-1.81 (m, 4H), 1.65-1.68 (m, 2H).

Example 153: Synthesis of (E)-N,N-Diethyl-3-(5-(4-(3-(piperidin-1-yl)propylamino)-1,6-naphthyridin-2-yl)thiophen-2-yl)acrylamide

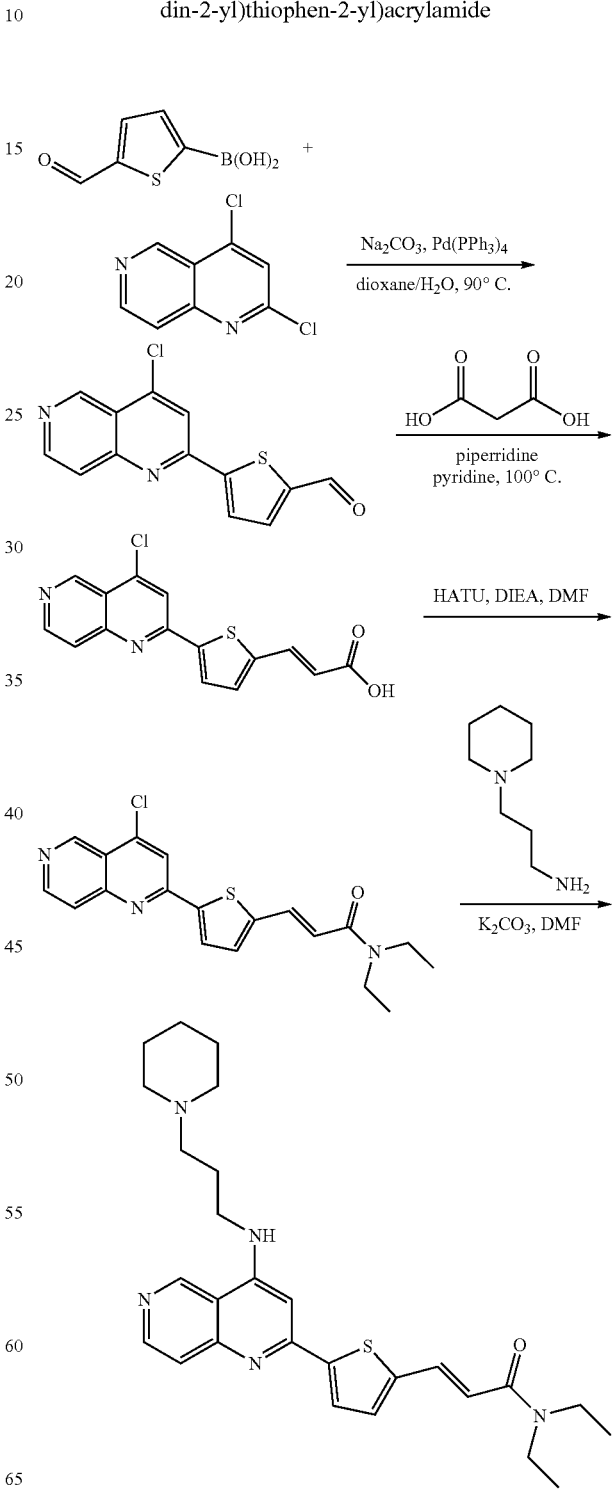

Step 1

The mixture of 5-formylthiophen-2-ylboronic acid (2.0 g, 12.8 mmol), 2,4-dichloro-1,6-naphthyridine (2.4 g, 12.06 mmol), Pd(PPh$_3$)$_4$ (1.5 g, 1.28 mmol) and Na$_2$CO$_3$ (2.8 g, 26.4 mmol) in 1,4-dioxane (20 mL) and H$_2$O (5 mL) was stirred at 90° C. under N$_2$ for 3 hrs. The reaction mixture was concentrated and purified by flash column chromatography (silica gel, eluting with 9% to 33% EA/PE) to afford 5-(4-chloro-1,6-naphthyridin-2-yl)furan-2-carbaldehyde (1.26 mg, 36%) as yellow solid. LC-MS (ESI): 275.1 (M+1)$^+$.

Step 2

Malonic acid (227 mg, 2.18 mmol) was added to the mixture of 5-(4-chloro-1,6-naphthyridin-2-yl)thiophene-2-carbaldehyde (500 mg, 1.83 mmol), piperidine (1 drop) and pyridine (5 mL). After stirred at 100° C. overnight, the mixture was diluted with EA (10 mL) and washed with water (10 mL×3). The water layer was acidified to pH=2 with 1N aq. HCl solution, extracted with EA (10 mL×3), dried over Na$_2$SO$_4$, and concentrated to afford (E)-3-(5-(4-chloro-1,6-naphthyridin-2-yl)furan-2-yl)acrylic acid (470 mg, 81.5%) as brown solid. LC-MS(ESI): 317.3 (M+1)$^+$.

Step 3

The mixture of (E)-3-(5-(4-chloro-1,6-naphthyridin-2-yl)thiophen-2-yl)acrylic acid (100 mg, 0.31 mmol), diethylamine (100 mg, 1.36 mmol), HATU (145 mg, 0.38 mmol) and DIPEA (82 mg, 0.63 mmol) in DMF (2 mL) was stirred at room temperature overnight. The reaction mixture was quenched with water (5 mL), extracted with EtOAc (5 mL×3). The combined organic layer was washed with water (10 mL×3) and brine (20 mL), dried over Na$_2$SO$_4$, concentrated and purified by prep-TLC to afford (E)-3-(5-(4-chloro-1,6-naphthyridin-2-yl)thiophen-2-yl)-N,N-diethylacrylamide (110 mg, 93.6%) as yellow solid. LC-MS (ESI): 372.5 (M+1)$^+$. $^1$H NMR (DMSO-d6) δ 9.52 (s, 1H), 8.83 (d, J=5.9 Hz, 1H), 8.59 (s, 1H), 8.23 (d, J=4.0 Hz, 1H), 7.92-7.86 (m, 1H), 7.68 (d, J=15.1 Hz, 1H), 7.61 (d, J=4.0 Hz, 1H), 7.01 (d, J=15.1 Hz, 1H), 3.59-3.49 (m, 2H), 3.41-3.36 (m, 2H), 1.18 (t, J=7.0 Hz, 3H), 1.08 (t, J=7.0 Hz, 3H).

Step 4

To a solution of (E)-3-(5-(4-chloro-1,6-naphthyridin-2-yl)thiophen-2-yl)-N,N-diethylacrylamide (110 mg, 0.29 mmol) in DMF (2 mL) were added 3-(piperidin-1-yl)propan-1-amine (55 mg, 0.38 mmol) and K$_2$CO$_3$ (82 mg, 0.59 mmol). After stirred at 70° C. overnight, the reaction mixture was quenched with water (2 mL), extracted with DCM (5 mL×3), washed with water (10 mL×3) and brine (10 mL), dried over Na$_2$SO$_4$, concentrated and purified by prep-PLC to afford (E)-N,N-diethyl-3-(5-(4-(3-(piperidin-1-yl)propylamino)-1,6-naphthyridin-2-yl)thiophen-2-yl)acrylamide (54 mg, 38.2%) as yellow solid. HPLC/UV purity: 100%; LC-MS (ESI): 478.2 (M+1)$^+$. $^1$H NMR (METHANOL-d4) δ 9.38 (s, 1H), 8.52 (d, J=6.0 Hz, 1H), 7.87 (d, J=3.9 Hz, 1H), 7.75 (d, J=15.1 Hz, 1H), 7.71 (d, J=6.0 Hz, 1H), 7.42 (d, J=3.9 Hz, 1H), 7.06 (s, 1H), 6.93 (d, J=15.1 Hz, 1H), 3.60 (q, J=7.1 Hz, 2H), 3.55-3.49 (m, 4H), 2.58-2.51 (m, 6H), 2.09-1.96 (m, 2H), 1.74-1.62 (m, 4H), 1.48-1.53 (m, 2H), 1.32 (t, J=7.1 Hz, 3H), 1.22 (t, J=7.1 Hz, 3H).

Example 154: Synthesis of (E)-N-(1-Methylpiperidin-4-yl)-3-(5-(4-(3-(piperidin-1-yl)propylamino)-1,6-naphthyridin-2-yl)thiophen-2-yl)acrylamide

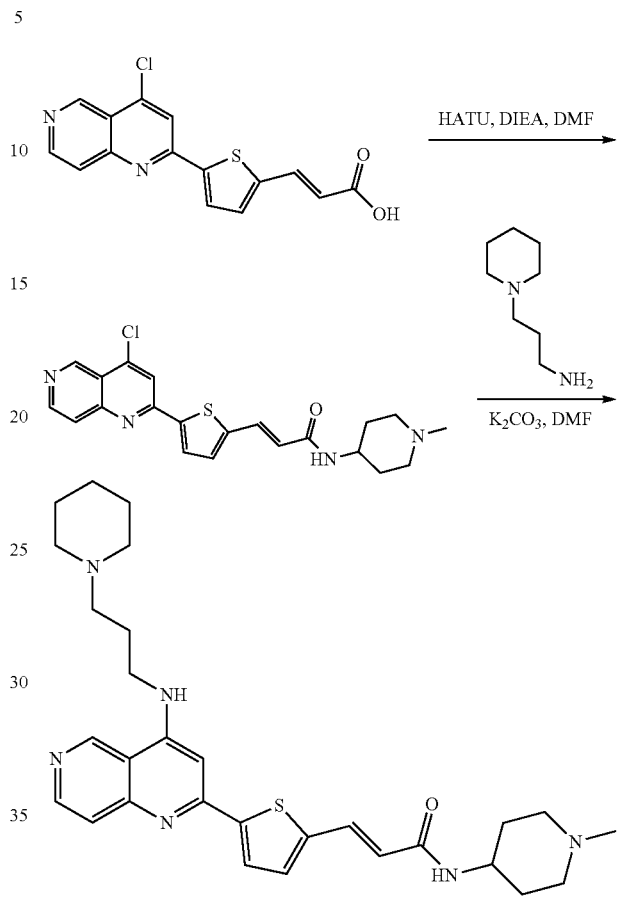

Step 1

The mixture of (E)-3-(5-(4-chloro-1,6-naphthyridin-2-yl)thiophen-2-yl)acrylic acid (100 mg, 0.31 mmol), 1-methylpiperidin-4-amine (72 mg, 0.63 mmol), HATU (145 mg, 0.38 mmol) and DIPEA (82 mg, 0.63 mmol) in DMF (2 mL) was stirred at room temperature overnight. The reaction mixture was quenched with water (5 mL), extracted with EA (5 mL×3), washed with water (10 mL×3) and brine (20 mL), dried over Na$_2$SO$_4$, concentrated and purified by prep-TLC to afford (E)-3-(5-(4-chloro-1,6-naphthyridin-2-yl)thiophen-2-yl)-N-(1-methylpiperidin-4-yl)acrylamide (103 mg, 78.9%) as yellow solid. LC-MS (ESI): 414.8 (M+1)$^+$.

Step 2

To a solution of (E)-3-(5-(4-chloro-1,6-naphthyridin-2-yl)thiophen-2-yl)-N-(1-methylpiperidin-4-yl)acrylamide (103 mg, 0.25 mmol) in DMF (2 mL) were added 3-(piperidin-1-yl)propan-1-amine (46 mg, 0.32 mmol) and K$_2$CO$_3$ (69 mg, 0.5 mmol). After stirred at 70° C. overnight, the reaction mixture was quenched with water (2 mL), extracted with DCM (5 mL×3). The combined organic layer was washed with water (10 mL×3) and brine (10 mL), and dried over Na$_2$SO$_4$. After filtration, the filtrate was concentrated and purified by prep-TLC to afford (E)-N-(1-methylpiperidin-4-yl)-3-(5-(4-(3-(piperidin-1-yl)propylamino)-1,6-naphthyridin-2-yl)thiophen-2-yl)acrylamide (12 mg, 9.3%) as yellow solid. HPLC/UV purity: 100%; LC-MS (ESI): 519.2 (M+1)+. ¹H NMR (METHANOL-d4) δ: 9.35 (s, 1H), 8.51 (d, J=6.0 Hz, 1H), 7.82 (d, J=3.9 Hz, 1H), 7.72-7.62 (m, 2H), 7.34 (d, J=3.9 Hz, 1H), 7.01 (s, 1H), 6.52 (d, J=15.5 Hz, 1H), 3.87-3.75 (m, 1H), 3.50 (t, J=6.8 Hz, 2H), 2.90 (d, J=12.0 Hz, 2H), 2.56-2.45 (m, 6H), 2.32 (s, 3H), 2.20 (t, J=10.8 Hz, 2H), 2.10-1.95 (m, 4H), 1.72-1.58 (m, 7H), 1.58-1.47 (m, 3H).

Example 155: Synthesis of Piperazin-1-yl(6-(4-(3-(piperidin-1-yl)propylamino)-1,6-naphthyridin-2-yl)benzo[d]thiazol-2-yl)methanone

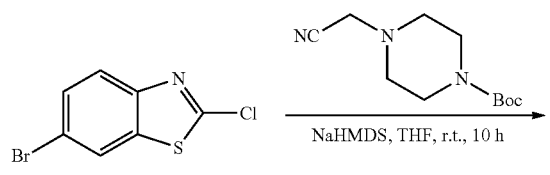

Steps 1 and 2

NaHMDS (4.9 mL, 2M) was added to a solution of 6-bromo-2-chlorobenzo[d]thiazole (1 g, 4.0 mmol) and tert-butyl 4-(cyanomethyl)piperazine-1-carboxylate (1 g, 4.4 mmol) in dry THF (20 mL) under Ar atmosphere at 0° C. The mixture was stirred overnight at room temperature. Then NiO₂·H₂O (1.77 g, 16.1 mmol) was added and the resulting mixture was stirred for another 10 hrs at room temperature. Solid was filtered off and washed with MeOH. The combined solution was concentrated and purified by silica gel chromatography (silica gel, eluting with 10% EA in PE) to afford tert-butyl 4-(6-bromobenzo[d]thiazole-2-carbonyl)piperazine-1-carboxylate (0.6 g, 58.8%) as white solid. LC-MS (ESI): 426.5 (M+1)+.

Steps 3 and 4

The mixture of tert-butyl 4-(6-bromobenzo[d]thiazole-2-carbonyl)piperazine-1-carboxylate (300 mg, 0.7 mmol), 4,4,4',4',5,5,5',5'-octamethyl-2,2'-bi(1,3,2-dioxaborolane) (232 mg, 0.91 mmol), Pd(dppf)Cl₂ (51 mg, 0.07 mmol) and KOAC (207 mg, 2.1 mmol) in 1,4-dioxane (5 mL) was heated to 100° C. and held for 18 hrs under N₂ atmosphere. The mixture was cooled to room temperature, and then 2-chloro-N-(3-(piperidin-1-yl)propyl)-1,6-naphthyridin-4- amine (100 mg, 0.32 mmol), Pd(PPh$_3$)$_4$ (285 mg, 0.25 mmol) and Na$_2$CO$_3$ (105 mg, 0.99 mmol) in 1,4-dioxane (5 mL) and H$_2$O (1 mL) was added. The resulting mixture was heated to 110° C. and held for 18 hrs under N$_2$ atmosphere. The mixture was concentrated under reduced pressure and the residue was purified by flash column chromatography (silica gel, eluting with CH$_2$Cl$_2$ to 10% Methanol/CH$_2$Cl$_2$) to afford tert-butyl 4-(6-(4-(3-(piperidin-1-yl)propylamino)-1,6-naphthyridin-2-yl)benzo[d]thiazole-2-carbonyl)piperazine-1-carboxylate (30 mg, 6.9%). LC-MS (ESI): 616.7 (M+1)$^+$.

Step 5

To a solution of tert-butyl 4-(6-(4-(3-(piperidin-1-yl)propylamino)-1,6-naphthyridin-2-yl)benzo[d]thiazole-2-carbonyl)piperazine-1-carboxylate (30 mg, 0.05 mmol) in DCM was added TFA (0.5 mL). After stirred at room temperature for 2 h, the reaction mixture was concentrated and purified by prep-TLC to afford piperazin-1-yl(6-(4-(3-(piperidin-1-yl)propylamino)-1,6-naphthyridin-2-yl)benzo[d]thiazol-2-yl)methanone (14 mg, 56%) as yellow solid. HPLC/UV purity: 98%; LC-MS (ESI): 516.2 (M+1)$^+$. $^1$H NMR (METHANOL-d4) δ: 9.75 (s, 1H), 8.87 (d, J=5.2 Hz, 2H), 8.39 (d, J=8.7 Hz, 1H), 8.26 (d, J=8.7, 1.7 Hz, 1H), 7.94 (d, J=6.0 Hz, 1H), 7.36 (s, 1H), 3.86 (t, J=6.9 Hz, 2H), 3.61 (d, J=11.8 Hz, 2H), 3.50-3.43 (m, 4H), 3.40-3.34 (m, 6H), 2.98 (t, J=11.7 Hz, 2H), 2.40-2.25 (m, 2H), 1.98-1.95 (m, 2H), 1.85-1.77 (m, 3H), 1.59-1.52 (m, 1H).

Example 156: Synthesis of Morpholino(6-(4-(3-(piperidin-1-yl)propylamino)-1,6-naphthyridin-2-yl)benzo[d]thiazol-2-yl)methanone

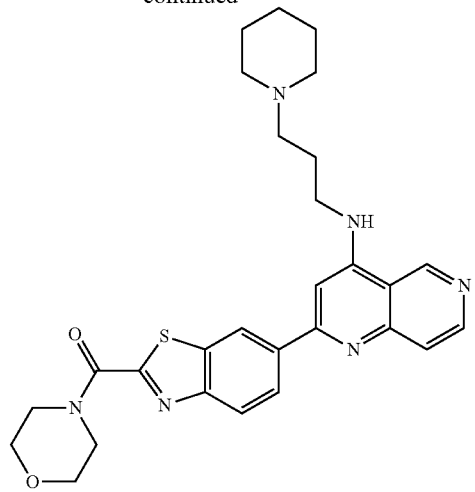

Morpholino(6-(4,4,5,5-tetramethyl-1,3,2-dioxaborolan-2-yl)benzo[d]thiazol-2-yl)methanone was synthesized in a similar fashion as Example 155, Steps 1-3.

A 10-mL microwave vial was charged with morpholino (6-(4,4,5,5-tetramethyl-1,3,2-dioxaborolan-2-yl)benzo[d]thiazol-2-yl)methanone (147 mg, 0.39 mmol), 2-chloro-N-(3-(piperidin-1-yl)propyl)-1,6-naphthyridin-4-amine (100 mg, 0.33 mmol), Pd(PPh$_3$)$_4$ (189 mg, 0.16 mmol), Na$_2$CO$_3$ (69 mg, 0.65 mmol), 1,4-dioxane (5 mL) and H$_2$O (1 mL). The brown solution was heated in a Biotage Initiator Eight Microwave Reactor at 110° C. for 1 h. The reaction mixture was concentrated and purified by silica gel chromatography (silica gel, eluting with 10% methanol in DCM) to give morpholino(6-(4-(3-(piperidin-1-yl)propylamino)-1,6-naphthyridin-2-yl)benzo[d]thiazol-2-yl)methanone as white solid (11.6 mg, 5.7%). HPLC/UV purity: 96%; LC-MS (ESI): 517.2 (M+1)$^+$ 0.1H NMR (METHANOL-d4) δ 9.36 (s, 1H), 8.66 (s, 1H), 8.47 (s, 1H), 8.19 (d, J=7.8 Hz, 1H), 8.10 (d, J=6.6 Hz, 1H), 7.69 (s, 1H), 7.04 (s, 1H), 4.30-4.37 (m, 2H), 3.73-3.79 (m, 6H), 3.52-3.56 (m, 2H), 2.92-2.95 (m, 6H), 2.05-2.09 (m, 2H), 1.68-1.70 (m, 4H), 1.48-1.52 (m, 2H).

Example 157: Synthesis of N,N-Diethyl-6-(4-(3-(piperidin-1-yl)propylamino)-1,6-naphthyridin-2-yl)benzo[d]oxazole-2-carboxamide

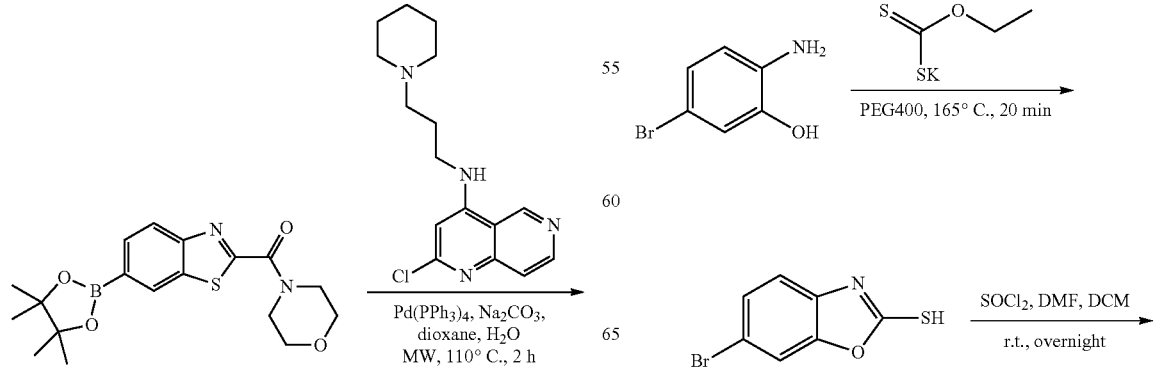

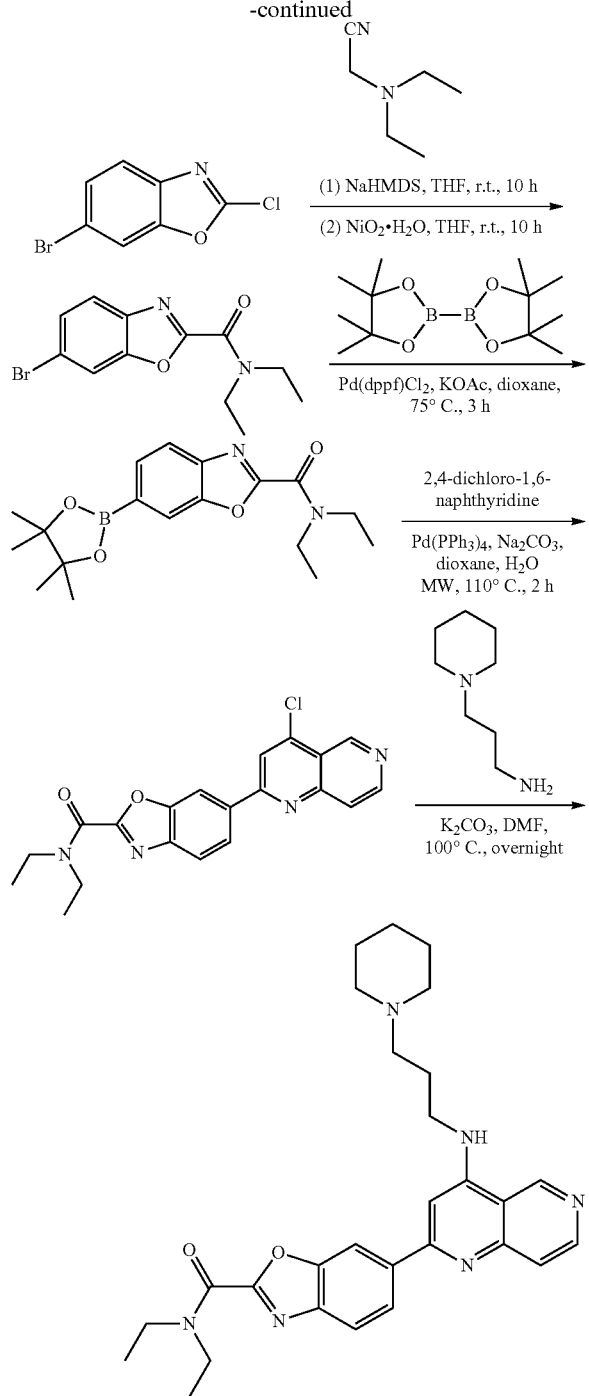

Step 1

2-Amino-5-bromophenol (2.00 g, 10.6 mmol) and potassium o-ethyldithiocarbonate (4.26 g, 26.6 mmol) were mixed in a 25 mL microwave vial with 12 mL of PEG400. The reaction mixture was stirred at 165° C. for 20 minutes in a Biotage Initiator Eight Microwave Reactor. The reaction mixture was diluted with water (500 mL), acidified to pH=3~4 with CH$_3$COOH. The precipitate was filtered and air-dried to give crude 6-Bromobenzo[d]oxazole-2-thiol (2.3 g) as powder, which can be used in the next step without further purification.

Step 2

SOCl$_2$ (5.6 mL) and DMF (2.8 mL) were added to a stirred solution of 6-bromobenzo[d]oxazole-2-thiol (2.30 g, 10 mmol) in DCM (30 mL) at 0° C. The reaction mixture was stirred till the solution was clear. Then the reaction mixture was stirred at room temperature overnight. After completion of the reaction, the mixture was poured into cold water (56 mL), neutralized with Na$_2$CO$_3$ (solid) carefully over 10 minutes and extracted with DCM. The combined organic layers were washed with brine, dried over Na$_2$SO$_4$ and concentrated. The crude product was purified by silica gel chromatography (silica gel, eluting with PE) to afford 6-bromo-2-chlorobenzo[d]oxazole (1.46 g, 62.9%) as white solid. LC-MS (ESI): 232.0 (M+1)$^+$.

Step 3

NaHMDS (6 mL, 12 mmol) was added to a solution of 6-bromo-2-chlorobenzo[d]oxazole (1.16 g, 4.99 mmol) and 2-(diethylamino)acetonitrile (0.84 mL, 6.49 mmol) in dry THF (50 mL) under Ar atmosphere at 0° C. The mixture was warmed to room temperature and stirred overnight. Then NiO$_2$·H$_2$O (2.2 g, 20 mmol) was added and the resulting mixture was stirred for another 10 hrs at room temperature. Insoluble solid was filtered off and washed with MeOH. The filtrate was concentrated and purified by silica gel chromatography (silica gel, eluting with 10% EA in PE) to afford 6-bromo-N,N-diethylbenzo[d]oxazole-2-carboxamide (0.57 g, 38.5%) as white solid. LC-MS (ESI): 297.0 (M+1)$^+$.

Step 4

The mixture of 6-bromo-N,N-diethylbenzo[d]oxazole-2-carboxamide (0.63 g, 2.11 mmol), 4,4,4',4',5,5,5',5'-octamethyl-2,2'-bi(1,3,2-dioxaborolane) (3.2 g, 12.66 mmol), Pd(dppf)Cl$_2$ (0.17 g, 0.211 mmol), KOAc (0.41 g, 4.22 mmol) and 1,4-dioxane (20 mL) was stirred at 75° C. under Ar for 3 hrs. The mixture was cooled to room temperature and filtered. The organic phase was concentrated and purified by silica gel chromatography (silica gel, eluting with 10% EA in PE) to afford N,N-diethyl-6-(4,4,5,5-tetramethyl-1,3,2-dioxaborolan-2-yl)benzo[d]oxazole-2-carboxamide (0.63 g, 86.3%) as white solid. LC-MS (ESI): 345.2 (M+1)$^+$.

Step 5

A 10-mL microwave vial was charged with N,N-diethyl-6-(4,4,5,5-tetramethyl-1,3,2-dioxaborolan-2-yl)benzo[d]oxazole-2-carboxamide (100 mg, 0.29 mmol), 2,4-dichloro-1,6-naphthyridine (52 mg, 0.26 mmol), Pd(PPh$_3$)$_4$ (168 mg, 0.15 mmol), Na$_2$CO$_3$ (62 mg, 0.58 mmol), 1,4-dioxane (5 mL) and H$_2$O (1 mL). The brown solution was heated in a Biotage Initiator Eight Microwave Reactor at 110° C. for 1 h. The reaction mixture was concentrated and purified by silica gel chromatography (silica gel, eluting with 10% methanol in DCM) to give 6-(4-chloro-1,6-naphthyridin-2-yl)-N,N-diethylbenzo[d]oxazole-2-carboxamide as white solid (90 mg, 81.4%). HPLC/UV purity: 96%; LC-MS (ESI): 382.1 (M+1)$^+$.

Step 6

The mixture of 6-(4-chloro-1,6-naphthyridin-2-yl)-N,N-diethylbenzo[d]oxazole-2-carboxamide (90 mg, 0.24 mmol), 3-(piperidin-1-yl)propan-1-amine (45 mg, 0.32 mmol), and K₂CO₃ (72 mg, 0.52 mmol) in DMF (2 mL) was stirred at 70° C. for 8 hrs. The reaction mixture was filtered, concentrated and purified by TLC to give N,N-Diethyl-6-(4-(3-(piperidin-1-yl)propylamino)-1,6-naphthyridin-2-yl)benzo[d]oxazole-2-carboxamide (10.2 mg, 8.86%) as white solid. HPLC/UV purity: 98%; LC-MS (ESI): 486.8 (M+1)⁺. ¹H NMR (METHANOL-d4) δ: 9.78 (s, 1H), 8.89 (d, J=6.0 Hz, 1H), 8.49 (s, 1H), 8.14 (s, 2H), 7.96 (d, J=6.0 Hz, 1H), 7.35 (s, 1H), 3.99-3.82 (m, 4H), 3.70-3.64 (m, 2H), 3.61 (d, J=12.7 Hz, 3H), 2.98 (t, J=12.3 Hz, 2H), 2.40-2.26 (m, 2H), 1.99-1.95 (m, 2H), 1.92-1.72 (m, 4H), 1.60-1.49 (m, 1H), 1.40 (t, J=7.0 Hz, 3H), 1.33 (t, J=7.1 Hz, 3H).

Example 158: Synthesis of N,N-Diethyl-6-(4-(3-(piperidin-1-yl)propylamino)-1,6-naphthyridin-2-yl)benzo[d]thiazole-2-carboxamide

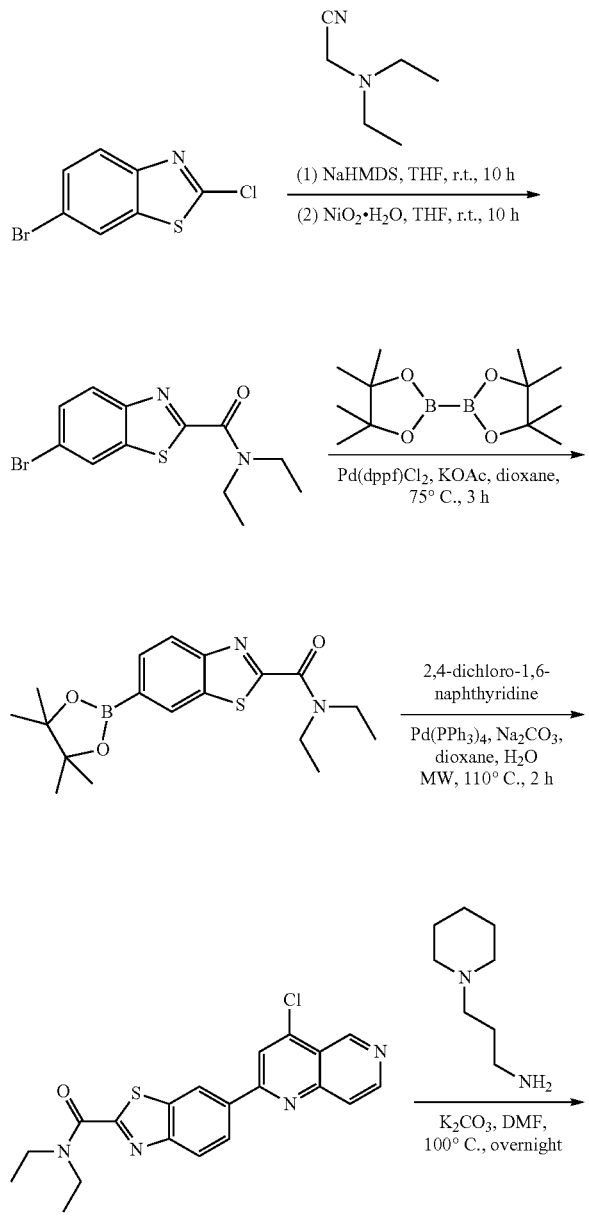

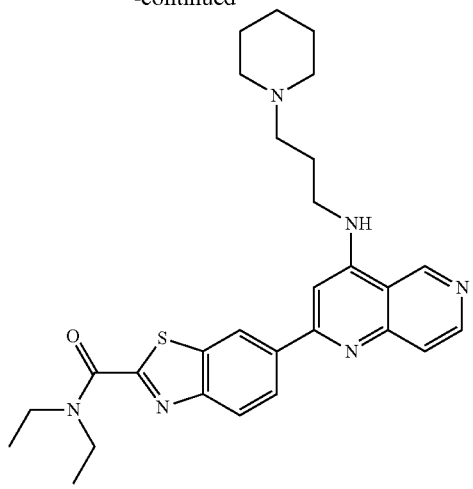

Step 1

NaHMDS (2.9 mL, 5.8 mmol) was added to a solution of 6-bromo-2-chlorobenzo[d]thiazole (0.60 g, 2.41 mmol) and 2-(diethylamino)acetonitrile (0.41 mL, 3.14 mmol) in dry THF (40 mL) under Ar atmosphere at 0° C. The mixture was warmed to room temperature and stirred overnight. Then NiO₂·H₂O (1.06 g, 9.7 mmol) was added and the resulting mixture was stirred for another 10 h. Insoluble solid was filtered off and the filtrate was concentrated. The residue was purified by silica gel chromatography (silica gel, eluting with 10% EA in PE) to afford 6-bromo-N,N-diethylbenzo[d]thiazole-2-carboxamide (0.46 g, 60.5%) as white solid. LC-MS (ESI): 313.0 (M+1)⁺.

Step 2

The mixture of 6-bromo-N,N-diethylbenzo[d]thiazole-2-carboxamide (0.26 g, 0.84 mmol), 4,4,4',4',5,5,5',5'-octamethyl-2,2'-bi(1,3,2-dioxaborolane) (1.28 g, 5.04 mmol), Pd(dppf)Cl₂ (69 mg, 0.08 mmol), KOAc (0.16 g, 1.68 mmol) and 1,4-dioxane (10 mL) was stirred at 75° C. under Ar₂ for 3 hrs. The mixture was cooled to room temperature and filtered. The organic phase was concentrated and purified by silica gel chromatography (silica gel, eluting with 10% EA in PE) to afford N,N-diethyl-6-(4,4,5,5-tetramethyl-1,3,2-dioxaborolan-2-yl)benzo[d]thiazole-2-carboxamide (0.42 g, 28.6%) as white solid. LC-MS (ESI): 361.2 (M+1)⁺.

Step 3

A 20-mL microwave vial was charged with N,N-diethyl-6-(4,4,5,5-tetramethyl-1,3,2-dioxaborolan-2-yl)benzo[d]thiazole-2-carboxamide (213.4 mg, 0.59 mmol), 2,4-dichloro-1,6-naphthyridine (94.3 mg, 0.47 mmol), Pd(PPh₃)₄ (274 mg, 0.24 mmol), Na₂CO₃ (100 mg, 0.95 mmol), 1,4-dioxane (10 mL) and H₂O (2 mL). The resulting brown solution is stirred at 110° C. for 2 hrs in a Biotage Initiator Eight Microwave Reactor. The resulting solutions were concentrated and purified via silica gel chromatography (silica gel, eluting with 10% methanol in DCM) to give 6-(4-chloro-1,6-naphthyridin-2-yl)-N,N-diethylbenzo[d]thiazole-2-carboxamide (50 mg, 26.7%) as yellow solid. LC-MS (ESI): 397.3 (M+1)⁺.

Step 4

To a solution of 6-(4-chloro-1,6-naphthyridin-2-yl)-N,N-diethylbenzo[d]thiazole-2-carboxamide (308.8 mg, 0.778 mmol) in DMF (5 mL) were added 3-(piperidin-1-yl)propan-1-amine (0.247 mL, 1.556 mmol) and $K_2CO_3$ (430.1 mg, 3.11 mmol). After stirred at 100° C. overnight, the reaction mixture was quenched with water (2 mL), extracted with DCM (5 mL×3). The combined organic layers was washed with water (10 mL×3) and brine (10 mL), and dried over $Na_2SO_4$. After filtration, the filtrate was concentrated and purified by prep-TLC to afford N,N-diethyl-6-(4-(3-(piperidin-1-yl)propylamino)-1,6-naphthyridin-2-yl)benzo[d]thiazole-2-carboxamide (92.2 mg, 23.5%) as yellow solid. HPLC/UV purity: 100%; LC-MS (ESI): 503.3 $(M+1)^+$. $^1$H NMR (METHANOL-d4) δ: 9.77 (s, 1H), 8.90 (d, J=6.0 Hz, 1H), 8.82 (s, 1H), 8.38 (d, J=8.5, 5.7 Hz, 1H), 8.21 (d, J=8.6, 1.8 Hz, 1H), 7.95 (d, J=6.0 Hz, 1H), 7.36 (s, 1H), 4.22-4.04 (m, 2H), 3.88 (t, J=6.9 Hz, 2H), 3.65 (dt, J=21.6, 10.6 Hz, 4H), 3.36-3.34 (m, 2H), 2.97 (dd, J=25.5, 13.1 Hz, 2H), 2.42-2.25 (m, 2H), 1.97 (d, J=15.2 Hz, 2H), 1.82 (dt, J=26.7, 13.2 Hz, 3H), 1.59-1.50 (m, 1H), 1.41 (t, J=6.9 Hz, 3H), 1.33 (t, J=7.1 Hz, 3H).

Pharmaceutical Compositions

Example A-1: Parenteral Pharmaceutical Composition

To prepare a parenteral pharmaceutical composition suitable for administration by injection (subcutaneous, intravenous), 1-1000 mg of a water-soluble salt of a compound described herein, or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection Example A-2: Oral Solution To prepare a pharmaceutical composition for oral delivery, a sufficient amount of a compound described herein, or a pharmaceutically acceptable salt thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound described herein, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 1-1000 mg of a compound described herein, or a pharmaceutically acceptable salt thereof, is mixed with starch or other suitable powder blend. The mixture is incorporated into an oral dosage unit such as a hard gelatin capsule, which is suitable for oral administration.

In another embodiment, 1-1000 mg of a compound described herein, or a pharmaceutically acceptable salt thereof, is placed into Size 4 capsule, or size 1 capsule (hypromellose or hard gelatin) and the capsule is closed.

Example A-5: Topical Gel Composition

To prepare a pharmaceutical topical gel composition, a compound described herein, or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

Biology Examples

Example B-1: Enzyme Assay of Inhibition of LMPTP-A

Phosphatase assays were performed in buffer containing 50 mM Bis-Tris, pH 6.0, 1 mM DTT and 0.01% Triton X-100 at 37° C. For assays conducted with 3-O-methylfluorescein phosphate (OMFP) as substrate, fluorescence was monitored continuously at λex=485 and λem=525 nm. For assays conducted with para-nitrophenylphosphate (pNPP) as substrate, the reaction was stopped by addition of 2× reaction volume of 1 M NaOH, and absorbance was measured at 405 nm. $IC_{50}$ values of compounds of Formula (I), (II), (III), or (IV) were determined from plots of inhibitor concentration versus percentage of enzyme activity. For inhibitor selectivity assays, each PTP was incubated with either 0.4 mM OMFP or 5 mM pNPP in the presence of 40 μM compound or DMSO. Equal units of enzyme activity, comparable to the activity of 10 nM human LMPTP-A, were used. For the inhibitor reversibility assay, 50 nM human LMPTP-A was pre-incubated with 10 μM of compound of Formula (I), (II), (III), or (IV) or DMSO for 5 min. The enzyme was diluted 100× in phosphatase assay buffer containing 0.4 mM OMFP and fluorescence was measured at the indicated time points.

Representative data for exemplary compounds disclosed herein is presented in Table 6.

TABLE 6

| Name | $IC_{50}$ |
|---|---|
| N,N-diethyl-4-(4-(3-(piperidin-1-yl)propylamino)-1,6-naphthyridin-2-yl)benzamide | A |
| N-(2-(dimethylamino)ethyl)-1-methyl-5-(4-((3-(piperidin-1-yl)propyl)amino)-1,6-naphthyridin-2-yl)-1H-indole-2-carboxamide | A |
| 1-methyl-N-(1-methylpiperidin-4-yl)-5-(4-((3-(piperidin-1-yl)propyl)amino)-1,6-naphthyridin-2-yl)-1H-indole-2-carboxamide | A |
| 1-methyl-5-(4-((3-(piperidin-1-yl)propyl)amino)-1,6-naphthyridin-2-yl)-N-(piperidin-4-yl)-1H-indole-2-carboxamide | A |
| ethyl 1-methyl-5-(4-((3-(piperidin-1-yl)propyl)amino)-1,6-naphthyridin-2-yl)-1H-indole-2-carboxylate | A |
| 4-(4-((3-(piperidin-1-yl)propyl)amino)-1,6-naphthyridin-2-yl)benzoic acid | A |
| 4-(4-((3-(piperidin-1-yl)propyl)amino)-1,6-naphthyridin-2-yl)-N-(piperidin-4-yl)benzamide | A |
| 4-(4-((3-(piperidin-1-yl)propyl)amino)-1,6-naphthyridin-2-yl)-N-(2-(pyridin-4-yl)ethyl)benzamide | A |
| N-(2-(dimethylamino)ethyl)-4-(4-((3-(piperidin-1-yl)propyl)amino)-1,6-naphthyridin-2-yl)benzamide | A |
| 1-methyl-N-(3-(4-methylpiperazin-1-yl)propyl)-5-(4-((3-(piperidin-1-yl)propyl)amino)-1,6-naphthyridin-2-yl)-1H-indole-2-carboxamide | A |

TABLE 6-continued

| Name | IC$_{50}$ |
|---|---|
| 1-methyl-5-(4-((3-(piperidin-1-yl)propyl)amino)-1,6-naphthyridin-2-yl)-N-(2-(pyridin-4-yl)ethyl)-1H-indole-2-carboxamide | A |
| 1-methyl-5-(4-((3-(piperidin-1-yl)propyl)amino)-1,6-naphthyridin-2-yl)-N-(tetrahydro-2H-pyran-4-yl)-1H-indole-2-carboxamide | A |
| N-(1,1-dioxidotetrahydro-2H-thiopyran-4-yl)-1-methyl-5-(4-((3-(piperidin-1-yl)propyl)amino)-1,6-naphthyridin-2-yl)-1H-indole-2-carboxamide | A |
| N,N-diethyl-4-(4-((3-(piperidin-1-yl)propyl)amino)-1,6-naphthyridin-2-yl)-3-(trifluoromethyl)benzamide | A |
| 4-(4-((3-(piperidin-1-yl)propyl)amino)-1,6-naphthyridin-2-yl)-N-(piperidin-4-yl)-3-(trifluoromethyl)benzamide | B |
| 1-methyl-5-(4-(3-(piperidin-1-yl)propylamino)-1,6-naphthyridin-2-yl)-N-(tetrahydro-2H-thiopyran-4-yl)-1H-indole-2-carboxamide | A |
| 1-methyl-N-(1-methylpiperidin-4-yl)-5-(4-(propylamino)-1,6-naphthyridin-2-yl)-1H-indole-2-carboxamide | A |
| 1-methyl-5-(4-(methylamino)-1,6-naphthyridin-2-yl)-N-(1-methylpiperidin-4-yl)-1H-indole-2-carboxamide | B |
| 5-(4-(ethylamino)-1,6-naphthyridin-2-yl)-1-methyl-N-(1-methylpiperidin-4-yl)-1H-indole-2-carboxamide | A |
| 1-methyl-N-(1-methylpiperidin-4-yl)-5-(4-((4-(pyrrolidin-1-ylmethyl)phenyl)amino)-1,6-naphthyridin-2-yl)-1H-indole-2-carboxamide | A |
| N-(3-(piperidin-1-yl)propyl)-5-(4-((3-(piperidin-1-yl)propyl)amino)-1,6-naphthyridin-2-yl)-1H-benzo[d]imidazole-2-carboxamide | A |
| methyl 3-carbamoyl-4-(4-((3-(piperidin-1-yl)propyl)amino)-1,6-naphthyridin-2-yl)benzoate | B |
| 5-(4-methoxy-1,6-naphthyridin-2-yl)-1-methyl-N-(1-methylpiperidin-4-yl)-1H-indole-2-carboxamide | C |
| 3-cyano-N,N-diethyl-4-(4-((3-(piperidin-1-yl)propyl)amino)-1,6-naphthyridin-2-yl)benzamide | B |
| N1,N1-diethyl-4-(4-((3-(piperidin-1-yl)propyl)amino)-1,6-naphthyridin-2-yl)isophthalamide | B |
| 1-methyl-5-(4-(methylamino)-1,6-naphthyridin-2-yl)-1H-indole-2-carboxamide | B |
| 3-cyano-N-(1-methylpiperidin-4-yl)-4-(4-((3-(piperidin-1-yl)propyl)amino)-1,6-naphthyridin-2-yl)benzamide | B |
| 1-methyl-N-(1-methylpiperidin-4-yl)-5-(4-(3-(piperidin-1-yl)propoxy)-1,6-naphthyridin-2-yl)-1H-indole-2-carboxamide | B |
| 5-(4-((3-(piperidin-1-yl)propyl)amino)-1,6-naphthyridin-2-yl)-N-(piperidin-4-yl)-1H-benzo[d]imidazole-2-carboxamide | A |
| 5-(4-(methylamino)-1,6-naphthyridin-2-yl)-N-(3-(piperidin-1-yl)propyl)-1H-benzo[d]imidazole-2-carboxamide | B |
| 5-(4-(ethylamino)-1,6-naphthyridin-2-yl)-N-(3-(piperidin-1-yl)propyl)-1H-benzo[d]imidazole-2-carboxamide | B |
| N-(2-(dimethylamino)ethyl)-5-(4-(3-(piperidin-1-yl)propylamino)-1,6-naphthyridin-2-yl)-1H-benzo[d]imidazole-2-carboxamide | A |
| N-(3-(4-methylpiperazin-1-yl)propyl)-5-(4-((3-(piperidin-1-yl)propyl)amino)-1,6-naphthyridin-2-yl)-1H-benzo[d]imidazole-2-carboxamide | A |
| piperazin-1-yl(5-(4-((3-(piperidin-1-yl)propyl)amino)-1,6-naphthyridin-2-yl)-1H-benzo[d]imidazol-2-yl)methanone | A |
| N,N-diethyl-5-(4-((3-(piperidin-1-yl)propyl)amino)-1,6-naphthyridin-2-yl)-1H-benzo[d]imidazole-2-carboxamide | B |
| (1-ethyl-5-(4-((3-(piperidin-1-yl)propyl)amino)-1,6-naphthyridin-2-yl)-1H-benzo[d]imidazol-2-yl)(4-ethylpiperazin-1-yl)methanone | A |
| (4-ethylpiperazin-1-yl)(5-(4-((3-(piperidin-1-yl)propyl)amino)-1,6-naphthyridin-2-yl)-1H-benzo[d]imidazol-2-yl)methanone | A |
| N-(3-(piperidin-1-yl)propyl)-5-(4-(3-(piperidin-1-yl)propylamino)-1,6-naphthyridin-2-yl)benzo[b]thiophene-2-carboxamide | B |
| N,N-diethyl-4-(4-(3-(piperidin-1-yl)propylamino)-1,5-naphthyridin-2-yl)benzamide | C |
| N,N-diethyl-4-(4-(3-(piperidin-1-yl)propylamino)-1,7-naphthyridin-2-yl)benzamide | C |
| N,N-diethyl-4-(2-(3-(piperidin-1-yl)propylamino)-1,8-naphthyridin-4-yl)benzamide | C |
| N,N-diethyl-4-(4-(3-(piperidin-1-yl)propylamino)-1,8-naphthyridin-2-yl)benzamide | C |
| N,N-Diethyl-4-(4-((3-morpholinopropyl)amino)-1,6-naphthyridin-2-yl)benzamide | B |
| N,N-Diethyl-4-(4-((2-(piperidin-1-yl)ethyl)amino)-1,6-naphthyridin-2-yl)benzamide | B |
| N,N-Diethyl-4-(4-((3-(piperazin-1-yl)propyl)amino)-1,6-naphthyridin-2-yl)benzamide | B |
| N,N-Diethyl-4-(4-((3-(4-(methylsulfonyl)piperazin-1-yl)propyl)amino)-1,6-naphthyridin-2-yl)benzamide | B |
| N,N-Diethyl-4-(4-((1-methylpiperidin-4-yl)amino)-1,6-naphthyridin-2-yl)benzamide | B |
| 4-(4-((2-(Dimethylamino)ethyl)amino)-1,6-naphthyridin-2-yl)-N,N-diethylbenzamide | B |
| N,N-diethyl-4-(4-(3-(4-methylpiperazin-1-yl)propylamino)-1,6-naphthyridin-2-yl)benzamide | B |
| N,N-diethyl-4-(4-(2-morpholinoethylamino)-1,6-naphthyridin-2-yl)benzamide | B |
| N,N-diethyl-4-(4-(2-(4-methylpiperazin-1-yl)ethylamino)-1,6-naphthyridin-2-yl)benzamide | B |
| N,N-diethyl-4-(4-(tetrahydro-2H-pyran-4-ylamino)-1,6-naphthyridin-2-yl)benzamide | B |
| N,N-diethyl-4-(4-(2-(piperazin-1-yl)ethylamino)-1,6-naphthyridin-2-yl)benzamide | B |
| N,N-diethyl-4-(4-(2-(4-(methylsulfonyl)piperazin-1-yl)ethylamino)-1,6-naphthyridin-2-yl)benzamide | B |
| N,N-Diethyl-4-(4-(4-methoxyphenylamino)-1,6-naphthyridin-2-yl)benzamide | B |
| 4-(4-((4-(Dimethylamino)phenylamino)-1,6-naphthyridin-2-yl)-N,N-diethylbenzamide | B |
| 4-(4-(4-((Dimethylamino)methyl)phenylamino)-1,6-naphthyridin-2-yl)-N,N-diethylbenzamide | B |
| N,N-Diethyl-4-(4-(4-(2-methoxyethylamino)phenylamino)-1,6-naphthyridin-2-yl)benzamide | B |
| 4-(4-((2-(1,1-Dioxidothiomorpholino)ethyl)amino)-1,6-naphthyridin-2-yl)-N,N-diethylbenzamide | B |
| 4-(4-((3-(1,1-Dioxidothiomorpholino)propyl)amino)-1,6-naphthyridin-2-yl)-N,N-diethylbenzamide | B |
| N,N-Diethyl-4-(4-(1-methylpyrrolidin-3-ylamino)-1,6-naphthyridin-2-yl)benzamide | B |
| N,N-Diethyl-4-(4-(piperidin-4-ylamino)-1,6-naphthyridin-2-yl)benzamide | B |
| N-(1-Methylpiperidin-4-yl)-4-(4-((1-methylpyrrolidin-3-yl)amino)-1,6-naphthyridin-2-yl)benzamide | B |
| 4-(4-((1-Methylpyrrolidin-3-yl)amino)-1,6-naphthyridin-2-yl)-N-(3-(piperidin-1-yl)propyl)benzamide | B |
| N-(3-(Piperidin-1-yl)propyl)-4-(4-(piperidin-4-ylamino)-1,6-naphthyridin-2-yl)benzamide | B |
| N-(1-Methylpiperidin-4-yl)-4-(4-(piperidin-4-ylamino)-1,6-naphthyridin-2-yl)benzamide | B |
| N,N-diethyl-4-(4-(pyrrolidin-3-ylamino)-1,6-naphthyridin-2-yl)benzamide | B |
| N-(3-(Piperidin-1-yl)propyl)-4-(4-(pyrrolidin-3-ylamino)-1,6-naphthyridin-2-yl)benzamide | B |
| N-(1-Methylpiperidin-4-yl)-4-(4-(pyrrolidin-3-ylamino)-1,6-naphthyridin-2-yl)benzamide | B |
| N-(1-Methylpiperidin-4-yl)-4-(4-((1-methylpiperidin-4-yl)amino)-1,6-naphthyridin-2-yl)benzamide | B |
| N-(3-(Piperidin-1-yl)propyl)-4-(4-((tetrahydro-2H-pyran-4-yl)amino)-1,6-naphthyridin-2-yl)benzamide | B |
| N-(3-(Piperidin-1-yl)propyl)-4-(4-((pyridin-4-ylmethyl)amino)-1,6-naphthyridin-2-yl)benzamide | B |
| N-(1-Methylpiperidin-4-yl)-4-(4-((tetrahydro-2H-pyran-4-yl)amino)-1,6-naphthyridin-2-yl)benzamide | A |
| 4-(8-Bromo-4-((3-(piperidin-1-yl)propyl)amino)-1,6-naphthyridin-2-yl)-N,N-diethylbenzamide | C |
| 4-(8-Bromo-4-((3-(piperidin-1-yl)propyl)amino)-1,6-naphthyridin-2-yl)-N-(1-methylpiperidin-4-yl)benzamide | C |
| N,N-Diethyl-4-(8-methyl-4-((3-(piperidin-1-yl)propyl)amino)-1,6-naphthyridin-2-yl)benzamide | C |
| 4-(8-Methyl-4-((3-(piperidin-1-yl)propyl)amino)-1,6-naphthyridin-2-yl)-N-(1-methylpiperidin-4-yl)benzamide | C |
| 4-(8-Methyl-4-((3-(piperidin-1-yl)propyl)amino)-1,6-naphthyridin-2-yl)-N-(3-(piperidin-1-yl)propyl)benzamide | C |
| N-(3-(piperidin-1-yl)propyl)-5-(4-((3-(piperidin-1-yl)propyl)amino)-1,6-naphthyridin-2-yl)picolinamide | C |
| N-(1-methylpiperidin-4-yl)-5-(4-((3-(piperidin-1-yl)propyl)amino)-1,6-naphthyridin-2-yl)picolinamide | B |
| 1-methyl-5-(4-(4-(piperidin-1-ylmethyl)benzylamino)-1,6-naphthyridin-2-yl)-N-(piperidin-4-yl)-1H-indole-2-carboxamide | A |
| 1-methyl-N-(1-methylpiperidin-4-yl)-5-(4-(4-(piperidin-1-ylmethyl)benzylamino)-1,6-naphthyridin-2-yl)-1H-indole-2-carboxamide | A |
| (1-methyl-5-(4-(4-(piperidin-1-ylmethyl)benzylamino)-1,6-naphthyridin-2-yl)-1H-indol-2-yl)(4-methylpiperazin-1-yl)methanone | A |
| 1-methyl-N-((1-methylpiperidin-4-yl)methyl)-5-(4-(4-(piperidin-1-ylmethyl)benzylamino)-1,6-naphthyridin-2-yl)-1H-indole-2-carboxamide | A |

TABLE 6-continued

| Name | IC$_{50}$ |
|---|---|
| 1-methyl-5-(4-(methyl(3-(piperidin-1-yl)propyl)amino)-1,6-naphthyridin-2-yl)-N-(1-methylpiperidin-4-yl)-1H-indole-2-carboxamide | B |
| 1-Methyl-N-(1-methylpiperidin-4-yl)-5-(4-(4-(piperidin-1-yl)butan-2-ylamino)-1,6-naphthyridin-2-yl)-1H-indole-2-carboxamide | B |
| 1-Methyl-N-(1-methylpiperidin-4-yl)-5-(4-(((1-methylpiperidin-4-yl)amino)-1,6-naphthyridin-2-yl)-1H-indole-2-carboxamide | A |
| (1-Methyl-5-(4-((1-methylpiperidin-4-yl)amino)-1,6-naphthyridin-2-yl)-1H-indol-2-yl)(4-methylpiperazin-1-yl)methanone | A |
| 1-Methyl-5-(4-((1-methylpiperidin-4-yl)amino)-1,6-naphthyridin-2-yl)-N-((1-methylpiperidin-4-yl)methyl)-1H-indole-2-carboxamide | A |
| 1-Methyl-5-(4-((1-methylpiperidin-4-yl)amino)-1,6-naphthyridin-2-yl)-N-(3-(piperidin-1-yl)propyl)-1H-indole-2-carboxamide | B |
| N-(1-Methylpiperidin-4-yl)-6-(4-(3-(piperidin-1-yl)propylamino)-1,6-naphthyridin-2-yl)-1H-indole-2-carboxamide | B |
| N-(3-(Piperidin-1-yl)propyl)-6-(4-(3-(piperidin-1-yl)propylamino)-1,6-naphthyridin-2-yl)-1H-indole-2-carboxamide | B |
| N-(2-(Dimethylamino)ethyl)-6-(4-(3-(piperidin-1-yl)propylamino)-1,6-naphthyridin-2-yl)-1H-indole-2-carboxamide | B |
| 6-(4-(3-(Piperidin-1-yl)propylamino)-1,6-naphthyridin-2-yl)-N-(2-(pyridin-4-ypethyl)-1H-indole-2-carboxamide | A |
| 6-(4-(3-(Piperidin-1-yl)propylamino)-1,6-naphthyridin-2-yl)-N-(piperidin-4-yl)-1H-indole-2-carboxamide | B |
| (4-Ethylpiperazin-1-yl)(6-(4-(3-(piperidin-1-yl)propylamino)-1,6-naphthyridin-2-yl)-1H-indol-2-yl)methanone | A |
| N,N-diethyl-3-(4-(4-((3-(piperidin-1-yl)propyl)amino)-1,6-naphthyridin-2-yl)phenoxy)propanamide | C |
| N-(1-methylpiperidin-4-yl)-3-(4-(4-((3-(piperidin-1-yl)propyl)amino)-1,6-naphthyridin-2-yl)phenoxy)propanamide | C |
| N-((1-ethylpiperidin-4-yl)methyl)-3-(4-(4-((3-(piperidin-1-yl)propyl)amino)-1,6-naphthyridin-2-yl)phenoxy)propanamide | C |
| 3-(4-(4-(ethyl(3-(piperidin-1-yl)propyl)amino)-1,6-naphthyridin-2-yl)phenoxy)-N-((1-ethylpiperidin-4-yl)methyl)propanamide | C |
| 4-cyano-5-(4-((3-(piperidin-1-yl)propyl)amino)-1,6-naphthyridin-2-yl)-N-(piperidin-4-yl)-1H-benzo[d]imidazole-2-carboxamide | B |
| (4-ethylpiperazin-1-yl)(5-(4-((4-(pyrrolidin-1-ylmethyl)phenyl)amino)-1,6-naphthyridin-2-yl)-1H-benzo[d]imidazol-2-yl)methanone | C |
| N-(3-(piperidin-1-yl)propyl)-5-(4-((4-(pyrrolidin-1-ylmethyl)phenyl)amino)-1,6-naphthyridin-2-yl)-1H-benzo[d]imidazole-2-carboxamide | A |
| N-(2-(dimethylamino)ethyl)-5-(4-((4-(pyrrolidin-1-ylmethyl)phenyl)amino)-1,6-naphthyridin-2-yl)-1H-benzo[d]imidazole-2-carboxamide | A |
| N-(3-(4-methylpiperazin-1-yl)propyl)-5-(4-((4-(pyrrolidin-1-ylmethyl)phenyl)amino)-1,6-naphthyridin-2-yl)-1H-benzo[d]imidazole-2-carboxamide | C |
| 5-(4-((3-(piperidin-1-yl)propyl)amino)-1,6-naphthyridin-2-yl)-N-(2-(pyridin-4-yl)ethyl)-1H-benzo[d]imidazole-2-carboxamide | A |
| N-(1-Methylpiperidin-4-yl)-6-(4-(3-(piperidin-1-yl)propylamino)-1,6-naphthyridin-2-yl)-3H-imidazo[4,5-b]pyridine-2-carboxamide | A |
| N-(1-methylpiperidin-4-yl)-2-(4-(4-(3-(piperidin-1-yl)propylamino)-1,6-naphthyridin-2-yl)phenoxy)acetamide | C |
| N-(3-(piperidin-1-yl)propyl)-2-((4-(4-((3-(piperidin-1-yl)propyl)amino)-1,6-naphthyridin-2-yl)benzyl)oxy)acetamide | B |
| N,N-diethyl-2-((4-(4-((3-(piperidin-1-yl)propyl)amino)-1,6-naphthyridin-2-yl)benzyl)oxy)acetamide | B |
| N-(1-methylpiperidin-4-yl)-2-((4-(4-((3-(piperidin-1-yl)propyl)amino)-1,6-naphthyridin-2-yl)benzyl)oxy)acetamide | A |
| N-((1-ethylpiperidin-4-yl)methyl)-2-(4-(4-(3-(piperidin-1-yl)propylamino)-1,6-naphthyridin-2-yl)benzyloxy)acetamide | B |
| N-((1-methylpiperidin-4-yl)methyl)-2-(4-(4-(3-(piperidin-1-yl)propylamino)-1,6-naphthyridin-2-yl)benzyloxy)acetamide | A |
| N-(2-(4-methyl-1,4-diazepan-1-yl)ethyl)-2-(4-(4-(3-(piperidin-1-yl)propylamino)-1,6-naphthyridin-2-yl)benzyloxy)acetamide | A |
| 2-(4-(4-(3-(piperidin-1-yl)propylamino)-1,6-naphthyridin-2-yl)benzyloxy)-N-(piperidin-4-ylmethyl)acetamide | A |
| N-(2-(1-methylpiperidin-4-yl)ethyl)-2-(4-(4-(3-(piperidin-1-yl)propylamino)-1,6-naphthyridin-2-yl)benzyloxy)acetamide | A |
| N-(1-Methylpiperidin-4-yl)-3-(4-(4-(3-(piperidin-1-yl)propylamino)-1,6-naphthyridin-2-yl)benzyloxy)propanamide | A |
| methyl-N-(1-methylpiperidin-4-yl)-5-(4-((3-(piperidin-1-yl)propyl)amino)-1,6-naphthyridin-2-yl)-1H-pyrrolo[3,2-b]pyridine-2-carboxamide | B |
| 1-methyl-5-(4-((3-(piperidin-1-yl)propyl)amino)-1,6-naphthyridin-2-yl)-1H-pyrrolo[3,2-b]pyridine-2-carboxamide | B |
| (E)-N-(1-Methylpiperidin-4-yl)-3-(4-(4-(3-(piperidin-1-yl)propylamino)-1,6-naphthyridin-2-yl)phenyl)acrylamide | A |
| (E)-N-(2-(Dimethylamino)ethyl)-3-(4-(4-(3-(piperidin-1-yl)propylamino)-1,6-naphthyridin-2-yl)phenyl)acrylamide | A |
| (E)-N-(3-(Piperidin-1-yl)propyl)-3-(4-(4-(3-(piperidin-1-yl)propylamino)-1,6-naphthyridin-2-yl)phenyl)acrylamide | A |
| (E)-N-((1-Methylpiperidin-4-yl)methyl)-3-(4-(4-(3-(piperidin-1-yl)propylamino)-1,6-naphthyridin-2-yl)phenyl)acrylamide | A |
| (E)-N-(2-(1-Methylpiperidin-4-yl)ethyl)-3-(4-(4-(3-(piperidin-1-yl)propylamino)-1,6-naphthyridin-2-yl)phenyl)acrylamide | A |
| (E)-N-((1-Ethylpiperidin-4-yl)methyl)-3-(4-(4-(3-(piperidin-1-yl)propylamino)-1,6-naphthyridin-2-yl)phenyl)acrylamide | B |
| (E)-N-(2-(4-Methyl-1,4-diazepan-1-yl)ethyl)-3-(4-(4-(3-(piperidin-1-yl)propylamino)-1,6-naphthyridin-2-yl)phenyl)acrylamide | A |
| (E)-N,N-Diethyl-3-(4-(4-((4-(pyrrolidin-1-ylmethyl)phenyl)amino)-1,6-naphthyridin-2-yl)phenyl)acrylamide | B |
| N-(1-Methylpiperidin-4-yl)-3-(4-(4-(1-methylpiperidin-4-ylamino)-1,6-naphthyridin-2-yl)phenyl)propanamide | A |
| N,N-Diethyl-3-(4-(4-(1-methylpiperidin-4-ylamino)-1,6-naphthyridin-2-yl)phenyl)propanamide | A |
| N-((1-Methylpiperidin-4-yl)methyl)-3-(4-(4-(3-(piperidin-1-yl)propylamino)-1,6-naphthyridin-2-yl)phenyl)propanamide | A |
| N-(2-(1-Methylpiperidin-4-yl)ethyl)-3-(4-(4-(3-(piperidin-1-yl)propylamino)-1,6-naphthyridin-2-yl)phenyl)propanamide | A |
| 3-(4-(4-(3-(Piperidin-1-yl)propylamino)-1,6-naphthyridin-2-yl)phenyl)-N-(piperidin-4-yl)propanamide | A |
| N-(2-(Diethylamino)-2-oxoethyl)-3-(4-(4-(3-(piperidin-1-yl)propylamino)-1,6-naphthyridin-2-yl)phenyl)propenamide | A |
| N-(1-Ethylpiperidin-4-yl)-3-(4-(4-(3-(piperidin-1-yl)propylamino)-1,6-naphthyridin-2-yl)phenyl)propanamide | A |
| N-(2-(4-Methyl-1,4-diazepan-1-yl)ethyl)-3-(4-(4-(3-(piperidin-1-yl)propylamino)-1,6-naphthyridin-2-yl)phenyl)propanamide | A |
| N-(2-(1-methylpiperidin-4-yl)ethyl)-3-(4-(4-((3-(piperidin-1-yl)propyl)amino)-1,6-naphthyridin-2-yl)phenyl)propiolamide | B |
| N-((1-methylpiperidin-4-yl)methyl)-3-(4-(4-((3-(piperidin-1-yl)propyl)amino)-1,6-naphthyridin-2-yl)phenyl)propiolamide | B |
| N-(2-(1-methylazepan-4-ypethyl)-3-(4-(4-((3-(piperidin-1-yl)propyl)amino)-1,6-naphthyridin-2-yl)phenyl)propiolamide | B |
| (Z)-N'-hydroxy-N-(1-methylpiperidin-4-yl)-4-(4-((3-(piperidin-1-yl)propyl)amino)-1,6-naphthyridin-2-yl)benzimidamide | B |
| (Z)-4-(8-chloro-4-((3-(piperidin-1-yl)propyl)amino)-1,6-naphthyridin-2-yl)-N'-hydroxy-N-(1-methylpiperidin-4-yl)benzimidamide | C |
| (Z)-N'-methoxy-N-(1-methylpiperidin-4-yl)-4-(4-(3-(piperidin-1-yl)propylamino)-1,6-naphthyridin-2-yl)benzimidamide | A |
| N-(3-(piperidin-1-yl)propyl)-6-(4-(3-(piperidin-1-yl)propylamino)-1,6-naphthyridin-2-yl)benzo[b]thiophene-2-carboxamide | A |
| N-(2-(dimethylamino)ethyl)-6-(4-(3-(piperidin-1-yl)propylamino)-1,6-naphthyridin-2-yl)benzo[b]thiophene-2-carboxamide | B |
| N-(1-methylpiperidin-4-yl)-6-(4-(3-(piperidin-1-yl)propylamino)-1,6-naphthyridin-2-yl)benzo[b]thiophene-2-carboxamide | A |
| 6-(4-(3-(piperidin-1-yl)propylamino)-1,6-naphthyridin-2-yl)-N-(piperidin-4-yl)benzo[b]thiophene-2-carboxamide | A |
| N,N-diethyl-6-(4-(3-(piperidin-1-yl)propylamino)-1,6-naphthyridin-2-yl)benzo[b]thiophene-2-carboxamide | A |
| N-(1-ethylpiperidin-4-yl)-6-(4-(3-(piperidin-1-yl)propylamino)-1,6-naphthyridin-2-yl)benzo[b]thiophene-2-carboxamide | A |
| (4-methylpiperazin-1-yl)(6-(4-(3-(piperidin-1-yl)propylamino)-1,6-naphthyridin-2-yl)benzo[b]thiophen-2-yl)methanone | A |
| Piperazin-1-yl(6-(4-(3-(piperidin-1-yl)propylamino)-1,6-naphthyridin-2-yl)benzo[b]thiophen-2-yl)methanone | A |
| (4-ethylpiperazin-1-yl)(6-(4-(3-(piperidin-1-yl)propylamino)-1,6-naphthyridin-2-yl)benzo[b]thiophen-2-yl)methanone | B |
| (E)-N,N-Diethyl-3-(5-(4-((3-(piperidin-1-yl)propyl)amino)-1,6-naphthyridin-2-yl)furan-2-yl)acrylamide | B |
| (E)-N-(2-(1-Methylpiperidin-4-yl)ethyl)-3-(5-(4-((3-(piperidin-1-yl)propyl)amino)-1,6-naphthyridin-2-yl)furan-2-yl)acrylamide | B |
| (E)-N-(1-Methylpiperidin-4-yl)-3-(5-(4-((3-(piperidin-1-yl)propyl)amino)-1,6-naphthyridin-2-yl)furan-2-yl)acrylamide | C |
| (E)-3-(5-(4-(3-(Piperidin-1-yl)propylamino)-1,6-naphthyridin-2-yl)thiophen-2-yl)acrylic acid | B |
| (E)-N,N-Diethyl-3-(5-(4-(3-(piperidin-1-yl)propylamino)-1,6-naphthyridin-2-yl)thiophen-2-yl)acrylamide | C |
| (E)-N-(1-Methylpiperidin-4-yl)-3-(5-(4-(3-(piperidin-1-yl)propylamino)-1,6-naphthyridin-2-yl)thiophen-2-yl)acrylamide | B |

TABLE 6-continued

| Name | IC$_{50}$ |
|---|---|
| Piperazin-1-yl(6-(4-(3-(piperidin-1-yl)propylamino)-1,6-naphthyridin-2-yl)benzo[d]thiazol-2-yl)methanone | B |
| Morpholino(6-(4-(3-(piperidin-1-yl)propylamino)-1,6-naphthyridin-2-yl)benzo[d]thiazol-2-yl)methanone | B |
| N,N-Diethyl-6-(4-(3-(piperidin-1-yl)propylamino)-1,6-naphthyridin-2-yl)benzo[d]oxazole-2-carboxamide | B |
| N,N-Diethyl-6-(4-(3-(piperidin-1-yl)propylamino)-1,6-naphthyridin-2-yl)benzo[d]thiazole-2-carboxamide | B |

A: IC$_{50}$ is ≤ 1 µM;
B: IC$_{50}$ > 1 µM and < 20 µM; and
C: IC$_{50}$ ≥ 20 µM.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inhibiting low molecular weight protein tyrosine phosphatase (LMPTP) activity in a mammal comprising administering to the mammal a compound of Formula (I), or a pharmaceutically acceptable salt or solvate thereof, wherein the mammal has insulin resistance, metabolic syndrome, type 2 diabetes, cardiovascular disease, or combinations thereof; and
wherein Formula (I) is

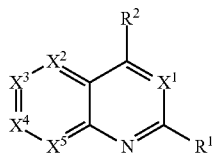

Formula (I)

wherein,
$R^1$ is

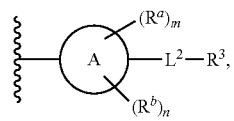

and $R^2$ is —$Z^1$-$L^4$-$R^4$;

Ⓐ is an aryl;
each $R^a$ is independently halogen, —CN, —OH, —OR$^{13}$, —SR$^{13}$, —S(=O)R$^{13}$, —S(=O)$_2$R$^{13}$, —N(R$^{12}$)S(=O)$_2$R$^{13}$, —S(=O)$_2$NR$^{12}$R$^{13}$, —C(=O)R$^{13}$, —OC(=O)R$^{13}$, —CO$_2$R$^{12}$, —OCO$_2$R$^{13}$, —NH$_2$, —NR$^{12}$R$^{13}$, —C(=O)NH$_2$, —C(=O)NR$^{12}$R$^{13}$, —OC(=O)NH$_2$, —OC(=O)NR$^{12}$R$^{13}$, —NR$^{12}$C(=O)NH$_2$, —NR$^{12}$C(=O)NR$^{12}$R$^{13}$, —NR$^{12}$C(=O) R$^{13}$, —NR$^{12}$C(=O) OR$^{13}$, substituted or unsubstituted C$_1$-C$_6$ alkyl, or unsubstituted C$_1$-C$_6$ fluoroalkyl;
each $R^b$ is independently substituted or unsubstituted C$_1$-C$_6$ alkyl, or unsubstituted C$_1$-C$_6$ fluoroalkyl;
m is 0, 1, or 2;
n is 0, 1, or 2;

$L^2$ is -$L^7$-$Y^1$—;
  $L^7$ is absent, substituted or unsubstituted C$_1$-C$_4$ alkylene, —CH=CH—, —C≡C—, substituted or unsubstituted C$_3$-C$_6$ cycloalkylene, —$Y^2$-$L^8$-, or -$L^8$-$Y^2$-$L^8$-;
  $Y^1$ is —C(=O)NR$^c$—, —C(=O)—, or —C(=O)O—;
  each $L^8$ is independently substituted or unsubstituted C$_1$-C$_4$ alkylene or substituted or unsubstituted C$_3$-C$_6$ cycloalkylene;
  $Y^2$ is —O—, —S—, —S(=O)—, —SO$_2$—, or —NR$^c$—;
  each $R^c$ is independently H or substituted or unsubstituted C$_1$-C$_6$ alkyl;
$R^3$ is H or -$L^3$-$R^5$;
  $L^3$ is absent or substituted or unsubstituted C$_1$-C$_6$ alkylene;
  $R^5$ is H, substituted or unsubstituted C$_3$-C$_{10}$ cycloalkyl, substituted or unsubstituted C$_2$-C$_{10}$ heterocycloalkyl, substituted or unsubstituted aryl, or substituted or unsubstituted heteroaryl;
or $R^3$ and $R^c$ are taken together with the N atom to which they are attached to form a substituted or unsubstituted N-containing heterocycle;
$Z^1$ is —NR$^d$—, —O—, or —S—;
$L^4$ is absent or -$L^5$-$L^6$-;
  $L^5$ is substituted or unsubstituted C$_1$-C$_6$ alkylene, substituted or unsubstituted arylene, or substituted or unsubstituted heteroarylene;
  $L^6$ is absent, substituted or unsubstituted C$_1$-C$_6$ alkylene, —NR$^6$—, —C(=O)NR$^6$—, —NR$^6$C(=O)—, or —NR$^6$C(=O)NR$^6$—;
$R^4$ is substituted or unsubstituted C$_3$-C$_{10}$ cycloalkyl, substituted or unsubstituted C$_2$-C$_{10}$ heterocycloalkyl, substituted or unsubstituted aryl, or substituted or unsubstituted heteroaryl;
or $R^4$ and $R^6$ are taken together with the N atom to which they are attached to form a substituted or unsubstituted N-containing heterocycle;
$X^1$ is CR$^7$;
$X^2$ is CR$^8$;
$X^3$ is N;
$X^4$ is CR$^{10}$;
$X^5$ is CR$^{11}$;
$R^7$, $R^8$, $R^{10}$, and $R^{11}$ are each independently selected from the group consisting of H, halogen, —CN, —OH, —OR$^{13}$, —SR$^{13}$, —S(=O)R$^{13}$, and —S(=O)$_2$R$^{13}$;
each $R^{12}$ is independently selected from the group consisting of H, C$_1$-C$_6$ alkyl, and C$_1$-C$_6$ fluoroalkyl;
each $R^{13}$ is independently selected from the group consisting of C$_1$-C$_6$ alkyl, C$_1$-C$_6$ fluoroalkyl, a substituted or unsubstituted C$_3$-C$_6$ cycloalkyl, a substituted or unsubstituted C$_2$-C$_6$ heterocycloalkyl, a substituted or unsubstituted aryl, a substituted or unsubstituted heteroaryl, a substituted or unsubstituted —C$_1$-C$_4$ alkylene-C$_3$-C$_{10}$ cycloalkyl, a substituted or unsubstituted —C$_1$-C$_4$ alkylene-C$_2$-C$_{10}$ heterocycloalkyl, a substituted or unsubstituted —C$_1$-C$_4$ alkylene-aryl, and a substituted or unsubstituted —C$_1$-C$_4$ alkylene-heteroaryl;
or when $R^{12}$ and $R^{13}$ are attached to the same N atom then $R^{12}$ and $R^{13}$ are taken together with the N atom to which they are attached to form a substituted or unsubstituted C$_2$-C$_{10}$ heterocycle.

2. The method of claim 1, wherein the compound of Formula (I) has the structure of Formula (II), or a pharmaceutically acceptable salt or solvate thereof:

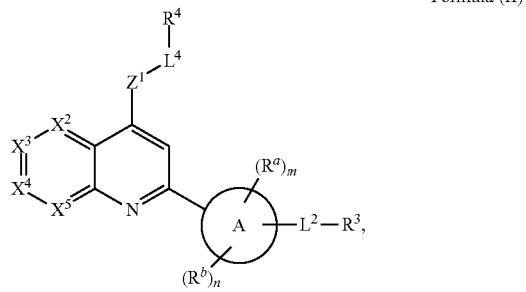

Formula (II)

each $R^a$ is independently halogen, —CN, —OH, —OR$^{13}$, —SR$^{13}$, —S(=O)R$^{13}$, —S(=O)$_2$R$^{13}$, —N(R$^{12}$)S(=O)$_2$R$^{13}$, —S(=O)$_2$NR$^{12}$R$^{13}$, —C(=O)R$^{13}$, —OC(=O)R$^{13}$, —CO$_2$R$^{12}$, —OCOR$^{13}$, —NR$^{12}$R$^{13}$, —C(=O)NR$^{12}$R$^{13}$, —OC(=O)NR$^{12}$R$^{13}$, —NR$^{12}$C(=O)NR$^{12}$R$^{13}$, —NR$^{12}$C(=O)R$^{13}$, —NR$^{12}$C(=O)OR$^{13}$, unsubstituted C$_1$-C$_6$ alkyl, or unsubstituted C$_1$-C$_6$ fluoroalkyl;

each $R^b$ is independently unsubstituted C$_1$-C$_6$ alkyl, or unsubstituted C$_1$-C$_6$ fluoroalkyl.

3. The method of claim 1, or a pharmaceutically acceptable salt or solvate thereof, wherein:

(A) is a phenyl or a naphthyl.

4. The method of claim 1, wherein the compound of Formula (I) has the structure of Formula (III), or a pharmaceutically acceptable salt or solvate thereof:

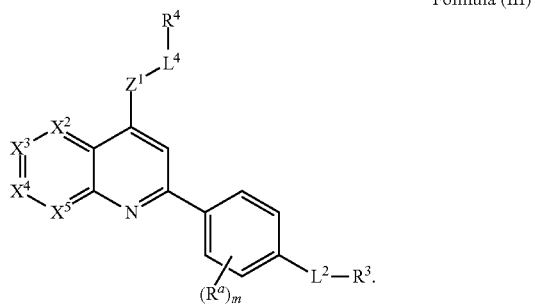

Formula (III)

5. The method of claim 1, or a pharmaceutically acceptable salt or solvate thereof, wherein:
$R^7$, $R^8$, $R^{10}$, and $R^{11}$ are each independently selected from the group consisting of H, halogen, —CN, —OH, —OR$^{13}$, —SR$^{13}$, —S(=O)R$^{13}$, and —S(=O)$_2$R$^{13}$.

6. The method of claim 1, or a pharmaceutically acceptable salt or solvate thereof, wherein:
$R^7$, $R^8$, $R^{10}$, and $R^{11}$ are each independently selected from the group consisting of H, halogen, —CN, —OH, —OR$^{13}$, and —SR$^{13}$.

7. The method of claim 1, or a pharmaceutically acceptable salt or solvate thereof, wherein:
$R^7$, $R^8$, $R^{10}$, and $R^{11}$ are each independently selected from the groups consisting of H, halogen, —CN, and —OH.

8. The method of claim 1, or a pharmaceutically acceptable salt or solvate thereof, wherein:
$R^7$, $R^8$, $R^{10}$, and $R^{11}$ are each independently selected from the group consisting of H, and halogen.

9. The method of claim 1, or a pharmaceutically acceptable salt or solvate thereof, wherein:
$R^7$, $R^8$, $R^{10}$, and $R^{11}$ are H.

10. The method of claim 1, or a pharmaceutically acceptable salt or solvate thereof, wherein:
$L^7$ is absent, substituted or unsubstituted C$_1$-C$_4$ alkylene, —CH=CH—, —C≡C—, or substituted or unsubstituted C$_3$-C$_6$ cycloalkylene;
$Y^2$ is —O—, —S—, or —NR$^c$—;
$R^3$ is H or -L$^3$-R$^5$;
  $L^3$ is absent or unsubstituted C$_1$-C$_6$ alkylene;
  $R^5$ is H, substituted or unsubstituted C$_3$-C$_1$ cycloalkyl, substituted or unsubstituted C$_2$-C$_{10}$ heterocycloalkyl, substituted or unsubstituted aryl, or substituted or unsubstituted heteroaryl.

11. The method of claim 1, or a pharmaceutically acceptable salt or solvate thereof, wherein:
$Z^1$ is —NR$^d$— or —O—;
$L^5$ is substituted or unsubstituted C$_1$-C$_6$ alkylene, substituted or unsubstituted C$_1$-C$_6$ heteroalkylene, substituted or unsubstituted phenylene or substituted or unsubstituted monocyclic heteroarylene;
$L^6$ is absent, substituted or unsubstituted C$_1$-C$_6$ alkylene, substituted or unsubstituted C$_1$-C$_6$ heteroalkylene, —NR$^6$—, —C(=O)NR$^6$—, —NR$^6$C(=O)—, or —NR$^6$C(=O)NR$^6$—;
$R^4$ is substituted or unsubstituted C$_3$-C$_{10}$ cycloalkyl, substituted or unsubstituted C$_2$-C$_{10}$ heterocycloalkyl, substituted or unsubstituted phenyl, or substituted or unsubstituted monocyclic heteroaryl.

12. The method of claim 1, or a pharmaceutically acceptable salt or solvate thereof, wherein:
$L^5$ is substituted or unsubstituted C$_1$-C$_6$alkylene;
$L^6$ is absent or —NR$^6$—;
$R^4$ is substituted or unsubstituted monocyclic C$_2$-C$_6$ heterocycloalkyl.

13. The method of claim 1, or a pharmaceutically acceptable salt or solvate thereof, wherein:
$L^5$ is —CH$_2$CH$_2$—, —CH$_2$CH$_2$CH$_2$—, or —CH$_2$CH$_2$CH$_2$CH$_2$—.

14. The method of claim 1, or a pharmaceutically acceptable salt or solvate thereof, wherein:
$R^4$ is substituted or unsubstituted monocyclic C$_2$-C$_6$ heterocycloalkyl that is a substituted or unsubstituted aziridinyl, substituted or unsubstituted azetidinyl, substituted or unsubstituted pyrrolidinyl, substituted or unsubstituted morpholinyl, substituted or unsubstituted thiomorpholinyl, substituted or unsubstituted piperidinyl, substituted or unsubstituted piperazinyl, or substituted or unsubstituted azepanyl;
or $R^4$ and $R^6$ are taken together with the N atom to which they are attached to form a substituted or unsubstituted monocyclic N-containing C$_2$-C$_6$ heterocycloalkyl that is a substituted or unsubstituted aziridinyl, substituted or unsubstituted azetidinyl, substituted or unsubstituted pyrrolidinyl, substituted or unsubstituted morpholinyl, substituted or unsubstituted thiomorpholinyl, substituted or unsubstituted piperidinyl, substituted or unsubstituted piperazinyl, or substituted or unsubstituted azepanyl.

15. The method of claim 1, wherein the compound is:
N,N-diethyl-4-(4-(3-(piperidin-1-yl)propylamino)-1,6-naphthyridin-2-yl)benzamide;
4-(4-((3-(piperidin-1-yl)propyl)amino)-1,6-naphthyridin-2-yl)benzoic acid;

4-(4-((3-(piperidin-1-yl)propyl)amino)-1,6-naphthyridin-2-yl)-N-(piperidin-4-yl)benzamide;
4-(4-((3-(piperidin-1-yl)propyl)amino)-1,6-naphthyridin-2-yl)-N-(2-(pyridin-4-yl)ethyl)benzamide;
N-(2-(dimethylamino)ethyl)-4-(4-((3-(piperidin-1-yl)propyl)amino)-1,6-naphthyridin-2-yl)benzamide;
N,N-diethyl-4-(4-((3-(piperidin-1-yl)propyl)amino)-1,6-naphthyridin-2-yl)-3-(trifluoromethyl)benzamide;
4-(4-((3-(piperidin-1-yl)propyl)amino)-1,6-naphthyridin-2-yl)-N-(piperidin-4-yl)-3-(trifluoromethyl)benzamide;
methyl 3-carbamoyl-4-(4-((3-(piperidin-1-yl)propyl)amino)-1,6-naphthyridin-2-yl)benzoate;
3-cyano-N,N-diethyl-4-(4-((3-(piperidin-1-yl)propyl)amino)-1,6-naphthyridin-2-yl)benzamide;
N1,N1-diethyl-4-(4-((3-(piperidin-1-yl)propyl)amino)-1,6-naphthyridin-2-yl)isophthalamide;
3-cyano-N-(1-methylpiperidin-4-yl)-4-(4-((3-(piperidin-1-yl)propyl)amino)-1,6-naphthyridin-2-yl)benzamide;
N,N-diethyl-4-(4-(3-(piperidin-1-yl)propylamino)-1,5-naphthyridin-2-yl)benzamide;
N,N-diethyl-4-(4-(3-(piperidin-1-yl)propylamino)-1,7-naphthyridin-2-yl)benzamide;
N,N-diethyl-4-(4-(3-(piperidin-1-yl)propylamino)-1,8-naphthyridin-2-yl)benzamide;
N,N-Diethyl-4-(4-((3-morpholinopropyl)amino)-1,6-naphthyridin-2-yl)benzamide;
N,N-Diethyl-4-(4-((2-(piperidin-1-yl)ethyl)amino)-1,6-naphthyridin-2-yl)benzamide;
N,N-Diethyl-4-(4-((3-(piperazin-1-yl)propyl)amino)-1,6-naphthyridin-2-yl)benzamide;
N,N-Diethyl-4-(4-((3-(4-(methylsulfonyl)piperazin-1-yl)propyl)amino)-1,6-naphthyridin-2-yl)benzamide;
N,N-Diethyl-4-(4-((1-methylpiperidin-4-yl)amino)-1,6-naphthyridin-2-yl)benzamide;
4-(4-((2-(Dimethylamino)ethyl)amino)-1,6-naphthyridin-2-yl)-N,N-diethylbenzamide;
N,N-diethyl-4-(4-(3-(4-methylpiperazin-1-yl)propylamino)-1,6-naphthyridin-2-yl)benzamide;
N,N-diethyl-4-(4-(2-morpholinoethylamino)-1,6-naphthyridin-2-yl)benzamide;
N,N-diethyl-4-(4-(2-(4-methylpiperazin-1-yl)ethylamino)-1,6-naphthyridin-2-yl)benzamide;
N,N-diethyl-4-(4-(tetrahydro-2H-pyran-4-ylamino)-1,6-naphthyridin-2-yl)benzamide;
N,N-diethyl-4-(4-(2-(piperazin-1-yl)ethylamino)-1,6-naphthyridin-2-yl)benzamide;
N,N-diethyl-4-(4-(2-(4-(methylsulfonyl)piperazin-1-yl)ethylamino)-1,6-naphthyridin-2-yl)benzamide;
N,N-Diethyl-4-(4-(4-methoxyphenylamino)-1,6-naphthyridin-2-yl)benzamide;
4-(4-(4-(Dimethylamino)phenylamino)-1,6-naphthyridin-2-yl)-N,N-diethylbenzamide;
4-(4-(4-((Dimethylamino)methyl)phenylamino)-1,6-naphthyridin-2-yl)-N,N-diethylbenzamide;
N,N-Diethyl-4-(4-(4-(2-methoxyethylamino)phenylamino)-1,6-naphthyridin-2-yl)benzamide;
4-(4-((2-(1,1-Dioxidothiomorpholino)ethyl)amino)-1,6-naphthyridin-2-yl)-N,N-diethylbenzamide;
4-(4-((3-(1,1-Dioxidothiomorpholino) propyl)amino)-1,6-naphthyridin-2-yl)-N,N-diethylbenzamide;
N,N-Diethyl-4-(4-(1-methylpyrrolidin-3-ylamino)-1,6-naphthyridin-2-yl)benzamide;
N,N-Diethyl-4-(4-(piperidin-4-ylamino)-1,6-naphthyridin-2-yl)benzamide;
N-(1-Methylpiperidin-4-yl)-4-(4-((1-methylpyrrolidin-3-yl)amino)-1,6-naphthyridin-2-yl)benzamide;
4-(4-((1-Methylpyrrolidin-3-yl)amino)-1,6-naphthyridin-2-yl)-N-(3-(piperidin-1-yl)propyl)benzamide;
N-(3-(Piperidin-1-yl)propyl)-4-(4-(piperidin-4-ylamino)-1,6-naphthyridin-2-yl)benzamide;
N-(1-Methylpiperidin-4-yl)-4-(4-(piperidin-4-ylamino)-1,6-naphthyridin-2-yl)benzamide;
N,N-diethyl-4-(4-(pyrrolidin-3-ylamino)-1,6-naphthyridin-2-yl)benzamide;
N-(3-(Piperidin-1-yl)propyl)-4-(4-(pyrrolidin-3-ylamino)-1,6-naphthyridin-2-yl)benzamide;
N-(1-Methylpiperidin-4-yl)-4-(4-(pyrrolidin-3-ylamino)-1,6-naphthyridin-2-yl)benzamide;
N-(1-Methylpiperidin-4-yl)-4-(4-((1-methylpiperidin-4-yl)amino)-1,6-naphthyridin-2-yl)benzamide;
N-(3-(Piperidin-1-yl)propyl)-4-(4-((tetrahydro-2H-pyran-4-yl)amino)-1,6-naphthyridin-2-yl)benzamide;
N-(3-(Piperidin-1-yl)propyl)-4-(4-((pyridin-4-ylmethyl)amino)-1,6-naphthyridin-2-yl)benzamide;
N-(1-Methylpiperidin-4-yl)-4-(4-((tetrahydro-2H-pyran-4-yl)amino)-1,6-naphthyridin-2-yl)benzamide;
4-(8-Bromo-4-((3-(piperidin-1-yl) propyl)amino)-1,6-naphthyridin-2-yl)-N,N-diethylbenzamide;
4-(8-Bromo-4-((3-(piperidin-1-yl) propyl)amino)-1,6-naphthyridin-2-yl)-N-(1-methylpiperidin-4-yl)benzamide;
N,N-Diethyl-4-(8-methyl-4-((3-(piperidin-1-yl)propyl)amino)-1,6-naphthyridin-2-yl)benzamide;
4-(8-Methyl-4-((3-(piperidin-1-yl) propyl)amino)-1,6-naphthyridin-2-yl)-N-(1-methylpiperidin-4-yl)benzamide;
4-(8-Methyl-4-((3-(piperidin-1-yl) propyl)amino)-1,6-naphthyridin-2-yl)-N-(3-(piperidin-1-yl)propyl)benzamide;
N,N-diethyl-3-(4-(4-((3-(piperidin-1-yl) propyl)amino)-1,6-naphthyridin-2-yl)phenoxy)propanamide;
N-(1-methylpiperidin-4-yl)-3-(4-(4-((3-(piperidin-1-yl)propyl)amino)-1,6-naphthyridin-2-yl)phenoxy)propanamide;
N-((1-ethylpiperidin-4-yl)methyl)-3-(4-(4-((3-(piperidin-1-yl)propyl)amino)-1,6-naphthyridin-2-yl)phenoxy)propanamide;
3-(4-(4-(ethyl(3-(piperidin-1-yl)propyl)amino)-1,6-naphthyridin-2-yl) phenoxy)-N-((1-ethylpiperidin-4-yl)methyl)propanamide;
N-(1-methylpiperidin-4-yl)-2-(4-(4-(3-(piperidin-1-yl)propylamino)-1,6-naphthyridin-2-yl)phenoxy)acetamide;
N-(3-(piperidin-1-yl)propyl)-2-((4-(4-((3-(piperidin-1-yl)propyl)amino)-1,6-naphthyridin-2-yl)benzyl)oxy)acetamide;
N,N-diethyl-2-((4-(4-((3-(piperidin-1-yl) propyl)amino)-1,6-naphthyridin-2-yl)benzyl)oxy)acetamide;
N-(1-methylpiperidin-4-yl)-2-((4-(4-((3-(piperidin-1-yl)propyl)amino)-1,6-naphthyridin-2-yl)benzyl)oxy)acetamide;
N-((1-ethylpiperidin-4-yl)methyl)-2-(4-(4-(3-(piperidin-1-yl)propylamino)-1,6-naphthyridin-2-yl)benzyloxy)acetamide;
N-((1-methylpiperidin-4-yl)methyl)-2-(4-(4-(3-(piperidin-1-yl)propylamino)-1,6-naphthyridin-2-yl)benzyloxy)acetamide;
N-(2-(4-methyl-1,4-diazepan-1-yl)ethyl)-2-(4-(4-(3-(piperidin-1-yl) propylamino)-1,6-naphthyridin-2-yl)benzyloxy)acetamide;
2-(4-(4-(3-(piperidin-1-yl) propylamino)-1,6-naphthyridin-2-yl)benzyloxy)-N-(piperidin-4-ylmethyl)acetamide;

N-(2-(1-methylpiperidin-4-yl)ethyl)-2-(4-(4-(3-(piperidin-1-yl) propylamino)-1,6-naphthyridin-2-yl)benzyloxy)acetamide;

N-(1-Methylpiperidin-4-yl)-3-(4-(4-(3-(piperidin-1-yl) propylamino)-1,6-naphthyridin-2-yl)benzyloxy)propanamide;

(E)-N-(1-Methylpiperidin-4-yl)-3-(4-(4-(3-(piperidin-1-yl) propylamino)-1,6-naphthyridin-2-yl)phenyl)acrylamide;

(E)-N-(2-(Dimethylamino)ethyl)-3-(4-(4-(3-(piperidin-1-yl) propylamino)-1,6-naphthyridin-2-yl)phenyl)acrylamide;

(E)-N-(3-(Piperidin-1-yl)propyl)-3-(4-(4-(3-(piperidin-1-yl)propylamino)-1,6-naphthyridin-2-yl)phenyl)acrylamide;

(E)-N-((1-Methylpiperidin-4-yl)methyl)-3-(4-(4-(3-(piperidin-1-yl)propylamino)-1,6-naphthyridin-2-yl)phenyl)acrylamide;

(E)-N-(2-(1-Methylpiperidin-4-yl)ethyl)-3-(4-(4-(3-(piperidin-1-yl) propylamino)-1,6-naphthyridin-2-yl)phenyl)acrylamide;

(E)-N-((1-Ethylpiperidin-4-yl)methyl)-3-(4-(4-(3-(piperidin-1-yl)propylamino)-1,6-naphthyridin-2-yl)phenyl)acrylamide;

(E)-N-(2-(4-Methyl-1,4-diazepan-1-yl)ethyl)-3-(4-(4-(3-(piperidin-1-yl)propylamino)-1,6-naphthyridin-2-yl)phenyl) acrylamide;

(E)-N,N-Diethyl-3-(4-(4-((4-(pyrrolidin-1-ylmethyl)phenyl)amino)-1,6-naphthyridin-2-yl)phenyl)acrylamide;

N-(1-Methylpiperidin-4-yl)-3-(4-(4-(1-methylpiperidin-4-ylamino)-1,6-naphthyridin-2-yl)phenyl)propanamide;

N,N-Diethyl-3-(4-(4-(1-methylpiperidin-4-ylamino)-1,6-naphthyridin-2-yl)phenyl)propanamide;

N-((1-Methylpiperidin-4-yl)methyl)-3-(4-(4-(3-(piperidin-1-yl)propylamino)-1,6-naphthyridin-2-yl)phenyl)propanamide;

N-(2-(1-Methylpiperidin-4-yl)ethyl)-3-(4-(4-(3-(piperidin-1-yl)propylamino)-1,6-naphthyridin-2-yl)phenyl)propanamide;

3-(4-(4-(3-(Piperidin-1-yl)propylamino)-1,6-naphthyridin-2-yl)phenyl)-N-(piperidin-4-yl)propanamide;

N-(2-(Diethylamino)-2-oxoethyl)-3-(4-(4-(3-(piperidin-1-yl) propylamino)-1,6-naphthyridin-2-yl)phenyl)propenamide;

N-(1-Ethylpiperidin-4-yl)-3-(4-(4-(3-(piperidin-1-yl)propylamino)-1,6-naphthyridin-2-yl)phenyl)propanamide;

N-(2-(4-Methyl-1,4-diazepan-1-yl)ethyl)-3-(4-(4-(3-(piperidin-1-yl) propylamino)-1,6-naphthyridin-2-yl)phenyl)propanamide;

N-(2-(1-methylpiperidin-4-yl)ethyl)-3-(4-(4-((3-(piperidin-1-yl) propyl)amino)-1,6-naphthyridin-2-yl)phenyl) propiolamide;

N-((1-methylpiperidin-4-yl)methyl)-3-(4-(4-((3-(piperidin-1-yl)propyl)amino)-1,6-naphthyridin-2-yl)phenyl) propiolamide;

N-(2-(1-methylazepan-4-yl)ethyl)-3-(4-(4-((3-(piperidin-1-yl)propyl)amino)-1,6-naphthyridin-2-yl)phenyl)propiolamide;

(Z)—N'-hydroxy-N-(1-methylpiperidin-4-yl)-4-(4-((3-(piperidin-1-yl) propyl)amino)-1,6-naphthyridin-2-yl) benzimidamide;

(Z)-4-(8-chloro-4-((3-(piperidin-1-yl) propyl)amino)-1,6-naphthyridin-2-yl)-N'-hydroxy-N-(1-methylpiperidin-4-yl)benzimidamide;

(Z)—N'-methoxy-N-(1-methylpiperidin-4-yl)-4-(4-(3-(piperidin-1-yl)propylamino)-1,6-naphthyridin-2-yl) benzimidamide;

or a pharmaceutically acceptable salt or solvate thereof.

16. The method of claim 4, wherein the method comprises administering to the mammal a pharmaceutical composition comprising a compound of Formula (I), or a pharmaceutically acceptable salt or solvate thereof, and at least one pharmaceutically acceptable excipient.

17. A method of treating insulin resistance, metabolic syndrome, type 2 diabetes or a combination thereof in a mammal comprising administering to the mammal a compound of Formula (I), or a pharmaceutically acceptable salt or solvate thereof:

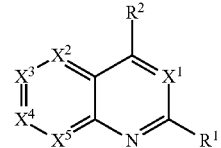

Formula (I)

wherein,
R¹ is

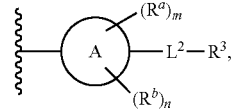

and R² is —Z¹-L⁴-R⁴;

$\bigcirc\!\!\!\!\!\text{A}$ is an aryl;

each $R^a$ is independently halogen, —CN, —OH, —OR¹³, —SR¹³, —S(=O)R¹³, —S(=O)₂R¹³, —N(R¹²)S(=O)₂R¹³, —S(=O)₂NR¹²R¹³, —C(=O)R¹³, —OC(=O)R¹³, —CO₂R¹², —OCO₂R¹³, —NH₂, —NR¹²R¹³, —C(=O)NH₂, —C(=O)NR¹²R¹³, —OC(=O)NH₂, —OC(=O) NR¹²R¹³, —NR¹²C(=O)NH₂, —NR¹²C(=O) NR¹²R¹³, —NR¹²C(=O) R¹³, —NR¹²C(=O)OR¹³, substituted or unsubstituted C₁-C₆ alkyl, or unsubstituted C₁-C₆ fluoroalkyl;

each $R^b$ is independently substituted or unsubstituted C₁-C₆ alkyl, or unsubstituted C₁-C₆ fluoroalkyl;

m is 0, 1, or 2;
n is 0, 1, or 2;
L² is -L⁷-Y¹—;
L⁷ is absent, substituted or unsubstituted C₁-C₄ alkylene, —CH=CH—, —C≡C—, substituted or unsubstituted C₃-C₆ cycloalkylene, —Y²-L⁸-, or -L⁸-Y²-L⁸-;
Y¹ is —C(=O)NR$^c$—, —C(=O)—, or —C(=O)O—;
each L⁸ is independently substituted or unsubstituted C₁-C₄ alkylene or substituted or unsubstituted C₃-C₆ cycloalkylene;
Y² is —O—, —S—, —S(=O)—, —SO₂—, or —NR$^c$—;
each R$^c$ is independently H or substituted or unsubstituted C₁-C₆ alkyl;
R³ is H or -L³-R⁵;
L³ is absent or substituted or unsubstituted C₁-C₆ alkylene;

$R^5$ is H, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl;

or $R^3$ and $R^c$ are taken together with the N atom to which they are attached to form a substituted or unsubstituted N-containing heterocycle;

$Z^1$ is —$NR^d$—, —O—, or —S—;

$L^4$ is absent or -$L^5$-$L^6$-;

$L^5$ is substituted or unsubstituted $C_1$-$C_6$ alkylene, substituted or unsubstituted arylene or substituted or unsubstituted heteroarylene;

$L^6$ is absent, substituted or unsubstituted $C_1$-$C_6$ alkylene, —$NR^6$—, —C(=O)$NR^6$—, —$NR^6$C(=O)—, or —$NR^6$C(=O)$NR^6$—;

$R^4$ is substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl;

or $R^4$ and $R^6$ are taken together with the N atom to which they are attached to form a substituted or unsubstituted N-containing heterocycle;

$X^1$ is $CR^7$;

$X^2$ is $CR^8$;

$X^3$ is N;

$X^4$ is $CR^{10}$;

$X^5$ is $CR^{11}$;

$R^7$, $R^8$, $R^{10}$, and $R^{11}$ are each independently selected from the group consisting of H, halogen, —CN, —OH, —$OR^{13}$, —$SR^{13}$, —S(=O)$R^{13}$, and —S(=O)$_2R^{13}$;

each $R^{12}$ is independently selected from the group consisting of H, $C_1$-$C_6$ alkyl, and $C_1$-$C_6$ fluoroalkyl;

each $R^{13}$ is independently selected from the group consisting of $C_1$-$C_6$ alkyl, $C_1$-$C_6$ fluoroalkyl, a substituted or unsubstituted $C_3$-$C_6$ cycloalkyl, a substituted or unsubstituted $C_2$-$C_6$ heterocycloalkyl, a substituted or unsubstituted aryl, a substituted or unsubstituted heteroaryl, a substituted or unsubstituted —$C_1$-$C_4$ alkylene-$C_3$-$C_{10}$ cycloalkyl, a substituted or unsubstituted —$C_1$-$C_4$ alkylene-$C_2$-$C_{10}$ heterocycloalkyl, a substituted or unsubstituted —$C_1$-$C_4$ alkylene-aryl, and a substituted or unsubstituted —$C_1$-$C_4$ alkylene-heteroaryl;

or when $R^{12}$ and $R^{13}$ are attached to the same N atom then $R^{12}$ and $R^{13}$ are taken together with the N atom to which they are attached to form a substituted or unsubstituted $C_2$-$C_{10}$ heterocycle.

18. The method of claim 17, further comprising administering an additional therapeutic agent to the mammal.

\* \* \* \* \*